United States Patent
Greco et al.

(10) Patent No.: US 10,717,981 B2
(45) Date of Patent: Jul. 21, 2020

(54) THERAPEUTIC COMPOSITIONS AND METHODS OF MAKING AND USING THE SAME

(71) Applicant: Advanced ReGen Medical Technologies, LLC, Houston, TX (US)

(72) Inventors: Steven John Greco, Houston, TX (US); Pranela Rameshwar, Newark, NJ (US); Khadidiatou Guiro, Houston, TX (US); Seda Ayer, Houston, TX (US)

(73) Assignee: Advanced ReGen Medical Technologies, LLC, Houston, TX (US)

( * ) Notice: Subject to any disclaimer, the term of this patent is extended or adjusted under 35 U.S.C. 154(b) by 0 days.

(21) Appl. No.: 16/250,940

(22) Filed: Jan. 17, 2019

(65) Prior Publication Data

US 2019/0218558 A1    Jul. 18, 2019

Related U.S. Application Data

(60) Provisional application No. 62/618,998, filed on Jan. 18, 2018, provisional application No. 62/619,002, (Continued)

(51) Int. Cl.
*C12N 15/11* (2006.01)
*A61K 48/00* (2006.01)
(Continued)

(52) U.S. Cl.
CPC ........ *C12N 15/1137* (2013.01); *A61K 31/185* (2013.01); *A61K 31/4741* (2013.01);
(Continued)

(58) Field of Classification Search
CPC .............. C12N 15/113; C12N 15/1137; A61K 31/713; A61K 31/53; A61K 31/4741; A61K 31/185
See application file for complete search history.

(56) References Cited

U.S. PATENT DOCUMENTS 2,984,164 A    5/1961  Melle
3,083,939 A    4/1963  Gallagher, Jr.
(Continued)

FOREIGN PATENT DOCUMENTS

CA    2845280      2/2012
EP    2 687 219    1/2014
(Continued)

OTHER PUBLICATIONS

Lam et al. (Molecular Therapy—Nucleic Acids (2015) vol. 4: pp. 1-20).*

(Continued)

*Primary Examiner* — Terra C Gibbs
(74) *Attorney, Agent, or Firm* — Knobbe, Martens, Olson & Bear, LLP

(57) ABSTRACT

Disclosed herein are polynucleotide agents (including interfering RNA agents (RNAi)), small molecule agents, and synthetic cells, methods of making the same, and their use as therapeutics against age-related dysfunction and/or cellular dysfunction that results in various disease states. In some embodiments, one or more agents as disclosed herein can be used to target and/or decrease the expression of the paired-box protein 5 (PAX5) gene, protein phosphatase, $Mg^{2+}/Mn^{2+}$ dependent 1F (PPM1F) gene, or both. Also disclosed herein are methods for the preparation and use of synthetic cells prepared by in vitro and/or in vivo manipulation using one or more cellular factors, polynucleotide agents, and/or small molecule agents. Disclosed herein is the use of these cells as therapeutic cells that treat age-related dysfunction and/or cellular dysfunction resulting in various disease states.

24 Claims, 133 Drawing Sheets

Specification includes a Sequence Listing.

Related U.S. Application Data filed on Jan. 18, 2018, provisional application No. 62/632,274, filed on Feb. 19, 2018, provisional application No. 62/743,345, filed on Oct. 9, 2018.

(51) Int. Cl.

| | | |
|---|---|---|
| C07H 21/02 | (2006.01) | |
| C07H 21/04 | (2006.01) | |
| C12N 15/113 | (2010.01) | |
| A61K 31/713 | (2006.01) | |
| A61K 31/53 | (2006.01) | |
| A61K 31/4741 | (2006.01) | |
| A61K 31/185 | (2006.01) | |

(52) U.S. Cl.
CPC ............ *A61K 31/53* (2013.01); *A61K 31/713* (2013.01); *C12N 15/113* (2013.01); *C12N 2310/14* (2013.01); *C12N 2310/141* (2013.01)

(56) References Cited

U.S. PATENT DOCUMENTS

| | | |
|---|---|---|
| 3,122,333 A | 2/1964 | Steele et al. |
| 3,436,081 A | 4/1969 | Unger |
| 8,257,973 B2 | 9/2012 | Park et al. |
| 8,747,915 B1 | 6/2014 | Giampapa |
| 8,945,558 B2 | 2/2015 | Kobara |
| 9,828,603 B2 | 11/2017 | Marbán et al. |
| 9,994,814 B2 | 6/2018 | Giampapa |
| 2004/0199935 A1 | 10/2004 | Chapman |
| 2005/0158285 A1 | 7/2005 | Giampapa |
| 2006/0188986 A1 | 8/2006 | Millar et al. |
| 2007/0025973 A1 | 2/2007 | Fitzsimmons et al. |
| 2007/0196918 A1 | 8/2007 | Sayre et al. |
| 2008/0213812 A1 | 9/2008 | Andrews et al. |
| 2008/0260704 A1 | 10/2008 | Riordan et al. |
| 2008/0268429 A1 | 10/2008 | Pietrzkowski |
| 2009/0011004 A1 | 1/2009 | Lutz et al. |
| 2009/0317369 A1 | 12/2009 | Hosoda et al. |
| 2009/0318345 A1 | 12/2009 | Fibbe et al. |
| 2011/0003008 A1 | 1/2011 | Lim |
| 2011/0177054 A1 | 7/2011 | Gibbings et al. |
| 2011/0258716 A1 | 10/2011 | Baltimore et al. |
| 2011/0300112 A1 | 12/2011 | Marbán et al. |
| 2012/0093885 A1 | 4/2012 | Sahoo et al. |
| 2012/0253102 A1 | 10/2012 | Marbán et al. |
| 2012/0258093 A1 | 10/2012 | Butler-Browne et al. |
| 2012/0321723 A1 | 12/2012 | Bruno et al. |
| 2013/0017176 A1 | 1/2013 | Hosoda et al. |
| 2013/0177593 A1 | 7/2013 | Gunn et al. |
| 2013/0195899 A1 | 8/2013 | Ichim et al. |
| 2013/0209528 A1 | 8/2013 | Levi et al. |
| 2013/0236428 A1 | 9/2013 | Giampapa |
| 2013/0302285 A1 | 11/2013 | Fong et al. |
| 2013/0336935 A1 | 12/2013 | Niedernhofer et al. |
| 2014/0004601 A1 | 1/2014 | Lim |
| 2014/0031256 A1 | 1/2014 | Lim |
| 2014/0088006 A1 | 3/2014 | Tsyrolva et al. |
| 2014/0120066 A1 | 5/2014 | Yeghiazarians et al. |
| 2014/0121171 A1 | 5/2014 | Muňoz-Cánoves et al. |
| 2014/0127284 A1 | 5/2014 | Cheresh |
| 2015/0023935 A1 | 1/2015 | Giampapa |
| 2015/0174166 A1 | 6/2015 | Giampapa |
| 2015/0203844 A1 | 7/2015 | Marbán et al. |
| 2015/0273113 A1 | 10/2015 | Marbán et al. |
| 2015/0328263 A1 | 11/2015 | Kaushal |
| 2016/0108370 A1 | 4/2016 | Greco et al. |
| 2016/0145571 A1 | 5/2016 | Giampapa |
| 2017/0087087 A1 | 3/2017 | Leonard et al. |
| 2017/0107581 A1 | 4/2017 | Kawauchi et al. |
| 2017/0173076 A1 | 6/2017 | Greco et al. |
| 2017/0275699 A1 | 9/2017 | Kawauchi et al. |
| 2017/0290860 A1 | 10/2017 | Marbán et al. |
| 2017/0304368 A1 | 10/2017 | Marbán et al. |
| 2017/0314019 A1 | 11/2017 | Greco et al. |
| 2018/0100149 A1 | 4/2018 | Marbán et al. |
| 2018/0360878 A1 | 12/2018 | Giampapa |
| 2018/0371465 A1 | 12/2018 | Hinkle |
| 2019/0000888 A1 | 1/2019 | Marbán et al. |

FOREIGN PATENT DOCUMENTS

| | | | |
|---|---|---|---|
| EP | 2 823 039 A1 | 1/2015 | |
| EP | 2 984 164 A1 | 2/2016 | |
| EP | 3 122 333 A1 | 2/2017 | |
| EP | 3 436 081 A1 | 2/2019 | |
| JP | 2017510582 A | 4/2017 | |
| JP | 6353073 B2 | 7/2018 | |
| KR | 10-2008-0049917 | 6/2008 | |
| KR | 20170139701 A | 5/2017 | |
| TW | 201739458 A | 11/2017 | |
| WO | WO 2004/048555 | 6/2004 | |
| WO | WO 2006/007529 | 1/2006 | |
| WO | WO 2006/052925 | 5/2006 | |
| WO | WO 2007/016245 | 2/2007 | |
| WO | WO 2007/109223 | 9/2007 | |
| WO | WO 2008/066330 | 6/2008 | |
| WO | WO-2008103135 A2 * | 8/2008 | ........... C12N 15/113 |
| WO | WO 2009/086425 | 7/2009 | |
| WO | WO 2009105044 | 8/2009 | |
| WO | WO 2011/029903 | 3/2011 | |
| WO | WO 2012/020307 | 2/2012 | |
| WO | WO 2012/149557 | 11/2012 | |
| WO | WO 2012/162741 | 12/2012 | |
| WO | WO 2013/048734 | 4/2013 | |
| WO | WO 2013/066368 | 5/2013 | |
| WO | WO 2013/134513 | 9/2013 | |
| WO | WO 2013/170170 | 11/2013 | |
| WO | WO 2014/013258 | 1/2014 | |
| WO | WO 2014028493 A2 | 2/2014 | |
| WO | WO 2014028493 A3 | 2/2014 | |
| WO | WO 2014/169077 | 10/2014 | |
| WO | WO 2015/052527 | 4/2015 | |
| WO | WO 2015/073625 | 5/2015 | |
| WO | WO 2015/085096 | 6/2015 | |
| WO | WO 2015095794 | 6/2015 | |
| WO | WO 2015/120150 | 8/2015 | |
| WO | WO 2015/148534 | 10/2015 | |
| WO | WO 2015/182781 A1 | 12/2015 | |
| WO | WO 2015/190542 A1 | 12/2015 | |
| WO | WO 2016/054591 | 4/2016 | |
| WO | WO 2016/057560 | 4/2016 | |
| WO | WO 2017/190000 | 4/2017 | |
| WO | WO 2009/011546 | 1/2019 | |
| WO | WO 2019/028223 | 2/2019 | |

OTHER PUBLICATIONS

PPM1F Wikipedia downloaded from https://en.wikipedia.org/wiki/PPM1F on Sep. 9, 2019.*
U.S. Appl. No. 14/922,353, filed Oct. 26, 2015, Greco, Steven John, et al.
U.S. Appl. No. 15/128,660, filed Sep. 23, 2016, Giampapa, Vincent C., et al.
U.S. Appl. No. 15/581,705, filed Apr. 28, 2017, Greco, Steven John, et al.
U.S. Appl. No. 16/111,832, filed Aug. 24, 2018, Giampapa, Vincent C.
Baker, Darren J. et al., "Clearance of p16Ink4a-positive senescent cells delays ageing-associated disorders" Nature, Nov. 1, 2011, vol. 479, No. 7372, pp. 232-236.
Bougel, S. et al., 'PAX5 activates the transcription of the human telomerase reverse transcriptase gene in B cells', J. Pathol. 2010, vol. 220, No. 1, pp. 87-96.
He, X. et al., "Human Fibroblast Reprogramming to Pluripotent Stem Cells Regulated by the miR19a/b-PTEN Axis" PLOS One, Apr. 16, 2014, vol. 9, No. 4, p. e95213.
International Search Report and Written opinion for PCT Application No. PCT/US2019/014061, dated May 8, 2019 7 pages.
Jurmeister, S. et. al., 'MicroRNA-200c represses migration and invasion of breast cancer cells by targeting actin-regulatory proteins

(56) References Cited

OTHER PUBLICATIONS

FHOD1 and PPM1F', Mol. Cell. Biol., Feb. 2012, vol. 32, No. 3, pp. 633-651.
Li, Zhonghan et al, "Small RNA-mediated regulation of iPS cell generation", EMBO Journal, Feb. 1, 2011, vol. 30, pp. 823-834.
Liang, J., et al., "MicroRNA-103a inhibits gastric cancer cell proliferation, migration and invasion by targeting c-Myb" Cell Proliferation, Dec. 22, 2014, vol. 48, No. 1, pp. 78-85.
Lu, D., et al., 'The miR-155-PU.1 axis acts on Pax5 to enable efficient terminal B cell differentiation', J. Exp. Med., 2014, vol. 211, No. 11, pp. 2183-2198.
Melief, Sara et al., "Multipotent stromal cells skew monocytes towards an anti-inflammatory interleukin-10-producing phenotype by production of interleukin-6," Haematologica, Jan. 24, 2013, 98(6): pp. 888-895.
NCBI Reference Sequence No. NM_014634.3, 'Homo sapiens protein phosphatase, Mg2+/Mn2+ dependent 1F (PPM1F), mRNA', Oct. 16, 2017.
NCBI Reference Sequence No. NM_016734.2, 'Homo sapiens paired box 5 (PAX5), transcript variant 1, mRNA', Nov. 30, 2017.
NCBI Reference Sequence No. NR_030350.1, 'Homo sapiens microRNA 619 (MIR619), microRNA', Jun. 26, 2017.
Suh, Mi-Ra, et al., "Human embryonic stem cells express a unique set of mircoRNAs" Development Biology, May 6, 2004, vol. 270, No. 2, pp. 488-498.
Tu, S.H. et al., 'Protein phosphatase Mg2+/Mn2+ dependent 1F promotes smoking-induced breast cancer by inactivating phosphorylated-p53-induced signals', Oncotarget, Oct. 18, 2016, vol. 7, No. 47, pp. 77516-77531.
Yu, Bin et al., "Exosomes secreted from GATA-4 overexpressing mesenchymal stem calls serve as a reservoir of anti-apoptotic microRNAs for cardioprotection" International Journal of Cardiology, Dec. 23, 2014, vol. 182, pp. 349-360.
Yu, Ge et al., "MicroRNA-19a targets tissue factor to inhibit colon cancer cells migration and invasion" Molecular and Cellular Biochemistry, May 12, 2013, vol. 380, No. 1-2, pp. 239-247.
Response to Office Action filed May 31, 2019, in U.S. Appl. No. 14/922,353.
Response to Final Office Action filed May 15, 2019, in U.S. Appl. No. 15/128,660.
Response to Final Office Action filed Apr. 2, 2019, in U.S. Appl. No. 15/581,705.
Rejenevie Therapeutics [rejenevie]. (published on May 15, 2019). "The Science Behind Immune Restoration," [Video file]. Retrieved from https://youtu.be/alKFhloo-L4, (transcript provided herewith).
Rejenevie Therapeutics [rejenevie]. (published Jun. 10, 2019). "10 Steps to Immune Restoration with Rejenevie," [Video file]. Retrieved from https://youtu.be/ulCaTglXXf8, (transcript provided herewith).
Rejenevie Therapeutics [rejenevie]. (published May 10, 2019). "FAQs for Patients: Restoration & Young Donors," [Video file]. Retrieved from https://youtu.be/GOm_Q5nTbPM, (transcript provided herewith).
Rejenevie Therapeutics [rejenevie]. (published May 10, 2019). "FAQs for Patients: Okyanos & Post-Treatment Testing," [Video file]. Retrieved from https://youtu.be/YU-v4yic36l, (transcript provided herewith).
Rejenevie Therapeutics [rejenevie]. (published May 10, 2019). "FAQs For Patients: Screening, Mobilization & Treatment," [Video file]. Retrieved from https://youtu.be/V3NIJ-emB1U, (transcript provided herewith).
Rejenevie Therapeutics [rejenevie]. (published on May 23, 2019). "The Science Behind The Transwell System," [Video file]. Retrieved from https://youtu.be/Y75UXv747IQ, (transcript provided herewith).
R Y Niyazova et al: "The interaction of miRNAs with mRNAs of the cell cycle genes in lung cancer", Proceedings of the Moscow Conference on Computational Molecular Biology (MCCMB'15), Jul. 2015, XP55595996.
Shi-Jie Zhang et al: "miR-1303 Targets Claudin-18 Gene to Modulate Proliferation and Invasion of Gastric Cancer Cells", Digestive Diseases and Sciences, vol. 59, No. 8, Mar. 20, 2014, pp. 1754-1763, XP55595270.
Ajijola et al., "Ventricular Tachycardia in Ischemic Heart Disease Substrates", Indian Heart Journal, 2014, pp. S24-S34, S28 & S30, vol. 66, Supplement 1.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Archundia, A., et al., "Direct cardiac injection of G-CSF mobilized bone-marrow stem-cells improves ventricular unction in old myocardial infarction," Life Sciences, Apr. 21, 2005, pp. 279-283, vol. 78, Elsevier Inc.
Baglio, S. R., et al,. "Mesenchymal stem cell secreted vesicles provide novel opportunities in (stem) cell-free herapy," Friontiers in Physiology, Sep. 6, 2012, pp. 1-11, vol. 3.
Beelen, Dietrich W., et al., "Transplantation of Filgrastim-Mobilized Peripheral Blood Stem Cells From HLA-Identical Sibling or Alternative Family Donors in Patients With Hematologic Malignancies: A Prospective Comparison on Clinical Outcome, Immune Reconstitution, and Hematopoietic Chimerism," Blood, Dec. 15, 1997, pp. 4725-4735, vol. 90 No. 12, The American Society of Hematology.
Chen et al., "Mesenchymal Stem Cell Secretes Microparticles Enriched in Pre-MicroRNAs", Nucleic Acids Research, 2010, vol. 38, No. 1, pp. 215-224.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Conboy, Irina M. et al, "Rejuvenation of aged progenitor cells by exposure to a young systemic environment", Nature, vol. 433, No. 7027, Feb. 17, 2005, pp. 760-764.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Guan, X, et al., "miR-223 regulates adipogenic and osteogenic differentiation of mesenchymal stem cells through a CI EBPs/miR-223/FGFR2 regulatory feedback loop," Stem Cells, 2015, pp. 1589-1600, vol. 33, AlphaMed Press.
Halley-Stott, Richard P., et al., "Nuclear reprogramming," Development at a Glance, 2013, vol. 2468-2471, The Company of Biologists Ltd.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hoetzenecker, Konrad, et al., "Mononuclear cell secretome protects from experimental autoimmune myocarditis," European Heart Journal, Jan. 15, 2013, pp. 676-685, vol. 36, No. 11.
Hsieh, J.-Y., et al., "miR-146a-5p circuitry uncouples cell proliferation and migration, but not differentiation, in human mesenchymal stem cells," Nucleic Acids Research, 2013, pp. 9753-9763, vol. 41, No. 21.
Hu et al., "MicroRNA-210 as a Novel Therapy for Treatment of Ischemic Heart Disease", Circulation, Sep. 14, 2010, vol. 122, Supplement 11, S124-S131, pp. 17.
Ibrahim et al., "Exosomes as Critical Agents of Cardiac Regeneration Triggered by Cell Therapy", Stem Cell Reports, May 6, 2014, vol. 2, pp. 606-619.
Ibrahim, A., et al. "Exosomes: Fundamental Biology and Roles in Cardiovascular Physiology," Annu. Rev. Physiol., 78, 68-83, 2017.
Ibrahim et al., "Microrna-Containing Exosomes from Cardiosphere-Derived Cells Stimulate Cardiomyocyte Proliferation and Angiogenesis

(56) References Cited

OTHER PUBLICATIONS in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
Iglesias, D. M., "Stem Cell Microvesicles Transfer Cystinosin to Human Cystinotic Cells and Reduce Cystine Accumulation in Vitro," PLOS One, Aug. 13, 2012, pp. 1-9, vol. 7, No. 8.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Kamdar et al., "Dystrophin-Deficient Cardiomyopathy", Journal of the American College of Cardiology, 2016, vol. 67, No. 21, pp. 2533-2546.
Kim, Mi Jung, et al., "Age-related Deterioration of Hematopoietic Stem Cells," International Journal of Stem Cells, 2008, 99. 55-63, vol. 1, No. 1.
Kooijmans et al., "PEGylated and Targeted Extracellular Vesicles Display Enhanced Cell Specificity and Circulation Time", Journal of Controlled Release, 2016, vol. 224, pp. 77-85.
Kordelas, L., et al., "MSC-derived exosomes: a novel tool to treat therapy-refractory graft-versus-host disease," Leukemia, Jan. 21, 2014, pp. 970-973, vol. 28, Macmillan Publishers Limited.
Kroschinsky, Frank, et al., "Single-dose pegfilgrastim for the mobilization of allogeneic CD34+ peripheral blood progenitor cells in healthy family and unrelated donors," Haematologica, Dec. 1, 2005, pp. 1665-1671, vol. 90, No. 12, Ferrata Storti Foundation.
Lai et al., "Exosome Secreted by MSC Reduces Myocardial lschemia/Reperfusion Injury", Stem Cell Research, 2010, vol. 4, pp. 214-222.
Lavasani, Mitra, et al., "Muscle-derived stem/ progenitor cell dysfunction limits healthspan and lifespan in a murine □rogeria model," Nature Communications, Jan. 3, 2012, pp. 1-12, vol. 3, No. 608, Macmillan Publishers Limited.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li, Shu-Hong, et al., "Reconstitution of aged bone marrow with young cells repopulates cardiac-resident bone arrow :lerived progenitor cells and prevents cardiac dysfunction after a myocardial infarction", European Heart Journal, Apr. 16, 2012, pp. 1157-1167, vol. 34, No. 15.
McCullagh, Karl J A: "Can a young muscle's stem cell secretome prolong our lives?", Stem Cell Research & Therapy, vol. 3, May 2012.
Melamed, Doran, et al., "Aging and neoteny in the B lineage," Blood, 2012, vol. 120, No. 20.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Mildner, Michael, et al., "Secretome of Peripheral Blood Mononuclear Cells Enhances Wound Healing," PLoS One, Mar. 22, 2013, pp. 1-8, vol. 8, No. 3.
Mittelbrunn, Maria, et al., "Unidirectional transfer of MicroRNA-loaded exosomes from T cell to antigen-presenting cells," Nature Communications, 2011, vol. 2, Article No. 282, 10 pages.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.

Ple et al., "The Repertoire and Features of Human Platelet microRNAs,"(Plos One (2012) vol. 7(12), article# e507 46, 14 pages). (Year: 2012).
Rando, Thomas A., et al., "Aging, Rjuvenation, and Epigenetic Reprogramming: Resetting the Aging Clock," Cell, Jan. 20, 2012, vol. 148, pp. 46-57, Elsevier Inc.
Ratajczak M Z et al: "Pivotal role of paracrine effects in stem cell therapies in regenerative medicine: can we translate stem cell-secreted paracrine factors and microvesicles into better therapeutic strategies?", Leukemia (Basingstoke), vol. 26, No. 6, Jun. 2012.
Rathore (2011, Preparative Biochemistry and Biotechnology, 41 :398-421).
Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.
Scaria et al., "Host-Virus Genome Interactions: Marco Roles for MicroRNAs", Cellular Microbiology, 2007, vol. 9, No. 12, pp. 2784-2794.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen, Jinhui, et al., "Transplantation of mesenchymal stem cells from young donors delays aging in mice," Scientific Reports, 2011, vol. 1, Article No. 67, 8 pages.
Shmazaki, T., et al., "Heterochronic microRNAs in temporal specification of neural stem cells: application toward rejuvenation," NPJ Aging and Mechanisms of Disease, Jan. 7, 2016, pp. 1-6, vol. 2, No. 15014, Japanese Society of Anti-Aging Medicine/Macmillan Publishers Limited.
Simonsson, Stina, et al., "DNA demethylation is necessary for the epigenetic reprogramming of somatic cell nuclei," Nature Cell Biology, Oct. 2004, vol. 6, No. 10, pp. 984-990, Nature Publishing Group.
Singhal, Nishant, et al., "Chromatin-Remodeling Components of the BAF Complex Facilitate Reprogramming," Cell, Jun. 11, 2010, vol. 141, pp. 943-955, Elsevier Inc.
Sun, Yun, et al., "Rescuing replication and osteogenesis of aged mesenchymal stem cells by exposure to a young extracellular matrix," The FASEB Journal, May 2011, vol. 25, No. 5, pp. 1474-1485.
Tatsumi, Kimiko et al: "Granulocyte-Colony Stimulation Factor Increases Donor Mesenchymal Stem Cells in Bone Marrow and Their Mobilization Into Peripheral Circulation but Does Not Repair Dystrophic Heart After Bone Marrow Transplantation", Gire J, 2008.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
U.S. Appl. No. 13/785,691, filed Mar. 5, 2013 including prosecution history.
U.S. Appl. No. 14/509,523, filed Oct. 8, 2014 including prosecution history.
U.S. Appl. No. 14/577,978, filed Dec. 19, 2014 including prosecution history.
U.S. Appl. No. 14/889,942, filed Nov. 9, 2015 including prosecution history.
U.S. Appl. No. 14/922,353, filed Oct. 26, 2015 including prosecution history.
U.S. Appl. No. 15/128,660, filed Sep. 23, 2016 including prosecution history.
U.S. Appl. No. 15/581,705, filed Apr. 28, 2017 including prosecution history.
U.S. Appl. No. 16/111,832, filed Aug. 24, 2018 including prosecution history.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.

(56) References Cited

OTHER PUBLICATIONS

Yu, B., et aL, "Exosomes Derived from Mesenchymal Stem Cells," International Journal of Molecular Sciences, Mar. 17, 2014, pp. 4142-4157, vol. 15.

Sugihara et al., "Carnosine induces intestinal cells to secrete exosomes that activate neuronal cells." PLOS One (2019) 14(5)e:0217394; pp. 1-17.

Response to Office Action filed Oct. 9, 2019, in U.S. Appl. No. 14/922,353.

Response to Final Office Action filed Sep. 26, 2019, in U.S. Appl. No. 15/128,660.

Response to Final Office Action filed Oct. 22, 2019, in U.S. Appl. No. 15/581,705.

\* cited by examiner

```
SEQ ID NO: 1
agttccttaa tcatttcacg gtgccttcgg acgcttttt tccacctaaa acgtttagtt      60
tcagctcagt gatcagctac cccagctcgg cggggagcg gaaggcttga attattccga     120
cctgtgagcg gcccctggca ccaaaaaaaa aaaaaaaaaa aaaaaaaaaa gaaaaaaaaa    180
ggcacaaaaa agtggaaact tttccctgtc cattccatca agtcctgaaa aatcaaaatg    240
gatttagaga aaaattatcc gactcctcgg accagcagga caggacatgg aggagtgaat    300
cagcttgggg gggtttttgt gaatggacgg ccactccogg atgtagtccg ccagaggata    360
gtggaacttg ctcatcaagg tgtcaggccc tgcgacatct ccaggcagct tcgggtcagc    420
catggttgtg tcagcaaaat tcttggcagg tattatgaga caggaagcat caagcctggg    480
gtaattggag gatccaaacc aaaggtcgcc acacccaaag tggtggaaaa aatcgctgaa    540
tataaacgcc aaaatcccac catgtttgcc tgggagatca gggaccggct gctggcagag    600
cgggtgtgtg acaatgacac cgtgcctagc gtcagttcca tcaacaggat catccggaca    660
aaagtacagc agccacccaa ccaaccagtc ccagcttcca gtcacagcat agtgtccact    720
ggctccgtga cgcaggtgtc ctcggtgagc acggattcgg ccggctcgtc gtactccatc    780
agcggcatcc tgggcatcac gtcccccagc gccgacacca acaagcgcaa gagagacgaa    840
ggtattcagg agtctccggt gccgaacggc cactcgcttc cgggcagaga cttcctccgg    900
aagcagatgc ggggagactt gttcacacag cagcagctgg aggtgctgga ccgcgtgttt    960
gagaggcagc actactcaga catcttcacc accacagagc ccatcaagcc cgagcagacc   1020
acagagtatt cagccatggc ctcgctggct ggtgggctgg acgacatgaa ggccaatctg   1080
gccagcccca ccctgctga catcgggagc agtgtgccag gccgcagtc ctaccccatt    1140
gtgacaggcc gtgacttggc gagcacgacc ctcccgggt accctccaca cgtccccccc   1200
gctggacagg gcagctactc agcaccgacg ctgacaggga tggtgcctgg gagtgagttt   1260
tccgggagtc cctacagcca ccctcagtat tcctcgtaca acgactcctg gaggttcccc   1320
aacccggggc tgcttggctc ccctactat tatagcgctg ccgcccgagg agccgcccca   1380
cctgcagccg ccactgccta tgaccgtcac tgaccttgg agccaggcgg gcaccaaaca   1440
ctgatggcac ctattgaggg tgacagccac ccagccctcc tgaagatagc cagagagccc   1500
atgagaccgt ccccagcat ccccacttg cctgaagctc ccctcttcct ctcttcctcc   1560
agggactctg gggcctttg gtgggccgt tggacttctg gatgcttgtc tatttctaaa   1620
agccaatcta tgagcttctc ccgatggcca ctgggtctct gcaaaccaat agactgtcct   1680
gcaaataacc gcagcccag cccagcctgc ctgtcctcca gctgtctgac tatccatcca   1740
```

FIG. 3P(1)

```
tcataaccac cccagcctgg gaaggagagc ttgcttttgt tgcttcagca gcacccatgt    1800
aaataccttc ttgctttct gtgggcctga aggtccgact gagaagactg ctccaccccat   1860
gatgcatctc gcactcttgg tgcatcaccg gacatcttag acctatggca gagcatcctc   1920
tctgccctgg gtgaccctgg caggtgcgct cagagctgtc ctcaagatgg aggatgctgc   1980
ccttgggccc cagcctcctg ctcatccctc cttctttagt atctttacga ggagtctcac   2040
tgggctggtt gtgctgcagg ctccccctga ggcccctctc caagaggagc acactttggg   2100
gagatgtcct ggtttcctgc ctccatttct ctgggaccga tgcagtatca gcagctcttt   2160
tccagatcaa agaactcaaa gaaaactgtc tgggagattc ctcagctact tttccgaagc   2220
agaatgtcat ccgaggtatt gattacattg tggactttga atgtgagggc tggatgggac   2280
gcaggagatc atctgatccc agccaaggag gggcctgagc ctctccctac tccctcagcc   2340
cctggaacgg tgttttctga ggcatgccca ggttcaggtc acttcggaca cctgccatgg   2400
acacttcacc caccctccag gaccccagca agtggattct gggcaagcct gttccggtga   2460
tgtagacaat aattaacaca gaggacttt ccccacaccc agatcacaaa cagcctacag    2520
ccagaacttc tgagcatcct ctcggggcag accctcccg tcctcgtgga gcttagcagg    2580
cagctgggca tggaggtgct ggggctgggg cagatgccta atttcgcaca atgcatgccc   2640
acctgttgat ctaagggcc gcgatggtca gggccacggc caagggccac gggaacttgg    2700
agagggagct tggagaactc actgtgggct agggtggtca gaggaagcca gcagggaaga   2760
tctggggac agaggaaggc ctcctgaggg aggggcagga gagcagtgag gagctgctgt    2820
gtgacctggg agtgattttg acatgggggt gccaggtgcc atcatctctt tacctggggc   2880
cttaattcct tgcatagtct ctcttgtcaa gtcagaacag ccaggtagag cccttgtcca   2940
aacctgggct gaatgacagt gatgagaggg ggcttggcct tcttaggtga caatgtcccc   3000
catatctgta tgtcaccagg atggcagaga gccagggcag agagagactg gacttgggat   3060
cagcaggcca ggcaggtctt gtcctggtcc tggccacatg tctttgctgt gggacctcag   3120
acaaaaccct gcacctcttt gagccttggc tgccttggtg cagcagggtc atctgtaggg   3180
ccaccccaca gctctttcct tccctcctc tctccaggga gccggggctg tgagaggatc    3240
atctgggca ggccctccac ttccaagcaa gcagatgggg gtgggcacct gaggcccaat    3300
aatatttgga ccaagtggga aacaagaaca ctcggagggg cgggaatcag aagagcctgg   3360
aaaaagacct agcccaactt cccttgtggg aaactgaggc ccagcttggg gaaggccagg   3420
accatgcagg gagaaaaagc agacttcctc tggccaccgc taagtatttt gttccctaag   3480
tccccacag ggtggtggaa cagaagagaa aactaaggct cagcaaggtg gagtcctcaa    3540
gcagtgactg gtgggggtgg ggctgggact cgggctcctg accccaacc catggtgttc    3600
cctgtcaccc tggtctatcc acatctccta ttcctgagga gagttgacag taagagcagt   3660
gagagatggt tctgggcccc atgccctaga caatcagtct gtaagaactg ccaaggaagc   3720
ctggtcaccc aggccaggga tggagccag cgagctcaca gcaggcacat gcacccccgc    3780
```

FIG. 3P(1) (continued)

```
cccoacccag aacctgcggg gcaaagaagg gaggtagttg gggccagagt ccacctccag    3840
gagccagggt gagctggctg cagcttccac ctgtcaggta aggtaggaga aggtatgtta    3900
cctggcatct ctctccctgc ctccctccat ttagcaggaa gtggtggggt cagggtctt    3960
cagcacagac ttcttgagcc tctgccccct gtcacccttc ttttggaatg atgtgtaccc    4020
acatctttgg atcctgccct ccttgtggtt ccaggctgtt gggaggaggt cagcctcccc    4080
tgaaccagct gcctgaggca tgcagcatcc ttcctcggca aagcccacct ggctcacagc    4140
ggcccctct ccccatcctg ttcctcttct tgccctgtaa tgagctcccc ccataccttt    4200
cctccctcac ctgaggcttt gctggtcctc agattggttt tgtatttgtg agacaaccac    4260
ttgactcctg ggctgccagg cggaagcaca agcgcacatg gatgcacacg gatgttctca    4320
cacacacacg cccgctctca ccaattcaca gcacctgtg gtccagcgga gctgcctggg    4380
agcttggtga ggatggctcc aaaggacaca agccgttgag tagatgccag agaattctga    4440
atggaaaaca caagtccggg gcctcaccag catcgtggca gaaggcctgg ggcatttctc    4500
catgggcctt cttccctgtg ttcgagctct gacttttgga aaaggacatt gtggatttta    4560
tgaaaatttc tcataccatc agtctagctc caacctagaa aaattggatg atatatcaaa    4620
cccaacatcc ctttcccaag gcaccttagt taaggctagc ccttccataa ctgacattgt    4680
acggtgcttt gcaatcctca accactctgt ggagcaaaga gcatgatgcc tactttatag    4740
acggggaaat tgacatttgg ggctctcacg gcaacataga ggcgaagtga attctcagat    4800
ctccaggccc cattctctct ccacggagtt gtgctcctgt catgggagtg tatggcttaa    4860
agacactccc ccaccccat tccctagaaa tccccagac ccacaatcag gcaagaaaga    4920
acagggaccc agaggctggc ctgacctagg ggcctgcagg ttggcggctt tgtttcctaa    4980
gaacattgaa acctgcggag tctttgacca aatccacaac agtgcttctg aggtttcatc    5040
cagactcttt cccagctgtc cctgaggttc agagggtatc agagtcaatt caaggccatg    5100
ccataatccc tgaccaggcc tggacatggg tccagccctg actccagggg tccaggtgcc    5160
aaggtcatgt gctgtccccc acttcccttt ctttgccttc gcactttgga acaggctcca    5220
ggcctggctg tgacagtatg caggagtgcc caagccaggg ccaccagggt gtccacagcc    5280
cctggaaaca cagatcacaa tctcaagtcc cctgaatgaa ctgcttcctg ggtgaacggg    5340
gtggtgtagc cttgccactc gggcagcgca ccagacagta cggtgcagca gtgccgaga    5400
tgcccagaag tgtgcctgcc ccctgagtg gcattcaagt atgaaaactt gtaaaatttt    5460
ctgtcggcct aaagaaaaat gtccatgggc caaacttgac ccactgggca ccagcctgtg    5520
agccccaatg cctgtcaatt gccccctttc tcattcacct cctgtcctt gttgcagatt    5580
tggaggagat gggagcccag agaggtgaga gatgtgcttc agggtgtcca gcaaggcagg    5640
ggtagaaacg ggcacgccca gagcctgcca ctctcccagg cctcatcttg ggctcttgca    5700
agtcttgcgc tttgaagatg gagttgggtg gaaggtcaga ggcgctgggg acgggattgg    5760
```

FIG. 3P(1) (continued)

```
ggagctgctg ggttttcagg ggaggtcagt gctgcttggg cacctttcac atgtgcaggg    5820
aagagactca gatgtggcca cagggcactg aggggtgaaa tccatttacc agaagtcacg    5880
ctccagaacg actgccagc cttggcagcc agtggctcca gccacccct cctcatgaca    5940
ttcagccaga attgagctcc aagccaggga agcaaatctt aaaaaccaac caagcaccct    6000
gacacagccc tagaaacacg atgagtctga aatacagctt cccaggaggg gagtctaaga    6060
tacagcttcc cgggagggtg gaaaccaact cctgcccac ggccaggcca ggcccaggca    6120
ggcatgggtg gatcccacag ggctctgagc tagaccggct ccacggtggc cccactacga    6180
ggccagttct gcagtcttgg ccttgtcacc catcgagagg ctgctctgat ggttcccagc    6240
cacacaccag ctctcctggg gaaactattt ctttcgttct tttggcctcg gagaggtccg    6300
aggcaagtac atttcttaaa aggtaataaa atgcattatt ggaaagttgg acagtcaggc    6360
cacgactcct agccacggc gtgccccacc tcccagcagc ccttcagcc ccttgccct     6420
gttgccccaa acctcagggt tccctcttgc atattcatgg gggaaccaca gtgctgatgt    6480
gtacttcccc actgtcagct cggctgcacc tcgtgtggcg ccaggtccca agggcctctg    6540
cagaggccag gctgtgagcc ccttgcctgc ctgctccct gatgaggcaa cagcttctct    6600
gaaatgagct gccggccagg agcaggcagg caccagcctg tctttccttt tctggtaatt    6660
cctcagcact gaggctccgt tcctgggcac cccaggattg aagggaacct cagaatcatg    6720
tcactgccat tctagagttt caatccaagg ggtcccttt agctcatctc caagatgggt    6780
aaacgtagcc accattcaga aagcccagaa attcttgttc ccacatctta gaccctgag     6840
caacacaagg agaaaatgca gctgcttacc tattaatatc tactgaggga caatcagcaa    6900
agcctcaaag gagtcgtctc aggtagggta cttggcctgt ggcaggagag acagaggcac    6960
aaacccaccc acccatcagc ttccggtggc tgatcggggc ccagggaggg aagcaggtga    7020
aacagcaggg tgggggtgac ttggcagtcg tgcatctcct ccccgactct gaggcctggc    7080
aggaggaggc cacaccagcc tcacctgccc tgaccccgc ccccaccct gtgaccctgt     7140
ggctatggcc gctggtcgcc cttgtcccca aaatcaccat gcctgtggcc acgtccctca    7200
tcttctccaa aagcatcatt aagaacaagt gattttggat gatggatttt tgatttacaa    7260
acggcgcatt tcccttggag tggaacagaa aggaaaccat ttaatggcgc ccttcttttc    7320
aagcatgaat acatttaat gaaactattt tattgtattt gaggaaatgg agagttgaac    7380
attccaacca atcaatagcc aattaattgc tataaagcta aaagaaaat aataaatcc     7440
tgagtctatt ttaaacactg caaaagttc agagcctcag aatctggcct tcccctccat    7500
aaggtgcacg agcatgtaaa cacacacaca cacacacaca cacacacaca cacactcact    7560
cactcccta caccctcagac atacttgaaa ctcagaaaca gcactgagtc tccccatgcc    7620
aattcttgcc tgctgtcttc gacttgggtc agagaaggtg agcagacccg gcagcagcct    7680
gtcccggggc tcaggaagag gcaggcccat cccctggcc caagcaccca gcacaacaga    7740
```

FIG. 3P(1) (continued)

```
gggtggcggg cagtgagggc ctggcgttgc ctgggcccca cttctcagcc ccagctgctg    7800
ggcctccaag gttgggctga ggatggagtt ttggctctgg gtttgccctg actcctgctg    7860
gaagacgctg ccctggtttt tcaccctcta gtggccttgg acattgagta tttgtagaaa    7920
tgcagattac attgcaaatg gaaacctttg ccaggaagac acatgcattt tgcttttaat    7980
tctttgagac atttgatttt gtcttaggga ctgacctttc agcatcaaag aaatacatat    8040
ctactgtatc cgccaaagtt tgtgatgcct gcatagacgc ttacttgtaa aaaaaaaaa    8100
atacaaaaaa atacaaaaaa accaacaaca aaaccacaa ttgaattgcc tttgaaagtg    8160
ggagatgatc tgtctccaac ggattgaaaa aaaaaaatgc ttcttaaaaa atgtgtatgt    8220
tttgtattct ttttttctag tagaaaataa ctgacttgaa atattggtgg ttttttttctt   8280
agtgacgtgt gttgcttttg tgtgtaataa tatttgaatg taattacagc agtgccaatt    8340
tgccaaagat gttggacata ttttttcttt tgggagga gggcagggct agggqtggga      8400
cttgggagaa aacaggggtg gggttttggt ttaatttttt ttttactttt ttttccttgt    8460
caaacctgaa atttgtggct tccttttaag ttaaatggtt gactgcaaca cctttatttt    8520
agattagttg gagaaacatg caataagatt ggcgtagttt caatatctgt gtgtcttttc    8580
atgagtggct gttacttgtg aagaattgat tttatgtaac ctttatgtga gataattatt    8640
tgtaaatatt tgccataatt ttattggttc ctaaaataaa agtaattttt taagttcaga    8700
aaaa                                                                 8704
```

FIG. 3P(1) (continued)

```
SEQ ID NO:2
ctgtccattc catcaagtcc tgaaaaatca aaatggattt agagaaaact tacccgactc      60
ctcggaccgg caggacagga catggaggag tgaatcagct tgggggggtt tttgtgaacg     120
gacggccact cccggatgta gtccgccaga ggatagtgga acttgctcat caaggtgtca    180
ggccctgcga catctccagg cagcttcgag tcagccatgg ttgtgtcagc aaaatccttg    240
gcaggtatta tgagacgggg agcatcaagc ctggggtaat tggaggatcc aaaccaaagg    300
tgccacacc caaagtggtg gaaaaaatcg ctgagtataa acgccaaaat cccaccatgt     360
ttgcctggga gatcagggac cggctgctag cagaacgcgt gtgtgacaat gacaccgtgc    420
ccagcgtcag ttccatcaac aggatcatcc ggacaaaggt gcagcagccg cccaaccagc    480
cggtgccggc ttccagccac agcatagtgt ccacgggctc agtgacgcag gtgtcgtcgg    540
tgagcacgga ctcagccggc tcctcgtact ccatcagcgg catcctgggc atcacgtccc    600
ccagtgctga caccaacaag cgcaagagag atgaaggtgt tccggagtcc ccggtgccca    660
acggccactc cctgccgggc cgagacttcc tccggaagca gatgcgagga gacctgttca    720
cgcagcagca gctggaggtg ctggaccgcg tgttcgagag gcagcactac gcggacatct    780
tcaccaccac ggagcccatc aagcccgagc agaccactga gtattcagcc atggcctcgc    840
tggctggagg gctggacgac atgaaggcca acctgaccag cccccacccca gctgacatcg    900
ggagcagcgt gccagggccg cagtcctacc ccattgtgac aggccgcgac ttggcgagca    960
cgactctccc cgggtaccct ccgcacgtcc cccggccgg acaggcagc tactcagcgc     1020
cgacgctgac agggatggtg cctggagtg agttttccgg gagcccctac agccaccctc     1080
agtacccctc gtacaacgac tcctggaggt tccccaaccc gggggctgctc ggctcccgt    1140
actattacag tgccgctgcc cggggggctg cccccgcctgc agctgccact gcctatgacc    1200
gtcactgacc ct                                                         1212
```

FIG. 3P(2)

SEQ ID NO:3

```
gaaagaaaaa aaaagaaagg aagaaagaaa agaaaaaaga aaaagaaaag aaagaaaaag      60
aagcacacaa aaaaagtgga aactttttcc ctcgtccact tcaagttctg aaaatcaaaa     120
tggatttaga gaaaaattac ccgactcctc ggagcggcag gacaggacat ggaggagtga     180
atcagcttgg gggggttttt gtgaatggac ggccacttcc ggatgtagtc cgccaaagga     240
tagtggaact tgctcatcaa ggtgtcaggc cctgcgacat ctcaaggcag cttcgagtca     300
gccatggttg tgtcagcaaa attcttggca ggtattatga gacggggagc atcaagcctg     360
gggtaattgg aggatccaaa ccaaaggtcg ccacgcccaa agtggtggaa aaaatcgctg     420
agtataaacg ccaaaatccc accatgtttg cctgggagat cagggaccgg ctgctggcgg     480
aacgtgtgtg tgacaatgac acggtgccca gcgtcagttc catcaacagg atcatccgga     540
caaaagtaca gcaaccaccc aaccagccgg tcccagcttc cagtcacagt atagtgtcca     600
cgggctccgt gacgcaggtg tcgtcggtga gcacggactc ggccggctcc tcgtactcca     660
tcagcggcat cctgggcatc acctccccca gcgccgacac caacaagcgc aagagagatg     720
aaggtattca ggaatctcca gtgccaaacg gtcactccct gccaggcaga gatttcctcc     780
ggaagcagat gcggggagac ctgttcacgc agcagcagct ggaggtgctg gaccgcgtgt     840
ttgagaggca gcactactcg gacatcttca ccaccacaga gcccatcaag cccgagcaga     900
ccaccgagta ttcagcgatg gcttcgctgg ctggagggct ggatgacatg aaggccaacc     960
tgaccagtcc cacccccgcc gacattggga gcagcgtgcc tgggccgcag tcctatccca    1020
ttgtgacagg ccgtgacttg cgcagcacga ccctccccgg gtaccctccg cacgtccccc    1080
ccgccggaca gggcagctac tcagcaccga cgctgacagg gatggtgcct gggagtgagt    1140
tctccgggag ccctacagc caccctcagt atcctctgta caacgactcc tggaggttcc    1200
ccaacccggg gctgcttgcc tccccgtact attacagcgc cgcagcccga ggagctgccc    1260
cgccagcagc cgccactgcc tacgaccggc actgaccctc ggagccaggc gggcgccaag    1320
cacttatcac acatatcact gagggcggta gcctctcggc ccctccgaag atggccagag    1380
gggccagcg agaccatcct ccagcaatcc ccactcgcct gaaactccct cccaaccttt    1440
tcttgccaag gactctgggg ctctatggta aggctgttag acttctagac acgcgtgtgt    1500
ttctaagagt caatcagcga gctgctccca acagcaactg ggtctctgca aagcaacgga    1560
ctattctgca gacaactgta gccccagcct agcctgccag tccccagctg tctgaccatc    1620
cacctgtctt cctgccccag gcctgggaag gagagcttgc ttttgtcact tcaacagcac    1680
ccatgtaaat accttcttgc tttttttgtgg gcctgagggt ccaactgagg cagaccgcct    1740
ccccattatg catccagtac tcccgatgtg tcacaggaca tcttagacct gtgtgcagag    1800
cattccctct gtcctggctg ccccccacag gtgggcttgt agttgtcctt gagactaagg    1860
```

FIG. 3P(3)

```
atgcccacct cagggcccag cctcctgctc attgctactt cttcaacgtc tggactagga      1920
gtcttgttgg actggttatg cttcacgctt ccccctgag accctcctc aggagaaaca         1980
cactggagag ttgccctggc ttcctgactc ccattttcc tgggcccagt gcagtgtgag        2040
cagctcttct tccatagcaa aggactcaga gaacaaagaa ctgtctggga gattcctcag       2100
ctactttct aaagtaagat gctgtccaag gtgctgaccg cattgtggac tcagtgctgc        2160
ggctgggcag gacccagaag accatagtcc aaggcgagga ctcccaagcc cctggaacca      2220
ctgaactgaa ctgggatgtg tttctgaggt gttcccaggc tcatatcaca ttggacaccc      2280
accatggaca tttcttccac cctccaggat gctagagagt ggattctggg caagcctgtc     2340
cctgccatgt agacaataat tcacaaaaag gaagttcttg caccaaggac cacaaacccc     2400
tacagcagtc agccagaact tcctgatcag cctctcccaa ttcctgtgga gcccagtgtg    2460
cagttgggac tagaggtgct ggggtgggag cagatgccta actgcacagt gggtatatac     2520
ctattgatgc aggggttgt gatggtcagc accatggcca agggccctg gagcctggag         2580
tgggagtttg gagaactcac tgtaggctgg agtggtcaga aaaactacc tgggagaatg      2640
tgggggacag aggaaggcct tctggggagag tgaggaactg gtgtgtgaac taggagtgat    2700
tttgaaatag gggttccagg ggccactatc tctttgcctg ggacctcaat tccttcaata    2760
atctctcttg ccagctccaa gcagccaggt ggaggtctgt ccaaatctgg gctgaattac    2820
agtgatgaca atggactttg ccatctcatg tgacaggata cccaatgtct acatgtcacc    2880
aagttggcaa agagctgggg cagagcagag cctgcacttg aggctattgg ccctgagagg    2940
tcttatcctg gccacaccat ttccttgctg taggacctca gacaagaccc tcacctctct    3000
gagtctccac tgctttggta cagcagggtc acctgcaggg ccatcctata gttctctcct    3060
cagcttcctc tttccccaga tgctgggct gtgactgggt catctggggc aagtcctcta     3120
cttataagca agcgtaagag ttgggcatct gagtcctgct aatatttgga ccaaatggga    3180
aataagaaca cccaaagaga tgagaatcag ccttgaggaa gatctagccc agctcccctc    3240
agggggaaact gaggcccagt ttggggaagc ccagtatgat gcagggaaat agaacagata    3300
tcctctggcc actatcaagt gtttttctccc caacatccta caaggtggtg gaagagaaga   3360
ggaaacaagc ttaccaaggt ggaggccaca ggcagtgact ggcagaggta gggctgggat    3420
tcaaccccc aaccctggc acaaggtgat catccttcca tccctgggga gggaagttga     3480
cagtgagggc agtgggagat cgttctgggc ccactgccac agatagagtg ttctgggctg    3540
ttagaactgc caagaaagcc caggcaccca gggcagaggt ggagccagtg ggctcaccat    3600
aggcacaccc acctccttgg aacctgctgg gcaaagaaga gaggcagctg ggggcagagc    3660
ccaccttcag gaacaggatg aaccagctcc agcctccacc tgccaggcaa ggtaggagaa    3720
ggaatgtcat ctggcctctc ctttcctcct tcctcccctc cttcccttcc acaggaaatg   3780
```

FIG. 3P(3) (continued)

```
gttggctcag gagtctgaag cacaggctct tggcctcttg cacccacatc tttggtcttc    3840
atccctcctt gtggtctcag gatattggga ggtcagcctt tcctgaacca actgcctaaa    3900
gcacacactg tccttcctca tcaaagccca gccggctcca ttctgttcct tctcttgccc    3960
tgtgatgagg tccccccata cctctcctct ctccccgag gctctgctgg tcttcagatt     4020
gcatttgtat ttattagaca accacttgat tcctgggctg ccaggaagaa gcacaagagc    4080
acatggatgt acacgcatgt tctcacacat gtacctgctc tctccagctc agggtacaca    4140
cactgcccag tggaacgcct gggagcttgg agagaaaggt tccaaaggac acaagccgtt    4200
gagtaaatgc cagagaattc tgaatggaaa acacaaggcc agagctctca cgaacattgt    4260
ggctggaggc ctgggcact cctccatggg ctttcagccc tatgttccag ctctgaattt     4320
tggaaaggac cttgtggatt ttatgaaaaa gcttcatatc attagtctag ctccagcctt    4380
gaaaaatctg atgacatatc aaatccaatc tccctttcc aaggcgcctt aggtagggtt     4440
agcccttca taactcacat ttgtatggtg ctttgcaatc cttgaccatt ccctggggca     4500
aagaccacaa tgcctattct acagatggta aaactgagat ttggggtttg catggcaaga    4560
gagagtaaa gtgaattctc agatctctgg gccccattct ctccacag aattgtgctc       4620
ttgtcatgag agcatgtggc ttagacaaat gcttcaatcc cctagaaacc ccctagaccc    4680
acaaggagga aaaaagaac agggacccag aggctgccct gaccaaatag cctggggctt     4740
ggtggcattg ccagtctacc ttgattctca ttaacaccaa acctgcaaag tctttgccca    4800
gatgcattca tatcagtgcc tctgaggttt tatccacact tcttccctgc tgggtcctga    4860
gcctccaagg ggatcagacc acaccattag ccctggcaga gctagacac gggcccgcct     4920
ccaactccca gggtctaaga ttccagggtt atgagatgtc ccctcactgg ggttcagaca    4980
tcagccctgt ttgtgacaac acgtaggagt cccccagcag ggccctcaga gcagccacag    5040
gcctgggaaa cacagatcgc aatctcaagg gccctgaact gctgcttccc aggttcagac    5100
ggagtaatct tgtcgctcag gccgggccag aggcaaccag agggcttgcc ccaaccaaca    5160
gcattcaaat gtgaaagctt ttaaaatgct cttccagcca aaaacctaca tttgtgggcc    5220
agatttgacc caccaaccac tagcacataa ctcccaactt ttgtccagtg ctcccttct     5280
ccttcacttg ctcttcattg aagatctggg ggagatggga accagagag ggatgggctt     5340
caggttttag gcagtcactg tcagggacaa gcatccccag tccttacccc ctccctcctc    5400
accccgggct cttgcagacc atttgggctt tgaagtggat gggatagaac agtttggggg    5460
tggtgggggt ggagggacta ttggcttcga gaggaggtca gtgccttgcc gctgggtct    5520
ttcatatgtg tgggaaagtg ccccagatgt ggccacaggg cactgaaggt tgaaatccct    5580
ttatgagaag tcgtatccca gagcaattgc cctgcctttg gcagcctctg caccagcta   5640
cccctcttct ggatgacatt tcagctagaa tttagctcca agccatgggg agcaaatctc    5700
aaaaataaac caagcactcc tgacaaatac ttagaaacaa gatatgtctg agacacagct    5760
```

FIG. 3P(3) (continued)

```
gcccggaggg tagagacaaa tccaggcccc tggagaagcc aggtccaggc tgaagtgggt    5820
ggatccctca gcactctggg caacaccagc tcccgggtgg cccagctaa  gaagctggct    5880
ttgcaaccat ggccttgtca cccatctagg ggcctgcctc tgatggtttc caggcacgca    5940
cgtcagtgct cccggagaat ttattccttt agttcttttg gcctcggaga ggtccaaggc    6000
aagtgcattt cttaaaaggt aacaaaacat tatcggaaag ttggacagtc aggccatgac    6060
tcctagccgg cagtctgccc cacctccag  cagcccttc  agccctggc  cctctgacga    6120
cccttacct  caggattccc tcttgcatat tcatggcgga gccacagtgt tgatccgaac    6180
ttccccaatg tcagctcgtg gctgcgcctc cagagtggcg gccaggtccc caggggctgc    6240
tgcggagggc tggaagtgag tccctggcct gcttctcgac gtgggcggct tgctaggagc    6300
agccaggcac cagactttct ttcattcact gtgatttctc gacactgggg ttccgttccc    6360
ggaccccccc acccaccacc cacccaggga tccaaggaga cctcaggatc ttgtccctgc    6420
cgatctaagc tgcagtgcat gtatttccag gggtccattt agtccatggc tgagttgggg    6480
gtaaatgtaa ccaccacgca gtaagtctag atagtctcct tccaacatct tagaccccaa    6540
agcagcacaa ggagaaaacg cagctgttta tctatttatg gaggaaatct taatgaattc    6600
taaaatggag ttggtctcag gtagcgtact tggcctgtga gtgggacaag gcgggtagga    6660
atcccacctg atttcagctc tagacagctc tgagcatggc tgggaaggg  agcatgtgaa    6720
acagcagggg gcggggcaga tcggagttag tgccccttg  cctgatctaa ggcctgcctg    6780
gaggaggtca agctgagcac ccgccccaag atcgggccca cccagtcctg caactatggc    6840
caccaggcca ccctcatccc caaaatcacc acgcataagg ccaagtccct catcatctct    6900
aaaggcacca ttaagaacaa gtgattttgg atgatggatt tttgatttac aaacggtgca    6960
tttcccttgg agtggaacag aaaggaaacc acttaatggc tcccttattt tcaagcatga    7020
atacatttta atgaaactat tttattgtat ttgaggaaat ggagagttga acattccaac    7080
caatcgatag ccaattaatt gctataaagc taaaaataaa taagtcttga gtcttttga     7140
aatgccctg  cagaactccg agcctccgga tcaggccttg ccctccatat gtgcgcctgt    7200
gtgtacatgc attcccacat gcgcacccct gcacctcaga catacttgaa actcagagat    7260
cgtgctgagt ctcctcatgc caattcttgc ctgctctcct cgcctctggt cagagatggt    7320
gagcagacct ggcagcagcc catgatgggg ctcaggaaga ggcagggcca tcccttggcc    7380
cggcaccacc agctcagtgt ggggatact  gggcagtgag ggcccctcg  ttggccccca    7440
ctgctgagcc tccaagtctg ggccgagggt ggaaatttga cttgggtttt gccctgactc    7500
ttgctggaag atgctgtcct ggttcttcac cctctagtgg cctttggaca ttgagtattt    7560
atagaaataa atgcagatta cattgcaagt ggaactcttt gccaggaaga cacatggatt    7620
tagcttctca ttctttgaga catttgactt tgtcttaggg actgaccttc cagcatcaaa    7680
gaaatacata tctactgtat ccgccaaagt ttgtgatgcc tgcatagacg cttacttgta    7740
aaaaaaaaaa aaaaaaaaaa aaaaa                                          7765
```

FIG. 3P(3) (continued)

SEQ ID NO:4

| | | | | | |
|---|---|---|---|---|---|
| gggaaaaaag | gaaagaaaaa | gaaagaaaaa | agaaaaaaga | aagaaaaaga | agcacacaca | 60 |
| aaaagtggaa | acttttctc | cctgtccact | tcatcaagtt | ctggaaaatc | aaaatggatt | 120 |
| tagagaaaaa | ttacccgact | cctcggaccg | gcaggacagg | acatggagga | gtgaatcagc | 180 |
| ttgggggggt | ttttgtgaat | ggacggccac | tcccggatgt | agtccgccaa | aggatagtgg | 240 |
| aacttgctca | tcaaggtgtc | aggccctgcg | acatctcaag | gcagcttcga | gtcagccatg | 300 |
| gttgtgtcag | caaaattctt | ggcaggtatt | atgagacggg | gagcatcaag | cctggtgtaa | 360 |
| ttggaggatc | caaaccaaag | gtcgccacgc | ccaaagtggt | ggaaaaaatt | gctgagtata | 420 |
| aacgccaaaa | tcccaccatg | tttgcctggg | agatcaggga | ccggctgctg | gcggaacggg | 480 |
| tgtgtgacaa | tgacacggtg | cccagcgtca | gttccatcaa | caggatcatc | cggactaaag | 540 |
| tacaacaacc | cccgaaccag | ccggtcccag | cttccagtca | cagcatagtg | tccacgggct | 600 |
| ccgtgacgca | ggtgtcgtcg | gtgagcacgc | actcggccgc | ctcctcgtac | tccatcagcg | 660 |
| gtatcctggg | catcacgtct | cccagcgcag | acaccaacaa | gcgcaagaga | gatgaaggta | 720 |
| ttcaggagtc | tccggtgccg | aacggccact | cactgccagg | cagagacttc | ctccggaagc | 780 |
| agatgcgggg | agaactgttc | acgcagcagc | agctggaggt | gctggaccgc | gtgtttgaga | 840 |
| ggcagcacta | ctcggacatc | ttcaccacca | cagagcccat | caagcccgag | cagaccactg | 900 |
| agtactcagc | tatggcctcg | ctggctggag | ggctggatga | catgaaggcc | aacctgacca | 960 |
| gtcccactcc | caccgacatt | gggagcagcg | tgcccgggcc | acagtcctac | cccattgtga | 1020 |
| caggccgtga | cttggcgagc | acgacccctcc | ccgggtaccc | tccgcacgtc | cccccgccg | 1080 |
| gacaaggcag | ctactcagca | ccgacgctga | cagggatggc | gcctgggagt | gagttttccg | 1140 |
| ggagccccta | cagccaccct | cagtatccct | catacaacga | ctcctggagg | ttccccaacc | 1200 |
| cggggctgct | cggctcccca | tactattaca | gcgccgctgc | ccgaggggct | gccccacctg | 1260 |
| cagccgccac | tgcctatgac | cgtcactgac | cctcggagcc | aggcaggcgc | caagcactta | 1320 |
| taacacatat | cactgagggc | gatagcctct | cagcccctct | gaagatggcc | agagggcc | 1380 |
| aacgagacca | tccccagca | accctcactc | acctgaaact | ccctcccaac | cttttcctgc | 1440 |
| cagggactct | ggggttccat | ggtaaggctg | ttggacttgt | agacatgcgt | ccatttctaa | 1500 |
| gagtcaatca | gtgagcttct | cccaacagca | gctgggtctc | tgcaaaccaa | cggactattc | 1560 |
| ttcagacaac | tatagcccca | gcctagcctg | ccagtcccca | gctgtctgac | catccacctg | 1620 |
| tcttcctgcc | ccaggctgg | gaaggagagc | ttgcttttgt | cgcttcaaca | gcacccatgt | 1680 |
| aaataccttc | ttgctttttt | gtgggcctga | gggtccagct | gagcggacag | cccacccatt | 1740 |
| atgcatccac | tactcccgat | gtgtcacagg | aaatcttaga | cctgtgtgca | gagtatcccc | 1800 |
| tctgttctgg | ctgccccca | agggtgggct | tggagttttc | cttgagacta | aggatgccca | 1860 |

FIG. 3P(4)

```
cctcagggcc cagcctcctg ctcattgcta cttctttaac gtctggacta ggagtctcat    1920
tgggctagtt atgcttcaag cttcccccct gagaaccctc ctcaggagaa acacactctg    1980
gagagatgcc ctggcttcct gacttcattt ccctgggccc aatgcagtgt gagcagctct    2040
tttccatatc aaaggactca aagagaactg tctgggagag tcttcagcta ctactctaaa    2100
gtaagatgct gtccaaggtg ctgactgcat tgcggacttt gaatgctagg gctggacagg    2160
acccaggaga ccatagtcct aggcgggaac cccaagcccc tggaaccact gaactgaact    2220
gggacgtgtt ttctgaggaa ttcccaggtt catatcatac cggacaccca ccgtggacat    2280
ttctcccacc ctccaggatg ccagagagtg gattctgggc aagcctgtcc ctgccatgta    2340
gacaatgatt aacaaaaagg actttcctgc actgaggacc acaaacacct acagaagtca    2400
gccagaactt cctgatcaac ccctcc                                         2426
```

FIG. 3P(4) (continued)

```
SEQ ID NO:5
agcagcttgc gggacacgga gccgcgagga gacagctgag gcccgcggag accagggggt      60
gaagcctgga gaccctcttg ccctggccta gctgcaggcc cccgggatgc tttgggcatg     120
tcctctggag cccacagaa gagcagccca atggccagtg gagctgagga gaccccaggc      180
ttcctggaca cgctcctgca agacttccca gccctgctga acccagagga ccctctgcca     240
tggaaggccc cagggacggt gctcagccag gaggaggtgg agggcgagct ggctgagctg     300
gccatgggct ttctgggcag caggaaggcc ccgccaccac ttgctgctgc tctggcccac     360
gaagcagttt cacagctgct acagacagac ctttccgaat tcaggaagtt gcccagggag     420
gaagaagaag aggaggagga cgatgacgag gaggaaaagg ccctgtgac cttgctggat      480
gcccaaagcc tggcacagag tttctttaac cgcctttggg aagtcgccgg ccagtggcag     540
aagcaggtgc cattggctgc ccgggcctca cagcggcagt ggctggtctc catccacgcc     600
atccggaaca ctcgccgcaa gatggaggac cggcacgtgt ccctcccttc cttcaaccag     660
ctcttcggct tgtctgaccc tgtgaaccgc gcctactttg ctgtgtttga tggtcacgga     720
ggcgtggatg ctgcgaggta cgccgctgtc cacgtgcaca ccaacgctgc ccgccagcca     780
gagctgccca cagacctga gggagccctc agagaagcct tccggcgcac cgaccagatg      840
tttctcagga aagccaagcg agagcggctg cagagcggca ccacaggtgt gtgtgcgctc     900
attgcaggag cgaccctgca cgtcgcctgg ctcggggatt cccaggtcat tttggtacag     960
cagggacagg tggtgaagct gatggagcca cacagaccag aacggcagga tgagaaggcg    1020
cgcattgaag cattgggtgg ctttgtgtct cacatggact gctggagagt caacgggacc    1080
ctggccgtct ccagagccat cggggatgtc ttccagaagc cctacgtgtc tggggaggcc    1140
gatgcagctt ccggggcgct gacgggctcc gaggactacc tgctgcttgc ctgtgatggc    1200
ttctttgacg tcgtacccca ccaggaagtt gttggcctgg tccagagcca cctgaccagg    1260
cagcaggca gcgggctccg tgtcgccgag gagctggtgg ctgcggcccg ggagcggggc    1320
tcccacgaca acatcacggt catggtggtc ttcctcaggg accccaaga gctgctggag     1380
ggcgggaacc agggagaagg ggaccccag gcagaaggga ggaggcagga cttgccctcc     1440
agccttccag aacctgagac ccaggctcca ccaagaagct aggtggtttc caggccctg     1500
ccctccctt cctccatcc ttgtccttct ctccctcaga agcctcagga cccaacaggt      1560
ggcaggcagt ggacagggtg cccgcccac agtgctttcc ccagcacccc agagccagtc     1620
gggacacccc ccgcagcccg tcctggtggc tgtggaactg cactgggtgg cgggcagatg    1680
gtggaaggca gcttaggaga cctcaccaaa gagaagatgg accggctctt gctcccagct    1740
cctattaggc ccggggtggg accagaggtc ataggtgccc aacggcagcc aaaccaaaga    1800
cactggtgtg catggggcag catggttgtg cacgtgggac cctggggcgg acccaggagc    1860
```

FIG. 3P(5) (continued)

```
caaactcttg aagcaccccc tgggtcaggc ccagcagcgg agtggccagc cccagtttcc    1920
cattgctcct ctctgcggcc agggccaggt gggttcatat ttacagatat gcccagccag    1980
tcctggtcgg ccacaccagt gtcccaaaga ggagagcgca gcagagccag gggtctgttc    2040
tgtagcagcc accccctgc ccccactcca gggcagccat gatgtgcttg ggcccaccag     2100
ggccttccgg gctgctctct tccctgagcc cggaaccggc gacgcacatg tgtcttttgt    2160
tggtgtgttt gttttttcc agggaggtct aattccgaag cagtattcca ggttttctct    2220
ttgttttatc agtgccaaga tgacctgttg tgtcatataa tttaagcaga gcttagcatt    2280
tattttattc tttagaaaac ttaagtattt actttttaa agctattttt caaggaacct     2340
tttttgcag tattattgaa tttatttct aaatcaggat tgaaacagga acttttccag      2400
gtggtgttaa taagccattc aagtgcctta cacagctttg aagaaactag gactgcagtg    2460
ggctcggata ggcccattga ggttttagaa aaagcaggat ttgttttgtt agggaggcat    2520
gattttggtg agatctttct ggaagagttt tccgcctctt tgtgatgctg aacacccca    2580
aggttctccc ctccccgc tgcccaggtg actggcagga gctgcgactg ccacgtagtg    2640
gtgcctgggc ccgacagcgg ggctctgggc atcccgggtg accttggcc atctgcctgc    2700
attcccaccc ccttgggcct ggctggatcc caggcagagg gaccttgctg ctgtgtgatt   2760
ggaacattcc caaatatctt gtgaatttgt aatcaaattg gtctcattgg gaaagactct    2820
taattaagag gctcaggcaa gcacagaggc agccgtggg tctctgtctc agtctggagg    2880
cagcagggat gctgctggga gtccatggca caggccacag cccctcacct tgccgcggtg    2940
gctggcagca cgctgcctt gctctgcccc atgccctgaa caggcatgag agctccacgt    3000
cccctagtgc accctgagag ggggctcaca agtgaccgat cctgggtgcc tcagggagct    3060
cactgagggc gtgcaaagtt gaaagtggca aggctggggg agggtgtcgg gtagagggaa   3120
gagggcaggg ggctagggga ggactcagag gccatctgca gggccaagcc acaggaaggg    3180
ctgagctgga ggtgggcagg gctgctccag gcaggtcaga gcagtgcagg gggaggagag    3240
gagaaaggga ggaagctggg ctgtgtggtc cccatgaagg cattcagagt ccacctgcag    3300
acagcgagag cccaggaag gtttgcacag ctgtgcccca agcaccttgg cctcctctca    3360
gctcgccgag gaggcacgct agagccgcct tcccggtggg agccctctgt cccacaggga    3420
gcggggagcc agctttgctg gggccctacc tgcatgccca gccttacccc tcattctcac    3480
agcacagatg aggttgagac catgcagtca atgcattgct taaggtctct tatttacaaa    3540
aaaaaaccct aaacatagtc gctgtcattc agacattcag agaatggttg gccacaaaca    3600
atgaccaagt attgcttggc ttaacttgaa ggcctgctgt ctccttctgg gggtcaggga    3660
cgcagctcca ccctcaccac tagcccaccc tgcccgtggg cataaccttg acgaagagag    3720
agaatgattg gcatctgctt ttctcttttc tttgctaata attctgttcc tggctgccga    3780
gagtgaagtt tcaccatgtg gaggtttggc tcctatcacc tggtggtctg attcatacccc   3840
```

FIG. 3P(5) (continued)

```
tagcctgagg ctccactgga agatctcgca gcctcagtgt atgggaaacc ctttccccag      3900
gcttgtccca gcactgccgc tccccacccc tgagccagga ccccagagga tggccatgcc      3960
ccgtgcctgg cagaggtctg gtgccagcac tgggagctgc tccgcccttg ccttggggcc      4020
gagggagccc tcgtccaccc ctgcacagca gctgggcaca gaggagcgct cttccatctt      4080
gaccaggact gcaccaagaa gcaccaggtg tcttcagcct ccaacctccg gggcgacctt      4140
ctcttccagc cacagtccca tgagggcccc tagccaggga cactggtctg taaattgtaa      4200
tcctttctcc agcccagctc tccacttgtt ccttgtgtga gctgagcagg cagtgcacct      4260
ctgagtgtcc cttttgtaag gccaggggt tgcactgagt ctgcagaggc cgcgacctcc       4320
tagaacgctg tgggtgcagg tgagccggcg tgtcctgggg agatgctgcc agcacacagg      4380
ggccctcctg ctgccagcag gttggggtgg ttaagtctta ttagtgtcta ttcttaaaat      4440
taagtgggct ggagaagaat ggagctccac atgccagcac cgtatatgga atacaaaagc      4500
tggggaagca gggcctgcct tacaggtgtg gctgactctg agcccaggcc tgcagggtg       4560
gagggcagtc cctcagaatc ccagaggcag tcccagcctc agaacccagg ataggaaatg      4620
ggtgtgttta gtggggaaag ggacggggtg cagacggcag ggccagtatg gggcccctc       4680
cctctcctct cctctcctat ggtgagccca gcgtgggcac cgggccgtct cagccgtgtt      4740
cccagggctg ggaggacagc tctggcccctt cttaggccta gcctcgtccc aagctaaatg     4800
taagccagtt gggctgtgtt aaaggaagca gtgttttttgg ttcgattctg cctctgtagc    4860
tcaagggggg cagcccccag agtcctgtgc attctgccaa ggctccatag ctttgccaaa     4920
tgcacggagc tctgccattc cggtgcagtg caggccttgc gaagggttta tctgcgttcg     4980
tctcggtggg cttctcctgc atgggagttg tgttcctgtg caaggggggag ctttgctcca    5040
ggacaggatg actgtcttcc ctattcttag ggacaagtcc caagatgcca gaaaggcagt    5100
ctcccaagga cccaccatgc agaagtgtca ataaaccaca agttctgaa                 5149
```

FIG. 3P(5) (continued)

SEQ ID NO:6

```
cggccaggga cgggaagtgg gcggggccgg ccagagcagc gagctgggcg cggagccgcc        60
gagtggcagg gtgaagacta actggaaccc tggcggcagg cccccggga tgctctgggc       120
atggcctctg gagccctaca ggagagcagc cagatggcag aggagacact gggcttcctg       180
gacatgctcc tctgcgactt tccagcccca ctgagcccag acagccctct gccgtggaag       240
gtgccaggga cagtgctgag gcaggaggag gtggaaggcg agctggccga gctggcgatg       300
ggtttcctgg gcagcaggaa tgctccgcca ccacttgctt cgtgtctggc ccatgaggca       360
gtttccaagc tgctgcaggc ggacctttcc gaattcagga agaagcccag gcaggaggag       420
gatgacgacg cagaagagga gaaggccct gtgaccttgc tggatgctga gggcctggtg       480
aggactttct ttaaccagct ctgggaagta tgcagccggt ggcagaagca ggtgccctcg       540
actgcccagg ctccgcagag gcagtggctg gtctccatcc acgccatccg gaacactcgc       600
cgcaagatgg aggaccggca cgtgtgcctt tcggccttca accagctctt cggcctgtcc       660
gaccccgtgg accgcgccta ctttgccgtg tttgacggtc acggcggggt ggacgctgcg       720
aggtacgctg ctgcacacgt gcatgcccat gctgcccgcc ggccggagct acctacagac       780
cctgcagggg ccctcaggga agccttccgg cgcaccgacg agatgtttct gtggaaagcc       840
aagcgagagc ggctgcagag cggcaccacc ggcgtgtgcg cgctcatcgc gggaaagacc       900
ctgcacgtcg cctggctcgg agactctcag gtcatcctgg tgcagcaggg acaggtggtg       960
aagctgatgg agccgcacag acccgagcga caggacgagc gggagcgcat cgaggcgctg      1020
ggtggcttcg tgtctcacat ggactgctgg agagtcaacg ggaccctggc tgtctccaga      1080
gccatcgggg atgtcttcca gaagccctac gtgtctgggg aggcggatgc agcctcccag      1140
gagctgacgg gctccgagga ctacctgctg ctcgcctgcg acggcttttt cgacgttgtc      1200
ccccaccatg aggttgctgg cctcgtgcag agccacctgg tcaggcagca gggcagtggg      1260
ctacacgtcg ccgaggagct ggtggctgca gcccgggagc ggggctccca cgacaacatc      1320
acagtcatgg tggtcttcct cagggacccc cgagccctgc tggagggcgg ggcccagggg      1380
gcaggggact tgccctctgg cctctcagag ccagagacca acaccacc gagaagctag       1440
gaggtcccag ccctggccc caccctgtga ccctccgtca gatgccttag gacctgatgg      1500
ctagcagtgc aggtggcacc gcccgcgcag tgctttgccc agcccccgag cccctcgtgt      1560
tgcttgcatt ggcccatccc gggggatggg atctgcactg ggtggtgagt gtcgcgccct      1620
gctggtggta ggcagtggga cggcaggatc tccaagggag cctaggaaga gacctcacca      1680
cggagccaag gccaggaggt gggccggcc ttgctcccgg tcaggcaggg gctggaccag      1740
aggccacagg cgccaggcga gcactcaggg cagcaggaca cagcatgggg ggccatcggg      1800
cagacctggg agccacggac attttcaaga gcgtcctggg tgcccggcac aggtttctca      1860
```

```
ctggctccac gctgcccaca gccgcgaggg ctcagatccg cagatgcgcc tggcgggtcc   1920
ctgctggccg agccggcttc cccaccagga aaaagggag caccaggcat ctggtctgct    1980
gcatcgccca ccactggtga cacgcctgcc ctggcctccc tggtccccca tccctggagc   2040
gcccggggag gggggtctca gaatgaccat gcgcgccttt catttgcggt cttttgtcag   2100
ggagcagtca gattcagaag cagtatttca gggctgtctt tttcgtcagt gccaaggtac   2160
ctgatgtgtc atgtaactta gacagggctt agtgtttggt ttatccctta ggaaactaag   2220
tattgatttt tttttttttt aggggaaacg tcttttgcag tattactgaa ttttttttcc   2280
cctaaatcag gactgagaca aaatttttcc aggtggtgtt aataagccat tcagtgcctt   2340
aaacagccta aggtgaggct ggaagtgccg ggcctctgac ggattccgcc aagcatgttg   2400
cagttcttac aaaggattta ttttgtcaga gtggcatgat tcgggctaga gttcttcctg   2460
gaagagttct gtctttgtga cgtgccactg actccgtgt ggagttgaaa ggggcaggc    2520
tgggcgaggg ctccccgcag aggccaggc cactggagag aggagcctgg gggcccgact   2580
cgcggtggtg ggcagggctg tgcaggcaga gaccagcaca tctgggaagg gcagtgggtg   2640
gctttggctt agctgaggct tcaggagaat gtcacggggt ggggggggc aggggaagt    2700
gggaggaagc ttggcgtcag gtcgccaagg ccatgaggtc ctgtggttca gagtccccc   2760
actgtagtgg ggccccaggg agcaatccca gctgcactga ggggaacctc ggcccttctc   2820
acccaggaa gggggtggatg gtgagagccg ccctgctga ggccagtcca ccatccagca   2880
agaaaggagg agcttgcagc ctcagggctc accccactc ccacggcagg gaagcagcag   2940
ctgagacgga cggtcagtgc cttgctccag ggctcgtgac agaaagcatc tcagacatgg   3000
tcactgcaac tcagagaggg tttggtggcc aacatgacca ggtattgctc catttaactt   3060
gaaggcccct ctgccttctg ggggcccgaa gcctcctcgt gagccctcc cagcaccagg    3120
ctggcacgag gggggatgtg gccccaccct tcactaccag cccagccacc catgggcatg   3180
accttaatgg aaggagggt caatggtttc tttgcgagtc tcactcggtt gacagctacc   3240
aagagtggag cttcaccca tggagtctgg gtcatgttca tgctccggcc caaggcccaa   3300
agcacaggag atctctccat gcttgtccca gtgtctccc cacctgagc caggctgagt   3360
caaaggctcc cgccccccac ccaccaggct gcctggcaga ggccttggct gtctggtgca   3420
gcctgggagc tgctggtcct tgccttgaga ccaagggagt ccccgctctc ccgctgcccc   3480
gggcctgacc tggtgcgtgc acccaggcac ggaggaggtc tcttccatct tgacagagcc   3540
cctgggcacc ttcaccctct gcgagtcctg gcccacttcc tctccaggcc acaggcactg   3600
ctctgtaagc cttgatccct ttctcaagtc ctagctttgc cactagctca ttttggggc    3660
tgagcaagcc gttgccctc cctggcctc agtttcccct tttagggcac agggttgcac    3720
tgagtctgtg cagcagctcc tggaacttgg gaggtgcagg ggctgcttgc ggtgagcctg   3780
gtgcagcagg ggagctactg ccggtgctga ggcccgcc accgccagca gggaggggtg    3840
```

FIG. 3P(6) (continued)

```
attaagtact attggtgtct attcttaaat ttaagtgggt tggaaaagaa tcgctgcaga    3900
tgccagcacc tcacgtgggt gcaaaagctg gagagccggc cctgccttca caggtagggc    3960
tgatgctgag cagcgggggt ggcagaagcg taggctccct cctcaggcgt gggggcctg     4020
ggaggggcag ggcgccgccg ggccccagg ggcttctagt caagctccca acctgctgac    4080
accctggagg caaacgcgtg gcctccctga cccagactgt ccttggagtc caggactagg    4140
aaatggatgt gttatggggg gagagtgaca ggcgggcccc acgggagaag cacaggctct   4200
ctgaggtccg cggtcatttc tgacgacccc tgcccttggc cgcagtcctg cctcccgcc    4260
ctccctgggc cggcacgcgg ccccggcct cgcccttcc cctgcgtccc ggctacctca    4320
gcagtattcc cagggctggg gggcagctct ggctgttcct ggacctggcc cccacccgag   4380
ctaaacggaa accgggtggg cctgtgcaaa ataagctgtt ttggtttgat tttggctgta    4440
gcccaagggg gcagcccag gaggcctgcg ctttagcttt gccaaacgtg ccacgccggc    4500
ctcgccaagg gtttatccgc acatctcagt gggttcctgg gagtggtgca agggggtct    4560
tgttctgaga caggatggcg gtcccctgt ccacagggac aagtcctagc gtgagggggc    4620
cagaagggca gtctcctccc agggccactg tgctcaagtg tcaataaacc acaagttgtg   4680
aaaccctgt                                                            4689
```

FIG. 3P(6) (continued)

```
SEQ ID NO:7
ggggcgggga ggcccggggc gcggggccgg tggcctctct gaggcgtgca gcgagtgaat      60
accacctgga atcccaacag agaccccgg  catgctctgg gcatggcctc tggagcccca     120
ccgcagagca gccacacggc agaggagatc ccaggcttcc tggacgcctt cctctgcgac     180
tttccagccc cgctgagcct ggagcccct  ttgccatgga agctcccggg acctgtgctg     240
agccaggagg aggtggaagg cgagctgacc gagctggcga tgggcttcct gagcaacagg     300
agcgctccac ctccacttgc tgcatctctg gcccatgagg cagtttccca gctgctacag     360
accgaccttt ctgaattcag gaagttgccc aggcaggagg aggaagaaga tgacgatgag     420
gaagagaagg ccctgtgac  cttgctggat gccaagggcc tggcacgaag ctgctttaac     480
cagctctggg aagtatgcag ccagtggcag aagcaggtgc cctcaactgc ccaggttcct     540
cagcggcagt ggctggtctc catgcatgcc atccggaata cacgccgcaa gatggaggac     600
cggcatgtgt gccttcccgc cttcaatcag ctcttcggcc tgtcggaccc cgtggaccga     660
gcctactttg ccgtgttcga tggtcacgga ggggtggacg ctgcacagta cgccgccgtg     720
cacgtgcaca ccaatctggc ccgccagccg gagctgctca cggacccgc  gggagccctc     780
agagaagcct tccggcacac cgatgagatg tttctctgga agccaagcg  agagcggctg     840
cagagcggca ctacaggggt gtgcgcactc atcgtgggaa agaccctgca catcgcctgg     900
cttggggact cccaggtcat cctggtgcag cagggacagg tggtgaagct gatggagcct     960
cacaggcctg agcgacagga tgagaaggag cgcattgagg cgctgggcgg cttcgtgtcc    1020
cacatggact gctggagagt caacgggacc ctggccgtgt ccagagccat cggggacgtg    1080
ttccagaagc cctacgtgtc agggaggcg  gactcggcct ctcggagct  gacggctcc    1140
gaggactacc tgctgctggc ctgcgacggc ttcttcgacg tgtcccca  ccaggaggtc    1200
gcgggcctcg tccacagcca cctggcccgg cagcagggca gcggctgca  ggttgcgag    1260
gagctggtgg ccgcggccg  ggagcggggc tcccacgaca acatcacggt catggtggtc    1320
ttcctcaggg acccccgaga cctactgaag ggcggggccc aggggacagg ggatgtgccc    1380
tctggcctct cacagccaga gaccagcact ccgcagagca gctaggaggt gtaggcccc     1440
tgcccccacc cgcacccctc ccctcagatg ccttaggacc cgacaggcgg tggcgggcag    1500
gcgggtgcca cctcagtgc  ttcccaggg  cccgaaccc  cctgctgca tcagtccatc    1560
ctggtgtctg gggaactgca ctgggtggtg gtgttattca tgcccgctc  gggcaggcag    1620
tggggtggcc tggatcccca aaggaggcct agggaagaga cctcaccaaa gagaagatga    1680
cccaagaagt ggagcagctc ttgctcccag ccccactggg taggggcagg gccagaggcc    1740
acaggcgcgg gccacagcca gaccaaagac actgggcctg tgcccggggc agcaggatgc    1800
tgcacgtgag tccccgggca gacccaggag cgacggacat ttccaagcgt gtcctgggcg    1860
```

FIG. 3P(7)

```
cctggctcag gcttctcgtt tgctcctcac tggccacggc tgggaggccc cagtctctac      1920
agatgggcct ggctgggcct ggcctgccaa gctggcttcc cgagtgggga gagcggcccc      1980
tggggaggga ggcgcaccag ggatctggtc tgcagtgggt gctcacggcc cccagcctcc      2040
ctgcccccct gcccccccat cccgcgcaca cccagggagg gggaggtcag aacgatgaca      2100
cgtgtgtctt tttatttgtg ggcttttcc cccccaggga agtctaactc agaagcagta       2160
tttcaggttt ttgcctttgt tttgtcagtg ccaagttgac ctgttgtgtc atataactta      2220
agcagagctt agcatttatt ttattcttag aaaacttaag tattgatttt ttttttttt       2280
gaagaaactt cttttgcagt attactgaat tttttttttcc taaatcagga ttgaaacaaa     2340
cacttttcca ggtggtgtta ataagccatt caagtgcctt aaacagcttt aggtaaggct      2400
agacccgccg ggcctgggac ggattctaat aggcatgctt cagtttttta caaaagcagg      2460
atttattttg ttctagtggc atgatttttgg ctagaattct tcccggacga gttctttcca    2520
cttgtcatga ttccattcgc tgctggaagt tagcaaagca gccctaaga gcgtaggctg       2580
tgctgtgcta cctgggccag accacggggcc tcgggagct ccgggtgacc atggcccgc       2640
cagcctcct ccacaccttg gccttgctgc tcatgtctca tgtctcatgt ctctggttgg       2700
tgcccaggct gagggactga gctccttgaa gcgggttcct cgtttgactg gaatgttcta      2760
gaatgtcttg tgttagtaat cgagtcggtt tcattgggaa acacgctgaa gaggccttgg     2820
caagtccgaa gcaggctggg gggctttggc ttggtttgga gcctgtcccg ctcacctgcc     2880
ccacagcccc caaaaccctc ctgtctcccg ctcgccatgg ctgtcaccct ctgccacctg      2940
gctctgccca cagcctaact gcctcaggga gggctccaca ttccctagca tgctctgggc     3000
aggtgaggct tgggagccac gaaacccag gtgcctggct gctcacatcc agtgaggcgg      3060
atatggcatg tgtgtcaagt tggaagtggc aggttaggtg gagtccaggc agaagtcaag     3120
ggccatgaga gagggatctc tggtgggagg acccaggcct acaggcctgg gaagagcatt     3180
aggtagctga gctgaggctt ctagagaatg tcgctgggag atgggcagca ggagggagct     3240
tggcaccagc ccccaggcca ggaggtccgc agagtccacc cgcagtagcc aggcccagc      3300
aaagagagcg cagggaggac cctgatcgcg tgcacagagg gagccctgct gacgaggaag      3360
cgggcagttg ggagcctcgg gggccctcag cccagggaag ggcagtgggt gagatgcccc     3420
cctccaggcc ccagacaagc ggaccctgac acaggaaggg agggagccag ctcgggcagg     3480
cagtgggca gtgaggtgcc accgcaggc tggcgctta cccctcactc ccacagcagg        3540
gatagagctg ctcggatgat ggggtcagtg ccgtggaaat gatgggaagt accttaaaca     3600
ccacaattcc aagaaggttt ggtaggagcc aacagtgacc ttgtgttgcc ccacttaacc     3660
ggaaggccct gctgctctcc gggggtccaa agccttctt cggccttcc cggcccaggg       3720
ccggcaggag gtggcacgtg gccctgccct tcaccaccag cctggctgct cctgggcatg     3780
```

```
atcttagcag atggaggaag cacgagcttc tgtttttctc atttctttgc taatcttatt    3840
ccgtgattgc catcaggagt gcggcttcac ccgtggggcc cggatcccc acgtgatggt     3900
ctgactcctg cccgggctcg aggctctccc aggagatctc tccaggcttg tcccagtgcc    3960
caccccgcct ctggcagagg cctctgctgt ctggtgctgc ccatccttgc cttggggctg    4020
agggcgccct tgttcatgct gcacagacgc tggctttgtg caagcaccta ggcacagagg    4080
cctcttccct cttgaccagg ggctggtcag ccttgaaagt cctggcccc cttctcttca    4140
ggccacagtc cgaggagggc ccctagccgg gccccccttc ccaaccctcg ccttgccact    4200
agctcattgt gtgagctgag caagtcctgg agccttcctg ggcctcagtt tctcctttag    4260
agggtacagg gttgcactgg atttgtgtgg cagatcctgg aattctggag gttcaggggc    4320
cagcctggtg catcctgggg agccgcggcc agtgccgcgg gagcccgccc ccccccge      4380
cccgaccgcc agcagggagg ggtgatgaag tattattagt gtctattctt gcagctaagt    4440
gggttggaag agaaaggagc cgcagacgct ggcgccgtat gtggatcaca agctggggcc    4500
caggtggagc tgagcccagg cagcggcagg ggggcagcag gtgccaggcc cggggacaag    4560
gcagggctcg gccgcgccct ccgcgcccag tcgtgctgcc agcctgctgc cgtgcggggc    4620
cgggtgcgcg gcctccccga cctcgcttgt cctcgcgccc aggactagga aagggtgcg     4680
ctgcaggggg gacggtggcg ggcccaggcc ccctggaga ggcccggagc cagccttggg     4740
ccgcagcccc gtgtcccgcc ccctccctc gtgggtgccc cggctacctc agcagtattc     4800
cagggctcgg gcgcggcccg ggcgggtcta ggcctggccc tgacggggc tgcaccgaag     4860
cccaatgggc ccgtgcaaaa taagctggtt tgggtttgct tctgcctgta gcccacggga    4920
ggcagcccca ggaggcccgc gcttctcgtc gaggctccac agctttgcca aatgcgccga    4980
gctttgccat tcagtgcgcc gtgccagcct tgccaagggt tcatctctgc acgtctcagc    5040
agggctcctg ggagaggtgt tctctgcaag gggcgtcttg ttccaagacg ggatggccat    5100
tgcccttgtc tgcagggcca agtcccagga tgtgggggca gaaactcagt ctcctcccag    5160
gggtcactgt gctcaagtgt caataaacca cgagttttga accctga                   5208
```

FIG. 3P(7) (continued)

SEQ ID NO:8

```
gcccgccgtc cgactgcgcc tgcgcggagc ccgcggcggc gggggacggg aagtgggcgg      60
ggtcggccag gagcggctcg cggggtccgg agtggcggag tagcagagtg aagatcacct     120
ggaaccccgg cagagccccc ccgggatgct gtggacatgg cctctggaga cccacagcag     180
agcagccaaa tggcagagga gatcccgggc ttcctggatg ccttcctcca tgacttccca     240
gccccactga gcccagagag cccttttgcca tggaaggtcc aggaacagt gctgagtcag     300
gaggaggtgg agggtgagct ggccgagctg gcgatgggct tcctgagcag caggaatgct     360
cccccaccac ttgcttcatg tctggcccac gaagcggttt cccagctgct gcagatggac     420
ctttctgaat tcaggaaatt gcccagacag gaggaggagg aggaggagga ggaggaagat     480
gacaacgagg aagagaaggc ccctgtgacc ctgctggatg ccaagggcct ggcgcgaagt     540
ttctttaacc agctctggga agtatgcagc cagtggcaga agcaggtgcc ctcgagtgcc     600
cgggttcctc agcggcagtg gctggtctcc atccatgcca tccggaatac tcgccgcaaa     660
atggaggacc ggcacgtgtg ccttcctgcc ttcaaccagc tctttggcct gtctgacccc     720
gtggaccgag cctactttgc tgtgtttgat ggccatggag gggtggacgc tgcaaggtat     780
gctgctgtac atgtgcacgc caacgtggcc cacggccgg agctgcccac agacccgcg      840
ggagccctca gagaagcctt ccggcacaca gatgagatgt tcctctggaa agccaagcga     900
gagcggctgc agagtggcac cacgggtgtg tgcgctttca ttgcgggaaa gaccctgcat     960
gttgcctggc tcgggactc ccaggtcatc ctggtgcaac agggacaggt ggtgaagctg    1020
atggagccgc acagacctga gcgacaggat gagaaggagc gtattgaagc gctgggcggc    1080
tttgtgtctc acatggactg ctggagagtc aacgggaccc tggctgtgtc tagagccatt    1140
ggggatgtct ttcagaagcc ctacgtgtca ggagaggccg actcagcctc ccgggagctg    1200
acaggctctg aggactacct gctgctggcc tgtgatggct tcttcgatgt cgtccccac     1260
caggaggtcg cgggcctcgt ccagagccac ttggtcaggg agcagggcag cggctgcag    1320
gttgctgagg agctggtggc tgcagcccgg gagcgggct cccacgataa catcacagtc    1380
atggtggtct tcctcaggga cccccaagac ctgctgaagg gcagggccca gggggtagga    1440
gacgtgccca ctggcctcgc agagccaggg accaatgctc cacagagacg ctaggaggtg    1500
caggctccct gccectacce cgtaacccte ccctcagat gcttaggac ccgacaggtg      1560
atggtggaca gtgggtgcca ccctcacagt gctttcccag ggcccaagt ctccgtgct     1620
gcttgcattg gcccatcctg gtggctgtgg aactggactg ggtcgtgggg gatgtgccct    1680
gctcggacag gcagtgggat ggccttgttc tttgaaggag gcctaggaa gagacctcac    1740
caaagaaaag acgacccaag aagtggagca gctcttgctc ccagccccat caggtagggg    1800
gctcaggtgg ggaccacagc cagaccaaag atgctgggca tgtgcatggg gcagcaggat    1860
```

```
gctgcatgag cccccaggca gacccaggag ccacggacat tccaagtgc aacctgggtg      1920 tccagcacag gtttctcact tgctcctcac tgggccgcca tgggaggctc gtctccgctg      1980
acgcacctgg cctcccgagc cagcttccca aattggggag aacagagcac cagggacctg      2040
gtctgcagtg aatgctcaca gcccccagcc tccctggttc cctcccgtcc cgcacacacc      2100
cagtgagagg aaggtcagaa tgacaacgag gtgtgtgtct tcagtttgtg gtcttttttt      2160
tttttttcca ggacagtcga actcagaagc agtatttcag gttttgtct ttgttttgtc       2220 agtgccaagg tgacctgttg tgtcatgtaa cttaagcaga gcttagcatt tatttattc      2280 ttggaaacct taagtattga tttttttttt ttggaagaaa cttcttttgc agtattactg      2340 aattttttc ctaaatcagg attgaagcaa cacttttcc aggtggtgtt aataagccat       2400
tcaagtgcct taaacagctt taggtgaggc tagaaccgcc gggcctggga tggattctac      2460
taggcatgtt taagtttta caagagcagg atttattttg ttatagtggc atgattcag      2520 ctagaattct tcccactcca cttcctttct gccccttgt gatgcgattt gctgctgaca       2580
gtcagcaaag cagctgaaag agcatgagct atgctgcaca gcctgggcca gacctagggg      2640
ctctgggagt tcaggtgac catggcacct cccccagcct ccctatgcac ctcagtcctg      2700
ctgcccatgt ctctggctgg tccccaggct gaggaactga gctccatgag caggcttctc      2760
atttgactgg aatgtcctag aacgtctcgt gttggtaatc gaattggttt ccttgggaaa      2820
cacacttacg aggccttggc aagtctggag gcagcctggg gggttctggc tctgtttgga      2880
gtctgtccat ccacctgccc cacagctccc caaaccctc ctcctgtttc ttgcccacca      2940
tggcggcacc ctctgttacc ttgctttgcc cacagcctga ccacctgggg gagagctcta      3000
cgttccctag catgccctgg gcaggtgagg ctcagaagcc acgaagcttg ggtgactcag      3060
gctactcaca tccagtgagg cagatatagc atgtgtgttg agctagaagt ggcagggctg      3120
ggtgaagagt ctggcagaga ggggtctctg tgggaggacc caggcctaca ggtctgggaa      3180
gagcggtggg tggctttgga ggctcgtgga gaatgtcact gggaggtggg cagcaggagg      3240
aagcttggca ctgtgtcccc caggccagaa tccacctgca gtagcaaggc tccaggaagg      3300
tgggagctgg gagagccttg gcggcactca tcagcccggg gaagggcaga cttggtaaga      3360 gccacccac tgaggcccga gggctgtgca gcaggagggg tgggagccag ctctgggcag      3420 gcagggggc aatgggggat gccgcccaca ggctcagcac tcacccctac tctcaccgca      3480
gggatgaaga agccaagatg atgtggtcag tgccatgctc aagggctcgt gacagaaaaa      3540
gtatcttaaa tgtggtcacc gcagttcaga gaaggtttgg tgggagccaa caatgacctg      3600
gtattgccgc acttaatctg aaggccctgc tgccttctgg gggccagaag cccctctttt      3660
ggcccttccc agcgcagggc cggcaagagg tggcatgtgg ccctaccag cctggctgcc      3720 cctgagcatg accttaacag aggaaagagg tgtgggcttg tttttctcat ttctttgcta      3780
atcttattct gggattgcca tcaagagtgg ggtttcacct ttggagtctg gactccccac      3840
```

FIG. 3P(8) (continued)

```
gtggtggtct gattcctgcc cagactcaag gctccaccag gagatctctc caggcttgtc    3900
ccagtgccca cccctctcgt ctgtgagagg cccttgccat ctggtgctgc tcagccttgc    3960
cttgaggcgg agggagccct tgttcccact gcgcagatgc tggctttgtg caagcaccta    4020
ggcatagagg tctcttccct cttgaccagg gaggactggg agccactggg catcttcagc    4080
ctctgaaagt cctagccac ctccttgtca ggccacagtc ccaagaaggc ctctagccag     4140
gacccaact ctagaagcct cagtcccctt ctcaaatccc cactttgcca ctagctcatt     4200
atatgagctg agcaagtcgt tgaacctcct tgggcccct tttctccttt ataggacaca     4260
gggttgcacg gaatctgtgc agcagatctt ggaattttgg aggttcgggg cccatcgagg    4320
gcaagcctgg cacatcctgg agagctgcta ccagtgctaa gggaaccctc ccctctgct    4380
agtgggaggg gtggttaagt atcattagtg tctattctta caattaagtg ggttggaaag    4440
gaatggagct acagttgcta gccgtatatg gaacacagaa gctggagaga gggagccctg    4500
cttttacagg tagagctgat cccaagccag caggaggagg agaggcagac agactcagct    4560
gcctccctct gcaggtgtga ggctgaaggg cagggcacag ccagcgtctc ccttgccttt    4620
tagtcaagct cccaacctgc tgaaatccag aggcagatgc atggcctccc tgacccagct    4680
tgtcctcagc atccaggact aggaaagggg tgtgctttac tggggacagt gatgggggca    4740
ggcctcactg gggaagcaca ggccctctga ggtcctgagc cagcctttgg ccacagtcct    4800
atctcccct acccttgaa accagcatgt ggccctcgtc cctacccta taatgccagt       4860
tctgagttcc ggcttgggtg tctggccact tcagcagtag tcccagggct tgggtcacag    4920
ctctggcagt tcctaggcct ggccccgaca agagccaaat gggcacctta agggcctgtg    4980
caaaataagc tgttttggt ttaattctgc ctgtagccca aaggaggcag cccaggagg      5040
cccacgcttt tgccgaggc tccacagctt tgccaaatgc gccgagcttt gccattcaca     5100
tgccatgcca gccttgccaa gggtttattt gtgcacgtct cagcagggct cctggagag     5160
gtgttctctg caaggtgcat cttgttccaa gatgggacta ctatttcccc tgtgtgcagg    5220
ggcaagtccc aggagaagag ggccagaaac acagtctctt cccagggtc actgtgctca     5280
agtgtcaata aaccacgagt tttgaaaccc tgt                                 5313
```

FIG. 3P(8) (continued)

SEQ ID NO:9
ccggugaugu agacaauaau uaaca                                        25

FIG. 3P(9)

SEQ ID NO:10
gcaagagagg aagguauuca gga                                          23

FIG. 3P(10)

SEQ ID NO:11
gccuuaauuc cuugcaauag ucucuc                                       26

FIG. 3P(11)

SEQ ID NO:12
guugagacca ugcagucaau gcatt                                        25

FIG. 3P(12)

SEQ ID NO:13
agaccuuucc gaauucagga agutg                                        25

FIG. 3P(13)

SEQ ID NO:14
caccaagaag cuaggugguu uccag                                        25

FIG. 3P(14)

SEQ ID NO:15
gcugggauua caggcaugag cc                                           22

FIG. 3P(15)

SEQ ID NO:16
cgcccaccuc agcccuccaa aaugcuggga uuacaggcau gagccacugc ggucgaccau  60
gaccuggaca uguuugugcc caguacuguc aguuugcag                         99

FIG. 3P(16)

SEQ ID NO:17
uuuagagacg gggucuugcu cu                                              22

FIG. 3P(17)

SEQ ID NO:18
ggcugggcaa cauagcgaga ccucaacucu acaauuuuuu uuuuuuaaa uuuagagac        60 ggggucuugc ucuguugcca ggcuuu                                          86

FIG. 3P(18)

SEQ ID NO:19
cuccgggacg gcugggc                                                    17

FIG. 3P(19)

SEQ ID NO:20
accuccggga cggcugggcg ccggcggccg ggagauccgc gcuuccugaa uccggccgg       60 cccgcccggc gcccguccgc ccgcggguc                                       89

FIG. 3P(20)

```
SEQ ID NO:21
ctccccggta aagtctcgcg gtgctgccgg gctcagccc  gtctcctcct cttgctccct      60
cggccgggcg gcggtgactg tgcaccgacg tcggcgcggg ctgcaccgcc gcgtccgccc     120
gcccgccagc atggccacca ccgccacctg caccgtttc  accgacgact accagctctt     180
cgaggagctt ggcaagggtg ctttctctgt ggtccgcagg tgtgtgaaga aacctccac      240
gcaggagtac gcagcaaaaa tcatcaatac caagaagttg tctgccggg  atcaccagaa     300
actagaacgt gaggctcgga tatgtcgact tctgaaacat ccaaacatcg tgcgcctcca     360
tgacagtatt tctgaagaag ggtttcacta cctcgtgttt gaccttgtta ccggcgggga     420
gctgtttgaa gacattgtgg ccagagagta ctacagtgaa gcagatgcca gccactgtat     480
acatcagatt ctggagagtg ttaaccacat ccaccagcat gacatcgtcc acagggacct     540
gaagcctgag aacctgctgc tggcgagtaa atgcaagggt gccgccgtca agctggctga     600
ttttggccta gccatcgaag tacagggaga gcagcaggct tggtttggtt ttgctggcac     660
ccaggttac  ttgtcccctg aggtcttgag gaaagatccc tatggaaaac ctgtggatat     720
ctgggctgc  ggggtcatcc tgtatatcct cctggtgggc tatcctccct tctgggatga     780
ggatcagcac aagctgtatc agcagatcaa ggctggagcc tatgatttcc catcaccaga     840
atgggacacg gtaactcctg aagccaagaa cttgatcaac cagatgctga ccataaaccc     900
agcaaagcgc atcacggctg accaggctct caagcacccg tgggtctgtc aacgatccac     960
ggtggcatcc atgatgcatc gtcaggagac tgtggagtgt ttgcgcaagt tcaatgcccg    1020
gagaaaactg aagggtgcca tcctcacgac catgcttgtc tccaggaact tctcagctgc    1080
caaaagccta ttgaacaaga agtcggatgg cggtgtcaag ccacagagca caacaaaaa     1140
cagtctcgta agcccagccc aagagccgc  gcccttgcag acggccatgg agccacaaac    1200
cactgtggta cacaacgcta cagatgggat caagggctcc acagagagct gcaacaccac    1260
cacagaagat gaggacctca aagctgcccc gctccgcact gggaatggca gctcggtgcc    1320
tgaaggacgg agctcccggg acagaacagc ccctctgca  ggcatgcagc ccagccttc     1380
tctctgctcc tcagccatgc gaaaacagga gatcattaag attacagaac agctgattga    1440
agccatcaac aatggggact tgaggcccta cacgaagatt tgtgatccag gcctcacttc    1500
ctttgagcct gaggcccttg gtaacctcgt ggagggggatg gatttccata gttttactt     1560
tgagaatctc ctgtccaaga acagcaagcc tatccatacc accatcctaa acccacacgt    1620
ccacgtgatt ggggaggacg cagcgtgcat cgcctacatc cgcctcaccc agtacatcga    1680
cgggcagggt cggcctcgca ccagccagtc agaagagacc cggtctggc  accgtcggga    1740
tggcaagtgg ctcaatgtcc actatcactg ctcagggcc  cctgccgcac cgctgcagtg    1800
```

FIG. 3P(21)

```
agctcagcca cagggggcttt aggagattcc agccggaggt ccaaccttcg cagccagtgg    1860
ctctggaggg cctgagtgac agcggcagtc ctgtttgttt gaggtttaaa acaattcaat    1920
tacaaaagcg gcagcagcca atgcacgccc ctgcatgcag ccctcccgcc cgcccttcgt    1980
gtctgtctct gctgtaccga ggtgttttt acatttaaga aaaaaaaaa agaaaaaaag      2040
attgtttaaa aaaaaagga atccatacca tgatgcgttt taaaccacc gacagccctt      2100
gggttggcaa gaaggcagga gtatgtatga ggtccatcct ggcatgagca gtggctcacc    2160
caccggcctt gaagaggtga gcttggcctc tctggtcccc atggacttag ggggaccagg    2220
caagaactct gacagagctt tgggggccgt gatgtgattg cagctcctga ggtggcctgc    2280
ttaccccagg tctaggaatg aacttctttg gaacttgcat aggcgcctag aatggggctg    2340
atgagaacat cgtgaccatc agacctactt gggagagaac gcagagctcc cagcctgctg    2400
tggaggcagc tgagaagtgg tggcctcagg actgagagcc cggacgttgc tgtactgtct    2460
tgtttagtgt agaagggaag agaattggtg ctgcagaagt gtacccgcca tgaagccgat    2520
gagaaacctc gtgttagtct gacatgcact cactcatcca tttctatagg atgcacaatg    2580
catgtgggcc ctaatattga ggccttatcc ctgcagctag gaggggggag ggttgttgct    2640
gctttgcttc gtgtttctt ctaacctggc aaggagagag ccaggccctg gtcagggctc     2700
ccgtgccgcc tttggcggtt ctgtttctgt gctgatctgg accatctttg tcttgccttt    2760
tcacggtagt ggtccccatg ctgaccctca tctgggcctg ggccctctgc caagtgccc     2820
tgtgggatgg gaggagtgag gcagtgggag aagaggtggt ggtcgtttct atgcattcag    2880
gctgcctttg gggctgcctc ccttcttatt cttccttgct gcacgtccat ctctttcct    2940
gtctttgaga ttgacctgac tgctctggca agaagaagag gtgtccttac agaggcctct    3000
ttactgacca actgaagtat agacttactg ctggacaatc tgcatgggca tcacccctcc    3060
ccgcatgtaa cccaaaagag gtgtccagag ccaaggcttc taccttcatt gtccctctct    3120
gtgctcaagg agttccattc caggaggaag agatctatac cctaagcaga tagcaaagaa    3180
gataatggag gagcaattgg tcatggcctt ggtttccctc aaaacaacgc tgcagattta    3240
tctgcacaaa catctccact tttgggggaa aggtgggtag attccagttc cctggactac    3300
cttcaggagg cacgagagct gggagaagag gcaaagctac aggtttactt gggagccagc    3360
tgagaagaga gcagactcac aggtgctggt gcttggattt agccaggctc ctccgagcac    3420
ctcatgcatg tcccagcccc tgggccctag cccttcctg ccctgcagtc tgcagtgcca    3480
gcacgcaaat cccttcacca cagggtttcg ttttgctggc ttgaagacaa atggtcttag    3540
aattcattga gacccatagc ttcatatggc tgctccagcc ccacttctta gcattcttac    3600
tcctcttctg gggctaatgt cagcatctat agacaataga ctattaaaaa atcacctttt    3660
aaacaagaaa cggaaggcat ttgatgcaga attttgcat gacaacatag aaataattta     3720
aaaatagtgt ttgttctgaa tgttggtaga cccttcatag ctttgttaca atgaaacctt    3780
gaactgaaaa tatttaataa aataaccttt aaacagtc                            3818
```

FIG. 3P(21) (continued)

SEQ ID NO:22

| | | | | | | | | | | | | | | |
|---|---|---|---|---|---|---|---|---|---|---|---|---|---|---|

Met Asp Leu Glu Lys Asn Tyr Pro Thr Pro Arg Thr Ser Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
                100                 105                 110

Glu Ile Arg Asp Arg Leu Leu Ala Glu Arg Val Cys Asp Asn Asp Thr
            115                 120                 125

Val Pro Ser Val Ser Ser Ile Asn Arg Ile Ile Arg Thr Lys Val Gln
        130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
        210                 215                 220

Arg Gly Asp Leu Phe Thr Gln Gln Gln Leu Glu Val Leu Asp Arg Val
225                 230                 235                 240

FIG. 3P(22)

```
Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
                260                 265                 270

Gly Leu Asp Asp Met Lys Ala Asn Leu Ala Ser Pro Thr Pro Ala Asp
                275                 280                 285

Ile Gly Ser Ser Val Pro Gly Pro Gln Ser Tyr Pro Ile Val Thr Gly
                290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Ser
                340                 345                 350

Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
                370                 375                 380

Ala Thr Ala Tyr Asp Arg His
385                 390
```

FIG. 3P(22) (continued)

SEQ ID NO:23

| | | | | | | | | | | | | | | |
|---|---|---|---|---|---|---|---|---|---|---|---|---|---|---|
| Met | Asp | Leu | Glu | Lys | Thr | Tyr | Pro | Thr | Pro | Arg | Thr | Gly | Arg | Thr | Gly |
| 1 | | | | 5 | | | | | 10 | | | | | 15 | |
| His | Gly | Gly | Val | Asn | Gln | Leu | Gly | Gly | Val | Phe | Val | Asn | Gly | Arg | Pro |
| | | | 20 | | | | | 25 | | | | | 30 | | |
| Leu | Pro | Asp | Val | Val | Arg | Gln | Arg | Ile | Val | Glu | Leu | Ala | His | Gln | Gly |
| | | 35 | | | | | 40 | | | | | 45 | | | |
| Val | Arg | Pro | Cys | Asp | Ile | Ser | Arg | Gln | Leu | Arg | Val | Ser | His | Gly | Cys |
| | 50 | | | | | 55 | | | | | 60 | | | | |
| Val | Ser | Lys | Ile | Leu | Gly | Arg | Tyr | Tyr | Glu | Thr | Gly | Ser | Ile | Lys | Pro |
| 65 | | | | | 70 | | | | | 75 | | | | | 80 |
| Gly | Val | Ile | Gly | Gly | Ser | Lys | Pro | Lys | Val | Ala | Thr | Pro | Lys | Val | Val |
| | | | | 85 | | | | | 90 | | | | | 95 | |
| Glu | Lys | Ile | Ala | Glu | Tyr | Lys | Arg | Gln | Asn | Pro | Thr | Met | Phe | Ala | Trp |
| | | | 100 | | | | | 105 | | | | | 110 | | |
| Glu | Ile | Arg | Asp | Arg | Leu | Leu | Ala | Glu | Arg | Val | Cys | Asp | Asn | Asp | Thr |
| | | 115 | | | | | 120 | | | | | 125 | | | |
| Val | Pro | Ser | Val | Ser | Ser | Ile | Asn | Arg | Ile | Ile | Arg | Thr | Lys | Val | Gln |
| | 130 | | | | | 135 | | | | | 140 | | | | |
| Gln | Pro | Pro | Asn | Gln | Pro | Val | Pro | Ala | Ser | Ser | His | Ser | Ile | Val | Ser |
| 145 | | | | | 150 | | | | | 155 | | | | | 160 |
| Thr | Gly | Ser | Val | Thr | Gln | Val | Ser | Ser | Val | Ser | Thr | Asp | Ser | Ala | Gly |
| | | | | 165 | | | | | 170 | | | | | 175 | |
| Ser | Ser | Tyr | Ser | Ile | Ser | Gly | Ile | Leu | Gly | Ile | Thr | Ser | Pro | Ser | Ala |
| | | | 180 | | | | | 185 | | | | | 190 | | |
| Asp | Thr | Asn | Lys | Arg | Lys | Arg | Asp | Glu | Gly | Val | Pro | Glu | Ser | Pro | Val |
| | | 195 | | | | | 200 | | | | | 205 | | | |
| Pro | Asn | Gly | His | Ser | Leu | Pro | Gly | Arg | Asp | Phe | Leu | Arg | Lys | Gln | Met |
| | | 210 | | | | | 215 | | | | | 220 | | | |
| Arg | Gly | Asp | Leu | Phe | Thr | Gln | Gln | Gln | Leu | Glu | Val | Leu | Asp | Arg | Val |
| 225 | | | | | 230 | | | | | 235 | | | | | 240 |

FIG. 3P(23)

```
Phe Glu Arg Gln His Tyr Ala Asp Ile Phe Thr Thr Thr Glu Pro Ile
                245                 250                 255

Lys Pro Glu Gln Thr Thr Glu Tyr Ser Ala Met Ala Ser Leu Ala Gly
                260                 265                 270

Gly Leu Asp Asp Met Lys Ala Asn Leu Thr Ser Pro Thr Pro Ala Asp
                275                 280                 285

Ile Gly Ser Ser Val Pro Gly Pro Gln Ser Tyr Pro Ile Val Thr Gly
                290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Pro
                340                 345                 350

Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
                370                 375                 380

Ala Thr Ala Tyr Asp Arg His
385                 390
```

FIG. 3P(23) (continued)

SEQ ID NO:24

| | | | | | | | | | | | | | | |
|---|---|---|---|---|---|---|---|---|---|---|---|---|---|---|
|Met|Asp|Leu|Glu|Lys|Asn|Tyr|Pro|Thr|Pro|Arg|Ser|Gly|Arg|Thr|Gly|

1 5 10 15

His Gly Gly Val Asn Gln Leu Gly Gly Val Phe Val Asn Gly Arg Pro
20 25 30

Leu Pro Asp Val Val Arg Gln Arg Ile Val Glu Leu Ala His Gln Gly
35 40 45

Val Arg Pro Cys Asp Ile Ser Arg Gln Leu Arg Val Ser His Gly Cys
50 55 60

Val Ser Lys Ile Leu Gly Arg Tyr Tyr Glu Thr Gly Ser Ile Lys Pro
65 70 75 80

Gly Val Ile Gly Gly Ser Lys Pro Lys Val Ala Thr Pro Lys Val Val
85 90 95

Glu Lys Ile Ala Glu Tyr Lys Arg Gln Asn Pro Thr Met Phe Ala Trp
100 105 110

Glu Ile Arg Asp Arg Leu Leu Ala Glu Arg Val Cys Asp Asn Asp Thr
115 120 125

Val Pro Ser Val Ser Ser Ile Asn Arg Ile Ile Arg Thr Lys Val Gln
130 135 140

Gln Pro Pro Asn Gln Pro Val Pro Ala Ser Ser His Ser Ile Val Ser
145 150 155 160

Thr Gly Ser Val Thr Gln Val Ser Ser Val Ser Thr Asp Ser Ala Gly
165 170 175

Ser Ser Tyr Ser Ile Ser Gly Ile Leu Gly Ile Thr Ser Pro Ser Ala
180 185 190

Asp Thr Asn Lys Arg Lys Arg Asp Glu Gly Ile Gln Glu Ser Pro Val
195 200 205

Pro Asn Gly His Ser Leu Pro Gly Arg Asp Phe Leu Arg Lys Gln Met
210 215 220

Arg Gly Asp Leu Phe Thr Gln Gln Gln Leu Glu Val Leu Asp Arg Val
225 230 235 240

FIG. 3P(24)

```
Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
                260                 265                 270

Gly Leu Asp Asp Met Lys Ala Asn Leu Thr Ser Pro Thr Pro Ala Asp
                275                 280                 285

Ile Gly Ser Ser Val Pro Gly Pro Gln Ser Tyr Pro Ile Val Thr Gly
        290                 295                 300

Arg Asp Leu Ala Ser Thr Thr Leu Pro Gly Tyr Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Pro
                340                 345                 350

Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
        370                 375                 380

Ala Thr Ala Tyr Asp Arg His
385                 390
```

FIG. 3P(24) (continued)

SEQ ID NO:25

| | | | | | | | | | | | | | | |
|---|---|---|---|---|---|---|---|---|---|---|---|---|---|---|
Met Asp Leu Glu Lys Asn Tyr Pro Thr Pro Arg Thr Gly Arg Thr Gly
1           5               10              15

His Gly Gly Val Asn Gln Leu Gly Gly Val Phe Val Asn Gly Arg Pro
            20              25              30

Leu Pro Asp Val Val Arg Gln Arg Ile Val Glu Leu Ala His Gln Gly
            35              40              45

Val Arg Pro Cys Asp Ile Ser Arg Gln Leu Arg Val Ser His Gly Cys
50              55              60

Val Ser Lys Ile Leu Gly Arg Tyr Tyr Glu Thr Gly Ser Ile Lys Pro
65              70              75              80

Gly Val Ile Gly Gly Ser Lys Pro Lys Val Ala Thr Pro Lys Val Val
            85              90              95

Glu Lys Ile Ala Glu Tyr Lys Arg Gln Asn Pro Thr Met Phe Ala Trp
            100             105             110

Glu Ile Arg Asp Arg Leu Leu Ala Glu Arg Val Cys Asp Asn Asp Thr
            115             120             125

Val Pro Ser Val Ser Ser Ile Asn Arg Ile Ile Arg Thr Lys Val Gln
            130             135             140

Gln Pro Pro Asn Gln Pro Val Pro Ala Ser Ser His Ser Ile Val Ser
145             150             155             160

Thr Gly Ser Val Thr Gln Val Ser Ser Val Ser Thr Asp Ser Ala Gly
            165             170             175

Ser Ser Tyr Ser Ile Ser Gly Ile Leu Gly Ile Thr Ser Pro Ser Ala
            180             185             190

Asp Thr Asn Lys Arg Lys Arg Asp Glu Gly Ile Gln Glu Ser Pro Val
            195             200             205

Pro Asn Gly His Ser Leu Pro Gly Arg Asp Phe Leu Arg Lys Gln Met
            210             215             220

Arg Gly Glu Leu Phe Thr Gln Gln Gln Leu Glu Val Leu Asp Arg Val
225             230             235             240

FIG. 3P(25)

```
Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
                260                 265                 270

Gly Leu Asp Asp Met Lys Ala Asn Leu Thr Ser Pro Thr Pro Thr Asp
                275                 280             285

Ile Gly Ser Ser Val Pro Gly Pro Gln Ser Tyr Pro Ile Val Thr Gly
        290                 295                 300

Arg Asp Leu Ala Ser Thr Thr Leu Pro Gly Tyr Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Pro
                340                 345                 350

Ser Tyr Asn Asp Ser Trp Arg Phe Pro Asn Pro Gly Leu Leu Gly Ser
            355                 360                 365

Pro Tyr Tyr Tyr Ser Ala Ala Ala Arg Gly Ala Ala Pro Pro Ala Ala
        370                 375                 380

Ala Thr Ala Tyr Asp Arg His
385                 390
```

FIG. 3P(25) (continued)

SEQ ID NO:26

Met Ser Ser Gly Ala Pro Gln Lys Ser Ser Pro Met Ala Ser Gly Ala
1               5                   10                  15

Glu Glu Thr Pro Gly Phe Leu Asp Thr Leu Leu Gln Asp Phe Pro Ala
                20                  25                  30

Leu Leu Asn Pro Glu Asp Pro Leu Pro Trp Lys Ala Pro Gly Thr Val
            35                  40                  45

Leu Ser Gln Glu Glu Val Glu Gly Glu Leu Ala Glu Leu Ala Met Gly
        50                  55                  60

Phe Leu Gly Ser Arg Lys Ala Pro Pro Leu Ala Ala Ala Leu Ala
65              70                  75                      80

His Glu Ala Val Ser Gln Leu Leu Gln Thr Asp Leu Ser Glu Phe Arg
                85                  90                  95

Lys Leu Pro Arg Glu Glu Glu Glu Glu Glu Asp Asp Asp Glu Glu
                100                 105                 110

Glu Lys Ala Pro Val Thr Leu Leu Asp Ala Gln Ser Leu Ala Gln Ser
        115                 120                 125

Phe Phe Asn Arg Leu Trp Glu Val Ala Gly Gln Trp Gln Lys Gln Val
        130                 135                 140

Pro Leu Ala Ala Arg Ala Ser Gln Arg Gln Trp Leu Val Ser Ile His
145                 150                 155                 160

Ala Ile Arg Asn Thr Arg Arg Lys Met Glu Asp Arg His Val Ser Leu
                165                 170                 175

Pro Ser Phe Asn Gln Leu Phe Gly Leu Ser Asp Pro Val Asn Arg Ala
                180                 185                 190

Tyr Phe Ala Val Phe Asp Gly His Gly Gly Val Asp Ala Ala Arg Tyr
            195                 200                 205

Ala Ala Val His Val His Thr Asn Ala Ala Arg Gln Pro Glu Leu Pro
        210                 215                 220

Thr Asp Pro Glu Gly Ala Leu Arg Glu Ala Phe Arg Arg Thr Asp Gln
225                 230                 235                 240

FIG. 3P(26)

```
Met Phe Leu Arg Lys Ala Lys Arg Glu Arg Leu Gln Ser Gly Thr Thr
            245                 250                 255

Gly Val Cys Ala Leu Ile Ala Gly Ala Thr Leu His Val Ala Trp Leu
            260                 265                 270

Gly Asp Ser Gln Val Ile Leu Val Gln Gln Gly Gln Val Val Lys Leu
            275                 280                 285

Met Glu Pro His Arg Pro Glu Arg Gln Asp Glu Lys Ala Arg Ile Glu
290                     295                 300

Ala Leu Gly Gly Phe Val Ser His Met Asp Cys Trp Arg Val Asn Gly
305                 310                 315                 320

Thr Leu Ala Val Ser Arg Ala Ile Gly Asp Val Phe Gln Lys Pro Tyr
                325                 330                 335

Val Ser Gly Glu Ala Asp Ala Ala Ser Arg Ala Leu Thr Gly Ser Glu
            340                 345                 350

Asp Tyr Leu Leu Leu Ala Cys Asp Gly Phe Phe Asp Val Val Pro His
        355                 360                 365

Gln Glu Val Val Gly Leu Val Gln Ser His Leu Thr Arg Gln Gln Gly
        370                 375                 380

Ser Gly Leu Arg Val Ala Glu Glu Leu Val Ala Ala Arg Glu Arg
385                 390                 395                 400

Gly Ser His Asp Asn Ile Thr Val Met Val Val Phe Leu Arg Asp Pro
                405                 410                 415

Gln Glu Leu Leu Glu Gly Gly Asn Gln Gly Glu Gly Asp Pro Gln Ala
            420                 425                 430

Glu Gly Arg Arg Gln Asp Leu Pro Ser Ser Leu Pro Glu Pro Glu Thr
            435                 440                 445

Gln Ala Pro Pro Arg Ser
450
```

FIG. 3P(26) (continued)

SEQ ID NO:27

| | | | | | | | | | | | | | | |
|---|---|---|---|---|---|---|---|---|---|---|---|---|---|---|
| Met<br>1 | Ala | Ser | Gly | Ala<br>5 | Leu | Gln | Glu | Ser | Ser<br>10 | Gln | Met | Ala | Glu | Glu<br>15 | Thr |

Met Ala Ser Gly Ala Leu Gln Glu Ser Ser Gln Met Ala Glu Glu Thr
1           5                   10                  15

Leu Gly Phe Leu Asp Met Leu Leu Cys Asp Phe Pro Ala Pro Leu Ser
            20                  25                  30

Pro Asp Ser Pro Leu Pro Trp Lys Val Pro Gly Thr Val Leu Arg Gln
            35                  40                  45

Glu Glu Val Glu Gly Glu Leu Ala Glu Leu Ala Met Gly Phe Leu Gly
        50                  55                  60

Ser Arg Asn Ala Pro Pro Leu Ala Ser Cys Leu Ala His Glu Ala
65                  70                  75                  80

Val Ser Lys Leu Leu Gln Ala Asp Leu Ser Glu Phe Arg Lys Lys Pro
                85                  90                  95

Arg Gln Glu Glu Asp Asp Ala Glu Glu Lys Ala Pro Val Thr
                100                 105                 110

Leu Leu Asp Ala Glu Gly Leu Val Arg Thr Phe Phe Asn Gln Leu Trp
            115                 120                 125

Glu Val Cys Ser Arg Trp Gln Lys Gln Val Pro Ser Thr Ala Gln Ala
        130                 135                 140

Pro Gln Arg Gln Trp Leu Val Ser Ile His Ala Ile Arg Asn Thr Arg
145                 150                 155                 160

Arg Lys Met Glu Asp Arg His Val Cys Leu Ser Ala Phe Asn Gln Leu
                165                 170                 175

Phe Gly Leu Ser Asp Pro Val Asp Arg Ala Tyr Phe Ala Val Phe Asp
            180                 185                 190

Gly His Gly Gly Val Asp Ala Ala Arg Tyr Ala Ala Ala His Val His
            195                 200                 205

Ala His Ala Ala Arg Arg Pro Glu Leu Pro Thr Asp Pro Ala Gly Ala
        210                 215                 220

Leu Arg Glu Ala Phe Arg Arg Thr Asp Glu Met Phe Leu Trp Lys Ala
225                 230                 235                 240

FIG. 3P(27)

```
Lys Arg Glu Arg Leu Gln Ser Gly Thr Thr Gly Val Cys Ala Leu Ile
                245                 250                 255

Ala Gly Lys Thr Leu His Val Ala Trp Leu Gly Asp Ser Gln Val Ile
                260                 265                 270

Leu Val Gln Gln Gly Gln Val Val Lys Leu Met Glu Pro His Arg Pro
                275                 280                 285

Glu Arg Gln Asp Glu Arg Glu Arg Ile Glu Ala Leu Gly Gly Phe Val
                290                 295                 300

Ser His Met Asp Cys Trp Arg Val Asn Gly Thr Leu Ala Val Ser Arg
305                     310                 315                 320

Ala Ile Gly Asp Val Phe Gln Lys Pro Tyr Val Ser Gly Glu Ala Asp
                325                 330                 335

Ala Ala Ser Gln Glu Leu Thr Gly Ser Glu Asp Tyr Leu Leu Leu Ala
                340                 345                 350

Cys Asp Gly Phe Phe Asp Val Val Pro His His Glu Val Ala Gly Leu
                355                 360                 365

Val Gln Ser His Leu Val Arg Gln Gln Gly Ser Gly Leu His Val Ala
                370                 375                 380

Glu Glu Leu Val Ala Ala Arg Glu Arg Gly Ser His Asp Asn Ile
385                     390                 395                 400

Thr Val Met Val Val Phe Leu Arg Asp Pro Arg Ala Leu Leu Glu Gly
                405                 410                 415

Gly Ala Gln Gly Ala Gly Asp Leu Pro Ser Gly Leu Ser Glu Pro Glu
                420                 425                 430

Thr Asn Thr Pro Pro Arg Ser
                435
```

FIG. 3P(27) (continued)

SEQ ID NO:28

| | | | | | | | | | | | | | | |
|---|---|---|---|---|---|---|---|---|---|---|---|---|---|---|
Met Ala Ser Gly Ala Pro Pro Gln Ser Ser His Thr Ala Glu Glu Ile
1 5 10 15

Pro Gly Phe Leu Asp Ala Phe Leu Cys Asp Phe Pro Ala Pro Leu Ser
20 25 30

Leu Glu Pro Pro Leu Pro Trp Lys Leu Pro Gly Pro Val Leu Ser Gln
35 40 45

Glu Glu Val Glu Gly Glu Leu Thr Glu Leu Ala Met Gly Phe Leu Ser
50 55 60

Asn Arg Ser Ala Pro Pro Leu Ala Ala Ser Leu Ala His Glu Ala
65 70 75 80

Val Ser Gln Leu Leu Gln Thr Asp Leu Ser Glu Phe Arg Lys Leu Pro
85 90 95

Arg Gln Glu Glu Glu Glu Asp Asp Glu Glu Glu Lys Ala Pro Val
100 105 110

Thr Leu Leu Asp Ala Lys Gly Leu Ala Arg Ser Cys Phe Asn Gln Leu
115 120 125

Trp Glu Val Cys Ser Gln Trp Gln Lys Gln Val Pro Ser Thr Ala Gln
130 135 140

Val Pro Gln Arg Gln Trp Leu Val Ser Met His Ala Ile Arg Asn Thr
145 150 155 160

Arg Arg Lys Met Glu Asp Arg His Val Cys Leu Pro Ala Phe Asn Gln
165 170 175

Leu Phe Gly Leu Ser Asp Pro Val Asp Arg Ala Tyr Phe Ala Val Phe
180 185 190

Asp Gly His Gly Gly Val Asp Ala Ala Gln Tyr Ala Ala Val His Val
195 200 205

His Thr Asn Leu Ala Arg Gln Pro Glu Leu Leu Thr Asp Pro Ala Gly
210 215 220

Ala Leu Arg Glu Ala Phe Arg His Thr Asp Glu Met Phe Leu Trp Lys
225 230 235 240

FIG. 3P(28)

```
Ala Lys Arg Glu Arg Leu Gln Ser Gly Thr Thr Gly Val Cys Ala Leu
            245                 250                 255

Ile Val Gly Lys Thr Leu His Ile Ala Trp Leu Gly Asp Ser Gln Val
            260                 265                 270

Ile Leu Val Gln Gln Gly Gln Val Val Lys Leu Met Glu Pro His Arg
            275                 280                 285

Pro Glu Arg Gln Asp Glu Lys Glu Arg Ile Glu Ala Leu Gly Gly Phe
            290                 295                 300

Val Ser His Met Asp Cys Trp Arg Val Asn Gly Thr Leu Ala Val Ser
305                 310                 315                 320

Arg Ala Ile Gly Asp Val Phe Gln Lys Pro Tyr Val Ser Gly Glu Ala
            325                 330                 335

Asp Ser Ala Ser Arg Glu Leu Thr Gly Ser Glu Asp Tyr Leu Leu Leu
            340                 345                 350

Ala Cys Asp Gly Phe Phe Asp Val Val Pro His Gln Glu Val Ala Gly
            355                 360                 365

Leu Val His Ser His Leu Ala Arg Gln Gln Gly Ser Gly Leu Gln Val
            370                 375                 380

Ala Glu Glu Leu Val Ala Ala Arg Glu Arg Gly Ser His Asp Asn
385                 390                 395                 400

Ile Thr Val Met Val Val Phe Leu Arg Asp Pro Arg Asp Leu Leu Lys
            405                 410                 415

Gly Gly Ala Gln Gly Thr Gly Asp Val Pro Ser Gly Leu Ser Gln Pro
            420                 425                 430

Glu Thr Ser Thr Pro Gln Ser Ser
            435                 440
```

FIG. 3P(28) (continued)

SEQ ID NO:29

```
Met Ala Ser Gly Asp Pro Gln Gln Ser Ser Gln Met Ala Glu Glu Ile
1               5                   10                  15

Pro Gly Phe Leu Asp Ala Phe Leu His Asp Phe Pro Ala Pro Leu Ser
            20                  25                  30

Pro Glu Ser Pro Leu Pro Trp Lys Val Pro Gly Thr Val Leu Ser Gln
            35                  40                  45

Glu Glu Val Glu Gly Glu Leu Ala Glu Leu Ala Met Gly Phe Leu Ser
        50                  55                  60

Ser Arg Asn Ala Pro Pro Leu Ala Ser Cys Leu Ala His Glu Ala
65              70                  75                  80

Val Ser Gln Leu Leu Gln Met Asp Leu Ser Glu Phe Arg Lys Leu Pro
                85                  90                  95

Arg Gln Glu Glu Glu Glu Glu Glu Glu Glu Asp Asp Asn Glu Glu
                100                 105                 110

Glu Lys Ala Pro Val Thr Leu Leu Asp Ala Lys Gly Leu Ala Arg Ser
            115                 120                 125

Phe Phe Asn Gln Leu Trp Glu Val Cys Ser Gln Trp Gln Lys Gln Val
            130                 135                 140

Pro Ser Ser Ala Arg Val Pro Gln Arg Gln Trp Leu Val Ser Ile His
145                 150                 155                 160

Ala Ile Arg Asn Thr Arg Arg Lys Met Glu Asp Arg His Val Cys Leu
                165                 170                 175

Pro Ala Phe Asn Gln Leu Phe Gly Leu Ser Asp Pro Val Asp Arg Ala
                180                 185                 190

Tyr Phe Ala Val Phe Asp Gly His Gly Gly Val Asp Ala Ala Arg Tyr
            195                 200                 205

Ala Ala Val His Val His Ala Asn Val Ala His Arg Pro Glu Leu Pro
            210                 215                 220

Thr Asp Pro Ala Gly Ala Leu Arg Glu Ala Phe Arg His Thr Asp Glu
225                 230                 235                 240
```

FIG. 3P(29)

```
Met Phe Leu Trp Lys Ala Lys Arg Glu Arg Leu Gln Ser Gly Thr Thr
            245             250             255

Gly Val Cys Ala Phe Ile Ala Gly Lys Thr Leu His Val Ala Trp Leu
            260             265             270

Gly Asp Ser Gln Val Ile Leu Val Gln Gln Gly Val Val Lys Leu
            275             280             285

Met Glu Pro His Arg Pro Glu Arg Gln Asp Glu Lys Glu Arg Ile Glu
    290             295             300

Ala Leu Gly Gly Phe Val Ser His Met Asp Cys Trp Arg Val Asn Gly
305             310             315             320

Thr Leu Ala Val Ser Arg Ala Ile Gly Asp Val Phe Gln Lys Pro Tyr
            325             330             335

Val Ser Gly Glu Ala Asp Ser Ala Ser Arg Glu Leu Thr Gly Ser Glu
            340             345             350

Asp Tyr Leu Leu Leu Ala Cys Asp Gly Phe Phe Asp Val Val Pro His
            355             360             365

Gln Glu Val Ala Gly Leu Val Gln Ser His Leu Val Arg Glu Gln Gly
    370             375             380

Ser Gly Leu Gln Val Ala Glu Glu Leu Val Ala Ala Arg Glu Arg
385             390             395             400

Gly Ser His Asp Asn Ile Thr Val Met Val Val Phe Leu Arg Asp Pro
                405             410             415

Gln Asp Leu Leu Lys Gly Arg Ala Gln Gly Val Gly Asp Val Pro Thr
            420             425             430

Gly Leu Ala Glu Pro Gly Thr Asn Ala Pro Gln Arg Arg
            435             440             445
```

FIG. 3P(29) (continued)

SEQ ID NO:30

Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
            20                  25                  30

Lys Lys Thr Ser Thr Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65              70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
                100                 105                 110

Ala Ser His Cys Ile His Gln Ile Leu Glu Ser Val Asn His Ile His
            115                 120                 125

Gln His Asp Ile Val His Arg Asp Leu Lys Pro Glu Asn Leu Leu Leu
        130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
            195                 200                 205

Val Gly Tyr Pro Pro Phe Trp Asp Glu Asp Gln His Lys Leu Tyr Gln
        210                 215                 220

Gln Ile Lys Ala Gly Ala Tyr Asp Phe Pro Ser Pro Glu Trp Asp Thr
225                 230                 235                 240

FIG. 3P(30)

Val Thr Pro Glu Ala Lys Asn Leu Ile Asn Gln Met Leu Thr Ile Asn
            245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
            275                 280                 285

Glu Cys Leu Arg Lys Phe Asn Ala Arg Arg Lys Leu Lys Gly Ala Ile
            290                 295                 300

Leu Thr Thr Met Leu Val Ser Arg Asn Phe Ser Ala Lys Ser Leu
305                 310                 315                 320

Leu Asn Lys Lys Ser Asp Gly Gly Val Lys Pro Gln Ser Asn Asn Lys
            325                 330                 335

Asn Ser Leu Val Ser Pro Ala Gln Glu Pro Ala Pro Leu Gln Thr Ala
            340                 345                 350

Met Glu Pro Gln Thr Thr Val Val His Asn Ala Thr Asp Gly Ile Lys
            355                 360                 365

Gly Ser Thr Glu Ser Cys Asn Thr Thr Thr Glu Asp Glu Asp Leu Lys
            370                 375                 380

Ala Ala Pro Leu Arg Thr Gly Asn Gly Ser Ser Val Pro Glu Gly Arg
385                 390                 395                 400

Ser Ser Arg Asp Arg Thr Ala Pro Ser Ala Gly Met Gln Pro Gln Pro
            405                 410                 415

Ser Leu Cys Ser Ser Ala Met Arg Lys Gln Glu Ile Ile Lys Ile Thr
            420                 425                 430

Glu Gln Leu Ile Glu Ala Ile Asn Asn Gly Asp Phe Glu Ala Tyr Thr
            435                 440                 445

Lys Ile Cys Asp Pro Gly Leu Thr Ser Phe Glu Pro Glu Ala Leu Gly
            450                 455                 460

Asn Leu Val Glu Gly Met Asp Phe His Lys Phe Tyr Phe Glu Asn Leu
465                 470                 475                 480

Leu Ser Lys Asn Ser Lys Pro Ile His Thr Thr Ile Leu Asn Pro His
            485                 490                 495

FIG. 3P(30) (continued)

```
Val His Val Ile Gly Glu Asp Ala Ala Cys Ile Ala Tyr Ile Arg Leu
            500                 505                 510

Thr Gln Tyr Ile Asp Gly Gln Gly Arg Pro Arg Thr Ser Gln Ser Glu
            515                 520                 525

Glu Thr Arg Val Trp His Arg Arg Asp Gly Lys Trp Leu Asn Val His
        530                 535                 540

Tyr His Cys Ser Gly Ala Pro Ala Ala Pro Leu Gln
545                 550                 555
```

FIG. 3P(30) (continued)

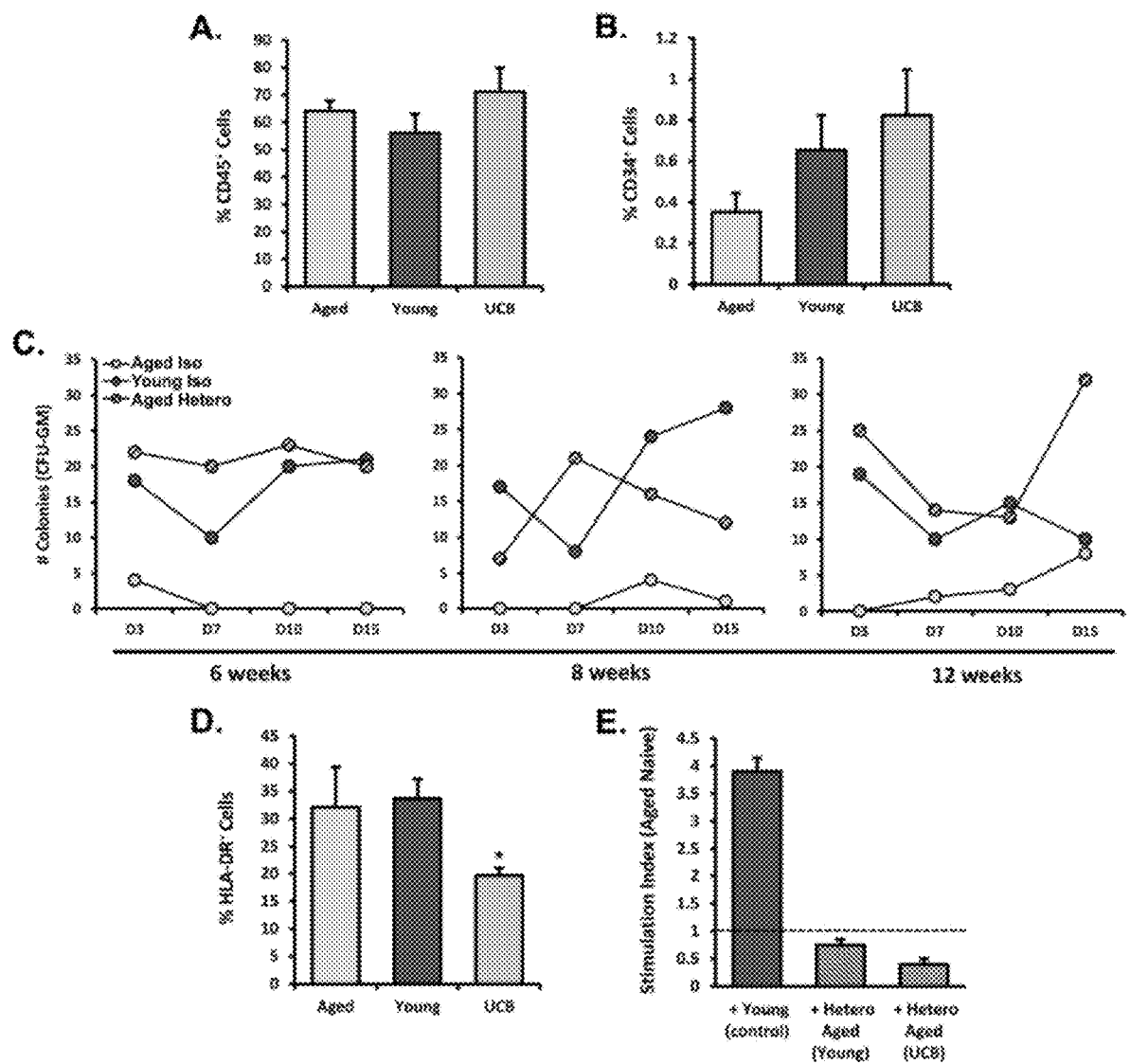
FIG. 4A-E

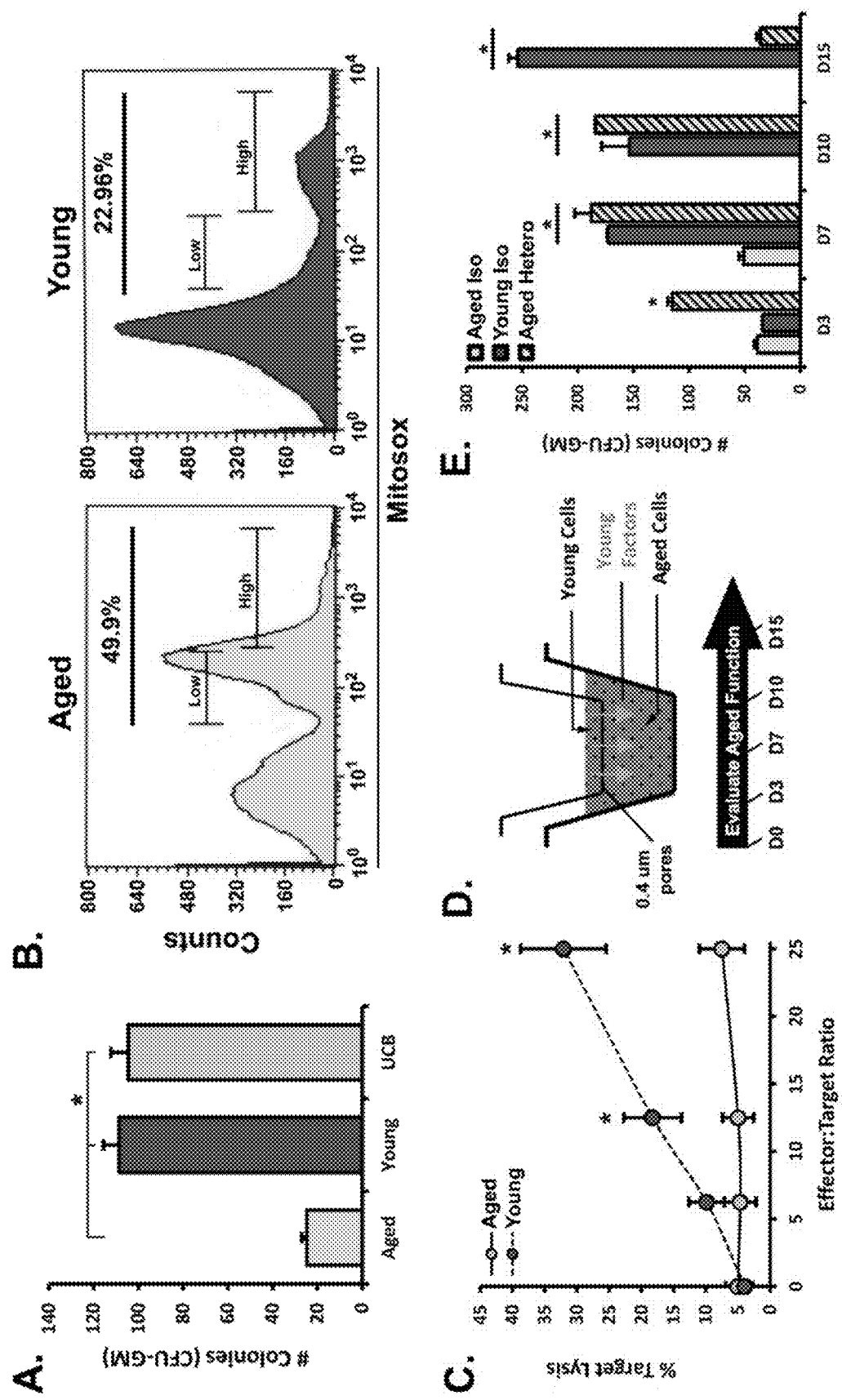
FIG. 5A-E

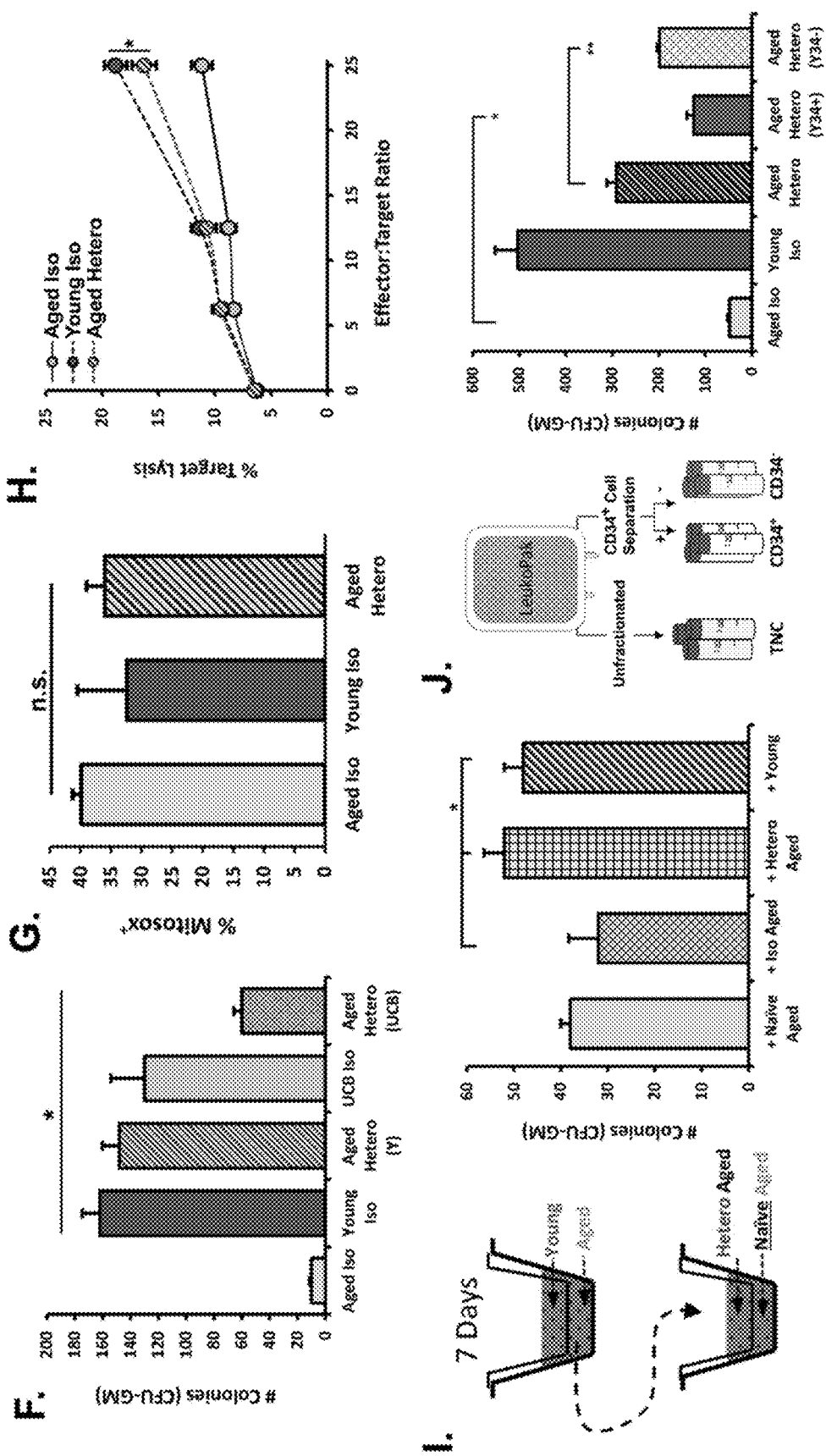
FIG. 5F-J

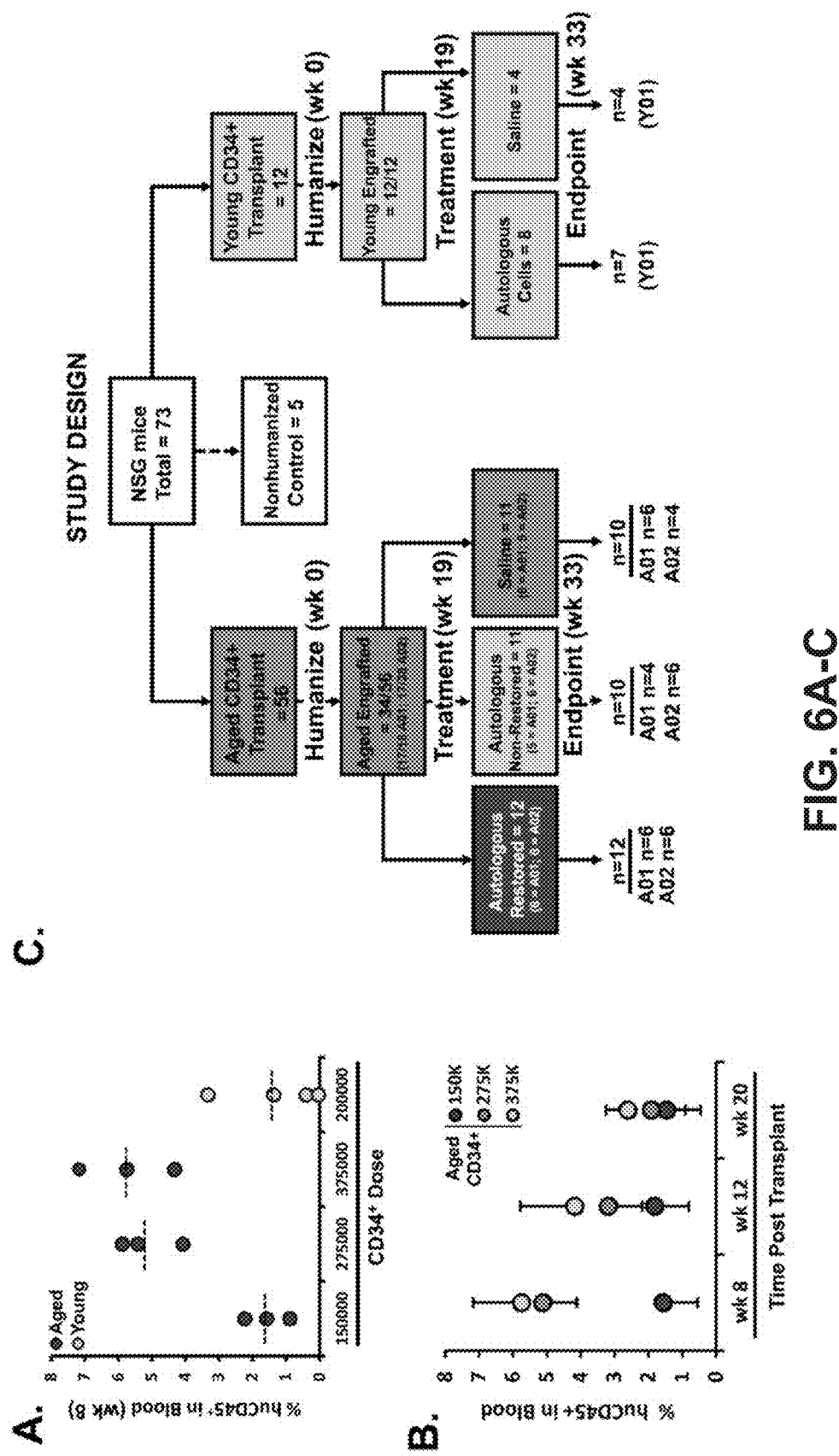
FIG. 6A-C

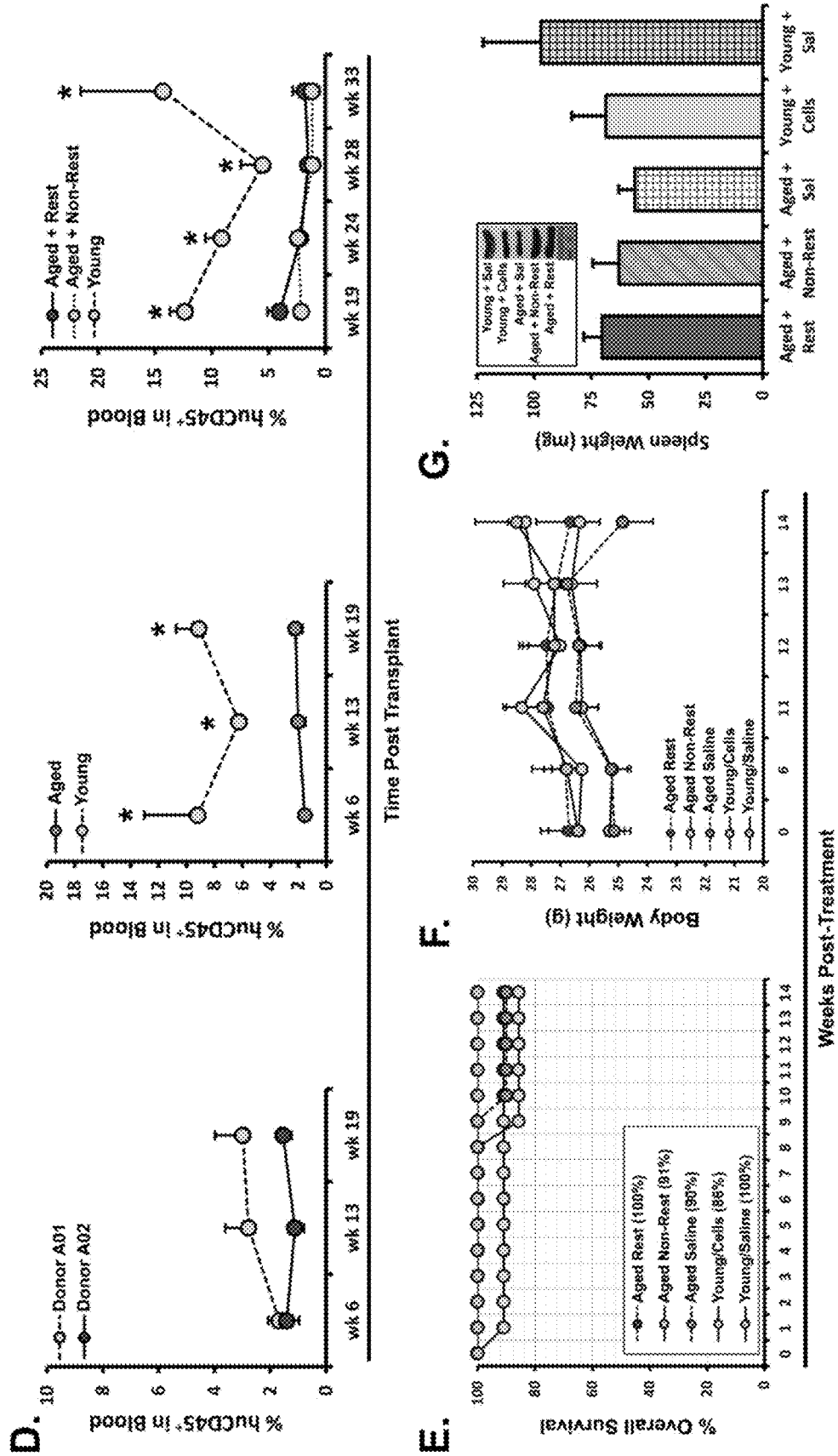
FIG. 6D-G

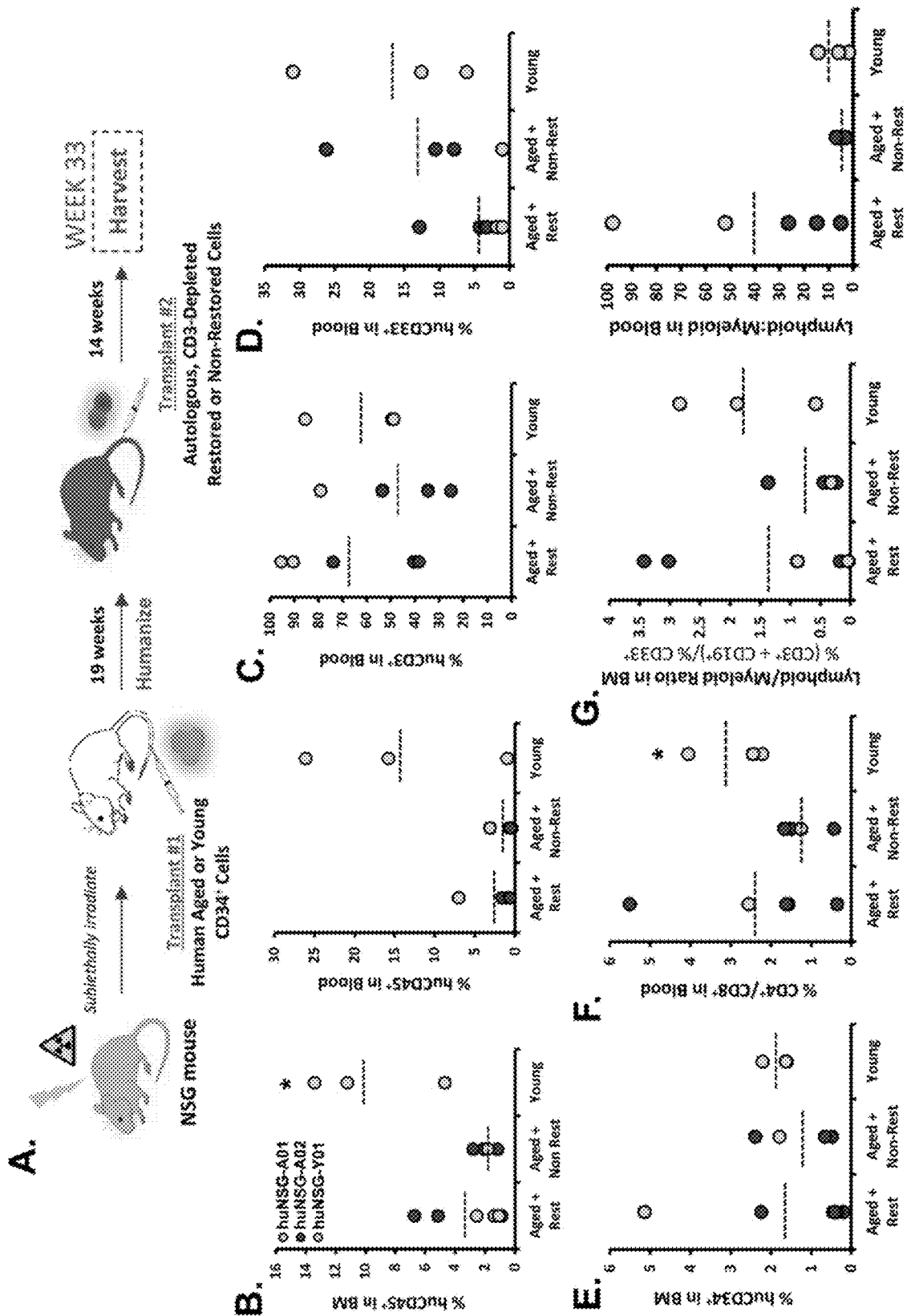
FIG. 7A-G

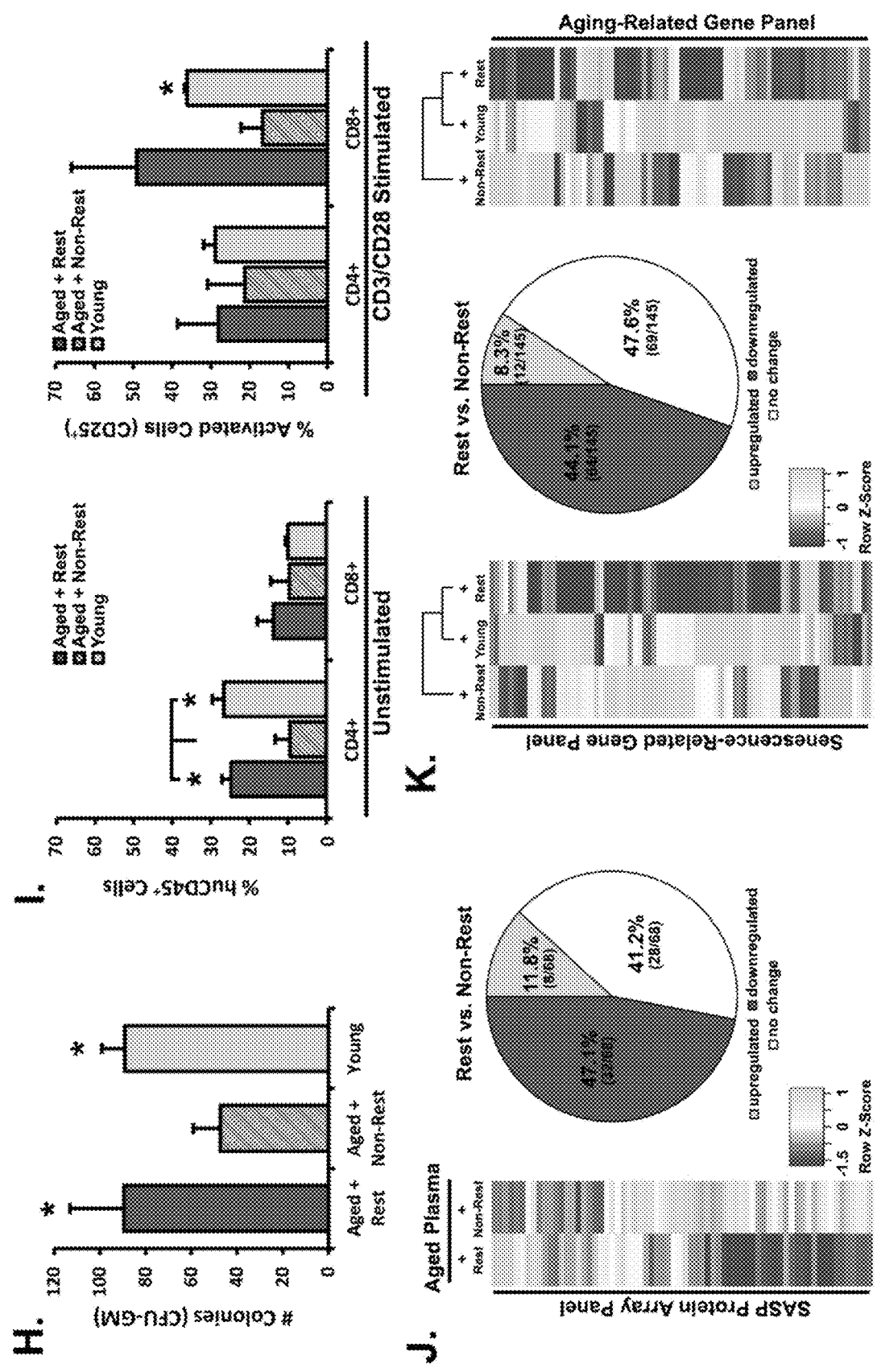
FIG. 7H-K

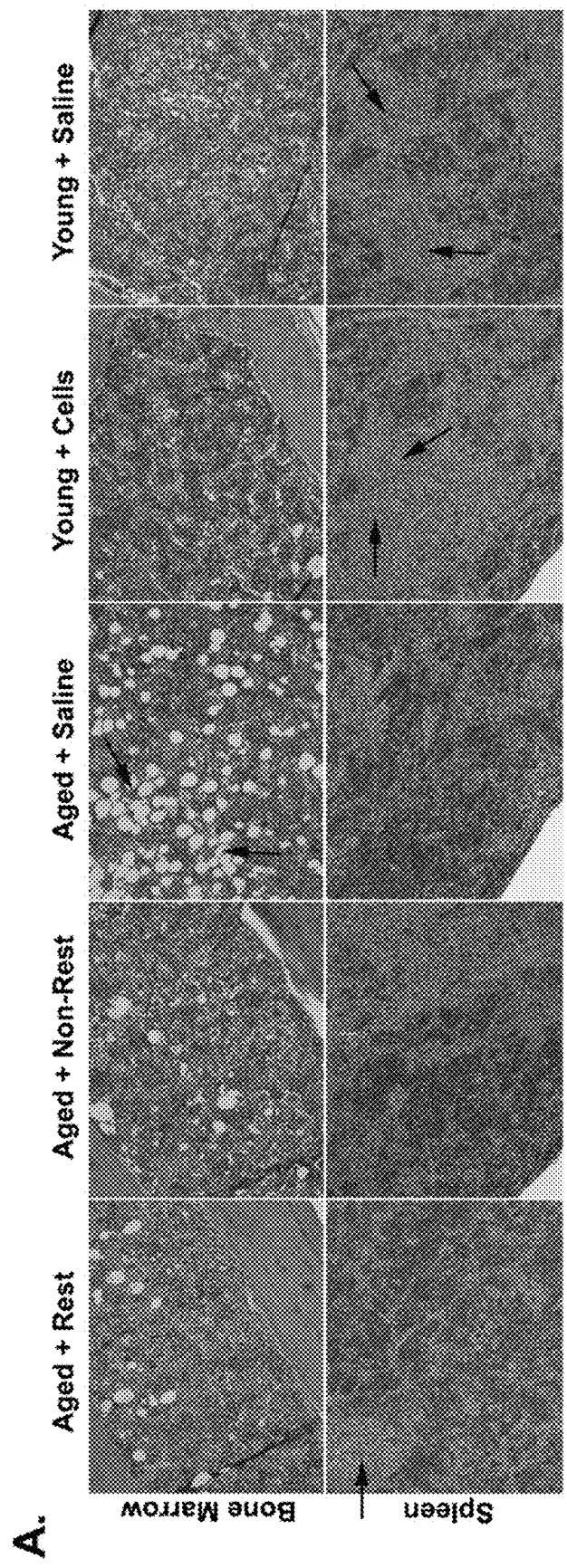
FIG. 8A-B

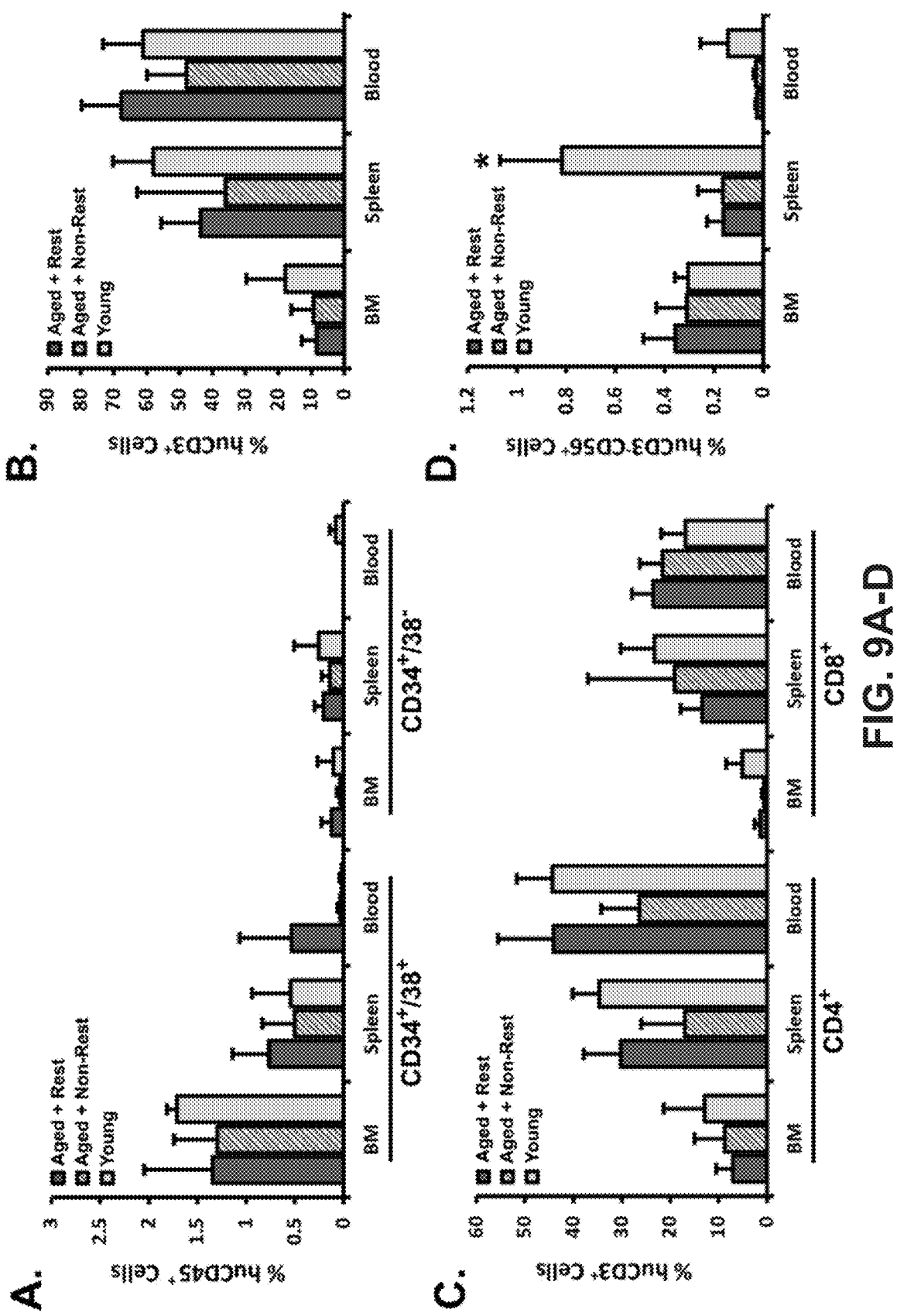
FIG. 9A-D

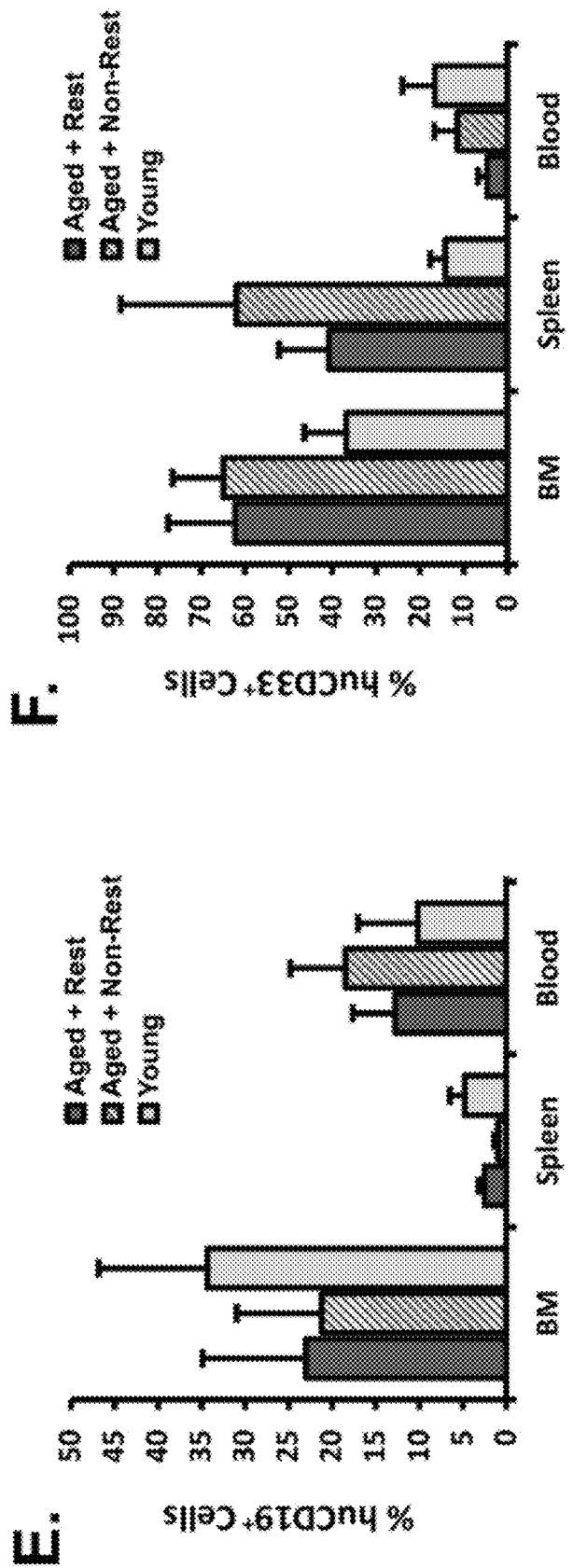
FIG. 9E-F

SASP Protein Array Panel: Rest vs. Non-Rest (+/- 2-fold change)

| Upregulated | No Change | | Downregulated | |
|---|---|---|---|---|
| • BFGF | • CTACK | • Lymphotactin | • ANG | • IL-11 |
| • BMP-4 | • Eotaxin | • MCP-2 | • AXL | • IL-13 |
| • CTLA-4 | • ENA-78 | • MCP-4 | • CXCL-16 | • MIP-3α |
| • EOTAXIN-2 | • Fas | • MIF | • FGF-7 | • MMP-1 |
| • IGFBP-3 | • Fas- Ligand | • MIP-1α | • GRO | • MMP-2 |
| • IGFBP-6 | • G-CSF | • MMP-7 | • CCL16 | • MMP-3 |
| • IL-8 | • GM-CSF | • MMP-8 | • HGF | • RANTES |
| • MCP-1 | • GRO-α | • MMP-9 | • ICAM-1 | • SCF |
| | • ICAM-3 | • MMP-10 | • IFN-γ | • TARC |
| | • IGFBP-4 | • OSM | • IGFBP-1 | • TGF-β1 |
| | • IL-15 | • PF-4 | • IGFBP-2 | • TIMP-2 |
| | • Leptin | • PlGF | • IL-1α | • TNF-α |
| | • Leptin R | • P-Selectin | • IL-1β | • sTNF RI |
| | • L-Selectin | • VEGF | • IL-6 | • sTNF RII |
| | | | • IL-6R | • TRAIL R3 |
| | | | • IL-7 | • VCAM-1 |

C. Aging/Senescence Gene Panel: Rest vs. Non-Rest (± 1.5-fold change)

| Upregulated | No Change | | | Downregulated | |
|---|---|---|---|---|---|
| CASP1 | AKT1 | LYZ | | ABL1 | MAP2K1 |
| CCR1 | ANXA5 | MAP2K6 | | ALDH1A3 | MAP2K3 |
| CD14 | ARID1A | MAPK14 | | ANGEL2 | MDM2 |
| CLU | ATM | MBP | | ANXA3 | MRPL43 |
| COL3A1 | BMI1 | MORC3 | | ARL6IP6 | NDUFB11 |
| CREG1 | BUB1B | MYC | | CCNE1 | PANX1 |
| CXCL16 | C3AR1 | NBN | | CDK2 | PDCD6 |
| FCER1G | C5AR1 | NFKB1 | | CDK6 | PIK3CA |
| ID1 | CALR | PCNA | | CDKN1C | POLRMT |
| IFNG | CCNA2 | PHF3 | | CDKN2B | POT1 |
| TLR4 | CCRB1 | PLAU | | CDKN2C | RB1 |
| TWIST1 | CCND1 | PRKCD | | CDKN2D | RBL1 |
| | CD44 | PTEN | | CHEK1 | RNF144B |
| | CDC25C | RAP1A | | CITED2 | S100A8 |
| | CDK4 | RBL2 | | COL1A1 | S100A9 |
| | CDKN1A | SERPINB2 | | E2F1 | SERPINE1 |
| | CDKN1B | SNAP23 | | ETS2 | SIRT1 |
| | CDKN2A | SOD1 | | FBXL16 | SIRT3 |
| | CHEK2 | SOD2 | | FCGBP | SIRT6 |
| | E2F3 | TFB1M | | FCGR1A | SMAD2 |
| | EGR1 | TFB2M | | FOXO1 | SPARC |
| | ELAVL1 | TGFB1 | | GADD45A | TEBF1 |
| | ELP3 | TGFB1I1 | | HRAS | TERF2 |
| | EP300 | THBS3 | | IGF1R | TERT |
| | ETS1 | TINF2 | | IGFBP3 | TFAM |
| | FCGR2A | TLR2 | | IGFBP7 | TMEM33 |
| | FN1 | TMEM135 | | ING1 | TOLLIP |
| | GLB1 | TPP1 | | IRF5 | TP53 |
| | GSK3B | TXNIP | | LMNB1 | TP53BP1 |
| | HSF1 | VIM | | LMNB2 | VPS13C |
| | IGF1 | VWA5A | | LSM5 | WRN |
| | IRF3 | ZFR | | LTF | ZBTB10 |
| | IRF7 | ZMPSTE24 | | | |
| | JAKMIP3 | ZNF23 | | | |
| | LMNA | | | | |

FIG. 10C

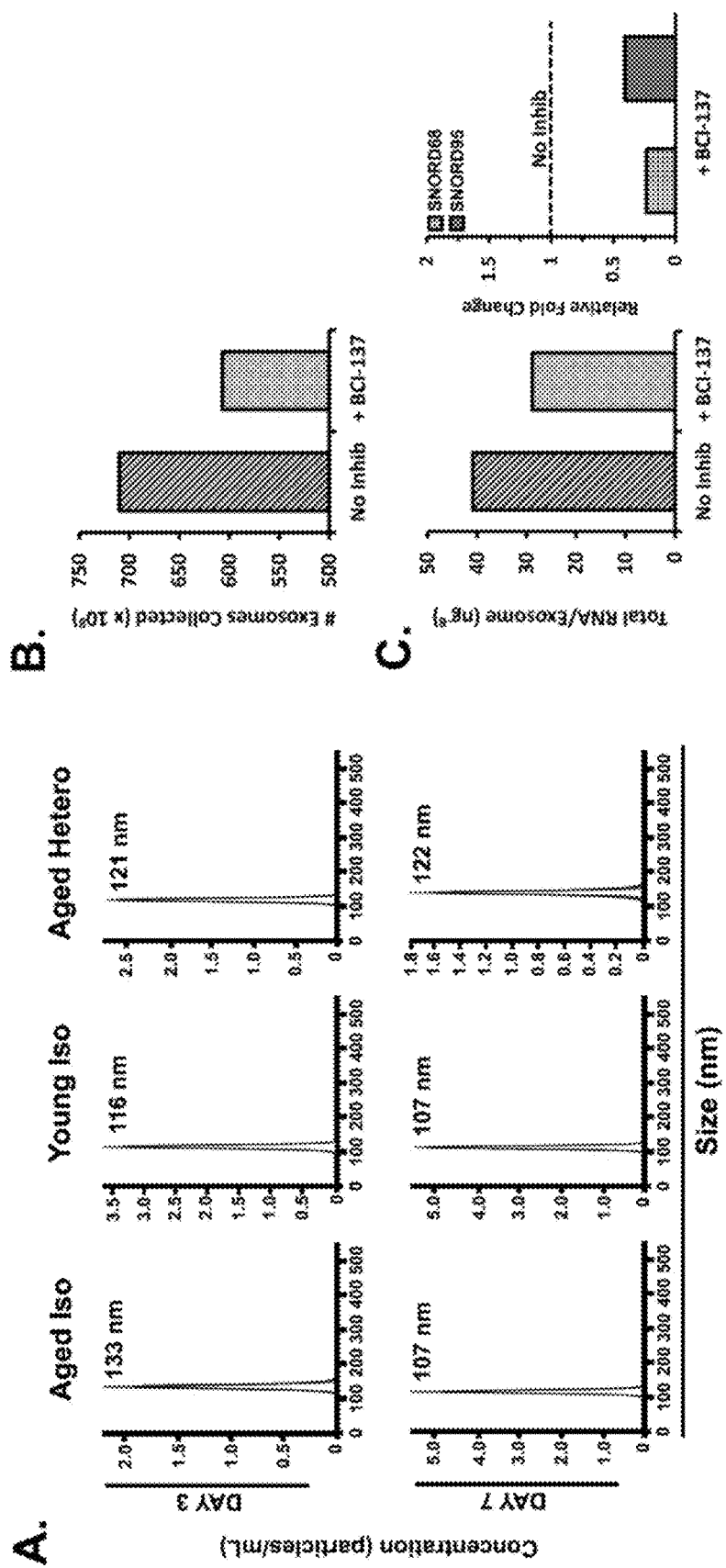
FIG. 11A-C

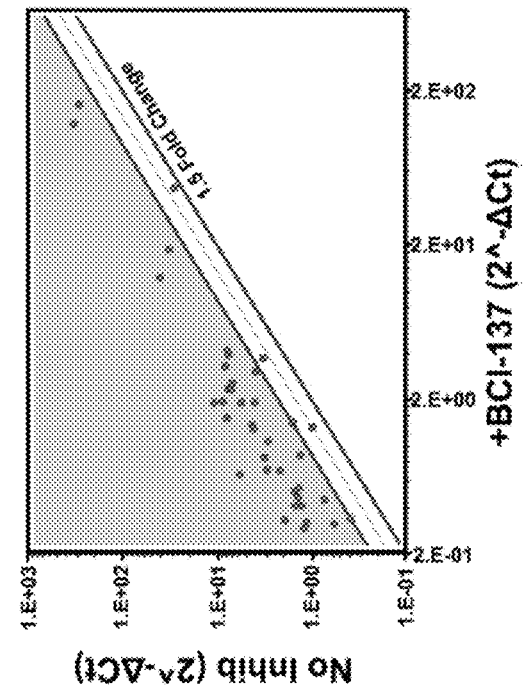
FIG. 11D-E

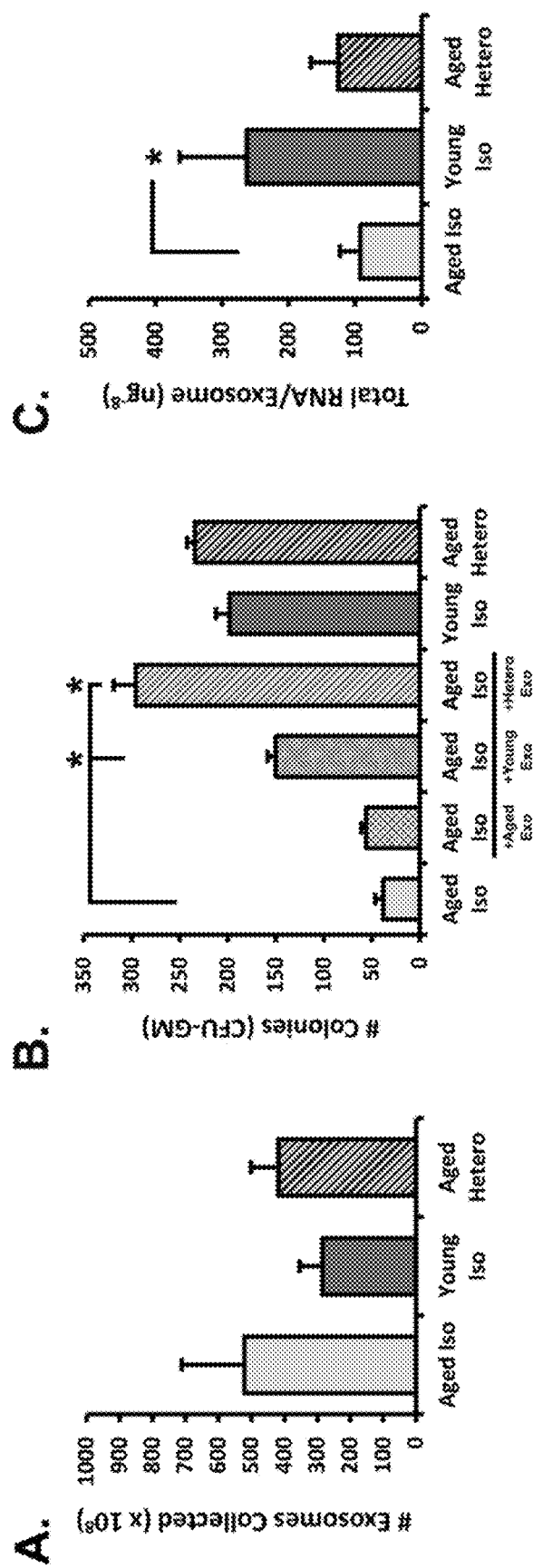
FIG. 12A-C

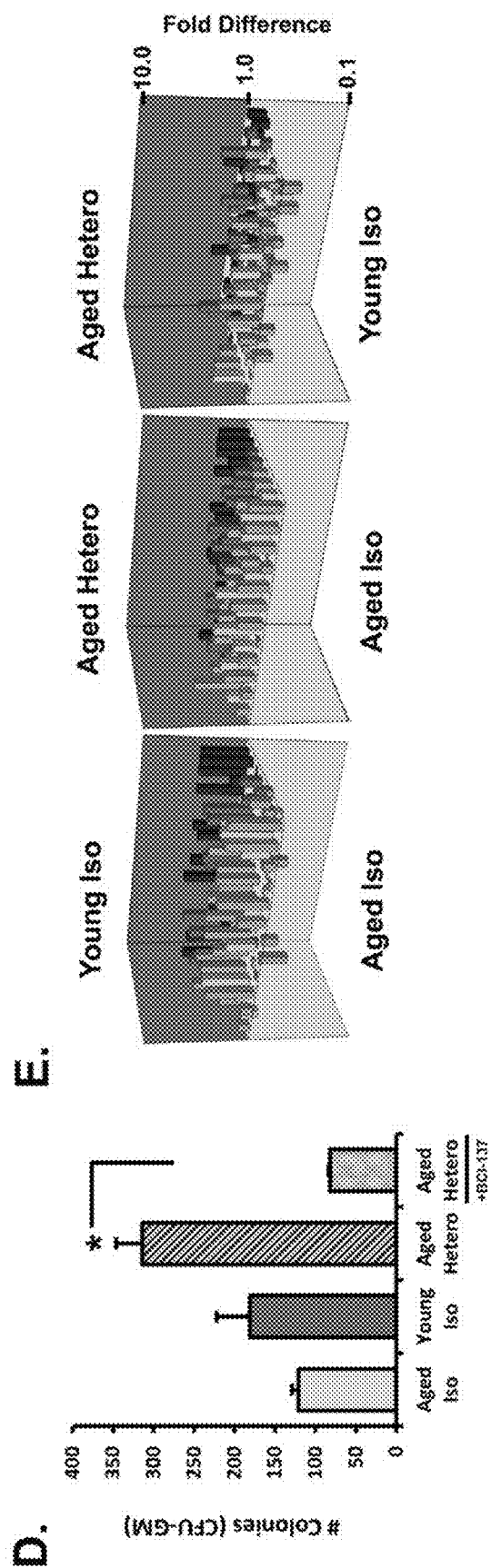
FIG. 12D-E

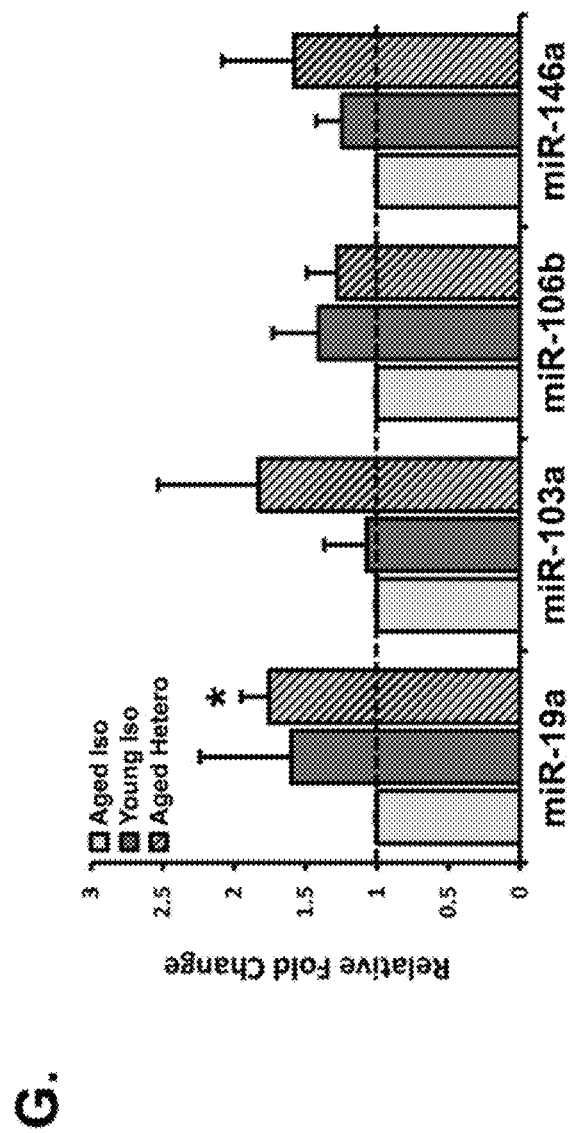
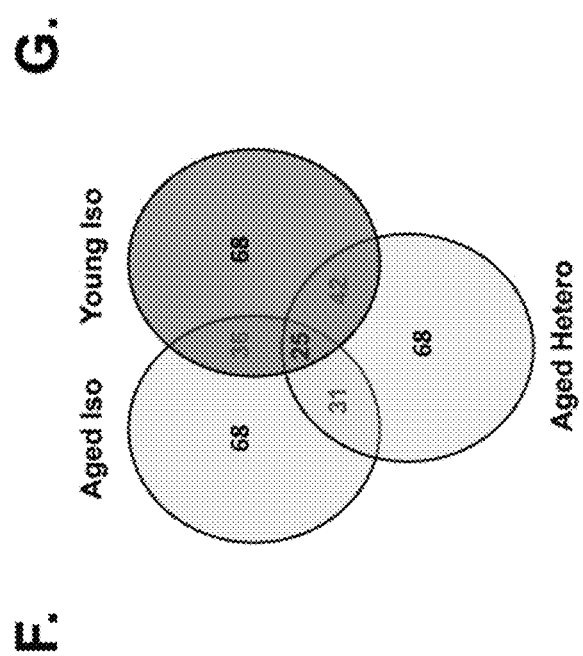
FIG. 12F-G

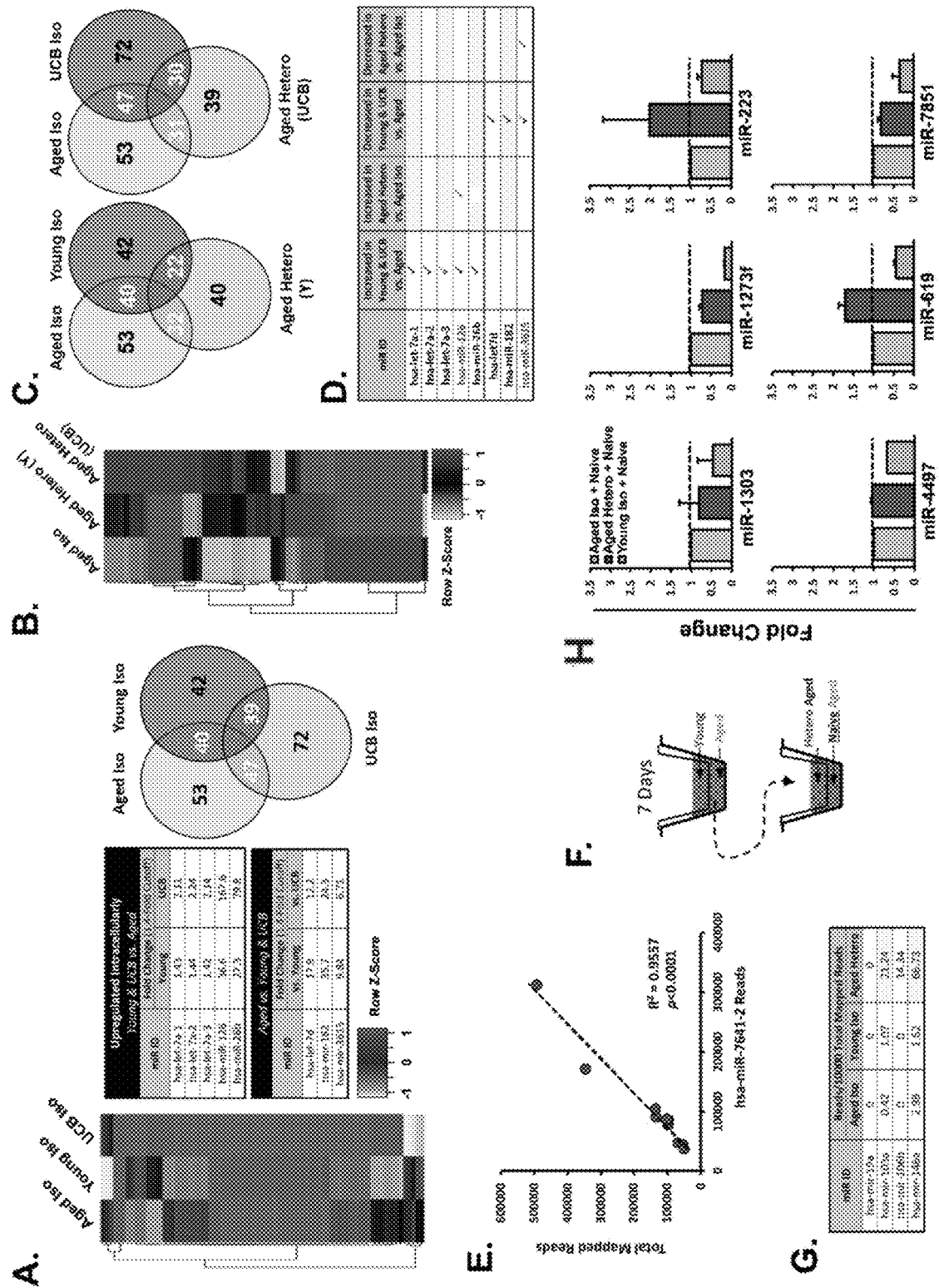
FIG. 13 A-H

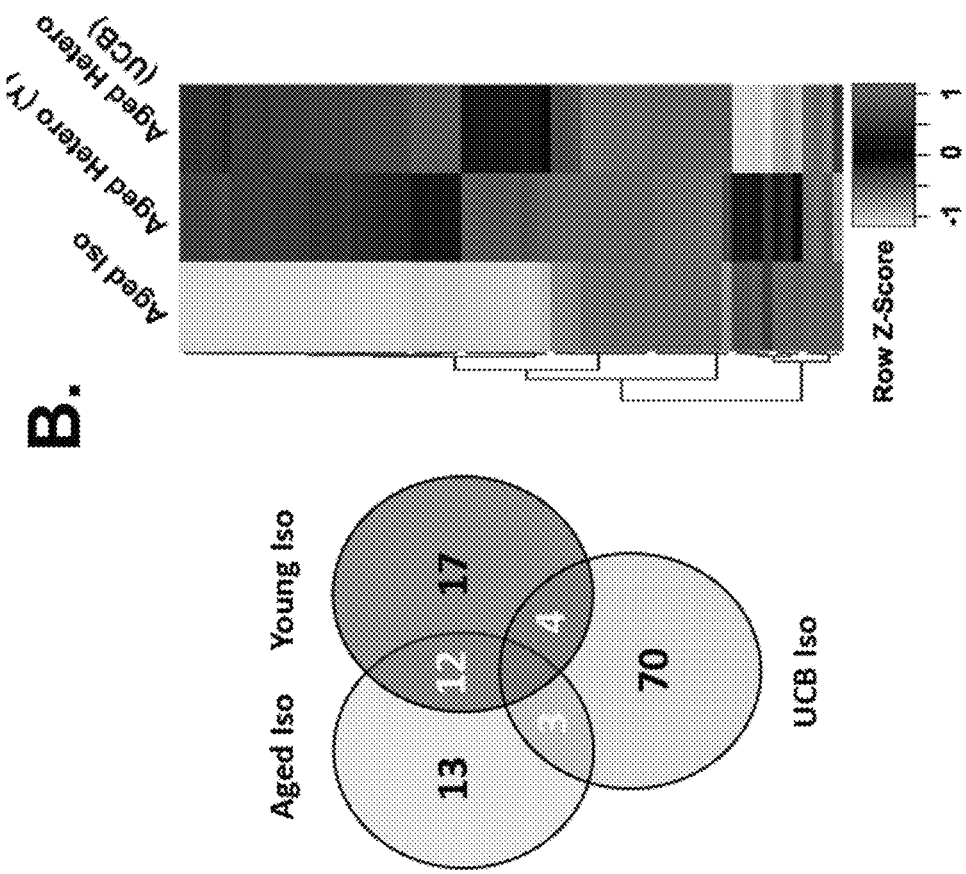
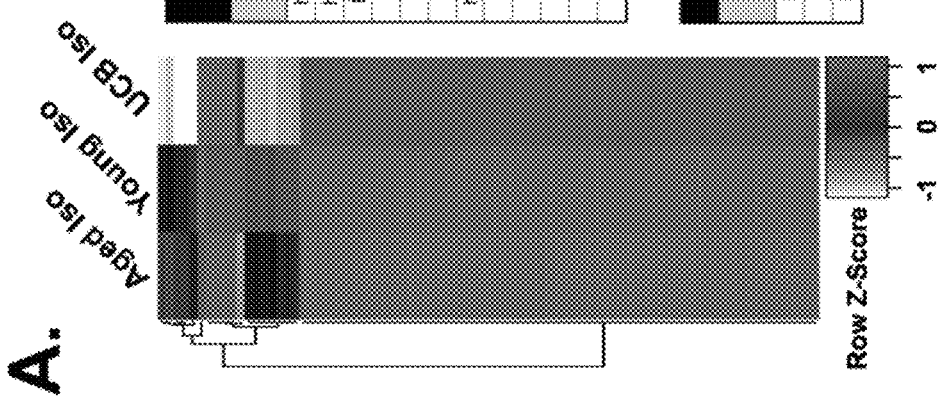
FIG. 14A-B

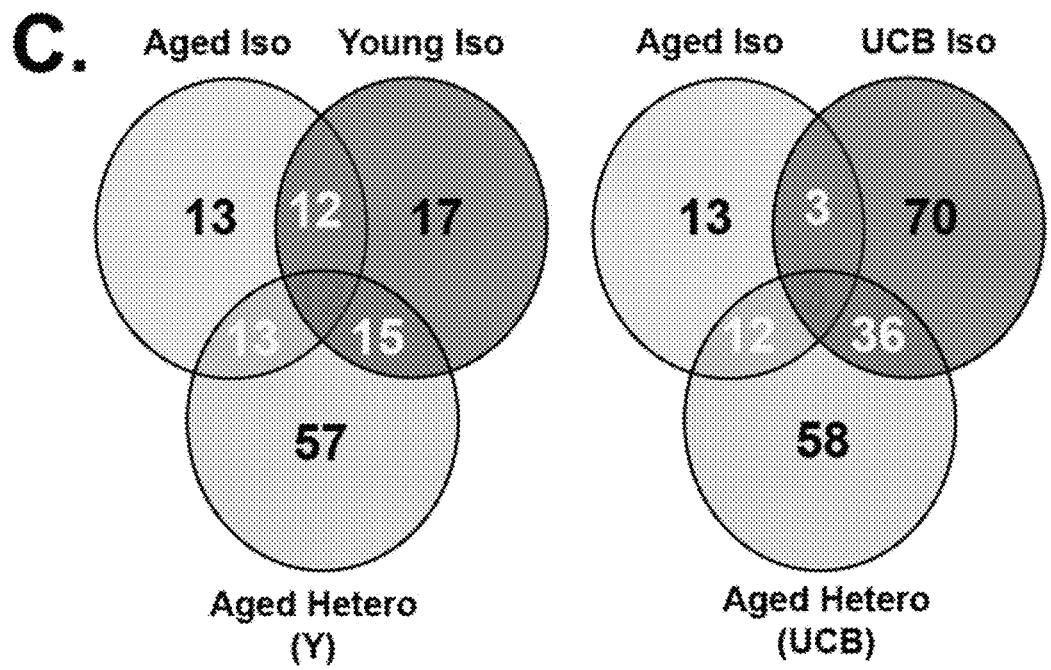
FIG. 14C-D

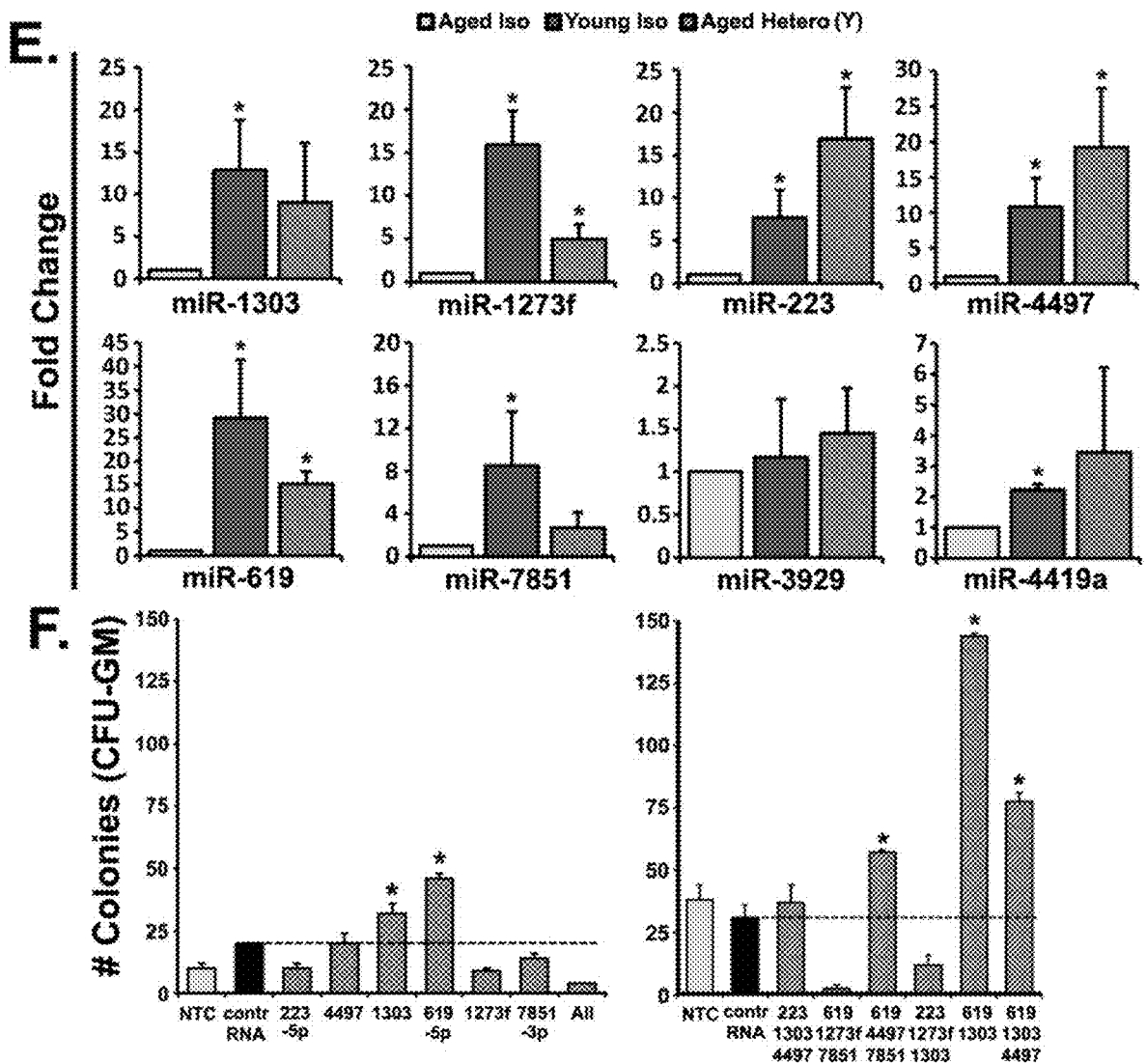
FIG. 14E-F

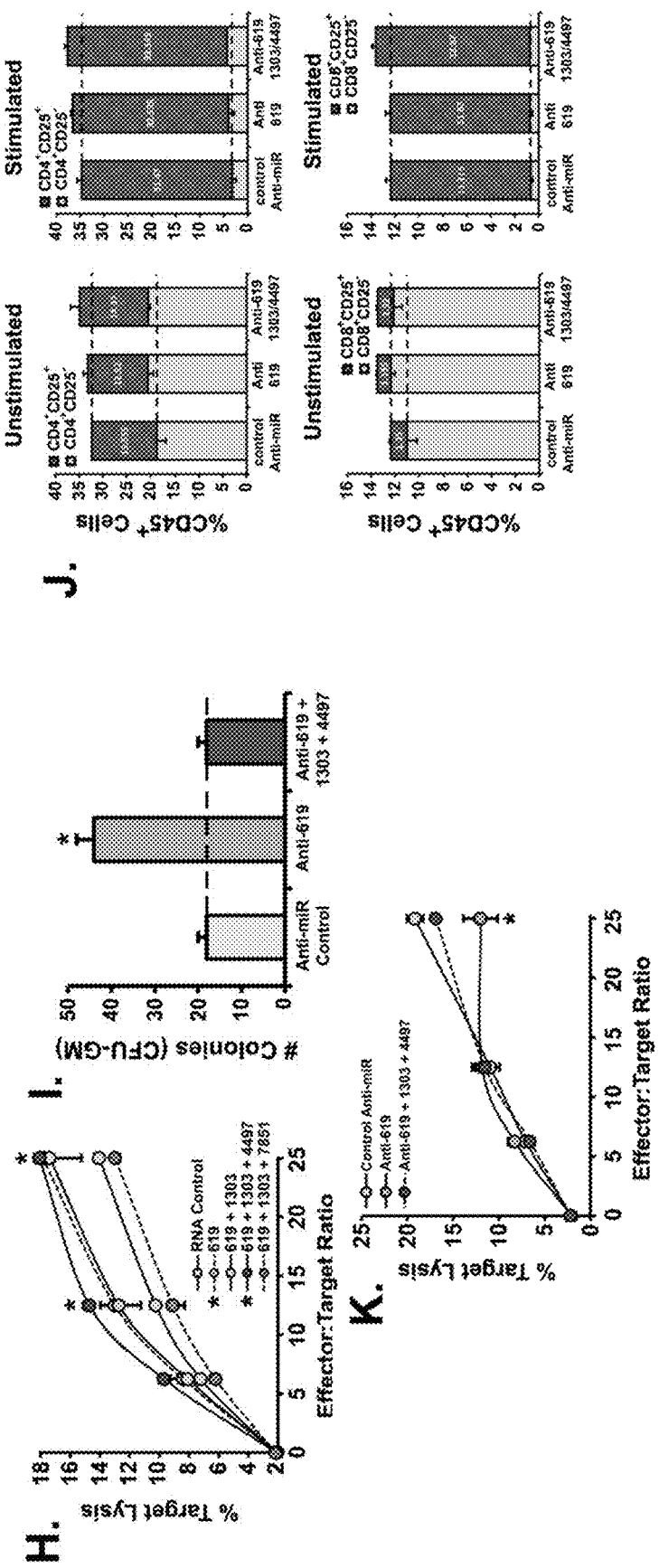
FIG. 14H-K

A.

| | Up-regulated microRNAs | | Down-regulated microRNAs | |
|---|---|---|---|---|
| miR ID | Fold Change (1.5-Fold Cutoff) | miR ID | Fold Change (1.5-Fold Cutoff) | |
| hsa-miR-3182 | 540.7 | hsa-miR-92a-1 | -8.84 | |
| hsa-miR-222 | 480.2 | hsa-miR-3529 | -12.9 | |
| hsa-miR-148b | 374.6 | hsa-miR-7-1 | -13.4 | |
| hsa-miR-8086 | 256.7 | hsa-miR-7-3 | -14.2 | |
| hsa-miR-629 | 242.5 | hsa-miR-7-2 | -14.5 | |
| hsa-miR-126 | 226.4 | hsa-miR-103b-2 | -25.6 | |
| hsa-miR-223 | 200.4 | hsa-miR-103b-1 | -27.9 | |
| hsa-miR-1273a | 183.8 | hsa-miR-103a-1 | -31.7 | |
| hsa-miR-183 | 176 | hsa-miR-103a-2 | -32.8 | |
| hsa-miR-148a | 3.8 | hsa-miR-92a-2 | -46.9 | |
| hsa-miR-21 | 2.5 | hsa-miR-26a-1 | -56.4 | |
| hsa-miR-532 | 2.1 | hsa-miR-26a-2 | -58.2 | |
| hsa-let-7i | 2.1 | hsa-miR-423 | -58.4 | |
| hsa-miR-99b | 2 | hsa-miR-3184 | -63.7 | |
| hsa-miR-378a | 2 | hsa-let-7a-2 | -105 | |
| hsa-miR-1246 | 1.9 | hsa-let-7a-3 | -109 | |
| hsa-miR-146a | 1.9 | hsa-let-7a-1 | -110 | |
| hsa-miR-30e | 1.8 | hsa-let-7f-1 | -289 | |
| hsa-miR-30d | 1.8 | hsa-let-7f-2 | -295 | |
| hsa-miR-25 | 1.7 | hsa-miR-146b | -331 | |
| hsa-let-7g | 1.7 | hsa-miR-486-2 | -693 | |
| hsa-miR-10a | 1.6 | hsa-miR-486-1 | -700 | |
| hsa-let-7d | 1.6 | | | |
| hsa-miR-191 | 1.6 | | | |
| hsa-miR-185 | 1.5 | | | |
| hsa-miR-140 | 1.5 | | | |
| hsa-miR-1307 | 1.5 | | | |

| miR ID | Fold Change (1.5-Fold Cutoff) | miR ID | Fold Change (1.5-Fold Cutoff) | miR ID | Fold Change (1.5-Fold Cutoff) |
|---|---|---|---|---|---|
| hsa-miR-1246 | 590.5 | hsa-miR-320a | 13.6 | hsa-miR-1273a | -5.4 |
| hsa-miR-21 | 338.1 | hsa-miR-89b | 13.2 | hsa-miR-1273f | -5.5 |
| hsa-miR-146b | 240.3 | hsa-miR-1291 | 12.7 | hsa-miR-1303 | -5.5 |
| hsa-let-7i | 190.6 | hsa-miR-142 | 9.3 | hsa-miR-4497 | -5.5 |
| hsa-let-7g | 158.9 | hsa-miR-26b | 8.4 | hsa-miR-619 | -5.5 |
| hsa-let-7f-2 | 141.1 | hsa-miR-23a | 8.0 | hsa-miR-222 | -7.0 |
| hsa-miR-148a | 104.1 | hsa-miR-361 | 7.7 | hsa-miR-7641-1 | -10.9 |
| hsa-let-7a-1 | 90.1 | hsa-miR-10a | 7.4 | hsa-miR-3929 | -56.5 |
| hsa-miR-146a | 81.7 | hsa-let-7d | 7.2 | hsa-miR-7851 | -72.4 |
| hsa-miR-30d | 66.2 | hsa-miR-126 | 6.9 | hsa-miR-1273e | -93.0 |
| hsa-miR-151a | 59.6 | hsa-miR-532 | 6.7 | hsa-miR-2052 | -106.9 |
| hsa-miR-92a-1 | 59.0 | hsa-miR-148b | 6.0 | hsa-miR-5096 | -135.6 |
| hsa-miR-92a-2 | 54.6 | hsa-miR-106b | 5.2 | hsa-miR-4419a | -145.4 |
| hsa-let-7f-1 | 54.3 | hsa-miR-27a | 4.5 | hsa-miR-566 | -146.5 |
| hsa-miR-25 | 44.6 | hsa-miR-7-1 | 4.2 | hsa-miR-3960 | -169.1 |
| hsa-miR-378a | 44.3 | hsa-miR-181b-1 | 4.1 | hsa-miR-6073 | -594.2 |
| hsa-miR-150 | 38.2 | hsa-miR-221 | 4.0 | | |
| hsa-miR-140 | 33.9 | hsa-miR-3529 | 3.9 | | |
| hsa-miR-26a-1 | 29.2 | hsa-miR-181b-2 | 3.8 | | |
| hsa-miR-26a-2 | 29.0 | hsa-miR-7-2 | 3.7 | | |
| hsa-miR-1248 | 22.7 | hsa-miR-27b | 3.7 | | |
| hsa-miR-423 | 20.9 | hsa-miR-1307 | 3.6 | | |
| hsa-miR-3184 | 20.6 | hsa-miR-223 | 3.5 | | |
| hsa-miR-191 | 19.4 | hsa-miR-363 | 3.5 | | |
| hsa-miR-28 | 19.3 | hsa-miR-7-3 | 3.5 | | |
| hsa-let-7a-3 | 18.8 | hsa-miR-143 | 3.2 | | |
| hsa-let-7a-2 | 18.7 | hsa-miR-101-2 | 3.1 | | |
| hsa-miR-486-1 | 18.0 | hsa-miR-185 | 3.1 | | |
| hsa-miR-486-2 | 17.4 | hsa-miR-22 | 3.0 | | |
| hsa-miR-181a-2 | 16.7 | hsa-miR-24-2 | 2.9 | | |
| hsa-miR-181a-1 | 15.4 | hsa-miR-629 | 2.9 | | |
| hsa-miR-342 | 15.0 | hsa-miR-584 | 2.8 | | |
| hsa-miR-30e | 14.4 | hsa-miR-101-1 | 2.7 | | |
| hsa-miR-155 | 13.9 | | | | |

| miR ID | Fold Change (1.5-Fold Cutoff) | miR ID | Fold Change (1.5-Fold Cutoff) | miR ID | Fold Change (1.5-Fold Cutoff) |
|---|---|---|---|---|---|
| hsa-miR-361 | 780 | hsa-miR-101-2 | 1.84 | hsa-miR-3539 | -83.3 |
| hsa-miR-3182 | 643 | hsa-miR-1248 | 1.84 | hsa-miR-7-1 | -86.3 |
| hsa-miR-26b | 361 | hsa-miR-126 | 1.84 | hsa-miR-7-3 | -91.7 |
| hsa-miR-222 | 348 | hsa-miR-128-1 | 1.84 | hsa-miR-7-2 | -93.6 |
| hsa-miR-1273e | 341 | hsa-miR-128-2 | 1.84 | hsa-miR-185 | -97.4 |
| hsa-miR-17 | 340 | hsa-miR-1291 | 1.84 | hsa-let-7d | -119 |
| hsa-miR-8086 | 278 | hsa-miR-142 | 1.84 | hsa-miR-103b-2 | -165 |
| hsa-miR-148b | 273 | hsa-miR-150 | 1.84 | hsa-miR-103b-1 | -179 |
| hsa-miR-20a | 3.56 | hsa-miR-155 | 1.84 | hsa-let-7f-1 | -186 |
| hsa-miR-93 | 3.47 | hsa-miR-181a-1 | 1.84 | hsa-miR-103a-1 | -204 |
| hsa-miR-25 | 3.35 | hsa-miR-181a-2 | 1.84 | hsa-miR-103a-2 | -211 |
| hsa-miR-10a | 2.88 | hsa-miR-181b-1 | 1.84 | hsa-miR-92a-2 | -302 |
| hsa-miR-221 | 2.84 | hsa-miR-181b-2 | 1.84 | hsa-miR-26a-1 | -363 |
| hsa-miR-1246 | 2.78 | hsa-miR-183 | 1.84 | hsa-miR-26a-2 | -375 |
| hsa-miR-320a | 2.59 | hsa-miR-192 | 1.84 | hsa-miR-423 | -376 |
| hsa-miR-532 | 2.44 | hsa-miR-223 | 1.84 | hsa-miR-3184 | -410 |
| hsa-miR-106b | 2.37 | hsa-miR-23a | 1.84 | hsa-miR-486-2 | -446 |
| hsa-miR-140 | 2.35 | hsa-miR-27b | 1.84 | hsa-miR-486-1 | -450 |
| hsa-miR-30d | 2.35 | hsa-miR-342 | 1.84 | hsa-miR-4419a | -556 |
| hsa-miR-3615 | 2.31 | hsa-miR-363 | 1.84 | hsa-let-7a-2 | -676 |
| hsa-miR-99b | 2.31 | hsa-miR-3653 | 1.84 | hsa-let-7a-3 | -703 |
| hsa-miR-28 | 2.28 | hsa-miR-584 | 1.84 | hsa-let-7a-1 | -711 |
| hsa-miR-30e | 2.18 | hsa-miR-629 | 1.84 | | |
| hsa-let-7b | 2.14 | hsa-miR-92a-1 | 1.8 | | |
| hsa-miR-1307 | 2.01 | hsa-miR-182 | 1.79 | | |
| hsa-miR-21 | 2.01 | hsa-miR-146a | 1.76 | | |
| hsa-let-7g | 1.96 | hsa-miR-151a | 1.62 | | |
| hsa-miR-101-1 | 1.84 | hsa-miR-191 | 1.61 | | |

FIG. 15D

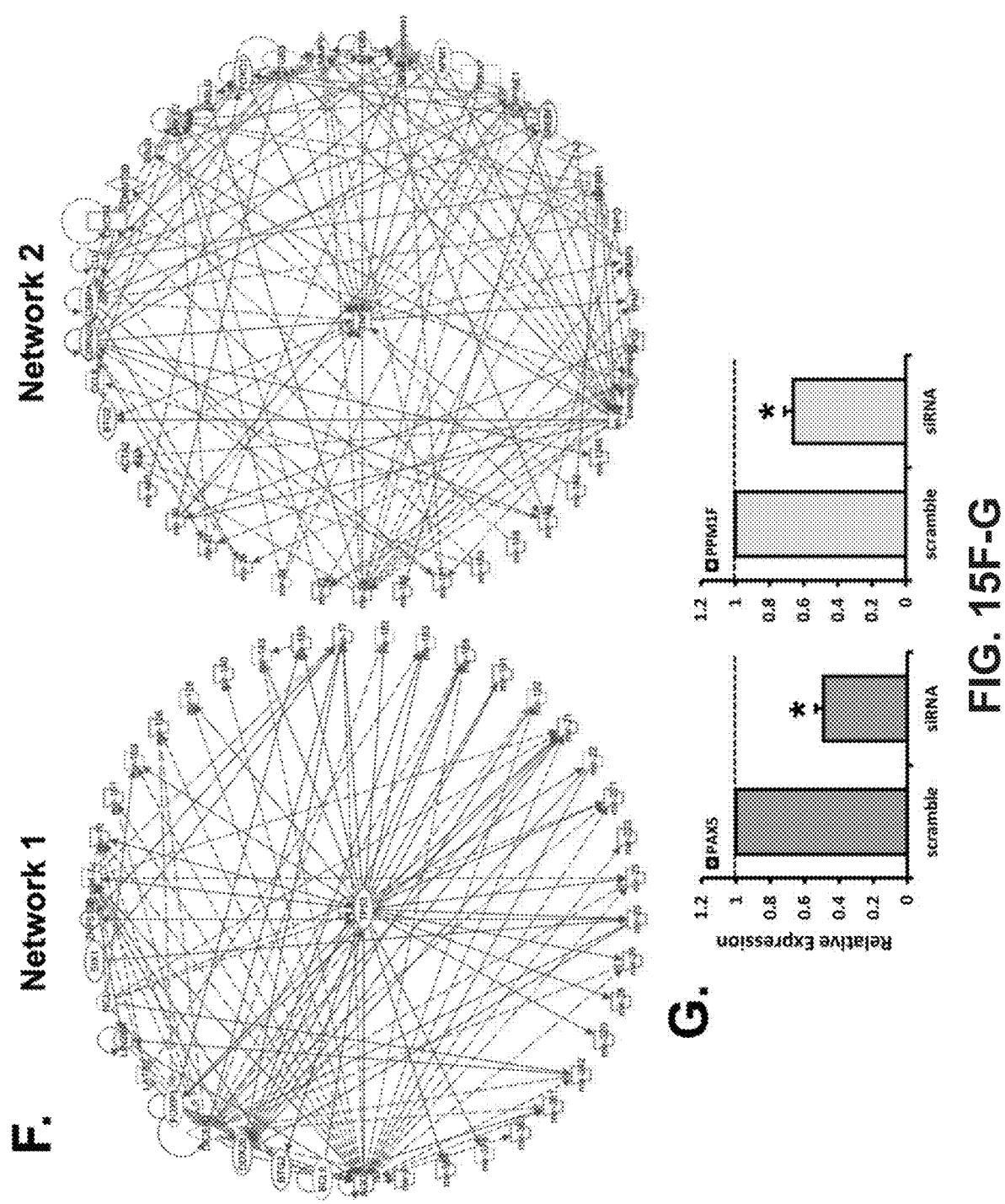
FIG. 15F-G

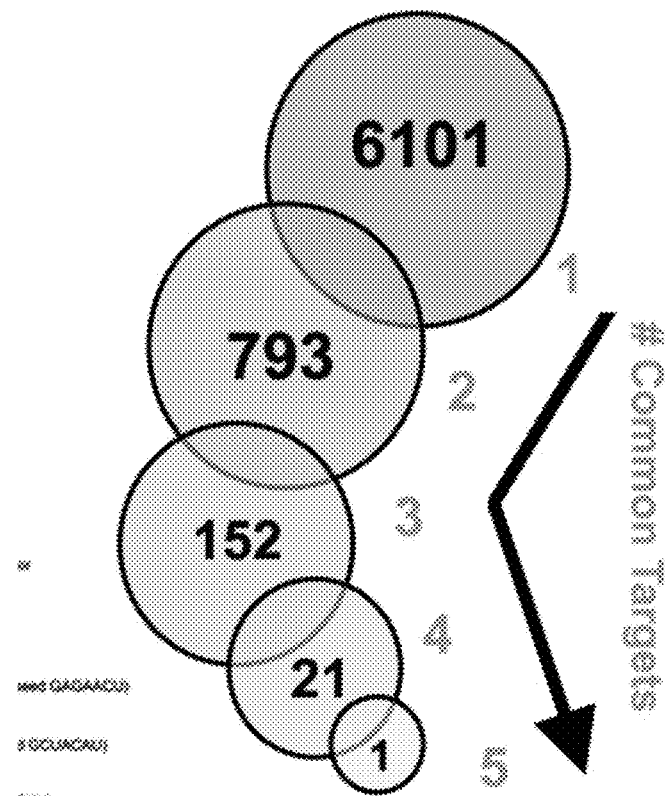
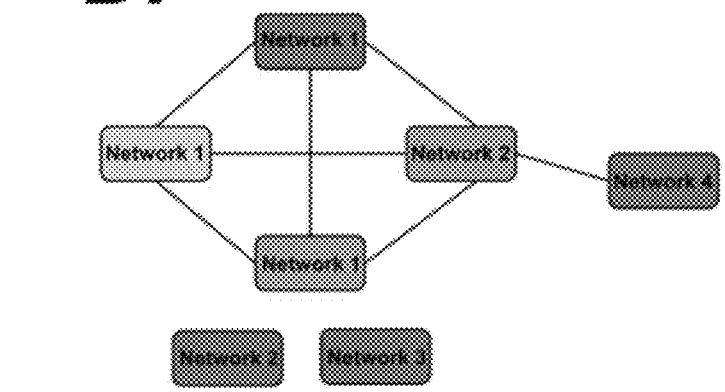
FIG. 16C-D

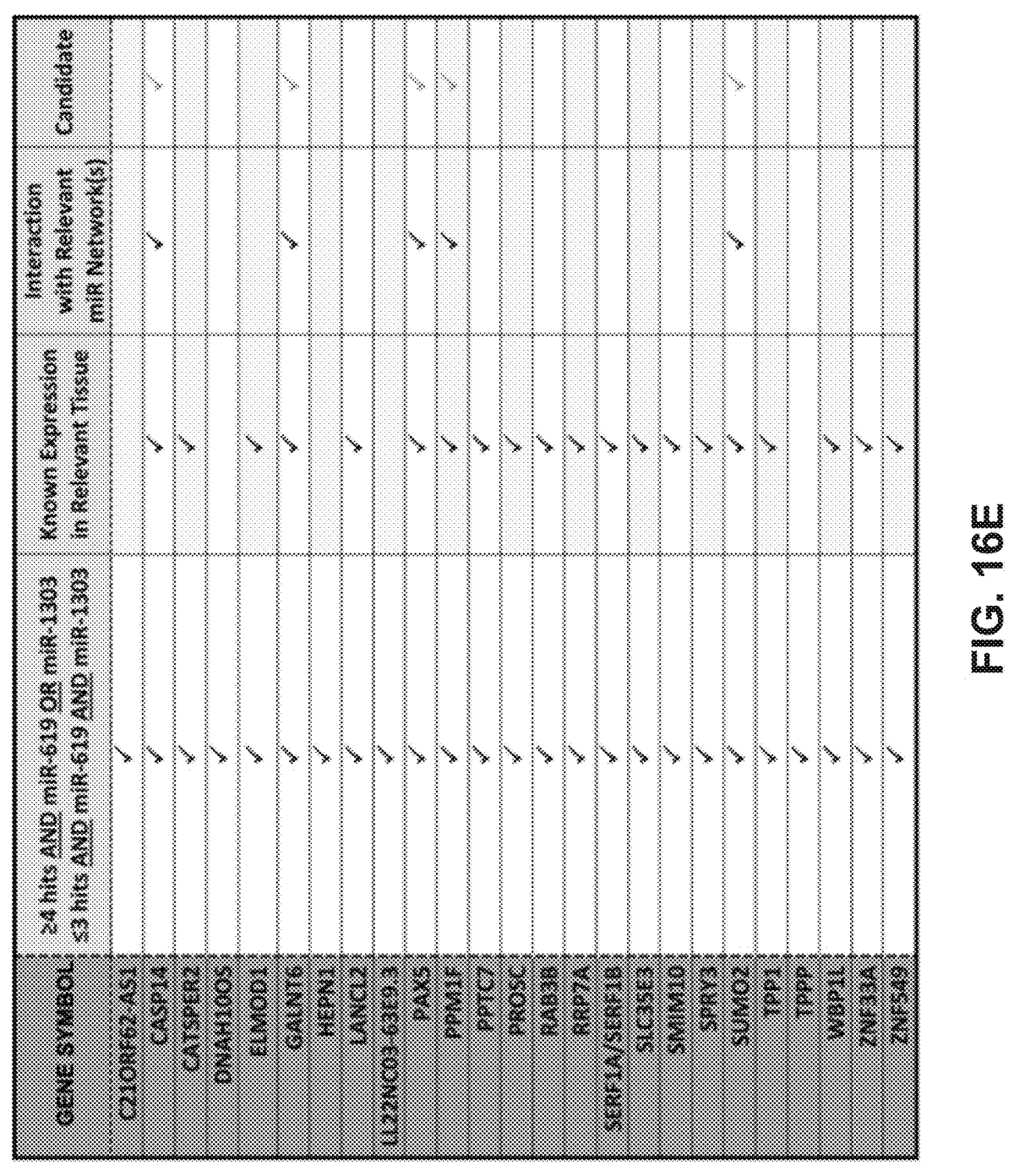

| GENE SYMBOL | ≥4 hits AND miR-619 OR miR-1303 / ≤3 hits AND miR-619 AND miR-1303 | Known Expression in Relevant Tissue | Interaction with Relevant miR Network(s) | Candidate |
|---|---|---|---|---|
| C21ORF2-AS1 | ✓ | | | |
| CASP14 | ✓ | | | ✓ |
| CATSPER2 | ✓ | | | |
| DNAH10OS | ✓ | | | |
| ELMOD1 | ✓ | ✓ | | |
| GALNT6 | ✓ | | ✓ | ✓ |
| HEPN1 | ✓ | ✓ | | |
| LANCL2 | ✓ | | | |
| LL22NC03-63E9.3 | ✓ | ✓ | ✓ | ✓ |
| PAX5 | ✓ | ✓ | | |
| PPM1F | ✓ | ✓ | ✓ | ✓ |
| PPTC7 | ✓ | ✓ | ✓ | |
| PROSC | ✓ | ✓ | | |
| RAB3B | ✓ | ✓ | | |
| RRP7A | ✓ | ✓ | | |
| SERF1A/SERF1B | ✓ | ✓ | | |
| SLC35E3 | ✓ | ✓ | | |
| SMIM10 | ✓ | ✓ | | |
| SPRY3 | ✓ | ✓ | ✓ | ✓ |
| SUMO2 | ✓ | ✓ | | |
| TPI1 | ✓ | ✓ | | |
| TPPP | ✓ | ✓ | | |
| WBP1L | ✓ | ✓ | | |
| ZNF33A | ✓ | ✓ | | |
| ZNF549 | ✓ | ✓ | | |

FIG. 16E

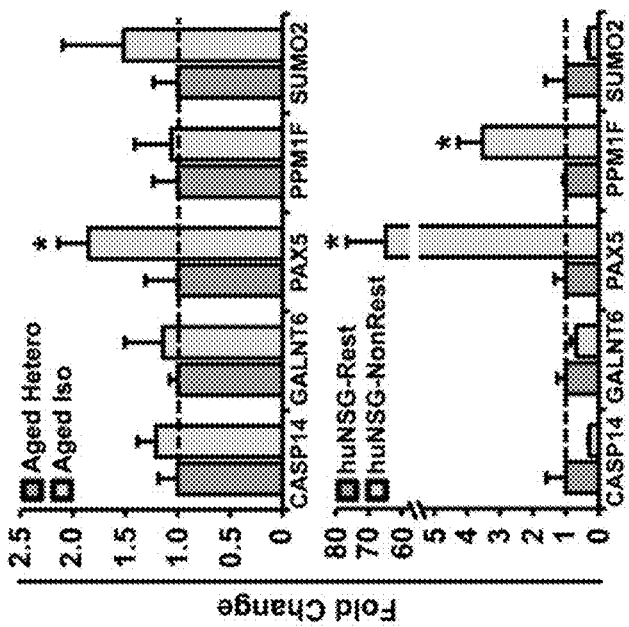
FIG. 16F-G

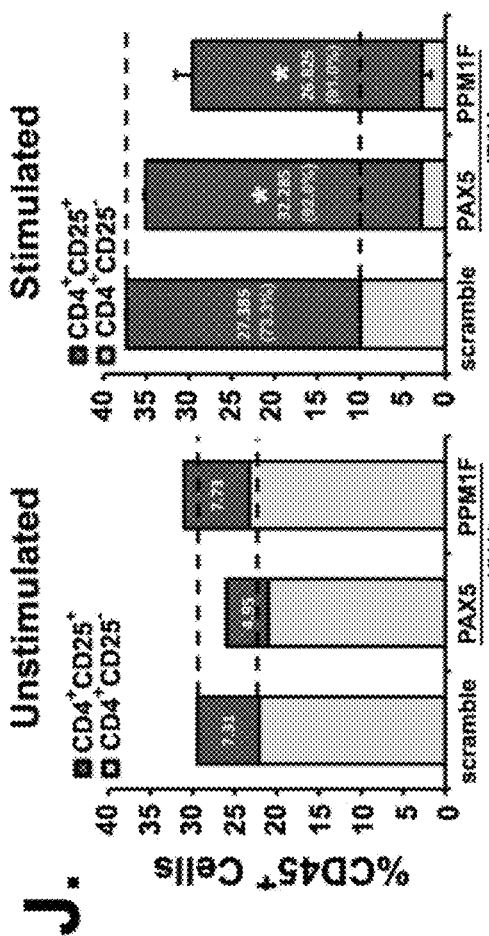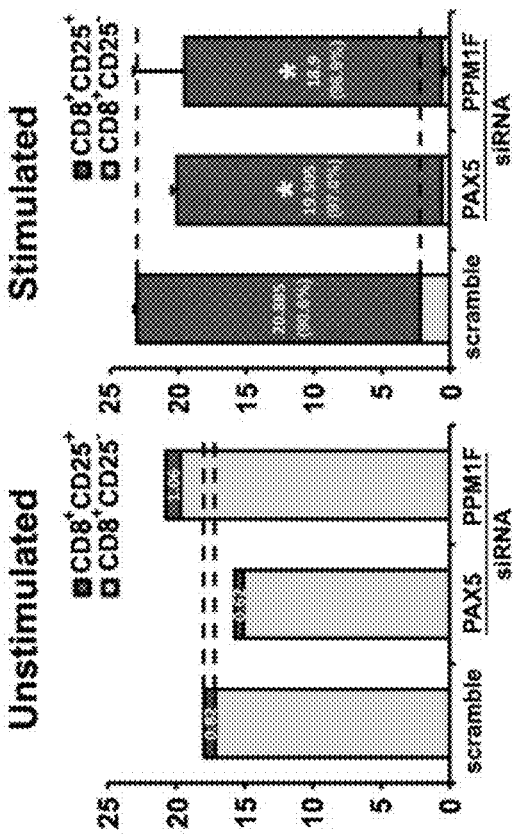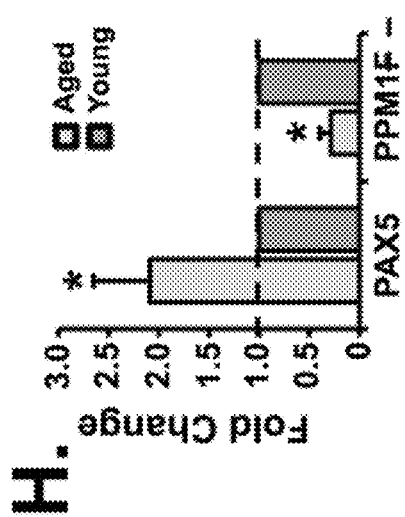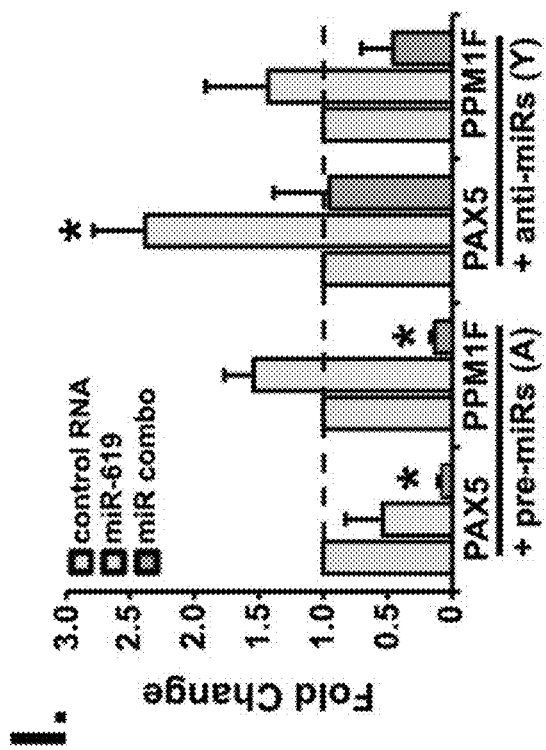
FIG. 16H-J

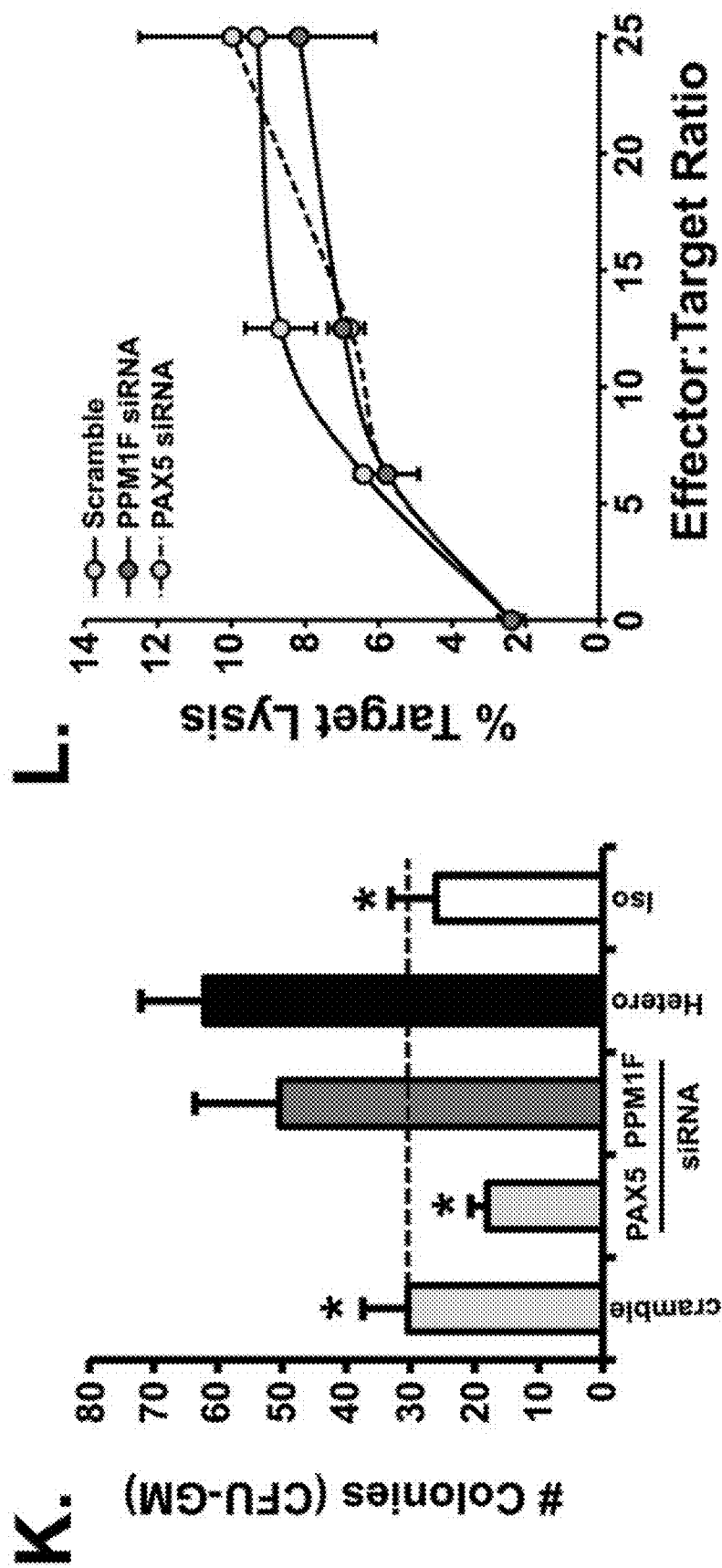
FIG. 16K-L

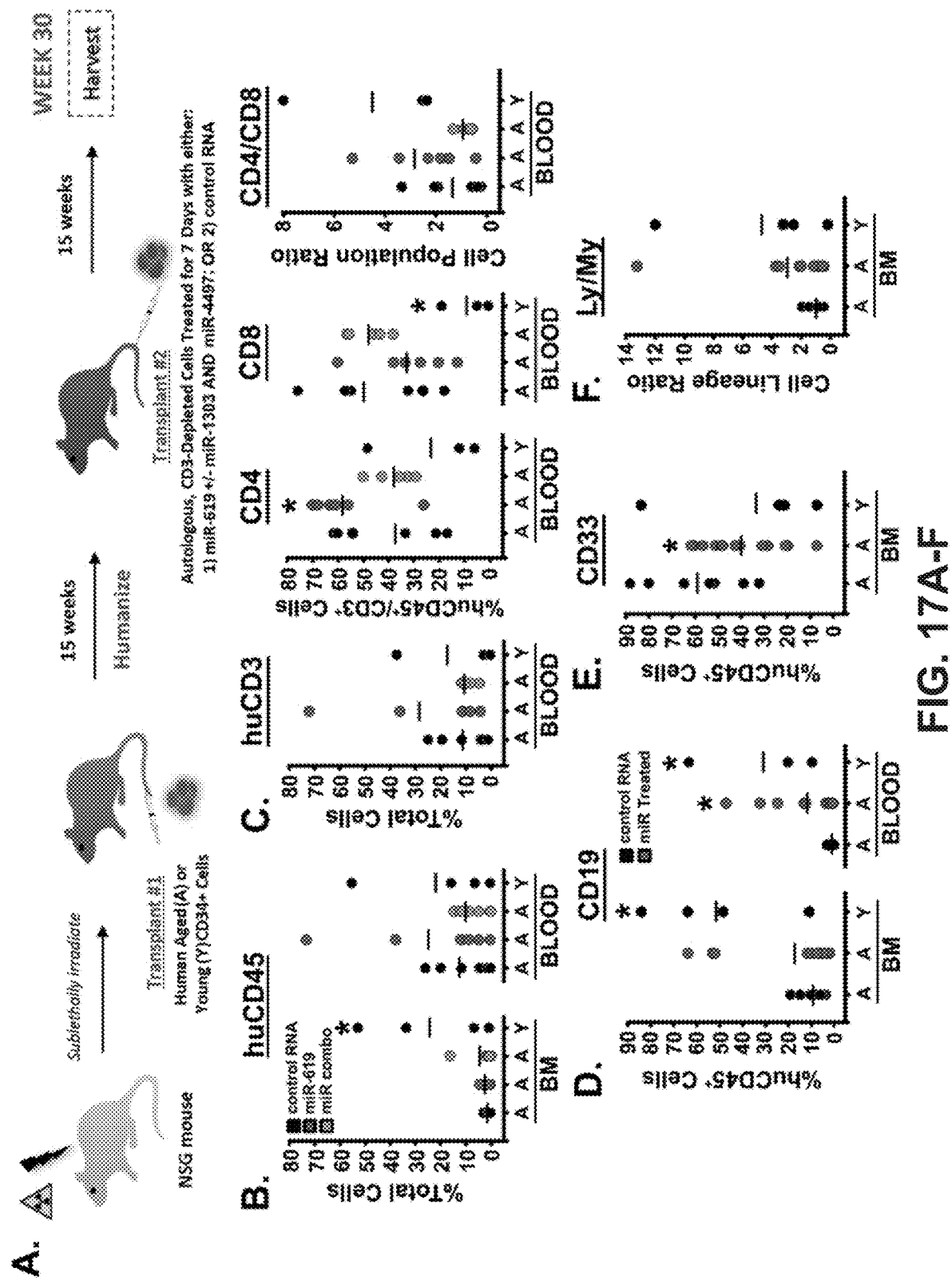
FIG. 17A-F

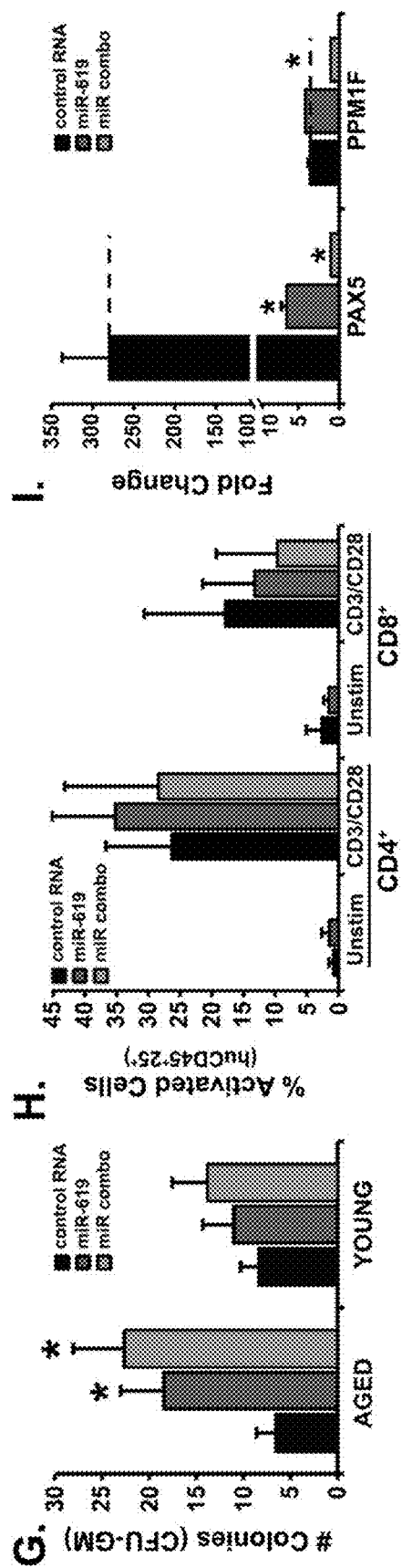
FIG. 17G-I

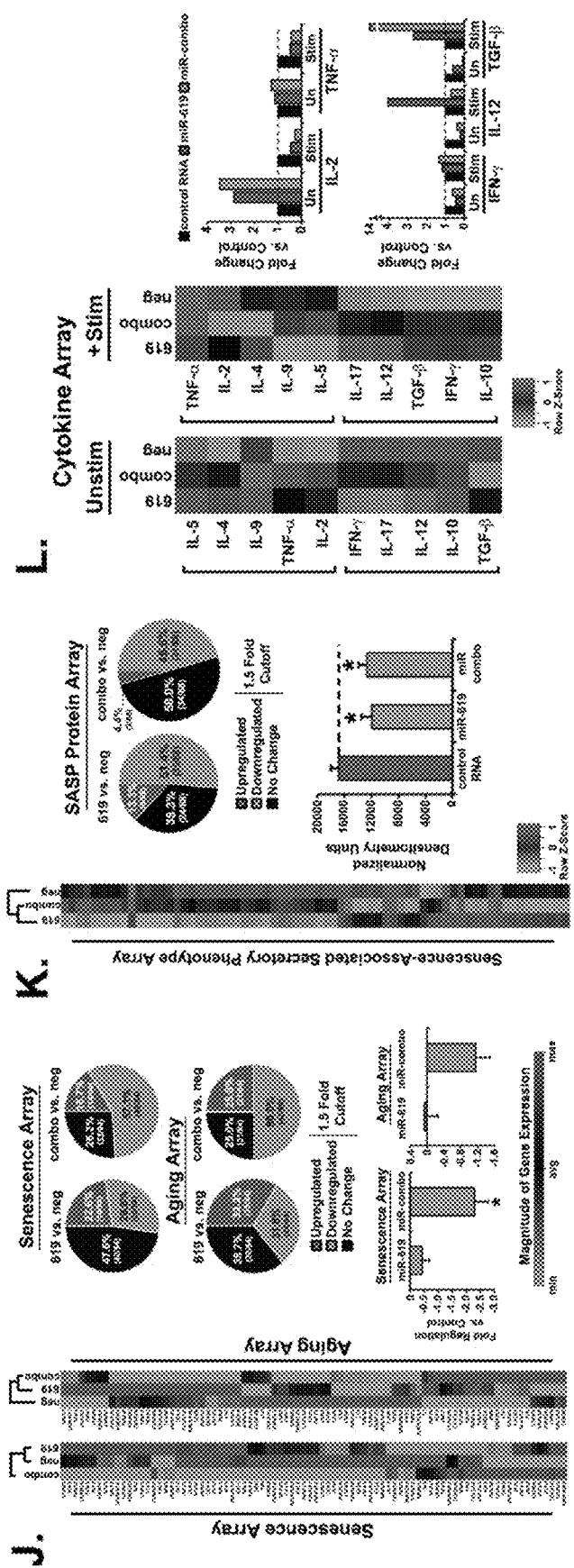
FIG. 17J-L

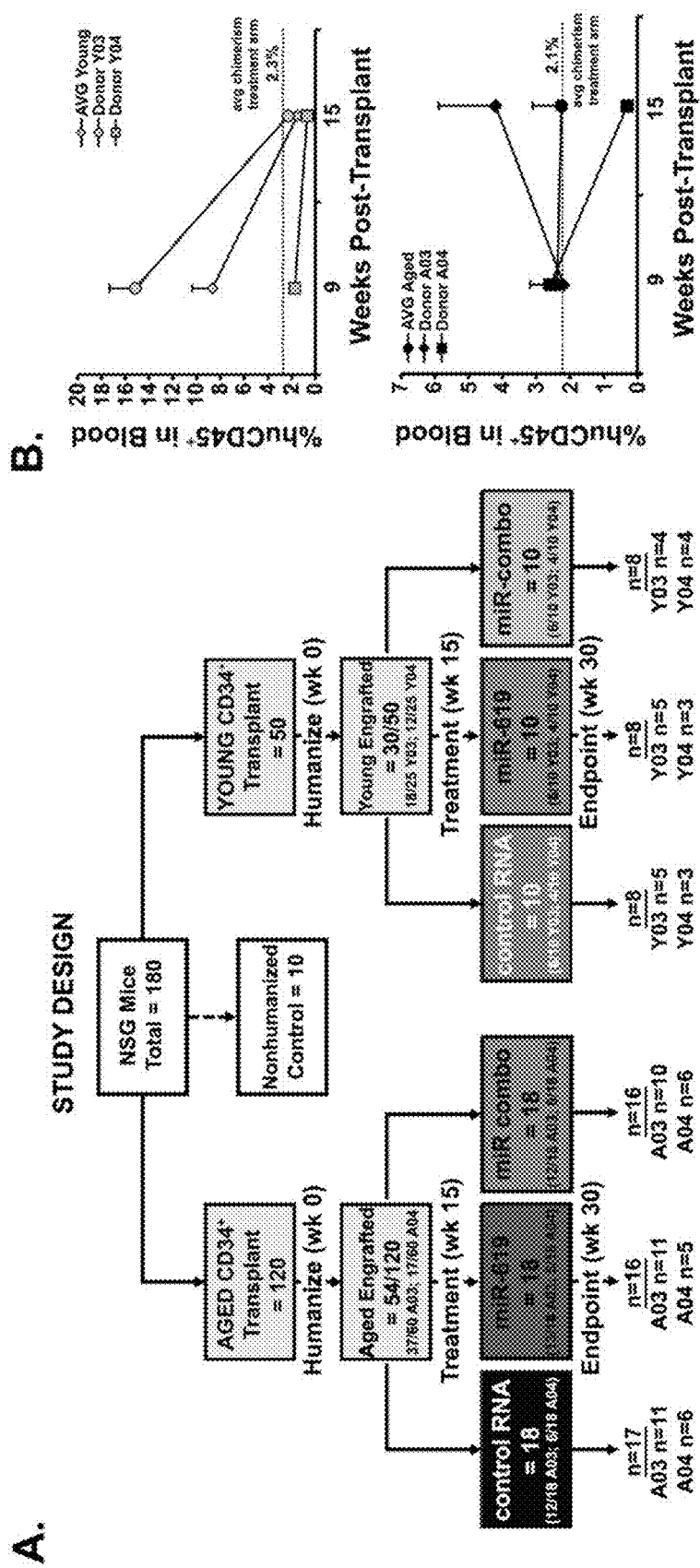
FIG. 18A-B

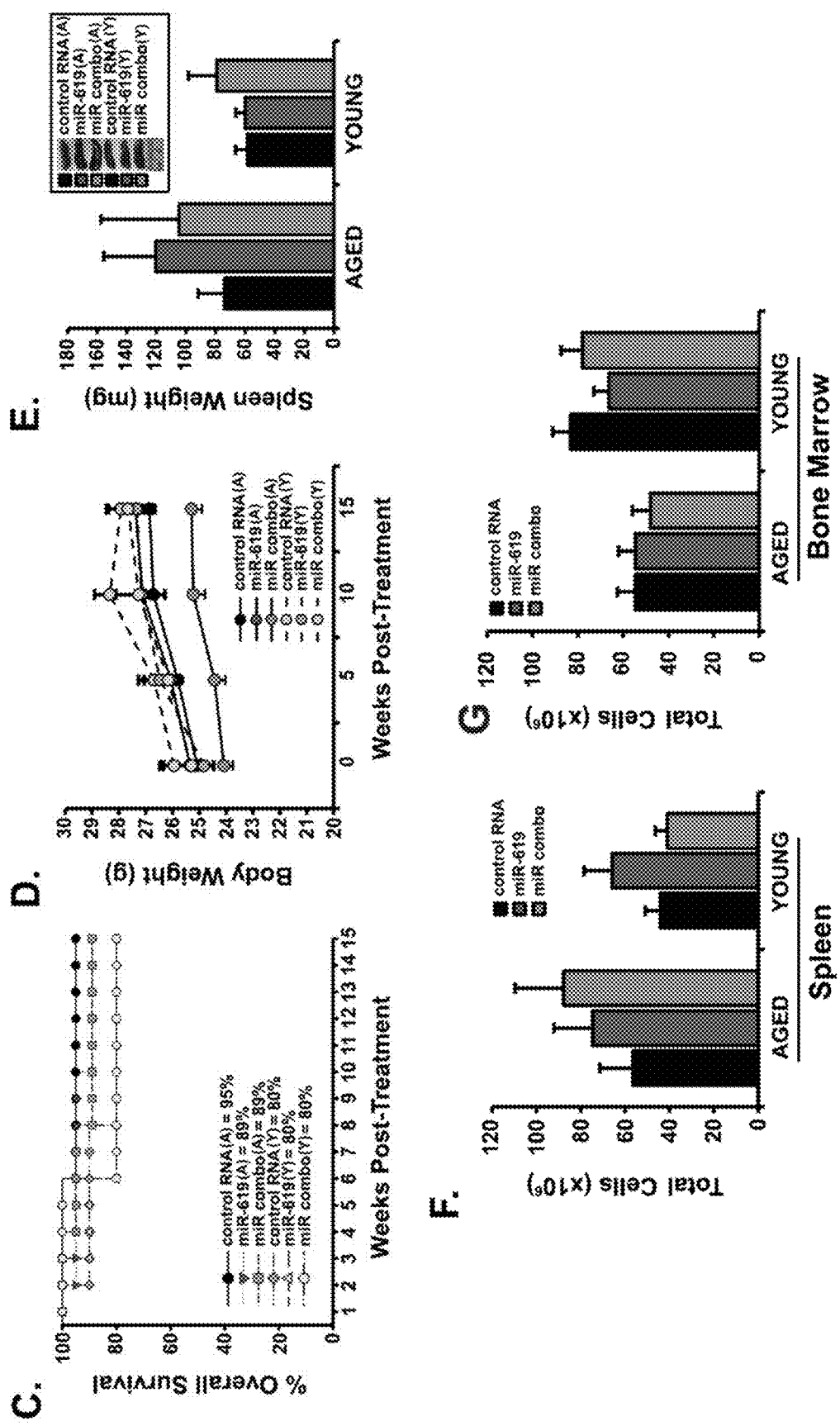
FIG. 18C-G

B.

| KEY | TISSUE | AVG. SCORE | | | | NOTES |
|---|---|---|---|---|---|---|
| | | Aged control RNA | Aged miR-619 | Aged miR-combo | Young control RNA | |
| Histologic Scoring<br><br>0 = Control tissue<br>1 = No difference vs. age-matched control<br>2 = Minor pathology noted vs. control<br>3 = Major pathology noted vs. control (necrosis, tumor formation) | Brain | 0 | 1 | 1 | 0 | |
| | Intestine | 0 | 1 | 1 | 0 | |
| | Liver | 0 | 1 | 1 | 0 | |
| | Heart | 0 | 1 | 1 | 0 | |
| | Lungs | 0 | 1 | 1 | 0 | |
| | Kidney | 0 | 1 | 1 | 0 | |
| | Spleen | 0 | 1 | 1 | 0 | *Enlarged spleen detected for all groups due to extra-medullary hematopoiesis* |
| | Skin | 0 | 1 | 1 | 0 | |
| | Muscle | 0 | 1 | 1 | 0 | |
| | Bone Marrow | 0 | 1 | 1 | 0 | *There is mild to moderate increase in cellularity of hematopoietic elements in bone marrow for miR-combo vs. miR-619* |

FIG. 19B

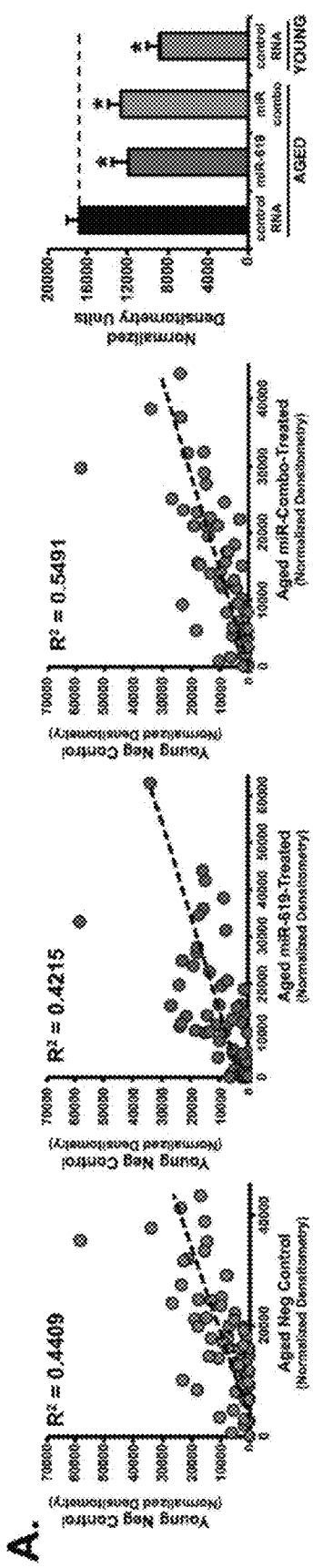
FIG. 20A-C

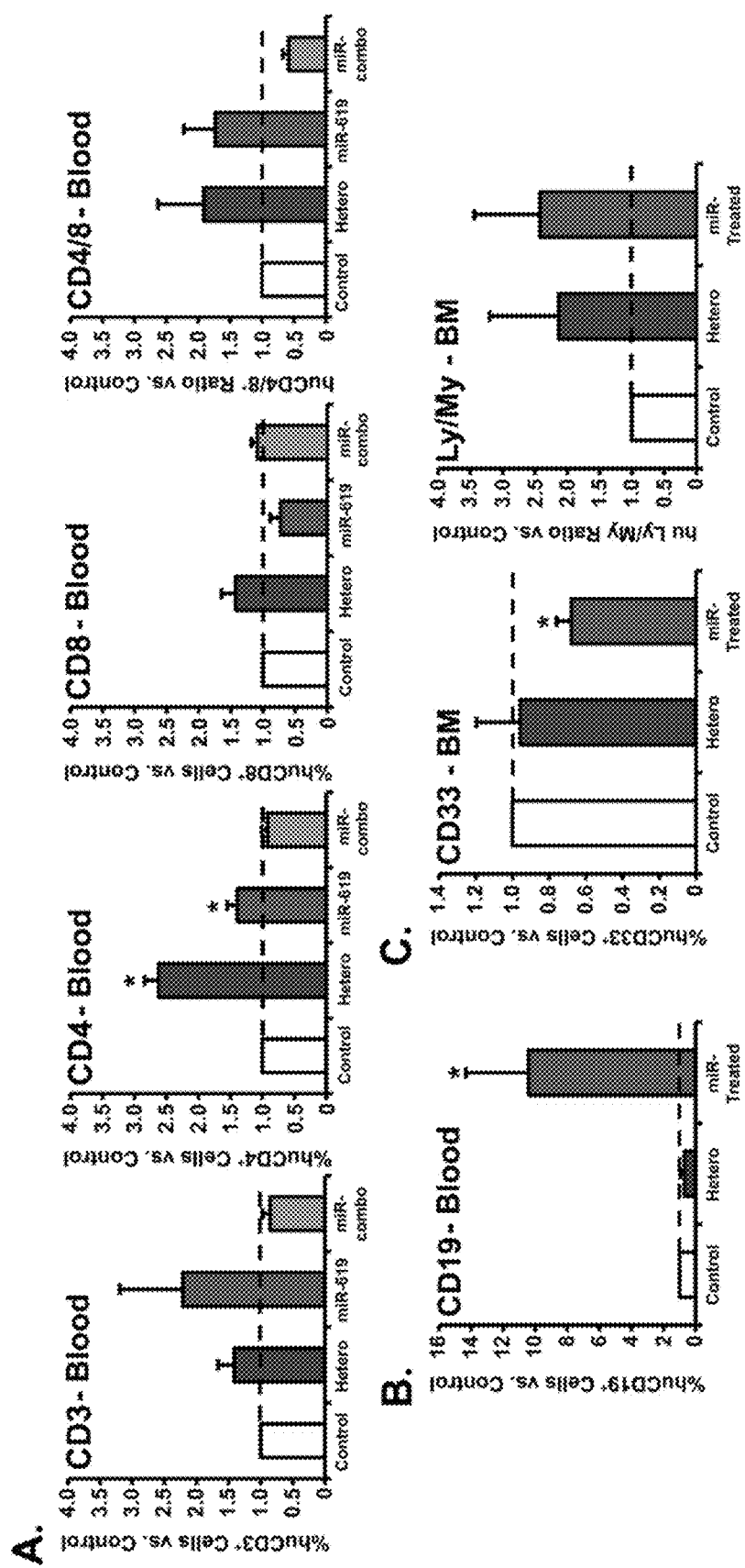
FIG. 21A-C

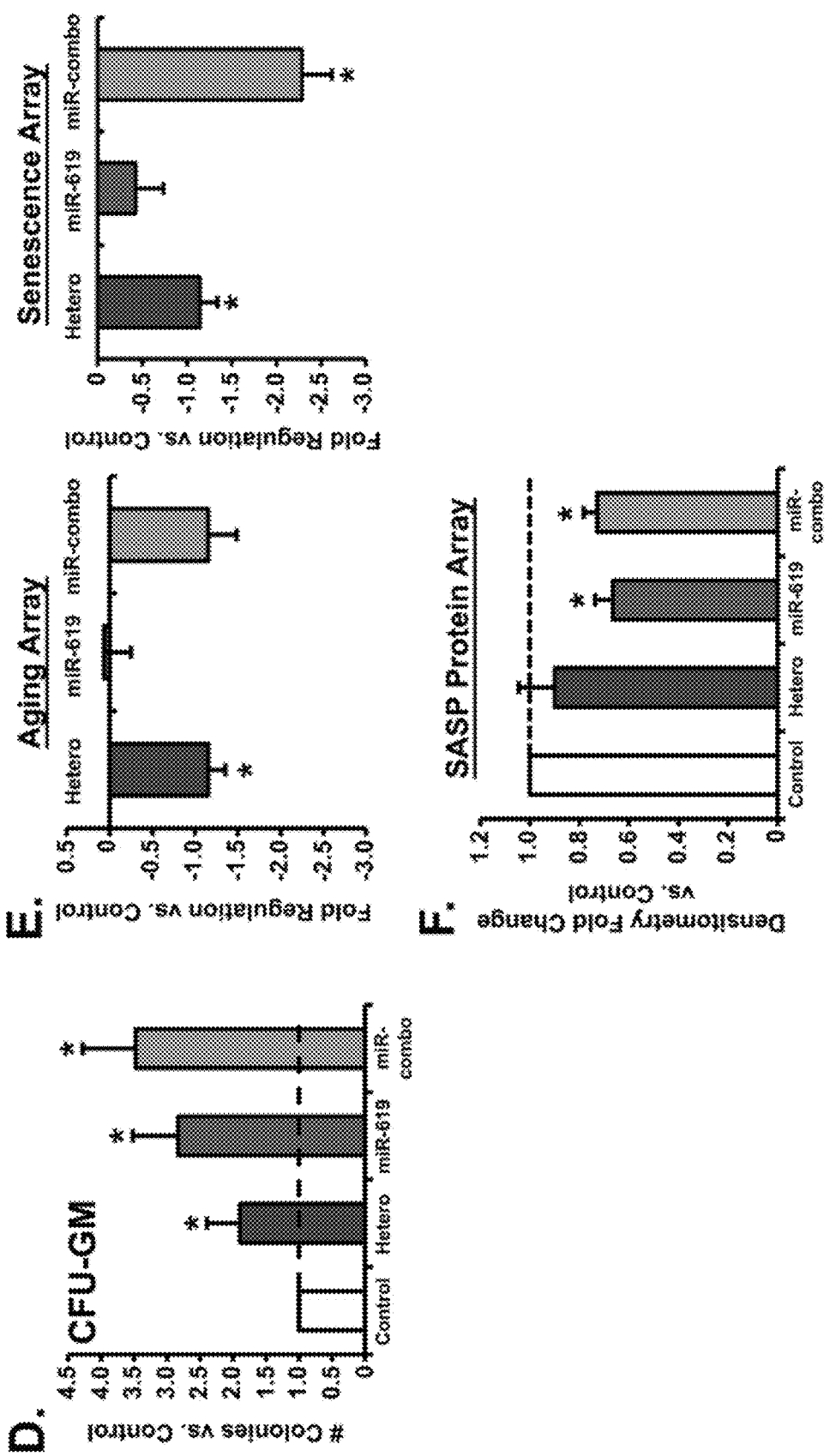
FIG. 21D-F

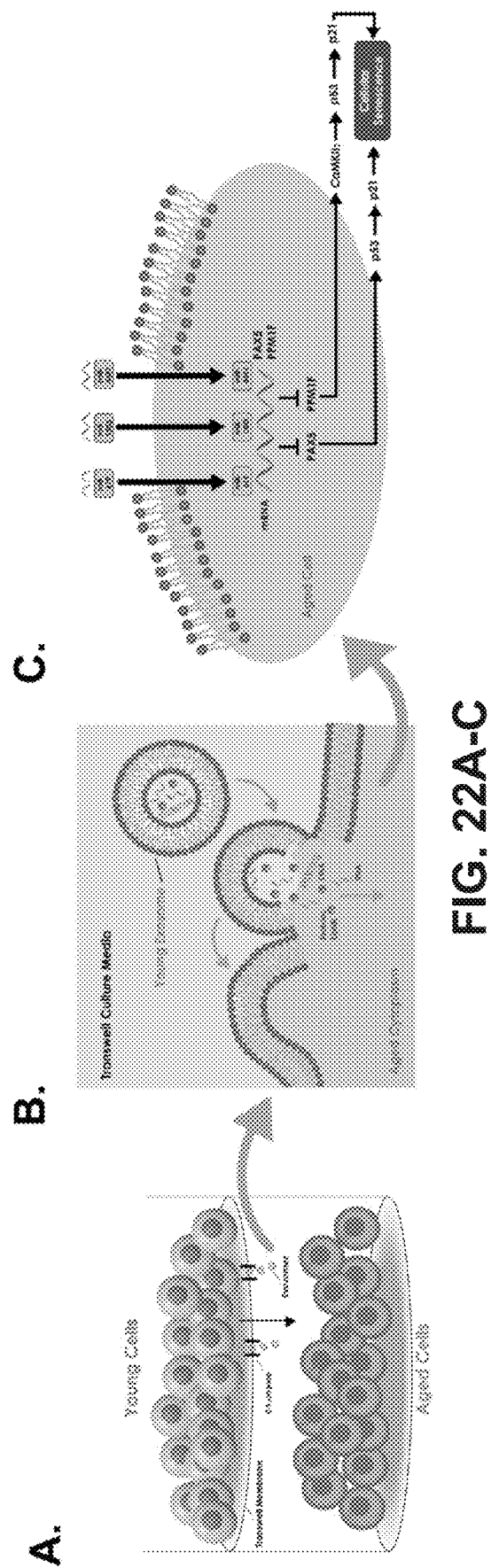
FIG. 22A-C

SEQUENCE LISTING

```
<160> NUMBER OF SEQ ID NOS: 30

<210> SEQ ID NO 1
<211> LENGTH: 8704
<212> TYPE: DNA
<213> ORGANISM: Homo sapiens

<400> SEQUENCE: 1
agttccttaa tcatttcacg gtgccttcgg acgctttttt tccacctaaa acgtttagtt      60
tcagctcagt gatcagctac cccagctcgg cggggagcg gaaggcttga attattccga      120
cctgtgagcg gcccctggca ccaaaaaaaa aaaaaaaaaa aaaaaaaaaa gaaaaaaaaa      180
ggcacaaaaa agtggaaact tttccctgtc cattccatca agtcctgaaa aatcaaaatg      240
gatttagaga aaaattatcc gactcctcgg accagcagga caggacatgg aggagtgaat      300
cagcttgggg gggtttttgt gaatggacgg ccactcccgg atgtagtccg ccagaggata      360
gtggaacttg ctcatcaagg tgtcaggccc tgcgacatct ccaggcagct tcgggtcagc      420
catggttgtg tcagcaaaat tcttggcagg tattatgaga caggaagcat caagcctggg      480
gtaattggag gatccaaacc aaaggtcgcc acacccaaag tggtggaaaa aatcgctgaa      540
tataaacgcc aaaatcccac catgtttgcc tgggagatca gggaccggct gctggcagag      600
cgggtgtgtg acaatgacac cgtgcctagc gtcagttcca tcaacaggat catccggaca      660
```

-continued

```
aaagtacagc agccacccaa ccaaccagtc ccagcttcca gtcacagcat agtgtccact    720
ggctccgtga cgcaggtgtc ctcggtgagc acggattcgg ccggctcgtc gtactccatc    780
agcggcatcc tgggcatcac gtcccccagc gccgacacca acaagcgcaa gagagacgaa    840
ggtattcagg agtctccggt gccgaacggc cactcgcttc cgggcagaga cttcctccgg    900
aagcagatgc ggggagactt gttcacacag cagcagctgg aggtgctgga ccgcgtgttt    960
gagaggcagc actactcaga catcttcacc accacagagc ccatcaagcc cgagcagacc   1020
acagagtatt cagccatggc ctcgctggct ggtgggctgg acgacatgaa ggccaatctg   1080
gccagcccca cccctgctga catcgggagc agtgtgccag gccgcagtc ctacccatt    1140
gtgacaggcc gtgacttggc gagcacgacc ctccccgggt accctccaca cgtccccccc   1200
gctggacagg gcagctactc agcaccgacg ctgacaggga tggtgcctgg gagtgagttt   1260
tccgggagtc cctacagcca ccctcagtat tcctcgtaca cgactcctg gaggttcccc   1320
aacccggggc tgcttggctc cccctactat tatagcgctg ccgcccgagg agccgcccca   1380
cctgcagccg ccactgccta tgaccgtcac tgacccttgg agccaggcgg gcaccaaaca   1440
ctgatggcac ctattgaggg tgacagccac ccagccctcc tgaagatagc cagagagccc   1500
atgagaccgt cccccagcat cccccacttg cctgaagctc ccctcttcct ctcttcctcc   1560
agggactctg ggcccttttg gtggggccgt tggacttctg gatgcttgtc tatttctaaa   1620
agccaatcta tgagcttctc ccgatggcca ctgggtctct gcaaaccaat agactgtcct   1680
gcaaataacc gcagccccag cccagcctgc ctgtcctcca gctgtctgac tatccatcca   1740
tcataaccac cccagcctgg gaaggagagc ttgcttttgt tgcttcagca gcacccatgt   1800
aaatacttc ttgcttttct gtgggcctga aggtccgact gagaagactg ctccacccat   1860
gatgcatctc gcactcttgg tgcatcaccg gacatcttag acctatggca gagcatcctc   1920
tctgccctgg gtgaccctgg caggtgcgct cagagctgtc ctcaagatgg aggatgctgc   1980
ccttgggccc cagcctcctg ctcatccctc cttctttagt atctttacga ggagtctcac   2040
tgggctggtt gtgctgcagg ctccccctga ggcccctctc caagaggagc acactttggg   2100
gagatgtcct ggtttcctgc ctccatttct ctgggaccga tgcagtatca gcagctcttt   2160
tccagatcaa agaactcaaa gaaaactgtc tgggagattc ctcagctact tttccgaagc   2220
agaatgtcat ccgaggtatt gattacattg tggactttga atgtgagggc tggatgggac   2280
gcaggagatc atctgatccc agccaaggag gggcctgagg ctctccctac tccctcagcc   2340
cctggaacgt tgttttctga ggcatgccca ggttcaggtc acttcggaca cctgccatgg   2400
acacttcacc caccctccag gaccccagca agtggattct gggcaagcct gttccggtga   2460
tgtagacaat aattaacaca gaggactttc ccccacaccc agatcacaaa cagcctacag   2520
ccagaacttc tgagcatcct ctcggggcag accctccccg tcctcgtgga gcttagcagg   2580
cagctgggca tggaggtgct ggggctgggg cagatgccta atttcgcaca atgcatgccc   2640
acctgttgat ctaaggggcc gcgatggtca gggcacggc caagggccac gggaacttgg    2700
agagggagct tggagaactc actgtgggct agggtggtca gaggaagcca gcagggaaga   2760
tctggggac agaggaaggc ctcctgaggg aggggcagga gagcagtgag gagctgctgt    2820
gtgacctggg agtgattttg acatgggggt gccaggtgcc atcatctctt tacctggggc   2880
cttaattcct tgcatagtct ctcttgtcaa gtcagaacag ccaggtagag cccttgtcca   2940
aacctgggct gaatgacagt gatgagaggg ggcttggcct tcttaggtga caatgtcccc   3000
catatctgta tgtcaccagg atggcagaga gccagggcag agagagactg gacttgggat   3060
```

```
cagcaggcca ggcaggtctt gtcctggtcc tggccacatg tctttgctgt gggacctcag    3120
acaaaaccct gcacctcttt gagccttggc tgccttggtg cagcagggtc atctgtaggg    3180
ccaccccaca gctctttcct tcccctcctc tctccaggga gccggggctg tgagaggatc    3240
atctggggca ggccctccac ttccaagcaa gcagatgggg gtgggcacct gaggcccaat    3300
aatatttgga ccaagtggga acaagaaca ctcggagggg cgggaatcag aagagcctgg     3360
aaaaagacct agcccaactt cccttgtggg aaactgaggc ccagcttggg gaaggccagg    3420
accatgcagg gagaaaaagc agacttcctc tggccaccgc taagtatttt gttccctaag    3480
tcccccacag ggtggtggaa cagaagagaa aactaaggct cagcaaggtg gagtcctcaa    3540
gcagtgactg gtgggggtgg ggctgggact cgggctcctg accccaacc catggtgttc     3600 cctgtcaccc tggtctatcc acatctccta ttcctgagga gagttgacag taagagcagt    3660
gagagatggt tctgggcccc atgccctaga caatcagtct gtaagaactg ccaaggaagc    3720
ctggtcaccc aggccaggga tggagcccag cgagctcaca gcaggcacat gcaccccgc     3780 ccccacccag aacctgcggg gcaaagaagg gaggtagttg gggccagagt ccacctccag    3840
gagccagggt gagctggctg cagcttccac ctgtcaggta aggtaggaga aggtatgtta    3900
cctggcatct ctctccctgc ctccctccat ttagcaggaa gtggtggggt cagggtctt    3960 cagcacagac ttcttgagcc tctgcccct gtcacccttc ttttggaatg atgtgtaccc     4020
acatctttgg atcctgccct ccttgtggtt ccaggctgtt gggaggaggt cagcctcccc    4080
tgaaccagct gcctgaggca tgcagcatcc ttcctcggca aagcccacct ggctcacagc    4140
ggccccctct ccccatcctg ttcctcttct tgccctgtaa tgagctcccc ccatacctt     4200 cctccctcac ctgaggcttt gctggtcctc agattggttt tgtatttgtg agacaaccac    4260
ttgactcctg ggctgccagg cggaagcaca agcgcacatg gatgcacacg gatgttctca   4320
cacacacacg cccgctctca ccaattcaca gcacctcgtg gtccagcgga gctgcctggg   4380
agcttggtga ggatggctcc aaaggacaca agccgttgag tagatgccag agaattctga   4440
atggaaaaca caagtccggg gcctcaccag catcgtggca gaaggcctgg ggcatttctc   4500
catgggcctt cttccctgtg ttcgagctct gacttttgga aaaggacatt gtggatttta   4560
tgaaaatttc tcataccatc agtctagctc caacctagaa aaattggatg atatatcaaa   4620
cccaacatcc ctttcccaag gcaccttagt taaggctagc ccttccataa ctgacattgt   4680
acggtgcttt gcaatcctca accactctgt ggagcaaaga gcatgatgcc tactttatag   4740
acggggaaat tgacatttgg ggctctcacg gcaacataga ggcgaagtga attctcagat   4800
ctccaggccc cattctctct ccaccgagtt gtgctcctgt catgggagtg tatggcttaa   4860
agacactccc ccaccccat tccctagaaa tcccccagac ccacaatcag gcaagaaaga    4920
acagggaccc agaggctggc ctgacctagg ggcctgcagg ttggcggctt tgtttcctaa   4980
gaacattgaa acctgcggag tctttgacca aatccacaac agtgcttctg aggtttcatc   5040
cagactcttt cccagctgtc cctgaggttc agagggtatc agagtcaatt caaggccatg   5100
ccataatccc tgaccaggcc tggacatggg tccagccctg actccagggg tccaggtgcc   5160
aaggtcatgt gctgtccccc acttcccttt ctttgccttc gcactttgga acaggctcca   5220
ggcctggctg tgacagtatg caggagtgcc caagccaggg ccaccagggt gtccacagcc   5280
cctggaaaca cagatcacaa tctcaagtcc cctgaatgaa ctgcttcctg ggtgaacggg   5340
gtggtgtagc cttgccactc gggcagcgca ccagacagta cggtgcagca gtgcccgaga   5400
```

```
tgcccagaag tgtgcctgcc ccctgagtg gcattcaagt atgaaaactt gtaaaatttt    5460
ctgtcggcct aaagaaaaat gtccatgggc caaacttgac ccactgggca ccagcctgtg    5520
agccccaatg cctgtcaatt gccccctttc tcattcacct cctgtccttt gttgcagatt    5580
tggaggagat gggagcccag agaggtgaga gatgtgcttc agggtgtcca gcaaggcagg    5640
ggtagaaacg ggcacgccca gagcctgcca ctctcccagg cctcatcttg ggctcttgca    5700
agtcttgcgc tttgaagatg gagttggggtg gaaggtcaga ggcgctgggg acgggattgg   5760
ggagctgctg ggttttcagg ggaggtcagt gctgcttggg cacctttcac atgtgcaggg    5820
aagagactca gatgtggcca cagggcactg aggggtgaaa tccatttacc agaagtcacg    5880
ctccagaacg actgcccagc cttggcagcc agtggctcca gccacccctc ctcatgaca    5940
ttcagccaga attgagctcc aagccaggga agcaaatctt aaaaaccaac caagcaccct   6000
gacacagccc tagaaacacg atgagtctga atacagcttc cccaggaggg gagtctaaga   6060
tacagcttcc cgggagggtg gaaaccaact cctgccccac ggccaggcca ggcccaggca   6120
ggcatgggtg gatcccacag ggctctgagc tagaccggct ccacggtggc cccactacga   6180
ggccagttct gcagtcttgg ccttgtcacc catcgagagg ctgctctgat ggttcccagc   6240
cacacaccag ctctcctggg gaaactattt ctttcgttct tttggcctcg gagaggtccg   6300
aggcaagtac atttcttaaa aggtaataaa atgcattatt ggaaagttgg acagtcaggc   6360
cacgactcct agcccacggc gtgcccacc tcccagcagc cccttcagcc ccttgccct    6420
gttgccccaa acctcagggt tccctcttgc atattcatgg gggaaccaca gtgctgatgt   6480
gtacttcccc actgtcagct cggctgcacc tcgtgtggcg ccaggtccca agggcctctg   6540
cagaggccag gctgtgagcc ccttgcctgc ctgctcccct gatgaggcaa cagcttctct   6600
gaaatgagct gccggccagg agcaggcagg caccagcctg tctttccttt tctggtaatt   6660
cctcagcact gaggctccgt tcctgggcac cccaggattg aagggaacct cagaatcatg   6720
tcactgccat tctagagttt caatccaagg ggtccccttt agctcatctc caagatgggt   6780
aaacgtagcc accattcaga aagcccagaa attcttgttc ccacatctta gaccctgag    6840
caacacaagg agaaaatgca gctgcttacc tattaatatc tactgaggga caatcagcaa   6900
agcctcaaag gagtcgtctc aggtagggta cttggcctgt ggcaggagag acagaggcac   6960
aaacccaccc acccatcagc ttccggtggc tgatcggggc ccaggagggg aagcaggtga   7020
aacagcaggg tgggggtgac ttggcagtcg tgcatctcct cccgactct gaggcctggc    7080
aggaggaggc cacaccagcc tcacctgccc tgaccccgc ccccaccct gtgaccctgt    7140
ggctatggcc gctggtcgcc cttgtcccca aaatcaccat gcctgtggcc acgtccctca   7200
tcttctccaa aagcatcatt aagaacaagt gatttggat gatggatttt tgatttacaa    7260
acggcgcatt tcccttggag tggaacagaa aggaaaccat ttaatggcgc ccttctttc    7320
aagcatgaat acatttaat gaaactattt tattgtattt gaggaaatgg agagttgaac    7380
attccaacca atcaatagcc aattaattgc tataaagcta aaaagaaaat aaataaatcc   7440
tgagtctatt ttaaacactg caaaagttc agagcctcag aatctggcct tcccctccat    7500
aaggtgcacg agcatgtaaa cacacacaca cacacacaca cacacacaca cacactcact   7560
cactccccta cacctcagac atacttgaaa ctcagaaaca gcactgagtc tccccatgcc   7620
aattcttgcc tgctgtcttc gacttgggtc agagaaggtg agcagacccg gcagcagcct   7680
gtcccggggc tcaggaagag gcaggcccat ccctggccc caagcaccca gcacaacaga   7740
gggtggcggg cagtgagggc ctggcgttgc ctgggcccca cttctcagcc ccagctgctg   7800
```

```
ggcctccaag gttgggctga ggatggagtt ttggctctgg gtttgccctg actcctgctg    7860
gaagacgctg ccctggtttt tcaccctcta gtggccttgg acattgagta tttgtagaaa    7920
tgcagattac attgcaaatg aaacctttg ccaggaagac acatgcattt tgcttttaat    7980
tctttgagac atttgatttt gtcttaggga ctgacctttc agcatcaaag aaatacatat    8040
ctactgtatc cgccaaagtt tgtgatgcct gcatagacgc ttacttgtaa aaaaaaaaa    8100 atacaaaaaa atacaaaaaa accaacaaca aaaccacaa ttgaattgcc tttgaaagtg    8160
ggagatgatc tgtctccaac ggattgaaaa aaaaaaatgc ttcttaaaaa atgtgtatgt    8220
tttgtattct ttttttctag tagaaaataa ctgacttgaa atattggtgg tttttttctt    8280
agtgacgtgt gttgcttttg tgtgtaataa tatttgaatg taattacagc agtgccaatt    8340
tgccaaagat gttggacata ttttctttt tggggagga gggcagggct aggggtggga    8400
cttgggagaa acaggggtg gggttttggt ttaattttt ttttactttt ttttccttgt    8460
caaacctgaa atttgtggct tccttttaag ttaaatggtt gactgcaaca cctttatttt    8520
agattagttg gagaaacatg caataagatt ggcgtagttt caatatctgt gtgtcttttc    8580
atgagtggct gttacttgtg aagaattgat tttatgtaac ctttatgtga gataattatt    8640
tgtaaatatt tgccataatt ttattggttc ctaaaataaa agtaatttt taagttcaga    8700 aaaa                                                                  8704

<210> SEQ ID NO 2
<211> LENGTH: 1212
<212> TYPE: DNA
<213> ORGANISM: Equus caballus

<400> SEQUENCE: 2
ctgtccattc catcaagtcc tgaaaaatca aatggatttt agagaaaact tacccgactc      60
ctcggaccgg caggacagga catggaggag tgaatcagct tggggggggtt tttgtgaacg     120 gacggccact cccggatgta gtccgccaga ggatagtgga acttgctcat caaggtgtca     180
ggccctgcga catctccagg cagcttcgag tcagccatgg ttgtgtcagc aaaatccttg     240
gcaggtatta tgagacgggg agcatcaagc ctggggtaat tggaggatcc aaaccaaagg     300
tcgccacacc caaagtggtg gaaaaaatcg ctgagtataa acgccaaaat cccaccatgt     360
ttgcctggga gatcagggac cggctgctag cagaacgcgt gtgtgacaat gacaccgtgc     420
ccagcgtcag ttccatcaac aggatcatcc ggacaaaggt gcagcagccg cccaaccagc     480
cggtgccggc ttccagccac agcatagtgt ccacgggctc agtgacgcag gtgtcgtcgg     540
tgagcacgga ctcagccggc tcctcgtact ccatcagcgg catcctgggc atcacgtccc     600
ccagtgctga caccaacaag cgcaagagag atgaaggtgt tccggagtcc ccggtgccca     660
acggccactc cctgccgggc cgagacttcc tccggaagca gatgcgagga gacctgttca     720
cgcagcagca gctggaggtg ctggaccgcg tgttcgagag cagcactac gcggacatct     780 tcaccaccac ggagcccatc aagcccgagc agaccactga gtattcagcc atggcctcgc     840
tggctggagg gctggacgac atgaaggcca acctgaccag ccccacccca gctgacatcg     900
ggagcagcgt gccagggccg cagtcctacc ccattgtgac aggccgcgac ttggcgagca     960
cgactctccc cgggtaccct ccgcacgtcc cccggccgg acagggcagc tactcagcgc    1020
cgacgctgac agggatggtg cctgggagtg agttttccgg gagcccctac agccaccctc    1080
agtacccctc gtacaacgac tcctggaggt tccccaaccc ggggctgctc ggctccccgt    1140
```

| actattacag tgccgctgcc cgggggggctg ccccgcctgc agctgccact gcctatgacc | 1200 |
| gtcactgacc ct | 1212 |

<210> SEQ ID NO 3
<211> LENGTH: 7765
<212> TYPE: DNA
<213> ORGANISM: Canis lupus

<400> SEQUENCE: 3

| gaaagaaaaa aaaagaaagg aagaaagaaa agaaaaaaga aaaagaaag aaagaaaaag | 60 |
| aagcacacaa aaaaagtgga aacttttttcc ctcgtccact tcaagttctg aaaatcaaaa | 120 |
| tggatttaga gaaaaattac ccgactcctc ggagcggcag gacaggacat ggaggagtga | 180 |
| atcagcttgg gggggttttt gtgaatggac ggccacttcc ggatgtagtc cgccaaagga | 240 |
| tagtggaact tgctcatcaa ggtgtcaggc cctgcgacat ctcaaggcag cttcgagtca | 300 |
| gccatggttg tgtcagcaaa attcttggca ggtattatga gacggggagc atcaagcctg | 360 |
| gggtaattgg aggatccaaa ccaaaggtcg ccacgcccaa agtggtggaa aaaatcgctg | 420 |
| agtataaacg ccaaaatccc accatgtttg cctgggagat cagggaccgg ctgctggcgg | 480 |
| aacgtgtgtg tgacaatgac acggtgccca gcgtcagttc catcaacagg atcatccgga | 540 |
| caaaagtaca gcaaccaccc aaccagccgg tcccagcttc cagtcacagt atagtgtcca | 600 |
| cgggctccgt gacgcaggtg tcgtcggtga gcacggactg ggccggctcc tcgtactcca | 660 |
| tcagcggcat cctgggcatc acctcccccca gcgccgacac caacaagcgc aagagagatg | 720 |
| aaggtattca ggaatctcca gtgccaaacg gtcactccct gccaggcaga gatttcctcc | 780 |
| ggaagcagat gcggggagac ctgttcacgc agcagcagct ggaggtgctg gaccgcgtgt | 840 |
| ttgagaggca gcactactcg gacatcttca ccaccacaga gcccatcaag cccgagcaga | 900 |
| ccaccgagta ttcagcgatg gcttcgctgg ctggagggct ggatgacatg aaggccaacc | 960 |
| tgaccagtcc caccccccgcc gacattggga gcagcgtgcc tggccgcag tcctatccca | 1020 |
| ttgtgacagg ccgtgacttg gcgagcacga ccctccccgg gtaccctccg cacgtccccc | 1080 |
| ccgccggaca gggcagctac tcagcaccga cgctgacagg gatggtgcct gggagtgagt | 1140 |
| tctcccggga gccccctacagc cacccctcagt atccctcgta caacgactcc tggaggttcc | 1200 |
| ccaacccggg gctgcttggc tccccgtact attacagcgc cgcagcccga ggagctgccc | 1260 |
| cgccagcagc cgccactgcc tacgaccggc actgaccctc ggagccaggc gggcgccaag | 1320 |
| cacttatcac acatatcact gagggcggta gcctctcggc ccctccgaag atggccagag | 1380 |
| gggcccagcg agaccatcct ccagcaatcc ccactcgcct gaaactccct cccaacctttt | 1440 |
| tcttgccaag gactctgggg ctctatggta aggctgttag acttctagac acgcgtgtgt | 1500 |
| ttctaagagt caatcagcga gctgctccca acagcaactg ggtctctgca aagcaacgga | 1560 |
| ctattctgca gacaactgta gccccagcct agcctgccag tcccagctg tctgaccatc | 1620 |
| cacctgtctt cctgccccag gcctgggaag agagcttgc ttttgtcact tcaacagcac | 1680 |
| ccatgtaaat accttcttgc ttttttgtgg gcctgagggt ccaactgagg cagaccgcct | 1740 |
| ccccattatg catccagtac tcccgatgtg tcacaggaca tcttagacct gtgtgcagag | 1800 |
| cattccctct gtcctggctg ccccccacag gtgggcttgt agttgtcctt gagactaagg | 1860 |
| atgcccacct cagggcccag cctctgctc attgctactt cttcaacgtc tggactagga | 1920 |
| gtcttgttgg actggttatg cttcacgctt ccccctgag acccttcctc aggagaaaca | 1980 |
| cactggagag ttgccctggc ttcctgactc ccatttttcc tgggcccagt gcagtgtgag | 2040 |

```
cagctcttct tccatagcaa aggactcaga gaacaaagaa ctgtctggga gattcctcag    2100
ctacttttct aaagtaagat gctgtccaag gtgctgaccg cattgtggac tcagtgctgc    2160
ggctgggcag gacccagaag accatagtcc aaggcgagga ctcccaagcc cctggaacca    2220
ctgaactgaa ctgggatgtg tttctgaggt gttcccaggc tcatatcaca ttggacaccc    2280
accatggaca tttcttccac cctccaggat gctagagagt ggattctggg caagcctgtc    2340
cctgccatgt agacaataat tcacaaaaag gaagttcttg caccaaggac cacaaacccc    2400
tacagcagtc agccagaact tcctgatcag cctctcccaa ttcctgtgga gcccagtgtg    2460
cagttgggac tagaggtgct ggggtgggag cagatgccta actgcacagt gggtatatac    2520
ctattgatgc agggggttgt gatggtcagc accatggcca agggcccctg gagcctggag    2580
tgggagtttg gagaactcac tgtaggctgg agtggtcaga aaaaactacc tgggagaatg    2640
tgggggacag aggaaggcct tctgggagag tgaggaactg gtgtgtgaac taggagtgat    2700
tttgaaatag gggttccagg ggccactatc tctttgcctg ggacctcaat tccttcaata    2760
atctctcttg ccagctccaa gcagccaggt ggaggtctgt ccaaatctgg gctgaattac    2820
agtgatgaca atggactttg ccatctcatg tgacaggata cccaatgtct acatgtcacc    2880
aagttggcaa agagctgggg cagagcagag cctgcacttg aggctattgg ccctgagagg    2940
tcttatcctg gccacaccat ttccttgctg taggacctca gacaagaccc tcacctctct    3000
gagtctccac tgctttggta cagcagggtc acctgcaggg ccatcctata gttctctcct    3060
cagcttcctc tttccccaga tgctggggct gtgactgggt catctggggc aagtcctcta    3120
cttataagca agcgtaagag ttgggcatct gagtcctgct aatatttgga ccaaatggga    3180
aataagaaca cccaaagaga tgagaatcag ccttgaggaa gatctagccc agctccctc    3240 aggggaaact gaggcccagt ttggggaagc ccagtatgat gcagggaaat agaacagata    3300
tcctctggcc actatcaagt gttttctccc caacatccta caaggtggtg aagagaaga    3360 ggaaacaagc ttaccaaggt ggaggccaca ggcagtgact ggcagaggta gggctgggat    3420 tcaaccccc aaccctggc acaaggtgat catccttcca tccctgggga gggaagttga    3480
cagtgagggc agtgggagat cgttctgggc ccactgccac agatagagtg ttctgggctg    3540
ttagaactgc caagaaagcc caggcaccca gggcagaggt ggagccagtg ggctcaccat    3600
aggcacaccc acctccttgg aacctgctgg gcaaagaaga gaggcagctg ggggcagagc    3660
ccaccttcag gaacaggatg aaccagctcc agcctccacc tgccaggcaa ggtaggagaa    3720
ggaatgtcat ctggcctctc ctttcctcct tccctccctc cttcccttcc acaggaaatg    3780
gttggctcag gagtctgaag cacaggctct tggcctcttg cacccacatc tttggtcttc    3840
atccctcctt gtggtctcag gatattggga ggtcagcctt tcctgaacca actgcctaaa    3900
gcacacactg tccttcctca tcaaagccca gccggctcca ttctgttcct tctcttgccc    3960
tgtgatgagg tcccccata cctctcctct ctccccgag gctctgctgg tcttcagatt    4020
gcatttgtat ttattagaca accacttgat tcctgggctg ccaggaagaa gcacaagagc    4080
acatggatgt acacgcatgt tctcacacat gtacctgctc tctccagctc agggtacaca    4140
cactgcccag tggaacgcct gggagcttgg agagaaaggt tccaaaggac acaagccgtt    4200
gagtaaatgc cagagaattc tgaatggaaa acacaaggcc agagctctca cgaacattgt    4260
ggctggaggc ctggggcact cctccatggg ctttcagccc tatgttccag ctctgaattt    4320
tggaaaggac cttgtggatt ttatgaaaaa gcttcatatc attagtctag ctccagcctt    4380
```

```
gaaaaatctg atgacatatc aaatccaatc tcccttttcc aaggcgcctt aggtagggtt    4440 agcccttca taactcacat ttgtatggtg ctttgcaatc cttgaccatt ccctggggca    4500
aagaccacaa tgcctattct acagatggta aaactgagat ttggggtttg catggcaaga    4560
gagaggtaaa gtgaattctc agatctctgg gccccattct ctctccacag aattgtgctc    4620
ttgtcatgag agcatgtggc ttagacaaat gcttcaatcc cctagaaacc ccctagaccc    4680
acaaggagga aaaaagaac agggacccag aggctgccct gaccaaatag cctgggcttt    4740
ggtggcattg ccagtctacc ttgattctca ttaacaccaa acctgcaaag tctttgccca    4800
gatgcattca tatcagtgcc tctgaggttt tatccacact tcttccctgc tgggtcctga    4860
gcctccaagg ggatcagacc acaccattag ccctggcaga gctagacac gggcccgcct    4920 ccaactccca gggtctaaga ttccaggggtt atgagatgtc ccctcactgg ggttcagaca    4980
tcagccctgt ttgtgacaac acgtaggagt cccccagcag ggccctcaga gcagccacag    5040
gcctgggaaa cacagatcgc aatctcaagg gccctgaact gctgcttccc aggttcagac    5100
ggagtaatct tgtcgctcag gccgggccag aggcaaccag agggcttgcc ccaaccaaca    5160
gcattcaaat gtgaaagctt ttaaaatgct cttccagcca aaaacctaca tttgtgggcc    5220
agatttgacc caccaaccac tagcacataa ctcccaactt ttgtccagtg ctcccttct    5280 ccttcacttg ctcttcattg aagatctggg ggagatggga acccagagag ggatgggctt    5340 caggtttag gcagtcactg tcagggacaa gcatccccag tccttacccc ctccctcctc    5400
accccgggct cttgcagacc atttgggctt tgaagtggat gggatagaac agtttggggg    5460
tggtgggggt ggagggacta ttggcttcga gaggaggtca gtgccttgcc gctgggtct    5520 ttcatatgtg tgggaaagtg ccccagatgt ggccacaggg cactgaaggt tgaaatccct    5580
ttatgagaag tcgtatccca gagcaattgc cctgcctttg gcagcctctg gcaccagcta    5640
cccctcttct ggatgacatt tcagctagaa tttagctcca agccatgggg agcaaatctc    5700
aaaaataaac caagcactcc tgacaaatac ttagaaacaa gatatgtctg agacacagct    5760
gcccggaggg tagagacaaa tccaggcccc tggagaagcc aggtccaggc tgaagtgggt    5820
ggatccctca gcactctggg caacaccagc tcccgggtgg ccccagctaa gaagctggct    5880
ttgcaaccat ggccttgtca cccatctagg ggcctgcctc tgatggtttc caggcacgca    5940
cgtcagtgct cccggagaat ttattccttt agttcttttg gcctcggaga ggtccaaggc    6000
aagtgcattt cttaaaaggt aacaaaacat tatcggaaag ttggacagtc aggccatgac    6060
tcctagccgg cagtctgccc cacctcccag cagccccttc agcccctggc cctctgacga    6120
ccccttacct caggattccc tcttgcatat tcatggcgga gccacagtgt tgatccgaac    6180
ttccccaatg tcagctcgtg gctgcgcctc cagagtggcg gccaggtccc caggggctgc    6240
tgcggagggc tggaagtgag tccctggcct gcttctcgac gtgggcggct tgctaggagc    6300
agccaggcac cagactttct ttcattcact gtgatttctc gacactgggg ttccgttccc    6360
ggaccccccc acccaccacc caccccagga tccaaggaga cctcaggatc ttgtccctgc    6420
cgatctaagc tgcagtgcat gtatttccag gggtccattt agtccatggc tgagttgggg    6480
gtaaatgtaa ccaccacgca gtaagtctag atagtctcct tccaacatct tagaccccaa    6540
agcagcacaa ggagaaaacg cagctgttta tctatttatg gaggaaatct taatgaattc    6600
taaaatggag ttggtctcag gtagcgtact tggcctgtga gtgggacaag gcgggtagga    6660
atcccacctg atttcagctc tagacagctc tgagcatggc tggggaaggg agcatgtgaa    6720
acagcagggg gcggggcaga tcggagttag tgcccccttg cctgatctaa ggcctgcctg    6780
```

```
gaggaggtca agctgagcac ccgccccaag atcgggccca cccagtcctg caactatggc    6840
caccaggcca ccctcatccc caaaatcacc acgcataagg ccaagtccct catcatctct    6900
aaaggcacca ttaagaacaa gtgattttgg atgatggatt tttgatttac aaacggtgca    6960
tttcccttgg agtggaacag aaaggaaacc acttaatggc tcccttattt tcaagcatga    7020
atacatttta atgaaactat tttattgtat ttgaggaaat ggagagttga acattccaac    7080
caatcgatag ccaattaatt gctataaagc taaaaataaa taagtcttga gtcttttga     7140 aatgcccctg cagaactccg agcctccgga tcaggccttg ccctccatat gtgcgcctgt    7200
gtgtacatgc attcccacat gcgcacccct gcacctcaga catacttgaa actcagagat    7260
cgtgctgagt ctcctcatgc caattcttgc ctgctctcct cgcctctggt cagagatggt    7320
gagcagacct ggcagcagcc catgatgggg ctcaggaaga ggcagggcca tcccttggcc    7380
cggcaccacc agctcagtgt gggggatact gggcagtgag ggcccctcg ttggccccca     7440 ctgctgagcc tccaagtctg ggccgagggt ggaaatttga cttgggtttt gccctgactc    7500
ttgctggaag atgctgtcct ggttcttcac cctctagtgg cctttggaca ttgagtattt    7560
atagaaataa atgcagatta cattgcaagt ggaactcttt gccaggaaga cacatggatt    7620
tagcttctca ttctttgaga catttgactt tgtcttaggg actgaccttc cagcatcaaa    7680
gaaatacata tctactgtat ccgccaaagt ttgtgatgcc tgcatagacg cttacttgta    7740
aaaaaaaaaa aaaaaaaaaa aaaaa                                         7765

<210> SEQ ID NO 4
<211> LENGTH: 2426
<212> TYPE: DNA
<213> ORGANISM: Felis catus

<400> SEQUENCE: 4
gggaaaaaag gaaagaaaaa gaaagaaaaa agaaaaaaga aagaaaaaga agcacacaca      60
aaaagtggaa acttttctc cctgtccact tcatcaagtt ctggaaaatc aaaatggatt     120
tagagaaaaa ttacccgact cctcggaccg gcaggacagg acatggagga gtgaatcagc     180
ttgggggggt ttttgtgaat ggacggccac tcccggatgt agtccgccaa aggatagtgg     240
aacttgctca tcaaggtgtc aggccctgcg acatctcaag gcagcttcga gtcagccatg     300
gttgtgtcag caaaattctt ggcaggtatt atgagacggg gagcatcaag cctggtgtaa     360
ttggaggatc caaaccaaag gtcgccacgc ccaaagtggt ggaaaaaatt gctgagtata     420
aacgccaaaa tcccaccatg tttgcctggg agatcaggga ccggctgctg gcggaacggg     480
tgtgtgacaa tgacacggtg cccagcgtca gttccatcaa caggatcatc cggactaaag     540
tacaacaacc cccgaaccag ccggtcccag cttccagtca cagcatagtg tccacgggct     600
ccgtgacgca ggtgtcgtcg gtgagcacgg actcggccgg ctcctcgtac tccatcagcg     660
gtatcctggg catcacgtct cccagcgcag acaccaacaa gcgcaagaga gatgaaggta     720
ttcaggagtc tccggtgccg aacggccact cactgccagg cagagacttc ctccggaagc     780
agatgcgggg agaactgttc acgcagcagc agctggaggt gctggaccgc gtgtttgaga     840
ggcagcacta ctcggacatc ttcaccacca cagagcccat caagcccgag cagaccactg     900
agtactcagc tatggcctcg ctggctggag ggctggatga catgaaggcc aacctgacca     960
gtcccactcc caccgacatt gggagcagcg tgccgggcc acagtcctac cccattgtga    1020
caggccgtga cttggcgagc acgaccctcc ccgggtaccc tccgcacgtc cccccgccg    1080
```

```
gacaaggcag ctactcagca ccgacgctga cagggatggt gcctgggagt gagttttccg    1140 ggagcccta cagccaccct cagtatccct catacaacga ctcctggagg ttccccaacc    1200
cggggctgct cggctcccca tactattaca gcgccgctgc ccgaggggct gccccacctg    1260
cagccgccac tgcctatgac cgtcactgac cctcggagcc aggcaggcgc caagcactta    1320
taacacatat cactgagggc gatagcctct cagcccctct gaagatggcc agaggggccc    1380
aacgagacca tcccccagca accctcactc acctgaaact ccctcccaac cttttcctgc    1440
cagggactct ggggttccat ggtaaggctg ttggacttgt agacatgcgt ccatttctaa    1500
gagtcaatca gtgagcttct cccaacagca gctgggtctc tgcaaaccaa cggactattc    1560
ttcagacaac tatagcccca gcctagcctg ccagtcccca gctgtctgac catccacctg    1620
tcttcctgcc ccaggcctgg aaggagagc ttgcttttgt cgcttcaaca gcacccatgt    1680
aaataccttc ttgctttttt gtgggcctga gggtccagct gagcggacag cccacccatt    1740
atgcatccac tactcccgat gtgtcacagg aaatcttaga cctgtgtgca gagtatcccc    1800
tctgttctgg ctgcccccca agggtgggct tggagttttc cttgagacta aggatgccca    1860
cctcagggcc cagcctcctg ctcattgcta cttctttaac gtctggacta ggagtctcat    1920
tgggctagtt atgcttcaag cttccccct gagaaccctc ctcaggagaa acacactctg    1980
gagagatgcc ctggcttcct gacttcattt ccctgggccc aatgcagtgt gagcagctct    2040
tttccatatc aaaggactca aagagaactg tctgggagag tcttcagcta ctactctaaa    2100
gtaagatgct gtccaaggtg ctgactgcat tgcggacttt gaatgctagg gctggacagg    2160
acccaggaga ccatagtcct aggcgggaac cccaagcccc tggaaccact gaactgaact    2220
gggacgtgtt ttctgaggaa ttcccaggtt catatcatac cggacaccca ccgtggacat    2280
ttctcccacc ctccaggatg ccagagagtg gattctgggc aagcctgtcc ctgccatgta    2340
gacaatgatt aacaaaaagg actttcctgc actgaggacc acaaacacct acagaagtca    2400
gccagaactt cctgatcaac ccctcc                                         2426
```

<210> SEQ ID NO 5
<211> LENGTH: 5149
<212> TYPE: DNA
<213> ORGANISM: Homo sapiens

<400> SEQUENCE: 5

```
agcagcttgc gggacacgga gccgcgagga gacagctgag gcccgcggag accagggggt      60
gaagcctgga gaccctcttg ccctggccta gctgcaggcc cccggatgc tttgggcatg     120 tcctctggag ccccacagaa gagcagccca atggccagtg gagctgagga gaccccaggc    180
ttcctggaca cgctcctgca agacttccca gccctgctga cccagagga ccctctgcca    240 tggaaggccc cagggacggt gctcagccag gaggaggtgg agggcgagct ggctgagctg    300
gccatgggct ttctgggcag caggaaggcc ccgccaccac ttgctgctgc tctgccccac    360
gaagcagttt cacagctgct acagacagac ctttccgaat tcaggaagtt gcccagggag    420
gaagaagaag aggaggagga cgatgacgag gaggaaaagg cccctgtgac cttgctggat    480
gcccaaagcc tggcacagag tttctttaac cgcctttggg aagtcgccgg ccagtggcag    540
aagcaggtgc cattggctgc ccgggcctca cagcggcagt ggctggtctc catccacgcc    600
atccggaaca ctcgccgcaa gatggaggac cggcacgtgt ccctcccttc cttcaaccag    660
ctcttcggct tgtctgaccc tgtgaaccgc gcctactttg ctgtgtttga tggtcacgga    720
ggcgtggatg ctgcgaggta cgccgctgtc cacgtgcaca ccaacgctgc ccgccagcca    780
```

```
gagctgccca cagaccctga gggagccctc agagaagcct tccggcgcac cgaccagatg    840
tttctcagga aagccaagcg agagcggctg cagagcggca ccacaggtgt gtgtgcgctc    900
attgcaggag cgaccctgca cgtcgcctgg ctcggggatt cccaggtcat tttggtacag    960
cagggacagg tggtgaagct gatggagcca cacagaccag aacggcagga tgagaaggcg   1020
cgcattgaag cattgggtgg ctttgtgtct cacatggact gctggagagt caacgggacc   1080
ctggccgtct ccagagccat cggggatgtc ttccagaagc cctacgtgtc tggggaggcc   1140
gatgcagctt cccgggcgct gacgggctcc gaggactacc tgctgcttgc ctgtgatggc   1200
ttctttgacg tcgtacccca ccaggaagtt gttggcctgg tccagagcca cctgaccagg   1260
cagcagggca gcgggctccg tgtcgccgag gagctggtgg ctgcggcccg ggagcgggc    1320
tcccacgaca acatcacggt catggtggtc ttcctcaggg accccaaga gctgctggag    1380
ggcgggaacc agggagaagg ggaccccag gcagaaggga ggaggcagga cttgccctcc    1440
agccttccag aacctgagac ccaggctcca ccaagaagct aggtggtttc caggcccctg   1500
ccctcccctt cctcccatcc ttgtccttct ctccctcaga gcctcagga cccaacaggt    1560
ggcaggcagt ggacagggtg cccgccccac agtgctttcc ccagcacccc agagccagtc   1620
gggacacccc ccgcagcccg tcctggtggc tgtggaactg cactgggtgg cgggcagatg   1680
gtggaaggca gcttaggaga cctcaccaaa gagaagatgg accggctctt gctcccagct   1740
cctattaggc ccggggtggg accagaggtc ataggtgccc aacggcagcc aaaccaaaga   1800
cactggtgtg catggggcag catggttgtg cacgtgggac cctggggcgg acccaggagc   1860
caaactcttg aagcaccccc tgggtcaggc ccagcagcgg agtggccagc cccagtttcc   1920
cattgctcct ctctgcggcc agggccaggt gggttcatat ttacagatat gcccagccag   1980
tcctggtcgg ccacaccagt gtcccaaaga ggagagcgca gcagagccag gggtctgttc   2040
tgtagcagcc accccctgc ccccactcca gggcagccat gatgtgcttg gcccaccag    2100
ggccttccgg gctgctctct tccctgagcc cggaaccggc gacgcacatg tgtcttttgt   2160
tggtgtgttt gttttttcc agggaggtct aattccgaag cagtattcca ggttttctct   2220
ttgttttatc agtgccaaga tgacctgttg tgtcatataa tttaagcaga gcttagcatt   2280
tatttattc tttagaaaac ttaagtattt acttttttaa agctatttt caaggaacct    2340
ttttttgcag tattattgaa tttatttct aaatcaggat tgaaacagga acttttccag    2400
gtggtgttaa taagccattc aagtgcctta cacagctttg aagaaactag gactgcagtg   2460
ggctcggata ggcccattga ggttttttaga aagcaggat ttgttttgtt agggaggcat    2520
gattttggtg agatctttct ggaagagttt tccgcctctt tgtgatgctg aacacccca    2580
aggttctccc ctccccccgc tgcccaggtg actggcagga gctgcgactg ccacgtagtg   2640
gtgcctgggc ccgacagcgg ggctctgggc atcccgggtg accttggccc atctgcctgc   2700
attcccaccc cctgggcct ggctggatcc caggcagagg gaccttgctg ctgtgtgatt    2760
ggaacattcc caaatatctt gtgaatttgt aatcaaattg gtctcattgg gaaagactct   2820
taattaagag gctcaggcaa gcacagaggc agcccgtggg tctctgtctc agtctggagg   2880
cagcagggat gctgctggga gtccatggca caggccacag cccctcacct tgccgcggtg   2940
gctggcagca cgcctgcctt gctctgcccc atgccctgaa caggcatgag agctccacgt   3000
cccctagtgc accctgagag ggggctcaca agtgaccgat cctgggtgcc tcagggagct   3060
cactgagggc gtgcaaagtt gaaagtggca aggctggggg agggtgtcgg gtagagggaa   3120
```

```
gagggcaggg ggctagggga ggactcagag gccatctgca gggccaagcc acaggaaggg    3180
ctgagctgga ggtgggcagg gctgctccag gcaggtcaga gcagtgcagg gggaggagag    3240
gagaaaggga ggaagctggg ctgtgtggtc cccatgaagg cattcagagt ccacctgcag    3300
acagcgagag ccccaggaag gtttgcacag ctgtgcccca agcaccttgg cctcctctca    3360
gctcgccgag gaggcacgct agagccgcct tcccgtgggg agccctctgt cccacaggga    3420
gcggggagcc agctttgctg gggccctacc tgcatgccca gccttacccc tcattctcac    3480
agcacagatg aggttgagac catgcagtca atgcattgct taaggtctct tatttacaaa    3540
aaaaaacctt aaacatagtc gctgtcattc agacattcag agaatggttg cccacaaaca    3600
atgaccaagt attgcttggc ttaacttgaa ggcctgctgt ctccttctgg gggtcaggga    3660
cgcagctcca ccctcaccac tagcccaccc tgcccgtggg cataaccttg acgaagagag    3720
agaatgattg gcatctgctt ttctcttttc tttgctaata attctgttcc tggctgccga    3780
gagtgaagtt tcaccatgtg gaggtttggc tcctatcacc tggtggtctg attcataccc    3840
tagcctgagg ctccactgga agatctcgca gcctcagtgt atgggaaacc ctttccccag    3900
gcttgtccca gcactgccgc tccccacccc tgagccagga ccccagagga tggccatgcc    3960
ccgtgcctgg cagaggtctg gtgccagcac tgggagctgc tccgcccttg ccttggggcc    4020
gagggagccc tcgtccaccc ctgcacagca gctgggcaca gaggagcgct cttccatctt    4080
gaccaggact gcaccaagaa gcaccaggtg tcttcagcct ccaacctccg gggcgacctt    4140
ctcttccagc cacagtccca tgagggcccc tagccaggga cactggtctg taaattgtaa    4200
tccttctcc agcccagctc tccacttgtt ccttgtgtga gctgagcagg cagtgcacct    4260
ctgagtgtcc cttttgtaag gcccaggggt tgcactgagt ctgcagaggc cgcgacctcc    4320
tagaacgctg tgggtgcagg tgagccggcg tgtcctgggg agatgctgcc agcacacagg    4380
ggccctcctg ctgccagcag gttggggtgg ttaagtctta ttagtgtcta ttcttaaaat    4440
taagtgggct ggagaagaat ggagctccac atgccagcac cgtatatgga atacaaaagc    4500
tggggaagca gggcctgcct tacaggtgtg gctgactctg agcccaggcc tgcaggggtg    4560
gagggcagtc cctcagaatc ccagaggcag tcccagcctc agaacccagg ataggaaatg    4620
ggtgtgttta gtggggaaag ggacggggtg cagacggcag ggccagtatg gggcccctc    4680
cctctcctct cctctcctat ggtgagccca gcgtgggcac cgggccgtct cagccgtgtt    4740
cccagggctg ggaggacagc tctggcccctt cttaggccta gcctcgtccc aagctaaatg    4800
taagccagtt gggctgtgtt aaaggaagca gtgttttttgg ttcgattctg cctctgtagc    4860
tcaagggggg cagcccccag agtcctgtgc attctgccaa ggctccatag ctttgccaaa    4920
tgcacggagc tctgccattc cggtgcagtg caggccttgc gaagggttta tctgcgttcg    4980
tctcggtggg cttctcctgc atgggagttg tgttcctgtg caaggggggag ctttgctcca    5040
ggacaggatg actgtcttcc ctattcttag ggacaagtcc caagatgcca gaaaggcagt    5100
ctcccaagga cccaccatgc agaagtgtca ataaaccaca agttctgaa                 5149

<210> SEQ ID NO 6
<211> LENGTH: 4689
<212> TYPE: DNA
<213> ORGANISM: Equus caballus

<400> SEQUENCE: 6
cggccaggga cgggaagtgg gcggggccgg ccagagcagc gagctgggcg cggagccgcc      60
gagtggcagg gtgaagacta actggaaccc tggcggcagg cccccgggga tgctctgggc    120
```

```
atggcctctg gagccctaca ggagagcagc cagatggcag aggagacact gggcttcctg        180
gacatgctcc tctgcgactt tccagcccca ctgagcccag acagccctct gccgtggaag        240
gtgccaggga cagtgctgag gcaggaggag gtggaaggcg agctggccga gctggcgatg        300
ggtttcctgg gcagcaggaa tgctccgcca ccacttgctt cgtgtctggc ccatgaggca        360
gtttccaagc tgctgcaggc ggaccttttc c gaattcagga agaagcccag gcaggaggag       420
gatgacgacg cagaagagga gaaggcccct gtgaccttgc tggatgctga gggcctggtg        480
aggactttct ttaaccagct ctgggaagta tgcagccggt ggcagaagca ggtgccctcg        540
actgcccagg ctccgcagag gcagtggctg gtctccatcc acgccatccg gaacactcgc        600
cgcaagatgg aggaccggca cgtgtgcctt tcggccttca accagctctt cggcctgtcc        660
gaccccgtgg accgcgccta ctttgccgtg tttgacggtc acggcggggt ggacgctgcg        720
aggtacgctg ctgcacacgt gcatgcccat gctgcccgcc ggccggagct acctacagac        780
cctgcagggg ccctcaggga agccttccgg cgcaccgacg agatgtttct gtggaaagcc        840
aagcgagagc ggctgcagag cggcaccacc ggcgtgtgcg cgctcatcgc gggaaagacc        900
ctgcacgtcg cctggctcgg agactctcag gtcatcctgg tgcagcaggg acaggtggtg        960
aagctgatgg agccgcacag acccgagcga caggacgagc gggagcgcat cgaggcgctg       1020
ggtggcttcg tgtctcacat ggactgctgg agagtcaacg ggaccctggc tgtctccaga       1080
gccatcgggg atgtcttcca gaagccctac gtgtctgggg aggcggatgc agcctcccag       1140
gagctgacgg gctccgagga ctacctgctg ctcgcctgcg acggcttttt cgacgttgtc       1200
ccccaccatg aggttgctgg cctcgtgcag agccacctgg tcaggcagca gggcagtggg       1260
ctacacgtcg ccgaggagct ggtggctgca gcccgggagc ggggctccca cgacaacatc       1320
acagtcatgg tggtcttcct cagggacccc cgagccctgc tggagggcgg ggcccagggg       1380 gcagggg act tgccctctgg cctctcagag ccagagacca acacaccacc gagaagctag       1440
gaggtcccag cccctggccc cacccctgtga ccctccgtca gatgccttag gacctgatgg       1500
ctagcagtgc agtggcacc gcccgcgcag tgctttgccc agcccccgag ccctcgtgt        1560 tgcttgcatt ggcccatccc ggggatggg atctgcactg ggtggtgagt gtcgcgccct       1620
gctggtggta ggcagtggga cggcaggatc tccaagggag cctaggaaga gacctcacca       1680
cggagccaag gccaggaggt gggccggccc ttgctcccgg tcaggcaggg gctggaccag       1740
aggccacagg cgccaggcga gcactcaggg cagcaggaca cagcatgggg ggccatcggg       1800
cagacctggg agccacggac attttcaaga gcgtcctggg tgcccggcac aggtttctca       1860
ctggctccac gctgcccaca gccgcgaggg ctcagatccg cagatgcgcc tggcgggtcc       1920
ctgctggcca gccggcttc cccaccagga aaaagggag caccaggcat ctggtctgct        1980
gcatcgccca ccactggtga cacgcctgcc ctggcctccc tggtccccca tccctggagc       2040
gcccggggag gggggtctca gaatgaccat gcgcgccttt catttgcggt cttttgtcag       2100
ggagcagtca gattcagaag cagtatttca gggctgtctt tttcgtcagt gccaaggtac       2160
ctgatgtgtc atgtaactta gacagggctt agtgtttggt ttatccctta ggaaactaag       2220
tattgatttt tttttttttt aggggaaacg tcttttgcag tattactgaa ttttttttcc       2280
cctaaatcag gactgagaca aaatttttcc aggtggtgtt aataagccat tcagtgcctt       2340
aaacagccta aggtgaggct ggaagtgccg ggctctgac ggattccgcc aagcatgttg        2400
cagttcttac aaaggattta ttttgtcaga gtggcatgat tcgggctaga gttcttcctg       2460
```

```
gaagagttct gtctttgtga cgtgccactg actcccgtgt ggagttgaaa ggggcagggc    2520
tgggcgaggg ctcccccgcag aggccagggc cactggagag aggagcctgg gggcccgact   2580
cgcggtggtg ggcagggctg tgcaggcaga gaccagcaca tctgggaagg gcagtgggtg    2640
gctttggctt agctgaggct tcaggagaat gtcacgggt ggggggggc agggggaagt     2700 gggaggaagc ttggcgtcag gtcgccaagg ccatgaggtc ctgtggttca gagtcccccc    2760
actgtagtgg ggccccaggg agcaatccca gctgcactga ggggaacctc ggcccttctc    2820
acccagggaa ggggtggatg gtgagagccg cccctgctga ggccagtcca ccatccagca    2880
agaaaggagg agcttgcagc ctcagggctc accccactc ccacggcagg gaagcagcag    2940
ctgagacgga cggtcagtgc cttgctccag ggctcgtgac agaaagcatc tcagacatgg    3000
tcactgcaac tcagagaggg tttggtggcc aacatgacca ggtattgctc catttaactt    3060
gaaggcccct ctgccttctg ggggcccgaa gcctcctcgt gagcccctcc cagcaccagg    3120
ctggcacgag gggggatgtg gccccaccct tcactaccag cccagccacc catgggcatg    3180
accttaatgg aaggaggggt caatggtttc tttgcgagtc tcactcggtt gacagctacc    3240
aagagtggag cttcacccca tggagtctgg gtcatgttca tgctccggcc caaggcccaa    3300
agcacaggag atctctccat gcttgtccca gtgtctcccc cacccctgagc caggctgagt   3360 caaaggctcc cgccccccac ccaccaggct gcctggcaga ggccttggct gtctggtgca    3420
gcctgggagc tgctggtcct tgccttgaga ccaagggagt ccccgctctc ccgctgcccc    3480
gggcctgacc tggtgcgtgc acccaggcac ggaggaggtc tcttccatct tgacagagcc    3540
cctgggcacc ttcaccctct gcgagtcctg gcccacttcc tctccaggcc acaggcactg    3600
ctctgtaagc cttgatccct ttctcaagtc ctagctttgc cactagctca ttttggggc     3660 tgagcaagcc gttgccctc cctgggcctc agtttcccct tttagggcac agggttgcac     3720
tgagtctgtg cagcagctcc tggaacttgg gaggtgcagg ggctgcttgc ggtgagcctg    3780
gtgcagcagg ggagctactg ccggtgctga ggccccgccc accgccagca gggaggggtg    3840
attaagtact attggtgtct attcttaaat ttaagtgggt tggaaaagaa tcgctgcaga    3900
tgccagcacc tcacgtgggt gcaaaagctg gagagccggc cctgccttca caggtagggc    3960
tgatgctgag cagcggggt ggcagaagcg taggctccct cctcaggcgt gggggggcctg    4020 ggaggggcag ggcgccgccg ggcccccagg ggcttctagt caagctccca acctgctgac    4080
accctggagg caaacgcgtg gcctccctga cccagactgt ccttggagtc caggactagg    4140
aaatggatgt gttatggggg gagagtgaca ggcgggcccc acgggagaag cacaggctct    4200
ctgaggtccg cggtcatttc tgacgacccc tgcccttggc cgcagtcctg cctccccgcc    4260
ctccctgggc cggcacgcgg ccccccggcct cgcccccttcc cctgcgtccc ggctacctca   4320
gcagtattcc cagggctggg gggcagctct ggctgttcct ggacctggcc cccacccgag    4380
ctaaacggaa accgggtggg cctgtgcaaa ataagctgtt ttggtttgat tttggctgta    4440
gcccaagggg gcagccccag gaggcctgcg ctttagcttt gccaaacgtg ccacgccggc    4500
ctcgccaagg gtttatccgc acatctcagt gggttcctgg gagtggtgca aggggggtct    4560
tgttctgaga caggatggcg gtccccctgt ccacagggac aagtcctagc gtgaggggc     4620 cagaagggca gtctcctccc agggccactg tgctcaagtg tcaataaacc acaagttgtg    4680
aaaccctgt                                                            4689

<210> SEQ ID NO 7
<211> LENGTH: 5208
```

<212> TYPE: DNA
<213> ORGANISM: Canis lupus

<400> SEQUENCE: 7

```
ggggcgggga ggcccggggc gcggggccgg tggcctctct gaggcgtgca gcgagtgaat      60
accacctgga atcccaacag agaccccegg catgctctgg gcatggcctc tggagcccca     120
ccgcagagca gccacacggc agaggagatc ccaggcttcc tggacgcctt cctctgcgac     180
tttccagccc cgctgagcct ggagccccct ttgccatgga agctcccggg acctgtgctg     240
agccaggagg aggtggaagg cgagctgacc gagctggcga tgggcttcct gagcaacagg     300
agcgctccac ctccacttgc tgcatctctg gcccatgagg cagtttccca gctgctacag     360
accgaccttt ctgaattcag gaagttgccc aggcaggagg aggaagaaga tgacgatgag     420
gaagagaagg cccctgtgac cttgctggat gccaagggcc tggcacgaag ctgctttaac     480
cagctctggg aagtatgcag ccagtggcag aagcaggtgc cctcaactgc ccaggttcct     540
cagcggcagt ggctggtctc catgcatgcc atccggaata cacgccgcaa gatggaggac     600
cggcatgtgt gccttcccgc cttcaatcag ctcttcggcc tgtcggaccc cgtggaccga     660
gcctactttg ccgtgttcga tggtcacgga ggggtggacg ctgcacagta cgccgccgtg     720
cacgtgcaca ccaatctggc ccgccagccg gagctgctca cggaccccgc gggagccctc     780
agagaagcct tccggcacac cgatgagatg tttctctgga aagccaagcg agagcggctg     840
cagagcggca ctacaggggt gtgcgcactc atcgtgggaa agaccctgca catcgcctgg     900
cttggggact cccaggtcat cctggtgcag cagggacagg tggtgaagct gatggagcct     960
cacaggcctg agcgacagga tgagaaggag cgcattgagg cgctgggcgg cttcgtgtcc    1020
cacatggact gctggagagt caacgggacc ctggccgtgt ccagagccat cggggacgtg    1080
ttccagaagc cctacgtgtc aggggaggcg gactcggcct ctcgggagct gacgggctcc    1140
gaggactacc tgctgctggc ctgcgacggc ttcttcgacg tcgtccccca ccaggaggtc    1200
gcgggcctcg tccacagcca cctggcccgg cagcagggca gcgggctgca ggttgccgag    1260
gagctggtgg ccgcggcccg ggagcgggc tcccacgaca acatcacggt catggtggtc    1320
ttcctcaggg acccccgaga cctactgaag gcgggccc aggggacagg ggatgtgccc    1380
tctggcctct cacagccaga gaccagcact ccgcagagca gctaggaggt gtaggccccc    1440
tgcccccacc cgcacccctc ccctcagatg ccttaggacc cgacaggcgg tggcgggcag    1500
gcgggtgcca tcctcagtgc ttccccaggg ccccgaaccc cctgctcgca tcagtccatc    1560
ctggtgtctg gggaactgca ctgggtggtg gtgttattca tgccccgctc gggcaggcag    1620
tggggtggcc tggatcccca aaggaggcct agggaagaga cctcaccaaa gagaagatga    1680
cccaagaagt ggagcagctc ttgctcccag cccactggg taggggcagg gccagaggcc    1740
acaggcgcgg gccacagcca gaccaaagac actgggcctg tgcccggggc agcaggatgc    1800
tgcacgtgag tccccgggca gacccaggag cgacggacat ttccaagcgt gtcctgggcg    1860
cctggctcag gcttctcgtt tgctcctcac tggccacggc tgggaggccc cagtctctac    1920
agatgggcct ggctgggcct ggcctgccaa gctggcttcc cgagtgggga gagcggcccc    1980
tggggaggga ggcgcaccag ggatctggtc tgcagtgggt gctcacggcc cccagcctcc    2040
ctgccccct gcccccccat cccgcgcaca cccaggagg gggaggtcag aacgatgaca    2100
cgtgtgtctt tttatttgtg ggcttttttcc ccccagggga agtctaactc agaagcagta    2160
tttcaggttt ttgcctttgt tttgtcagtg ccaagttgac ctgttgtgtc atataactta    2220
```

-continued

```
agcagagctt agcatttatt ttattcttag aaaacttaag tattgatttt tttttttttt    2280
gaagaaactt cttttgcagt attactgaat ttttttttcc taaatcagga ttgaaacaaa    2340
cacttttcca ggtggtgtta ataagccatt caagtgcctt aaacagcttt aggtaaggct    2400
agacccgccg ggcctgggac ggattctaat aggcatgctt cagttttttta caaaagcagg    2460 atttattttg ttctagtggc atgattttgg ctagaattct tcccggacga gttctttcca    2520
cttgtcatga ttccattcgc tgctggaagt tagcaaagca gcccctaaga gcgtaggctg    2580
tgctgtgcta cctgggccag accacgggcc tccggagctc ccgggtgacc atggccccgc    2640
cagcctccct ccacaccttg gccttgctgc tcatgtctca tgtctcatgt ctctggttgg    2700
tgcccaggct gagggactga gctccttgaa gcgggttcct cgtttgactg aatgttcta    2760 gaatgtcttg tgttagtaat cgagtcggtt tcattgggaa acacgctgaa gaggccttgg    2820
caagtccgaa gcaggctggg gggctttggc ttggtttgga gcctgtcccg ctcacctgcc    2880
ccacagcccc caaaaccctc ctgtctcccg ctcgccatgg ctgtcaccct ctgccacctg    2940
gctctgccca cagcctaact gcctcaggga gggctccaca ttccctagca tgctctgggc    3000
aggtgaggct tgggagccac gaaacccag gtgcctggct gctcacatcc agtgaggcgg    3060
atatggcatg tgtgtcaagt tggaagtggc aggttaggtg gagtccaggc agaagtcaag    3120
ggccatgaga gagggatctc tggtgggagg acccaggcct acaggcctgg gaagagcatt    3180
aggtagctga gctgaggctt ctagagaatg tcgctgggag atgggcagca ggaggagct    3240 tggcaccagc ccccaggcca ggaggtccgc agagtccacc cgcagtagcc aggccccagc    3300
aaagagagcg cagggaggac cctgatcgcg tgcacagagg gagccctgct gacgaggaag    3360
cgggcagttg ggagcctcgg gggccctcag cccaggaag ggcagtgggt gagatgcccc    3420
cctccaggcc ccagacaagc ggaccctgac acaggaaggg agggagccag ctcgggcagg    3480
cagtggggca gtgaggtgcc acccgcaggc tcggcgctta cccctcactc ccacagcagg    3540
gatagagctg ctcggatgat ggggtcagtg ccgtggaaat gatgggaagt accttaaaca    3600
ccacaattcc aagaaggttt ggtaggagcc aacagtgacc ttgtgttgcc ccacttaacc    3660
ggaaggccct gctgctctcc gggggtccaa agcccttctt cggcccttcc cggcccaggg    3720
ccggcaggag gtggcacgtg gccctgccct tcaccaccag cctggctgct cctgggcatg    3780
atcttagcag atggaggaag cacgagcttc tgttttttctc atttctttgc taatcttatt    3840
ccgtgattgc catcaggagt gcggcttcac ccgtggggcc cggatccccc acgtgatggt    3900
ctgactcctg cccgggctcg aggctctccc aggagatctc tccaggcttg tccagtgcc    3960 caccccgcct ctggcagagg cctctgctgt ctggtgctgc ccatccttgc cttgggctg    4020 agggcgccct tgttcatgct gcacagacgc tggctttgtg caagcaccta ggcacagagg    4080
cctcttccct cttgaccagg ggctggtcag ccttgaaagt cctggccccc cttctcttca    4140
ggccacagtc cgaggagggc ccctagccgg gccccccttc caaccctcg ccttgccact    4200 agctcattgt gtgagctgag caagtcctgg agccttcctg ggcctcagtt tctcctttag    4260
agggtacagg gttgcactgg atttgtgtgg cagatcctgg aattctggag gttcaggggc    4320
cagcctggtg catcctgggg agccgcggcc agtgccgcgg gagcccgccc cccccccgc    4380 cccgaccgcc agcaggagg ggtgatgaag tattattagt gtctattctt gcagctaagt    4440
gggttggaag agaaaggagc cgcagacgct ggcgccgtat gtggatcaca agctggggcc    4500
caggtggagc tgagcccagg cagcggcagg ggggcagcag gtgccaggcc cggggacaag    4560
gcagggctcg gccgcgccct ccgcgcccag tcgtgctgcc agcctgctgc cgtgcgggc    4620
```

```
cgggtgcgcg gcctccccga cctcgcttgt cctcgcgccc aggactagga aaggggtgcg    4680 ctgcagggggg gacggtggcg ggcccaggcc ccctggaga ggcccggagc cagccttggg    4740
ccgcagcccc gtgtcccgcc ccctccctc gtgggtgccc cggctacctc agcagtattc    4800
cagggctcgg gcgcggcccg ggcgggtcta ggcctggccc tgacggggggc tgcaccgaag    4860 cccaatgggc ccgtgcaaaa taagctggtt tgggtttgct tctgcctgta gcccacggga    4920
ggcagcccca ggaggcccgc gcttctcgtc gaggctccac agctttgcca aatgcgccga    4980
gctttgccat tcagtgcgcc gtgccagcct tgccaagggt tcatctctgc acgtctcagc    5040
agggctcctg ggagaggtgt tctctgcaag gggcgtcttg ttccaagacg ggatggccat    5100
tgcccttgtc tgcagggcca agtcccagga tgtgggggca gaaactcagt ctcctcccag    5160
gggtcactgt gctcaagtgt caataaaacca cgagttttga aaccctga                5208
```

<210> SEQ ID NO 8
<211> LENGTH: 5313
<212> TYPE: DNA
<213> ORGANISM: Felis catus

<400> SEQUENCE: 8

```
gcccgccgtc cgactgcgcc tgcgcggagc ccgcggcggc gggggacggg aagtgggcgg      60
ggtcggccag gagcggctcg cggggtccgg agtggcggag tagcagagtg aagatcacct     120
ggaaccccgg cagagccccc ccgggatgct gtggacatgg cctctggaga cccacagcag     180
agcagccaaa tggcagagga gatcccgggc ttcctggatg ccttcctcca tgacttccca     240
gccccactga gcccagagag ccctttgcca tggaaggtcc caggaacagt gctgagtcag     300
gaggaggtgg agggtgagct ggccgagctg gcgatgggct tcctgagcag caggaatgct     360 ccccccaccac ttgcttcatg tctggcccac gaagcggttt cccagctgct gcagatggac     420
ctttctgaat tcaggaaatt gcccagacag gaggaggagg aggaggagga ggaggaagat     480
gacaacgagg aagagaaggc ccctgtgacc ctgctggatg ccaagggcct ggcgcgaagt     540
ttctttaacc agctctggga agtatgcagc cagtggcaga agcaggtgcc ctcgagtgcc     600
cgggttcctc agcggcagtg gctggtctcc atccatgcca tccggaatac tcgccgcaaa     660
atggaggacc ggcacgtgtg ccttcctgcc ttcaaccagc tctttggcct gtctgacccc     720
gtggaccgag cctactttgc tgtgtttgat ggccatgaag gggtggacgc tgcaaggtat     780
gctgctgtac atgtgcacgc caacgtggcc caccggccgg agctgcccac agaccccgcg     840
ggagccctca gagaagcctt ccggcacaca gatgagatgt tcctctggaa agccaagcga     900
gagcggctgc agagtggcac cacgggtgtg tgcgctttca ttgcgggaaa gaccctgcat     960
gttgcctggc tcgggactc ccaggtcatc tggtgcaac agggacaggt ggtgaagctg    1020
atggagccgc acagacctga gcgacaggat gagaaggagc gtattgaagc gctgggcggc    1080
tttgtgtctc acatggactg ctggagagtc aacgggaccc tggctgtgtc tagagccatt    1140
ggggatgtct ttcagaagcc ctacgtgtca ggagaggccg actcagcctc ccgggagctg    1200
acaggctctg aggactacct gctgctggcc tgtgatggct tcttcgatgt cgtccccac    1260 caggaggtcg cggcctcgt ccagagccac ttggtcaggg agcagggcag cgggctgcag    1320
gttgctgagg agctggtggc tgcagcccgg gagcgggggct cccacgataa catcacagtc    1380
atggtggtct tcctcaggga cccccaagac ctgctgaagg gcagggccca gggggtagga    1440
gacgtgccca ctggcctcgc agagccaggg accaatgctc cacagagacg ctaggaggtg    1500
```

```
caggctccct gcccctaccc cgtaaccctc ccctcagat gccttaggac ccgacaggtg      1560
atggtggaca gtgggtgcca ccctcacagt gctttcccag ggccccaagt ctcccgtgct      1620
gcttgcattg gcccatcctg gtggctgtgg aactggactg ggtcgtgggg gatgtgccct      1680
gctcggacag gcagtgggat ggccttgttc tttgaaggag gcctagggaa gagacctcac      1740
caaagaaaag acgacccaag aagtggagca gctcttgctc ccagccccat caggtagggg      1800
gctcaggtgg ggaccacagc cagaccaaag atgctgggca tgtgcatggg gcagcaggat      1860
gctgcatgag cccccaggca gacccaggag ccacggacat ttccaagtgc aacctgggtg      1920
tccagcacag gtttctcact tgctcctcac tggccgccac tgggaggctc gtctccgctg      1980
acgcacctgg cctcccgagc cagcttccca aattggggag aacagagcac cagggacctg      2040
gtctgcagtg aatgctcaca gcccccagcc tccctggttc cctcccgtcc cgcacacacc      2100
cagtgagagg aaggtcagaa tgacaacgag gtgtgtgtct tcagtttgtg gtctttttt       2160 ttttttttcca ggacagtcga actcagaagc agtatttcag gtttttgtct ttgttttgtc      2220
agtgccaagg tgacctgttg tgtcatgtaa cttaagcaga gcttagcatt tattttattc      2280
ttggaaacct taagtattga tttttttttt ttggaagaaa cttcttttgc agtattactg      2340
aatttttttc ctaaatcagg attgaagcaa acacttttcc aggtggtgtt aataagccat      2400
tcaagtgcct taaacagctt taggtgaggc tagaaccgcc gggcctggga tggattctac      2460
taggcatgtt taagttttta caagagcagg atttatttg ttatagtggc atgatttcag       2520
ctagaattct tcccactcca cttcctttct gcccctttgt gatgcgattt gctgctgaca      2580
gtcagcaaag cagctgaaag agcatgagct atgctgcaca gcctgggcca gacctagggg     2640
ctctgggagt tcagggtgac catggcacct cccccagcct ccctatgcac ctcagtcctg      2700
ctgcccatgt ctctggctgg tccccaggct gaggaactga gctccatgag caggcttctc      2760
atttgactgg aatgtcctag aacgtctcgt gttggtaatc gaattggttt ccttgggaaa      2820
cacacttacg aggccttggc aagtctggag gcagcctggg gggttctggc tctgtttgga     2880
gtctgtccat ccacctgccc cacagctccc caaacccctc ctcctgtttc ttgcccacca     2940
tggcggcacc ctctgttacc ttgctttgcc cacagcctga ccacctgggg gagagctcta     3000
cgttccctag catgccctgg gcaggtgagg ctcagaagcc acgaagcttg ggtgactcag     3060
gctactcaca tccagtgagg cagatatagc atgtgtgttg agctagaagt ggcagggctg      3120
ggtgaagagt ctggcagaga ggggtctctg tgggaggacc caggcctaca ggtctgggaa     3180
gagcggtggg tggctttgga ggctcgtgga gaatgtcact gggaggtggg cagcaggagg     3240
aagcttggca ctgtgtcccc caggccagaa tccacctgca gtagcaaggc tccaggaagg     3300
tgggagctgg gagagccttg gcggcactca tcagcccggg gaagggcaga cttggtaaga     3360 gccacccac tgaggcccga gggctgtgca gcagggaggg tgggagccag ctctgggcag      3420 gcagggggc aatgggggat gccgcccaca ggctcagcac tcaccctac tctcaccgca       3480 gggatgaaga agccaagatg atgtggtcag tgccatgctc aagggctcgt gacagaaaaa     3540
gtatcttaaa tgtggtcacc gcagttcaga gaaggtttgg tgggagccaa caatgacctg     3600
gtattgccgc acttaatctg aaggccctgc tgccttctgg gggccagaag ccccctcttt     3660
ggcccttccc agcgcagggc cggcaagagg tggcatgtgg cccctaccag cctggctgcc     3720
cctgagcatg accttaacag aggaaagagg tgtgggcttg tttttctcat ttctttgcta      3780
atcttattct gggattgcca tcaagagtgg ggtttcacct ttggagtctg gactccccac      3840
gtggtggtct gattcctgcc cagactcaag gctccaccag gagatctctc caggcttgtc     3900
```

```
ccagtgccca cccctctcgt ctgtgagagg cccttgccat ctggtgctgc tcagccttgc    3960
cttgaggcgg agggagccct tgttcccact gcgcagatgc tggctttgtg caagcaccta    4020
ggcatagagg tctcttccct cttgaccagg gaggactggg agccactggg catcttcagc    4080
ctctgaaagt cctagcccac ctccttgtca ggccacagtc ccaagaaggc ctctagccag    4140
gaccccaact ctagaagcct cagtcccctt ctcaaatccc cactttgcca ctagctcatt    4200
atatgagctg agcaagtcgt tgaacctcct tgggcccccc tttctccttt ataggacaca    4260
gggttgcacg gaatctgtgc agcagatctt ggaattttgg aggttcgggg cccatcgagg    4320
gcaagcctgg cacatcctgg agagctgcta ccagtgctaa gggaaccctc cccctctgct    4380
agtgggaggg gtggttaagt atcattagtg tctattctta caattaagtg ggttggaaag    4440
gaatggagct acagttgcta gccgtatatg gaacacagaa gctggagaga gggagccctg    4500
cttttacagg tagagctgat cccaagccag caggaggagg agaggcagac agactcagct    4560
gcctccctct gcaggtgtga ggctgaaggg cagggcacag ccagcgtctc ccttgccttt    4620
tagtcaagct cccaacctgc tgaaatccag aggcagatgc atggcctccc tgacccagct    4680
tgtcctcagc atccaggact aggaaagggg tgtgctttac tggggacagt gatggggca    4740 ggcctcactg gggaagcaca ggccctctga ggtcctgagc cagccttttgg ccacagtcct    4800 atctccccct acccttttgaa accagcatgt ggccctcgtc cctacccta taatgccagt    4860 tctgagttcc ggcttgggtg tctggccact tcagcagtag tcccagggct tgggtcacag    4920
ctctggcagt tcctaggcct ggccccgaca agagccaaat gggcaccta agggcctgtg    4980 caaaataagc tgtttttggt ttaattctgc ctgtagccca aggaggcag ccccaggagg    5040 cccacgcttt tcgccgaggc tccacagctt tgccaaatgc gccgagcttt gccattcaca    5100
tgccatgcca gccttgccaa gggtttattt gtgcacgtct cagcagggct cctgggagag    5160
gtgttctctg caaggtgcat cttgttccaa gatgggacta ctatttcccc tgtgtgcagg    5220
ggcaagtccc aggagaagag ggccagaaac acagtctctt cccaggggtc actgtgctca    5280
agtgtcaata aaccacgagt tttgaaaccc tgt                                5313
```

<210> SEQ ID NO 9
<211> LENGTH: 25
<212> TYPE: DNA
<213> ORGANISM: Artificial Sequence
<220> FEATURE:
<223> OTHER INFORMATION: siRNA 1

<400> SEQUENCE: 9
ccggugaugu agacaauaau uaaca                                          25

<210> SEQ ID NO 10
<211> LENGTH: 23
<212> TYPE: DNA
<213> ORGANISM: Artificial Sequence
<220> FEATURE:
<223> OTHER INFORMATION: siRNA 2

<400> SEQUENCE: 10
gcaagagagg aagguauuca gga                                            23

<210> SEQ ID NO 11
<211> LENGTH: 26
<212> TYPE: DNA
<213> ORGANISM: Artificial Sequence
<220> FEATURE:

<223> OTHER INFORMATION: siRNA 3

<400> SEQUENCE: 11
gccuuaauuc cuugcaauag ucuctc                                            26

<210> SEQ ID NO 12
<211> LENGTH: 25
<212> TYPE: DNA
<213> ORGANISM: Artificial Sequence
<220> FEATURE:
<223> OTHER INFORMATION: siRNA 4

<400> SEQUENCE: 12
guugagacca ugcagucaau gcatt                                             25

<210> SEQ ID NO 13
<211> LENGTH: 25
<212> TYPE: DNA
<213> ORGANISM: Artificial Sequence
<220> FEATURE:
<223> OTHER INFORMATION: siRNA 5

<400> SEQUENCE: 13
agaccuuucc gaauucagga agutg                                             25

<210> SEQ ID NO 14
<211> LENGTH: 25
<212> TYPE: DNA
<213> ORGANISM: Artificial Sequence
<220> FEATURE:
<223> OTHER INFORMATION: siRNA 6

<400> SEQUENCE: 14
caccaagaag cuaggugguu uccag                                             25

<210> SEQ ID NO 15
<211> LENGTH: 22
<212> TYPE: RNA
<213> ORGANISM: Homo sapiens

<400> SEQUENCE: 15
gcugggauua caggcaugag cc                                                22

<210> SEQ ID NO 16
<211> LENGTH: 99
<212> TYPE: RNA
<213> ORGANISM: Homo sapiens

<400> SEQUENCE: 16
cgcccaccuc agccucccaa aaugcuggga uuacaggcau gagccacugc ggucgaccau        60
gaccuggaca uguuugugcc caguacuguc aguuugcag                              99

<210> SEQ ID NO 17
<211> LENGTH: 22
<212> TYPE: RNA
<213> ORGANISM: Homo sapiens

<400> SEQUENCE: 17
uuuagagacg gggucuugcu cu                                                22

<210> SEQ ID NO 18
<211> LENGTH: 86
<212> TYPE: RNA
<213> ORGANISM: Homo sapiens

<400> SEQUENCE: 18

| ggcugggcaa cauagcgaga ccucaacucu acaauuuuuu uuuuuuaaa uuuuagagac | 60 |
| gggucuugc ucuguugcca ggcuuu | 86 |

<210> SEQ ID NO 19
<211> LENGTH: 17
<212> TYPE: RNA
<213> ORGANISM: Homo sapiens

<400> SEQUENCE: 19

| cuccgggacg gcugggc | 17 |

<210> SEQ ID NO 20
<211> LENGTH: 89
<212> TYPE: RNA
<213> ORGANISM: Homo sapiens

<400> SEQUENCE: 20

| accuccggga cggcugggcg ccggcggccg ggagauccgc gcuuccugaa ucccggccgg | 60 |
| cccgcccggc gcccguccgc ccgcggguc | 89 |

<210> SEQ ID NO 21
<211> LENGTH: 3818
<212> TYPE: DNA
<213> ORGANISM: Homo sapiens

<400> SEQUENCE: 21

| ctccccggta aagtctcgcg gtgctgccgg gctcagcccc gtctcctcct cttgctccct | 60 |
| cggccgggcg gcggtgactg tgcaccgacg tcggcgcggg ctgcaccgcc gcgtccgccc | 120 |
| gcccgccagc atggccacca ccgccacctg cacccgtttc accgacgact accagctctt | 180 |
| cgaggagctt ggcaagggtg cttttctctgt ggtccgcagg tgtgtgaaga aaacctccac | 240 |
| gcaggagtac gcagcaaaaa tcatcaatac caagaagttg tctgcccggg atcaccagaa | 300 |
| actagaacgt gaggctcgga tatgtcgact tctgaaacat ccaaacatcg tgcgcctcca | 360 |
| tgacagtatt tctgaagaag ggtttcacta cctcgtgttt gaccttgtta ccggcgggga | 420 |
| gctgtttgaa gacattgtgg ccagagagta ctacagtgaa gcagatgcca gccactgtat | 480 |
| acatcagatt ctggagagtg ttaaccacat ccaccagcat gacatcgtcc acagggacct | 540 |
| gaagcctgag aacctgctgc tggcgagtaa atgcaagggt gccgccgtca agctggctga | 600 |
| ttttggccta gccatcgaag tacagggaga gcagcaggct tggtttggtt ttgctggcac | 660 |
| cccaggttac ttgtcccctg aggtcttgag gaaagatccc tatggaaaac ctgtggatat | 720 |
| ctgggcctgc ggggtcatcc tgtatatcct cctggtgggc tatcctccct ctgggatga | 780 |
| ggatcagcac aagctgtatc agcagatcaa ggctggagcc tatgatttcc catcaccaga | 840 |
| atgggacacg gtaactcctg aagccaagaa cttgatcaac cagatgctga ccataaaccc | 900 |
| agcaaagcgc atcacggctg accaggctct caagcacccg tgggtctgtc aacgatccac | 960 |
| ggtggcatcc atgatgcatc gtcaggagac tgtggagtgt ttgcgcaagt tcaatgcccg | 1020 |
| gagaaaactg aagggtgcca tcctcacgac catgcttgtc tccaggaact tctcagctgc | 1080 |
| caaaagccta ttgaacaaga agtcggatgg cggtgtcaag ccacagagca acaacaaaaa | 1140 |
| cagtctcgta agcccagccc aagagcccgc gccttgcag acggccatgg agccacaaac | 1200 |
| cactgtggta cacaacgcta cagatgggat caagggctcc acagagagct gcaacaccac | 1260 |

```
cacagaagat gaggacctca aagctgcccc gctccgcact gggaatggca gctcggtgcc    1320
tgaaggacgg agctcccggg acagaacagc cccctctgca ggcatgcagc cccagccttc    1380
tctctgctcc tcagccatgc gaaaacagga gatcattaag attacagaac agctgattga    1440
agccatcaac aatggggact ttgaggccta cacgaagatt tgtgatccag gcctcacttc    1500
ctttgagcct gaggcccttg gtaacctcgt ggaggggatg gatttccata agttttactt    1560
tgagaatctc ctgtccaaga acagcaagcc tatccatacc accatcctaa acccacacgt    1620
ccacgtgatt ggggaggacg cagcgtgcat cgcctacatc cgcctcaccc agtacatcga    1680
cgggcagggt cggcctcgca ccagccagtc agaagagacc cgggtctggc accgtcggga    1740
tggcaagtgg ctcaatgtcc actatcactg ctcaggggcc cctgccgcac cgctgcagtg    1800
agctcagcca caggggcttt aggagattcc agccggaggt ccaaccttcg cagccagtgg    1860
ctctggaggg cctgagtgac agcggcagtc ctgtttgttt gaggtttaaa acaattcaat    1920
tacaaaagcg gcagcagcca atgcacgccc ctgcatgcag ccctcccgcc cgcccttcgt    1980
gtctgtctct gctgtaccga ggtgtttttt acatttaaga aaaaaaaaa agaaaaaaag    2040 attgtttaaa aaaaaaagga atccatacca tgatgcgttt taaaaccacc gacagccctt    2100
gggttggcaa aaggcagga gtatgtatga ggtccatcct ggcatgagca gtggctcacc    2160
caccggcctt gaagaggtga gcttggcctc tctggtcccc atggacttag ggggaccagg    2220
caagaactct gacagagctt tgggggccgt gatgtgattg cagctcctga ggtggcctgc    2280
ttaccccagg tctaggaatg aacttctttg gaacttgcat aggcgcctag aatggggctg    2340
atgagaacat cgtgaccatc agacctactt gggagagaac gcagagctcc cagcctgctg    2400
tggaggcagc tgagaagtgg tggcctcagg actgagagcc cggacgttgc tgtactgtct    2460
tgtttagtgt agaagggaag agaattggtg ctgcagaagt gtaccgcca tgaagccgat    2520 gagaaacctc gtgttagtct gacatgcact cactcatcca tttctatagg atgcacaatg    2580
catgtgggcc ctaatattga ggccttatcc ctgcagctag gaggggagg ggttgttgct    2640 gctttgcttc gtgttttctt ctaacctggc aaggagagag ccaggccctg gtcagggctc    2700
ccgtgccgcc tttggcggtt ctgtttctgt gctgatctgg accatctttg tcttgccttt    2760
tcacggtagt ggtccccatg ctgacccctca tctgggcctg ggcctctgc caagtgcccc    2820 tgtgggatgg gaggagtgag gcagtgggag aagaggtggt ggtcgtttct atgcattcag    2880
gctgcctttg gggctgcctc ccttcttatt cttccttgct gcacgtccat ctcttttcct    2940
gtctttgaga ttgacctgac tgctctggca agaagaagag gtgtccttac agaggcctct    3000
ttactgacca actgaagtat agacttactg ctggacaatc tgcatgggca tcacccctcc    3060
ccgcatgtaa cccaaaagag gtgtccgag ccaaggcttc taccttcatt gtccctctct    3120
gtgctcaagg agttccattc caggaggaag agatctatac cctaagcaga tagcaaagaa    3180
gataatggag gagcaattgg tcatggcctt ggtttccctc aaaacaacgc tgcagattta    3240
tctgcacaaa catctccact tttggggaa aggtgggtag attccagttc cctggactac    3300
cttcaggagg cacgagagct gggagaagag gcaaagctac aggtttactt gggagccagc    3360
tgagaagaga gcagactcac aggtgctggt gcttggattt agccaggctc ctccgagcac    3420
ctcatgcatg tcccagcccc tgggccctag ccctttcctg ccctgcagtc tgcagtgcca    3480
gcacgcaaat cccttcacca cagggtttcg ttttgctggc ttgaagacaa atggtcttag    3540
aattcattga gacccatagc ttcatatggc tgctccagcc ccacttctta gcattcttac    3600
tcctcttctg gggctaatgt cagcatctat agacaataga ctattaaaaa atcacctttt    3660
```

```
aaacaagaaa cggaaggcat ttgatgcaga atttttgcat gacaacatag aaataattta    3720
aaaatagtgt ttgttctgaa tgttggtaga cccttcatag ctttgttaca atgaaacctt    3780
gaactgaaaa tatttaataa aataacctttt aaacagtc                           3818
```

<210> SEQ ID NO 22
<211> LENGTH: 391
<212> TYPE: PRT
<213> ORGANISM: Homo sapiens

<400> SEQUENCE: 22

```
Met Asp Leu Glu Lys Asn Tyr Pro Thr Pro Arg Thr Ser Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Ala Ser Pro Thr Pro Ala Asp
        275                 280                 285

Ile Gly Ser Ser Val Pro Gly Pro Gln Ser Tyr Pro Ile Val Thr Gly
    290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Ser
```

```
            340                 345                 350
Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
            370                 375                 380

Ala Thr Ala Tyr Asp Arg His
385                 390
```

<210> SEQ ID NO 23
<211> LENGTH: 391
<212> TYPE: PRT
<213> ORGANISM: Equus caballus

<400> SEQUENCE: 23

```
Met Asp Leu Glu Lys Thr Tyr Pro Thr Pro Arg Thr Gly Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
            115                 120                 125

Val Pro Ser Val Ser Ser Ile Asn Arg Ile Ile Arg Thr Lys Val Gln
            130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Val Pro Glu Ser Pro Val
            195                 200                 205

Pro Asn Gly His Ser Leu Pro Gly Arg Asp Phe Leu Arg Lys Gln Met
            210                 215                 220

Arg Gly Asp Leu Phe Thr Gln Gln Gln Leu Glu Val Leu Asp Arg Val
225                 230                 235                 240

Phe Glu Arg Gln His Tyr Ala Asp Ile Phe Thr Thr Thr Glu Pro Ile
            245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Thr Ser Pro Thr Pro Ala Asp
            275                 280                 285

Ile Gly Ser Ser Val Pro Gly Pro Gln Ser Tyr Pro Ile Val Thr Gly
            290                 295                 300

Arg Asp Leu Ala Ser Thr Thr Leu Pro Gly Tyr Pro Pro His Val Pro
305                 310                 315                 320
```

```
Pro Ala Gly Gln Gly Ser Tyr Ser Ala Pro Thr Leu Thr Gly Met Val
            325                 330                 335

Pro Gly Ser Glu Phe Ser Gly Ser Pro Tyr Ser His Pro Gln Tyr Pro
        340                 345                 350

Ser Tyr Asn Asp Ser Trp Arg Phe Pro Asn Pro Gly Leu Leu Gly Ser
            355                 360                 365

Pro Tyr Tyr Tyr Ser Ala Ala Arg Gly Ala Pro Pro Ala Ala
        370                 375                 380

Ala Thr Ala Tyr Asp Arg His
385                 390

<210> SEQ ID NO 24
<211> LENGTH: 391
<212> TYPE: PRT
<213> ORGANISM: Canis lupus

<400> SEQUENCE: 24

Met Asp Leu Glu Lys Asn Tyr Pro Thr Pro Arg Ser Gly Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Thr Ser Pro Thr Pro Ala Asp
        275                 280                 285

Ile Gly Ser Ser Val Pro Gly Pro Gln Ser Tyr Pro Ile Val Thr Gly
    290                 295                 300
```

```
Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
            325                 330                 335

Pro Gly Ser Glu Phe Ser Gly Ser Pro Tyr Ser His Pro Gln Tyr Pro
            340                 345                 350

Ser Tyr Asn Asp Ser Trp Arg Phe Pro Asn Pro Gly Leu Leu Gly Ser
            355                 360                 365

Pro Tyr Tyr Tyr Ser Ala Ala Arg Gly Ala Ala Pro Pro Ala Ala
370                 375                 380

Ala Thr Ala Tyr Asp Arg His
385                 390

<210> SEQ ID NO 25
<211> LENGTH: 391
<212> TYPE: PRT
<213> ORGANISM: Felis catus

<400> SEQUENCE: 25

Met Asp Leu Glu Lys Asn Tyr Pro Thr Pro Arg Thr Gly Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
            85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
            115                 120                 125

Val Pro Ser Val Ser Ser Ile Asn Arg Ile Ile Arg Thr Lys Val Gln
130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
            165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
            195                 200                 205

Pro Asn Gly His Ser Leu Pro Gly Arg Asp Phe Leu Arg Lys Gln Met
            210                 215                 220

Arg Gly Glu Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                    245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Thr Ser Pro Thr Pro Thr Asp
```

```
                   275                 280                 285
Ile Gly Ser Ser Val Pro Gly Pro Gln Ser Tyr Pro Ile Val Thr Gly
        290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

Pro Gly Ser Glu Phe Ser Gly Ser Pro Tyr Ser His Pro Gln Tyr Pro
                340                 345                 350

Ser Tyr Asn Asp Ser Trp Arg Phe Pro Asn Pro Gly Leu Leu Gly Ser
                355                 360                 365

Pro Tyr Tyr Tyr Ser Ala Ala Ala Arg Gly Ala Ala Pro Pro Ala Ala
                370                 375                 380

Ala Thr Ala Tyr Asp Arg His
385                 390

<210> SEQ ID NO 26
<211> LENGTH: 454
<212> TYPE: PRT
<213> ORGANISM: Homo sapiens

<400> SEQUENCE: 26

Met Ser Ser Gly Ala Pro Gln Lys Ser Pro Met Ala Ser Gly Ala
1               5                   10                  15

Glu Glu Thr Pro Gly Phe Leu Asp Thr Leu Leu Gln Asp Phe Pro Ala
                20                  25                  30

Leu Leu Asn Pro Glu Asp Pro Leu Pro Trp Lys Ala Pro Gly Thr Val
                35                  40                  45

Leu Ser Gln Glu Glu Val Glu Gly Leu Ala Glu Leu Ala Met Gly
        50                  55                  60

Phe Leu Gly Ser Arg Lys Ala Pro Pro Leu Ala Ala Ala Leu Ala
65                  70                  75                  80

His Glu Ala Val Ser Gln Leu Leu Gln Thr Asp Leu Ser Glu Phe Arg
                85                  90                  95

Lys Leu Pro Arg Glu Glu Glu Glu Glu Glu Asp Asp Asp Glu Glu
                100                 105                 110

Glu Lys Ala Pro Val Thr Leu Leu Asp Ala Gln Ser Leu Ala Gln Ser
                115                 120                 125

Phe Phe Asn Arg Leu Trp Glu Val Ala Gly Gln Trp Gln Lys Gln Val
                130                 135                 140

Pro Leu Ala Ala Arg Ala Ser Gln Arg Gln Trp Leu Val Ser Ile His
145                 150                 155                 160

Ala Ile Arg Asn Thr Arg Arg Lys Met Glu Asp Arg His Val Ser Leu
                165                 170                 175

Pro Ser Phe Asn Gln Leu Phe Gly Leu Ser Asp Pro Val Asn Arg Ala
                180                 185                 190

Tyr Phe Ala Val Phe Asp Gly His Gly Gly Val Asp Ala Ala Arg Tyr
                195                 200                 205

Ala Ala Val His Val His Thr Asn Ala Ala Arg Gln Pro Glu Leu Pro
                210                 215                 220

Thr Asp Pro Glu Gly Ala Leu Arg Glu Ala Phe Arg Arg Thr Asp Gln
225                 230                 235                 240

Met Phe Leu Arg Lys Ala Lys Arg Glu Arg Leu Gln Ser Gly Thr Thr
                245                 250                 255
```

```
Gly Val Cys Ala Leu Ile Ala Gly Ala Thr Leu His Val Ala Trp Leu
            260                 265                 270

Gly Asp Ser Gln Val Ile Leu Val Gln Gln Gly Gln Val Val Lys Leu
            275                 280                 285

Met Glu Pro His Arg Pro Glu Arg Gln Asp Glu Lys Ala Arg Ile Glu
    290                 295                 300

Ala Leu Gly Gly Phe Val Ser His Met Asp Cys Trp Arg Val Asn Gly
305                 310                 315                 320

Thr Leu Ala Val Ser Arg Ala Ile Gly Asp Val Phe Gln Lys Pro Tyr
                325                 330                 335

Val Ser Gly Glu Ala Asp Ala Ala Ser Arg Ala Leu Thr Gly Ser Glu
            340                 345                 350

Asp Tyr Leu Leu Leu Ala Cys Asp Gly Phe Phe Asp Val Val Pro His
            355                 360                 365

Gln Glu Val Val Gly Leu Val Gln Ser His Leu Thr Arg Gln Gln Gly
    370                 375                 380

Ser Gly Leu Arg Val Ala Glu Glu Leu Val Ala Ala Arg Glu Arg
385                 390                 395                 400

Gly Ser His Asp Asn Ile Thr Val Met Val Val Phe Leu Arg Asp Pro
                405                 410                 415

Gln Glu Leu Leu Glu Gly Gly Asn Gln Gly Glu Gly Asp Pro Gln Ala
            420                 425                 430

Glu Gly Arg Arg Gln Asp Leu Pro Ser Ser Leu Pro Glu Pro Glu Thr
            435                 440                 445

Gln Ala Pro Pro Arg Ser
    450

<210> SEQ ID NO 27
<211> LENGTH: 439
<212> TYPE: PRT
<213> ORGANISM: Equus caballus

<400> SEQUENCE: 27

Met Ala Ser Gly Ala Leu Gln Glu Ser Gln Met Ala Glu Glu Thr
1               5                   10                  15

Leu Gly Phe Leu Asp Met Leu Leu Cys Asp Phe Pro Ala Pro Leu Ser
            20                  25                  30

Pro Asp Ser Pro Leu Pro Trp Lys Val Pro Gly Thr Val Leu Arg Gln
            35                  40                  45

Glu Glu Val Glu Gly Glu Leu Ala Glu Leu Ala Met Gly Phe Leu Gly
    50                  55                  60

Ser Arg Asn Ala Pro Pro Pro Leu Ala Ser Cys Leu Ala His Glu Ala
65                  70                  75                  80

Val Ser Lys Leu Leu Gln Ala Asp Leu Ser Glu Phe Arg Lys Lys Pro
                85                  90                  95

Arg Gln Glu Glu Asp Asp Ala Glu Glu Lys Ala Pro Val Thr
    100                 105                 110

Leu Leu Asp Ala Glu Gly Leu Val Arg Thr Phe Phe Asn Gln Leu Trp
            115                 120                 125

Glu Val Cys Ser Arg Trp Gln Lys Gln Val Pro Ser Thr Ala Gln Ala
    130                 135                 140

Pro Gln Arg Gln Trp Leu Val Ser Ile His Ala Ile Arg Asn Thr Arg
145                 150                 155                 160

Arg Lys Met Glu Asp Arg His Val Cys Leu Ser Ala Phe Asn Gln Leu
                165                 170                 175
```

```
Phe Gly Leu Ser Asp Pro Val Asp Arg Ala Tyr Phe Ala Val Phe Asp
            180                 185                 190

Gly His Gly Gly Val Asp Ala Ala Arg Tyr Ala Ala Ala His Val His
            195                 200                 205

Ala His Ala Ala Arg Arg Pro Glu Leu Pro Thr Asp Pro Ala Gly Ala
    210                 215                 220

Leu Arg Glu Ala Phe Arg Arg Thr Asp Glu Met Phe Leu Trp Lys Ala
225                 230                 235                 240

Lys Arg Glu Arg Leu Gln Ser Gly Thr Thr Gly Val Cys Ala Leu Ile
                245                 250                 255

Ala Gly Lys Thr Leu His Val Ala Trp Leu Gly Asp Ser Gln Val Ile
            260                 265                 270

Leu Val Gln Gln Gly Gln Val Val Lys Leu Met Glu Pro His Arg Pro
        275                 280                 285

Glu Arg Gln Asp Glu Arg Glu Arg Ile Glu Ala Leu Gly Gly Phe Val
    290                 295                 300

Ser His Met Asp Cys Trp Arg Val Asn Gly Thr Leu Ala Val Ser Arg
305                 310                 315                 320

Ala Ile Gly Asp Val Phe Gln Lys Pro Tyr Val Ser Gly Glu Ala Asp
                325                 330                 335

Ala Ala Ser Gln Glu Leu Thr Gly Ser Glu Asp Tyr Leu Leu Leu Ala
            340                 345                 350

Cys Asp Gly Phe Phe Asp Val Val Pro His His Glu Val Ala Gly Leu
        355                 360                 365

Val Gln Ser His Leu Val Arg Gln Gln Gly Ser Gly Leu His Val Ala
    370                 375                 380

Glu Glu Leu Val Ala Ala Arg Glu Arg Gly Ser His Asp Asn Ile
385                 390                 395                 400

Thr Val Met Val Val Phe Leu Arg Asp Pro Arg Ala Leu Leu Glu Gly
                405                 410                 415

Gly Ala Gln Gly Ala Gly Asp Leu Pro Ser Gly Leu Ser Glu Pro Glu
            420                 425                 430

Thr Asn Thr Pro Pro Arg Ser
            435

<210> SEQ ID NO 28
<211> LENGTH: 440
<212> TYPE: PRT
<213> ORGANISM: Canis lupus

<400> SEQUENCE: 28

Met Ala Ser Gly Ala Pro Pro Gln Ser Ser His Thr Ala Glu Glu Ile
1               5                   10                  15

Pro Gly Phe Leu Asp Ala Phe Leu Cys Asp Phe Pro Ala Pro Leu Ser
            20                  25                  30

Leu Glu Pro Pro Leu Pro Trp Lys Leu Pro Gly Pro Val Leu Ser Gln
        35                  40                  45

Glu Glu Val Glu Gly Glu Leu Thr Glu Leu Ala Met Gly Phe Leu Ser
    50                  55                  60

Asn Arg Ser Ala Pro Pro Leu Ala Ala Ser Leu Ala His Glu Ala
65                  70                  75                  80

Val Ser Gln Leu Leu Gln Thr Asp Leu Ser Glu Phe Arg Lys Leu Pro
                85                  90                  95

Arg Gln Glu Glu Glu Glu Asp Asp Asp Glu Glu Glu Lys Ala Pro Val
```

```
            100                 105                 110
Thr Leu Leu Asp Ala Lys Gly Leu Ala Arg Ser Cys Phe Asn Gln Leu
            115                 120                 125

Trp Glu Val Cys Ser Gln Trp Lys Gln Val Pro Ser Thr Ala Gln
        130                 135                 140

Val Pro Gln Arg Gln Trp Leu Val Ser Met His Ala Ile Arg Asn Thr
145                 150                 155                 160

Arg Arg Lys Met Glu Asp Arg His Val Cys Leu Pro Ala Phe Asn Gln
                165                 170                 175

Leu Phe Gly Leu Ser Asp Pro Val Asp Arg Ala Tyr Phe Ala Val Phe
            180                 185                 190

Asp Gly His Gly Gly Val Asp Ala Ala Gln Tyr Ala Ala Val His Val
        195                 200                 205

His Thr Asn Leu Ala Arg Gln Pro Glu Leu Leu Thr Asp Pro Ala Gly
210                 215                 220

Ala Leu Arg Glu Ala Phe Arg His Thr Asp Glu Met Phe Leu Trp Lys
225                 230                 235                 240

Ala Lys Arg Glu Arg Leu Gln Ser Gly Thr Thr Gly Val Cys Ala Leu
                245                 250                 255

Ile Val Gly Lys Thr Leu His Ile Ala Trp Leu Gly Asp Ser Gln Val
            260                 265                 270

Ile Leu Val Gln Gln Gly Gln Val Val Lys Leu Met Glu Pro His Arg
        275                 280                 285

Pro Glu Arg Gln Asp Glu Lys Glu Arg Ile Glu Ala Leu Gly Gly Phe
    290                 295                 300

Val Ser His Met Asp Cys Trp Arg Val Asn Gly Thr Leu Ala Val Ser
305                 310                 315                 320

Arg Ala Ile Gly Asp Val Phe Gln Lys Pro Tyr Val Ser Gly Glu Ala
                325                 330                 335

Asp Ser Ala Ser Arg Glu Leu Thr Gly Ser Glu Asp Tyr Leu Leu Leu
            340                 345                 350

Ala Cys Asp Gly Phe Phe Asp Val Val Pro His Gln Glu Val Ala Gly
        355                 360                 365

Leu Val His Ser His Leu Ala Arg Gln Gln Gly Ser Gly Leu Gln Val
    370                 375                 380

Ala Glu Glu Leu Val Ala Ala Arg Glu Arg Gly Ser His Asp Asn
385                 390                 395                 400

Ile Thr Val Met Val Phe Leu Arg Asp Pro Arg Asp Leu Leu Lys
                405                 410                 415

Gly Gly Ala Gln Gly Thr Gly Asp Val Pro Ser Gly Leu Ser Gln Pro
            420                 425                 430

Glu Thr Ser Thr Pro Gln Ser Ser
            435                 440

<210> SEQ ID NO 29
<211> LENGTH: 445
<212> TYPE: PRT
<213> ORGANISM: Felis catus

<400> SEQUENCE: 29

Met Ala Ser Gly Asp Pro Gln Gln Ser Ser Gln Met Ala Glu Glu Ile
1               5                   10                  15

Pro Gly Phe Leu Asp Ala Phe Leu His Asp Phe Pro Ala Pro Leu Ser
            20                  25                  30
```

```
Pro Glu Ser Pro Leu Pro Trp Lys Val Pro Gly Thr Val Leu Ser Gln
         35                  40                  45

Glu Glu Val Glu Gly Glu Leu Ala Glu Leu Ala Met Gly Phe Leu Ser
 50                  55                  60

Ser Arg Asn Ala Pro Pro Leu Ala Ser Cys Leu Ala His Glu Ala
 65                  70                  75                  80

Val Ser Gln Leu Leu Gln Met Asp Leu Ser Glu Phe Arg Lys Leu Pro
                 85                  90                  95

Arg Gln Glu Glu Glu Glu Glu Glu Glu Asp Asp Asn Glu Glu
                100                 105                 110

Glu Lys Ala Pro Val Thr Leu Leu Asp Ala Lys Gly Leu Ala Arg Ser
         115                 120                 125

Phe Phe Asn Gln Leu Trp Glu Val Cys Ser Gln Trp Gln Lys Gln Val
     130                 135                 140

Pro Ser Ser Ala Arg Val Pro Gln Arg Gln Trp Leu Val Ser Ile His
145                 150                 155                 160

Ala Ile Arg Asn Thr Arg Arg Lys Met Glu Asp Arg His Val Cys Leu
                165                 170                 175

Pro Ala Phe Asn Gln Leu Phe Gly Leu Ser Asp Pro Val Asp Arg Ala
             180                 185                 190

Tyr Phe Ala Val Phe Asp Gly His Gly Gly Val Asp Ala Ala Arg Tyr
         195                 200                 205

Ala Ala Val His Val His Ala Asn Val Ala His Arg Pro Glu Leu Pro
     210                 215                 220

Thr Asp Pro Ala Gly Ala Leu Arg Glu Ala Phe Arg His Thr Asp Glu
225                 230                 235                 240

Met Phe Leu Trp Lys Ala Lys Arg Glu Arg Leu Gln Ser Gly Thr Thr
                245                 250                 255

Gly Val Cys Ala Phe Ile Ala Gly Lys Thr Leu His Val Ala Trp Leu
             260                 265                 270

Gly Asp Ser Gln Val Ile Leu Val Gln Gly Gln Val Val Lys Leu
         275                 280                 285

Met Glu Pro His Arg Pro Glu Arg Gln Asp Glu Lys Glu Arg Ile Glu
     290                 295                 300

Ala Leu Gly Gly Phe Val Ser His Met Asp Cys Trp Arg Val Asn Gly
305                 310                 315                 320

Thr Leu Ala Val Ser Arg Ala Ile Gly Asp Val Phe Gln Lys Pro Tyr
                325                 330                 335

Val Ser Gly Glu Ala Asp Ser Ala Ser Arg Glu Leu Thr Gly Ser Glu
             340                 345                 350

Asp Tyr Leu Leu Leu Ala Cys Asp Gly Phe Phe Asp Val Val Pro His
         355                 360                 365

Gln Glu Val Ala Gly Leu Val Gln Ser His Leu Val Arg Glu Gln Gly
     370                 375                 380

Ser Gly Leu Gln Val Ala Glu Glu Leu Val Ala Ala Arg Glu Arg
385                 390                 395                 400

Gly Ser His Asp Asn Ile Thr Val Met Val Phe Leu Arg Asp Pro
                405                 410                 415

Gln Asp Leu Leu Lys Gly Arg Ala Gln Gly Val Gly Asp Val Pro Thr
             420                 425                 430

Gly Leu Ala Glu Pro Gly Thr Asn Ala Pro Gln Arg Arg
         435                 440                 445
```

<210> SEQ ID NO 30
<211> LENGTH: 556
<212> TYPE: PRT
<213> ORGANISM: Homo sapiens

<400> SEQUENCE: 30

| Met | Ala | Thr | Thr | Ala | Thr | Cys | Thr | Arg | Phe | Thr | Asp | Asp | Tyr | Gln | Leu |
|---|---|---|---|---|---|---|---|---|---|---|---|---|---|---|---|
| 1 | | | | 5 | | | | | 10 | | | | | 15 | |

| Phe | Glu | Glu | Leu | Gly | Lys | Gly | Ala | Phe | Ser | Val | Val | Arg | Arg | Cys | Val |
| | | | 20 | | | | | 25 | | | | | 30 | | |

| Lys | Lys | Thr | Ser | Thr | Gln | Glu | Tyr | Ala | Ala | Lys | Ile | Ile | Asn | Thr | Lys |
| | | | 35 | | | | | 40 | | | | | 45 | | |

| Lys | Leu | Ser | Ala | Arg | Asp | His | Gln | Lys | Leu | Glu | Arg | Glu | Ala | Arg | Ile |
| | 50 | | | | | 55 | | | | | 60 | | | | |

| Cys | Arg | Leu | Leu | Lys | His | Pro | Asn | Ile | Val | Arg | Leu | His | Asp | Ser | Ile |
| 65 | | | | | 70 | | | | | 75 | | | | | 80 |

| Ser | Glu | Glu | Gly | Phe | His | Tyr | Leu | Val | Phe | Asp | Leu | Val | Thr | Gly | Gly |
| | | | | | 85 | | | | | 90 | | | | | 95 |

| Glu | Leu | Phe | Glu | Asp | Ile | Val | Ala | Arg | Glu | Tyr | Tyr | Ser | Glu | Ala | Asp |
| | | | | 100 | | | | | 105 | | | | | 110 | |

| Ala | Ser | His | Cys | Ile | His | Gln | Ile | Leu | Glu | Ser | Val | Asn | His | Ile | His |
| | | | 115 | | | | | 120 | | | | | 125 | | |

| Gln | His | Asp | Ile | Val | His | Arg | Asp | Leu | Lys | Pro | Glu | Asn | Leu | Leu | Leu |
| | 130 | | | | | 135 | | | | | 140 | | | | |

| Ala | Ser | Lys | Cys | Lys | Gly | Ala | Ala | Val | Lys | Leu | Ala | Asp | Phe | Gly | Leu |
| 145 | | | | | 150 | | | | | 155 | | | | | 160 |

| Ala | Ile | Glu | Val | Gln | Gly | Glu | Gln | Gln | Ala | Trp | Phe | Gly | Phe | Ala | Gly |
| | | | | | 165 | | | | | 170 | | | | | 175 |

| Thr | Pro | Gly | Tyr | Leu | Ser | Pro | Glu | Val | Leu | Arg | Lys | Asp | Pro | Tyr | Gly |
| | | | | 180 | | | | | 185 | | | | | 190 | |

| Lys | Pro | Val | Asp | Ile | Trp | Ala | Cys | Gly | Val | Ile | Leu | Tyr | Ile | Leu | Leu |
| | | | 195 | | | | | 200 | | | | | 205 | | |

| Val | Gly | Tyr | Pro | Pro | Phe | Trp | Asp | Glu | Asp | Gln | His | Lys | Leu | Tyr | Gln |
| | 210 | | | | | 215 | | | | | 220 | | | | |

| Gln | Ile | Lys | Ala | Gly | Ala | Tyr | Asp | Phe | Pro | Ser | Pro | Glu | Trp | Asp | Thr |
| 225 | | | | | 230 | | | | | 235 | | | | | 240 |

| Val | Thr | Pro | Glu | Ala | Lys | Asn | Leu | Ile | Asn | Gln | Met | Leu | Thr | Ile | Asn |
| | | | | | 245 | | | | | 250 | | | | | 255 |

| Pro | Ala | Lys | Arg | Ile | Thr | Ala | Asp | Gln | Ala | Leu | Lys | His | Pro | Trp | Val |
| | | | | 260 | | | | | 265 | | | | | 270 | |

| Cys | Gln | Arg | Ser | Thr | Val | Ala | Ser | Met | Met | His | Arg | Gln | Glu | Thr | Val |
| | | | 275 | | | | | 280 | | | | | 285 | | |

| Glu | Cys | Leu | Arg | Lys | Phe | Asn | Ala | Arg | Arg | Lys | Leu | Lys | Gly | Ala | Ile |
| | 290 | | | | | 295 | | | | | 300 | | | | |

| Leu | Thr | Thr | Met | Leu | Val | Ser | Arg | Asn | Phe | Ser | Ala | Ala | Lys | Ser | Leu |
| 305 | | | | | 310 | | | | | 315 | | | | | 320 |

| Leu | Asn | Lys | Lys | Ser | Asp | Gly | Val | Lys | Pro | Gln | Ser | Asn | Asn | Lys |
| | | | | 325 | | | | | 330 | | | | | 335 |

| Asn | Ser | Leu | Val | Ser | Pro | Ala | Gln | Glu | Pro | Ala | Pro | Leu | Gln | Thr | Ala |
| | | | 340 | | | | | 345 | | | | | 350 | | |

| Met | Glu | Pro | Gln | Thr | Thr | Val | Val | His | Asn | Ala | Thr | Asp | Gly | Ile | Lys |
| | | | 355 | | | | | 360 | | | | | 365 | | |

| Gly | Ser | Thr | Glu | Ser | Cys | Asn | Thr | Thr | Thr | Glu | Asp | Glu | Asp | Leu | Lys |
| | 370 | | | | | 375 | | | | | 380 | | | | |

-continued

```
Ala Ala Pro Leu Arg Thr Gly Asn Gly Ser Ser Val Pro Glu Gly Arg
385                 390                 395                 400

Ser Ser Arg Asp Arg Thr Ala Pro Ser Ala Gly Met Gln Pro Gln Pro
                405                 410                 415

Ser Leu Cys Ser Ser Ala Met Arg Lys Gln Glu Ile Ile Lys Ile Thr
            420                 425                 430

Glu Gln Leu Ile Glu Ala Ile Asn Asn Gly Asp Phe Glu Ala Tyr Thr
        435                 440                 445

Lys Ile Cys Asp Pro Gly Leu Thr Ser Phe Glu Pro Glu Ala Leu Gly
    450                 455                 460

Asn Leu Val Glu Gly Met Asp Phe His Lys Phe Tyr Phe Glu Asn Leu
465                 470                 475                 480

Leu Ser Lys Asn Ser Lys Pro Ile His Thr Thr Ile Leu Asn Pro His
            485                 490                 495

Val His Val Ile Gly Glu Asp Ala Ala Cys Ile Ala Tyr Ile Arg Leu
            500                 505                 510

Thr Gln Tyr Ile Asp Gly Gln Gly Arg Pro Arg Thr Ser Gln Ser Glu
        515                 520                 525

Glu Thr Arg Val Trp His Arg Arg Asp Gly Lys Trp Leu Asn Val His
    530                 535                 540

Tyr His Cys Ser Gly Ala Pro Ala Ala Pro Leu Gln
545                 550                 555
```

THERAPEUTIC COMPOSITIONS AND METHODS OF MAKING AND USING THE SAME

INCORPORATION BY REFERENCE TO ANY PRIORITY APPLICATIONS

This application is claims the benefit of priority to U.S. Provisional Application Nos. 62/618,998, filed Jan. 18, 2018, 62/619,002, filed Jan. 18, 2018, 62/632,274, filed Feb. 19, 2018, and 62/743,345, filed Oct. 9, 2018. The disclosures of each of the foregoing applications are hereby incorporated by reference in their entireties.

THE NAMES OF THE PARTIES TO A JOINT RESEARCH AGREEMENT

The claimed invention was made by, on behalf of, and/or in connection with one or more of the following parties to a joint research agreement between: University of Medicine and Dentistry of New Jersey, Rutgers, The State University of New Jersey, and Advanced Regen Medical Technologies, LLC. The agreement was in effect on and before the date the claimed invention was made, and the claimed invention was made as a result of activities undertaken within the scope of the agreement.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is ARGMT003A.TXT, the date of creation of the ASCII text file is Jan. 17, 2019, and the size of the ASCII text file is 96 KB.

FIELD

The present disclosure generally relates to compounds, compositions, methods of making thereof, and methods for the treatment of disease and for the improvement of one or more aspects of cellular function. Some embodiments pertain to methods of making the compounds and compositions disclosed herein, including manufacturing target cells for use in treatment.

BACKGROUND

Cellular dysfunctional and/or senescent cellular signaling is an important risk factor for most chronic diseases and is a primary factor for the majority of morbidity and health care expenditures in developed nations.

SUMMARY

Some embodiments disclosed herein pertain to interfering RNAs, small molecule inhibitors, and target cells, compositions thereof, and the use of the same in treating cellular dysfunction leading to various disease states. Some embodiments pertain to a method of reducing expression of a paired box 5 (PAX5) gene and reducing expression of a protein phosphatase 1F enzyme (PPM1F) gene in a cell using one or more interfering RNAs (RNAi(s)), small molecule compounds, or combinations thereof. In some embodiments, the method of reducing expression of the PAX5 gene and reducing expression of the PPM1F gene in a cell comprises contacting the cell with one or more interfering RNA(s) (RNAi(s)), wherein the one or more RNAi(s) include one or more of SEQ ID NO:9-SEQ ID NO:20. In some embodiments, the cell is maintained for a time sufficient to obtain inhibition of the PAX5 gene and the PPM1F gene, thereby reducing expression of the PAX5 gene and the PPM1F gene in that cell to provide a target cell.

Any of the embodiments described above, or described elsewhere herein, can include one or more of the following features or can lack one or more of the following features.

In some embodiments, the one or more RNAi(s) comprises SEQ ID NO:15. In some embodiments, the one or more RNAi(s) comprises at least one of SEQ ID NO:15, SEQ ID NO:17, and SEQ ID NO:19. In some embodiments, one or more RNAi(s) comprises at least one of SEQ ID NO:16, SEQ ID NO:18, and SEQ ID NO:20. In some embodiments, the one or more RNAi(s) further comprises at least one of SEQ ID NO:9, SEQ ID NO:10, SEQ ID NO:11, SEQ ID NO:12, SEQ ID NO:13, and SEQ ID NO:14.

In some embodiments, PAX5 expression is reduced by at least about 30%, 40%, 50%, 60%, 70%, 80%, 90%, 95%, 98%, 99%, or 99.9%. In some embodiments, PAX5 expression is reduced by at least about 70%. In some embodiments, PPM1F expression is reduced by at least about 30%, 40%, 50%, 60%, 70%, 80%, 90%, 95%, 98%, 99%, or 99.9%. In some embodiments, PPM1F expression is reduced by at least about 70%.

In some embodiments, the cell is contacted with the one or more RNAi(s) for a period of equal to or at least about 16 hours, 48 hours, or 72 hours. In some embodiments, the cell is isolated from a subject. In some embodiments, the cell is inside a subject. In some embodiments, the cell is a human cell.

Some embodiments pertain to the target cell made by contacting the cell with one or more interfering RNA(s) (RNAi(s)), wherein the one or more RNAi(s) include one or more of SEQ ID NO:9-SEQ ID NO:20. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a composition for reducing expression of a PAX5 gene and reducing the expression of a PPM1F gene, the composition comprising an acceptable carrier and an RNAi that is at least 80% to 100% identical to one or more of SEQ ID NO:9-SEQ ID NO:20. In some embodiments, the composition comprises an acceptable carrier and an RNAi that is at least 80% to 100% identical to SEQ ID NO:15. In some embodiments, the composition comprises or further comprises a microRNA that is at least 80% to 100% identical to SEQ ID NO:16. In some embodiments, the composition comprises or further comprises a microRNA that is at least 80% to 100% identical to SEQ ID NO:17. In some embodiments, the composition comprises or further comprises a microRNA that is at least 80% to 100% identical to SEQ ID NO:18. In some embodiments, the composition comprises or further comprises a microRNA that is at least 80% to 100% identical to SEQ ID NO:19. In some embodiments, the composition comprises or further comprises a microRNA that is at least 80% to 100% identical to SEQ ID NO:20. In some embodiments, the composition comprises or further comprises one or more of SEQ ID NO:9-14.

Some embodiments pertain to a method of treating a subject having a disease or disorder that would benefit from reduction in expression of a PAX5 gene and a reduction in expression of a PPM1F gene. In some embodiments, the method comprises administering to the subject a therapeutically effective amount of the target cell as disclosed elsewhere herein or the composition as disclosed elsewhere herein, thereby treating the subject.

Some embodiments pertain to an interfering RNA (RNAi) for reducing the expression of a paired box 5 (PAX5) gene, wherein the RNAi comprises 4 to 50 contiguous nucleotides having a polynucleotide sequence that is at least 80% to 100% complementary to a region of SEQ ID NO:1 (or SEQ ID NOs:2-4). In some embodiments, combinations of RNAi agents can be used (e.g., any one or more of SEQ ID NO:9-11 and 15-20 and/or RNAs that are at least 80% to 100% identical to those RNAi agents). In some embodiments, combinations of RNAi agents can be used (e.g., any one or more of SEQ ID NO:9-20 and/or RNAs that are at least 80% to 100% identical to those RNAi agents). In some embodiments, the RNAi is a short interfering RNA (siRNA), microRNA (miRNA), circular RNAs (circRNAs), short hairpin RNAs (shRNAs), long non-coding RNAs (lncRNAs); piwi-interacting RNAs (piRNA), small nucleolar RNA (snoRNAs), tRNA-derived small RNA (tsRNA), small rDNA-derived RNA (srRNA), or a small nuclear RNA (U-RNA). In some embodiments, the RNAi is an siRNA.

In some embodiments, RNAi hybridizes to the complimentary region of SEQ ID NO:1. In some embodiments, the RNAi comprises about 20 to 30 contiguous nucleotides. In some embodiments, the RNAi is at least 80% to 100% identical to the nucleotide sequence of SEQ ID NO:9. In some embodiments, the RNAi is at least 80% to 100% identical to the nucleotide sequence of SEQ ID NO:10. In some embodiments, the RNAi is at least 80% to 100% identical to the nucleotide sequence of SEQ ID NO: 11.

Some embodiments pertain to a composition for reducing expression of a PAX5 gene comprising the RNAi of any one of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20. In some embodiments, the composition comprises two or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20. In some embodiments, the composition further comprises a pharmaceutically acceptable carrier.

Some embodiments pertain to a method of reducing expression of a PAX5 gene in a cell. In some embodiments, the method comprises contacting a cell with the RNAi or RNAi(s) above or as disclosed elsewhere herein, combinations of the same, or a composition comprising the same. In some embodiments, the method comprises maintaining the cell for a time sufficient to obtain inhibition of the PAX5 gene, thereby reducing expression of the PAX5 gene in the cell. In some embodiments, the cell is isolated from or is inside a subject. In some embodiments, the subject is a human. In some embodiments, PAX5 expression is reduced by at least about 30%, 40%, 50%, 60%, 70%, 80%, 90%, 95%, 98%, 99%, or 99.9%. In some embodiments, PAX5 expression is reduced by at least about 70%. In some embodiments, the cell is contacted with the RNAi for a period of equal to or at least about 16 hours, 48 hours, or 72 hours. Some embodiments pertain to the cell made by a method as disclosed above or as disclosed elsewhere herein.

In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PAX5 gene. In some embodiments, the method comprises administering to the subject a therapeutically effective amount of cells that have been treated with the RNAi, combination of RNAi(s), or compositions containing RNAi(s) as disclosed above or elsewhere herein, thereby treating the subject.

Some embodiments pertain to an interfering RNA (RNAi) for reducing the expression of a PPM1F gene, wherein the RNAi comprises 4 to 50 contiguous nucleotides having a polynucleotide sequence that is at least 80% to 100% complementary to a region of SEQ ID NO:5 (or SEQ ID NOs:6-8). In some embodiments, combinations of RNAi agents can be used (e.g., any one or more of SEQ ID NO:12-20 and/or RNAs that are at least 80% to 100% identical to those RNAi agents). In some embodiments, combinations of RNAi agents can be used (e.g., any one or more of SEQ ID NO:9-20 and/or RNAs that are at least 80% to 100% identical to those RNAi agents). In some embodiments, the RNAi is a short interfering RNA (siRNA), microRNA (miRNA), circular RNAs (circRNAs), short hairpin RNAs (shRNAs), long non-coding RNAs (lncRNAs); piwi-interacting RNAs (piRNA), small nucleolar RNA (snoRNAs), tRNA-derived small RNA (tsRNA), small rDNA-derived RNA (srRNA), or a small nuclear RNA (U-RNA). In some embodiments, the RNAi is an siRNA.

In some embodiments, RNAi hybridizes to the complimentary region of SEQ ID NO:5. In some embodiments, the RNAi comprises about 20 to 30 contiguous nucleotides. In some embodiments, the RNAi is at least 80% to 100% identical to the nucleotide sequence of SEQ ID NO:12. In some embodiments, the RNAi is at least 80% to 100% identical to the nucleotide sequence of SEQ ID NO:13. In some embodiments, the RNAi is at least 80% to 100% identical to the nucleotide sequence of SEQ ID NO: 14.

Some embodiments pertain to a composition for reducing expression of a PPM1F gene comprising the RNAi of any one of SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some embodiments, the composition comprises two or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some embodiments, the composition further comprises a pharmaceutically acceptable carrier.

Some embodiments pertain to a method of reducing expression of a PPM1F gene in a cell. In some embodiments, the method comprises contacting a cell with the RNAi or RNAi(s) above or as disclosed elsewhere herein, combinations of the same, or a composition comprising the same. In some embodiments, the method comprises maintaining the cell for a time sufficient to obtain inhibition of the PPM1F gene, thereby reducing expression of the PPM1F gene in the cell. In some embodiments, the cell is isolated from or is inside a subject. In some embodiments, the subject is a human. In some embodiments, PPM1F expression is reduced by at least about 30%, 40%, 50%, 60%, 70%, 80%, 90%, 95%, 98%, 99%, or 99.9%. In some embodiments, PPM1F expression is reduced by at least about 70%. In some embodiments, the cell is contacted with the RNAi for a period of equal to or at least about 16 hours, 48 hours, or 72 hours. Some embodiments pertain to the cell made by a method as disclosed above or as disclosed elsewhere herein. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PPM1F gene. In some embodiments, the method comprises administering to the subject a therapeutically effective amount of cells that have been treated with the RNAi, combination of RNAi(s), or compositions containing RNAi(s) as disclosed above or elsewhere herein, thereby treating the subject.

Some embodiments pertain to a method for treating or preventing a disease state, comprising administering to a patient in need thereof a therapeutically effective dose of cells treated with one or more RNAi(s) of a PAX5 gene and/or of a PPM1F gene. In some embodiments, the one or more RNAi(s) is selected from any one or more of the RNA is as recited in elsewhere herein. In some embodiments, the disease state is an age related dysfunction. In some embodiments, the disease state is not an age-related dysfunction. In some embodiments, the disease state comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

Some embodiments pertain to a method for preparing a target cell. In some embodiments, the method comprises obtaining cells from a subject to provide at least one subject cell. In some embodiments, the method comprises exposing the at least one subject cell to one or more RNA is as recited in above or elsewhere herein to provide at least one target cell. In some embodiments, the at least one target cell is member of a population of cells comprising equal to or at least about 100, 1000, 10,000, 100,000, 1,000,000, or 10,000,000 cells. Some embodiments pertain to the target cell.

Some embodiments pertain to a method for treating or preventing cellular dysfunction in a patient. In some embodiments, the method comprises administering to a patient in need thereof a therapeutically effective dose of the target cell as disclosed above or elsewhere herein. In some embodiments, the cellular dysfunction is an age-related dysfunction. In some embodiments, the cellular dysfunction is not an age-related dysfunction.

Some embodiments pertain to an interfering RNA (RNAi) for reducing the expression of a paired any one of the CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, or ZNF549 gene. In some embodiments, the RNAi comprises 4 to 50 contiguous nucleotides having a polynucleotide sequence that is at least 80% to 100% complementary to a region of any one of the CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, or ZNF549 gene. In some embodiments, the RNAi comprises 4 to 50 contiguous nucleotides having a polynucleotide sequence that is at least 80% to 100% complementary to a region of any one or more of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

Some embodiments pertain to a method of reducing expression of a paired box 5 (PAX5) gene in a cell. In some embodiments, the method comprises contacting the cell with one or more interfering RNA(s) (RNAi(s)) wherein the one or more RNAi(s) comprises one or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, SEQ ID NO:20. In some embodiments, the method comprises maintaining the cell for a time sufficient to obtain inhibition of the PAX5 gene, thereby reducing expression of the PAX5 gene in that cell to provide a target cell. In some embodiments, the one or more RNAi(s) comprises at least one of SEQ ID NO:9, SEQ ID NO:10, and SEQ ID NO:11. In some embodiments, the one or more RNAi(s) comprises at least one of SEQ ID NO:15, SEQ ID NO:17, and SEQ ID NO:19. In some embodiments, the one or more RNAi(s) comprises at least one of SEQ ID NO:16, SEQ ID NO:18, and SEQ ID NO:20. In some embodiments, the cell is isolated from a subject or is inside the subject. In some embodiments, the subject is a human. In some embodiments, the PAX5 expression is reduced by at least about 30%, 40%, 50%, 60%, 70%, 80%, 90%, 95%, 98%, 99%, or 99.9%. In some embodiments, the PAX5 expression is reduced by at least about 70%. In some embodiments, the cell is contacted with the one or more RNAi(s) for a period of equal to or at least about 16 hours, 48 hours, or 72 hours.

Some embodiments pertain to a target cell made by the method disclosed above or as disclosed elsewhere herein. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PAX5 gene, the method comprising administering to the subject a therapeutically effective amount of one or more RNAi(s) selected from the group consisting of SEQ ID NO:9, SEQ ID NO:10, SEQ ID NO:11, SEQ ID NO:15, SEQ ID NO:16, SEQ ID NO:17, SEQ ID NO:18, SEQ ID NO:19, and SEQ ID NO:20 or a therapeutically effective amount of cells that have been treated with the one or more RNAi(s), thereby treating the subject.

Some embodiments pertain to a method for reducing the expression of a PAX5 gene, comprising exposing a cell to a composition comprising at least one isolated microRNA, wherein the at least one microRNA is at least 80% to 100% identical to any one or SEQ ID NO:15-20. Some embodiments pertain to a method for reducing the expression of a PAX5 gene, comprising exposing a cell to a composition comprising at least one isolated microRNA, wherein the at least one microRNA is at least 80% to 100% identical to SEQ ID NO:15. Some embodiments pertain to a method for reducing the expression of a PAX5 gene, comprising exposing a cell to a composition comprising at least one isolated microRNA, wherein the at least one microRNA is at least 80% to 100% identical to SEQ ID NO:16. In some embodiments, the composition comprises both SEQ ID NO: 15 and SEQ ID NO: 16. In some embodiments, the composition further comprises a microRNA that is at least 80% to 100% identical to SEQ ID NO:17. In some embodiments, the composition further comprises a microRNA that is at least 80% to 100% identical to SEQ ID NO:18. In some embodiments, the composition further comprises a microRNA that is at least 80% to 100% identical to SEQ ID NO:19. In some embodiments, the composition further comprises a microRNA that is at least 80% to 100% identical to SEQ ID NO:20.

Some embodiments pertain to a composition for reducing expression of a PAX5 gene comprising an acceptable carrier and at least one isolated microRNA that is at least 80% to 100% identical to SEQ ID NO:15. In some embodiments, the composition further comprises a microRNA that is at least 80% to 100% identical to SEQ ID NO:16. In some embodiments, the composition further comprises a microRNA that is at least 80% to 100% identical to SEQ ID NO:17. In some embodiments, the composition further comprises a microRNA that is at least 80% to 100% identical to SEQ ID NO:18. In some embodiments, the composition further comprises a microRNA that is at least 80% to 100% identical to SEQ ID NO:19. In some embodiments, the composition further comprises a microRNA that is at least 80% to 100% identical to SEQ ID NO:20.

Some embodiments pertain to a method of reducing expression of a PAX5 gene in a cell, the method comprising contacting the cell with the composition as disclosed above or elsewhere herein and maintaining the cell for a time sufficient to obtain inhibition of a PAX5 gene, thereby reducing expression of the PAX5 gene in the cell. In some embodiments, the cell is isolated from a subject. In some embodiments, the subject is a human. In some embodiments, PAX5 expression is reduced by at least about 30%, 40%, 50%, 60%, 70%, 80%, 90%, 95%, 98%, 99%, or 99.9%.

Some embodiments pertain to a method of treating a subject having a disease or disorder that would benefit from reduction in expression of a PAX5 gene, the method comprising administering to the subject a therapeutically effective amount of cells treated with the composition as disclosed above or elsewhere herein, thereby treating the subject. In some embodiments, the disease or disorder comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

Some embodiments pertain to a method of reducing expression of a PPM1F gene in a cell, the method comprising contacting the cell with one or more interfering RNA(s) (RNAi(s)), wherein the one or more RNAi(s) comprises one or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20. In some embodiments, the method comprises maintaining the cell for a time sufficient to obtain inhibition of the PAX5 gene, thereby reducing expression of the PAX5 gene in that cell to provide a target cell. In some embodiments, the one or more RNAi(s) comprises at least one of SEQ ID NO:12, SEQ ID NO:13, and SEQ ID NO:14. In some embodiments, the one or more RNAi(s) comprises at least one of SEQ ID NO:15, SEQ ID NO:17, and SEQ ID NO:19. In some embodiments, the one or more RNAi(s) comprises at least one of SEQ ID NO:16, SEQ ID NO:18, and SEQ ID NO:20. In some embodiments, the cell is isolated from a subject or is inside the subject. In some embodiments, the subject is a human. In some embodiments, the PPM1F expression is reduced by at least about 30%, 40%, 50%, 60%, 70%, 80%, 90%, 95%, 98%, 99%, or 99.9%. In some embodiments, the PPM1F expression is reduced by at least about 70%. In some embodiments, the cell is contacted with the one or more RNAi(s) for a period of equal to or at least about 16 hours, 48 hours, or 72 hours.

Some embodiments pertain to a target cell made by the method disclosed above or as disclosed elsewhere herein. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PPM1F gene, the method comprising administering to the subject a therapeutically effective amount of one or more RNAi(s) selected from the group consisting of SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 or a therapeutically effective amount of cells that have been treated with the one or more RNAi(s), thereby treating the subject.

Some embodiments pertain to a method for reducing the expression of a PPM1F gene, comprising exposing a cell to a composition comprising at least one isolated microRNA, wherein the at least one microRNA is at least 80% to 100% identical to any one or SEQ ID NO:15-20. Some embodiments pertain to a method for reducing the expression of a PPM1F gene, comprising exposing a cell to a composition comprising at least one isolated microRNA, wherein the at least one microRNA is at least 80% to 100% identical to SEQ ID NO:15. Some embodiments pertain to a method for reducing the expression of a PAX5 gene, comprising exposing a cell to a composition comprising at least one isolated microRNA, wherein the at least one microRNA is at least 80% to 100% identical to SEQ ID NO:16. In some embodiments, the composition comprises both SEQ ID NO: 15 and SEQ ID NO: 16. In some embodiments, the composition further comprises a microRNA that is at least 80% to 100% identical to SEQ ID NO:17. In some embodiments, the composition further comprises a microRNA that is at least 80% to 100% identical to SEQ ID NO:18. In some embodiments, the composition further comprises a microRNA that is at least 80% to 100% identical to SEQ ID NO:19. In some embodiments, the composition further comprises a microRNA that is at least 80% to 100% identical to SEQ ID NO:20.

Some embodiments pertain to a composition for reducing expression of a PPM1F gene comprising an acceptable carrier and at least one isolated microRNA that is at least 80% to 100% identical to SEQ ID NO:15. In some embodiments, the composition further comprises a microRNA that is at least 80% to 100% identical to SEQ ID NO:16. In some embodiments, the composition further comprises a microRNA that is at least 80% to 100% identical to SEQ ID NO:17. In some embodiments, the composition further comprises a microRNA that is at least 80% to 100% identical to SEQ ID NO:18. In some embodiments, the composition further comprises a microRNA that is at least 80% to 100% identical to SEQ ID NO:19. In some embodiments, the composition further comprises a microRNA that is at least 80% to 100% identical to SEQ ID NO:20.

Some embodiments pertain to a method of reducing expression of a PPM1F gene in a cell, the method comprising contacting the cell with the composition as disclosed above or elsewhere herein and maintaining the cell for a time sufficient to obtain inhibition of a PPM1F gene, thereby reducing expression of the PPM1F gene in the cell. In some embodiments, the cell is isolated from a subject. In some embodiments, the subject is a human. In some embodiments, PPM1F expression is reduced by at least about 30%, 40%, 50%, 60%, 70%, 80%, 90%, 95%, 98%, 99%, or 99.9%.

Some embodiments pertain to a method of treating a subject having a disease or disorder that would benefit from reduction in expression of a PPM1F gene, the method comprising administering to the subject a therapeutically effective amount of cells treated with the composition as disclosed above or elsewhere herein, thereby treating the subject. In some embodiments, the disease or disorder comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

Some embodiments pertain to a method of treating a subject having a disease or disorder that would benefit from reduction in expression of a PAX5 gene and a reduction in expression of the PPM1F gene, the method comprising administering to the subject a therapeutically effective amount of the composition disclosed above or elsewhere herein, thereby treating the subject. In some embodiments, the subject is suffering from one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

Some embodiments pertain to a method for preparing a target cell comprising obtaining cells from a subject to provide at least one subject cell. In some embodiments, the method comprises exposing the at least one subject cell to one or more miRNA including one or more SEQ ID NOS: 15-20 to provide at least one target cell. In some embodiments, the method comprises exposing the at least one subject cell to one or more siRNA including one or more SEQ ID NOS:9-14 to provide at least one target cell. In some embodiments, the at least one target cell is member of a population of cells comprising equal to or at least about 100, 1000, or 10,000 cells. Some embodiments pertain to a method for treating or preventing cellular dysfunction in a patient, comprising administering to a patient in need thereof a therapeutically effective dose of the target cell. In some embodiments, the cellular dysfunction is an age related dysfunction. In some embodiments, the cellular dysfunction is not an age related dysfunction. In some embodiments, the cellular dysfunction one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

Some embodiments pertain to one or more miRNAs for use in reducing the expression of PAX5 gene, wherein the miRNA comprises 4 to 50 contiguous nucleotides having a polynucleotide sequence that is at least 80% to 100% complementary to a region of SEQ ID NO: 1. Some embodiments pertain to miRNA for use in reducing the expression of a PPM1F, wherein the miRNA comprises 4 to 50 contiguous nucleotides having a polynucleotide sequence that is at least 80% to 100% complementary to a region of SEQ ID NO:5.

Some embodiments pertain to method for treating or preventing age related dysfunction, comprising administering to a patient in need thereof a therapeutically effective dose of one or more polycyclic aromatic compounds that antagonize or reduce the expression of PAX5 and/or PPM1F.

In some embodiments, the polycyclic compound is of formula I:

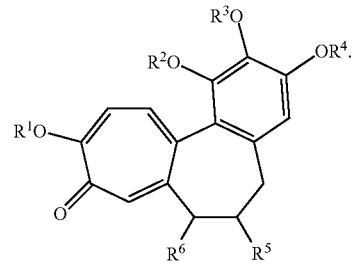

Formula I

In some embodiments, each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine ($C_1$ to $C_6$ alkyl optionally substituted), a di-substituted amine($C_1$ to $C_6$ alkyl optionally substituted), a diamino-group, and an optionally substituted polyether—having 1 to 6 repeat units. In some embodiments, each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, and a —($OR_B$—)$_o$OH, where $R_B$ is an optionally substituted $C_1$ to $C_6$ alkyl.

In some embodiments, the polycyclic compound is of formula II:

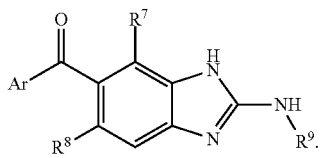

Formula II

In some embodiments, each of $R_7$, $R_8$, and $R_9$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units. In some embodiments, each of $R_7$, $R_8$, and $R_9$ is independently selected from —H, hydroxyl, halogen, $C_1$ to $C_6$ alkyl optionally substituted with halogen or hydroxy, and a —($OR_B$—)$_o$ OH, where $R_B$ is an optionally substituted $C_1$ to $C_6$ alkyl.

In some embodiments, the polycyclic compound is of formula III:

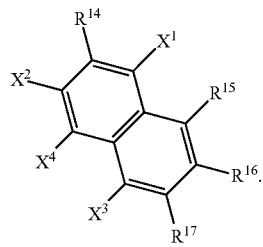

Formula III

In some embodiments, each of $X_1$, $X_2$, $X_3$, $X_4$ is independently selected from —H, hydroxyl, halogen, —$NH_2$, optionally substituted —$SO_2OR_{18}$. In some embodiments, each of $R_{14}$, $R_{15}$, $R_{16}$, $R_{17}$, and $R_{18}$ is independently selected from —H, hydroxyl, halogen, —$NH_2$, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether-having 1 to 6 repeat units. In some embodiments, $R_{14}$, $R_{15}$, $R_{16}$, $R_{17}$, and $R_{18}$ are independently selected from —H, hydroxyl, halogen, $C_1$ to $C_6$ alkyl optionally substituted with halogen or hydroxy, and a —($OR_B$—)$_o$ OH, where $R_B$ is an optionally substituted $C_1$ to $C_6$ alkyl.

In some embodiments, the compound of formula III is represented by the following structure:

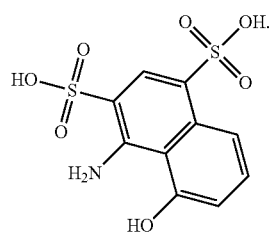

In some embodiments, the polycyclic compound is selected from the group consisting of:

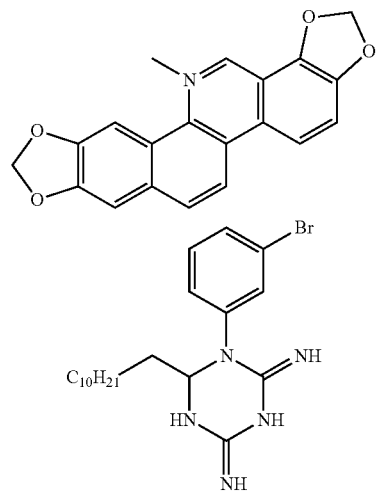

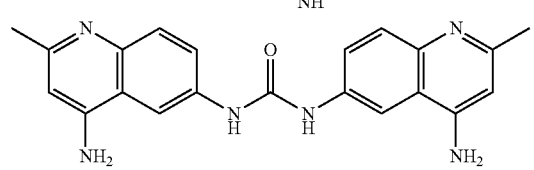

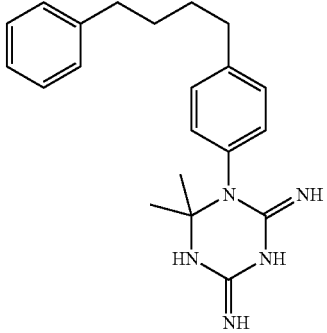

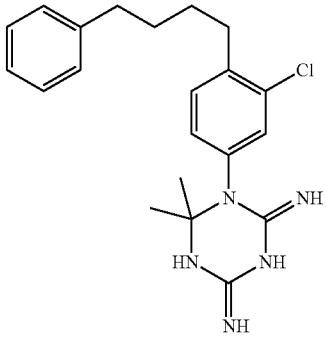

-continued

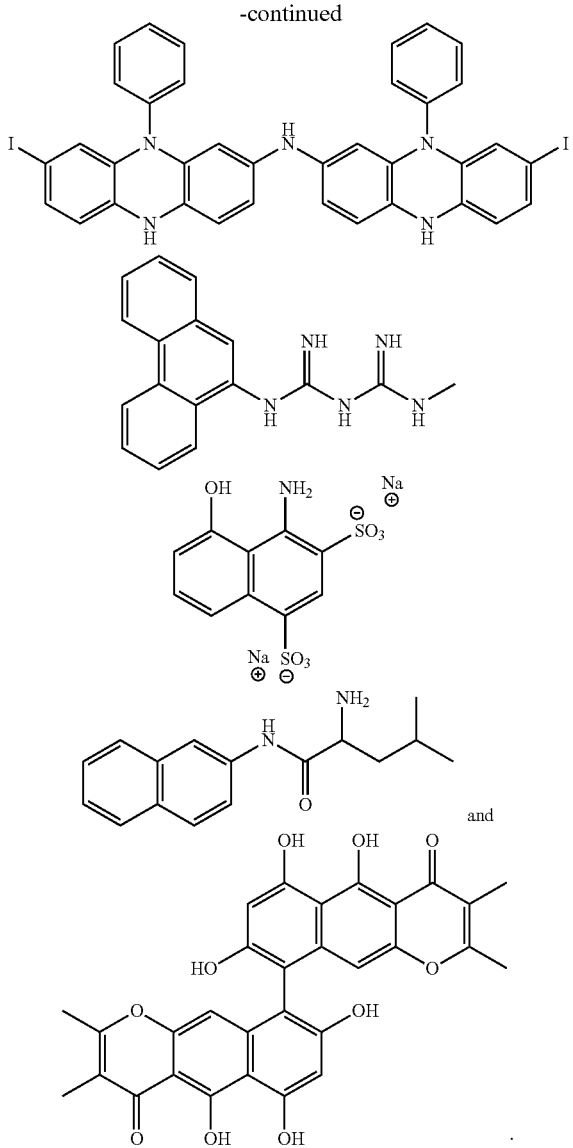

In some embodiments, the polycyclic compound is provided as a pharmaceutically acceptable salt.

Some embodiments pertain to a pharmaceutical composition comprising one or more polycyclic aromatic compounds and a pharmaceutically acceptable carrier. In some embodiments, the pharmaceutical compound comprises a polycyclic aromatic compound and an RNAi as disclosed elsewhere herein.

Some embodiments pertain to a method of preparing at least one cell, the method comprising providing at least one donor cell from a donor. In some embodiments, the method comprises providing at least one subject cell from a subject. In some embodiments, the method comprises providing at least one patient cell from a patient. In some embodiments, the method comprises exposing the subject cell to the donor cell to provide at least one intermediate cell. In some embodiments, the method comprises exposing the patient cell to the intermediate cell to provide a target cell. In some embodiments, exposing the subject cell to the donor cell comprises co-incubating the subject cell and the donor cell. In some embodiments, exposing the intermediate cell to the patient cell comprises co-incubating the intermediate cell and the patient cell. In some embodiments, the subject cell is exposed to the donor cell for a time sufficient for cellular material from the donor cell to interact with the subject cell, thereby providing the intermediate cell. In some embodiments, the patient cell is exposed to the intermediate cell for a time sufficient for cellular material from the intermediate cell to interact with the patient cell, thereby providing the target cell.

In some embodiments, each of the subject and the patient is older than the donor. In some embodiments, donor cell is a cell mobilized from blood from the donor. In some embodiments, the subject cell is a cell mobilized from blood from the subject. In some embodiments, the patient cell is a cell that is mobilized from blood from the patient.

In some embodiments, the method further comprises administering a mobilizing agent to one or more of the donor, the subject, and/or the patient. In some embodiments, the mobilizing agent is an organic molecule, synthetic or naturally derived, or a polypeptide, such as a growth factor or colony-stimulating factor or an active fragment or mimic thereof, a nucleic acid, a carbohydrate, an antibody, or another agent that acts to enhance migration of stem cells from bone marrow to peripheral blood. In some embodiments, one or more of the donor cell, the subject cell, and/or the patient cell are harvested directly from the bone marrow of the donor, the subject, and/or the patient. In some embodiments, the subject is the patient. In some embodiments, the donor is the patient at an earlier age. In some embodiments, the target cell is provided in a formulation or culture suitable for administration to the patient to provide a therapeutic effect to the patient.

In some embodiments, the at least one donor cell is member of a population of cells comprising equal to or at least about 10,000, 1,000,000, 10,000,000 cells. In some embodiments, the at least one subject cell is member of a population of cells comprising equal to or at least about 10,000, 1,000,000, 10,000,000 cells. In some embodiments, the at least one intermediate cell is member of a population of cells comprising equal to or at least about 10,000, 1,000,000, 10,000,000 cells. In some embodiments, the at least one target cell is member of a population of cells comprising equal to or at least about 10,000, 1,000,000, 10,000,000 cells. In some embodiments, one or more of the population of cells comprising the at least one donor cell, the population of cells comprising the at least one subject cell, the population of cells comprising the at least one intermediate cell, and/or the population of cells comprising the at least one target cell comprises one or more non-hematopoietic cells, mesenchymal stem cells, endothelial progenitor cells, hematopoietic stem cells, primitive hematopoietic stem cells, hematopoietic progenitor cells, differentiated hematopoietic cells, T—lymphocytes, natural killer cells, or combinations thereof.

Some embodiments pertain to a target cell prepared from the patient cell. In some embodiments, the target cell is non-senescent or has decreased senescent behavior, has increased innate immune function, increased telomere length, lower replicative stress relative to the patient cell, increased stem cell clonogenicity, increased cytotoxic function, increased mitogen- and antigen-induced lymphocyte proliferation and activation, decreased myeloid to lymphoid ratio, increased CD4 to CD8 T lymphocyte ratio, decreased expression of senescence-associated secretory proteins, and/or decreased expression of senescence- and aging-related genes.

Some embodiments pertain to a composition comprising a population of cells comprising the target cell prepared from the patient cell. In some embodiments, the composition comprises a pharmaceutically acceptable carrier. In some embodiments, pharmaceutically acceptable carrier comprises one or more of an aqueous solution, cell culture media, or an aqueous buffered solution. In some embodiments, the pharmaceutically acceptable carrier comprises an aqueous solution of sodium chloride. In some embodiments, the pharmaceutically acceptable carrier further comprises human serum albumin. In some embodiments, the sodium chloride is present at about 0.9% by weight and/or wherein the human serum albumin is present at about 0.5% by weight.

Some embodiments pertain to a method for treating or preventing age-related dysfunction, comprising administering the target cell prepared from the patient cell to the patient. In some embodiments, the dysfunction is age-related dysfunction. In some embodiments, the dysfunction is not an age-related dysfunction. In some embodiments, dysfunction includes one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, and Alzheimer's disease, leukemia, lymphoma, multiple sclerosis, Crohn's disease, HIV, influenza, pneumonia, lung cancer, melanoma, stroke, Parkinson's disease, multiple drug resistant *Staphylococcus aureus* (MRSA).

BRIEF DESCRIPTION OF THE DRAWINGS

FIGS. 3P1-3P30 depict the sequences for some embodiments of target genes, RNAi(s), and target proteins.

FIGS. 4A-E. Effect of young paracrine factors on aged hematopoietic and immune function. Total mononuclear cells (MNC) harvested from mobilized peripheral blood (MPB) of aged and young study donors, and umbilical cord blood (UCB) donors were measured for baseline levels of (A) CD45+ and (B) CD34+ cells, n=4. (C) Sustainability of aged cell restoration was measured by long-term culture-initiating cell (LTC-IC) assay. Aged cells from heterochronic and isochronic culture, and young controls, were harvested on days 3, 7, 10 and 15 of transwell culture and transferred to confluent monolayers of irradiated human stroma for long-term culture. At 6, 8 and 12 weeks after initial seeding, cells were harvested and evaluated by clonogenic assay for CFU-GM. (D) Baseline levels of HLA-DR was measured in aged, young and UCB donor samples, n=4. (E) To assess the immunogenic effects of heterochronic culture, the ability of restored aged cells to stimulate autologous naïve aged cells was measured by mixed lymphocyte reaction. Stimulation of naïve aged cells with young cells served as control, n=2. Results are presented as the mean±SEM. *p≤0.05 vs. control.

FIG. 5A-J. Effect of young paracrine factors on aged hematopoietic and immune function. (A) Total mononuclear cells (MNC) harvested from mobilized peripheral blood (MPB) of aged and young study donors, and umbilical cord blood (UCB) donors were measured for baseline hematopoietic differentiation by clonogenic assay. Results are presented as mean number of colony forming units—granulocyte, monocyte (CFU-GM), n=4. MPB cells from aged and young donors were also measured for baseline (B) oxidative stress and (C) cell-mediated cytotoxicity. Oxidative stress was measured by mitosox assay, and delineated into mitosox negative, low and high populations by flow cytometry. Cytotoxicity was quantified by flow cytometry to determine % target lysis at multiple effector to target ratios, with donor MNC as effector and K562 as target. (D) For assessing aged cell restoration by young paracrine factors, MNCs were co-cultured using a 0.4 um transwell insert to separate the aged (bottom chamber) and young (top chamber) cells. At select time points up to day 15, aged cells from heterochronic (aged/young) or isochronic culture (aged/aged), or young cells from isochronic culture (young/young) were harvested and evaluated for functional restoration by clonogenic assay (E). Cells harvested from heterochronic and isochronic control cultures at day 7 were evaluated for (F) clonogenicity, (G) oxidative stress and (H) cell-mediated cytotoxicity. For clonogenic assessment, restoration was compared among young and UCB heterochronic cultures and isochronic controls after 7 days. (I) To evaluate whether in vitro restoration can be propagated, aged and young cells from isochronic cultures (+iso aged, +young) or aged cells from heterochronic culture (+hetero aged) were harvested at day 7 and transferred to fresh transwell cultures with naïve aged cells. As control, naïve aged cells were also placed in isochronic culture (gray bar). After an additional 7 days, aged cells from the 2nd set of cultures were evaluated by clonogenic assay. (J) Part of each study donor LeukoPak MPB was separated into CD34+ and CD34− fractions during initial cell processing. To determine a role for young CD34+ cells in the mechanism of restoration, 7-day heterochronic cultures were setup with either CD34-purified (Y34+) or CD34-depleted (Y34−) young cells, and restoration measured by clonogenic assay. Results are presented as the mean±SEM, n=3, unless otherwise noted. *p≤0.05 vs. control.

FIG. 6A-G. Procedural and safety monitoring of huNSG mice. To determine the optimal dose for NSG engraftment, pilot study mice were transplanted with increasing doses of aged CD34+ cells and (A) initial engraftment, and (B) chimerism stability measured up to 20 weeks post-transplant. Human chimerism was determined by expression of huCD45 in blood. (C) Study design for huNSG aging cell restoration study. A total of 68 irradiated mice were transplanted with aged (n=56) or young (n=12) CD34+ cells, with 34 of 56 mice successfully engrafted with aged, and 12 of 12 mice successfully engrafted with young CD34+ cells. Chimerism cutoff for enrolling mice in the heterochronic and isochronic culture treatment arms was a minimum of 1% huCD45+ cells in blood. Mice displaying 0.5%-1% chimerism were enrolled in the saline treatment arms, and mice displaying <0.5% chimerism were not enrolled in the study at all. (D) Chimerism stability was monitored during the initial 19-week engraftment period and compared among individual aged donors (left plot) and among donor age group (middle plot). Chimerism stability after the 2nd transplant was monitored for 14 weeks up to study endpoint for all treatment groups (right plot). (E) Kaplan-Meier plot for huNSG overall survival (F) mouse body weights for the 14 weeks following the 2nd transplant are shown. Percent survival is displayed in the legend inset. (G) Mouse spleen weights at study endpoint, with spleen images in legend inset. Results are presented as the mean±SEM. *p≤0.05 vs. control.

FIG. 7A-K. Creation of a humanized mouse model to evaluate restoration of the aging lymphohematopoietic system. (A) Humanized mouse study design. 6-week old female NSG mice were sub-lethally irradiated and transplanted with human aged or young CD34+ cells. After 19 weeks to allow for engraftment and sustained human hematopoiesis, mice were transplanted with autologous, CD3-depleted cells from 7-day heterochronic (Aged+Rest, n=12) or isochronic control cultures (Aged+Non-Rest, n=11; Young, n=8). 14 weeks after the second transplant, mice were sacrificed and tissues harvested. (B) Bone marrow (BM) and blood was measured for human leukocyte chimerism by expression of huCD45 in all treatment groups. Mice humanized with cells from aged donors A01 and A02, and young donor Y01, were given the nomenclature huNSG-donor ID. huCD45+ cells from blood were probed for (C) human CD3 and (D) human CD33, and from BM for (E) human CD34. To determine changes in immune phenotype metrics related to aging, the ratio of (F) CD4+ to CD8+ human leukocytes in blood, and (G) lymphoid (CD3++CD19+) to myeloid (CD33+) human leukocytes in BM and blood were determined. (H) BM was harvested and colony forming ability measured by clonogenic assay. Colony formation from BM of non-humanized mice served as background control. (I) MNC were isolated from blood and cultured ex vivo in the absence (unstimulated, left graph) or presence (stimulated, right graph) of CD3/CD28-conjugated beads. After 72 h, human leukocytes were measured for CD4+ and CD8+ T cell activation by expression of the activation marker CD25. (J) Blood plasma from huNSG receiving restored or non-restored cells was isolated and the expression of 68 known senescence-associated secretory factors (SASFs) measured by custom protein array. Semi-quantitative densitometry was utilized to perform expression analysis, with a 1.5-fold cutoff for classifying up- or down-regulation, or no change. (K) Engrafted human cells were purified from mouse BM, and RNA isolated for gene expression studies evaluating 145 genes related to human senescence and aging by qPCR. Results were normalized to housekeeping genes and differential expression determined, with a 1.5-fold cutoff for classifying up- or down-regulation, or no change. Differential gene and protein expressions are represented by heatmap in J and K. Results are presented as the mean±SEM, unless otherwise noted. *$p \leq 0.05$ vs. control.

FIG. 8A-B. Histologic evaluation of tissues from huNSG treatment groups. At study endpoint, major organs and immune tissues were harvested. (A) H&E staining of mouse BM (top panels) and spleen (bottom panels), 10× magnification. (B) All harvested tissues were examined by a pathologist for tissue necrosis and tumorigenesis. Treatment groups were compared to age-matched control tissue for pathological comparison.

FIG. 9A-F. Phenotypic characterization of human hematopoietic and immune cells in huNSG immune tissues. Blood, BM and spleen from all treatment groups were harvested and measured for human leukocyte (huCD45+) populations, including (A) hematopoietic stem (CD34+38−) and progenitor cells (CD34+38+); (B) T cells (CD3+); (C) T helper (CD4+) and cytotoxic (CD8+) cells; (D) natural killer cells (CD3-56+); (E) B cells (CD19+); and (F) myeloid cells (CD33+). Results are presented as the mean±SEM.

FIG. 10A-C. Senescence- and aging-related gene and protein expression in huNSG treatment groups. (A) Scatterplots comparing senescence-associated secretory factor (SASF) expression in plasma of mice transplanted with either aged restored (left plot) or non-restored (right plot) cells compared to young. Values are normalized by background subtraction of SASF levels in non-humanized control NSG mice. Results are presented as mean densitometry units, with description of upregulated, downregulated and no change in expression SASFs listed in (B). (C) List of aging- and senescence-related genes whose expression is upregulated, downregulated or no change in human cells isolated from huNSG BM. Classifications in B and C are based on a 1.5-fold change cutoff.

FIG. 11A-F. Characterizing exosomes and exosomal miRNAs in heterochronic and isochronic cultures. (A) Nanoparticle tracking analysis (NTA) of exosomes isolated from 7-day heterochronic and isochronic cultures at day 3 and day 7. Effect of the AGO2 inhibitor, BCI-137, on exosome (B) production, (C) total (left panel), small (right panel) and (D) micro RNA content in heterochronic culture. Enrichment of exosomal miRNAs in cultures without inhibitor vs. with inhibitor is depicted by scatterplot in D with a 1.5-fold change cutoff. (E) Ingenuity Pathway Analysis (IPA) of commonly expressed miRNAs that are differentially expressed (1.5-fold cutoff) in exosomes of young vs. aged isochronic cultures. (F) Validation of miFinder qPCR array by individual qPCR experiments in array (left panels) and fresh donor samples (right panels). Gating scheme depicts miRNAs that are upregulated in young isochronic and heterochronic vs. aged isochronic cultures. Results are depicted by scatterplot with 1.25-fold and 1.05-fold cutoffs in array and fresh donor samples, respectively. Array and individual qPCR studies were normalized to RNU6, SNORD68 and SNORD95 and presented as fold change, with a value of 1 representing control.

FIG. 12A-G. Ascribing a role for exosomes in the mechanism of cellular restoration. (A) Exosomes were isolated from 7-day heterochronic and isochronic control cultures on day 4 and day 7, and then pooled and quantified by nanoparticle tracking analysis (NTA), n=4. (B) Pooled exosomes from A were added to fresh aged isochronic cultures (middle bars) at a dose of 1×106 exosomes/culture on day 0 and again on day 4 of 7-day culture. Non-supplemented heterochronic and isochronic cultures served as control. After 7 days, cells were harvested and measured for CFU-GM by clonogenic assay. (C) Total RNA was extracted from exosomes from A and quantified to determine total RNA content/exosome, n=8. (D) The AGO2 inhibitor, BCI-137, was added to heterochronic cultures upon initial seeding (far right bar) and effect on clonogenicity was established compared to no inhibitor and control isochronic cultures. (E) 3D plots comparing 84 commonly expressed miRNAs among exosomes harvested from isochronic (left panel) and heterochronic cultures (middle and right panels) by qPCR. Results were normalized to housekeeping genes within the array, and are presented as fold difference, with a value of 1 representing no change. (F) Venn diagrams illustrate expression of 68 of 84 commonly expressed miRNAs in exosomes isolated from all cultures. Overlapping areas represent miRNAs with less than 1.5-fold difference among groups. 25 of 68 expressed miRNA show no change among all groups. (G) Among exosomal miRNAs that were differentially expressed, only miR-19a, miR-103a, miR-106b and miR-146a were consistently upregulated in both young isochronic cultures and heterochronic cultures (striped bar). Results are presented as the mean±SEM, n=3, unless otherwise noted. Array and individual qPCR studies were normalized to RNU6, SNORD68 and SNORD95 and presented as fold change, with a value of 1 representing control. *$p \leq 0.05$ vs. control.

FIG. 13A-H. Characterizing the young intracellular miRnome and ascribing a role for miRNAs in the mechanism of restoration. (A) Small RNA was purified from aged, young and UCB isochronic cultures for whole miRnome sequencing. All miRNAs exhibiting greater than 100 mappable reads were further analyzed. Differential RNA expression is denoted by heatmap, with miRNA exhibiting greater than 1.4-fold difference among aged vs. UCB and young samples tabulated. Outer area of the Venn diagrams depicts total number of intracellular miRNAs with greater than 100 mappable reads in age-matched isochronic samples. Overlapping areas represent common miRNA among samples. (B, C) Similar studies as in A were carried out comparing miRNAs sequenced from aged isochronic and heterochronic (young-aged, UCB-aged) samples. (D) miRNA showing differential expression from A were compared to miRNA showing increased or decreased expression in heterochronic (aged-young) vs. aged isochronic cultures in B and C, and results tabulated to illustrate candidate miRNAs whose expression patterns are coincident with aged cell restoration. (E) Scatterplot depicting linear correlation between exosomal miR-7641-2 expression and total mappable reads, n=10. (G) Expression of early exosomal candidate miRNAs from miFinder array studies in sequencing dataset. Results are shown for isochronic and heterochronic cultures as average reads per 10000 total mapped reads. (H) To evaluate whether candidate exosomal miRNAs can be propagated after aged cell restoration, aged and young cells from 7-day isochronic cultures or aged cells from heterochronic culture were harvested at day 7 and transferred to fresh transwell cultures with naïve aged cells for an additional 7 days. On the 3rd (day 10) and 7th (day 14) day of the propagation culture, exosomes were isolated and probed for candidate miRNA expression by qPCR. Results were normalized to miR-7641-2 expression and presented as fold change, with a value of 1 representing control (gray bars). Results are presented as the mean±SEM, n=3, unless otherwise noted. *p≤0.05 vs. control.

FIG. 14A-K. Characterizing the young exosomal miRnome and ascribing a role for miRNAs in the mechanism of restoration. (A) Exosomes were isolated from aged, young or UCB isochronic cultures and small RNA purified for whole miRnome sequencing. All miRNAs exhibiting greater than 100 mappable reads were further analyzed. Differential RNA expression is denoted by heatmap, with miRNA exhibiting greater than 1.4-fold difference among aged and young samples tabulated. Outer area of the Venn diagrams depicts total number of exosomal miRNA with greater than 100 mappable reads in age-matched isochronic samples. Overlapping areas represent common miRNA among samples. (B, C) Similar studies as in A were carried out comparing miRNAs sequenced from exosomes of aged isochronic and heterochronic (young-aged, UCB-aged) samples. (D) miRNA showing differential expression from A were compared to miRNA showing increased expression in heterochronic (aged-young) vs. aged isochronic cultures in B and C, and results tabulated to illustrate candidate miRNAs whose expression patterns are coincident with aged cell restoration. (E) Exosomes collected from heterochronic and isochronic cultures of different study donors were used to validate expression of candidate miRNA by individual qPCR. Results were normalized to miR-7641-2 and presented as fold change, with a value of 1 representing aged control. (F) 6 of 8 miRNA passing qPCR validation were tested for their ectopic ability to restore aged cell function by clonogenic assay. Candidate miRNA were tested alone (left panel) or in various combinations (right panel) vs. negative control RNA (black bars) and non-transfected control (NTC, gray bars). (G) miRNA formulations demonstrating significant improvement in aged clonogenicity were further evaluated for ability to enhance CD4+(top panels) and CD8+ (bottom panels) T cell activation in aged donors. Cells were stimulated with anti-CD3 and -CD28 (right panels), or unstimulated (left panels), and T cell activation measured after 72 h by expression of the activation marker CD25. (H) Formulations demonstrating a significant effect on T cell activation in G were finally evaluated for ability to boost cell-mediated cytotoxicity compared to control RNA (gray circles). To investigate whether miRNA candidates also have a role in young cell function, cells from young study donors were transfected with candidate anti-miRNAs, either alone (anti-619) or in combination (anti-619, -1303 and -4497), and effect on (I) clonogenicity, (J) T cell activation and (K) cell-mediated cytotoxicity as in F, G and H, respectively, were determined compared to anti-miR control RNA. Results are presented as the mean±SEM, n=3, unless otherwise noted. *p≤0.05 vs. control.

FIG. 15A-G. Identification of potential young exosomal miRNA targets in aged cells. (A) Up- and downregulated intracellular miRNAs comparing aged heterochronic (aged-young) vs. isochronic cultures with a 1.5-fold cutoff, and their (B) predicted activation/inhibition networks after IPA. Up- and downregulated (C) exosomal miRNAs comparing UCB vs. aged isochronic and (D) intracellular miRNAs comparing aged heterochronic (aged-UCB) vs. isochronic cultures with a 1.5-fold cutoff. (E) Illustration of the top cellular functions (left graph) and canonical pathways (right graph) predicted by (F) these networks are shown. (G) Validation of siRNA knockdown of target candidates in cells from aged donors. Results were normalized to β-Actin expression and presented as fold change, with a value of 1 representing control (scrambled siRNA). Results are presented as the mean±SEM, n=3, unless otherwise noted. *p≤0.05 vs. control.

FIG. 16A-L. Identification of exosomal miRNA targets that promote restoration of aged cells. (A) miRNA that were differentially expressed in young exosomes compared to aged, and intracellularly in aged hetrochronic vs. isochronic cultures, were analyzed by Ingenuity Pathway Analysis (IPA). Illustration of the top cellular functions (left graph) and canonical pathways (right graph) predicted by these networks are shown. (B) Radial depiction of the young exosomal-aged heterochronic intracellular interactome. p53 is at the center of the overlapping network predictions. Direct interactions among the networks are displayed. (C) The 6 qPCR-validated miRNAs from the sequencing studies were probed for potential targets using the TargetScan human database. A total of 6101 potential targets were evaluated, with number of common targets within the group of 6 miRNA displayed within the descending concentric circles. 25 targets were identified that met the conditions, either: (1) ≥4 common hits among the miRNA group, including miR-619 OR miR-1303; or (2) ≤3 common hits among the group, including miR-619 AND miR-1303. Predicted expression of these targets was analyzed by IPA and (D) the resulting network predictions compared to the young exosomal and aged heterochronic intracellular miRNA interactome. (E) Targets satisfying the above miRNA hit conditions were tabulated and pared down based on expression in relevant tissues (target gene encodes verified protein; expression not limited solely to neural tissue) and predicted interaction with the miRNA interactome to (F) yield 5 potential downstream targets for functional validation. (G) RNA collected from aged cells in heterochronic or isochronic culture (top plot), or human cells purified from BM of huNSG transplanted with restored or non-restored cells (bottom plot), was probed for expression of candidate targets by qPCR. Results were normalized to β-Actin and presented as fold change. (H) Basal expression of PAX5 and PPM1F in aged donor cells (light gray bars) was determined by qPCR, with results presented as fold change versus young donor expression, which were arbitrarily assigned a value of 1. (I) Aged donor cells were transfected with candidate pre-miRs or control RNA (first and second groups of bars from left) and young donors were transfected with candidate anti-miRs or control RNA (third and fourth group of bars from left), and effect on expression of PAX5 and PPM1F was determined by qPCR, with results presented as fold change versus control RNA (light gray bars), which were arbitrarily assigned a value of 1. (J) Effect of siRNA knockdown of PAX5 or PPM1F on T cell activation was performed for CD4+(top panels) and CD8+(bottom panels) populations. Percent activated vs. total T cells is presented (right panels) for each condition. (K) Aged cells were transfected with siRNA to target candidates, PAX5 or PPM1F, or scrambled siRNA control (light gray bar), and effect on clonogenicity measured compared to heterochronic (black bar) and isochronic (white bar) controls. (L) Target knockdown cells were finally evaluated for ability to boost cell-mediated cytotoxicity compared to control RNA (gray circles). Results are presented as the mean±SEM, n=3, unless otherwise noted. *p≤0.05 vs. control.

FIG. 17A-L. Application of the humanized model of the aging lymphohematopoietic system to test cell-free methods of restoring aged function. (A) Humanized mice were created as in FIG. 2A using 2 different aged (A03, A04) and young donors (Y03, Y04), with the exception that 15 weeks was allowed for engraftment and sustained human hematopoiesis. Aged CD34+-engrafted mice were then transplanted with autologous, CD3-depleted cells that had been transfected for 7 days with either miR-619 alone (n=18), a miR-combo of -619, -1303 and -4497 (n=18) or control RNA (n=18). 15 weeks after the second transplant, mice were sacrificed, and tissues harvested. (B) Bone marrow (BM) and blood was measured for human leukocyte chimerism by expression of huCD45 in all treatment groups. huCD45+ cells from blood were probed for (C) human T cell populations in blood (from left to right; CD3, CD4, CD8 and CD4/CD8 ratio). Data from all mice transfected with either miR formulation (619 alone or in combination) were pooled and compared to negative control for (D) human B cell populations (CD19) in BM and blood, and (E) pan myeloid cells (CD33) and (F) lymphoid to myeloid ratio (CD3++CD19+/CD33+) in BM. (G) BM was harvested and colony forming ability measured by clonogenic assay. Colony formation from BM of non-humanized mice served as background control. (H) MNC were isolated from blood and cultured ex vivo in the absence (unstimulated) or presence (stimulated) of CD3/CD28-conjugated beads. After 72 h, human leukocytes were measured for CD4+ and CD8+ T cell activation by expression of the activation marker CD25. (I) Engrafted human cells were purified from mouse BM, and RNA isolated to examine gene expression of target candidates, PAX5 (left bars) and PPM1F (right bars), by qPCR. (J) Isolated RNA was also probed for microarray studies evaluating 145 genes related to human senescence and aging by qPCR. Results were normalized to housekeeping genes and differential expression determined, with a 1.5-fold cutoff for classifying up- or down-regulation, or no change. (K) Blood plasma was isolated and the expression of 68 known senescence-associated secretory factors (SASFs) measured by custom protein array. Semi-quantitative densitometry was utilized to perform expression analysis, with a 1.5-fold cutoff for classifying up- or down-regulation, or no change. Differential gene (J) and protein expressions (K) are represented by heatmap (left panel), pie charts (top panels) and bar graphs (bottom panels). (L) Conditioned cell culture media from H were probed for cytokine expression using a human T-cell cytokine array. Semi-quantitative densitometry was utilized to perform expression analysis, with non-conditioned culture media used as control for background subtraction. Differential cytokine expression is represented by heatmap (left panel) and bar graphs (right panels) which normalized to unstimulated control. Results are presented as the mean±SEM, unless otherwise noted. *p≤0.05 vs. control.

FIG. 18A-G. Procedural and safety monitoring of humanized mice from the cell-free restoration study. (A) Study design for the cell free restoration study in humanized mice. A total of 170 irradiated mice were transplanted with aged (n=120) or young (n=50) CD34+ cells, with 54 of 120 mice successfully engrafted with aged, and 30 of 50 mice successfully engrafted with young CD34+ cells. Chimerism cutoff for enrolling mice in the control and treatment arms was a minimum of 1% huCD45+ cells in blood. Mice displaying 0.5%-1% chimerism were enrolled in the saline treatment arms (not shown), and mice displaying <0.5% chimerism were not enrolled in the study at all. (B) Bleeds were performed on mice transplanted with aged (A03 or A04) and young donor (Y03 and Y04) CD34+ cells, and chimerism evaluated at 9- and 15-weeks post-transplant. Average chimerism of the aged (top graph) and young (bottom graph) donors enrolled in the study are shown. (C) Kaplan-Meier plot for huNSG overall survival post-treatment and (D) mouse body weights for the 15 weeks following the 2nd transplant are shown. Percent survival is displayed in the legend inset. (E) Mouse spleen weights at study endpoint, with spleen images in legend inset. Total (F) spleen and (G) bone marrow cellularity at study endpoint are displayed. Results are presented as the mean±SEM.

FIG. 19A-B. Histologic evaluation of tissues from huNSG treatment groups in expanded study. (A) At study endpoint, major organs and immune tissues were harvested. (A) H&E staining of mouse spleen (top panels) and bone marrow (bottom panels), 4× magnification. (B) All harvested tissues were examined by a pathologist for tissue necrosis and tumorigenesis. Treatment groups were compared to age-matched control tissue for pathological comparison.

FIG. 20A-C. Senescence- and aging-related gene and protein expression in huNSG treatment groups from expanded study. (A) Scatterplots comparing senescence-associated secretory factor (SASF) expression in plasma of mice transplanted with either aged+negative control (gray dot plot), aged+miR-619 or aged+miR-combo cells compared to young control. Values are normalized by background subtraction of SASF levels in non-humanized control NSG mice. Results are presented as mean densitometry units, with average total SASF expression among each group also shown for comparison (far right bar graph). Enumeration of SASFs upregulated, downregulated or not changed for miR-619 vs. control (left table) or miR-combo vs. control (right table) is listed in (B). (C) List of aging- and senescence-related genes whose expression is upregulated, downregulated or not changed in human cells isolated from huNSG BM in miR-combo treated mice vs. control. Classifications in B and C are based on a 1.5-fold change cutoff. Results are presented as the mean±SEM. *p≤0.05 vs. control.

21A-F. Comparative analysis of heterochronic- vs. miR-treated aged humanized mouse studies. To indirectly compare heterochronic- vs. miRNA-mediated cell restoration in the humanized mouse studies, data were normalized to non-restored isochronic control and negative RNA control mice, respectively. Results are presented as the mean±SEM with control values set to either 1 or 0. *p≤0.05 vs. control. Comparative data were presented for (A) human T cell populations in blood (from left to right; CD3, CD4, CD8 and CD4/CD8 ratio); (B) human B cell populations (CD19) in blood; (C) pan myeloid cells (CD33) and lymphoid to myeloid ratio (CD3++CD19+/CD33+) in BM; (D) colony forming ability measured by clonogenic assay; (E) aging (left graph) and senescence (right gray) arrays; and (F) SASP protein array.

22A-C. Cartoon depicting mechanism of cellular restoration. (A) Heterochronic transwell culture displaying young (top chamber) and aged (bottom chamber) cells in co-culture separated by a membrane containing 0.4 μm pores. Exosomes released by young cells penetrate the transwell pores and perfuse the aged cells in the bottom chamber. (B) The young exosomes fuse with the aged cell membranes to deliver their payload of RNA, DNA, lipids and proteins intracellularly to the aged cells. (C) Specific miRNAs that are elevated in the young cells, but not expressed basally by the aged cells (miR-619, -1303 and -4497), are delivered by the young exosomes into the aged cytoplasm where they selectively bind target mRNAs (PAX5, PPM1F) for translational repression. Both PAX5 and PPM1F have downstream targets that are involved in cellular senescence, including p53 and p21.

Figure 23:
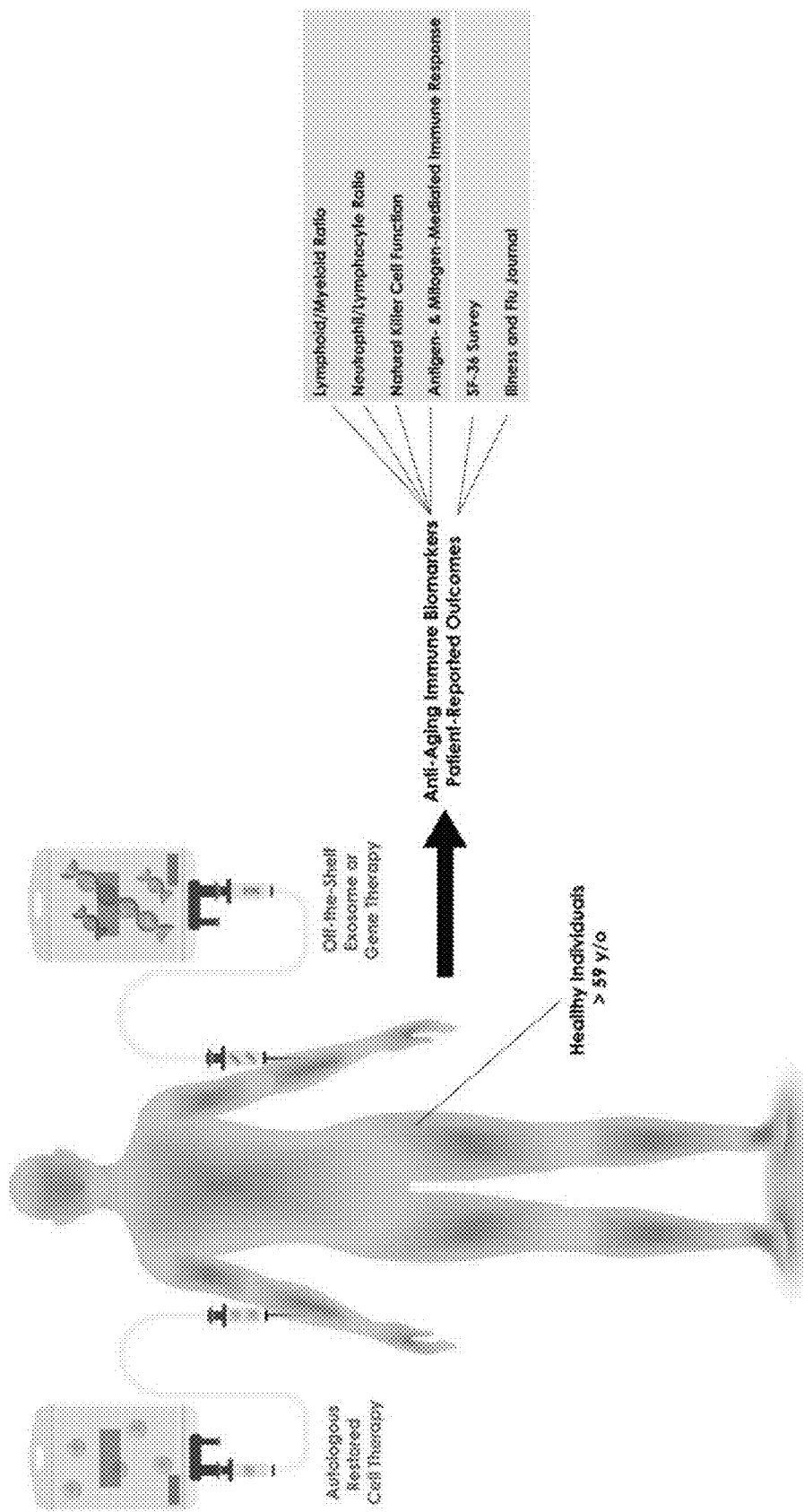

FIG. 23. Cartoon depicting clinical implementation of restoration technology. Two adoptive, autologous immune restoration therapies have been modeled in humanized mice, which could be translated to human studies. Studies would utilize aged, healthy individuals >59 y/o who had previously undergone stem cell mobilization and banking. Patients would be administered an autologous cell therapy utilizing either young cells (left) or an off-the-shelf biologic (right) as the restorative agent. Patients' immune function would be tested before and after treatment to assess safety and efficacy using a number of biomarker-based assays and patient reported outcomes.

Figure 24A:
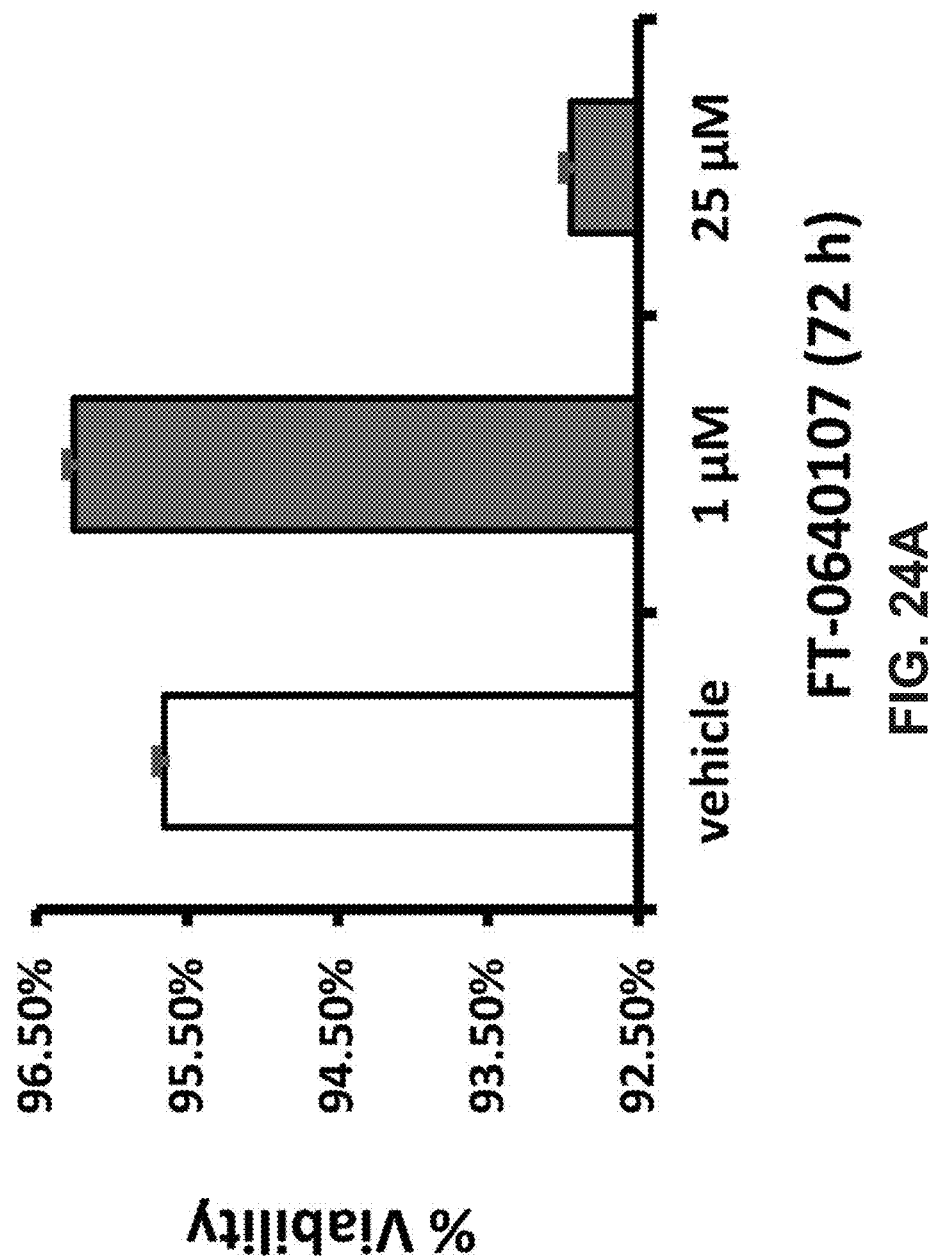
Figure 24B:
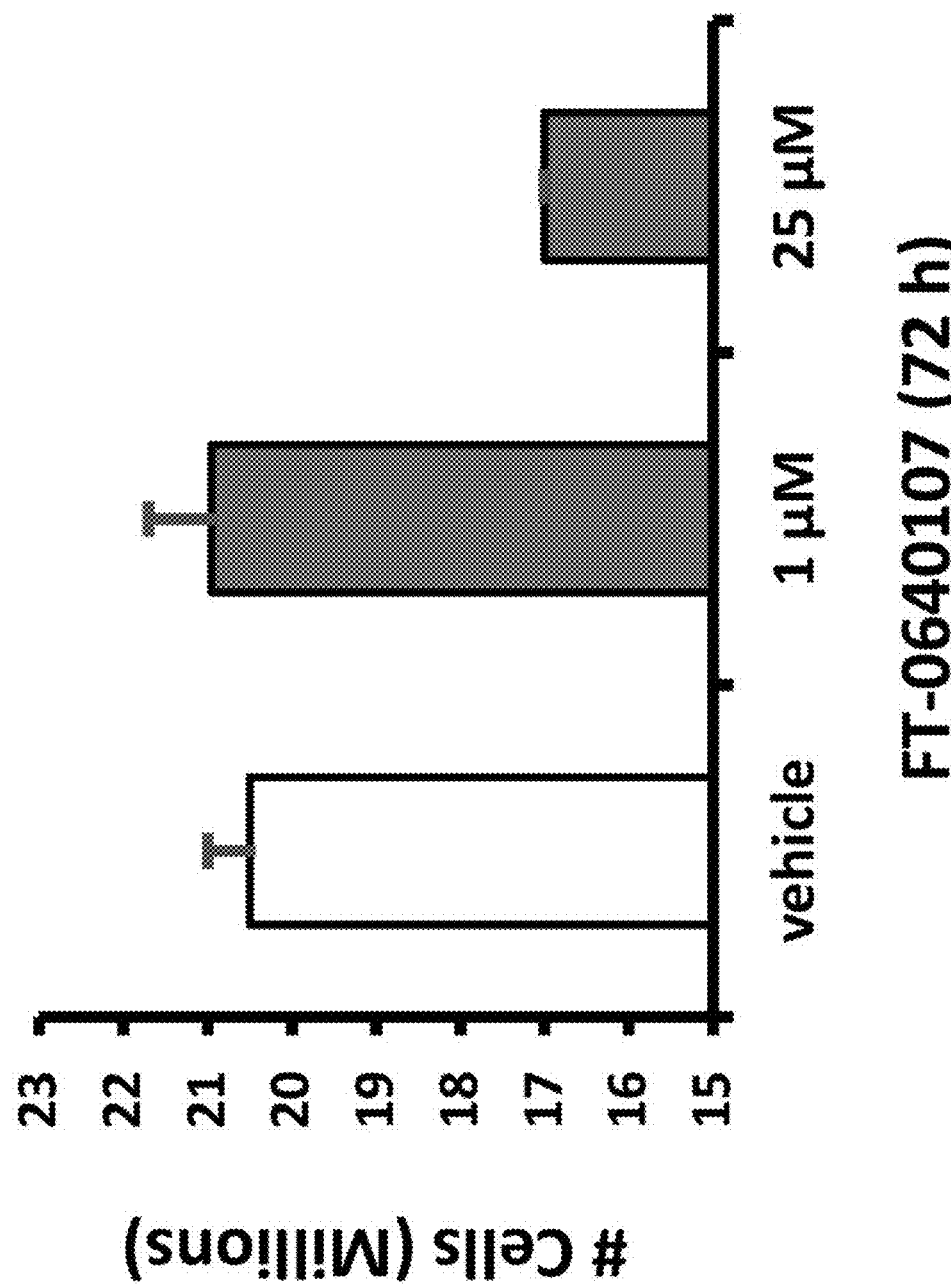

FIG. 24A-B show viability and cell number data for Example 3, respectively.

Figure 25:
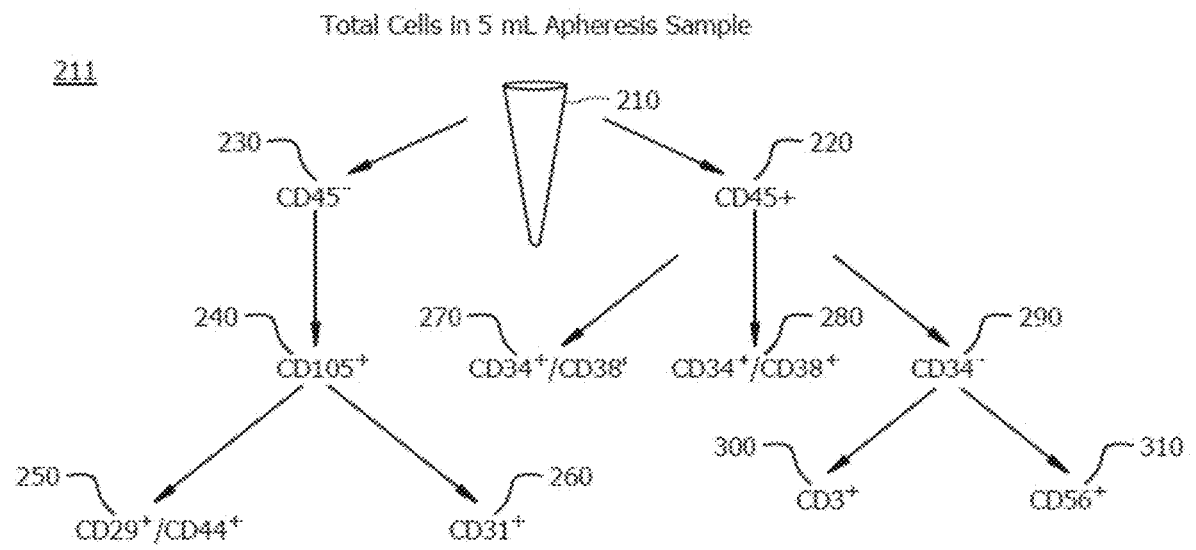

FIG. 25 is a depiction of an embodiment for immunophenotyping a cell sample.

Figure 26:
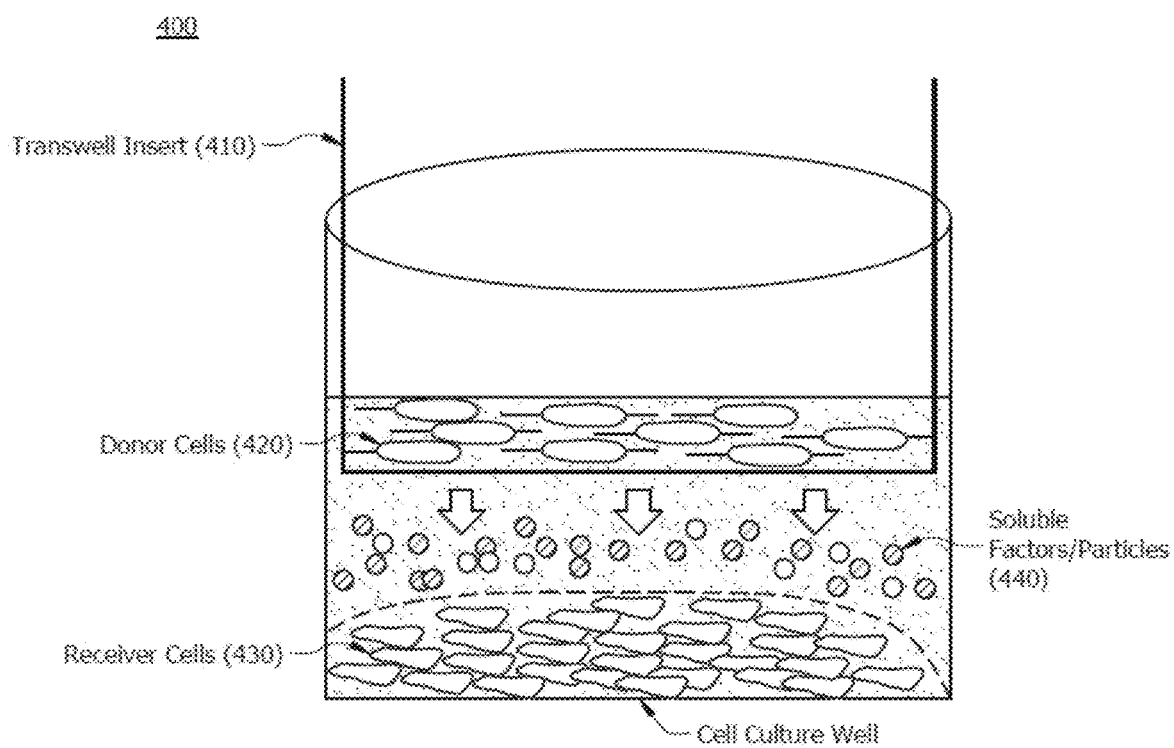

FIG. 26 is a depiction of an embodiment of a transwell co-culture experimental apparatus.

Figure 27:
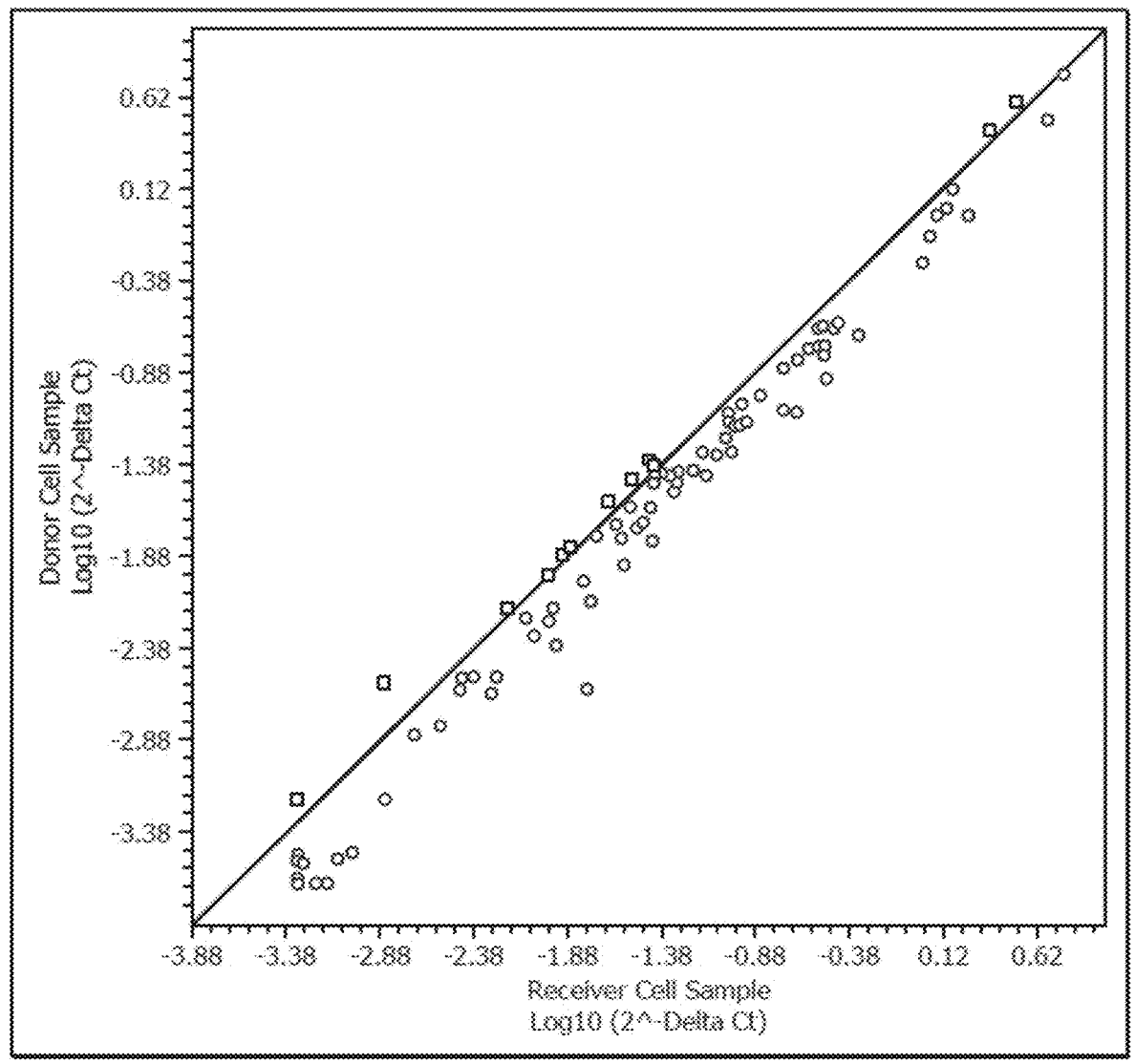

FIG. 27 is a plot of a gene expression analysis for donor cell samples and receiver cell samples.

Figure 28:
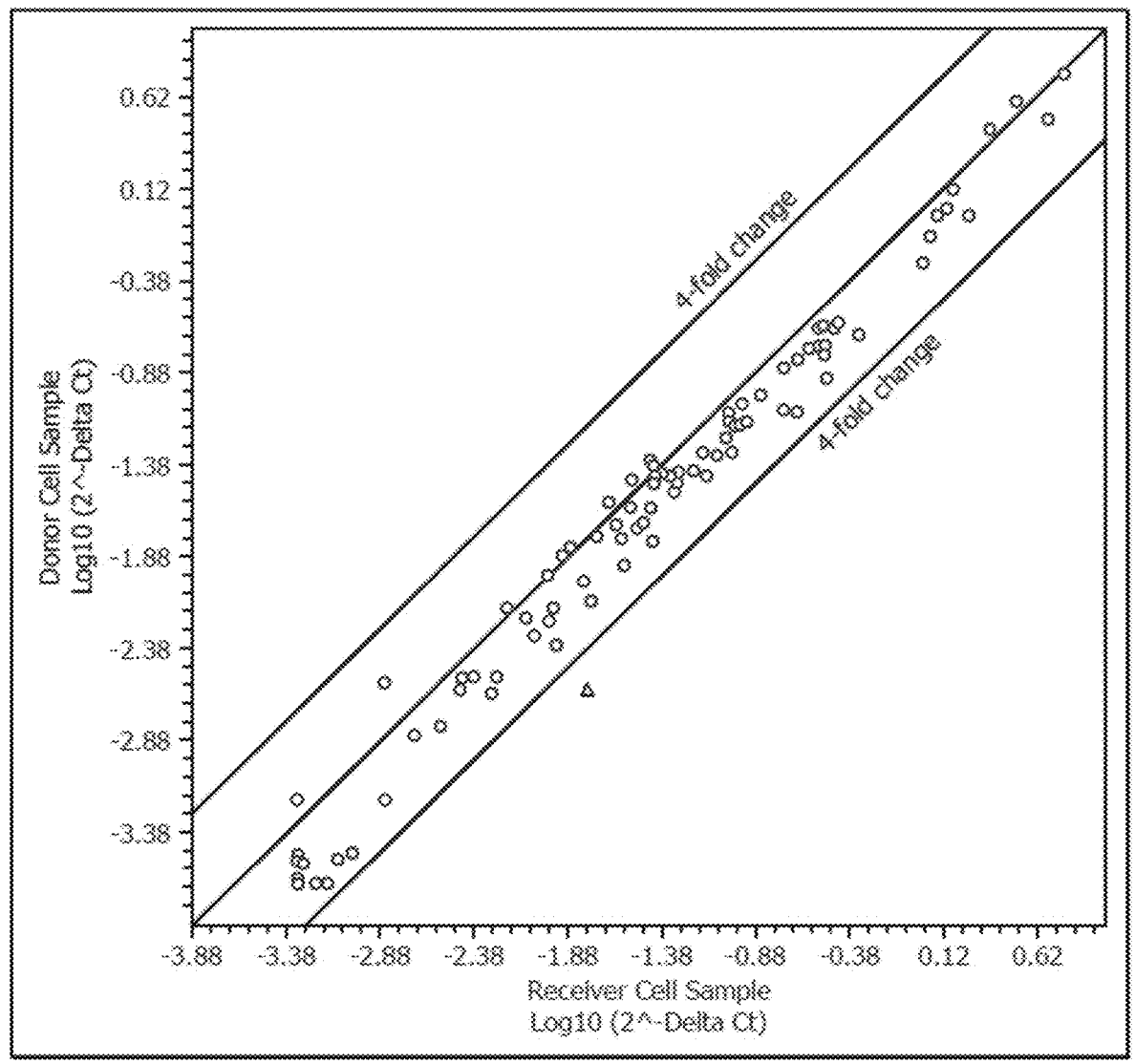

FIG. 28 is a plot of a protein expression analysis for donor cell samples and receiver cell samples.

Figure 29A:
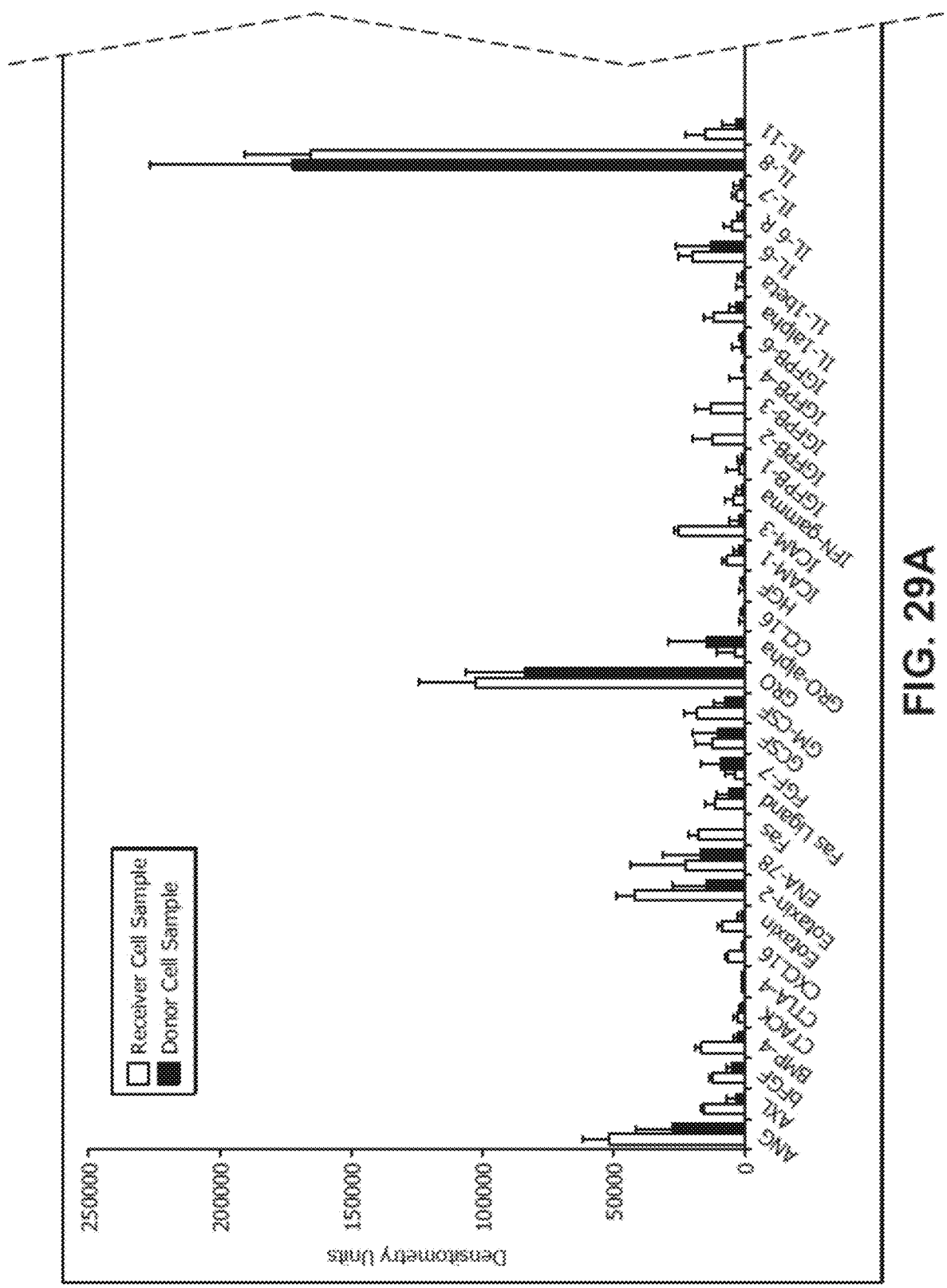

FIGS. 29A and B are a plot of a level of expression of the indicated proteins for the donor cell samples and receiver cell samples.

Figure 30:
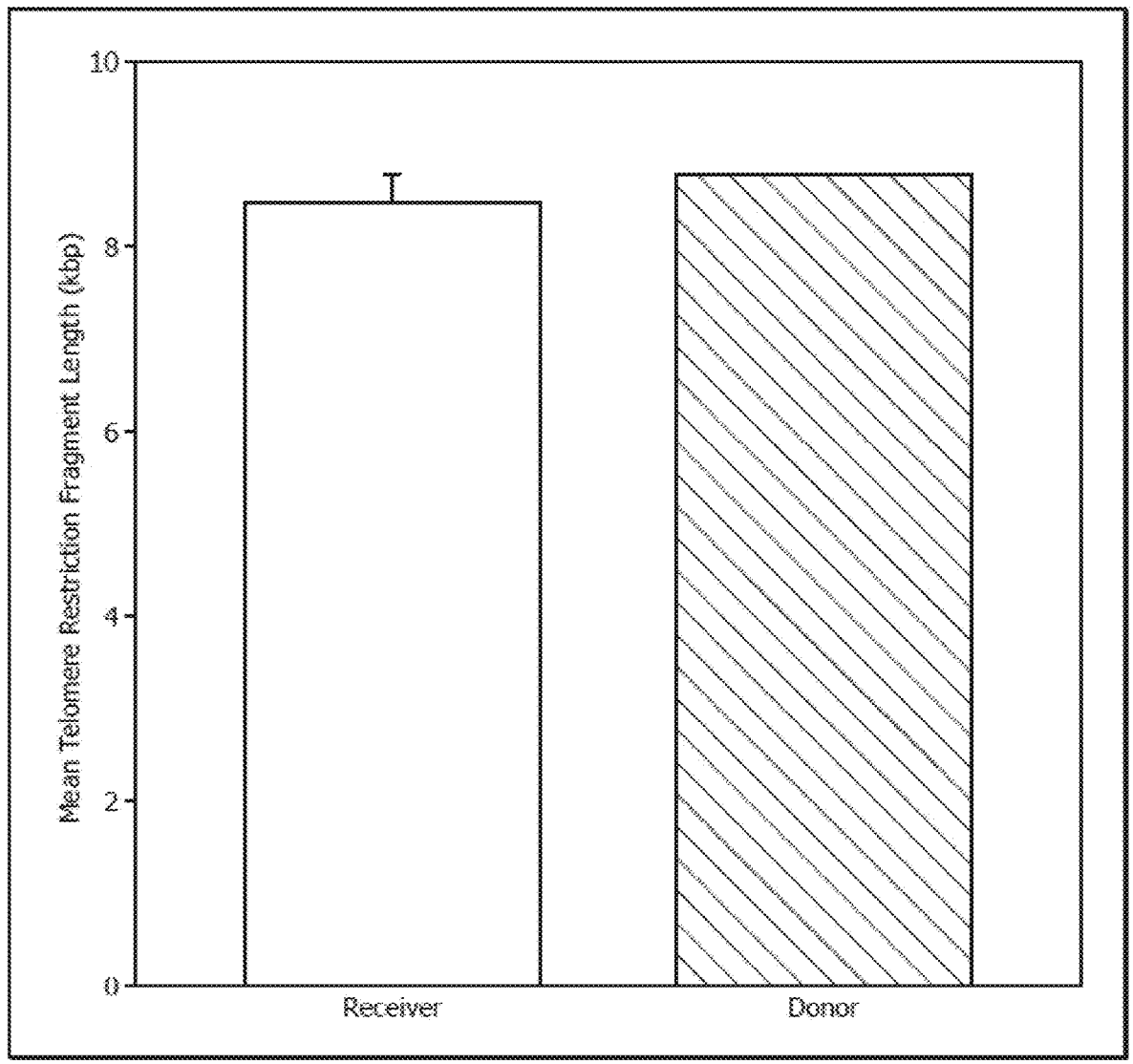

FIG. 30 is a plot of the average telomere length for the donor cell samples and receiver cell samples.

Figure 31:
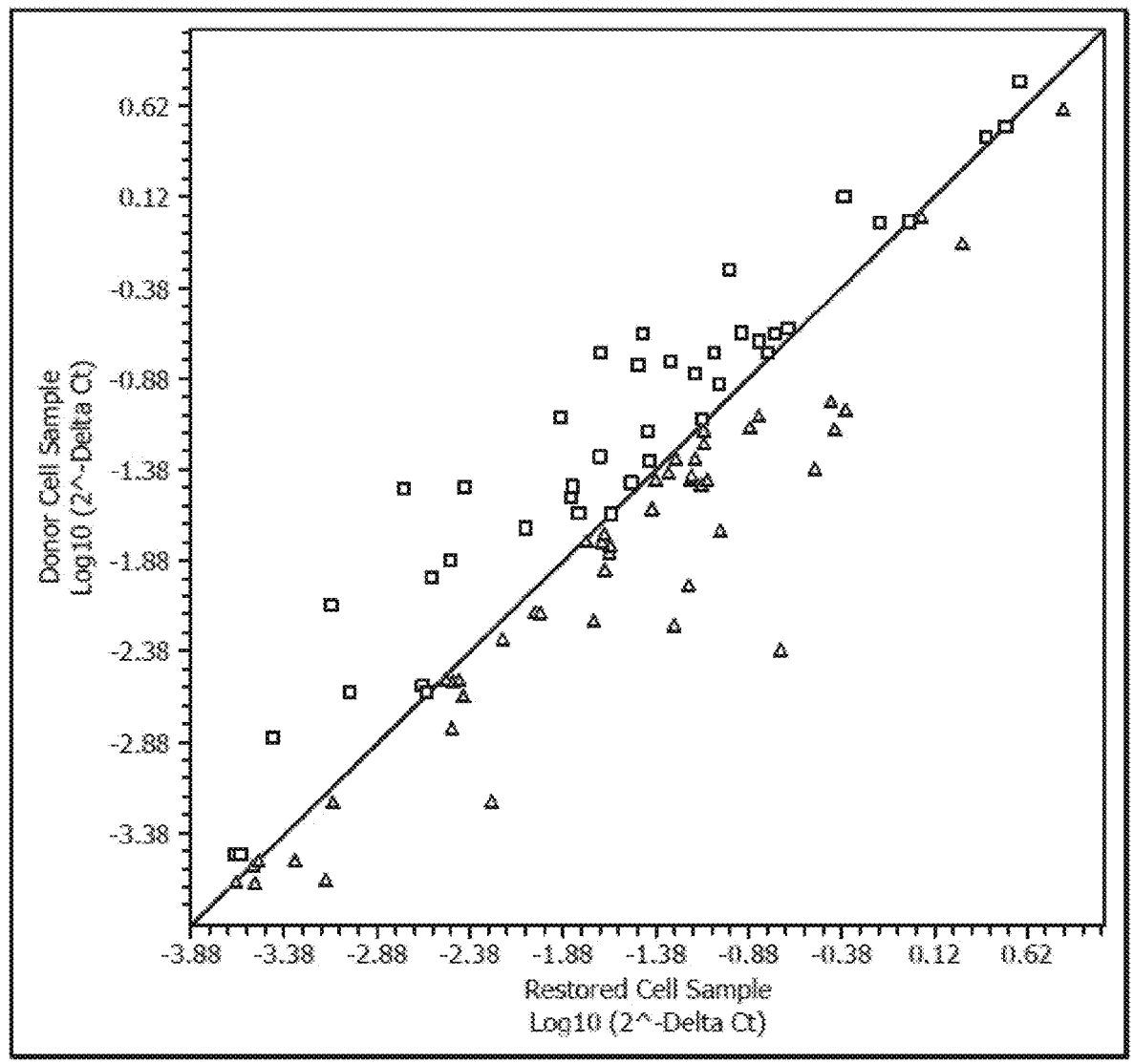

FIG. 31 is a plot of a gene expression analysis for baseline donor cell samples and restored cell samples.

Figure 32:
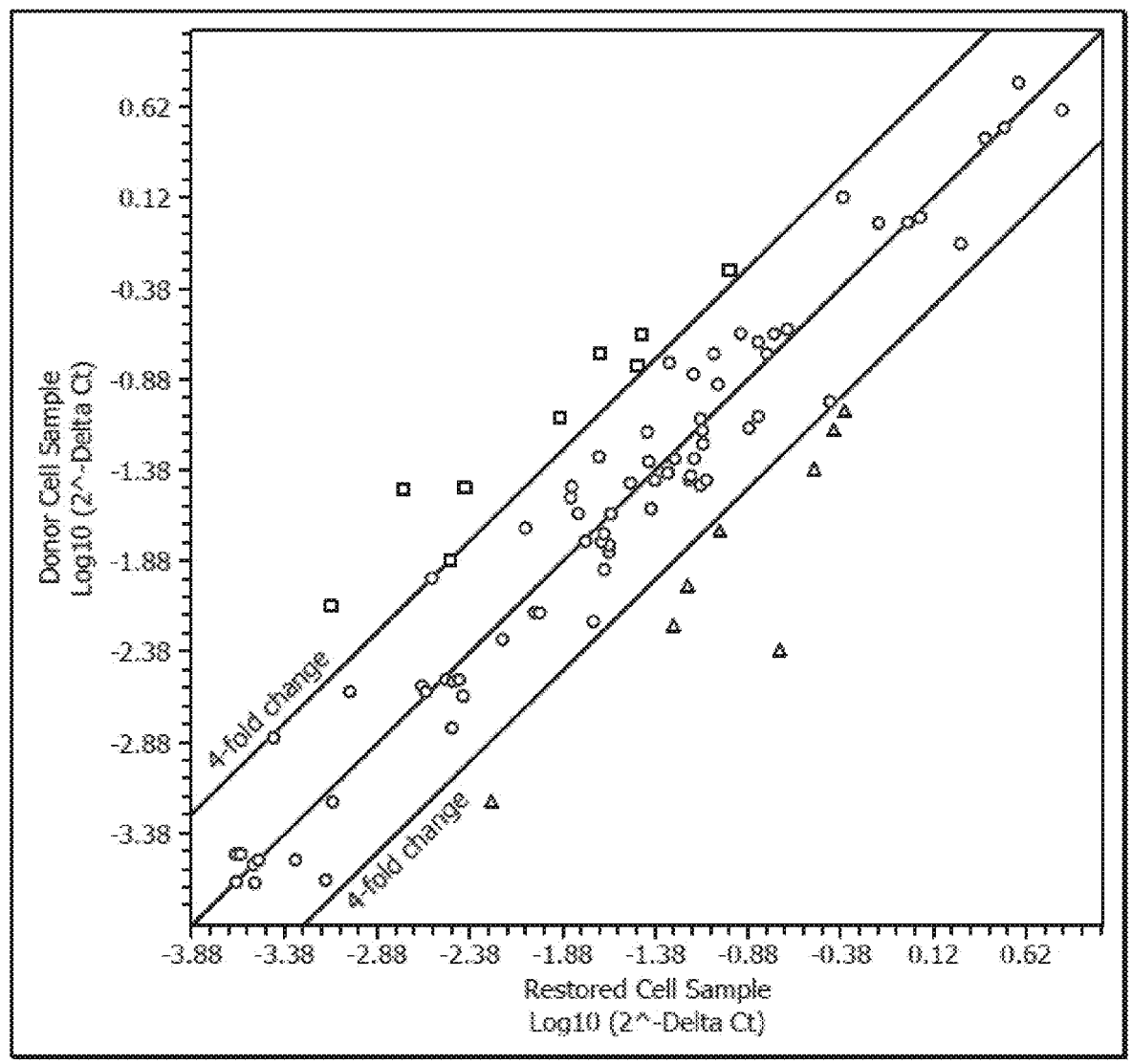

FIG. 32 is a plot of a protein expression analysis for baseline donor cell samples and restored cell samples.

Figure 33A:
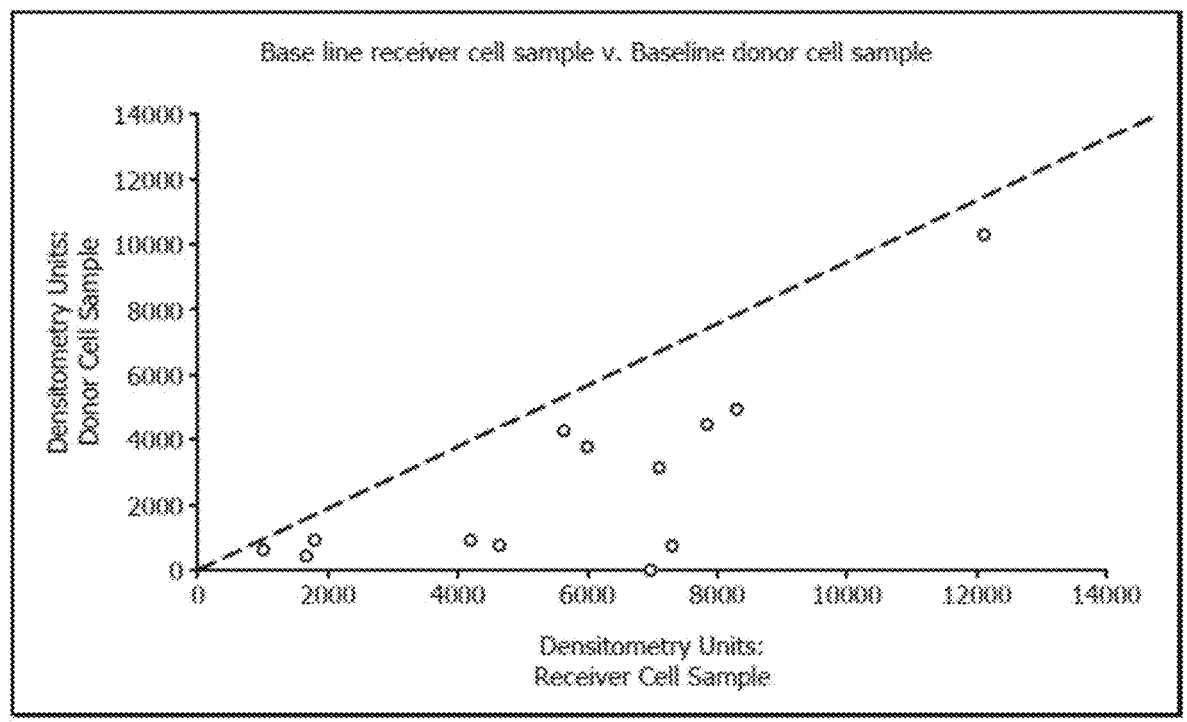

FIG. 33A is a plot of a protein expression analysis for baseline donor cell samples and baseline receiver cell samples.

Figure 33B:
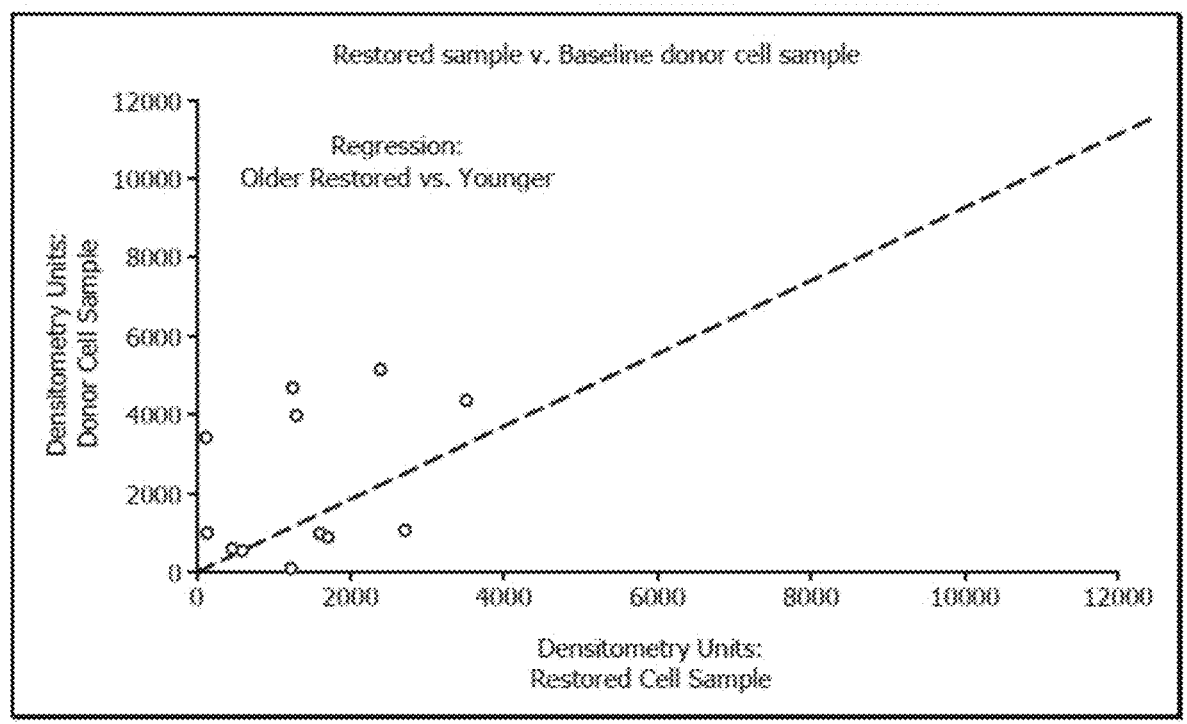

FIG. 33B is a plot of a protein expression analysis for baseline donor cell samples and baseline donor cell samples and restored cell samples.

Figure 34A:
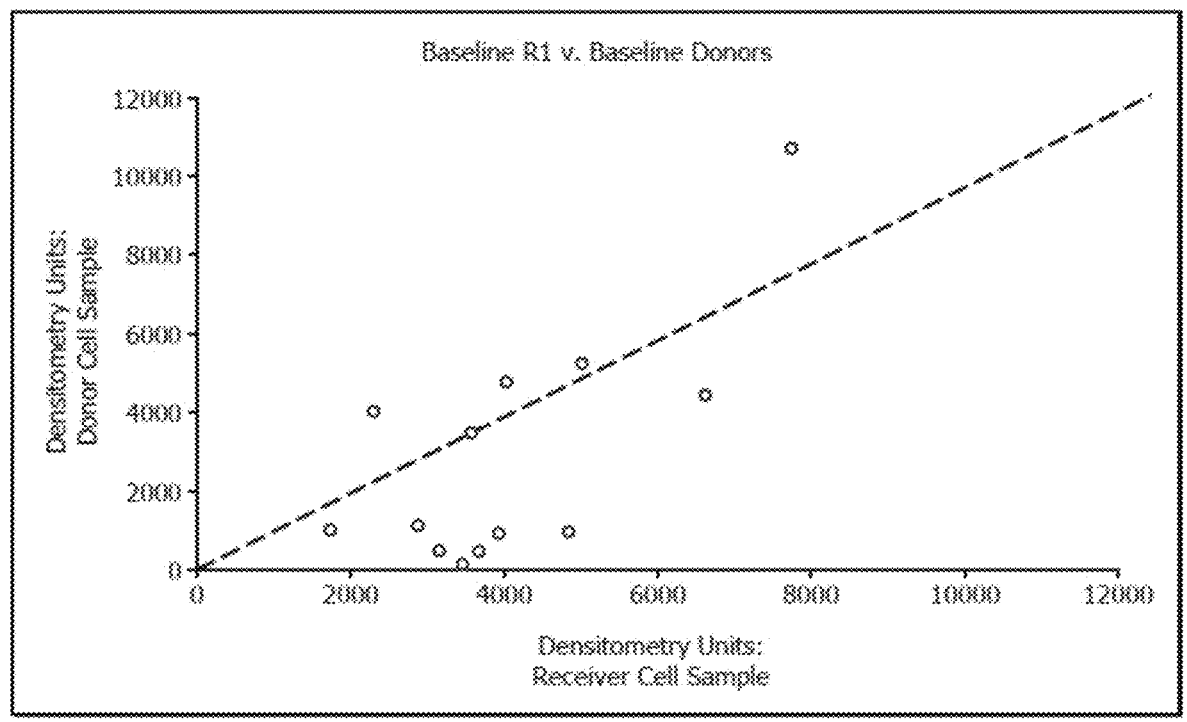

FIG. 34A is a plot of a protein expression analysis for the baseline donor cell sample and the baseline receiver cell sample R1.

Figure 34B:
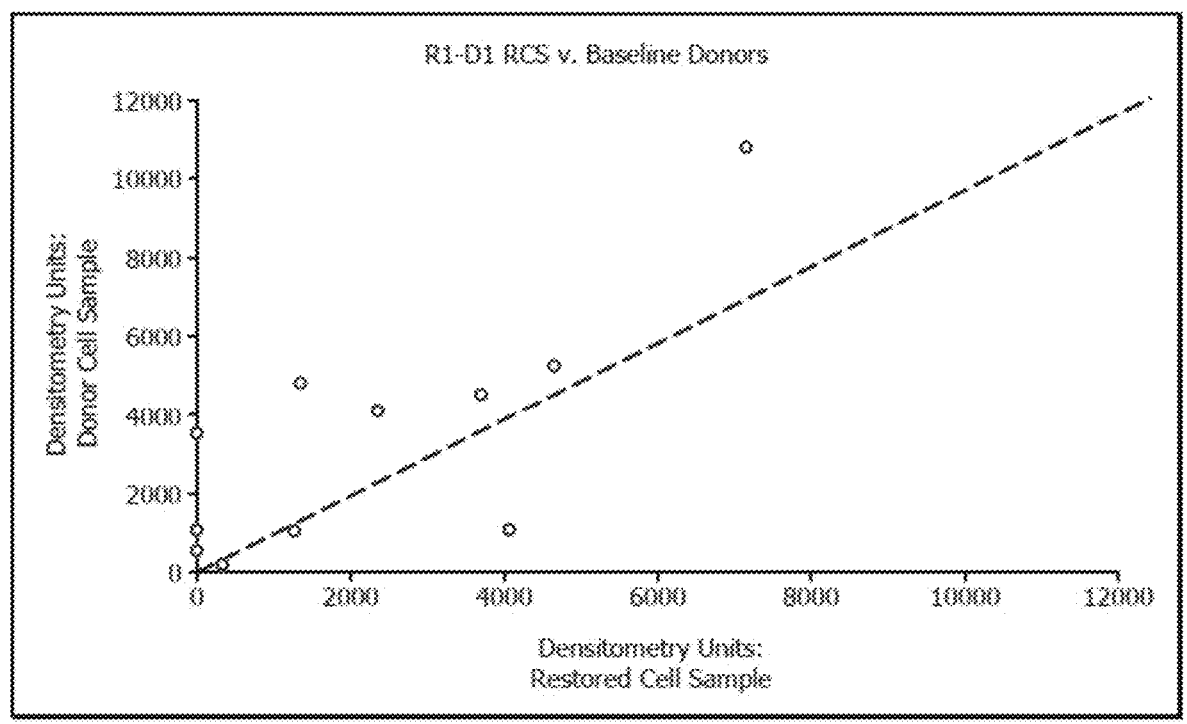

FIG. 34B is a plot of a protein expression analysis for the baseline donor cell sample and restored cell sample R1-D1.

Figure 34C:
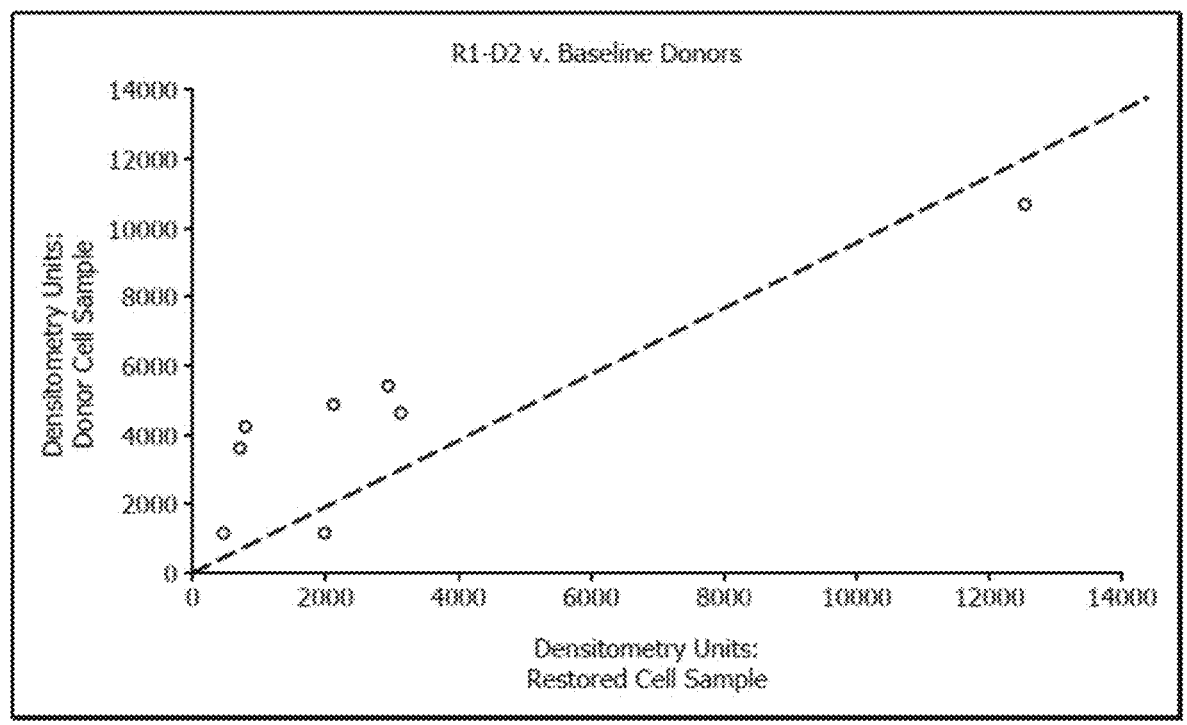

FIG. 34C is a plot of a protein expression analysis for the baseline donor cell sample and restored cell sample R1-D2.

Figure 34D:
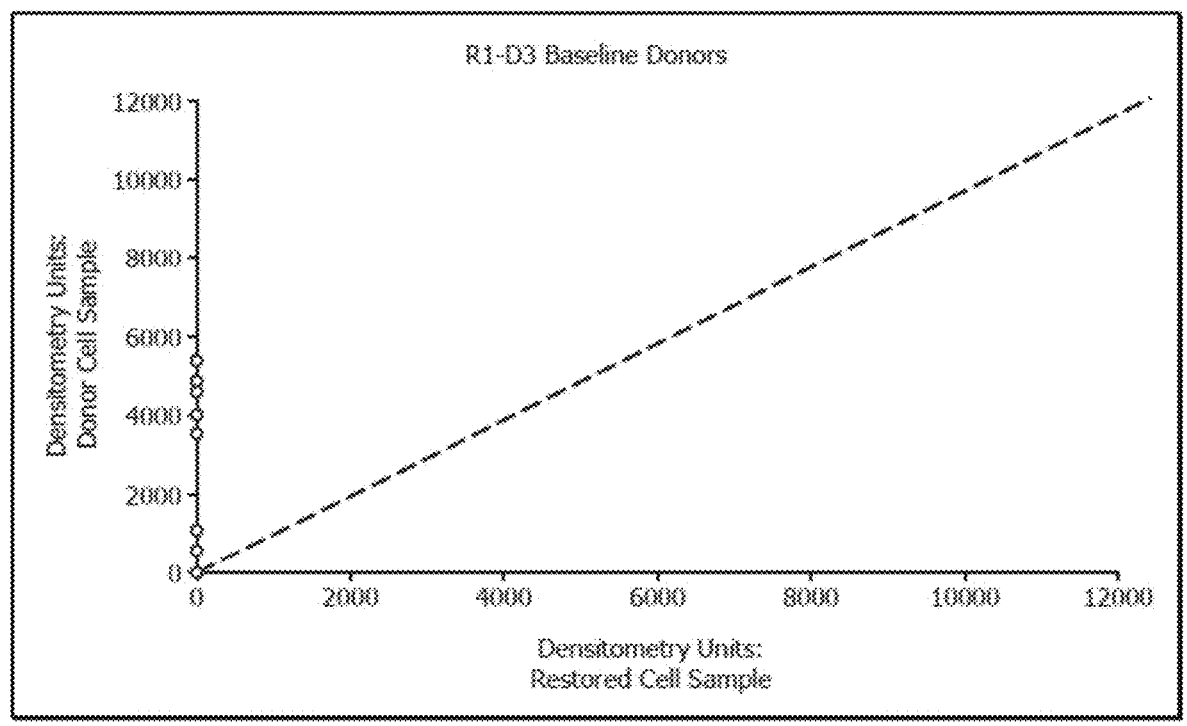

FIG. 34D is a plot of a protein expression analysis for the baseline donor cell sample and restored cell sample R1-D3.

Figure 35:
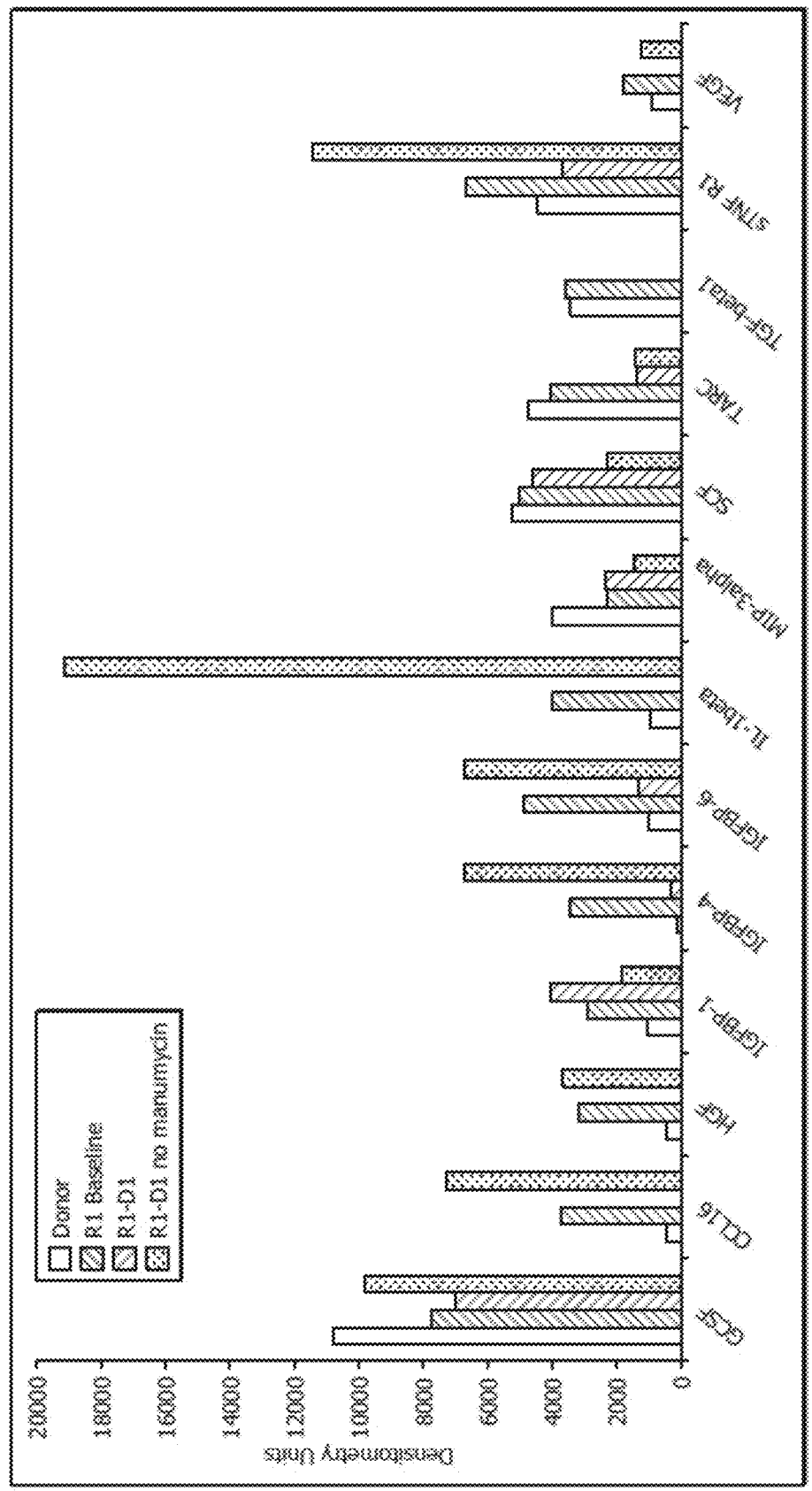

FIG. 35 is a plot of a level of protein expression in restored cells in the presence or absence of manumycin.

Figure 36:
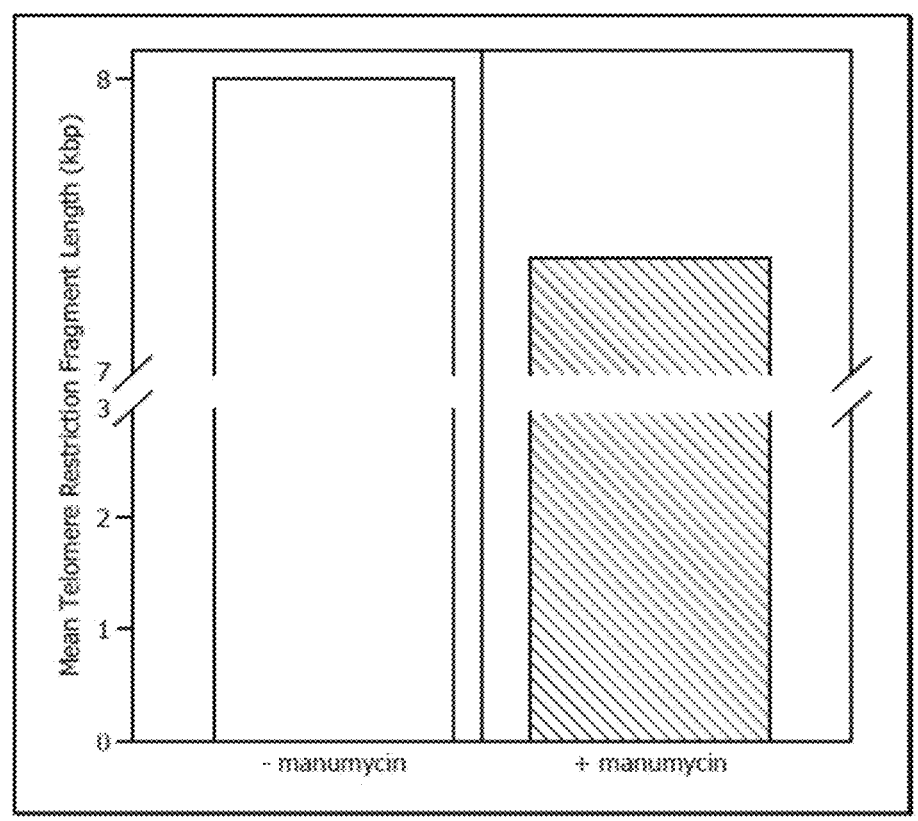

FIG. 36 is a plot of the telomere length for the restored cell sample from the donor cell sample-receiver cell sample pair R1-D1 in the presence or absence of manumycin.

Figure 37:
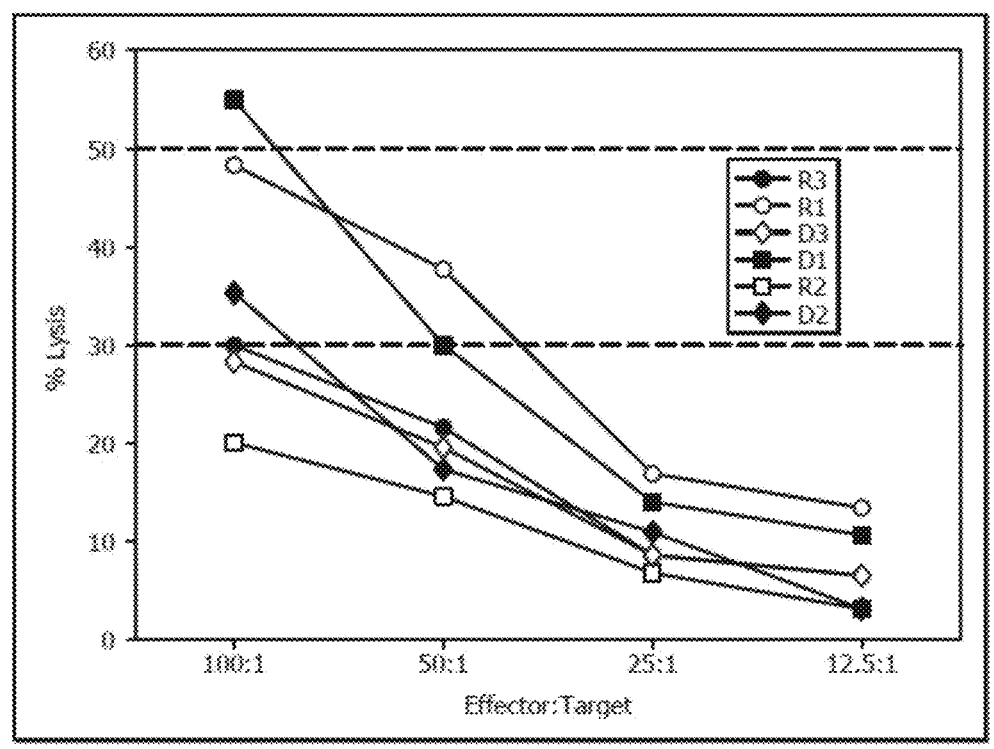
Figure 38:
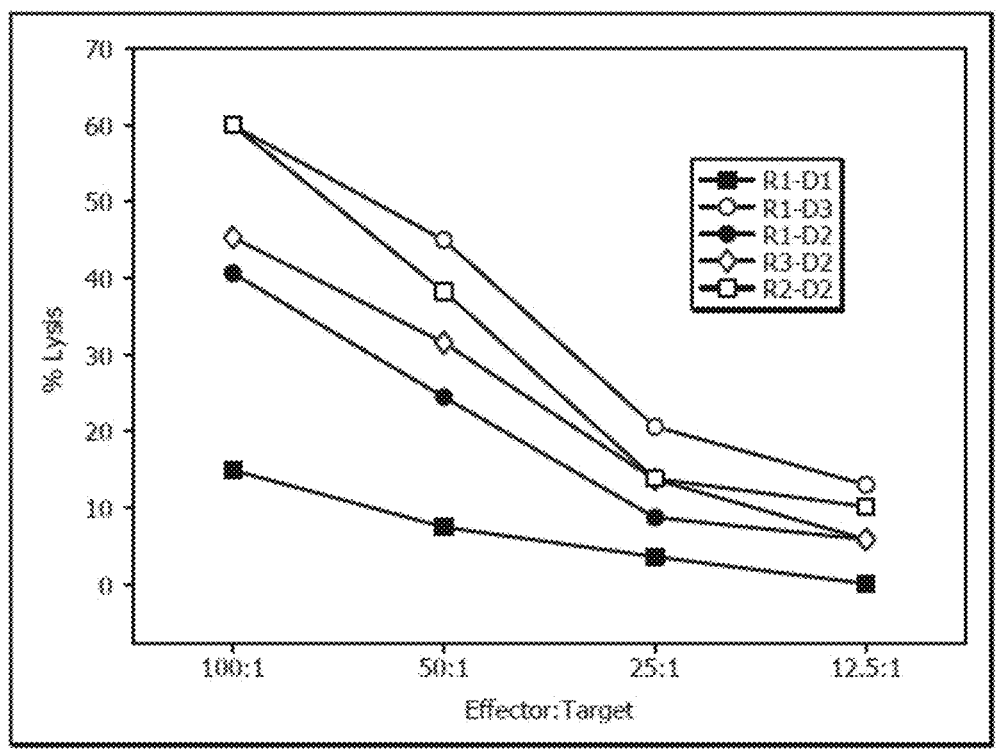

FIGS. 37 and 38 depict the results of the natural killer cell assay for the samples from Example 8.

Figure 39:
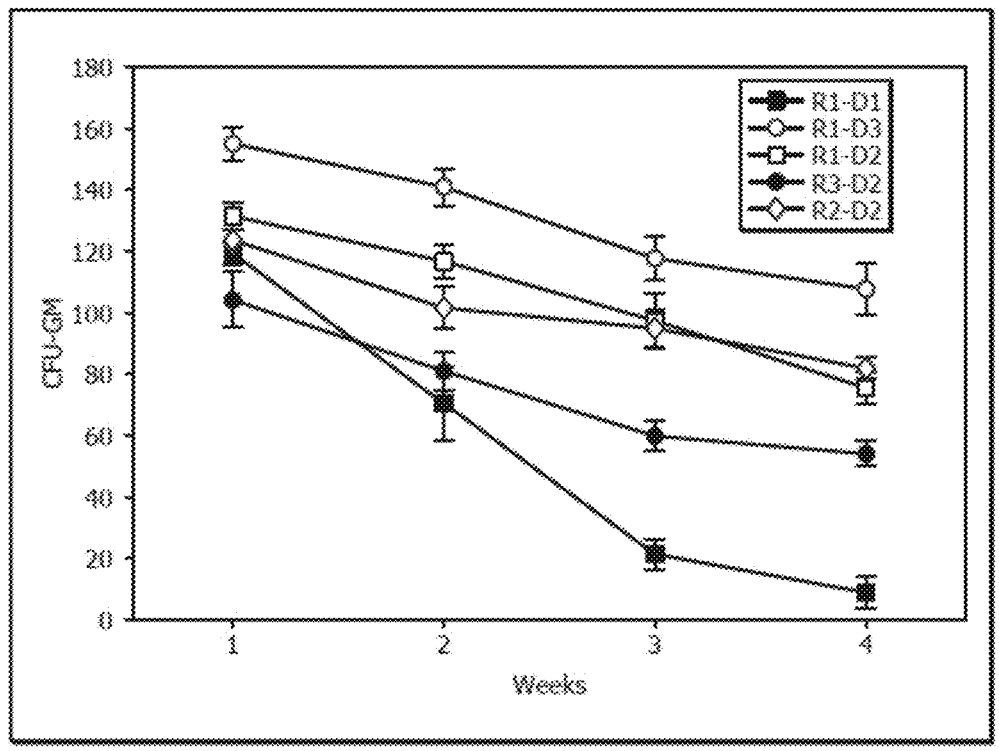

FIG. 39 depicts the results of the clonogenic assay for the samples from Example 8.

FIGS. 40A-D depict the results of a flow cytometry assay for the samples from Example 8.

Figure 41:
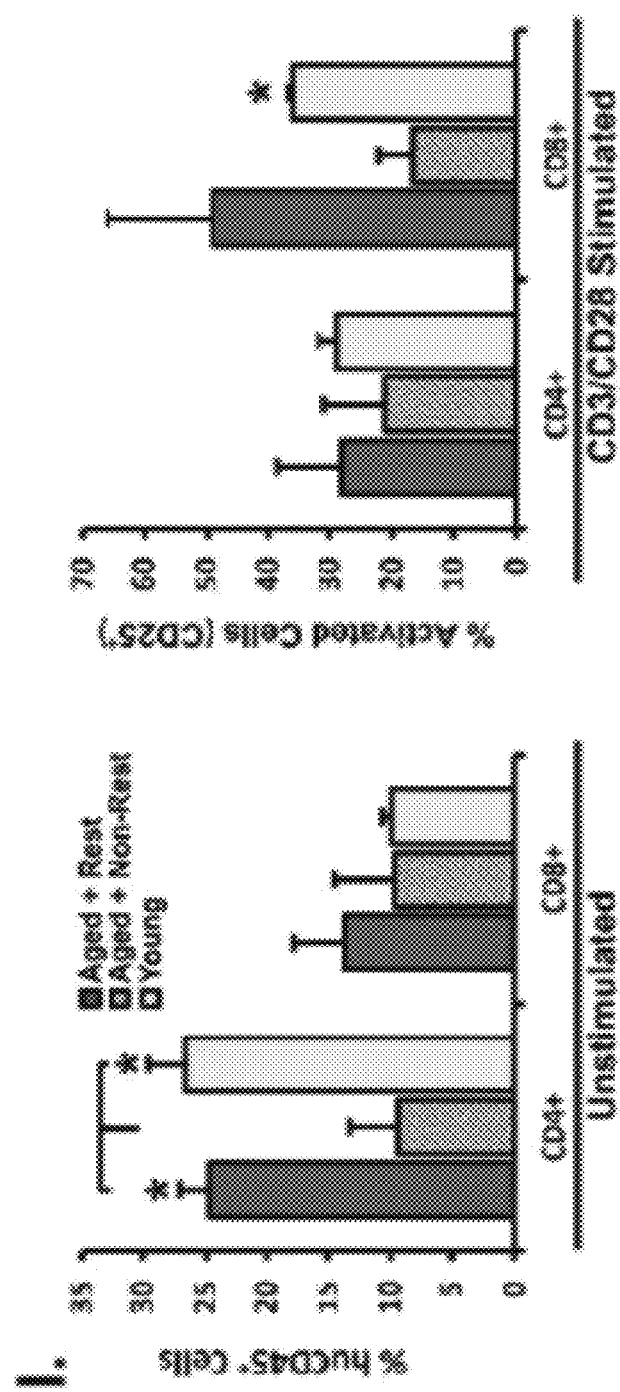

FIG. 41 depicts the results of a propagation of restoration experiment for the samples from Example 9.

DETAILED DESCRIPTION

Some embodiments disclosed herein provide polynucleotides, e.g., interfering polynucleotides, small molecules, which target the gene encoding the paired box 5 (PAX5) protein (e.g., as provided in, for example, any one of SEQ ID NOs:1-4), the gene encoding the protein phosphatase 1F enzyme (PPM1F) (e.g., as provided in, for example, any one of SEQ ID NOs:5-8), the gene encoding the calcium/calmodulin dependent protein kinase II gamma (CAMK2G) protein (e.g., as provided in, for example, SEQ ID NO:20), and/or that antagonize or disrupt the proteins themselves. In some embodiments, the polynucleotide agents bind to nucleic acids encoding one or more of PAX5, PPM1F, and CAMK2G via, e.g., Watson-Crick base pairing, and interfere with the normal function of the targeted nucleic acid. These methods and compositions including these interfering polynucleotide agents and compounds are useful for treating a subject who would benefit by a reduction in the levels or activity of a PAX5, PPM1F, and/or CAMK2G protein, such as a subject having a PAX5, PPM1F, and/or CAMK2G-associated disease, such as an age-related disease, cancer, an infectious disease, or the like as disclosed elsewhere herein. Some embodiments also provide methods and combination therapies for treating a subject having a disorder that would benefit from inhibiting or reducing the expression of a PAX5, PPM1F, and/or CAMK2G gene, e.g., a PAX5, PPM1F, and/or CAMK2G-associated disease. The combination therapies of the present invention include administering to a subject having a PAX5, PPM1F, and/or CAMK2G-associated disease, a polynucleotide as disclosed herein, a compound as disclosed herein, and/or an additional therapeutic agent suitable for treating the condition. Some embodiments disclosed herein pertain to a method of preparing target cells and/or the use of target cells for treating patients. In some embodiments, the cells have reduced expression of one or more of the PAX5, PPM1F, and/or CAMK2G gene.

The following description provides context and examples, but should not be interpreted to limit the scope of the inventions covered by the claims that follow in this specification or in any other application that claims priority to this specification. No single component or collection of components is essential or indispensable. For example, some embodiments may not include a fluid modifier. Any feature, structure, component, material, step, or method that is described and/or illustrated in any embodiment in this specification can be used with or instead of any feature, structure, component, material, step, or method that is described and/or illustrated in any other embodiment in this specification.

Terms

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human animals, including primates, cattle, sheep, goats, pigs, horses, cats, dogs, rabbits, rodents (e.g., rats or mice), monkeys, etc. Human subjects and patients include neonates, infants, juveniles, adults and geriatric subjects. The subject can be a subject "in need of" the methods disclosed herein can be a subject that is experiencing a disease state and/or is anticipated to experience a disease state, and the methods and compositions of the invention are used for therapeutic and/or prophylactic treatment. A subject can be a patient, which refers to a human presenting to a medical provider for diagnosis or treatment of a disease. A subject can be afflicted with or is susceptible to a disease or disorder but may or may not display symptoms of the disease or disorder. An aged patient or subject can be one having an age that is greater than or equal to about: 50, 60, 70, 80, 90, or ranges including and/or spanning the aforementioned values. A young subject or patient can be one having an age that is less than or equal to 30, 20, 10, or ranges including and/or spanning the aforementioned values.

The term "effective amount," as used herein, refers to that amount of a recited compound that imparts a modulating effect, which, for example, can be a beneficial or desirable effect (biological or clinical), to a subject afflicted with a disorder, disease or illness (or at risk of developing the same), including improvement in the condition of the subject (e.g., in one or more symptoms), delay or reduction in the progression of the condition, prevention or delay of the onset of the disorder, and/or change in clinical parameters, disease or illness, etc. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in age-related disease. In some embodiments, an improvement can be increase immune response in a subject. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein. In some embodiments, a "therapeutically effective amount" means a sufficient amount of the compositions disclosed herein to treat, prevent, and/or ameliorate one or more symptoms of the medical condition. It also may include a safe and tolerable amount of the compositions and/or agents disclosed herein, as based on industry and/or regulatory standards.

In some embodiments, the effectiveness of the compound is measured by the decrease in expression level of the protein of interest. For example, an effective decrease in expression can be at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc. As used herein, these can refer to a clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Those in need of treatment include those already affected by a disease or disorder or undesired physiological condition as well as those in which the disease or disorder or undesired physiological condition is to be prevented. In some embodiments, the subject is administered the compositions disclosed herein in a therapeutically effective amount sufficient for treating, preventing, and/or ameliorating one or more symptoms of a medical condition, disorder, disease, or dysfunction. Hereinafter, for simplicity, the unwanted condition which has been used interchangeably with the terms medical condition, disorder, disease, and dysfunction are collectively referred to as the "medical condition." As used herein, amelioration of the symptoms of the medical condition by administration of a particular composition of the type disclosed herein refers to any lessening, whether lasting or transient, which can be attributed to or associated with administration of compositions of the type disclosed herein. The term "treat" can also be used to denote a decrease in expression level of the protein in question.

As used herein, "pharmaceutically acceptable" refers to carriers, excipients, and/or stabilizers that are nontoxic to the cell or mammal being exposed thereto at the dosages and concentrations employed or that have an acceptable level of toxicity. A "pharmaceutically acceptable" "diluent," "excipient," and/or "carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" can refer to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A non-limiting example of a physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as TWEEN®, polyethylene glycol (PEG), and PLURONICS®. The composition, if desired, can also contain minor amounts of wetting, bulking, emulsifying agents, or pH buffering agents. These compositions can take the form of solutions, suspensions, emulsion, sustained release formulations and the like. The formulation should suit the mode of administration.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from equal to or at least about 10%, about 20%, about 30%, about 40%, about 50%, about 60%, about 70%, about 80%, about 90%, about 95%, about 98%, about 99%, substantially 100%, or 100% of the other components with which they were initially associated (or ranges including and/or spanning the aforementioned values). In some embodiments, isolated agents are more than about 80%, about 85%, about 90%, about 91%, about 92%, about 93%, about 94%, about 95%, about 96%, about 97%, about 98%, about 99%, substantially 100%, or 100% pure (or ranges including and/or spanning the aforementioned values). As used herein, a substance that is "isolated" may be "pure" (e.g., substantially free of other components). As used herein, the term "isolated cell" may refer to a cell not contained in a multi-cellular organism.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage. RNA are a class of single-stranded molecules, which in their natural state, can be transcribed from DNA in the cell nucleus or in the mitochondrion or chloroplast, containing along the strand a linear sequence of nucleotide bases that is complementary to the DNA strand from which it is transcribed: the composition of the RNA molecule is identical with that of DNA except for the substitution of the sugar ribose for deoxyribose and the substitution of the nucleotide base uracil for thymine. RNA may be in the form of siRNA, asymmetrical interfering RNA (aiRNA), microRNA (miRNA), mRNA, tRNA, rRNA, RNA, viral RNA (vRNA), and combinations thereof.

The term "deoxynucleotide", as used herein, refers to a nucleotide or polynucleotide lacking an OH group at the 2' or 3' position of a sugar moiety with appropriate bonding and/or 2', 3' terminal dideoxy, instead having a hydrogen bonded to the 2' and/or 3' carbon.

The terms "deoxyribonucleotide" and "DNA", as used herein, refer to a nucleotide or polynucleotide comprising at least one ribosyl moiety that has an H at its 2' position of a ribosyl moiety instead of an OH. DNA may be in the form of, e.g., antisense molecules, plasmid DNA, pre-condensed DNA, a PCR product, vectors (PAC, BAC, YAC, artificial chromosomes), expression cassettes, chimeric sequences, chromosomal DNA, or derivatives and combinations of these groups.

"Polynucleotide," or "nucleic acid," as used interchangeably herein, refers to polymers of nucleotides of any length, and includes DNA and RNA. The nucleotides can be deoxyribonucleotides, ribonucleotides, unmodified nucleotides or bases, modified nucleotides or bases, and/or their analogs, or any substrate that can be incorporated into a polymer by DNA or RNA polymerase. A polynucleotide may comprise modified nucleotides, such as methylated nucleotides and their analogs. The term "nucleic acid" as used herein refers to a polymer containing at least two deoxyribonucleotides or ribonucleotides in either single- or double-stranded form and includes DNA and RNA. Nucleic acids include nucleic acids containing known nucleotide analogs or modified backbone residues or linkages, including for example locked nucleic acid (LNA), unlocked nucleic acid (UNA), and zip nucleic acid (ZNA), which can be synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylases, and alkylhalides. "Oligonucleotide," as used herein, generally refers to short, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides. In some embodiments, the polynucleotides disclosed herein (e.g., RNAi(s)) can include one or more nucleotides that is not naturally occurring to, for example, improve the stability of the polynucleotide. Some non-natural nucleotide modifications can include: phosphorothioate linkages, boranophosphate linkages, locked nucleic acids, 2'-modified RNA, 4'-thio modified RNA, ribo-difluorotoluyl nucleotides, uncharged nucleic acid mimics, siRNA conjugates including but not limited to peptide additions or polyethylene glycol. In some embodiments, the polynucleotide does not include non-natural nucleotides.

As used herein, "sense sequence" refers to a polynucleotide or region that has the same nucleotide sequence, in whole or in part, as a target nucleic acid such as a messenger RNA or a sequence of DNA. When a sequence is provided, by convention, unless otherwise indicated, it is the sense sequence (or region), and the presence of the complementary antisense sequence (or region) is implicit.

As used herein, "antisense sequence" refers to a polynucleotide or region of a polynucleotide that is substantially complementary (e.g., 80% or more) 90, 85, 98, 99, or 100% complementary to a target nucleic acid of interest. An antisense sequence can be composed of a polynucleotide region that is RNA, DNA or chimeric RNA/DNA. Any nucleotide within an antisense sequence can be modified by including substituents coupled thereto, such as in a 2' modification. The antisense sequence can also be modified with a diverse group of small molecules and/or conjugates. For example, an antisense sequence may be complementary, in whole or in part, to a molecule of messenger RNA, an RNA sequence that is not mRNA (e.g., tRNA, rRNA, hnRNA, negative and positive stranded viral RNA and its complementary RNA) or a sequence of DNA that is either coding or non-coding.

As used herein, the term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

As used herein, "perfect complementarity" or "100% complementarity" refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 19-mers, if 17 base pairs on each strand or each region can hydrogen bond with each other, the polynucleotide strands exhibit 89.5% complementarity.

As used herein, "mismatch" includes situations in which Watson-Crick base pairing does not take place between a nucleotide of a antisense sequence and a nucleotide of a sense sequence, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. Examples of mismatches include, without limitation, an A across from a G, a C across from an A, a U across from a C, an A across from an A, a G across from a G, a C across from a C, and so on. Mismatches also include an abasic residue across from a nucleotide or modified nucleotide, an acyclic residue across from a nucleotide or modified nucleotide, a gap, or an unpaired loop. In its broadest sense, a mismatch includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position. Mismatches include a G across from an A, and an A across from a C. Some embodiments of a mismatch comprise an A across from an A, G across from a G, C across from a C, and U across from a U.

As used herein, "silencing" refers to an RNAi-mediated reduction in gene expression that can be measured by any number of methods including reporter methods such as for example luciferase reporter assay, PCR-based methods, Northern blot analysis, Branched DNA, western blot analysis, and other techniques.

The term "interfering RNA" or "RNAi" or "interfering RNA sequence" refers to single-stranded or double-stranded RNA, including short interfering RNA (siRNA), microRNA (miRNA), circular RNAs (circRNAs), short hairpin RNAs (shRNAs), long non-coding RNAs (lncRNAs); piwi-interacting RNAs (piRNA), small nucleolar RNA (snoRNAs), tRNA-derived small RNA (tsRNA), small rDNA-derived RNA (srRNA), or a small nuclear RNA (U-RNA). The sequence will not be the full length of the target gene, but some fragment thereof. These sequences can be used for reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. In some embodiments, interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Interfering RNA includes "small-interfering RNA" or "siRNA," e.g., interfering RNA of about 15-60, 15-50, or 5-40 (duplex) nucleotides in length, more typically about 15-30, 15-25, or 19-25 (duplex) nucleotides in length, and is, in some embodiments, about 20-30, 20-24, 21-22, or 21-23 (duplex) nucleotides in length (e.g., each complementary sequence of the double-stranded siRNA is 15-60, 15-50, 15-40, 15-30, 15-25, 19-25, or 20-30 nucleotides in length, about 20-24, 21-22, or 21-23 nucleotides in length, and the double-stranded siRNA is about 15-60, 15-50, 15-40, 5-30, 5-25, or 19-25 base pairs in length, preferably about 8-22, 9-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. Preferably, siRNA are chemically synthesized. siRNA can also be generated by cleavage of longer dsRNA (e.g., dsRNA greater than about 25 nucleotides in length) with the E coli RNase III or Dicer. These enzymes process the dsRNA into biologically active siRNA. Preferably, dsRNA are at least 50 nucleotides to about 100, 200, 300, 400, or 500 nucleotides in length A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops). A small hairpin RNA or short hairpin RNA (shRNA) is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. Suitable length of the interference RNA are about 5 to about 200 nucleotides, or 10-50 nucleotides or base pairs or 15-30 nucleotides or base pairs. In some embodiments, the interference RNA is substantially or completely complementary (such as at least about: 60%, 70%, 80%, 90%, 95%, 98%, 99%, 99.9%, 99.99%, 100%, or ranges including and/or spanning the aforementioned values) the corresponding target gene. In some embodiments, the interference RNA is modified, for example by incorporating non-naturally occurring nucleotides. In some embodiments, an "interfering RNA" or RNAi is an RNA having a structure characteristic of molecules that function to mediate inhibition or interference with of gene expression through an RNAi mechanism or an RNA strand comprising at least partially complementary portions that hybridize to one another to form such a structure. When an RNA comprises complementary regions that hybridize with each other, the RNA will be said to self-hybridize. An RNAi suitable for use in the present disclosure may include a portion that is substantially complementary to a target gene. An RNAi, optionally includes one or more nucleotide analogs or modifications. One of ordinary skill in the art will recognize that RNAi(s) that are synthesized in vitro can include ribonucleotides, deoxyribonucleotides, nucleotide analogs, modified nucleotides or backbones, etc., whereas RNAi(s) synthesized intracellularly, e.g., encoded by DNA templates, typically consist of RNA, which may be modified following transcription. Of particular interest herein are short RNAi(s), i.e., RNAi(s) consisting of one or more strands that hybridize or self-hybridize optionally having one or more mismatched or unpaired nucleotides within the duplex. RNAi(s) include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA. In some embodiments, RNAi refers to dsRNA-induced gene silencing, a cellular process that degrades RNA homologous to one strand of the dsRNA. Methods of mediating the RNAi effect involve small interfering RNA (siRNA), short hairpin RNA (shRNA) and bi-functional shRNA. The interfering RNAs (e.g., siRNA, shRNA), when introduced into cells, can be used to silence genes in mammalian systems where long dsRNAs prompt protein kinase R (PKR), RNase L, and interferon activities that result in non-specific RNA degradation and general shutdown of protein synthesis. Herein any RNA that can be used in the present disclosure to reduce the expression of mRNA of a target biomolecule are collectively termed RNAi.

As used herein, "short, interfering RNA" (siRNA) refers to a nucleic acid that may include a double-stranded portion between about 15-29 nucleotides in length and optionally further comprises a single-stranded overhang (e.g., 1-6 nucleotides in length) on either or both strands. The double-stranded portion is typically between 17-21 nucleotides in length, e.g., 19 nucleotides in length. The overhangs are typically present on the 3' end of each strand, are usually 2 nucleotides long, and are composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. Mismatches or unpaired nucleotides may or may not be present in the duplex formed by the two siRNA strands. One strand of an siRNA (the "antisense" or "guide" strand) includes a portion that hybridizes with a target nucleic acid, e.g., an mRNA transcript. In some embodiments, the antisense strand is perfectly complementary to the target over about 15-29 nucleotides, typically between 17-21 nucleotides, e.g., 19 nucleotides, meaning that the siRNA hybridizes to the target transcript without a single mismatch over this length. In some embodiments, one or more mismatches or unpaired nucleotides may be present in a duplex formed between the siRNA strand and the target transcript. In some embodiments, the siRNA may be single stranded.

As used herein, "short hairpin RNA" (shRNA) refers to a nucleic acid molecule comprising at least two complementary portions hybridized or capable of hybridizing to form a duplex structure sufficiently long to mediate RNAi (in some embodiments between 15-29 nucleotides in length), and at least one single-stranded portion, in some embodiments between approximately 1 and 10 nucleotides in length that forms a loop connecting the ends of the two sequences that form the duplex. The structure may further comprise an overhang. The duplex formed by hybridization of self-complementary portions of the shRNA has similar properties to those of siRNAs and, as described elsewhere herein, shRNAs are processed into siRNAs by the conserved cellular RNAi machinery. Thus, shRNAs are precursors of siRNAs and are similarly capable of inhibiting expression of a target transcript. As is the case for siRNA, an shRNA includes a portion that hybridizes with a target nucleic acid, e.g., an mRNA transcript and is, in some embodiments, perfectly complementary to the target over about 15-29 nucleotides, typically between 17-21 nucleotides, e.g., 19 nucleotides. However, in some embodiments, one or more mismatches or unpaired nucleotides may be present in a duplex formed between the shRNA strand and the target transcript. The shRNAs described herein can be useful in implementing gene silencing. In some embodiments, the RNAi structures disclosed herein when compared to duplexes having lengths that are similar or equivalent to the length of the stem of the hairpin in some instances are advantageous, due to the fact that the shRNAs described herein can be more efficient in RNA interference and less likely to induce cellular stress and/or toxicity. Additionally, the phrase "small hairpin RNA" and the term "shRNA" include nucleic acids that also contain moieties other than ribonucleotide moieties, including, but not limited to, modified nucleotides, modified internucleotide linkages, non-nucleotides, deoxynucleotides and analogs of the nucleotides mentioned thereof.

An RNAi is considered to be "targeted" to a transcript and to the gene that encodes the transcript if (1) the RNAi comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi and a 15 nucleotide portion of the transcript, under conditions (excluding temperature) typically found within the cytoplasm or nucleus of mammalian cells is no more than approximately 15° C. lower or no more than approximately 10° C. lower, than the Tm of a duplex that would be formed by the same 15 nucleotides of the RNAi and its exact complement; and/or (3) the stability of the transcript is reduced in the presence of the RNAi as compared with its absence. An RNAi targeted to a transcript is also considered targeted to the gene that encodes and directs synthesis of the transcript. A target region is a region of a target transcript that hybridizes with an antisense strand of an RNAi.

A "stringent hybridization" and "stringent hybridization wash conditions" in the context of nucleic acid hybridization are sequence dependent, and are different under different experimental parameters. Stringent hybridization conditions can include, e.g., hybridization in a buffer comprising 50% formamide, 5×SSC, and 1% SDS at 42° C., or hybridization in a buffer comprising 5×SSC and 1% SDS at 65° C. both with a wash of 0.2×SSC and 0.1% SDS at 65° C. Other stringent hybridization conditions can also include a hybridization in in a buffer of 40% formamide, 1 M NaCl, and 1% SDS at 37° C., and a wash in 1×SSC at 45° C. Alternatively, hybridization to filter-bound DNA in 0.5 M NaHPC-4, 7% sodium dodecyl sulfate (SDS), 1 mM EDTA at 65° C., and washing in 0.1×SSC/0.1% SDS at 68° C. can be employed. Additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency. Wash conditions may include, e.g. a salt concentration of about 0.02 molar at pH 7 and a temperature of at least about 501° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos As used herein, "expression vector" refers to a nucleic acid construct, generated recombinantly or synthetically, bearing a series of specified nucleic acid elements that enable transcription of a particular gene in a host cell. In some embodiments, gene expression is placed under the control of certain regulatory elements, such as constitutive or inducible promoters.

As used herein, "operably linked" refers to the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

The RNA induced silencing complex (RISC) refers to a multiprotein complex, specifically a ribonucleoprotein, which incorporates one strand of a single-stranded RNA (ssRNA) fragment, such as microRNA (miRNA), or double-stranded small interfering RNA (siRNA). The single strand acts as a template for RISC to recognize complementary messenger RNA (mRNA) transcript. Once found, one of the proteins in RISC, called Argonaute, activates and cleaves the mRNA. This process is called RNA interference.

As used herein, the term "small molecule" refers to a non-nucleotidyl, distinct organic compound with a molecular weight markedly lower (e.g., less than or equal to about: 900 Daltons, 1500 Daltons, 2000 Daltons, or ranges including and/or spanning the aforementioned values) compared to the molecular weight of biomolecules. The average size of a small molecule is on the order of less than or equal to about: 1 nm, 2 nm, 3 nm, or ranges including and/or spanning the aforementioned values. Many pharmaceutical drugs are small molecules that may help regulate biological processes.

For any particular non-nucleotidyl compound disclosed herein, the general structure or name presented is also intended to encompass all structural isomers, conformational isomers, and stereoisomers that may arise from a particular set of substituents, unless indicated otherwise. Thus, a general reference to a compound includes all structural isomers unless explicitly indicated otherwise; e.g., a general reference to pentane includes n-pentane, 2-methylbutane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that may arise from a particular set of substituents.

Whenever a group is described as being "optionally substituted" that group may be unsubstituted or substituted with one or more of the indicated substituents. Likewise, when a group is described as being "unsubstituted or substituted" (or "substituted or unsubstituted") if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl), a di-substituted amine(alkyl), a diamino-group, a polyamino, a diether-group, and a polyether-.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

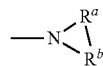

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by $\sim\!\sim\!\sim$, followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group

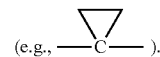

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted. As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "cycloalkyl(alkyl)" refer to an cycloalkyl group connected, as a substituent, via a lower alkylene group. The lower alkylene and cycloalkyl group of a cycloalkyl(alkyl) may be substituted or unsubstituted.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

As used herein, a "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N ($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N ($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N ($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "R$SO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "nitro" group refers to an "—NO₂" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO₂R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The terms "amino" and "unsubstituted amino" as used herein refer to a —NH₂ group.

A "mono-substituted amine" group refers to a "—NHR$_A$" group in which R$_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The R$_A$ may be substituted or unsubstituted. A mono-substituted amine group can include, for example, a mono-alkylamine group, a mono-$C_1$-$C_6$ alkylamine group, a mono-arylamine group, a mono-$C_6$-$C_{10}$ arylamine group and the like. Examples of mono-substituted amine groups include, but are not limited to, —NH(methyl), —NH(phenyl) and the like.

A "di-substituted amine" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_A$ and R$_B$ can independently be substituted or unsubstituted. A di-substituted amine group can include, for example, a di-alkylamine group, a di-$C_1$-$C_6$ alkylamine group, a di-arylamine group, a di-$C_6$-$C_{10}$ arylamine group and the like. Examples of di-substituted amine groups include, but are not limited to, —N(methyl)₂, —N(phenyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. A mono-substituted amine(alkyl) group can include, for example, a mono-alkylamine(alkyl) group, a mono-$C_1$-$C_6$ alkylamine($C_1$-$C_6$ alkyl) group, a mono-arylamine(alkyl group), a mono-$C_6$-$C_{10}$ arylamine($C_1$-$C_6$ alkyl) group and the like. Examples of mono-substituted amine(alkyl) groups include, but are not limited to, —CH₂NH(methyl), —CH₂NH(phenyl), —CH₂CH₂NH(methyl), —CH₂CH₂NH(phenyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. A di-substituted amine(alkyl) group can include, for example, a dialkylamine(alkyl) group, a di-$C_1$-$C_6$ alkylamine($C_1$-$C_6$ alkyl) group, a di-arylamine(alkyl) group, a di-$C_6$-$C_{10}$ arylamine($C_1$-$C_6$ alkyl) group and the like. Examples of di-substituted amine(alkyl)groups include, but are not limited to, —CH₂N(methyl)₂, —CH₂N(phenyl)(methyl), —CH₂N(ethyl)(methyl), —CH₂CH₂N(methyl)₂, —CH₂CH₂N(phenyl)(methyl), —NCH₂CH₂(ethyl)(methyl) and the like.

As used herein, the term "diamino-" denotes an a "—N(R$_A$)R$_B$—N(R$_C$)(R$_D$)" group in which R$_A$, R$_C$, and R$_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein R$_B$ connects the two "N" groups and can be (independently of R$_A$, R$_C$, and R$_D$) a substituted or unsubstituted alkylene group. R$_A$, R$_B$, R$_C$, and R$_D$ can independently further be substituted or unsubstituted.

As used herein, the term "polyamino" denotes a "—(N(R$_A$)R$_B$—)$_n$—N(R$_C$)(R$_D$)". For illustration, the term polyamino can comprise —N(R$_A$)alkyl-N(R$_A$)alkyl-N(R$_A$)alkyl-N(R$_A$)alkyl-H. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units. R$_A$, R$_C$, and R$_D$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein R$_B$ connects the two "N" groups and can be (independently of R$_A$, R$_C$, and R$_D$) a substituted or unsubstituted alkylene group. R$_A$, R$_C$, and R$_D$ can independently further be substituted or unsubstituted. As noted here, the polyamino comprises amine groups with intervening alkyl groups (where alkyl is as defined elsewhere herein).

As used herein, the term "diether-" denotes an a "—OR$_B$O—R$_A$" group in which R$_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein R$_B$ connects the two "0" groups and can be a substituted or unsubstituted alkylene group. R$_A$ can independently further be substituted or unsubstituted.

As used herein, the term "polyether" denotes a repeating —(OR$_B$—)$_n$OR$_A$ group. For illustration, the term polyether can comprise —Oalkyl-Oalkyl-Oalkyl-Oalkyl-OR$_A$. In some embodiments, the alkyl of the polyether is as disclosed elsewhere herein. While this example has only 4 repeat units, the term "polyether" may consist of 1, 2, 3, 4, 5, 6, 7, 8, 9, or 10 repeat units. R$_A$ can be a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_B$ can be a substituted or unsubstituted alkylene group. R$_A$ can independently further be substituted or unsubstituted. As noted here, the polyether comprises ether groups with intervening alkyl groups (where alkyl is as defined elsewhere herein and can be optionally substituted).

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C—N), a carbamoyl group (—C(O)NH$_2$), an N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$NR$_2$, and the like. An "organyl group," "organylene group," or "organic group" may be aliphatic, inclusive of being cyclic or acyclic, or may be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" may be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen-diphenyl ether; nitrogen-triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" may have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene may contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

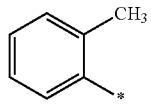 [SMILES: *c1ccccc1C]

A heteroarene is aromatic compound, with or without side chains, having a heteroatom within the aromatic ring or aromatic ring system (e.g. pyridene, indole, or benzofuran, among others). A "heteroaryl group" is a class of "heterocyclyl group" and is a univalent group formed by removing a hydrogen atom from a heteroaromatic ring or ring system carbon atom of a heteroarene compound.

Herein a "mobilizer" or a "mobilizer of hematopoietic stem cells or progenitor cells" (used interchangeably) refers to any substance, whether it is a small organic molecule, synthetic or naturally derived, or a polypeptide, such as a growth factor or colony-stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of stem cells (e.g., hematopoietic stem cells or hematopoietic progenitor/precursor cells) in the peripheral blood, thus allowing for a more accessible source of stem cells for use in the methods disclosed herein. Any mobilizer suitable for increasing the number of stem cells in the subject that are available to be harvested and is compatible with the other aspects of this disclosure may be utilized. In an embodiment, the mobilizer is a cytokine such as granulocyte colony-stimulating factor (G-CSF). A commercial example of a mobilizer suitable for use in the present disclosure is NEUPOGEN® (filgrastim) which is a prescription medication used to treat neutropenia that is commercially available from Amgen. Another example of a mobilizer suitable for use in the present disclosure is a recombinant methionyl human stem cell factor which is commercially available as STEMGEN® from Amgen. Yet another example of a mobilizer suitable for use in the present disclosure is plerixa for which is an inhibitor of the CXCR4 chemokine receptor and blocks binding of its cognate ligand, stromal cell-derived factor-1α (SCF-1α) and is commercially available as MOZOBIL® from Genzyme.

As used herein, "exosomes" refers to small membrane vesicles released by cells, which contain a subset of proteins, lipids, and nucleic acids derived from the parent cell. In some embodiments, exosomes deliver nucleotides to cells. In some embodiments, exosomes are produced naturally by cells. In other embodiments, synthetic exosomes that are not produced naturally can be used to deliver nucleotides to cells.

As used herein, "in vivo" is given its ordinary meaning and refers to the performance of a method inside living organisms, usually animals, mammals, including humans, and plants, as opposed to a tissue extract or dead organism.

As used herein, "ex vivo" is given its ordinary meaning and refers to the performance of a method outside a living organism with little alteration of natural conditions.

As used herein, "in vitro" is given its ordinary meaning and refers to the performance of a method outside of biological conditions, e.g., in a petri dish or test tube.

In some areas of this disclosure genes are capitalized and italicized while the gene product is capitalized but not italicized.

INTRODUCTION

Aging is a biological process and the leading risk factor for the chronic diseases that account for the bulk of morbidity, mortality and health costs. The complexity of organismal aging appears to be driven by cellular dysfunction at the macromolecular and/or organelle level, which ultimately leads to a decline in tissue function and the manifestation of disease. As cells age they undergo epigenetic alterations that lead to dynamic changes in gene expression and increased likelihood of oncogenesis and cellular transformation. A potent inducer of cellular senescence is epigenomic stress, which can result from direct DNA damage, dysfunctional telomeres, disrupted chromatin, or strong mitogenic signals.

Cell entry into the non-proliferative, yet metabolically active, state of senescence serves a protective role to avert transformation to an aberrant physiological form. However, senescent cells exhibit a profile of enhanced secretory factor production, termed the senescent-associated secretory phenotype (SASP). Many of the SASP factors are pro-inflammatory and/or tumor-supportive, thus cellular senescence is a fundamental aging mechanism tied to the progressive breakdown of tissue function with age. In particular, reduced function associated with an aging lymphohematopoietic system leads to compensatory increases in immune-related diseases, such as cancer. This decline in the lymphohematopoietic system and decreased immune surveillance is an important factor in the increased incidence of cancer, infectious diseases and immune-related disorders responsible for the majority of morbidity and health care expenditures in developed nations.

Epigenomic stress from sources other than age and/or other disease processes and disorders not associated with age can also lead to dysfunction that puts cells in a similar biological states to aged cells (e.g., pro-inflammatory and/or tumor-supportive status). These dysfunctions manifest in biological and physiological states that are similar to those found in aged cells.

There exists a need for compositions and methods that can intervene in the progressive breakdown of tissue function and may repair or stimulate aging or dysfunctional cells and tissues. Disclosed herein are methods, agents, and compositions for preventing or treating age-related dysfunction and/or dysfunction that is not related to aging but that manifests biological and physiological outcomes that are similar or the same as those found in aging cells. In some embodiments, the methods disclosed herein include administering agents that reduce the expression of a paired box 5 (PAX5) gene and/or reducing expression of a protein phosphatase 1F enzyme (PPM1F) gene. In some embodiments, this expression is reduced in a cell using one or more interfering RNAs (RNAi(s)), small molecule drug compounds, cells treated with such agents, or combinations thereof. In some embodiments, the methods include cell therapies. In some embodiments, cells are manipulated and to provide therapeutic cells which can be implanted in the body to achieve one or more therapeutic effects. In some embodiments, prepared therapeutic cells are exposed to patient cells to provide target cells. In some embodiments, target cells can be manipulated to provide additional therapeutic cells and/or can be reintroduced to the patient to achieve a therapeutic effect. In some embodiments, an RNAi that reduces the expression of PAX5, PPM1F, both, other genes as disclosed elsewhere herein, and/or genes encoding proteins disclosed herein is referred to as senescence-agent disruptors (SAD). Some embodiments pertain to methods of treating PAX5 and/or PPM1F gene mediated conditions in a patient.

PAX5 and PPM1F for Achieving Therapeutic Effect

Figure 1:
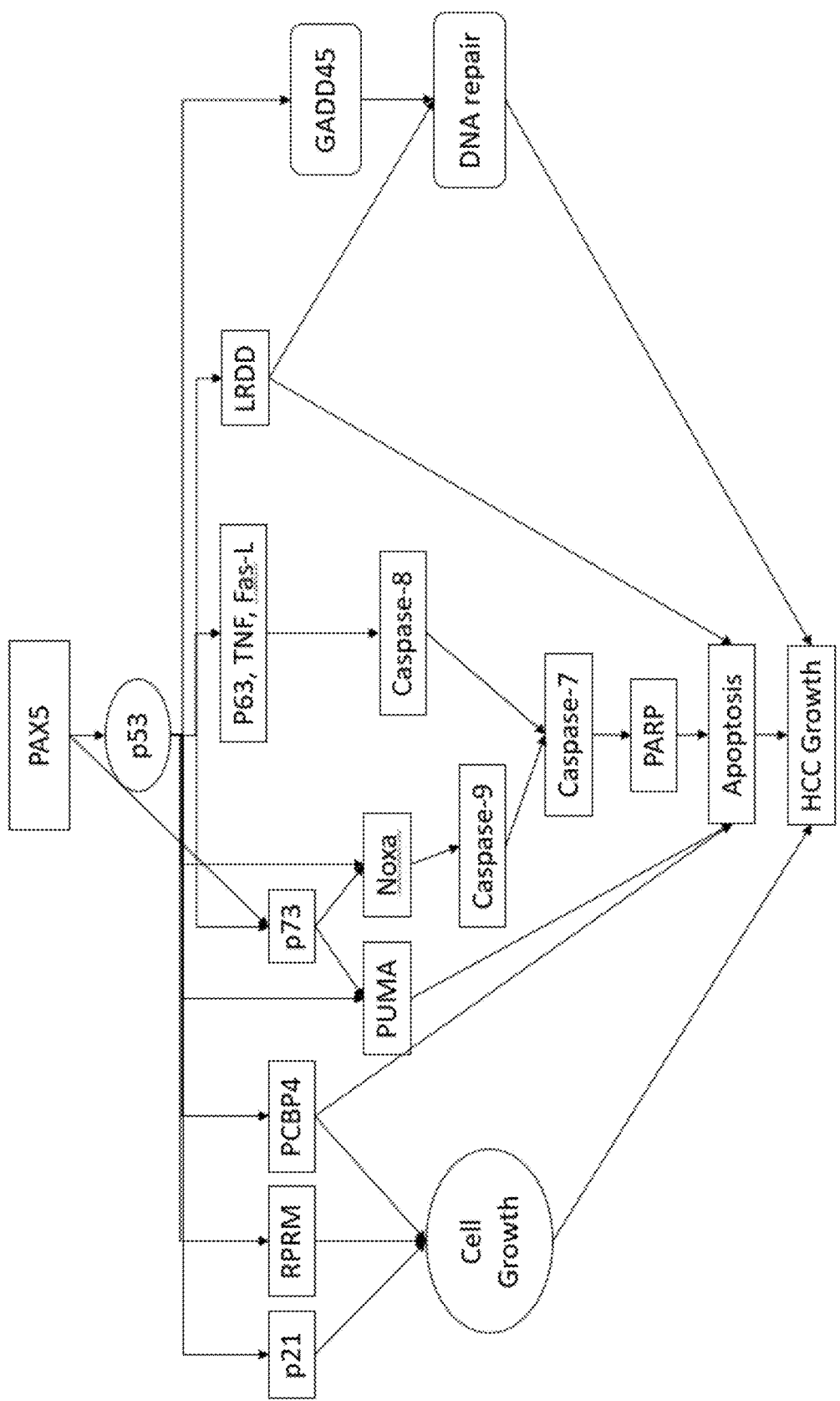
FIG. 1 depicts a paired box 5 (PAX5) signaling cascade.

B-cell lineage specific activator protein (BSAP) is expressed at early, but not late, stages of B-cell differentiation. BSAP is a nuclear protein in the paired-box (PAX) containing family of transcription factors involved in control of organ development and tissue differentiation. BSAP is encoded by the PAX5 gene which is primarily expressed in B lymphocytes and B-cell lymphomas, with additional expression in the developing central nervous system. As shown in FIG. 1, which illustrates the PAX5 signaling cascade, PAX5 function influences a number of cellular processes, including cell growth, DNA repair, apoptosis, and tumor growth (e.g., hepatocellular carcinoma or "HCC"). As shown, PAX5 also influences the p53 signaling pathway. Among other things, PAX5 up-regulates the effectors of p53-dependent apoptosis, including ligands responsible for extracellular death (e.g., TNF, Fas-L, adaptor protein LRDD, p53 family members p63 and p73, Bcl2 family members Noxa and PUMA). These ligands induce caspase dependent cellular apoptosis. PAX5 may increase p53 transcription target genes p21, RPRM, and PCBp4 resulting in cell growth arrest. PAX5 induced p53-dependent DNA repair occurs through GADD45, which protects against tumorigenesis through maintaining genomic stability. Some embodiments disclosed herein influence one or more of the molecules and ligands (e.g., through interfering RNA mechanism, etc.) to interrupt the normal PAX5 cascade.

A feature of the PAX gene family is a novel, highly conserved DNA-binding domain, known as the paired box. The PAX proteins (e.g., BSAP) are important regulators in early development, and alterations in the expression of their genes are thought to contribute to neoplastic transformation. Its expression has also been detected in developing CNS and testis, therefore, the PAX5 gene product may not only play an important role in B-cell differentiation, but also in neural development and spermatogenesis. Some embodiments disclosed herein influence the PAX5 gene or protein (e.g., through interfering RNA mechanism, through inhibition of the protein, etc.) to interrupt PAX5 function.

The protein phosphatase 1F enzyme (PP1F) is a member of the PP2C family of Ser/Thr protein phosphatases which are known to be negative regulators of cell stress response pathways. This phosphatase can interact with Rho guanine nucleotide exchange factors (PIX), and thus block the effects of p21-activated kinase 1 (PAK), a protein kinase mediating biological effects downstream of Rho GTPases. Calcium/calmodulin-dependent protein kinase II gamma (CAMK2G/CAMK-II) is found to be one of the substrates of this phosphatase. The overexpression of this phosphatase or CAMK2G has been shown to mediate caspase-dependent apoptosis. An alternatively spliced transcript variant has been identified, but its full-length nature has not been determined. Protein phosphatase 1F enzyme is encoded by the PPM1F gene. Some embodiments disclosed herein influence one or more of the molecules and ligands (e.g., through interfering RNA mechanism, etc.) to interrupt the normal PPM1F cascade.

Figure 2:
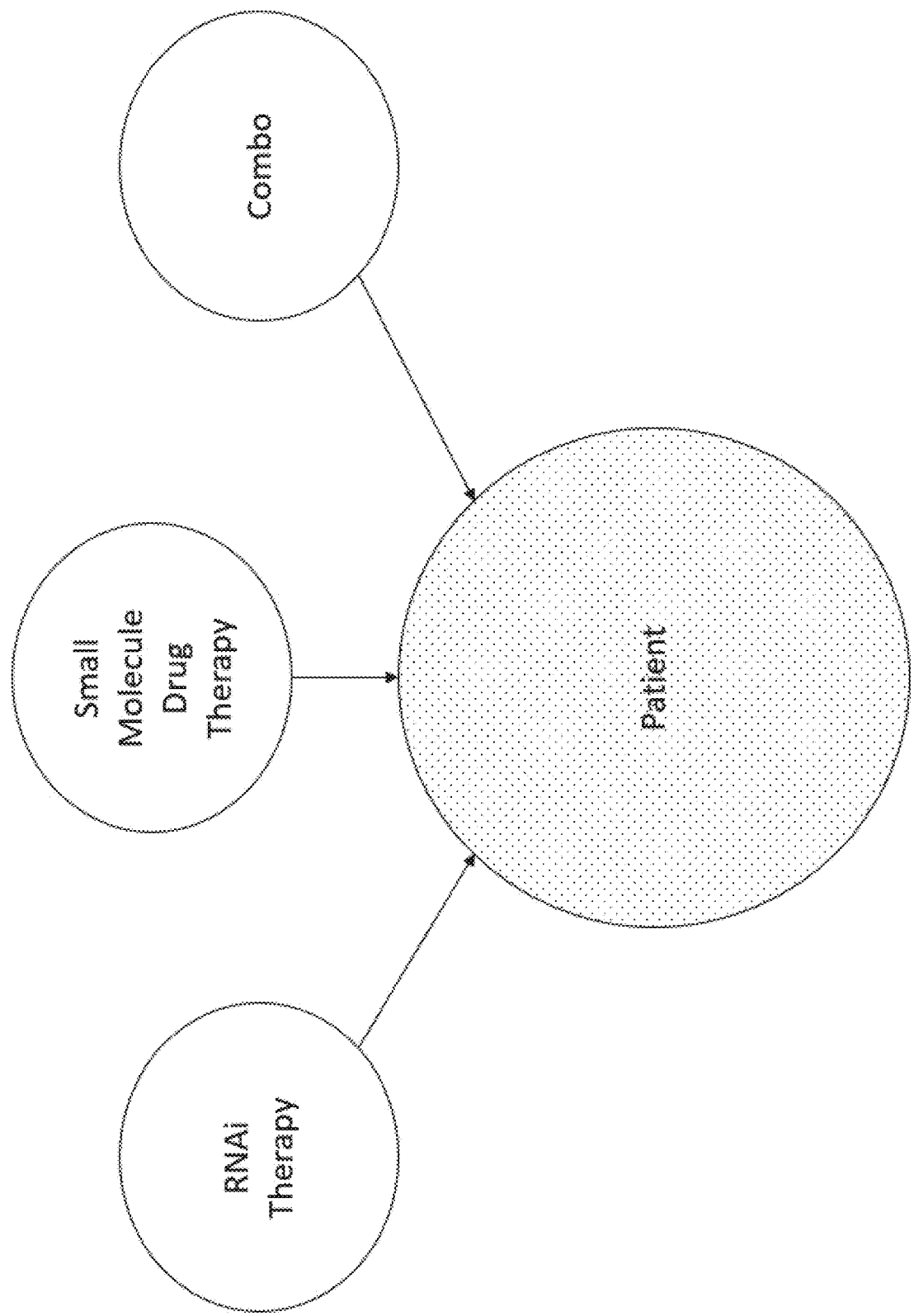
FIG. 2 depicts a chart displaying embodiments of strategies for treating a patient as disclosed herein.

As shown in FIG. 2, multiple strategies can be used to interfere with the PAX5 gene/protein and/or the PPM1F gene/protein. These approaches can involve using one or more of interfering RNA(s) (RNAi(s)), compounds that inhibit the PAX5 gene and/or the PPM1F gene, and/or using combinations of RNAi(s) and inhibitor compounds together. In other words, in some embodiments, the method of reducing expression of the PAX5 gene and/or reducing expression of the PPM1F gene in a cell comprises contacting the cell with one or more of interfering RNA(s) (RNAi(s)), compounds that inhibit the PAX5 gene and/or the PPM1F gene, and/or using combinations of RNAi(s) and inhibitor compounds together.

Figure 3A:
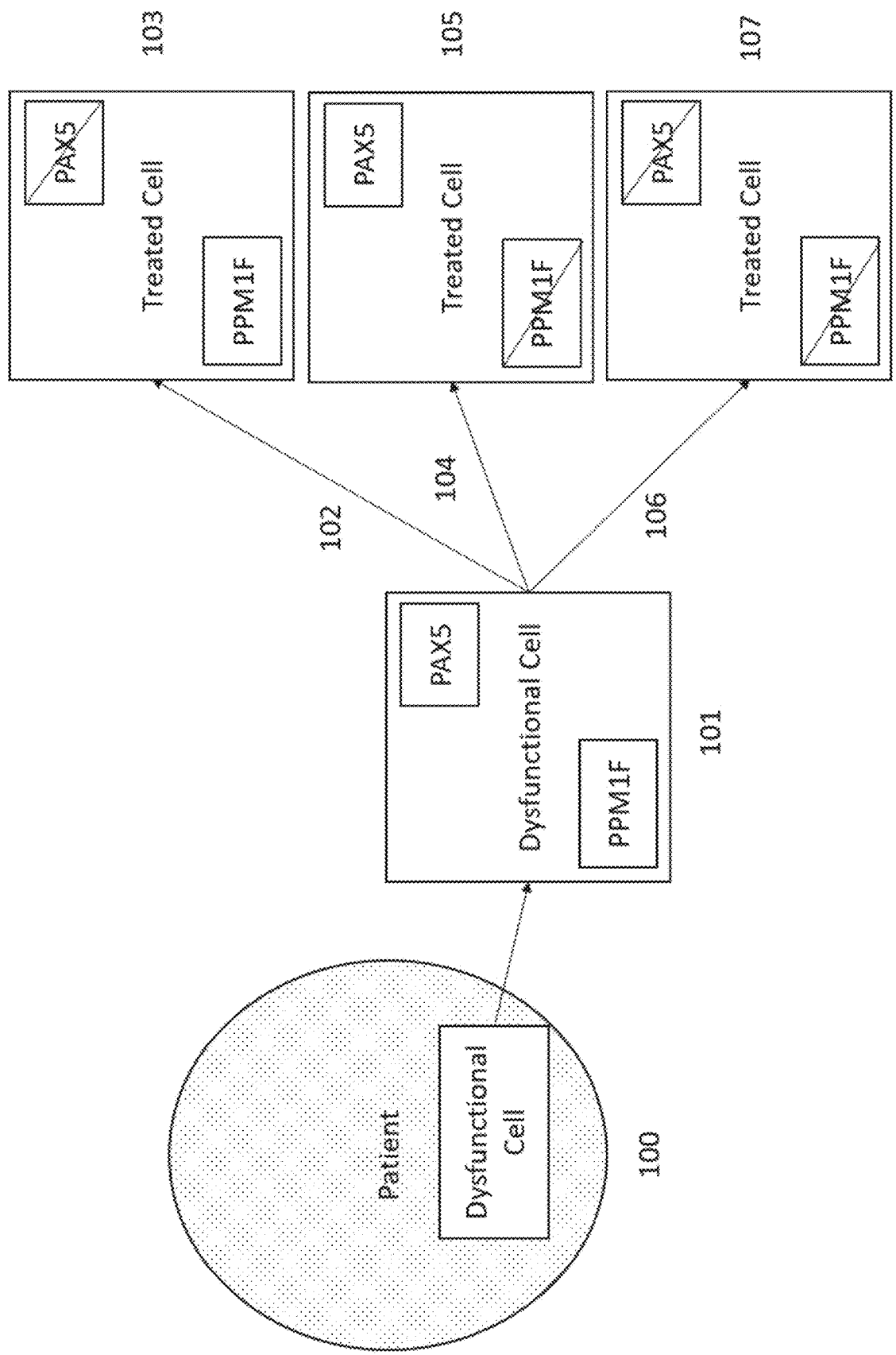
FIGS. 3A-O depict alternative strategies for treating a patient using the methods disclosed herein. (A) and (B) depict an embodiment of an ex vivo treatment strategy. (C) depicts an embodiment of an in vivo treatment strategy.
Figure 3B:
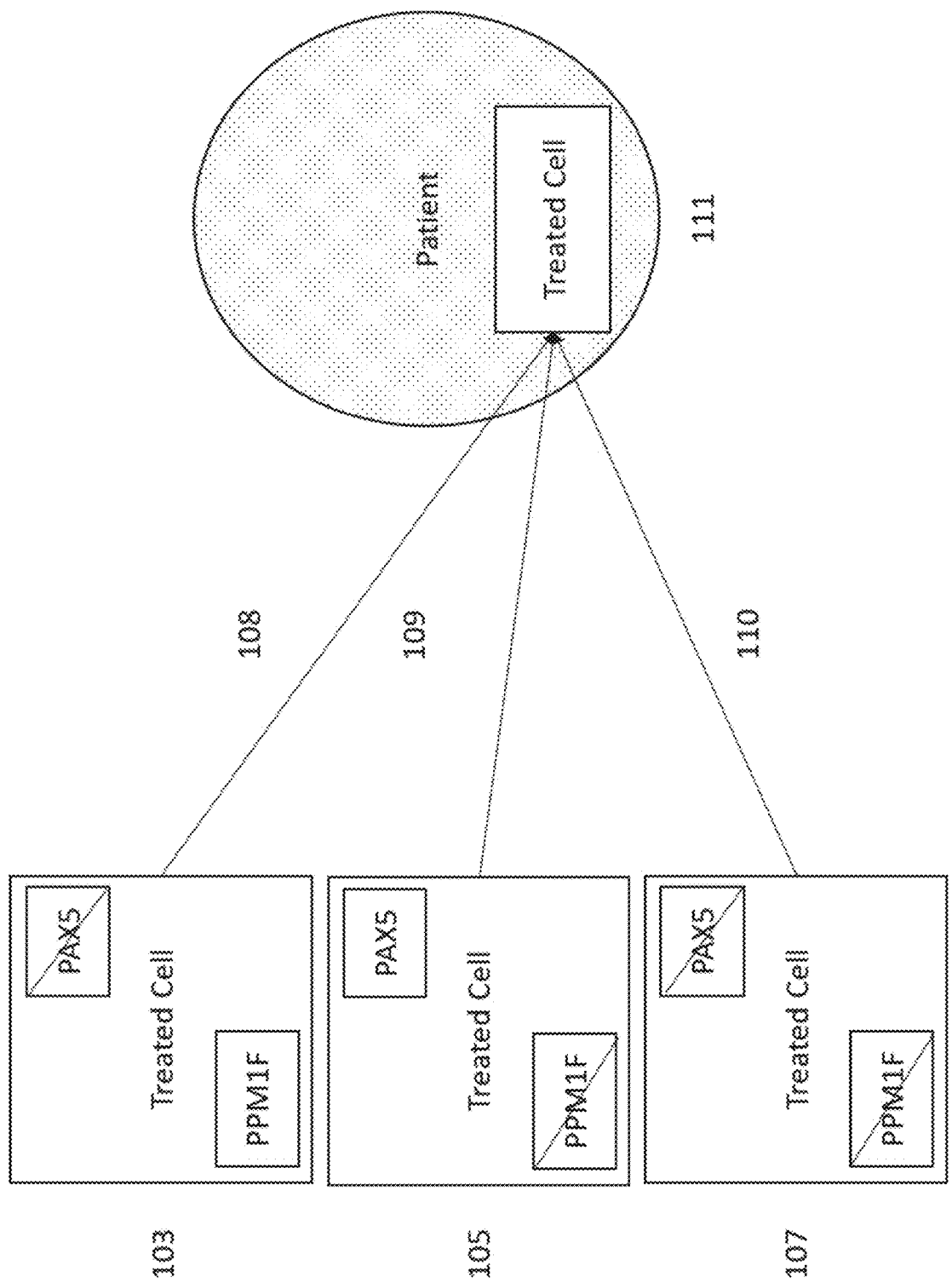

Additionally, in some embodiments, interference with one or more of the PAX5 or PPM1F genes and/or proteins can be achieved using a variety of strategies. For example, in some embodiments, as illustrated in FIGS. 3A-B, active agents can act upon cells ex vivo (FIG. 3A) that are then introduced in vivo (FIG. 3B). Alternatively, active agents can be introduced to a patient (e.g., systemically or locally) to act upon cells in vivo to illicit a therapeutic effect (FIG. 3C).

For example, in some embodiments, as shown in FIG. 3A, PAX5 and/or PPM1F interference and/or inhibition can be performed on cell 101 that is isolated from a patient 100. As shown, one or more RNAi(s) for PAX5, compounds that inhibit the PAX5 gene, and/or using combinations thereof (collectively interfering agents 102) can be used to treat the cell to inhibit the PAX5 gene, causing the down regulation of the PAX5 protein and affording a cell with improved cellular function 103. As shown, one or more RNAi(s) for PPM1F, compounds that inhibit the PPM1F gene, and/or using combinations thereof (collectively interfering agents 104) can be used to treat the cell to inhibit the PPM1F gene, causing the down regulation of the PPM1F protein and affording a cell with improved cellular function 105. As shown, one or more RNAi(s) for PAX5 and/or PPM1F, compounds that inhibit the PAX5 and/or PPM1F gene, and/or using combinations thereof (collectively interfering agents 106) can be used to treat the cell to inhibit the PAX5 and PPM1F gene, causing the down regulation of the PAX5 and PPM1F protein and affording a cell with improved cellular function 107.

As shown in FIG. 3B, each of these cells with improved cellular function 103, 105, 107 (e.g., a therapeutic cell) can be reintroduced 108, 109, 110 to the patient, resulting in a treated patient 111. In some embodiments, once in the body, the therapeutic cell can influence other cells in vivo to cause a broader therapeutic effect that can be long lasting.

Figure 3C:
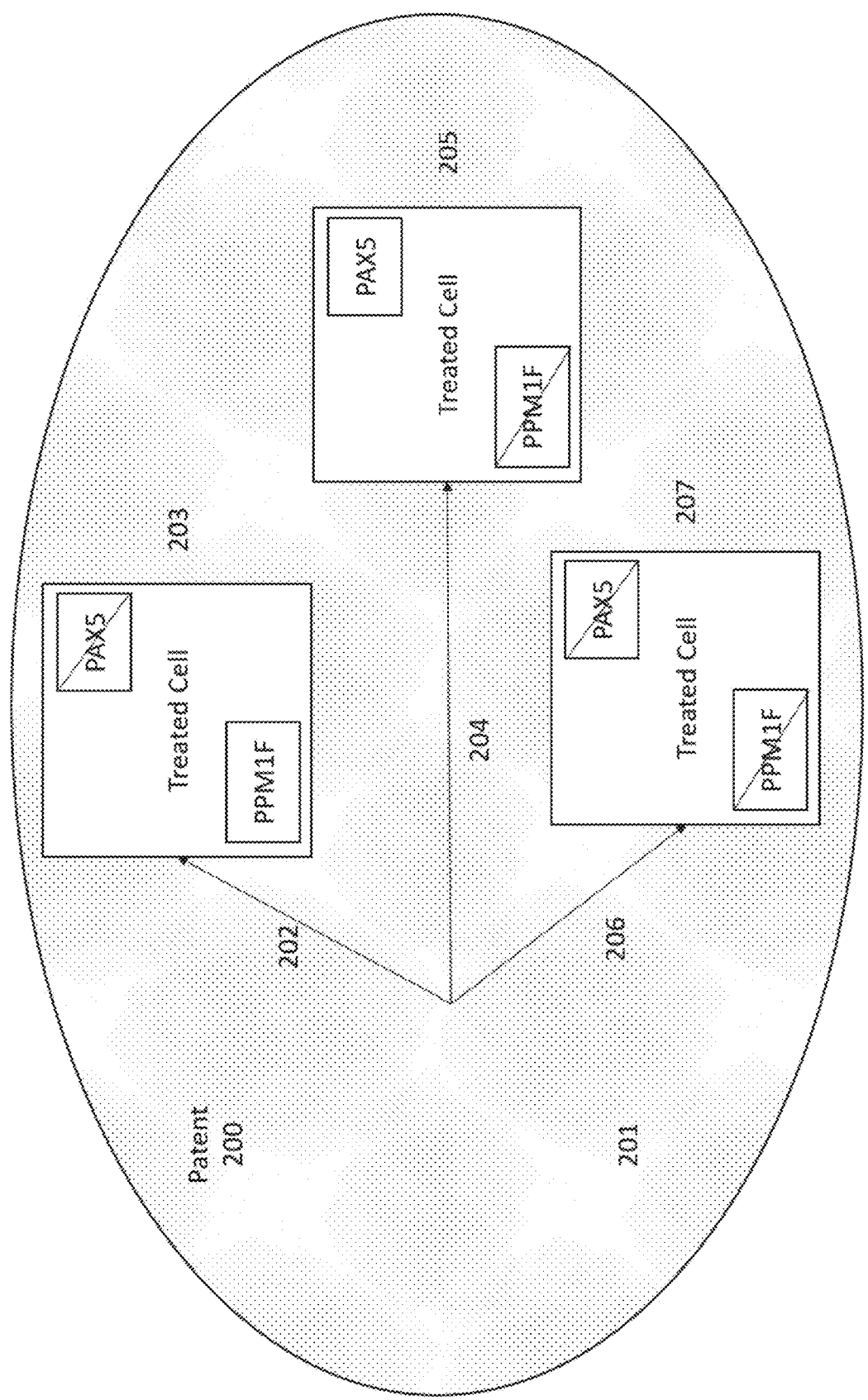

Alternatively, in some embodiments, as shown in FIG. 3C, PAX5 and/or PPM1F interference and/or inhibition can be performed on a cell that is in a patient 200. As shown, one or more RNAi(s) for PAX5, compounds that inhibit the PAX5 gene, and/or using combinations thereof (collectively interfering agents 202) can be used to treat the in vivo cell to inhibit the PAX5 gene, causing the down regulation of the PAX5 protein and affording a cell with improved cellular function 203. As shown, one or more RNAi(s) for PPM1F, compounds that inhibit the PPM1F gene, and/or using combinations thereof (collectively interfering agents 204) can be used to treat the cell in vivo to inhibit the PPM1F gene, causing the down regulation of the PPM1F protein and affording a cell with improved cellular function 205. As shown, one or more RNAi(s) for PAX5 and/or PPM1F, compounds that inhibit the PAX5 and/or PPM1F gene, and/or using combinations thereof (collectively interfering agents 206) can be used to treat the cell in vivo to inhibit the PAX5 and PPM1F gene, causing the down regulation of the PAX5 and PPM1F protein and affording a cell with improved cellular function 207.

In some embodiments, both the strategies of FIGS. 3A-3B and that of FIG. 3C can be used in combination (e.g., to achieve an enhanced effect and/or where one mode of therapy is more suited for a particular pathway than another). In some embodiments, additional potential treatment strategies include those shown in the flow charts of FIGS. 3C-30, which are described in more detail elsewhere herein.

Interfering RNAs

Some embodiments pertain to an interfering RNA (RNAi) that reduces the expression of a gene or protein. In some embodiments, by reducing the expression of a gene, for example, in a cell, one or more cellular benefits is achieved. In some embodiments, the benefits are related to treating one or more symptoms of aging and/or one or more symptoms of dysfunctional cellular processes. In some embodiments, the RNAi reduces the expression of one or more of the PAX5, PPM1F, and/or CAMK2G genes.

In some embodiments, a reduction of expression includes reducing expression by greater than or at least about: 1%, 5%, 10%, 30%, 40%, 50%, 60%, 70%, 80%, 90%, 95%, 98%, 99%, 99.9%, 100%, or ranges including and/or spanning the aforementioned values. In some embodiments, a reduction of expression includes at least one of of decreasing the amount of native protein synthesized, full length protein synthesized, decreasing the amount of functional protein synthesized, decreasing the amount of functional fragments of protein synthesized, and decreasing the amount of fragments of protein synthesized. Unless otherwise noted, reduced expression will denote a reduction of the expression of the functional protein.

In some embodiments, the RNAi comprises 4 to 50 contiguous nucleotides having a polynucleotide sequence that is at least 80% to 100% complementary to a region of a gene encoding a protein as disclosed elsewhere herein. In some embodiments, the RNAi comprises a polynucleotide sequence comprising 4 to 50 contiguous nucleotides having a polynucleotide sequence that is at least 80% to 100% complementary to a region of a gene of SEQ ID NO:1 (PAX5; homo sapien—as shown in FIG. 3P1), SEQ ID NO:2 (PAX5; *Equus caballus*—as shown in FIG. 3P2), SEQ ID NO:3 (PAX5; *Canis lupus*—as shown in FIG. 3P3), SEQ ID NO:4 (PAX5; *Felis catus*—as shown in FIG. 3P4), SEQ ID NO:5 (PPM1F; homo sapien—as shown in FIG. 3P5), SEQ ID NO:6 (PPM1F; *Equus caballus*—as shown in FIG. 3P6), SEQ ID NO:7 (PPM1F; *Canis lupus*—as shown in FIG. 3P7), and/or SEQ ID NO:8 (PPM1F; *Felis catus*—as shown in FIG. 3P8), SEQ ID NO:21 (CAMK2G; homo sapien—as shown in FIG. 3P21). In some embodiments, the RNAi comprises a polynucleotide sequence comprising 4 to 50 contiguous nucleotides having a polynucleotide sequence that is at least 80% to 100% complementary to a region of a gene of SEQ ID NO:1 or SEQ ID NO:5. Unless otherwise noted herein, reference to the PAX5 and/or the PPM1F gene will denote and/or include the human sequences as shown in FIG. 3P1 and FIG. 3P5, respectively. Unless otherwise noted herein, reference to the CAMK2G gene will denote and/or include the human sequence as shown in FIG. 3P21.

Sequences for various variants of the targets are presented in FIGS. 3P1-3P8 and 3P21. Conservation across organisms indicate sections of the sequences that could be used universally as iRNAs, while sections of variation demonstrate sequences that can be specific to various organisms. In some embodiments, interference with the expression of one or more of the genes of SEQ ID NOs: 1-8 and 21, results in a decreased amount of the coinciding proteins of those genes, for example, SEQ ID NOs: 22-30, respectively, being expressed and synthesized.

Some embodiments pertain to a method of reducing expression of a paired box 5 (PAX5) gene and reducing expression of a protein phosphatase 1F enzyme (PPM1F) gene using one or more interfering RNAs (RNAi(s)), compounds, or combinations thereof. While, in some embodiments, the RNAi is administered to a human (and/or to at least one human cell) to treat that human, in other embodiments, the RNAi is administered to, for example, a horse, dog, cat, or other mammal (and/or to at least one cell of the mammal). The nucleic acid sequence for the human PAX5 gene is provided as SEQ ID NO: 1. The nucleic acid sequences for the horse, dog, and cat PAX5 gene are provided as SEQ ID NO: 2, SEQ ID NO: 3, and SEQ ID NO: 4, respectively. The nucleic acid sequence for the human PPM1F gene is provided as SEQ ID NO: 5. The nucleic acid sequences for the horse, dog, and cat PPM1F gene is provided as SEQ ID NO: 6, SEQ ID NO: 7, and SEQ ID NO: 8, respectively.

Figure 3D:
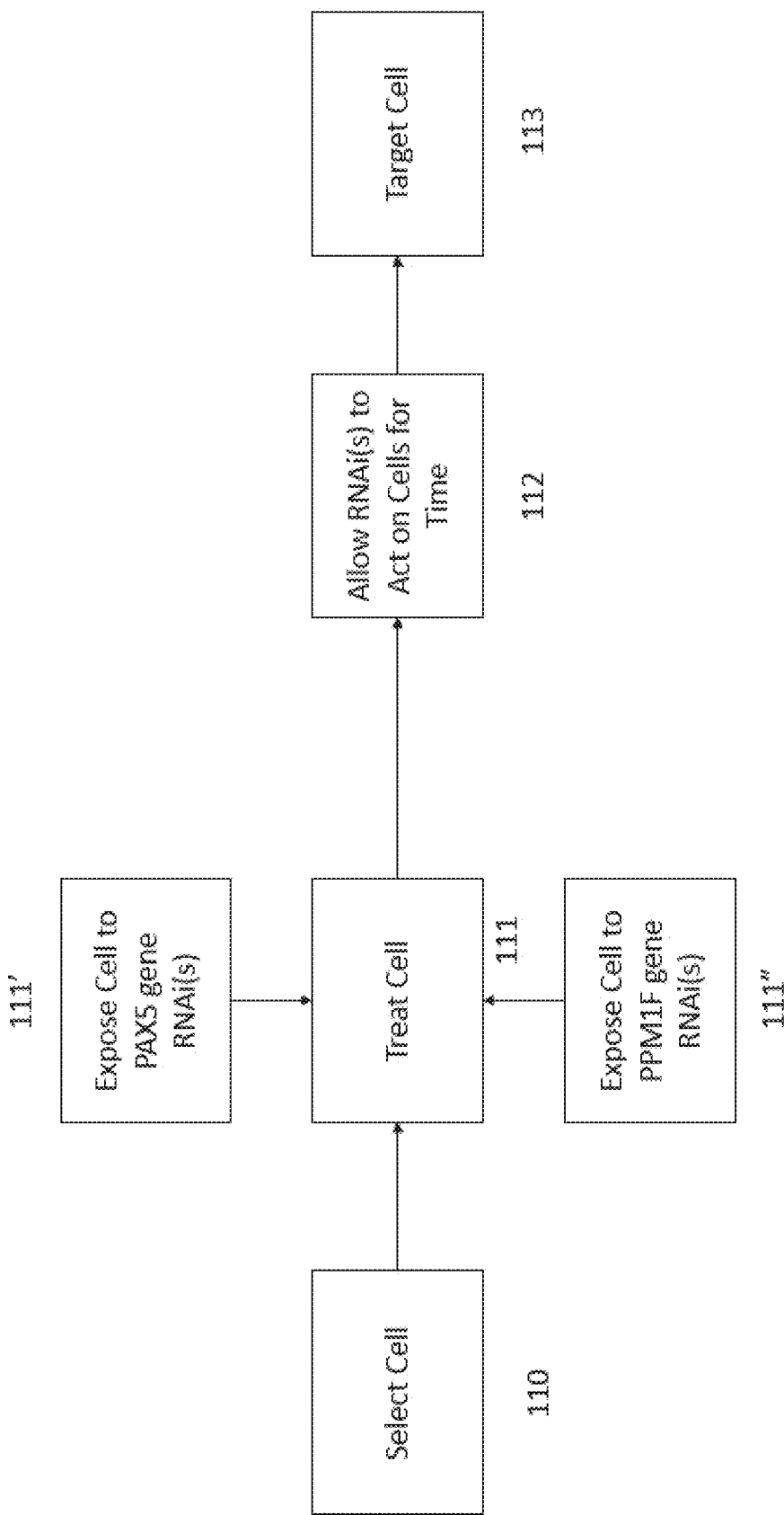
Figure 3E:
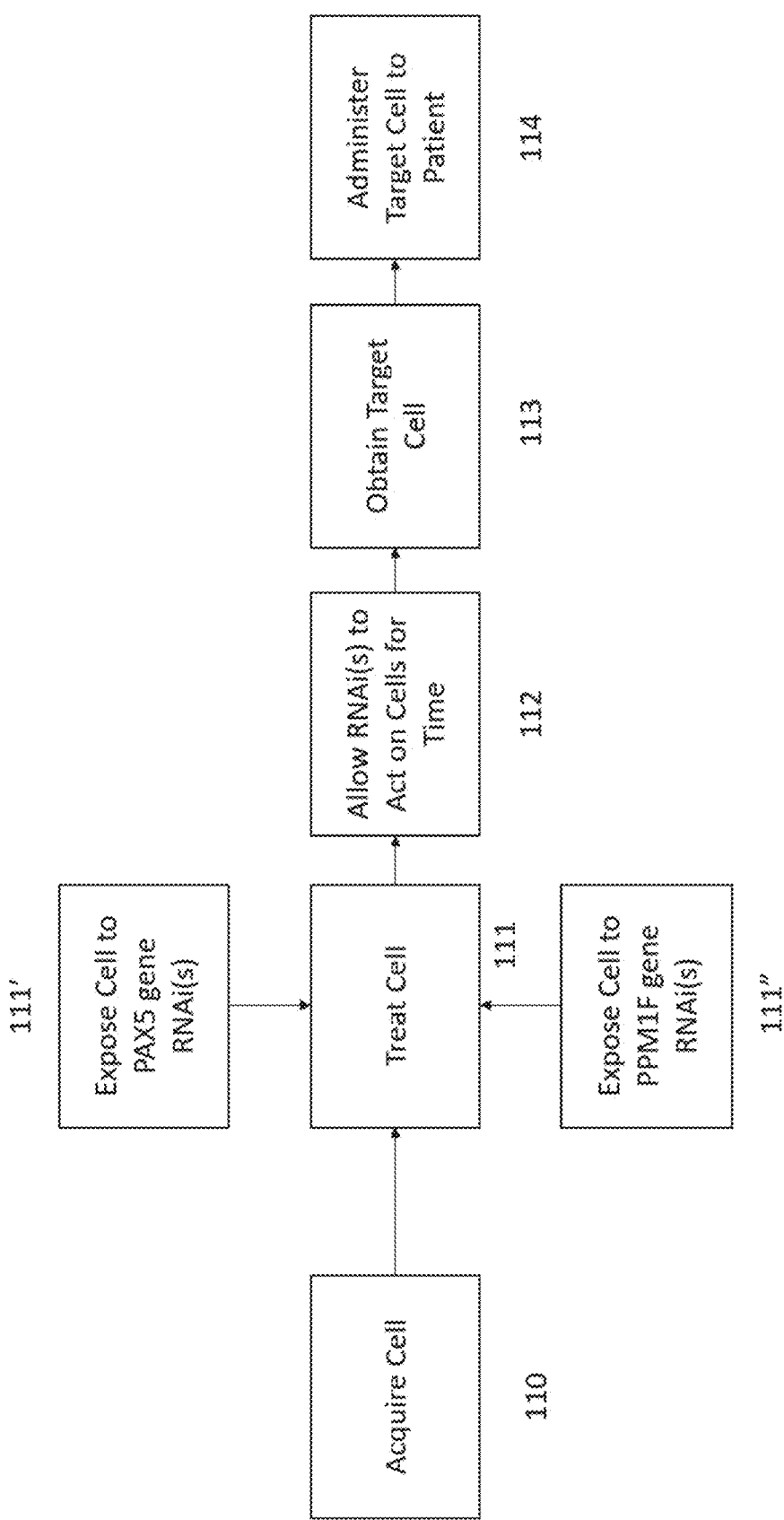

In some embodiments, as shown in FIGS. 3D and 3E, the method includes selecting or acquiring a patient cell 110. In some embodiments, as shown in FIG. 3C, the cell may be a cell in the body of the patient (for in vivo treatment) or isolated from the patient (for ex vivo and/or in vitro treatment). In some embodiments, as shown, the cell is treated by exposing it to one or more different PAX5 gene RNAi(s) 111'. In some embodiments, as shown, the cell is treated by exposing it to one or more different PPM1F gene RNAi(s) 111". In some embodiments, as shown, the RNAi(s) are allowed to act on the cell for a period of time 112. In some embodiments, as shown, this results in a target cell 113. In some embodiments, as shown in FIG. 3E, the cell can be reintroduced to the patient (e.g., where it was initially isolated from the patient). In some embodiments, the entire process is performed in vivo and, therefore, the cell need not be reintroduced to the patient.

Some embodiments pertain to a method of reducing expression of a calcium/calmodulin dependent protein kinase II gamma (CAMK2G) gene. In some embodiments, an RNAi is administered to a human and/or to at least one cell of a human. The nucleic acid sequence for the human CAMK2G gene is provided as SEQ ID NO: 21.

In some embodiments, the RNAi is a short interfering RNA (siRNA), microRNA (miRNA), circular RNAs (circRNAs), short hairpin RNAs (shRNAs), long non-coding RNAs (lncRNAs); piwi-interacting RNAs (piRNA), small nucleolar RNA (snoRNAs), tRNA-derived small RNA (tsRNA), small rDNA-derived RNA (srRNA), or a small nuclear RNA (U-RNA). In some embodiments, the RNAi is an siRNA.

In some embodiments, the number of contiguous nucleotides in the RNAi is less than or equal to about: 200, 150, 100, 50, 40, 30, 25, 20, 10, 4, or ranges including and/or spanning the aforementioned values. In some embodiments, the RNAi comprises about 20 to 30 contiguous nucleotides.

In some embodiments, the RNAi comprises a polynucleotide sequence comprising 4 to 50 contiguous nucleotides having a polynucleotide sequence that is at least 80% to 100% complementary to a region of a gene of any one of SEQ ID NOs:1-8 and 21. In some embodiments, the region of complementarity between the RNAi and a target sequence (e.g., a portion of SEQ ID NOs:1-8 and 21) may be substantially complementary (e.g., there is a sufficient degree of complementarity between the RNAi and a target nucleic acid to so that they specifically hybridize and induce a desired effect). In some embodiments, the RNAi is fully complementary to the target sequence (100% complementary). In some embodiments, the RNAi may include a contiguous nucleotide sequence comprising no more than 5 mismatches (e.g., no more than 1, no more than 2, no more than 3, no more than 4, or no more than 5 mismatches) when hybridizing to a target sequence, such as to the corresponding region of a portion of SEQ ID NOs:1-8 and 21. In some embodiments, the contiguous nucleotide sequence comprises no more than a single mismatch when hybridizing to the target sequence, such as the corresponding region of a portion of SEQ ID NOS:1-8 and 21. In some embodiments, RNAi hybridizes to a complimentary region (e.g., a target region) of any one of SEQ ID NOs:1-8 and 21, thereby interfering with the transcription of that gene. In some embodiments, the RNAi is complementary in one section (as noted above), but has a section with 1, 2, 3, 4, or more nucleotides that are not complementary.

In some embodiments, the RNAi comprises a polynucleotide chain comprising nucleotides that are complementary to polynucleotides that transcribe any one of SEQ ID NOs:1-8 and 21 (e.g., mRNA). The region of complementarity between the RNAi and a target sequence (e.g., a portion of mRNA that transcribes SEQ ID NOs:1-8 and 21) may be substantially complementary (e.g., there is a sufficient degree of complementarity between the RNAi and a target nucleic acid to so that they specifically hybridize and induce a desired effect). In some embodiments, the RNAi is fully complementary to the target sequence (e.g., 100% complementary). In some embodiments, the RNAi may include a contiguous nucleotide sequence comprising no more than 5 mismatches (e.g., no more than 1, no more than 2, no more than 3, no more than 4, or no more than 5 mismatches) when hybridizing to a target sequence, such as to the corresponding region of an mRNA encoding any one of SEQ ID NOs:1-8 and 21. In some embodiments, the contiguous nucleotide sequence comprises no more than a single mismatch when hybridizing to the target sequence, such as the mRNA encoding a region of a portion of SEQ ID NOs:1-8 and 21. In some embodiments, the RNAi hybridizes to a target nucleic acid molecule, such as the mRNA encoding PAX5, PPM1F, or CAMK2G, and comprises a contiguous nucleotide sequence which corresponds to the reverse complement of a nucleotide sequence of any one of SEQ ID NOs:1-8 and 21, or a fragment of any one of SEQ ID NOs:1-8 and 21. As will be appreciated by one of skill in the art, for double stranded RNAi, one sequence will be complementary to the target, while the other strand will be identical to the target. Thus, in some embodiments, any description provided herein regarding a sequence that is complementary to, can also describe a sequence that is the same as (when the hybridized chain is being referenced).

In some embodiments, the RNAi is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% complementary to a target sequence (or ranges including and/or spanning the aforementioned values). In some embodiments, the target sequence is a polynucleotide region of less than or equal to about: 200, 150, 100, 50, 40, 30, 25, 20, 10, or 4 (or ranges including and/or spanning the aforementioned values) nucleotides in length. In some embodiments, the RNAi is prepared synthetically and is not an RNAi that has been isolated from a natural source. In some embodiments, as disclosed elsewhere herein, the target region can include a region of the gene encoding the protein or a region of an mRNA transcribing the gene. In some embodiments, the target region is a region of any one of SEQ ID NOs:1-8 and 21, CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, ZNF549, a gene encoding any one of the molecules disclosed in FIGS. 1 and 22, or an mRNA transcribing any one of the foregoing. As noted herein, the sequence will be of an appropriate length and composition to allow for the correct hybridization, and can be, for example 10-50 nucleic acids in length. In some embodiments, the hybridization conditions are set to those for ex vivo therapy. In some embodiments, the hybridization is performed in a solution having a concentration of MgCl2 of equal to or less than about: 1 mM, 2.5 mM, 5 mM, 7.5 mM, 10 mM, or ranges including and/or spanning the aforementioned values. In some embodiments, the hybridization is performed in a solution having a temperature of equal to or at least about: 45° C., 50° C., 55° C., 60° C., 65° C., or ranges including and/or spanning the aforementioned values.

In some embodiments, combinations of various RNAi species can be used (e.g., in methods of treating patients and/or cells). In some embodiments, a plurality (e.g., 1, 2, 3, 4, 5, or more) RNAi(s) are administered. In some embodiments, the RNAi or RNAi(s) are isolated prior to use. In some embodiments, the RNAi(s) are synthesized. In some embodiments, the RNAi(s) are synthesized using, for example, PCR. In some embodiments, the members of a combination can be administered substantially simultaneously and/or sequentially. In some embodiments, when administered simultaneously, the RNAi(s) can be part of a composition. In some embodiments, combinations of RNAi species are not used and a single RNAi species can be administered. In some embodiments, the administered RNAi has a sequence that is identical to that of any one of SEQ ID NOs:9-20 (as shown in Table 1 below). In some embodiments, the RNAi or combination of RNAi(s) have sequences that are independently at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to any one of SEQ ID NOs:9-20 (or ranges including and/or spanning the aforementioned values). In some embodiments, multiple RNAi(s) having a mutual gene target (e.g., PAX5, PPM1F, CAMK2G, etc.) are used. For example, in some embodiments, two or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20, which each are RNAi(s) for PAX5, are used in combination to interfere with the PAX5 gene. In some embodiments, SEQ ID Nos: 12-20, which each are RNAi(s) for PPM1F, are used in combination to interfere with the PPM1F gene. In some embodiments, SEQ ID NOs: 15, 17, and 19, which each are RNAi(s) for the PAX5 and the PPM1F gene, are used in combination to interfere with those genes.

TABLE 1

Some embodiments of RNAi(s).

| SEQ ID NO: | Sequence | RNAi Type |
|---|---|---|
| 9 | CCGGUGAUGUAGACAAUAAUUAACA | siRNA |
| 10 | GCAAGAGAGGAAGGUAUUCAGGA | siRNA |

TABLE 1-continued

Some embodiments of RNAi(s).

| SEQ ID NO: | Sequence | RNAi Type |
|---|---|---|
| 11 | GCCUUAAUUCCUUGCAAUAGUCUCUC | siRNA |
| 12 | GUUGAGACCAUGCAGUCAAUGCAUU | siRNA |
| 13 | AGACCUUUCCGAAUUCAGGAAGUTG | siRNA |
| 14 | CACCAAGAAGCUAGGUGGUUUCCAG | siRNA |
| 15 | GCUGGGAUUACAGGCAUGAGCC | miRNA (miR-619-5p) |
| 16 | CGCCCACCUCAGCCUCCCAAAAUGC UGGGAUUACAGGCAUGAGCCACUGC GGUCGACCAUGACCUGGACAUGUUU GUGCCCAGUACUGUCAGUUUGCAG | shRNA (miR-619-5p stem loop) |
| 17 | UUUAGAGACGGGGUCUUGCUCU | miRNA (miR-1303) |
| 18 | GGCUGGGCAACAUAGCGAGACCUCA ACUCUACAAUUUUUUUUUUUUAAA UUUUAGAGACGGGGUCUUGCUCUGU UGCCAGGCUUU | shRNA (miR-1303 stem loop) |
| 19 | CUCCGGGACGGCUGGGC | miRNA (miR-4497) |
| 20 | ACCUCCGGGACGGCUGGGCGCCGGC GGCCGGGAGAUCCGCGCUUCCUGAA UCCCGGCCGGCCCGCCCGGCGCCCG UCCGCCCGCGGGUC | shRNA (miR-4497 stem loop) |

As disclosed elsewhere herein, some embodiments pertain to compositions for reducing expression of genes (e.g., PAX5, PPM1F, CAMK2G, etc.). In some embodiments, the composition comprises one or more of an RNAi, a small molecule inhibitor of a gene, and/or a pharmaceutically excipient, diluent, or carrier. In some embodiments, the composition comprises a single RNAi species or a plurality of different RNAi species. In some embodiments, the composition comprises a single small molecule inhibitor or a plurality of different small molecule inhibitors. In some embodiments, the composition lacks one or more of an RNAi, a small molecule inhibitor of PAX5, PPM1F, CAMK2G, and/or a pharmaceutically excipient, diluent, or carrier.

Figure 3F:
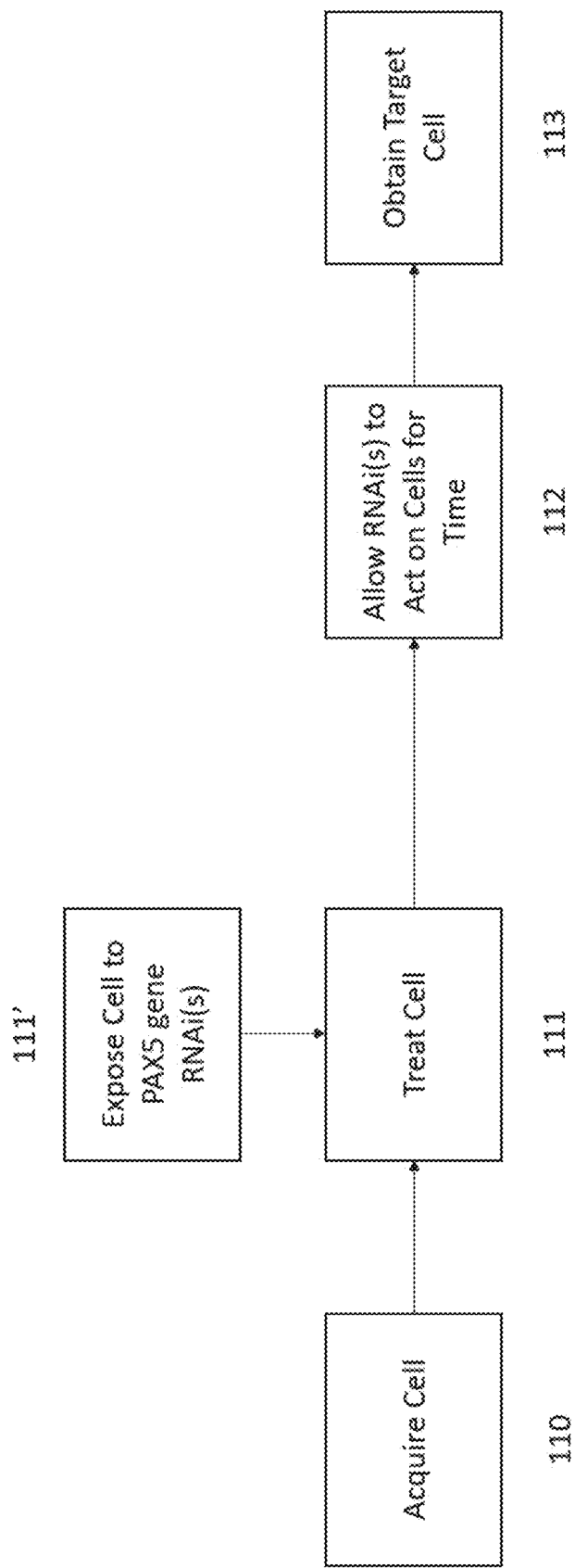
Figure 3G:
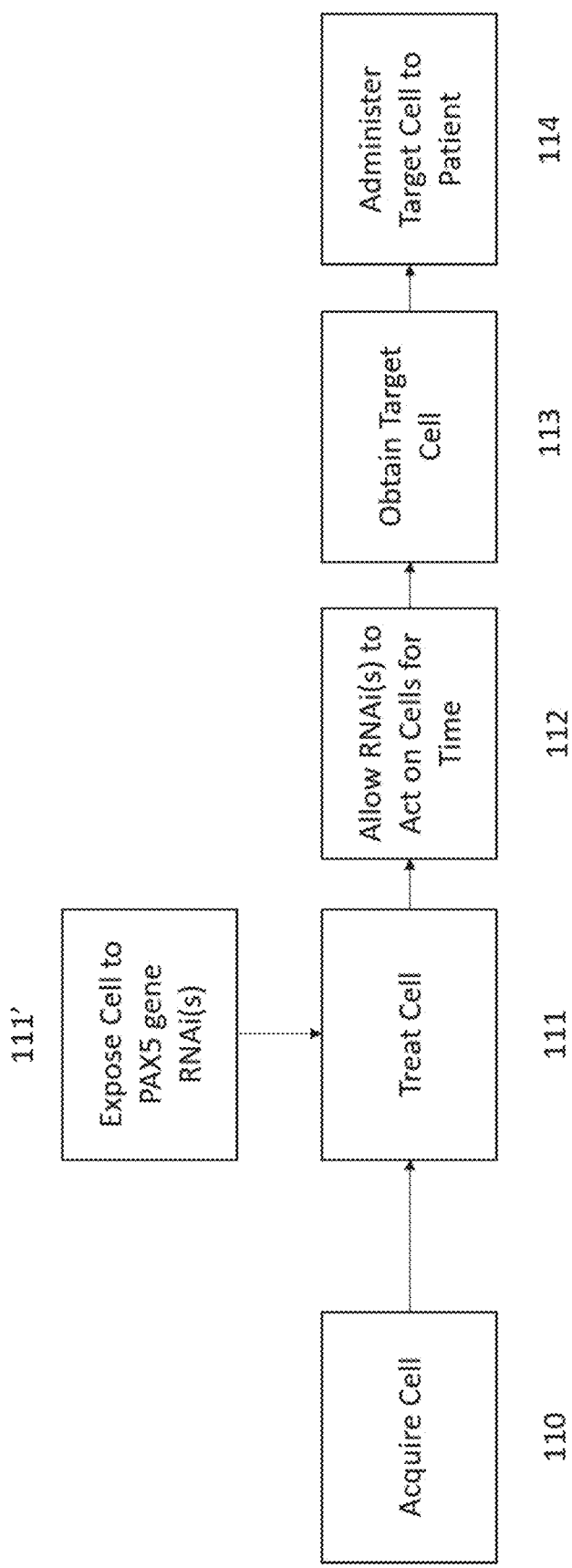

Some embodiments pertain to one or more RNAi(s) for reducing expression of a PAX5 gene. In some embodiments, as shown in FIGS. 3F and 3G, the method includes selecting or acquiring a patient cell 110. In some embodiments, as shown in FIG. 3C, the cell may be a cell in the body of the patient (for in vivo treatment) or isolated from the patient (for ex vivo and/or in vitro treatment). In some embodiments, as shown, the cell is treated by exposing it to one or more different PAX5 gene RNAi(s) 111'. In some embodiments, as shown, the RNAi(s) are allowed to act on the cell for a period of time 112. In some embodiments, as shown, this results in a target cell 113. In some embodiments, as shown in FIG. 3G, the target cell can be reintroduced to the patient (e.g, where it was initially isolated from the patient). In some embodiments, the entire process is performed in vivo and, therefore, the cell need not be reintroduced to the patient.

In some embodiments, the RNAi(s) for reducing expression of a PAX5 gene comprise any one or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20. In some embodiments, the RNAi(s) for reducing expression of a PAX5 gene is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to any one of SEQ ID NOs:9-11 or 15-20 (or ranges including and/or spanning the aforementioned values).

In some embodiments, an RNAi composition for reducing expression of a PAX5 gene is provided. In some embodiments, the composition comprises the one or more RNAi(s). In some embodiments, the composition comprises of any one or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20. In some embodiments, the composition for reducing expression of a PAX5 gene comprises RNAi(s) that are at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to any one of SEQ ID NOs:9-11 or 15-20 (or ranges including and/or spanning the aforementioned values). In some embodiments, the composition comprises two or more (e.g., 2, 3, 4, 5, 6, etc.) RNAi(s). In some embodiments, the composition comprises one or more a small molecule inhibitors of PAX5. In some embodiments, the composition comprises a pharmaceutically acceptable carrier. In some embodiments, the one or more RNAi(s) comprises SEQ ID NO:15. In some embodiments, the one or more RNAi(s) comprises at least one of SEQ ID NO:15, SEQ ID NO:17, and SEQ ID NO:19. In some embodiments, one or more RNAi(s) comprises at least one of SEQ ID NO:16, SEQ ID NO:18, and SEQ ID NO:20. In some embodiments, the one or more RNAi(s) further comprises at least one of SEQ ID NO:9, SEQ ID NO:10, SEQ ID NO:11, SEQ ID NO:12, SEQ ID NO:13, and SEQ ID NO:14.

Some embodiments pertain to a method of reducing expression of a PAX5 gene in a cell. In some embodiments, the method comprises contacting a cell with the RNAi or RNAi(s), combinations of therapeutics, or a composition comprising the same. In some embodiments, the method comprises maintaining the cell for a time sufficient to obtain inhibition of the PAX5 gene, thereby reducing expression of the PAX5 gene in the cell. In some embodiments, the cell is isolated from (FIGS. 3A-3B) or is inside a subject (FIG. 3C). In some embodiments, the cell is contacted with the RNAi for a period of equal to or at least about: 8 hours, 16 hours, 48 hours, 72 hours, or ranges including and/or spanning the aforementioned values.

Some embodiments pertain to the cell made by a method as disclosed above or as disclosed elsewhere herein. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PAX5 gene. In some embodiments, the method comprises administering to the subject a therapeutically effective amount of cells that have been treated with the RNAi, combination of RNAi(s), or compositions containing RNAi(s) as disclosed above or elsewhere herein, thereby treating the subject.

In some embodiments, the administration of the RNAi, combinations, or compositions disclosed herein result in a PAX5 expression that is reduced by at least about 30%, 40%, 50%, 60%, 70%, 80%, 90%, 95%, 98%, 99%, or 99.9%. In some embodiments, PAX5 expression is reduced by at least about 70%. In some embodiments, a reduction in the expression of PAX5 results in increased hematopoietic stem and progenitor cell clonogenicity, T cell activation and immune cell cytotoxicity and decreased expression of genes linked to cellular senescence and aging, as well as a decrease in the production of proteins composing the senescence-associated secretory phenotype (SASP). In some embodiments, PAX5 related diseases, such as age-related immune dysfunction are treated.

Figure 3H:
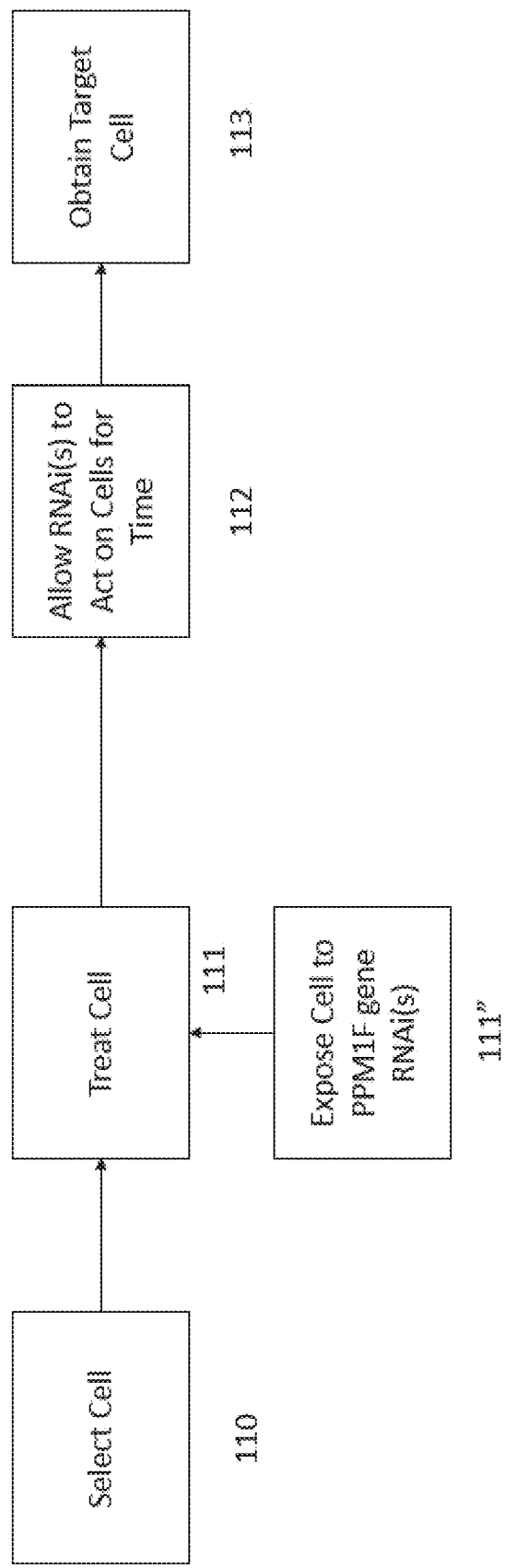
Figure 3I:
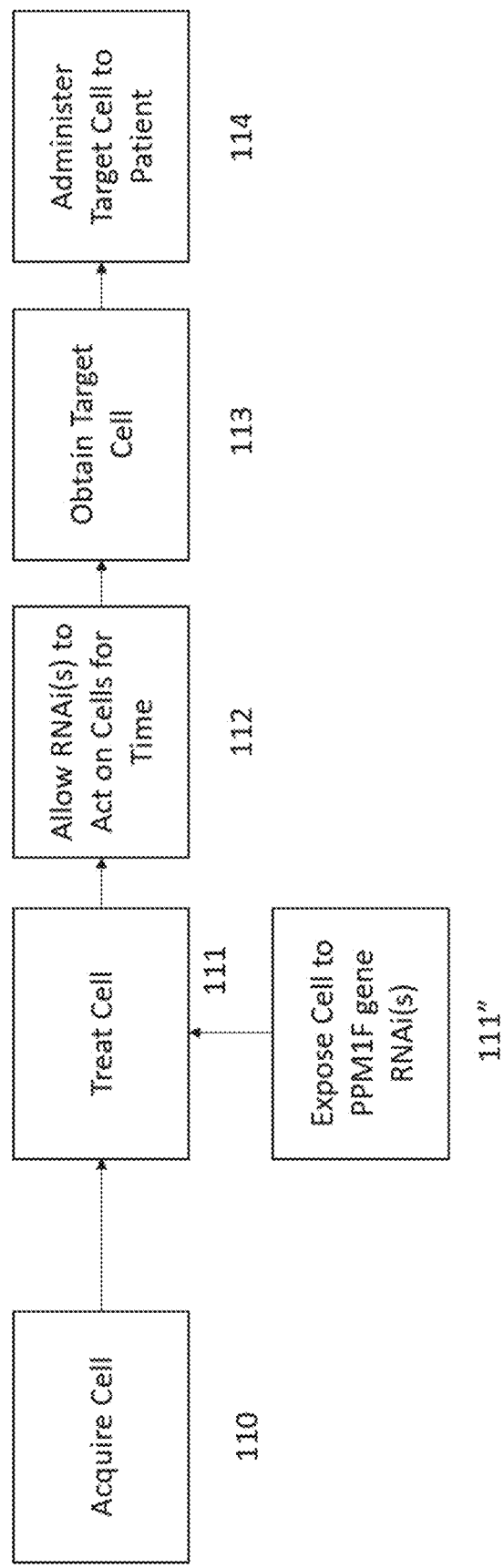

Some embodiments pertain to one or more RNAi(s) for reducing expression of a PPM1F gene. In some embodiments, as shown in FIGS. 3H and 3I, the method includes selecting or acquiring a patient cell 110. In some embodiments, as shown in FIG. 3C, the cell may be a cell in the body of the patient (for in vivo treatment) or isolated from the patient (for ex vivo and/or in vitro treatment). In some embodiments, as shown, the cell is treated by exposing it to one or more different PPM1F gene RNAi(s) 111'. In some embodiments, as shown, the RNAi(s) act within the cell for a period of time 112. In some embodiments, as shown, this results in a target cell 113. In some embodiments, as shown in FIG. 3I, the cell can be reintroduced to the patient (e.g., where it was initially isolated from the patient). In some embodiments, the entire process is performed in vivo and, therefore, the cell need not be reintroduced to the patient.

In some embodiments, the RNAi(s) for reducing expression of a PPM1F gene comprise any one or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some embodiments, the RNAi(s) for reducing expression of a PPM1F gene is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to any one of SEQ ID NOs:12-20 (or ranges including and/or spanning the aforementioned values). In some embodiments, the nucleic acid sequence is any one of the preceding identities to the denoted SEQ ID NO:, and the nucleic acid include additional nucleotides, for example 1, 2, 3, 4, 5, 6, 7, 8, 9, 10, 15, 20, 25, 30 or more additional nucleotides, in a second section, which is contiguous to the first section.

In some embodiments, an RNAi composition for reducing expression of a PPM1F gene is provided. In some embodiments, the composition comprises the one or more RNAi(s). In some embodiments, the composition comprises of any one or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some embodiments, the composition for reducing expression of a PPM1F gene comprises RNAi(s) that are at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to any one of SEQ ID NOs:14-20 (or ranges including and/or spanning the aforementioned values). In some embodiments, the composition comprises two or more (e.g., 2, 3, 4, 5, 6, etc.) RNAi(s). In some embodiments, the composition comprises one or more a small molecule inhibitors of PPM1F. In some embodiments, the composition comprises a pharmaceutically acceptable carrier. In some embodiments, the one or more RNAi(s) comprises SEQ ID NO:15. In some embodiments, the one or more RNAi(s) comprises at least one of SEQ ID NO:15, SEQ ID NO:17, and SEQ ID NO:19. In some embodiments, one or more RNAi(s) comprises at least one of SEQ ID NO:16, SEQ ID NO:18, and SEQ ID NO:20. In some embodiments, the one or more RNAi(s) further comprises at least one of SEQ ID NO:9, SEQ ID NO:10, SEQ ID NO:11, SEQ ID NO:12, SEQ ID NO:13, and SEQ ID NO:14.

Some embodiments pertain to a method of reducing expression of a PPM1F gene in a cell. In some embodiments, the method comprises contacting a cell with the RNAi or RNAi(s), combinations of therapeutics, or a composition comprising the same. In some embodiments, the method comprises maintaining the cell for a time sufficient to obtain inhibition of the PPM1F gene, thereby reducing expression of the PPM1F gene in the cell. In some embodiments, the cell is isolated from (FIGS. 3A-3B) or is inside a subject (FIG. 3C). In some embodiments, the cell is contacted with the RNAi for a period of equal to or at least about: 8 hours, 16 hours, 48 hours, 72 hours, or ranges including and/or spanning the aforementioned values.

Some embodiments pertain to the cell made by a method as disclosed above or as disclosed elsewhere herein. In some embodiments, the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

Some embodiments pertain to a method of treating a subject having a disease or disorder that would benefit from reduction in expression of a PPM1F gene. In some embodiments, the method comprises administering to the subject a therapeutically effective amount of cells that have been treated with the RNAi, combination of RNAi(s), or compositions containing RNAi(s) as disclosed above or elsewhere herein, thereby treating the subject.

In some embodiments, the administration of the RNAi, combinations, or compositions disclosed herein result in a PPM1F expression that is reduced by at least about 30%, 40%, 50%, 60%, 70%, 80%, 90%, 95%, 98%, 99%, or 99.9%. In some embodiments, PAX5 expression is reduced by at least about 70%. In some embodiments, a reduction in the expression of PPM1F results in increased hematopoietic stem and progenitor cell clonogenicity, T cell activation and immune cell cytotoxicity and decreased expression of genes linked to cellular senescence and aging, as well as a decrease in the production of proteins composing the senescence-associated secretory phenotype (SASP). In some embodiments, PPM1F related diseases, such as age-related immune dysfunction are treated.

In some embodiments, a reduction in the expression of CAMK2G results in increased hematopoietic stem and progenitor cell clonogenicity, T cell activation and immune cell cytotoxicity and decreased and decreased expression of genes linked to cellular senescence and aging, as well as a decrease in the production of proteins composing the senescence-associated secretory phenotype (SASP). In some embodiments, CAMK2G related diseases, such as age-related immune dysfunction are treated. In some embodiments, the expression of CAMK2G is reduced by equal to or at least about: 0.01%, 1%, 10%, 20%, 30%, 40%, 50%, 60%, 70%, 80%, 90%, 95%, 98%, 99%, 99.9%, 100%, or ranges including and/or spanning the aforementioned values.

In some embodiments, the method of reducing expression of the PAX5 gene and reducing expression of the PPM1F gene in a cell comprises contacting the cell with one or more interfering RNA(s) (RNAi(s)), wherein the one or more RNAi(s) include one or more of SEQ ID NOs:9-20. In some embodiments, the cell is maintained for a time sufficient to obtain inhibition of the PAX5 gene and the PPM1F gene, thereby reducing expression of the PAX5 gene and the PPM1F gene in that cell to provide a target cell.

In some embodiments, PPM1F and/or PAX5 expression is reduced by at least about: 0.01%, 1%, 10%, 20%, 30%, 40%, 50%, 60%, 70%, 80%, 90%, 95%, 98%, 99%, 99.9%, 100%, or ranges including and/or spanning the aforementioned values. In some embodiments, PPM1F and/or PAX5 expression is reduced by at least about 70%.

In some embodiments, the cell is contacted with the one or more RNAi(s) for a period of equal to or at least about: 8 hours, 16 hours, 48 hours, 72 hours, 84 hours, or ranges including and/or spanning the aforementioned values. In some embodiments, the cell is isolated from a subject. In some embodiments, the cell is inside a subject. In some embodiments, the cell is a human cell.

Some embodiments pertain to the target cell made by contacting the cell with one or more RNAi(s) that are at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to one or more of SEQ ID NOs:9-20.

In some embodiments, the target cell is non-senescent and/or has decreased senescent behavior. In some embodiments, a cell that is non-senescent and/or has decreased senescent releases fewer cytokines and other secreted proteins that are related to the inflammatory response and/or are tumor-supportive, also referred to as the senescence-associated secretory phenotype (SASP), decreased levels of genes linked to senescence and aging, including but not limited to p53, p21 and p16$^{INK4A}$. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging). In some embodiments, the target cell has decreased expression of senescence-associated secretory proteins, and/or decreased expression of senescence- and/or aging-related genes.

In some embodiments, the target cell has increased innate and adaptive immune function including increased T cell activation, and increased immune cell cytotoxicity. In some embodiments, as a result, the patient has less occurrences of sickness, periodically less episodes of general sickness including but not limited to the common cold, allergies, influenza, pneumonia, increased cancer immune surveillance resulting in clearance of pre-cancerous cells and lower incidence of cancer occurrence or relapse.

In some embodiments, the target cell has increased telomere length. Cells with a lower rate of aging-related telomere attrition display a lower rate of cellular senescence incidence. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging).

In some embodiments, the target cell has lower replicative stress relative to the patient cell. In some embodiments, these cells display a lower rate of cellular senescence incidence. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging).

In some embodiments, the target cell has increased stem cell clonogenicity. In some embodiments, this results in increased continuous production of a functional hematopoietics system comprised of immune cells exhibiting low levels of cellular senescence, increased immune activation and increased cytotoxic function. In some embodiments, these cells display a lower rate of cellular senescence incidence. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging), less occurrences of sickness, periodically less episodes of general sickness including but not limited to the common cold, allergies, influenza, pneumonia, increased cancer immune surveillance resulting in clearance of pre-cancerous cells and/or lower incidence of cancer occurrence or relapse.

In some embodiments, the target cell has increased cytotoxic function. In some embodiments, increased cytotoxic function helps reduce potentially cancerous cells from replicating, enhances the detection and clearance of pre-cancerous and cancerous cells by the innate and adaptive immune systems, and/or increases systemic immune surveillance to prevent the formation of circulating tumor cells.

In some embodiments, the target cell has increased mitogen- and/or antigen-induced lymphocyte proliferation and/or activation. In some embodiments, this results in the patient having less occurrences of sickness, periodically less episodes of general sickness including but not limited to the common cold, allergies, influenza, pneumonia, increased cancer immune surveillance resulting in clearance of pre-cancerous cells, and/or lower incidence of cancer occurrence or relapse.

In some embodiments, the target cell has decreased myeloid to lymphoid ratio. In some embodiments, this results in the patient having less occurrences of sickness, periodically less episodes of general sickness including but not limited to the common cold, allergies, influenza, pneumonia, increased cancer immune surveillance resulting in clearance of pre-cancerous cells, and/or lower incidence of cancer occurrence or relapse. In some embodiments, these cells display a lower rate of cellular senescence incidence. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging), less occurrences of sickness, periodically less episodes of general sickness including but not limited to the common cold, allergies, influenza, pneumonia, increased cancer immune surveillance resulting in clearance of pre-cancerous cells, and/or lower incidence of cancer occurrence or relapse. In some embodiments, a decreased myeloid to lymphoid ratio helps reduce potentially cancerous cells from replicating, enhances the detection and clearance of pre-cancerous and cancerous cells by the innate and adaptive immune systems, and/or increases systemic immune surveillance to prevent the formation of circulating tumor cells.

In some embodiments, the target cell has increased CD4 to CD8 T lymphocyte ratio. In some embodiments, this results in the patient having less occurrences of sickness, periodically less episodes of general sickness including but not limited to the common cold, allergies, influenza, pneumonia, increased cancer immune surveillance resulting in clearance of pre-cancerous cells and lower incidence of cancer occurrence or relapse. In some embodiments, these cells display a lower rate of cellular senescence incidence. In some embodiments, as a result, the patient has less soreness in joints, higher activity levels, less stiffness (e.g., in the legs, arms, and/or back), increased cognitive function, increased cardiovascular function, increased health span (e.g., which may include a decrease in the general incidence of age-related disease(s) over the course of chronological aging), less occurrences of sickness, periodically less episodes of general sickness including but not limited to the common cold, allergies, influenza, pneumonia, increased cancer immune surveillance resulting in clearance of pre-cancerous cells, and/or lower incidence of cancer occurrence or relapse. In some embodiments, an increased CD4 to CD8 T lymphocyte ratio helps reduce potentially cancerous cells from replicating, enhances the detection and clearance of pre-cancerous and cancerous cells by the innate and adaptive immune systems and/or increases systemic immune surveillance to prevent the formation of circulating tumor cells.

In some embodiments, a decrease in senescence is measured as a decrease scenescense indicators, such as any senescence cytokine or protein, a senescence related inflammatory cytokine, a senescence related tumor supportive cytokine, and/or as a decrease in the amount of senescnence related gene expression (e.g., p53, p21, p16INK4A, and/or any ligand disclosed in FIG. 1). In some embodiments, patients receiving treatment experience a decrease in the senescence indicators of equal to or at least about: 5%, 10%, 25%, 50%, 75%, 90%, or ranges including and/or spanning the aforementioned values. In some embodiments, soreness and/or stiffness is quantified by measuring pain during the movement of a joint (e.g., extending the leg at the knee or the arm at the elbow) using one or more of the following pain scales: Visual Analog Scale for Pain (VAS Pain), Numeric Rating Scale for Pain (NRS Pain), McGill Pain Questionnaire (MPQ), Short-Form McGill Pain Questionnaire (SF-MPQ), Chronic Pain Grade Scale (CPGS), Short Form-36 Bodily Pain Scale (SF-36 BPS), and Measure of Intermittent and Constant Osteoarthritis Pain (ICOAP). In some embodiments, in patients receiving treatment, pain, soreness, and/or stiffness decreases by equal to or at least about: 5%, 10%, 25%, 50%, 75%, 90%, or ranges including and/or spanning the aforementioned values. In some embodiments, cognitive function is quantified using one or more of the following cognition scales: Cognitive Function Composite Score, Fluid Cognition Composite Score (includes DCCS, Flanker, Picture Sequence Memory, Mini-Mental State Exam (MMSE), etc.). In some embodiments, cognition is improved in patients receiving treatment by equal to or at least about: 5%, 10%, 25%, 50%, 75%, 90%, or ranges including and/or spanning the aforementioned values. In some embodiments, cardiac function is measured using cardiac output (e.g., the measure of a heart's ability to pump). In some embodiments, cardiac output is improved in patients receiving treatment by equal to or at least about: 5%, 10%, 25%, 50%, 75%, 90%, or ranges including and/or spanning the aforementioned values. In some embodiments, life span is increased in patients receiving treatment by equal to or at least about: 5%, 10%, 15%, 25%, or ranges including and/or spanning the aforementioned values. In some embodiments, rates of sickness (e.g., occurrences of common cold, allergies, influenza, pneumonia, etc.) in patients receiving treatment decreases by equal to or at least about: 5%, 10%, 25%, 50%, 75%, 90%, or ranges including and/or spanning the aforementioned values. In some embodiments, telomere length in patients receiving treatment is higher by equal to or at least about: 5%, 10%, 25%, 50%, 75%, 90%, or ranges including and/or spanning the aforementioned values. In some embodiments, cytotoxic function in patients receiving treatment is higher by equal to or at least about: 5%, 10%, 25%, 50%, 75%, 90%, or ranges including and/or spanning the aforementioned values. In some embodiments, increased cancer cell surveillance is measured by an increase in the clearance of cancer cells from patients receiving treatment by equal to or at least about: 5%, 10%, 25%, 50%, 75%, 90%, or ranges including and/or spanning the aforementioned values. In some embodiments, cancer rates in patients receiving treatment is lower by equal to or at least about: 25%, 50%, 75%, 90%, or ranges including and/or spanning the aforementioned values. In some embodiments, the health of a treated patient is compared to the health of an untreated, control patient to determine any effect of the treatment. In some embodiments, the health of a treated patient is compared to the health of a that patient before treatment to determine any effect of the treatment.

Some embodiments pertain to a composition for reducing expression of a PAX5 gene and reducing the expression of a PPM1F gene (and/or the other genes encoding the other proteins disclosed herein), the composition comprising an acceptable carrier and an RNAi that is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to one or more of SEQ ID NOs:9-20. In some embodiments, the composition comprises an acceptable carrier and an RNAi that is at least 80% to 100% identical to SEQ ID NO:15. In some embodiments, the composition comprises or further comprises a microRNA that is at least 80% to 100% identical to SEQ ID NO:16. In some embodiments, the composition comprises or further comprises a microRNA that is at least 80% to 100% identical to SEQ ID NO:17. In some embodiments, the composition comprises or further comprises a microRNA that is at least 80% to 100% identical to SEQ ID NO:18. In some embodiments, the composition comprises or further comprises a microRNA that is at least 80% to 100% identical to SEQ ID NO:19. In some embodiments, the composition comprises or further comprises a microRNA that is at least 80% to 100% identical to SEQ ID NO:20. In some embodiments, the composition comprises or further comprises one or more of SEQ ID NOs:9-14.

In some embodiments, the RNAi or combination of RNAi(s) (e.g., siRNAs, microRNAs, etc.) are administered using a pharmaceutically acceptable carrier. In some embodiments the wherein the pharmaceutically acceptable carrier comprises one or more of nanoparticles composed of non-degradable and/or degradable biomaterials, micelles, liposomes, extracellular vesicles (native and/or synthetic), exosomes (native and/or synthetic), and/or microvesicles (native and/or synthetic). In some embodiments, the pharmaceutically acceptable carrier comprises a non-natural or synthetic exosome. In some embodiments, natural exosomes are not used as a carrier. In some embodiments, RNAi can be delivered to the targets cells for active transport-mediated uptake, by electroporation and/or by nucleofection.

In some embodiments, the RNAi or combination of RNAi(s) are administered using gene delivery vector. In some embodiments, the carrier is a viral vector. In some embodiments, a gene for the transcription of the RNAi is delivered to a cell which transcribes the RNAi. In some embodiments, the RNAi or combination of RNAi(s) are administered to other cells by a cell that transcribes the RNAi or RNAi(s) (e.g., through exosome, extracellular vesicles, etc.). In some embodiments, the cell transcribing the RNAi is treated by the RNAi it produces.

In some embodiments, a dose of RNAi(s) comprises equal to less than about: 0.001 μg, 0.01 μg, 0.1 μg, 1 μg, 10 μg, 100 μg, 1000 μg, or ranges including and/or spanning the aforementioned values.

Figure 3J:
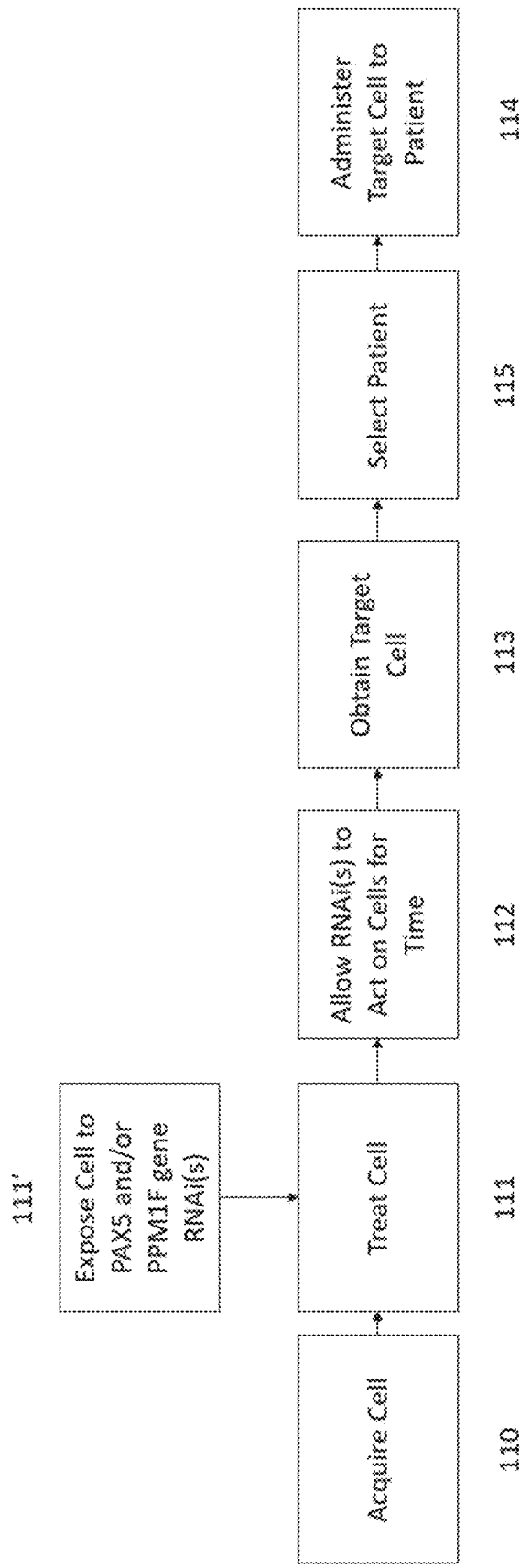

Some embodiments pertain to a method of treating a subject having a disease or disorder that would benefit from reduction in expression of a PAX5 gene and a reduction in expression of a PPM1F gene. As shown in FIG. 3J, in some embodiments, the method includes acquiring a patient cell 110. In some embodiments, as shown in FIG. 3C, the cell may be a cell in the body of the patient (for in vivo treatment) or isolated from the patient (for ex vivo and/or in vitro treatment), as shown in FIG. 3A-B. In some embodiments, as shown, the cell is treated by exposing it to one or more different PAX5 gene RNAi(s) 111' and/or one or more different PPM1F gene RNAi(s) 111'. In some embodiments, as shown, the RNAi(s) are allowed to act on the cell for a period of time 112. In some embodiments, as shown, this results in a target cell 113. In some embodiments, a patient suffering from a disease or disorder that would benefit from reduction of the expression of a PAX5 gene and a reduction in expression of a PPM1F gene is selected 115. In some embodiments, as shown in FIG. 3J, the cell can be administered to the patient (e.g, where it was initially isolated from the patient). In some embodiments, the method comprises administering to the subject a therapeutically effective amount of the target cell as disclosed elsewhere herein or the composition as disclosed elsewhere herein, thereby treating the subject.

Some embodiments pertain to a method for treating or preventing a disease state, comprising administering to a patient in need thereof a therapeutically effective dose of cells treated with one or more RNAi(s) of a PAX5 gene and/or of a PPM1F gene. In some embodiments, the one or more RNAi(s) is selected from any one or more of the RNA is as recited in elsewhere herein. In some embodiments, the disease state is an age related dysfunction. In some embodiments, the disease state is not an age-related dysfunction. In some embodiments, the disease state comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA). In some embodiments, the dysfunction is one in which PAX5 and/or PPM1F plays a direct role or is part of a pathway that is compromised. In some embodiments, PAX5 and/or PPM1F are not part of a compromised pathway, but allow for the recovery or increase in activity to address the disorder.

Some embodiments pertain to a method for preparing a target cell. In some embodiments, the method comprises obtaining cells from a subject to provide at least one subject cell. In some embodiments, the method comprises exposing the at least one subject cell to one or more RNAi(s) that is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical to one or more of SEQ ID NOs:9-20 to provide at least one target cell. In some embodiments, the at least one target cell is member of a population of cells comprising equal to or at least about 100, 1000, 10,000, 100,000, 1,000,000, or 10,000,000 cells. Some embodiments pertain to the target cell.

Some embodiments pertain to a method for treating or preventing cellular dysfunction in a patient. In some embodiments, the method comprises administering to a patient in need thereof a therapeutically effective dose of the target cell as disclosed above or elsewhere herein. In some embodiments, the method comprises administering to a patient in need thereof a therapeutically effective dose of one or more RNAi(s) and small molecule inhibitors. In some embodiments, the cellular dysfunction is an age-related dysfunction. In some embodiments, the cellular dysfunction is not an age-related dysfunction.

Some embodiments pertain to an interfering RNA (RNAi) for reducing the expression of a paired any one of the CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, or ZNF549 gene. In some embodiments, the RNAi comprises 4 to 50 contiguous nucleotides having a polynucleotide sequence that is at least about 60%, about 70%, about 80%, about 85%, about 86%, about 87%, about 88%, about 89%, about 90%, about 91%, about 92%, about 93%, about 94%, about 95%, about 96%, about 97%, about 98%, about 99%, about 99.9%, about 99.99%, or about 100% identical complementary (or anti-complementary) to a region of any one of the CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, or ZNF549 gene. In some embodiments, the RNAi comprises 4 to 50 contiguous nucleotides having a polynucleotide sequence that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to a region of any one or more of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

Some embodiments pertain to a method for reducing the expression of a PAX5 gene and/or PPM1F gene, comprising exposing a cell at least one isolated microRNA that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to any one or SEQ ID NO:15-20. Some embodiments pertain to a method for reducing the expression of a PAX5 and/or PPM1F gene, comprising exposing a cell to at least one isolated microRNA, wherein the at least one microRNA is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:15. Some embodiments pertain to a method for reducing the expression of a PAX5 gene and/or PPM1F, comprising exposing a cell to a composition comprising at least one isolated microRNA, wherein the at least one microRNA is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:16. In some embodiments, the method comprises administering both SEQ ID NO: 15 and SEQ ID NO: 16. In some embodiments, the method comprises administering a microRNA that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:17. In some embodiments, the method comprises administering a microRNA that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:18. In some embodiments, the method comprises administering a microRNA that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:19. In some embodiments, the method comprises administering a microRNA that is at least about 60%, about 70%, about 80%, about 85%, about 86%, about 87%, about 88%, about 89%, about 90%, about 91%, about 92%, about 93%, about 94%, about 95%, about 96%, about 97%, about 98%, or about 100% identical to SEQ ID NO:20.

In some embodiments, a nucleic acid is an oligonucleotide, an antisense oligonucleotide, an RNAi agent, a miRNA, immunomodulatory nucleic acid, an aptamer, a Piwi-interacting RNA (piRNA), a small nucleolar RNA (snoRNA), a ribozyme, a mRNA, a lncRNA, a ncRNA, an antigomir (e.g., an antagonist to a miRNA, lncRNA, ncRNA or other nucleic acid), or a portion thereof. In some embodiments, an interfering polynucleotide is provided. In some embodiments, the nucleic acids are single stranded oligonucleotides. In some embodiments, the nucleic acids are double stranded oligonucleotides. In some embodiments, the sequence of an antisense RNAi is complementary to the protein-coding sequence. The nucleic acids described herein may be any of a range of length of up to, but not necessarily 200 nucleotides in the case of antisense oligonucleotides, RNAi, siRNA, shRNA, iRNA, antagomirs. In some embodiments, the antisense RNA is modified, for example by incorporating non-naturally occurring nucleotides. In some embodiments, the nucleic acid is an interfering RNA, such as an siRNA, that specifically targets an RNA molecule, such as an mRNA, encoding a protein involved in a disease, such as cancer. In some embodiments, the disease is cancer, such as a solid tumor or hematological malignancy, and the interfering RNA targets mRNA encoding a protein involved in the cancer, such as a protein involved in regulating the progression of the cancer. In some embodiments, the nucleic acid is an interfering RNA, such as an siRNA, that specifically targets an RNA molecule, such as an mRNA, encoding a protein involved in negatively regulating an immune response. In some embodiments, the interfering RNA targets mRNA encoding a negative co-stimulatory molecule.

In some embodiments, the nucleic acids are miRNA. A microRNA (abbreviated miRNA) is a short ribonucleic acid (RNA) molecule found in eukaryotic cells. A microRNA molecule has very few nucleotides (an average of 22) compared with other RAs. miRNAs are post-transcriptional regulators that bind to complementary sequences on target messenger RNA transcripts (mRNAs), usually resulting in translational repression or target degradation and gene silencing. In some embodiments, the miRNAs substantially complementary (such as at least about 60%, 70%, 80%, 90%, 95%, 98%, 99%, 99.9%, or more identical to) the corresponding target gene. In some embodiments, the antisense RNA is modified, for example by incorporating non-naturally occurring nucleotides.

Some embodiments disclosed herein relate to compositions and methods for decreasing the extent of cellular senescence occurring in the lymphohematopoietic system of a subject. In some embodiments, a method of reducing the extent of cellular senescence occurring in the lymphohematopoietic system of a subject comprises administration of a composition comprising a microRNA (miR) that targets and decreases the expression of PAX5, PPM1F, or both in a subject. Aspects of the present disclosure are directed to compositions and methods for performing RNA-induced gene silencing (also called RNAi) of PAX5, PPM1F or both.

The compositions and methods disclosed herein may provide means of restoring an aging lymphohematopoietic system. Herein reference is made to the undifferentiated cells of the hematopoietic lineage including hematopoietic stem cells (HSCs), lymphoid progenitor cells (LPCs) and myeloid progenitor cells (MPCs) which are known collectively as lymphohaematopoietic progenitor cells (LPCs). LPCs and MPCs are each formed by the differentiation of HSCs.

Other examples of differentiated cells of the hematopoietic lineage include T lymphocytes, B lymphocytes, eosinophils, basophils, neutrophils, megakaryocytes, monocytes, macrophages erythrocytes, granulocytes, mast cells, dendritic cells and natural killer cells. The pathways of differentiation in the lymphohematopoietic system have been extensively characterized and the various cell stages are readily identifiable according to morphology and lineage-specific cell surface markers.

In some embodiments, the compositions and methodologies disclosed herein are utilized in the treatment of one or more ARDs that may be the result of an aging lymphohematopoietic system. In certain aspects, the present disclosure contemplates a polynucleotide comprising a unimolecular RNA, such as an shRNA. The shRNA can be a unimolecular RNA that includes a sense sequence, a loop region, and an antisense sequence (sometimes referred to as first and second regions) which together form a hairpin loop structure. A loop structure can also include deoxyribonucleotides, non-nucleotide monomers and reversible linkages such as S—S bonds, which can be formed by oxidation of —SH groups introduced into nucleotide residues.

The antisense and sense sequences of the RNAi may be substantially complementary to one other (about 80% complementary or more), where in certain aspects the antisense and sense sequences are 100% complementary to each other. In certain aspects, the antisense and sense sequences are too short to be processed by Dicer, and hence act through an alternative pathway to that of longer double-stranded RNAs. Additionally, the antisense and sense sequences within a unimolecular RNA of the present disclosure can be the same length, or differ in length by from about 1 base to about 5 bases. The loop can be any length, such as from 0 to 4 nucleotides (nt) in length or an equivalent length of non-nucleotidic linker, and or 2 nucleotides or an equivalent length of non-nucleotidic linker (e.g., a non-nucleotide loop having a length equivalent to 2 nt). In the case of a loop of zero nt, the antisense sequence is linked directly to the sense sequence, with part of one or both strands forming the loop. In another aspect of a zero-nt loop shRNA, the antisense sequence is about 18 or 19 nt and the sense sequence is shorter than the antisense sequence, so that one end of the antisense sequence forms the loop.

In one aspect, an shRNA described herein comprises a sequence complementary to a sequence of an mRNA of PAX5. PAX5 encodes the B-cell lineage specific activator protein (BSAP) which is a nuclear protein in the paired-box containing (PAX) family of transcription factors involved in control of organ development and tissue differentiation. BSAP is primarily expressed in B lymphocytes and B-cell lymphomas, with additional expression in the developing central nervous system. In an aspect of the present disclosure a method of treating an ARD comprises administering to a subject an RNAi that reduces the expression of BSAP. In some embodiments, the RNAi is an shRNA which acts to reduce the expression of BSAP by mechanisms such as mRNA disruption (e.g, hydrolysis, slicing) or translational repression.

In some embodiments, an RNAi for reducing the expression of BSAP comprises an shRNA having SEQ ID NOs: 9-11, or combinations thereof.

In some embodiments, the RNAi (e.g., shRNA) is capable of binding to a target sequence of PAX5 mRNA and reducing the expression of BSAP by from about 30% to about 100%, alternatively from about 30% to about 50%, alternatively from about 50% to about 75% or alternatively from about 75% to about 100% of the original expression level of BSAP. The expression level of BSAP in any particular cell type may be determined using any suitable methodology for determining protein expression level such as Western blots, high performance liquid chromatography, enzyme-linked immunosorbent assay, protein immunoprecipitation and the like.

In one aspect, an shRNA described herein comprises a sequence complementary to a sequence of an mRNA of PPM1F. PPM1F encodes Mg2+/Mn2+-dependent protein phosphatase 1F which belongs to the PP2C family of Ser/Thr protein phosphatases. PP2C family members are known as negative regulators of cell stress response pathways, including p38 MAPK, JNK and HOG signaling pathways. Known substrates of the phosphatase include Rho guanine nucleotide exchange factors (PIX) and calcium/calmodulin-dependent protein kinase II gamma. PPM1F is ubiquitous in various tissues and organs.

In some embodiments, an RNAi for downregulation of the expression of the gene product of PPM1F comprises an shRNA having SEQ ID Nos:12-14 or combinations thereof. In some embodiments, the RNAi (e.g, shRNA) is capable of binding to a target sequence of the PPM1F mRNA and reducing the expression of the Mg2+/Mn2+-dependent protein phosphatase 1F by from about 30% to about 100%, alternatively from about 30% to about 50%, alternatively from about 50% to about 75% or alternatively from about 75% to about 100% of the original expression level of Mg2+/Mn2+-dependent protein phosphatase 1F. The expression level of Mg2+/Mn2+-dependent protein phosphatase 1F in any particular cell type may be determined using any suitable methodology for determining protein expression level such as Western blots, high performance liquid chromatography, enzyme-linked immunosorbent assay, protein immunoprecipitation and the like.

In some aspects of the present disclosure, an RNAi (e.g., shRNA) that reduces the expression of the mRNA of PAX5, PPM1F or both comprises a modified nucleotide. One or more of the nucleotides present in the RNAi (e.g., shRNA) may be modified to achieve one or more user and/or process goals, such as increased stability. Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitromdole, or nebularine. The term "nucleotide" is also meant to include the N3' to P5' phosphoramidate, resulting from the substitution of a ribosyl 3' oxygen with an amine group. Further, the term nucleotide also includes those species that have a detectable label, such as for example a radioactive or fluorescent moiety, or mass label attached to the nucleotide.

In some aspects of the present disclosure, an RNAi (e.g., shRNA) that reduces the expression of the mRNA of PAX5, PPM1F or both is a component of an antibody conjugate. In some embodiments, any RNAi suitable for use in the reduction of the PAX5 or PPM1F may be utilized in the present disclosure. Additionally any suitable method of introducing such biomolecules to cells and/or administering such biomolecules is also contemplated. In some embodiments, the RNAi (e.g., shRNA) may be administered as a component of an antibody-RNAi (e.g., shRNA) conjugate. In some aspects, the antibody-shRNA conjugates specifically target senescent cells to deliver an shRNA molecule that reduces the expression of PAX5, PPM1F or both. The antibody-shRNA conjugates (or "complexes") include an antibody or functional fragment thereof that targets a cell to selectively deliver an associated shRNA molecule to the cell. In some embodiments, the cell is a cell of the lymphohematopoietic system, An antibody or functional antibody fragment is a molecule that includes one or more portions of an immunoglobulin or immunoglobulin-related molecule that specifically binds to, or is immunologically reactive with an age-related antigen or other age-related biomarker. The antibody may be a polyclonal antibody, a monoclonal antibody, or any suitable modified antibody. The term modified antibody includes, but is not limited to genetically engineered or otherwise modified forms of immunoglobulins, such as intrabodies, chimeric antibodies, fully human antibodies, humanized antibodies, and heteroconjugate antibodies (e.g., bispecific antibodies, diabodies, triabodies, and tetrabodies). The term functional antibody fragment includes one or more antigen binding fragments of an antibody alone or in combination with other molecules. The antibody-shRNA conjugates or complexes may be synthesized or constructed using any suitable conjugation method. In one aspect, the antibody-siRNA complex is constructed by a method of covalent conjugation. Synthesis of antibody-shRNA conjugates via a covalent construction strategy involves chemically linking an shRNA molecule to an antibody using a cleavable or non-cleavable.

In some aspects of the present disclosure, an RNAi (e.g., shRNA) that reduces the expression of the mRNA of PAX5, PPM1F or both is a component of a nucleic acid vector, or is encoded by a nucleic acid vector. A nucleic acid vector is any nucleic acid that functions to carry, harbor or express a nucleic acid of interest. Nucleic acid vectors can have specialized functions such as expression, packaging, pseudotyping, transduction or sequencing, for example. Nucleic acid vectors also can have, for example, manipulatory functions such as a cloning or shuttle vector. The structure of the vector can include any desired form that is feasible to make and desirable for a particular use. In an alternative aspect, a method of the present disclosure comprises introducing to the cells a vector capable of inducible or constitutive expression of one or more nucleotides of the type disclosed herein. For example, an expressible form of the shRNA may be located on a vector such as a plasmid, cosmid, phagemid, virus, and other vehicles derived from viral or bacterial sources.

In some embodiments, the RNAi (e.g., shRNA) that reduces the expression of the mRNA of PAX5, PPM1F or both is a component of a packaging construct. A packaging construct is a nucleic acid vector that encodes retroviral structural polypeptides sufficient for vector production. In some embodiments, the nucleotide vector is a viral vector comprises an oligonucleotide (e.g., siRNA, shRNA) that inhibits expression of the mRNA or gene product of PAX5, PPM1F or both. The viral vector may be a lentivirus vector, including an integrating lentivirus vector. A lentivirus is an icosahedral enveloped virus having a diploid RNA genome that becomes integrated into the host chromosome as a proviral DNA for genome replication. The lentiviral genome contains gag, pol and env genes which encode the structural polypeptides of the virion (p17, p24, p7 and p6); the viral enzymes protease, reverse transcriptase and integrase, and the envelope glycoproteins (gp120 and gp41), respectively.

In some aspects, the RNAi and/or SAD may be associated with a delivery material that facilitates entry of the SAD into the appropriate cells. In some embodiments, a SAD (e.g., an RNAi) of the type disclosed herein is associated with a liposome or niosome. In some embodiments, a SAD (e.g., an RNAi) is delivered using a viral vector. Liposomes are a form of vesicles that consist either of many, few or just one phospholipid bilayers. The polar character of the liposomal core enables polar drug molecules to be encapsulated. Amphiphilic and lipophilic molecules are solubilized within the phospholipid bilayer according to their affinity towards the phospholipids. Participation of nonionic surfactants instead of phospholipids in the bilayer formation results in niosomes. shRNA of the type disclosed herein (i.e., SADs) can be incorporated without loss of their activity within the hydrophobic domain of vesicle membranes, acting as a size-selective filter, only allowing passive diffusion of small solutes such as ions, nutrients and antibiotics. Thus, SADs may be encapsulated in a nanocage and are effectively protected from premature degradation by proteolytic enzymes.

In an aspect the SAD is associated with a dendrimer. Dendrimers are nanometer-sized, highly branched and monodisperse macromolecules with symmetrical architecture. They consist of a central core, branching units and terminal functional groups. The core together with the internal units, determine the environment of the nanocavities and consequently their solubilizing properties, whereas the external groups the solubility and chemical behavior of these polymers. Targeting effectiveness is affected by attaching targeting ligands at the external surface of dendrimers, while their stability and protection from the Mononuclear Phagocyte System (MPS) is being achieved by functionalization of the dendrimers with polyethylene glycol chains (PEG)

In some embodiments, the SAD is associated with a liquid crystal. Liquid crystals combine the properties of both liquid and solid states. They can be made to form different geometries, with alternative polar and non-polar layers (i.e., a lamellar phase) where aqueous drug solutions can be included.

In some embodiments, the SAD is associated with a nanoparticle. Nanoparticles (including nanospheres and nanocapsules of size 10-200 nm) are in the solid state and are either amorphous or crystalline. They are able to adsorb and/or encapsulate a drug, thus protecting it against chemical and enzymatic degradation. Nanocapsules are vesicular systems in which the drug is confined to a cavity surrounded by a unique polymer membrane, while nanospheres are matrix systems in which the drug is physically and uniformly dispersed. Nanoparticles as drug carriers can be formed from both biodegradable polymers and non-biodegradable polymers. In recent years, biodegradable polymeric nanoparticles have attracted considerable attention as potential drug delivery devices in view of their applications in the controlled release of drugs, in targeting particular organs/tissues, as carriers of DNA in gene therapy, and in their ability to deliver proteins, peptides and genes through the peroral route.

In some embodiments, the SAD is associated with a hydrogel. Hydrogels are three-dimensional, hydrophilic, polymeric networks capable of imbibing large amounts of water or biological fluids. The networks are composed of homopolymers or copolymers, and are insoluble due to the presence of chemical crosslinks (tie-points, junctions), or physical crosslinks, such as entanglements or crystallites. Hydrogels exhibit a thermodynamic compatibility with water, which allows them to swell in aqueous media. They are used to regulate drug release in reservoir-based, controlled release systems or as carriers in swellable and swelling-controlled release devices. On the forefront of controlled drug delivery, hydrogels as enviro-intelligent and stimuli-sensitive gel systems modulate release in response to pH, temperature, ionic strength, electric field, or specific analyte concentration differences. In these systems, release can be designed to occur within specific areas of the body (e.g., within a certain pH of the digestive tract) or also via specific sites (adhesive or cell-receptor specific gels via tethered chains from the hydrogel surface). Hydrogels as drug delivery systems can be very promising materials if combined with the technique of molecular imprinting.

SADS associated with one or more of the delivery systems disclosed herein may be considered as packaged therapeutic agents and are herein denoted "p-SADs." p-SADs may be further modified to improve properties such as bioavailability by modification of the packaging using any suitable methodology (e.g., conjugation with a targeting molecule).

In some embodiments, the present disclosure contemplates the utilization of SADs of the type disclosed herein as compositions for administration to a subject in need thereof. In some embodiments, the SADs may be a component of a pharmaceutical formulation that is administered locally or systemically to a subject. In some embodiments, SADs of the type disclosed herein are used in conjunction with a vehicle such as a nanoparticle, micelle, liposome, niosome, microsphere, cyclodextrin and the like. In some embodiments, such vehicles further comprise one or more elements to direct the carrier or vehicle to a particular cell, tissue or organ of a subject (e.g., cells of the lymphohematopoietic system).

In an aspect of the present disclosure, a subject experiencing an ARD may be administered a SAD of the type disclosed herein. The administration may involve targeting cells of the lymphohematopoietic system such using an adoptive therapy method comprising (i) obtaining lymphohematopoietic cells from the subject using any suitable methodology such as via mobilization of the stem cells into the peripheral blood, aspiration of the bone marrow, apheresis; (ii) transfecting or transducing the obtained cells with RNAi of the type disclosed herein and (iii) reintroducing the cells to the subject. An alternative methodology may comprise packaging an RNAi of the type disclosed herein such as via encapsulation and introducing the packaged RNAi to the bone marrow of a subject experiencing an ARD using any suitable administration route. The administration may involve targeting cells of the lymphohematopoietic system such using an adoptive therapy method comprising (i) obtaining lymphohematopoietic cells from the subject using any suitable methodology such as via mobilization of the stem cells into the peripheral blood, aspiration of the bone marrow, apheresis; (ii) transfecting or transducing the obtained cells with RNAi of the type disclosed herein using transposons such as sleeping beauty, crisper, CAS9, and zinc finger nucleases and (iii) reintroducing the cells to the subject. In such aspects, the expression of natural or synthetic nucleic acids encoding SADs of the type disclosed herein is typically achieved by operably linking a nucleic acid encoding the SAD polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

In some embodiments, one or more of CRISPR, antibodies, and/or RISC can be used to reduce the expression of one or more of the proteins disclosed herein.

Small Molecule Inhibitors

Disclosed herein is a method of decreasing the extent of cellular senescence occurring in the lymphohematopoietic system of a subject and/or treating an age-related disorder (ARD) that comprises administering to a subject in need thereof an effective amount of one or more of a RNAi, a chemical compound, and/or a target cell that has been treated with one of the foregoing. Some embodiments disclosed herein pertain to compositions and methods for decreasing the extent of cellular senescence occurring in the lymphohematopoietic system of a subject. In some embodiments, a method of decreasing the extent of cellular senescence occurring in the lymphohematopoietic system of a subject comprises administration of a composition comprising a polycyclic aromatic small molecule that targets and reduces the activity of the B-cell lineage specific activator protein, the protein phosphatase 1F enzyme or both in a subject. In some embodiments, the compositions and methodologies disclosed herein are utilized in the treatment of one or more age-related disorders.

Figure 3K:
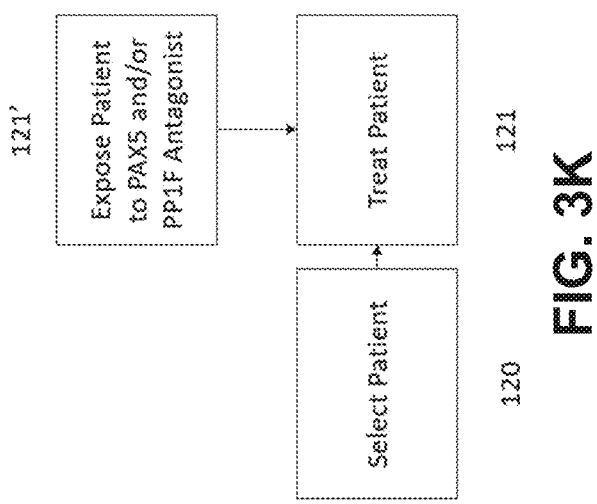

Disclosed herein is a composition or compound comprising a polycyclic aromatic small molecule capable of targeting BSAP and reducing the activity of BSAP. Also disclosed herein is a composition comprising a polycyclic aromatic small molecule capable of targeting PP1F and reducing the activity of PP1F. In some embodiments, as shown in FIG. 3K, a patient with a disease or disorder who could benefit from treatment with a PAX5 or PP1F inhibitor is selected 120. As shown in FIG. 3K, in some embodiments, one or more small molecules 121' can be administered to the patient to achieve a desired therapeutic result (e.g., lowering the accurrence of an ARD) 121.

Figure 3L:
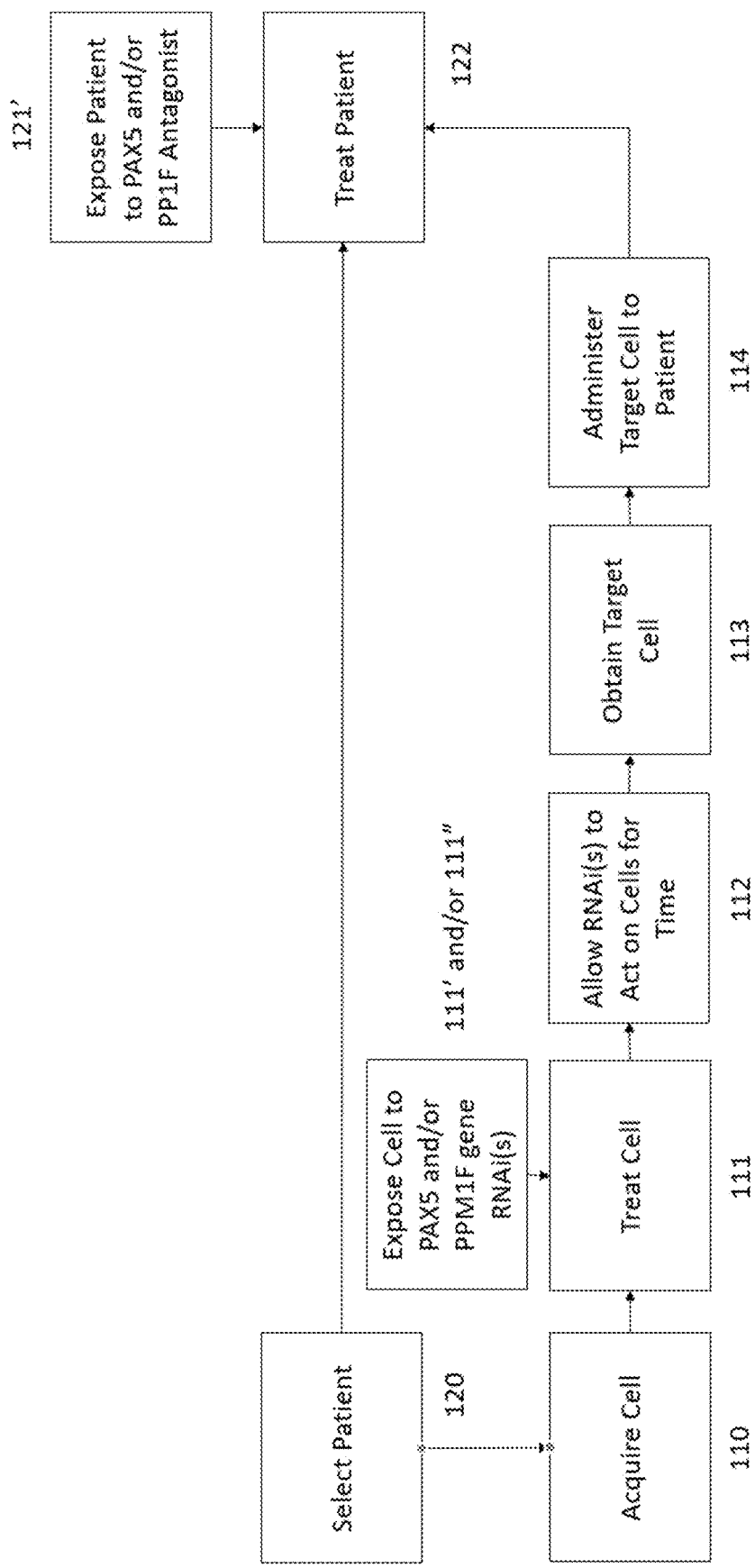

In some embodiments, as shown in FIG. 3L, alternatively, multiple therapies can be used in conjunction to achieve a desired therapeutic results. In some embodiments, as shown in FIG. 3K, a patient with a disease or disorder who could benefit from treatment with a PAX5 or PP1F inhibitor is selected 120. In some embodiments, as shown, a cell is acquired and treated by exposing it to one or more different PAX5 gene RNAi(s) and/or PPM1G gene RNAi(s) 111', 111". In some embodiments, as shown, the RNAi(s) are allowed to act on the cell for a period of time 112. In some embodiments, as shown, this results in a target cell 113. In some embodiments, as shown in FIG. 3L, the cell can be reintroduced to the patient (e.g, where it was initially isolated from the patient). In some embodiments, a small molecule PAX5 and/or PP1F inhibitor 121' is also administered to the patient. In some embodiments, as shown, the patient is thereby treated 122.

Figure 3M:
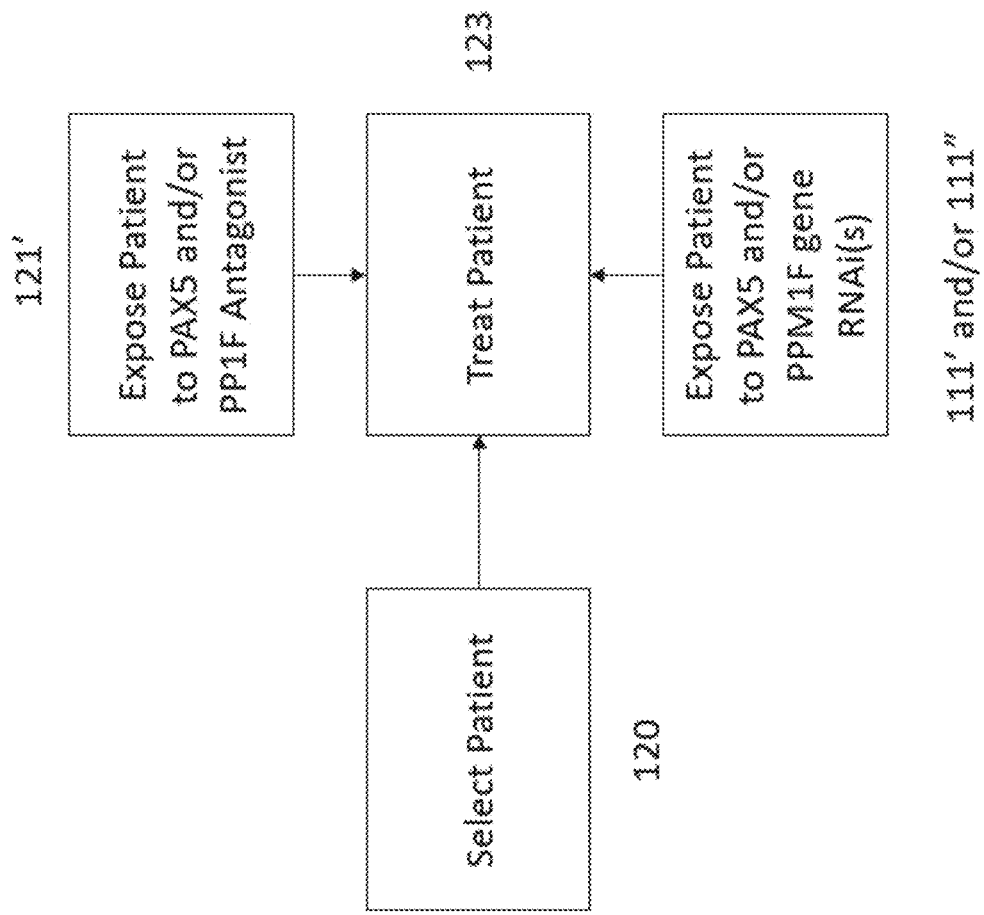

Alternatively, in some embodiments, as shown in FIG. 3M, treatment is performed entirely in vivo. In some embodiments, a patient with a disease or disorder who could benefit from treatment with a PAX5 or PP1F inhibitor and/or an antagonist of PAX5 and/or PP1F is selected 120. In some embodiments, as shown, one or more different PAX5 gene RNAi(s) and/or PPM1G gene RNAi(s) 111', 111" are administered to the patient. In some embodiments, a small molecule PAX5 and/or PP1F inhibitor 121' is also administered to the patient. In some embodiments, as shown, the patient is thereby treated 123.

In some embodiments, the polycyclic aromatic small molecule capable of targeting and reducing the activity of BSAP may be termed a BSAP small molecule inhibitor (BAP-MI). In some embodiments, the method of decreasing the extent of cellular senescence occurring in the lympho-hematopoietic system of a subject and/or treating an ARD disclosed herein comprises administering to a subject in need thereof an effective amount of a composition comprising a BAP-MI.

In some embodiments, the polycyclic aromatic small molecule may target one or more gene products wherein the gene products are endogenous to the subject. As used herein with respect to small molecules, the term "target" refers to action of a ligand (e.g., small molecule) recognizing, associating with, and/or binding to a target molecule (i.e., substrate) that is targeted by the ligand. In a further aspect, the polycyclic aromatic small molecule may reduce the activity of the one or more gene products relative to the activity of the gene products in an absence of the polycyclic aromatic small molecule. Non-limiting examples of gene products suitable for use as described herein (e.g., suitable for use as targets for the polycyclic aromatic small molecule to reduce the activity thereof) are the B-cell lineage specific activator protein (BSAP) (including the protein encoded by the PAX5 gene), the protein phosphatase 1F enzyme (PP1F), or both. In a further aspect, the method of decreasing the extent of cellular senescence occurring in the lymphohe-matopoietic system of a subject and/or treating an ARD disclosed herein comprises targeting and reducing the activity of BSAP and/or PP1F via administration of an effective amount of the polycyclic aromatic small molecule to a subject in need thereof.

In some embodiments, inhibition of the protein includes reducing its function by greater than or at least about: 1%, 5%, 10%, 30%, 40%, 50%, 60%, 70%, 80%, 90%, 95%, 98%, 99%, 99.9%, 100%, or ranges including and/or spanning the aforementioned values. In some embodiments, a reduction of function includes at least one of of decreasing the amount of native protein synthesized, decreasing the full length protein synthesized, decreasing the amount of functional protein synthesized, decreasing the amount of functional fragments of protein synthesized, and decreasing the amount of fragments of protein synthesized. Unless otherwise noted, reduced expression will denote a reduction of the synthesis of the functional protein. In some embodiments, markers for inhibition can include the monitoring protein expression of a molecule that is directly regulated by the target. In some embodiments, PAX5 inhibition can be measured by measuring the amount of p53 synthesized. In some embodiments, inhibition of the PAX5 protein includes reducing transcription of p53 by equal to or at least about: 1%, 5%, 10%, 30%, 40%, 50%, 60%, 70%, 80%, 90%, 95%, 98%, 99%, 99.9%, 100%, or ranges including and/or spanning the aforementioned values. In some embodiments, PPM1F inhibition can be measured by measuring the amount of CaMK2G synthesized. In some embodiments, inhibition of the PPM1F protein includes reducing transcription of CaMK2G by equal to or at least about: 1%, 5%, 10%, 30%, 40%, 50%, 60%, 70%, 80%, 90%, 95%, 98%, 99%, 99.9%, 100%, or ranges including and/or spanning the aforementioned values.

Figure 29B:
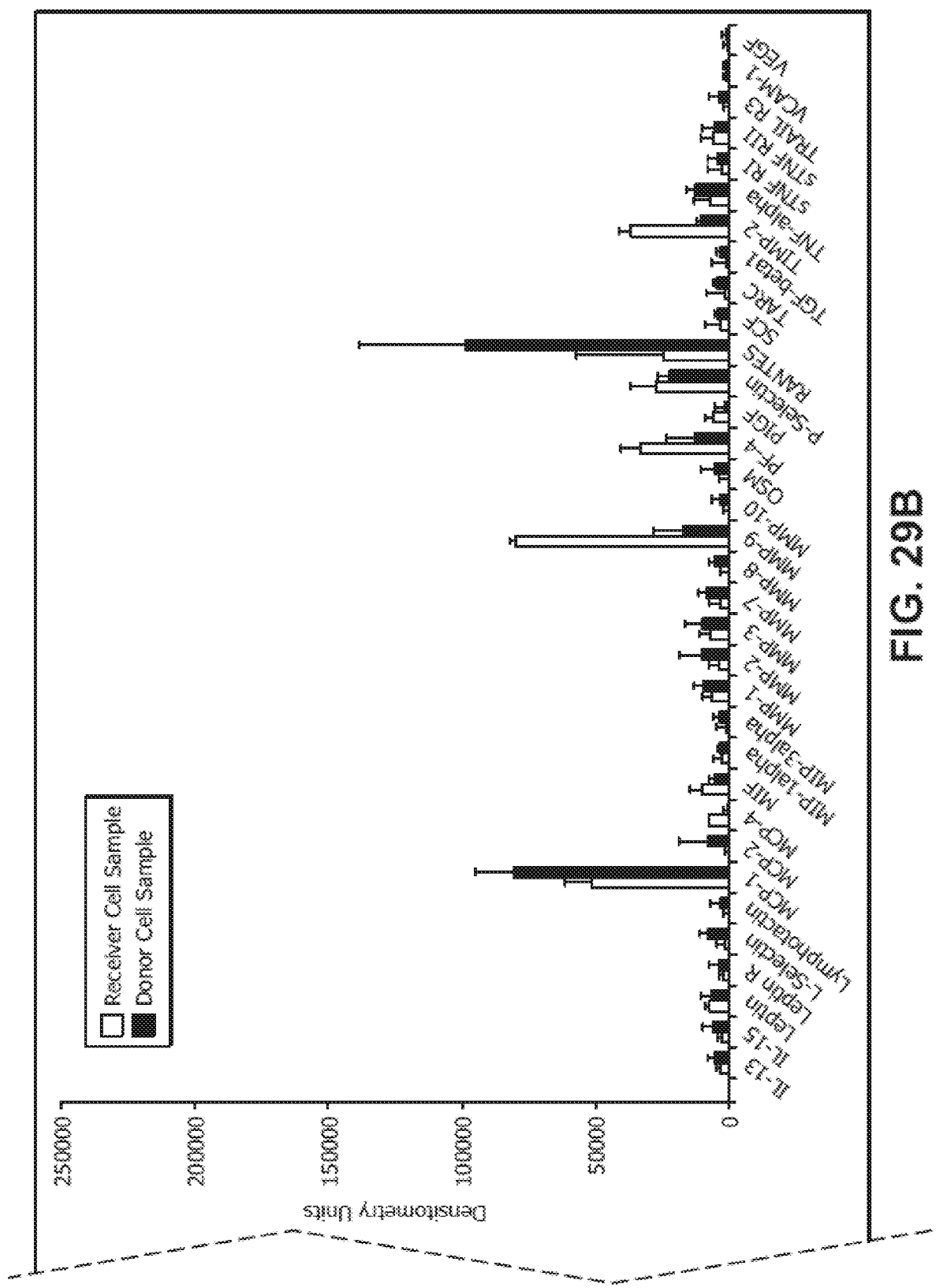

In some embodiments, in using a PAX5 protein inhibitor will reduce the function of one or more proteins including one or more of SEQ ID NO:22 (PAX5 protein; homo sapien—as shown in FIG. 3P22), SEQ ID NO:23 (PAX5 protein; *Equus caballus*—as shown in FIG. 3P23), SEQ ID NO:24 (PAX5 protein; *Canis lupus*—as shown in FIG. 3P24), SEQ ID NO:25 (PAX5 protein; *Felis catus*—as shown in FIG. 3P25), SEQ ID NO:26 (PP1F protein; homo sapien—as shown in FIG. 3P26), SEQ ID NO:27 (PP1F protein; *Equus caballus*—as shown in FIG. 3P27), SEQ ID NO:28 (PP1F protein; *Canis lupus*—as shown in FIG. 3P28), SEQ ID NO:29 (PP1F protein; *Felis catus*—as shown in FIG. 3P29), and SEQ ID NO:30 (calcium/calmodulin-dependent protein kinase; homo sapien—as shown in FIG. 3P30).

The BAP-MI suitable for use in the present disclosure may be any small molecule capable of targeting BSAP. In some embodiments, the BAP-MI may be a polycyclic arene, a polycyclic heteroarene, or combinations thereof; alternatively, a polycyclic arene; or alternatively, a polycyclic heteroarene. In yet a further aspect, the BAP-MI of the present disclosure may be a 6,7-dihydro-5H-benzoheptalen-9-one, a benzoimidazole, or combinations thereof; alternatively, a 6,7-dihydro-5H-benzoheptalen-9-one; or alternatively, a benzoimidazole.

In a particular aspect, the BAP-MI suitable for use in the present disclosure may comprise a member of the class of compounds known as mitotic inhibitors (mitogen spindle inhibitors). A mitotic inhibitor interferes with mitosis (i.e., cell division) by disrupting polymerization of microtubules, which are polymeric forms of the protein tubulin. Microtubules extend through the cell and facilitate the movement of cellular components, e.g., separation of chromosomes and other components of the cell before and during mitosis. Mitotic inhibitors interfere with the assembly and disassembly of tubulin into microtubules and thus interrupt cell division, usually during the mitosis (M) phase of the cell cycle. In some embodiments, the mitotic inhibitor suitable for use as a BSAP small molecule inhibitor may be colcemid (or demecolcine), colchicine, docetaxel, nocodazole, griseofulvin, paclitaxel, vinblastine, vincristine, vinorelbine, any analog or derivative thereof, or combinations thereof. In a further aspect, the mitotic inhibitor suitable for use as a BSAP small molecule inhibitor may be an ansamitocin, campothecin, a combretastatin, a cryptophycin, a curacin, cytochalasin B, discodermolide, a dolastatin, eleutherobin, epothilone A, epothilone B, a flavanol, a halichondrin, a halistatin, lysophosphatidic acid, a maytansinoid, phomopsin A, rhizoxin, a sarcodictyin, a spongistatin, steganacin, a subtilisin, any analog or derivative thereof, or combinations thereof. In a particular aspect, the mitotic inhibitor suitable for use as a BSAP small molecule inhibitor may be colcemid (or demecolcine), nocodazole, any analog or derivative thereof, or combinations thereof.

The BSAP small molecule inhibitors disclosed herein may have Structure BAP-MI 1, Structure BAP-MI 2, Structure Formula I (as disclosed elsewhere herein), Structure Formula II (as disclosed elsewhere herein), Structure Formula III (as disclosed elsewhere herein), or combinations thereof; alternatively, Structure BAP-MI 1; alternatively, Structure BAP-MI 2; alternatively, Structure Formula I; alternatively, Structure Formula II; alternatively, Structure Formula III.

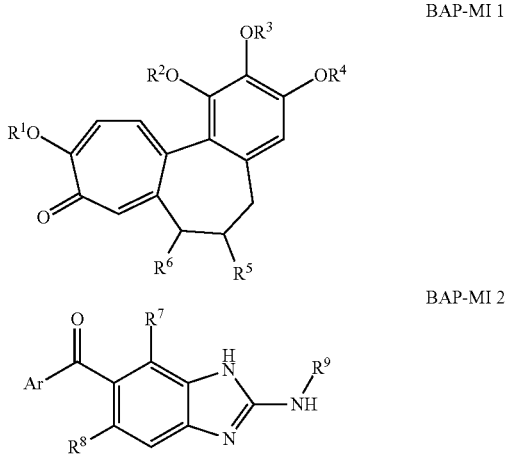

BAP-MI 1

BAP-MI 2

$R^1$, $R^2$, $R^3$, $R^4$, $R^5$, and $R^6$ of the BSAP small molecule inhibitor having Structure BAP-MI 1 are independent elements of the BSAP small molecule inhibitor having Structure BAP-MI 1 and are independently described herein. The independent descriptions of $R^1$, $R^2$, $R^3$, $R^4$, $R^5$, and $R^6$ can be utilized without limitation, and in any combination, to further describe the BSAP small molecule inhibitor having Structure BAP-MI 1. Similarly, Ar, $R^7$, $R^8$, and $R^9$ of the BSAP small molecule inhibitor having Structure BAP-MI 2 are independent elements of the BSAP small molecule inhibitor having Structure BAP-MI 2 and are independently described herein. The independent descriptions of Ar, $R^7$, $R^8$, and $R^9$ can be utilized without limitation, and in any combination, to further describe the BSAP small molecule inhibitor having Structure BAP-MI 2.

Generally, $R^1$, $R^2$, $R^3$, $R^4$, $R^7$, and/or $R^8$ of the respective BSAP small molecule inhibitors, which have an $R^1$, $R^2$, $R^3$, $R^4$, $R^7$, and/or $R^8$ each independently can be hydrogen, an organyl group, a hydrocarbyl group or an aromatic group; alternatively, hydrogen; alternatively, an organyl group; alternatively, a hydrocarbyl group; or alternatively, an aromatic group. In some embodiments, $R^1$, $R^2$, $R^3$, $R^4$, $R^7$, and/or $R^8$, independently can be a $C_1$ to $C_{30}$ organyl group; alternatively, a $C_1$ to $C_{20}$ organyl group; alternatively, a $C_1$ to Cis organyl group; alternatively, a $C_1$ to $C_{10}$ organyl group; or alternatively, a $C_1$ to $C_5$ organyl group. In some embodiments, $R^1$, $R^2$, $R^3$, $R^4$, $R^7$, and/or $R^8$ each independently can be a $C_1$ to $C_{30}$ hydrocarbyl group; alternatively, a $C_1$ to $C_{20}$ hydrocarbyl group; alternatively, a $C_1$ to Cis hydrocarbyl group; alternatively, a $C_1$ to $C_{10}$ hydrocarbyl group; or alternatively, a $C_1$ to $C_5$ hydrocarbyl group. In yet other aspects, $R_1$, $R^2$, $R^3$, $R^4$, $R^7$, and/or $R^8$ each independently can be a $C_3$ to $C_{30}$ aromatic group; alternatively, a $C_3$ to $C_{20}$ aromatic group; alternatively, a $C_3$ to Cis aromatic group; or alternatively, a $C_3$ to $C_{10}$ aromatic group.

In an aspect $R_1$, $R^2$, $R^3$, $R^4$, $R^7$, and/or $R^8$ each independently can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ heterocyclic group, a $C_3$ to $C_{30}$ substituted heterocyclic group, a $C_6$ to $C_{30}$ aryl group, a $C_6$ to $C_{30}$ substituted aryl group, a $C_3$ to $C_{30}$ heteroaryl group, or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ heterocyclic group; alternatively, a $C_3$ to $C_{30}$ substituted heterocyclic group; alternatively, a $C_6$ to $C_{30}$ aryl group; alternatively, a $C_6$ to $C_{30}$ substituted aryl group; alternatively, a $C_3$ to $C_{30}$ heteroaryl group; or alternatively, a $C_3$ to $C_{30}$ substituted heteroaryl group. In a further aspect $R^1$, $R^2$, $R^3$, $R^4$, $R^7$, and/or $R^8$ each independently can be a $C_1$ to Cis alkyl group, a $C_4$ to Cis cycloalkyl group, a $C_4$ to Cis substituted cycloalkyl group, a $C_3$ to Cis heterocyclic group, a $C_3$ to Cis substituted heterocyclic group, a $C_6$ to Cis aryl group, a $C_6$ to Cis substituted aryl group, a $C_3$ to Cis heteroaryl group, or a $C_3$ to Cis substituted heteroaryl group; alternatively, a $C_1$ to Cis alkyl group; alternatively, a $C_4$ to Cis cycloalkyl group; alternatively, a $C_4$ to Cis substituted cycloalkyl group; alternatively, a $C_3$ to Cis heterocyclic group; alternatively, a $C_3$ to Cis substituted heterocyclic group; alternatively, a $C_6$ to Cis aryl group; alternatively, a $C_6$ to Cis substituted aryl group; alternatively, a $C_3$ to Cis heteroaryl group; or alternatively, a $C_3$ to Cis substituted heteroaryl group. In a particular aspect $R_1$, $R^2$, $R^3$, $R^4$, $R^7$, and/or $R^8$ each independently can be a $C_1$ to $C_6$ alkyl group, a $C_4$ to $C_6$ cycloalkyl group, a $C_4$ to $C_6$ substituted cycloalkyl group, a $C_3$ to $C_6$ heterocyclic group, a $C_3$ to $C_6$ substituted heterocyclic group, a $C_6$ to $C_8$ aryl group, a $C_6$ to $C_8$ substituted aryl group, a $C_3$ to $C_6$ heteroaryl group, or a $C_3$ to $C_6$ substituted heteroaryl group; alternatively, a $C_1$ to $C_6$ alkyl group; alternatively, a $C_4$ to $C_6$ cycloalkyl group; alternatively, a $C_4$ to $C_6$ substituted cycloalkyl group; alternatively, a $C_3$ to $C_6$ heterocyclic group; alternatively, a $C_3$ to $C_6$ substituted heterocyclic group; alternatively, a $C_6$ to $C_8$ aryl group; alternatively, a $C_6$ to $C_8$ substituted aryl group; alternatively, a $C_3$ to $C_6$ heteroaryl group; or alternatively, a $C_3$ to $C_6$ substituted heteroaryl group.

The non-hydrogen substituents of any substituted $R^1$, $R^2$, $R^3$, $R^4$, $R^7$, and/or $R^8$ group independently can be a hydrocarbyl group. In some embodiments, each non-hydrogen substituent of any substituted $R^1$, $R^2$, $R^3$, $R^4$, $R^7$, and/or $R^8$ group independently can be a halide, a $C_1$ to $C_{10}$ hydrocarbyl group, or a $C_1$ to $C_{10}$ hydrocarboxy group. In some embodiments, each halide substituent for any substituted $R^1$, $R^2$, $R^3$, $R^4$, $R^7$, and/or $R^8$ group independently can be fluoride, chloride, bromide, or iodide; alternatively, fluoride or chloride.

Generally, $R^5$ and/or $R^6$ each independently can be a $C_1$ to $C_{30}$ hydrocarbyl aminyl group, a $C_4$ to $C_{30}$ cycloaminyl group, or a $C_4$ to $C_{30}$ substituted cycloaminyl group. In a further aspect, $R^5$ and/or $R^6$ each independently can be a $C_1$ to $C_{15}$ hydrocarbyl aminyl group, a $C_4$ to $C_{15}$ cycloaminyl group, or a $C_4$ to $C_{15}$ substituted cycloaminyl group. In still a further aspect, $R^5$ and/or $R^6$ each independently can be a $C_1$ to $C_5$ hydrocarbyl aminyl group, a $C_4$ to $C_5$ cycloaminyl group, or a $C_4$ to $C_5$ substituted cycloaminyl group. In some embodiments, each hydrocarbyl group of a hydrocarbyl aminyl group can be a $C_1$ to $C_{30}$ hydrocarbyl group; alternatively, a $C_1$ to $C_{15}$ hydrocarbyl group; or alternatively, a $C_1$ to $C_5$ hydrocarbyl group.

In some embodiments, Ar can be a pyridinyl group, a substituted pyridinyl group, a furyl group, a substituted furyl group, a thienyl group, or a substituted thienyl group. In some embodiments, the furyl (or substituted furyl) Ar group can be a fur-2-yl group, a substituted fur-2-yl group, a fur-3-yl group, or a substituted fur-3-yl group. In some embodiments, the thienyl (or substituted thienyl) Ar group be a thien-2-yl group, a substituted thien-2-yl group, a thien-3-yl group, or a substituted thien-3-yl group. Substituents for the substituted furyl groups and substituted thienyl groups are independently disclosed herein and can be utilized without limitation to further describe the substituted furyl groups and substituted thienyl groups which can be utilized as Ar. In some embodiments, each substituent for a substituted pyridinyl, furyl, and/or thienyl group that can be independently utilized as Ar can be a halogen, a hydrocarbyl group, or a hydrocarboxy group. In some aspects, each substituent for a substituted pyridinyl, furyl, and/or thienyl group can be a halogen, an alkyl group, or an alkoxy group.

In a particular aspect, $R^9$ may be represented by formula $COOR^{10}$ or by formula $C(O)R^{11}$; alternatively, by formula $COOR^{10}$; or alternatively by formula $C(O)R^{11}$. In a further aspect $R^{10}$ may be hydrogen, a $C_1$ to $C_{12}$ alkyl group, a $C_3$ to $C_{10}$ cycloalkyl group, a $C_6$ to $C_{12}$ aralkyl group, a phenyl group, or substituted phenyl group. In a further aspect, $R^{11}$ may be an amino group of formula $N(R^{12})_2$, wherein each $R^{12}$ independently may be hydrogen, a $C_1$ to $C_{12}$ alkyl group, a $C_3$ to $C_{10}$ cycloalkyl group, a $C_6$ to $C_{12}$ aralkyl group, a phenyl group, a substituted phenyl group, a pyridyl group, a substituted pyridyl group, a $C_1$ to $C_5$ hydroxyalkyl group, or a $C_1$ to $C_4$ dihydroxyalkyl group. In a further aspect, $R^{11}$ may be a cycloamino group selected from the group consisting of pyrolidino, piperidino, morpholino, piperazino, hexamethyleneimino, pyrrolino, or 3,4-didehydropiperidinyl optionally substituted by one or more $C_1$ to $C_{12}$ alkyl groups. In a still further aspect, $R^{11}$ may be a carbonylamino of formula $NR^{13}C(O)R^{12}$, wherein $R^{13}$ is hydrogen or a $C_1$ to $C_4$ alkyl group, and $R^{12}$ is a $C_1$ to $C_4$ alkyl group. In yet a further aspect, $R^{11}$ may be a sulfonylamino of formula $NR^{13}SO_2R^{12}$, wherein $R^{12}$ and $R^{13}$ may be the same, respectively, as any $R^{12}$ and $R^{13}$ previously disclosed herein. In some embodiments, each substituent for a substituted phenyl group (general or specific) or a substituted pyridyl group (general or specific) that can be utilized as $R^{10}$ and/or $R^{12}$ independently can be a halogen, a hydrocarbyl group, a nitro group or a hydrocarboxy group; alternatively, a halogen; alternatively, a hydrocarbyl group; alternatively, a nitro group; or alternatively, a hydrocarboxy group.

In some embodiments, the polycyclic compound is of formula I:

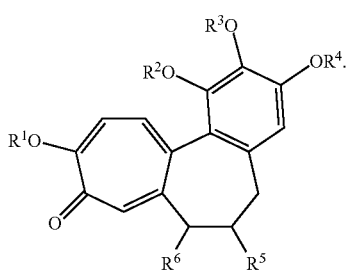

Formula I

In some embodiments, each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units. In some embodiments, each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, and a —$(OR_B$—$)_o$OH, where $R_B$ is an optionally substituted $C_1$ to $C_6$ alkyl.

In some embodiments, the polycyclic compound is of formula II:

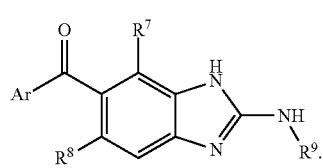

Formula II

In some embodiments, each of $R_7$, $R_8$, and $R_9$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units. In some embodiments, each of $R_7$, $R_8$, and $R_9$ is independently selected from —H, hydroxyl, halogen, $C_1$ to $C_6$ alkyl optionally substituted with halogen or hydroxy, and a —$(OR_B$—$)_o$OH, where $R_B$ is an optionally substituted $C_1$ to $C_6$ alkyl.

In some embodiments, the polycyclic compound is of formula III:

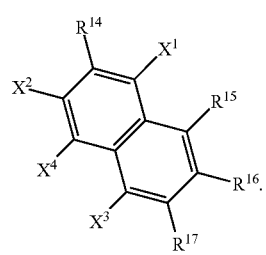

Formula III

In some embodiments, each of $X_1$, $X_2$, $X_3$, $X_4$ is independently selected from —H, hydroxyl, halogen, —$NH_2$, optionally substituted —$SO_2OR_{18}$. In some embodiments, each of $R_{14}$, $R_{15}$, $R_{16}$, $R_{17}$, and $R_{18}$ is independently selected from —H, hydroxyl, halogen, —$NH_2$, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether-having 1 to 6 repeat units. In some embodiments, $R_{14}$, $R_{15}$, $R_{16}$, $R_{17}$, and $R_{18}$ are independently selected from —H, hydroxyl, halogen, $C_1$ to $C_6$ alkyl optionally substituted with halogen or hydroxy, and a —$(OR_B$—$)_o$OH, where $R_B$ is an optionally substituted $C_1$ to $C_6$ alkyl.

In some embodiments, the compound of formula III is represented by the following structure:

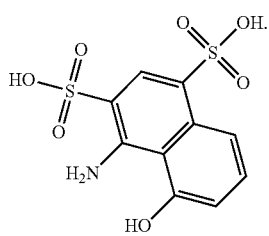 [SMILES: Nc1c(S(=O)(=O)O)cc(S(=O)(=O)O)c2cccc(O)c12]

In some embodiments, the polycyclic compound is provided as a pharmaceutically acceptable salt.

Some embodiments pertain to a pharmaceutical composition comprising one or more polycyclic aromatic compounds and a pharmaceutically acceptable carrier. In some embodiments, the pharmaceutical compound comprises a polycyclic aromatic compound and an RNAi as disclosed elsewhere herein.

Disclosed herein is a composition comprising a polycyclic aromatic small molecule capable of targeting PP1F (e.g., the protein resulting from the PPM1F gene) and reducing the activity of PP1F. In some embodiments, the polycyclic aromatic small molecule capable of targeting and reducing the activity of PP1F may be termed a PP1F small molecule inhibitor (P1F-MI). In some embodiments, the method of decreasing the extent of cellular senescence occurring in the lymphohematopoietic system of a subject and/or treating an ARD disclosed herein comprises administering to a subject in need thereof an effective amount of a composition comprising a P1F-MI.

The P1F-MI suitable for use in the present disclosure may be any small molecule capable of targeting PP1F. In some embodiments, the P1F-MI may be a polycyclic arene, a polycyclic heteroarene, or combinations thereof; alternatively, a polycyclic arene; or alternatively, a polycyclic heteroarene. In yet a further aspect, the P1F-MI of the present disclosure may be a benzophenanthridine, a benzophenanthridinium or combinations thereof; alternatively, a benzophenanthridine; or alternatively, a benzophenanthridinium. In yet a further aspect, the P1F-MI of the present disclosure may be a piperazine bisindole, a pyrazine bisindole, a guanidinium pyrazine bisindole, or combinations thereof; alternatively, a piperazine bisindole; alternatively, a pyrazine bisindole; or alternatively, a guanidinium pyrazine bisindole.

Natural products provide a bountiful source of compounds that potently inhibit the catalytic activity of PP1F. In a particular aspect, the P1F-MI suitable for use in the present disclosure may comprise a sanguinarine salt complex or combinations thereof. Sanguinarine is a polycyclic ammonium ion that is extracted from plants including the bloodroot plant (*Sanguinaria canadensis*) and the Mexican prickly poppy (*Argemone mexicana*). In some embodiments, the sanguinarine salt complex suitable for use as the P1F-MI as disclosed herein is represented by Structure P1F-MI 1 wherein X represents a monoanion.

Generally, the monoanion, X, of Structure P1F-MI 1 may be any monoanion suitable for use as a component of the sanguinarine salt complex. In some embodiments, the monoanion, X can be a halide, a carboxylate, a hydrocarboxide, a nitrate, a phosphate, a sulfate, or a chlorate. In a further aspect, the halide suitable for use as X can be fluoride, chloride, bromide, iodide, or any combination thereof; or alternatively, chloride. In a further aspect, the carboxylate suitable for use as X may be acetate, a propionate, trifluoroacetate, or any combination thereof. In a further aspect, the hydrocarboxide suitable for use as X may be an alkoxide, an aryloxide, or an aralkoxide. In a still further aspect, the P1F-MI suitable for use in the present disclosure may comprise sanguinarine chloride or a derivative thereof.

In a particular aspect, the P1F-MI suitable for use in the present disclosure may comprise a member of the dragmacidin family of small molecules or combinations thereof. The dragmacidins represent an emerging class of bioactive marine natural products obtained from a number of deep water sponges including Dragmacidon, Halicortex, Spongosorites, and Hexadella, and the tunicate Didemnum candid. Dragmacidin D, which has been found to serve as a potent inhibitor of serine-threonine protein phosphatases, has received particular attention as a lead compound for treating Parkinson's, Alzheimer's, and Huntington's diseases. In some embodiments, the P1F-MI suitable for use in the present disclosure may comprise dragmacidin A, dragmacidin B, dragmacidin C, dragmacidin D, dragmacidin E, dragmacidin F, or combinations thereof.

In a still further aspect, the PP1F small molecule inhibitor (P1F-MI) disclosed herein may have Structure P1F-MI 2, Structure P1F-MI 3, Structure P1F-MI 4, Structure P1F-MI 5, Structure P1F-MI 6, Structure P1F-MI 7, Structure P1F-MI 8, Structure P1F-MI 9, Structure P1F-MI 10, or combinations thereof; alternatively, Structure P1F-MI 2; alternatively, Structure P1F-MI 3; alternatively, Structure P1F-MI 4; alternatively, Structure P1F-MI 5; alternatively, Structure P1F-MI 6; alternatively, Structure P1F-MI 7; alternatively, Structure P1F-MI 8; alternatively, Structure P1F-MI 9; or alternatively, Structure P1F-MI 10.

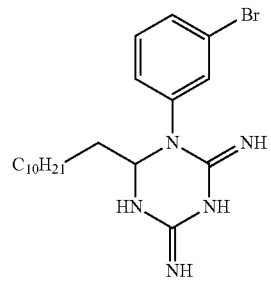

P1F-MI 2

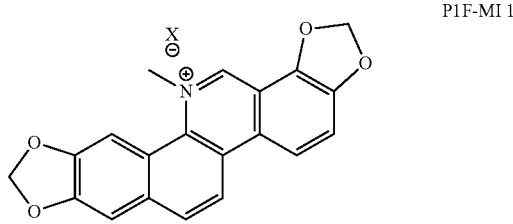

P1F-MI 1

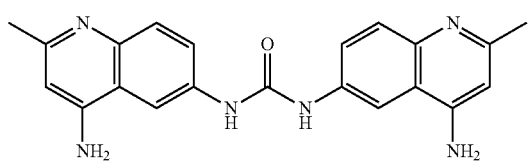

P1F-MI 3

P1F-MI 4

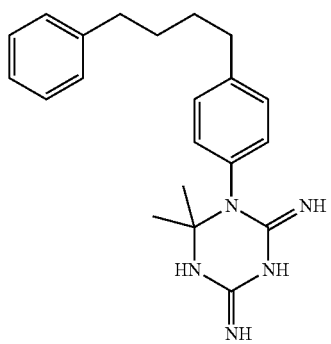

P1F-MI -5

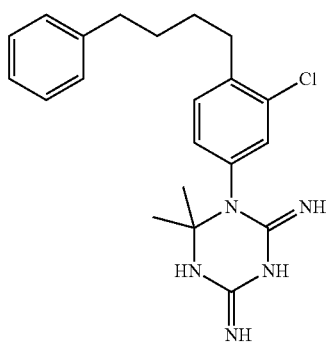

P1F-MI 6

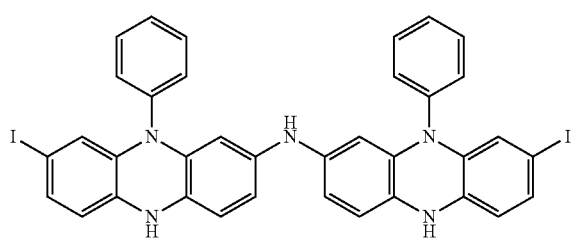

P1F-MI 7

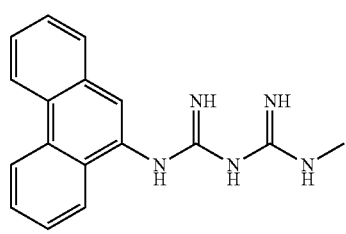

P1F-MI 8

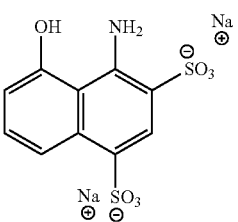

P1F-MI 9

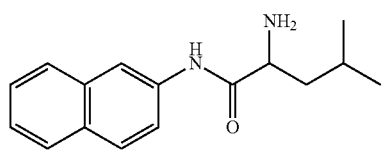

P1F-MI 10

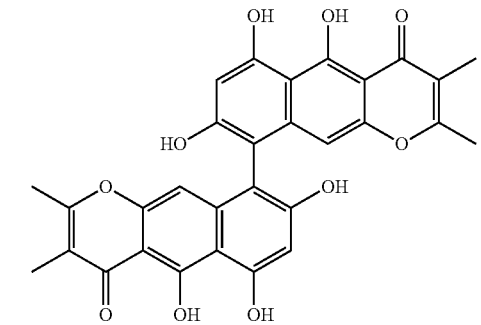

Some embodiments pertain to method for treating or preventing age related dysfunction or other cellular dysfunction, comprising administering to a patient in need thereof a therapeutically effective dose of one or more polycyclic aromatic compounds that antagonize or reduce the expression of PAX5 and/or PPM1F.

Disclosed herein are pharmaceutical formulations of one or more BSAP small molecule inhibitors (BAP-MIs), one or more PP1F small molecule inhibitors (P1F-MIs), or combinations thereof. The BAP-MIs and/or P1F-MIs described herein may be formulated in a variety of manners, and thus may additionally comprise one or more carriers of the type disclosed herein, and it is to be understood that various of the specific carriers disclosed herein may be used in combination. In this regard, a wide variety of carriers may be selected of either polymeric or non-polymeric origin. In one particular aspect, a wide variety of polymeric carriers may be utilized to contain and/or deliver one or more of the BAP-MIs discussed herein, one or more P1F-MIs discussed herein, or combinations thereof, including for example both biodegradable and non-biodegradable compositions. Representative examples of biodegradable compositions include one or more of albumin, collagen, gelatin, hyaluronic acid, starch, cellulose (methylcellulose, hydroxypropylcellulose, hydroxypropylmethylcellulose, hydroxyethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly(D,L-lactide-co-glycolide), poly(glycolide), poly (hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers. Representative examples of nondegradable polymers include one or more of poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polyproplene, polyamides (nylon 6,6), polyurethane, poly(ester urethanes), poly(ether urethanes), poly(ester-urea), polyethers (poly(ethylene oxide), poly(propylene oxide), PLURONICS® and poly(tetramethylene glycol)), silicone rubbers and vinyl polymers (polyvinylpyrrolidone, poly(vinyl alcohol), poly(vinyl acetate phthalate). Polymers may also be developed which are either anionic (e.g., alginate, carrageenin, carboxymethyl cellulose and poly(acrylic acid), or cationic (e.g., chitosan, poly-L-lysine, polyethylenimine, and poly (allyl amine)). Particularly preferred polymeric carriers include one or more of poly(ethylene-vinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with a polyethylene glycol (e.g., MePEG), and blends thereof.

Polymeric carriers can be fashioned in a variety of forms, with desired release characteristics and/or with specific desired properties. For example, polymeric carriers may be fashioned to release a BAP-MI or P1F-MI upon exposure to a specific triggering event such as pH. Representative examples of pH-sensitive polymers include one or more of poly(acrylic acid) and its derivatives (including for example, homopolymers such as poly(aminocarboxylic acid); poly (acrylic acid); poly(methyl acrylic acid), copolymers of such homopolymers, and copolymers of poly(acrylic acid) and acrylmonomers such as those discussed above. Other pH sensitive polymers include one or more polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water-soluble polymer. Likewise, polymeric carriers can be fashioned which are temperature sensitive.

Representative examples of thermogelling polymers, and their gelatin temperature (LCST (° C.)) include homopolymers such as poly(N-methyl-N-n-propylacrylamide), 19.8° C.; poly(N-n-propylacrylamide), 21.5° C.; poly(N-methyl-N-isopropylacrylamide), 22.3° C.; poly(N-n-propylmethacrylamide), 28.0° C.; poly(N-isopropylacrylamide), 30.9° C.; poly(N, n-diethylacrylamide), 32.0° C.; poly(N-isopropylmethacrylamide), 44.0° C.; poly(N-cyclopropylacrylamide), 45.5° C.; poly(N-ethylmethyacrylamide), 50.0° C.; poly(N-methyl-N-ethylacrylamide), 56.0° C.; poly(N-cyclopropylmethacrylamide), 59.0° C.; and poly(N-ethylacrylamide), 72.0° C. Moreover, thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, and PLURONICS® such as F-127, 10-15° C.; L-122, 19° C.; L-92, 26° C.; L-81, 20° C.; and L-61, 24° C.

A wide variety of forms may be fashioned by the polymeric carriers of the present disclosure, including for example, rod-shaped devices, pellets, slabs, or capsules. The BAP-MIs or P1F-MIs may be linked by occlusion in the matrices of the polymer, bound by covalent linkages, or encapsulated in microcapsules.

Compositions comprising one or more BAP-MIs disclosed herein, one or more P1F-MIs disclosed herein, or combinations thereof may be fashioned in any manner appropriate to the intended use. Within certain aspects, the composition comprising one or more BAP-MIs disclosed herein, one or more P1F-MIs disclosed herein, or combinations thereof should be biocompatible, and release one or more BAP-MIs and/or P1F-MIs over a period of several days to months. For example, "quick release" or "burst" compositions are provided that release greater than 10%, 20%, or 25% (w/v) of a BAP-MI (e.g. colcemid) and/or P1F-MI (e.g. sanguinarine chloride) over a period of 7 to 10 days. Such "quick release" compositions should, within certain aspects, be capable of releasing chemotherapeutic levels (where applicable) of a desired agent. Within other aspects, "low release" therapeutic compositions are provided that release less than 1% (w/v) of a BAP-MI and/or P1F-MI over a period of 7 to 10 days. Further, compositions comprising a BAP-MI and/or P1F-MI as disclosed herein should preferably be stable for several months and capable of being produced and maintained under sterile conditions.

Within further aspects, the compositions comprising one or more BAP-MIs disclosed herein, one or more P1F-MIs disclosed herein, or combinations thereof may be formulated for topical application. Representative examples include: ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoyl-phosphatidyl glycerol, ethyldiglycol (i.e., TRANSCUTOL®), or terpinolene; mixtures of isopropyl myristate and 1-hexyl-2-pyrrolidone, N-dodecyl-2-piperidinone or 1-hexyl-2-pyrrolidone. Other excipients may also be added to the above, including for example, acids such as oleic acid and linoleic acid, and soaps such as sodium lauryl sulfate. A preferred aspect would include buffered saline or water, antimicrobial agents (e.g., methylparaben, propylparaben), carrier polymer(s), such as celluloses (e.g., hydroxyethyl-cellulose) and (a) penetration or permeation enhancer(s) (e.g., ethoxydiglycol-TRANSCUTOL®, isopropyl myristate, ethylene glycol, 1-hexyl-2-pyrrolidone, D-limonene).

In a particular aspect, the compositions and methods disclosed herein may provide means of restoring an aging lymphohematopoietic system. Herein reference is made to the undifferentiated cells of the hematopoietic lineage including hematopoietic stem cells (HSCs), lymphoid progenitor cells (LPCs) and myeloid progenitor cells (MPCs) which are known collectively as lymphohaematopoietic progenitor cells (LPCs). LPCs and MPCs are each formed by the differentiation of HSCs.

Other examples of differentiated cells of the hematopoietic lineage include T lymphocytes, B lymphocytes, eosinophils, basophils, neutrophils, megakaryocytes, monocytes, macrophages erythrocytes, granulocytes, mast cells, dendritic cells and natural killer cells. The pathways of differentiation in the lymphohematopoietic system have been extensively characterized and the various cell stages are readily identifiable according to morphology and lineage-specific cell surface markers.

It should be noted that, while some of the results achieved are described as being a result of using either the small molecules disclosed herein or the RNAi(s) disclosed herein, it should be appreciated that the RNAi(s) and small molecules can accomplish one or more results disclosed for the other.

In some embodiments, the present disclosure contemplates the utilization of BAP-MIs and/or P1F-MIs which are hereinafter collectively referred to small inhibitory molecules (SIMs). In some embodiments, SIMs of the type disclosed herein are utilized as compositions for administration to a subject in need thereof. In some embodiments, the SIMs may be a component of a pharmaceutical formulation that is administered locally or systemically to a subject. In some embodiments, SIMs of the type disclosed herein are used in conjunction with a vehicle such as a nanoparticle, micelle, liposome, niosome, microsphere, cyclodextrin and the like. In some embodiments, such vehicles further comprise one or more elements to direct the carrier or vehicle to a particular cell, tissue or organ of a subject (e.g., cells of the lymphohematopoietic system).

Some embodiments pertain to a pharmaceutical composition comprising a polycyclic aromatic small molecule capable of targeting and reducing the activity of the B-cell lineage specific activator protein, the protein phosphatase 1F enzyme, or both when the composition is administered in an effective amount to a subject in need thereof, wherein the B-cell lineage specific activator protein is a gene product of the paired box 5 (PAX5) gene and the protein phosphatase 1F enzyme is a gene product of the PPM1F gene. Some embodiments pertain to a method of treatment comprising administering to a subject in need thereof a therapeutically effective amount of the pharmaceutical composition. In some embodiments, the subject has one or more medical conditions or age-related disorders selected from the group consisting of arthritis, atherosclerosis, breast cancer, cardiovascular disease, cataracts, chronic obstructive pulmonary disease, colorectal cancer, hypertension, osteoporosis, periodontitis, type 2 diabetes, and Alzheimer's disease.

Additional Embodiments of Cellular Methods

Also, disclosed herein are compositions and methods for improving and/or restoring one or more cellular functions. These cellular functions may be directly or indirectly associated with promoting cellular health in a subject. Herein the term "promoting cellular health" refers to alterations in parameters of cellular function that result in a perceived and/or quantifiable improvement in the viability state of cells and/or cell types. The viability state of a cell may be assessed using any suitable metric to evaluate parameters such as, but not limited to, cellular architecture, membrane organization and/or integrity, dynamic protein assemblies, molecular organization, and cellular responses to external signals. The compositions and methods disclosed herein may improve the viability state of a cell as assessed by any suitable methodology. In an embodiment, a subject having improved and/or restored cellular function via the compositions and/or methodologies disclosed herein exhibits a perceived and/or quantifiable improvement in one or more aspects of the subject's cellular and/or general health. Disclosed herein is a method comprising (i) obtaining a first cell sample from a first subject; (ii) obtaining a second cell sample from a second subject; (iii) culturing the first cell sample in the presence of at least a portion of a culture media of the second cell sample for a time period ranging from about 24 hours to about 6 weeks to produce a restoring composition; and (iv) contacting the restoring composition with the second cell sample for a period of time ranging from about 24 hours to about 6 weeks to produce a restored composition.

Also disclosed herein is a pharmaceutical formulation comprising an exosome isolated from a restoring composition and an active selected from the group consisting of antimicrobials, steroids, pain medications, anti-inflammatory agents, growth factors, cytokines, hormones, and combinations thereof.

In an embodiment, the subject is administered the compositions disclosed herein in a therapeutically effective amount sufficient for treating, preventing, and/or ameliorating one or more symptoms of a medical condition, disorder, disease, or dysfunction. Hereinafter, for simplicity, the unwanted condition which has been used interchangeably with the terms medical condition, disorder, disease, and dysfunction are collectively referred to as the "medical condition." As used herein, amelioration of the symptoms of the medical condition by administration of a particular composition of the type disclosed herein refers to any lessening, whether lasting or transient, which can be attributed to or associated with administration of compositions of the type disclosed herein. As used herein, a "therapeutically effective amount" means a sufficient amount of the compositions disclosed herein to treat, prevent, and/or ameliorate one or more symptoms of the medical condition. It also may include a safe and tolerable amount of the compositions disclosed herein, as based on industry and/or regulatory standards. As will be understood by the ordinarily skilled artisan an amount that proves to be a "therapeutically effective amount" in a given instance, for a particular subject, may not be effective for 100% of subjects similarly treated for the medical condition under consideration, even though such dosage is deemed a "therapeutically effective amount" by ordinarily skilled practitioners. The therapeutically effective amount for a particular individual may vary depending on numerous factors such as the nature of the medical condition, severity of the medical condition, subject weight, subject age, and the general health of the subject. It is contemplated that the therapeutically effective amount may be optimized by one or more healthcare professionals in consideration of the particular factors affecting a subject.

One or more compositions disclosed herein may comprise cells and/or cellular material obtained from a human subject. Herein the term "cellular material" refers to materials derived from, secreted by, and otherwise currently or previously associated with a cell.

In an embodiment, a method of the present disclosure comprises (i) obtaining a donor cell sample and a receiver cell sample; (ii) utilizing one or more analytical techniques to characterize the donor cell sample and receiver cell sample; (iii) contacting one or more components of the donor cell sample with the receiver cell sample to generate a restored cell sample; (iv) utilizing one or more analytical techniques to characterize the restored cell sample; and (v) utilizing the restored cell sample for treatment of a subject.

In an alternative embodiment, a method of the present disclosure comprises (i) obtaining a donor cell sample and a receiver cell sample; (ii) contacting one or more components of the donor cell sample with the receiver cell sample to generate a restored cell sample; and (iii) utilizing the restored cell sample for treatment of a subject.

In yet another embodiment, a method of the present disclosure comprises (i) obtaining a first cell sample from a first subject; (ii) obtaining a second cell sample from a second subject; (iii) culturing the first cell sample in the presence of at least a portion of a culture media of the second cell sample for a time period ranging from about 24 hours to about 6 weeks to produce a restoring composition; and (iv) contacting the restoring composition with the second cell sample for a period of time ranging from about 24 hours to about 6 weeks to produce a restored composition.

In still yet another aspect, a method of the present disclosure comprises (i) obtaining a first cell sample from a first receiver subject; (ii) obtaining a second cell sample from a second donor subject; (iii) culturing the first cell sample in the presence of at least a portion of a culture media of the second cell sample for a time period ranging from about 24 hours to about 6 weeks to produce a restored composition (v) obtaining a third cell sample from a third receiver subject and (vi) culturing the third cell sample in the presence of at least a portion of the culture media of the restored composition for a time period ranging from about 24 hours to about 6 weeks to produce a secondarily restored composition. In such aspects the first receiver subject and the third receiver subject are the sources of aged adult stem cells found in the first and third cell samples, respectively. Further in such aspects, the second donor subject who provides the second cell sample is characterized as chronologically younger than the first or third receiver subjects. In some embodiments, the secondarily restored composition may be utilized in a like manner to produce a tertiary restored composition and so forth.

In an embodiment, the donor cell sample is provided by a donor subject while the receiver cell sample is provided by a receiver subject. In some embodiments, the donor subject and receiver subject are the same. Alternatively, the donor subject and receiver subject are different. In an embodiment, the donor subject is chosen such that the difference in the age of the donor subject, designated x, and the age of the receiver subject, designated y, is greater than about 5 years, alternatively, greater than about 10 years, alternatively greater than about 15 years, alternatively greater than about 20 years, alternatively greater than about 25 years, or alternatively greater than about 30 years where y is greater than x. In an embodiment, the donor subject is chosen such that the difference in the age of the donor subject, x, and the age of the receiver subject, y, is from about 5 years to about 75 years, alternatively from about 10 years to about 60 years, alternatively from about 15 years to about 50 years, alternatively from about 20 years to about 40 years, or alternatively from about 20 years to about 30 years where y is greater than x.

In some embodiments, the difference in chronological age between the donor subject and receiver subject is equal to or greater than about 16 years, alternatively from about 16 years to about 80 years, alternatively from about 16 years to about 50 years, or alternatively from about 16 years to about 30 years and x is greater than y. In yet another embodiment, the difference in chronological age between the donor subject and the receiver subject is less than about 365 days.

In an embodiment, the donor subject and receiver subject are related by consanguinity. Alternatively, the donor subject and receiver subject are not related. In an embodiment, the receiver subject has a medical condition that is absent from or undiagnosed in the donor subject. In either of the above disclosed embodiments, the donor subject and the receiver subject are adults, i.e., have reached sexual maturity. Alternatively, in either of the above disclosed embodiments, the donor subject has reached sexual maturity. Alternatively, in either of the above disclosed embodiments, the receiver subject has reached sexual maturity.

In an embodiment, the receiver subject is identified as having one or more risk factors associated with the development of a medical condition. In yet another embodiment, the receiver subject has not been diagnosed with a medical condition and/or has not been identified as having one or more risk factors associated with the development of a medical condition. It is contemplated that the methodologies disclosed herein may be employed in the treatment of subjects having a medical condition for which additional therapies have been previously or are currently being employed. It is further contemplated that in an embodiment, a receiver subject has undergone or is currently undergoing one or more therapies for medical conditions not associated with the medical condition for which the subject will be treated using the compositions and methodologies disclosed herein. In an embodiment, the receiver subject has one or more age-related medical conditions.

In an embodiment, the donor cell sample, receiver cell sample, or both are obtained from a subject(s) who has undergone a Stage B preparation. In some embodiments, the donor cell sample, receiver cell sample, or both are obtained from a subject(s) who has undergone a Stage A preparation and a Stage B preparation.

In an embodiment, the donor cell sample, the receiver cell sample, or both are obtained from a subject that has undergone a Stage A preparation. Herein, a Stage A preparation of a subject comprises the utilization of methods and/or compositions to improve the subject's general health prior to obtaining a composition (i.e., donor cell sample or receiver cell sample) from the subject.

A nonlimiting example of a methodology to improve the subject's general health includes the administration of one or more metabolic mediators to the subject. Herein, metabolic mediator refers to a substance which, when present in insufficient amounts in the subject, is detrimental to the physiological and/or psychological state of the subject or whose presence positively impacts the physiological and/or psychological state of the subject. The subject may be administered a plurality of metabolic mediators prior to obtaining one or more compositions of the type disclosed herein from the subject.

In an embodiment, the metabolic mediator comprises a nutraceutical. Herein, a nutraceutical refers to a material that may be derived from a natural source and that provides health benefits. A nonlimiting example of a nutraceutical suitable for use in the Stage A preparation of a subject is commercially available as EVERYCELL®, HEALTHYCELL, or HEALTHYCELL PLUS from Cell Health Institute. Additional compositions suitable for use metabolic mediators in the present disclosure are described in U.S. Pat. No. 8,747,918 entitled "Dietary Supplement System for Multifunctional Anti-Aging Management and Method of Use" which is incorporated by reference herein in its entirety.

Another example of a methodology suitable for use in Stage A preparation of a subject comprises the administration of one or more pulsed electromagnetic fields (PEMF) to at least a portion of the subject's body prior to and/or concurrent with, obtaining a sample of the type disclosed herein. PEMF may be used to enhance the homing, engraftment, and/or differentiation of the adult stem cells.

Stage A preparation of a subject may be carried out for some period of time prior to, and/or concurrent with obtaining a cell sample of the type disclosed herein from the subject. For example, Stage A preparation of a subject may comprise administration of a nutraceutical to the subject at a particular dosage (e.g., 500 mg, twice daily) for a period of time greater than about 48 hours prior to obtaining a cell sample of the type disclosed herein from the subject. Alternatively, the nutraceutical is administered for a time period of from about 48 hours to about 1 year prior to obtaining a cell sample of the type disclosed herein from the subject, alternatively from about 1 week to about 9 months, or alternatively from about 1 month to about 6 months. In some embodiments, the subject may be administered or may self-administer the nutraceutical for any period of time prior to, concurrent with, or subsequent to the procurement of a cell sample.

In an embodiment, the donor cell sample, the receiver cell sample, or both are obtained from a subject that has undergone a Stage B preparation. In an embodiment, during a Stage B preparation, the subject (donor and/or receiver) undergoes at least one process for mobilizing the subject's stem cells. Herein "stem cells" are given their usual meaning which generally refers to cells which are not terminally differentiated and are therefore able to produce cells of other types. Stem cells are typically divided into three types, including totipotent, pluripotent, and multipotent. "Totipotent stem cells" can grow and differentiate into any cell in the body, and thus can grow into an entire organism. These cells are not capable of self-renewal. In mammals, the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew, as well as differentiate, to regenerate adult tissues. "Multipotent stem cells" are also referred to as "unipotent" and can only become particular types of cells, such as blood cells or bone cells.

In an embodiment, the donor and receiver cell samples comprise adult stem cells and/or adult stem cell material which refer to stem cells or stem cell material that are not embryonic in origin nor derived from embryos or fetal tissue. In an alternative embodiment, the donor cell sample comprises adult stem cells and/or adult stem cell material which refer to stem cells or stem cell material that are not embryonic in origin or derived from embryos or fetal tissue. In an embodiment, the donor and receiver cell samples comprise stem cells and/or stem cell material that are embryonic in origin and/or derived from embryos or fetal tissue. In an alternative embodiment, the donor cell sample comprises stem cells and/or stem cell material that are embryonic in origin and/or derived from embryos or fetal tissue.

In an embodiment, Stage B preparation comprises administering to a subject an effective amount of a mobilizer. An effective amount of a mobilizer may be determined by the ordinarily skilled artisan consistent with best medical practices and taking into account a variety of factors including, for example and without limitation, the subject's general health and body mass.

As known to one of ordinary skill in the art, stem cells have been identified in various organs and tissues, including brain, bone marrow, peripheral blood, blood vessels, skeletal muscle, skin, teeth, heart, gut, liver, ovarian epithelium, and testis. It is contemplated that utilization of Stage B preparation of a subject would be carried out when obtaining stem cells using bone marrow as the source. It is within the scope of this disclosure to conduct various embodiments of the present methods using cell samples comprising stem cells obtained from any of the tissues known to be a source of stem cells. In such embodiments, Stage B preparation of the subject may not be carried out.

In an embodiment, a donor subject, a receiver subject, or both undergo Stage A preparation. In an embodiment, a donor subject, a receiver subject, or both undergo Stage B preparation. In an embodiment, a donor subject, a receiver subject, or both do not undergo Stage A preparation. In an embodiment, a donor subject, a receiver subject, or both do not undergo Stage B preparation. In an embodiment, a donor subject and a receiver subject, or both undergo Stage A and Stage B preparation.

Subsequent to administration of the mobilizer, and after a suitable time period has elapsed; a cell sample (e.g., donor cell sample or receiver cell sample) may be harvested from a subject. The time period between administration of the mobilizer to the subject and harvesting of the cell sample may be varied to meet one or more user and/or process goals. In an embodiment, the time period between administration of the mobilizer and harvesting of the cell sample may range from about 24 hours to about 10 days, alternatively from about 48 hours to about 7 days, or alternatively from about 3 days to about 5 days.

In an embodiment, the cell sample is harvested from a subject using any suitable methodology, for example, using an extracorporeal therapy such as apheresis. Apheresis is a method used to collect only a specific part of the subject's blood. It works on the basis of centrifugation or rapid spinning of the blood. A pathway is established for the subject's blood and allows for connection to the apheresis device. The instrument uses small pumps to move blood and fluids through the system. One pump draws blood out of one arm or side of the catheter and directs it to the centrifuge where the blood is separated into red cell, white cell, and plasma layers. A portion of the white cell layer, which includes stem cells, and a small amount of plasma and red cells are diverted to a collection bag. The rest of the blood is returned to the subject in the other arm or the second side of the catheter. In such an embodiment, the cell sample is harvested using intravenous needles located in a vein in each arm of a subject. Blood may be removed from a first vein, passed through an extracorporeal circuit that separates out the cell sample of interest and the remaining material may be returned to a second vein.

In an embodiment, the donor cell sample and/or receiver cell sample are harvested from the bone marrow directly. For example, the cell sample may be harvested from the iliac crest of a subject. In such embodiments, bone marrow aspiration to obtain the cell sample may involve a healthcare provider locating the posterior iliac crest of the subject subsequent to carrying out standard precautions such as skin sterilization and the administration of a local anesthetic. A suitable needle with the stylet in place may be slowly advanced through the skin and subcutaneous tissue pointing towards the anterior superior iliac spine. Upon reaching the posterior iliac crest, the area may be penetrated by the needle until an adequate depth is reached. Once the needle is in place, the stylet may be removed, a syringe attached, and the aspiration performed.

In an embodiment, a plurality of stem cell collections (e.g., bone marrow aspirations) is carried out in order to obtain some user and/or process desired number of cells in the cell sample. For example, the number of cells collected may range from $1 \times 10^6$-$1.0 \times 10^9$ cells/kg of the subject weight, alternatively from about $2 \times 10^6$-$1.0 \times 10^8$ cells/kg of the subject weight, or alternatively from about $5 \times 10^6$-$1.0 \times 10^8$ cells/kg of the subject weight. Cell samples harvested as disclosed herein may be utilized without further processing in the methodologies disclosed herein. Alternatively, cell samples harvested as disclosed herein may be further processed using any methodology compatible with the compositions and methodologies disclosed herein. Alternatively, cell samples harvested as disclosed herein may be stored for some time period before being utilized in the methodologies and therapies disclosed herein. Storage of the cell samples may involve, for example, cryogenic preservation of the cell sample in a biocompatible solution to stabilize the sample for the duration of storage. "Biocompatible solution" refers to solutions in which the cell sample (e.g., donor and/or receiver) are suspended for use in the cellular restoration methodologies disclosed herein or for any other subsequent uses. Such biocompatible solutions may include saline and may further comprise other ingredients such as preservatives, antimicrobials, and the like.

In an embodiment, cell samples harvested as disclosed herein are stored for greater than about 24 hours prior to being utilized in the methodologies disclosed herein. Alternatively, the cell samples harvested as disclosed herein are stored for a period of time ranging from about 1 hour to about 20 years prior to being utilized in the methodologies disclosed herein. Alternatively, storage of a cell sample harvested as disclosed herein may be for a time period ranging from about 10 days to about 15 years, alternatively from about 30 days to about 10 years, or alternatively from about 30 days to about 5 years.

As will be understood by the ordinarily skilled artisan, the donor cell sample and/or receiver cell sample, as harvested, comprise a heterogeneous cell population. An aspect of the methodologies disclosed herein comprises identifying and quantifying the types and amounts of cells present in the donor cell sample and/or receiver cell sample. Any methodology suitable for characterizing the number and types of cells present in the donor cell sample and/or receiver sample may be employed. In an embodiment, the donor cell sample and/or receiver cell sample are characterized by immunophenotyping. Herein, immunophenotyping refers to the analysis of heterogeneous populations of cells for the purpose of identifying the presence and proportions of the various populations in the sample. Antibodies are used to identify cells by detecting specific antigens (termed markers) expressed by these cells. In an embodiment, the donor cell sample and/or receiver sample are characterized by immunophenotyping using techniques such as flow cytometry. In alternative embodiments, characterizations of the various cell types present in a donor cell sample and/or receiver cell sample may be carried out using any suitable methodology such as reverse transcriptase polymerase chain reaction (RT-PCR) or immunocytochemistry.

In an embodiment, the populations of cells or cell types present in the donor cell sample and/or receiver cell sample are identified based on the presence or absence or one or more cell surface markers. An embodiment of a flow cytometry protocol for the identification of the different populations of cells (e.g., cell types) in a donor cell sample and/or receiver cell sample, 211, is presented in FIG. 25. Referring to FIG. 25, a cell sample (donor and/or receiver sample) 210 is subjected to flow cytometry. In an embodiment, the donor cell sample and/or receiver cell sample 210 may be, at a first stage, sorted into hematopoietic cells 220 and non-hematopoietic cells 230 based on the presence or absence of CD45. CD45, also known as leukocyte common antigen (LCA), T200, B220, Ly5, and protein tyrosine phosphatase receptor type C (PTPRC) is a transmembrane glycoprotein of the leukocyte-specific-receptor-like protein tyrosine phosphatase family. It is expressed on all nucleated hematopoietic cells and can cover up to 10% of the cell surface area. CD45 functions as a regulator of T-cell and B-cell antigen receptor signaling and is a regulator of cell growth and cell differentiation.

In an embodiment, CD45− cells, identified as non-hematopoietic stem cells 230, may be further characterized on the basis of the presence or absence of CD105. CD105, also known as endoglin, HHT1, ORW, and SH-1 is a type I membrane glycoprotein located on cell surfaces and is a component of the TGFβ receptor complex. CD105 may play a role in hematopoiesis and angiogenesis. In an embodiment, a cell population that is both CD45− and CD105+, 240, is characterized as having both mesenchymal stem cells and endothelial progenitor cells.

In an embodiment, a cell population that is identified to be both CD45− and CD105+, 240, may be further sorted into mesenchymal stem cells and endothelial progenitor cells. In an embodiment, the mesenchymal stem cells are identified as being CD45−, CD105+, CD29+ and CD44+, 250. CD29, also known as platelet GPIIa, integrin β1, and GP is an integrin unit associated with very late antigen receptors and functions in cell adhesion. CD44, also known as ECMRII, H-CAM, Pgp-1, HUTCH-1, Hermes antigen, phagocytic glycoprotein I, extracellular matrix receptor III, GP90 lymphocyte homing/adhesion receptor, and hyaluronate receptor functions in cell adhesion and migration. In an embodiment, endothelial progenitor cells are identified as being CD45−, CD105+, and CD31+, 260. CD31, also known as PECAM-1, endoCAM, platelet endothelial cell adhesion molecule, and PECA-1 is a protein that in humans is encoded by the PECAM1 gene found on chromosome 17. CD31 is thought to function in cell adhesion, activation, and migration.

The method of the present disclosure may further comprise identifying the differing hematopoietic cell types present in the CD45+ cells, 220. In an embodiment, a population of the cells is identified as being primitive hematopoietic stem cells, 270, on the basis of being CD45+, CD34+ and CD38−. In an embodiment, a population of the cells is identified as being hematopoietic progenitor cells on the basis of being CD45+, CD34+ and CD38+, 280. CD34 also known as gp105-120 and hematopoietic progenitor cell antigen (HPCA-1) is a member of the family of single-pass transmembrane sialomucin proteins that are expressed on early hematopoietic and vascular tissues. CD34 is thought to function in cell adhesion. CD38, also known as ADP-ribosyl cyclase, T10, and cyclic ADP-ribose hydrolase 1 is a multifunctional ectonucleotidase encoded by the CD38 gene which is located on chromosome 4. In an embodiment, at least a portion of the cell population are CD45+ and CD34−, 290, and are identified as differentiated hematopoietic cells. In such an embodiment, the differentiated hematopoietic cells, 290, may be further defined as being T-lymphocytes, 300, or Natural Killer cells, 310. T-lymphocytes can be characterized as being CD45+, CD34−, and CD3+. CD3, also known as T3, is a protein complex and plays a role in cell adhesion between T-cells and other cell types. Natural Killer cells can be characterized as being CD45+, CD34−, and CD56+. CD56 also known as Leu-19, NKH-1, and neural cell adhesion molecule (NCAM) is a hemophilic binding glycoprotein that may function in cell-cell adhesion, neurite outgrowth, synaptic plasticity, and learning and memory.

In an embodiment, the donor cell sample and/or receiver sample may be characterized using the methodologies disclosed herein. Such characterizations may result in the identification of cell populations in the donor cell sample and/or receiver cell sample that include without limitation, non-hematopoietic cells, mesenchymal stem cells, endothelial progenitor cells, hematopoietic cells, primitive hematopoietic stem cells, hematopoietic progenitor cells, differentiated hematopoietic cells, T-lymphocytes, natural killer cells, or combinations thereof. It is contemplated that the surface markers described herein represent one methodology for the identification of cell populations present within the donor cell sample and/or receiver cell sample. As will be understood by the ordinarily skilled artisan, numerous markers and combination of markers other than those disclosed herein may be utilized to identify and characterize the cell populations present within the donor cell sample and/or receiver cell sample. Further, the identification of the various cell populations present in the donor cell sample and/or receiver cell sample may be carried out to the extent described herein, may include determination of the presence or absence of additional surface markers, may utilize fewer markers than disclosed herein, or may be carried out to a lesser extent such that fewer populations of cells within the donor cell sample and/or receiver cell sample are identified. In an embodiment, a method comprises excluding the identification of the different populations of cells present in a donor cell sample and/or receiver cell sample.

In an embodiment, a donor cell sample and/or receiver cell sample is obtained from a subject having undergone a Stage B preparation. In such embodiments, the donor cell sample and/or receiver cell sample may be further characterized based on the number of senescent cells and non-senescent cells present in the cell sample. Herein, non-senescent cells refer to the cells that retain the ability to divide many times over without showing replicative senescence. Herein senescent cells refer to cells having a long-term loss of proliferative capacity despite continued viability and metabolic activity.

Senescent cells may be identified using a variety of metrics that include for example loss of proliferation, morphological changes, decreased telomere lengths, increased S-β-GAL activity, the production of senescence-associated heterochromatic foci (SAHF), increased production of senescence-associated secretory factors (SASF), increased production of reactive oxygen species (ROS), increased DNA damage, decreased chaperone-mediated autophagy, or combinations thereof. It is contemplated that changes in the various metrics described are assessed relative to comparable cell types established to be non-senescent cells. Alternatively, the characteristics of the cell sample may be compared to literature values established for the analyzed metric in a corresponding non-senescent cell.

Non-senescent cells may characterized by the length of their telomeres and of the level of telomerase activity present in the cell. By way of a non-limiting example, non-senescent cells present in the donor cell sample may be characterized by telomere lengths greater than or equal to about 4 kilobases, alternatively 4.5 kilobases, or alternatively 5 kilobases. It will be understood by the ordinarily skilled artisan that teleomere lengths indicative of non-senescent cells may vary depending on the cell type. Consequently, for a particular cell type, the telomere length characteristic of a non-senescent cell may be determined by routine experimentation.

In an embodiment, Stage B preparation of the subject from which the donor cell sample and/or receiver cell sample is harvested results in the preferential mobilization of non-senescent cells. The result of the preferential mobilization of non-senescent cells may be a donor cell sample and/or receiver cell sample comprising greater than 90% non-senescent cells, alternatively greater than 91% non-senescent cells, alternatively greater than 92% non-senescent cells, alternatively greater than 93% non-senescent cells, alternatively greater than 94% non-senescent cells, alternatively greater than 95% non-senescent cells, alternatively greater than 96% non-senescent cells, alternatively greater than 97% non-senescent cells, alternatively greater than 98% non-senescent cells, or alternatively greater than 99% non-senescent cells. The percentage of non-senescent cells is based on the total number of cells present in the sample. In an embodiment, the donor cell sample and/or receiver cell sample comprise from about 90% non-senescent cells to about 99% non-senescent cells based on the total number of cells present in the sample.

In some embodiments, the non-senescent cells present in the donor cell sample and/or receiver cell sample may be identified using any suitable methodology. In such embodiments, the non-senescent cells may be separated from the senescent cells using any suitable process compatible with the present disclosure to result in a donor cell sample and/or receiver cell sample that comprises, consists essentially of, or consists of non-senescent cells. It is contemplated that such methodologies may be extended to further define a population of non-senescent cells having the presence or absence of particular cell surface markers and result in a donor cell sample and/or receiver cell sample comprising, consisting essentially of, or consisting of non-senescent cells of a particular type (e.g., non-senescent mesenchymal stem cells, non-senescent natural killer cells).

In an embodiment, the donor cell sample and/or receiver cell sample may be analyzed for the extent of expression of one or more genes and/or proteins associated with cellular senescence. Such analyses may be carried out using a restoration biomarker protein panel (RBPP) and/or restoration biomarker gene expression panel (RBGEP) of the types disclosed herein.

In an embodiment, the RBPP comprises a plurality of antibody probes for factors linked to cellular aging and senescence. For example, the RBPP may comprise greater than 5 antibody probes, alternatively greater than 10 antibody probes, or alternatively greater than 20 antibody probes. In an embodiment the RBPP comprises from 10 to 15 antibody probes. An example of a RBPP suitable for use in this disclosure is a protein array panel designated RBPP—X1 comprising antibody probes to the proteins listed in Table 2:

TABLE 2

| Name | Also Known As | Designated |
|---|---|---|
| granulocyte-colony stimulating factor | colony-stimulating factor 3 | G-CSF |
| chemokine ligand 26 | eotaxin-3, macrophage inflammatory protein 4-alpha, thymic stroma chemokine, and IMAC | CCL26 |
| hepatocyte growth factor | hepatocyte scatter factor (HSF), | HGF |
| insulin-like growth factor binding protein 1 | placental protein 12 (PP12) | IGFBP-1 |
| insulin-like growth factor binding protein 4 | | IGFBP-4 |
| insulin-like growth factor binding protein 6 | | IGFBP-6 |
| insulin-like growth factor beta | catabolin | IL-β |
| macrophage inflammatory protein 3 (MIP3A) | chemokine ligand 20, liver activation regulated chemokine (LARC) | MIP-3α |
| stem cell factor | KIT-ligand, KL, steel factor | SCF |
| thymus and activation regulated chemokine | chemokine ligand 17 (CCL17), | TARC |
| transforming growth factor beta 1 | | TGF-β1 |

TABLE 2-continued

| Name | Also Known As | Designated |
|---|---|---|
| tumor necrosis factor receptor superfamily member 1A | | sTNFR1 |
| vascular endothelial growth factor | | VEGF |

In some embodiments, the RBGEP may comprise greater than 5 gene probes, alternatively greater than 10 gene probes, or alternatively, greater than 20 gene probes. In some embodiments, the RBGEP comprises from 10 to 15 gene probes. In some aspects, the RBGEP comprises gene probes for factors linked to the regulation of cell cycle or the p53 pathway such as IFBP3, CSC25C, ABL1, CDKN2B, ALDH1A3, SIRT1, ING1, CITED2, CDKN1C, or a combination thereof. The RBGEP may further comprise gene probes for factors associated with regulation of inflammatory processes such as CDKN1A, IRF3, EGR1, IFNG, CDKN1B, NFKB1, SERPING2, IGFBP7, IRF7, or a combination thereof. The RBGEP may further comprise gene probes for factors associated with regulation of DNA damage related-processes such as PCNA, TERT, TP53BP1, or a combination thereof. The RBGEP may further comprise gene probes for factors associated with oxidative stress such as PRKCD, SOD1, NOX4, or a combination thereof. The RBGEP may further comprise gene probes for factors associated with cellular senescence such as CDKN2A, CDK6, TWIST, ATM, CCND1, ETS2, RBL2, BMI1, ETS1, or a combination thereof. The RBGEP may further comprise gene probes for factors associated with the MAPK pathway such as HRAS, MAP2K3, or both. The RBGEP may further comprise gene probes for factors associated with cytoskeletal function such as VIM, PIK3CA, THBS1, or a combination thereof. The RBGEP may further comprise gene probes for factors associated with the p16 effector pathway such as TBX3, TBX2 or a combination thereof. The RBGEP may further comprise gene probes for factors associated with insulin signaling such as IGFBP5. The RBGEP may further comprise gene probes for factors associated with cell adhesion such as CDL3A1, CD44, TGFB1A, CDL1A1, TGFB1 or a combination thereof. The RBGEP may further comprise gene probes for factors associated with the p53 effector pathway such as E2F1,MYC or both. An example of a RBGEP suitable for use in this disclosure, designated RBGEP-X1, is a gene panel comprising cDNA to the proteins listed in Table 3:

TABLE 3

| Gene | Protein Encoded |
|---|---|
| IGFBP3 | insulin-like growth factor binding protein 3 |
| HRAS | Transforming protein p21 |
| PRKCD | protein kinase C delta |
| AKT1 | alpha serine/threonine protein kinase |
| CHEK2 | checkpoint kinase 2 |
| MAPK14 | mitogen-activated protein kinase 14 |
| IGF1 | insulin-like growth factor |
| TWIST1 | Twist-related protein 1 |
| CDC25C | M-phase inducer phosphatase 3 |
| CCNA2 | cyclin-A2 |
| CDK5 | cell-division protein kinase 6 |
| CCNE1 | G1/S-specific cyclin E1 |
| CHEK1 | checkpoint kinase 1 |

In an embodiment, at least a portion of the donor cell sample and/or receiver cell sample are subjected to protein array analyses utilizing the RBPP—X1 array, gene expression analysis using the RBGEP-X1 array, or both. In alternative embodiments, at least a portion of the donor cell sample and/or receiver cell sample are subjected to protein array analyses, gene expression analyses or both utilizing any suitable protein and/or gene array.

In an embodiment, the donor cell sample, receiver cell sample, or both are subjected to at least one analytical technique to characterize the quality of the cell sample. Herein, the "quality" of the cell sample refers to factors used to characterize the cellular health of the sample and includes parameters such as the number and types of cells present in the sample; the ratio of senescent to non-senescent cells in the sample; the extent of expression of a group of genetic and/or protein biomarkers; the average telomere length of the cells in the sample; and the status of the innate immune function of the cells in the sample. Telomere length may be determined using any suitable methodology, for example, terminal restriction fragment (TRF) analysis. Innate immune function may be evaluated using any suitable methodology such as the $^{51}Cr$ cytotoxicity release natural killer cell assay. The donor cell sample quality may be an assessment of the ability of the cells in the sample to improve and/or restore one or more cellular functions of the cells in the receiver cell sample. The receiver cell sample quality may be an assessment of the ability of the cells in the sample to exhibit improvement and/or the restoration of one or more cellular functions when subjected to the compositions and methodologies disclosed herein.

The donor cell sample quality may be assigned a numerical value that ranges from 1 to 10 wherein a sample displaying positive characteristics for use in the improvement and/or restoration of cellular function of a receiver cell sample has a value of 10, and a sample exhibiting the fewest characteristics associated with the ability to improve/restore cellular function of a receiver cell sample has a value of 1. For example, each of the following factors may weigh positively in characterization of the quality of a donor cell sample; relatively long telomere length; high level of expression of cell viability-promoting genes and/or proteins; the presence of greater than about 90% non-senescent cells; and high levels of innate immune function. Donor cell samples displaying these characteristics may be given a sample quality value of 10.

The receiver cell sample quality may be assigned a numerical value that ranges from 1 to 10 wherein a sample having restorable or improvable cellular function has a value of 10, and a sample whose cellular function cannot be significantly improved and/or restored has a value of 1. For example, each of the following factors may weigh positively in characterization of the quality of a receiver cell sample; relatively long telomere length; moderate level of expression of senescence-promoting genes and/or proteins; and the presence of greater than about 90% non-senescent cells. Receiver cell samples displaying these characteristics may be given a sample quality value of 10.

Utilizing the quality metrics disclosed herein (e.g., telomere length, percentage of non-senescent cells), an aspect of the present disclosure comprises evaluating the quality of the donor cell sample and receiver cell sample and identifying samples suitable for use in the disclosed methodologies. For example, a receiver cell sample having a quality value of less than 3 may be deemed unsuitable for use in the presently disclosed methodologies. Similarly, a donor cell sample having a quality value of less than 3 may be deemed unsuitable for use in the present methodologies. In some embodiments, the a donor cell sample having a quality value of equal to or greater than 7 may be used in the methodologies disclosed herein with a receiver cell sample having a quality value of equal to or greater than 7. It is to be understood that the quality values may be assigned based on any number of metrics used to assess the quality of a donor cell sample and/or receiver cell sample. Consequently, based on the parameters used to make the assignment of a quality value, the characteristics associated with a particular quality value may differ.

In some embodiments, the donor cell sample and/or receiver cell sample having been subjected to one or more of the qualitative and quantitative characterizations described herein are further processed to provide some user and/or process desired sample containing a predetermined type and number of cells. The present disclosure contemplates the utilization of such characterized samples. For example, the characterized samples may be a component of a pharmaceutical formulation that is administered to a subject to ameliorate one or more medical conditions.

Alternatively, the donor cell sample and receiver cell sample may be utilized in the restoration methodologies disclosed herein.

In an embodiment, a method of cellular restoration comprises contacting the soluble factors and/or particles present in the media of a cultured donor cell sample with the receiver cell sample. For example, the donor cell sample may be cultured in appropriate media for a time period ranging from about 24 hours to about 6 weeks, alternatively, from about 1 week to about 5 weeks or alternatively, from about 2 weeks to about 4 weeks. Herein, the culture media, also known as the growth media, refers to a liquid or gel containing the appropriate nutrients to support the growth of cells. Suitable culture media may be chosen by the ordinarily skilled artisan with the benefits of the present disclosure. The culture media may then be removed from the donor cell sample using any suitable methodology (e.g., filtration, centrifugation) and the cell-free media then contacted with the receiver cell sample.

In an alternative embodiment, the method of cellular restoration comprises establishing a transwell culture of both the donor cell sample and receiver cell sample. Referring to FIG. 26, the transwell culture 400 may comprise an insert 410 having at least one permeable surface that allows the donor cells to uptake and secrete molecules on the basal and/or apical surfaces of the transwell. The transwell insert 410 may be comprised of any material compatible with the compositions and methodologies disclosed herein such as, for example, polyethylene terephthalate or polycarbonate. In an embodiment, the transwell insert 410 comprises a permeable membrane with a pore size ranging from 0.4 µm to 3.0 µm, alternatively from 0.4 µm to 2.0 µm, or alternatively from 0.4 µm to 1.0 µm. The transwell insert may have a pore size that allows for the passage of soluble factors and/or particles secreted or released from the donor cell sample to the lower compartment of the transwell where these materials contact the receiver cell sample. At least a portion of the donor cell sample 420 may be applied to the transwell insert 410 while the receiver cell sample 430 is positioned within the lower compartment of the transwell culture with an appropriate amount of culture media. The donor cell sample and receiver cell sample may be cultured in the transwell for a time period of from 24 hours to 6 weeks, alternatively, from 1 week to 5 weeks, or alternatively, from 2 weeks to 4 weeks. Soluble factors and/or particles of the appropriate size 440 are allowed to pass through the permeable membrane and contact the receiver cell sample 430 in the lower chamber of the transwell.

In an embodiment, the donor cell sample and receiver cell sample are recovered separately from the transwell culture. The donor cell sample, as recovered from the transwell culture, is hereinafter termed the altered donor cell sample (ADCS). The receiver cell sample as recovered from the transwell culture is termed the restored composition (RC). In an embodiment, the ADCS and/or RC may be further characterized using any of the methodologies disclosed herein. In some embodiments, at least a portion of the ADCS and/or RC are further processed, for example, the samples may be prepared for cryopreservation. In yet another embodiment, at least a portion of the RC is utilized to treat a subject.

Herein the RC refers to the cellular material subsequent to culturing with the soluble factors of the donor cell sample for the time periods disclosed herein. The RC is characterized by improvement in one or more of the following metrics when compared to the receiver cell sample; innate immune function, morphology, colony-forming ability, reduced expression of senescence-promoting factors; increased expression of cell-viability promoting factors, and the like. In an embodiment, the RC is characterized by the presence of cells having gene expression and protein expression patterns for cellular senescence associated agents (e.g., CDKN2A, CDK6, TWIST, ATM, CCND1, ETS2, RBL2, BMI1, and ETS1) that are quantitatively more similar to those of the donor cell sample than the receiver cell sample.

In one embodiment, a methodology disclosed herein comprises the preparation of a RC. The RC is derived from the receiver cell sample that is subjected to the methodologies disclosed herein, specifically by the restoration of at least a portion of the receiver cell sample. Herein, "restoration" refers to modification of a cell (e.g., stem cell) such that expression of one or more senescence-promoting agents is reduced and/or expression of one or more cell viability/cell function-promoting agents is increased. Without wishing to be limited by theory, the methodologies and compositions disclosed herein may result in the epigenetic modification of one or more cell types that results in at least one characteristic associated with improved cellular function when compared to an otherwise similar cell type not subjected to the compositions and methods disclosed herein. Herein, "epigenetic" refers to the heritable changes in gene activity and expression that occurs without alternation in DNA sequence. Nonlimiting examples of epigenetic modifications include posttranslational modifications such as DNA methylation, chromatin remodeling, and histone modification.

The RC comprises cells that may exhibit alterations in parameters of cellular and/or organismal physiology that result in a perceived and/or quantifiable improvement in the functional state of receiver cells and/or cell types, wherein perceived improvement is defined as semblance to the functional state of the donor cells and/or cell types. It is to be understood that the restored composition comprises cells and is derived from a corresponding receiver cell sample.

In an embodiment, a RC is characterized by the maintenance of the viability state of the cells and/or cell types in the composition as quantified, for example, by a cell vitality assay.

In an alternate embodiment, a RC is characterized by an increase in the viability state of the cells and/or cell types as quantified, for example, by a cell viability assay.

In an embodiment, a RC is characterized by a lack of change in the percentage of hematopoietic stem cells, hematopoietic progenitor cells, mesenchymal stem cells and endothelial progenitor cells, herein termed the "stem cell pool", compared to the receiver cell sample.

In an alternate embodiment, a RC is characterized by an increase in the stem cell pool in comparison to the receiver cell sample.

In an embodiment, a RC is characterized by cells that exhibit an improvement in cellular immune function in comparison to the corresponding receiver cell sample as quantified, for example, by natural killer cell cytotoxicity assay.

In an embodiment, a RC is characterized by cells that exhibit an improvement in cellular hematopoietic function as quantified, for example, by hematopoietic stem cell clonogenic assay in comparison to the corresponding receiver cell sample.

In an alternate embodiment, a RC is characterized by cells that exhibit an improvement in systematic hematopoietic and immune function of the subject when compared to the corresponding receiver cell sample as quantified, for example, by increased lymphopoiesis, increased ratio of CD4 to CD8 positive T cells, and/or improved immune surveillance. Improved immune surveillance can be determined by decreased incidences of microbial infection and tumor formation in the subject. Improved immune surveillance can also be measured by decreased rate of cancer incidence in the subject. Decreased rates of cancer incidence shall thereby confer to the subject an increased likelihood of prolonged organismal survival.

In an embodiment, a RC is characterized by cells that exhibit a minimization of replicative stress as determined, for example, by telomere length and/or telomerase activity when compared to the corresponding receiver cell sample.

In an embodiment, a RC is characterized by cells that exhibit a decreased expression of senescence-related genes when compared to the corresponding receiver cell sample, wherein senescence-related genes are defined, for example, as the RBGEP, by quantitative polymerase chain reaction.

In an embodiment, a RC is characterized by cells that exhibit a decreased expression of senescence-associated secretory factors when compared to the corresponding receiver cell sample, wherein senescence-associated secretory factors are exemplified in Table 2.

In an embodiment, a RC is characterized by cells that exhibit alterations in the epigenetic signature of the cells when compared to the corresponding receiver cell sample, wherein epigenetic signature is determined, for example, by chromatin immunoprecipitation sequencing (ChIP-Seq).

In an embodiment, a RC is characterized by cells that exhibit an increase in the rate of proteostasis when compared to the corresponding receiver cell sample which may be quantified, for example, by a Cyto-ID® Autogphagy Detection Kit.

In an embodiment, a RC is characterized by cells that exhibit a decrease in cellular oxidative stress when compared to the corresponding receiver cell sample, as quantified for example by the MitoSOX™ Red mitochondrial superoxide indicator kit.

In an embodiment, a RC is characterized by cells that exhibit a decrease in cellular senescence when compared to the corresponding receiver cell sample, as quantified, for example, by the Fluorometric Quantitative Cellular Senescence β-Gal Assay Kit.

In an embodiment, a RC is characterized by cells that exhibit the maintenance of mesenchymal stem cell function when compared to the corresponding receiver cell sample, wherein mesenchymal stem cell function is quantified, for example, by the colony forming unit-fibroblast (CFU-F) assay and/or ability to undergo lineage-specific differentiation into adipogenic, osteogenic and chondrogenic lineages.

In an alternate embodiment, a RC is characterized by cells that exhibit an increased mesenchymal stem cell function when compared to the corresponding receiver cell sample.

In an embodiment, a RC is characterized by cells that exhibit maintenance of endothelial progenitor function when compared to the corresponding receiver cell sample wherein endothelial progenitor function is quantified, for example, by tube formation assay.

In an alternate embodiment, a RC is characterized by cells that exhibit an increased endothelial progenitor function when compared to the corresponding receiver cell sample.

Herein, cellular restoration occurs following contact of the receiver cell sample with soluble factors and/or particles present in the donor cell sample (e.g., materials that pass through the permeable transwell insert). Consequently, the method of restoration comprises contact of the cell-free soluble factors and/or particles present in the media of a donor cell sample with a receiver cell sample. In some aspects, the donor cell sample is cultured in a suitable media and the media may then be separated from the donor cells to form a cell-free media which is utilized in the restoration of a receiver cell sample. Without wishing to be limited by theory, the soluble factors and/or particles present in the donor cell sample media that pass through the permeable transwell insert may include paracrine factors, microvesicles, exosomes, cellular fragments, and the like Herein paracrine factors refer to signaling molecules which are secreted into the immediate extracellular environment and diffuse over a short distance to a target cell. Microvesicles generally refer to small (e.g., 50 nm to 100 nm) fragments of plasma membrane thought to be shed by a variety of cell types. Exosomes generally refer to secreted extracellular vesicles that may contain biomolecules such as proteins, lipids, and RNA and function in cellular signaling. In some embodiments, the soluble factors and/or particles of the donor cell sample that contact the receiver cell sample comprise extracellular vesicles. Exosomes and microvesicles belong to a broader group of extracellular vesicles (EVs) that represent an important mode of intercellular communication by serving as vehicles for transfer between cells of membrane and cytosolic proteins, lipids, and RNA.

In an embodiment, the quality of the restoring composition can be adjusted by the presence of one or more materials that regulate the release of EVs. For example, the release of one or more EVs may be inhibited by the addition of small molecule inhibitors such as mannumycin A. Alternatively, the release of EVs may be promoted, for example, by activation of purinergic receptors with ATP, activation by lipopolysaccharides, plasma membrane depolarization, or increasing intracellular $Ca^{2+}$ concentrations.

It is a contemplated aspect of the present disclosure that cell-free media generated by culturing of the donor cell sample in a suitable media followed by removal of the cells and herein designated the restoring composition, may be further processed to separate individual constituents or groups of constituents based on like characteristics using any suitable methodology (e.g., ethanol precipitation, centrifugation gradients). In an embodiment, the individual constituents of the restoring composition may be analyzed for their ability to affect restoration of a receiver cell sample of the type disclosed herein. The present disclosure further contemplates utilization of one or more isolated constituents, or isolated groups of constituents, in the methodologies for cellular restoration. In an embodiment, cellular restoration of a receiver cell sample of the type disclosed herein is carried out utilizing an EV (e.g., exosome/microvesicle) isolated from a culture media of a donor cell sample. In another embodiment, cellular restoration of a receiver cell sample of the type disclosed herein is carried out utilizing cellular fragments isolated from a culture media of a donor cell sample.

In yet another aspect, the present disclosure contemplates utilization of the restored composition to generate a secondarily restored composition. In particular, the restored composition having the characteristics disclosed herein may be contacted with a third cell sample obtained from a third subject. The third cell sample may be evaluated via the methodologies disclosed herein for evaluation of cell samples (e.g., immunophenotyping). In some embodiments, the third cell sample is obtained from a subject having characteristics (e.g., chronological age, medical condition) disclosed for the first subject. Culturing of the third cell sample in the presence of the restored composition using the methods disclosed herein (e.g., transwell culture) may result in the formation of a secondarily restored composition. It is contemplated that the restoration processes disclosed herein can be propagated indefinitely such that a secondarily restored composition may likewise be utilized to produce a tertiary restored composition utilizing a fourth cell sample obtained from a fourth subject and so on. The extent to which the subsequently restored compositions (e.g., tertiary restored compositions) manifest the characteristics disclosed herein may be evaluated utilizing any suitable methodology (e.g., assay for increased endothelial progenitor function). In some embodiments, subsequently restored compositions (e.g., a secondarily restored composition) when evaluated using assays such as cell viability, the percentage of hematopoietic stem cells, extent of the stem cell pool, cellular hematopoietic and immune function, systematic hematopoietic and immune function, replicative stress, expression of senescence-related genes, level of senescence-associated secretory factors, alterations in epigenetic signature, rate of proteostasis, extent of cellular oxidative stress, extent of cellular senescence, maintenance or increase of mesenchymal stem cell function, maintenance or increase of endothelial progenitor function, or a combination thereof have results that are within from about 10% to about 90% of results obtained from assaying the restored composition, alternatively from about 20% to about 80% or alternatively from about 30% to about 70%.

Within the context of aspects comprising a donor and receiver cell sample, cellular restoration occurs following contact of the receiver cell sample with soluble factors and/or particles present in the donor cell sample (e.g., materials that pass through the permeable transwell insert). Likewise utilizing a first and second cell sample; the first cell sample is considered the receiver sample while the second cell sample is considered the donor sample. Once a restored composition is formed it can function as the donor sample in subsequent restorations.

Consequently, the method of restoration comprises contact of the cell-free soluble factors and/or particles present in the media of a donor cell sample with a receiver cell sample. In some aspects, the donor cell sample is cultured in a suitable media and the media may then be separated from the donor cells to form a cell-free media which is utilized in the restoration of a receiver cell sample. Without wishing to be limited by theory, the soluble factors and/or particles present in the donor cell sample media that pass through the permeable transwell insert may include paracrine factors, microvesicles, exosomes, cellular fragments, and the like Herein paracrine factors refer to signaling molecules which are secreted into the immediate extracellular environment and diffuse over a short distance to a target cell. Microvesicles generally refer to small (e.g., 50 nm to 100 nm) fragments of plasma membrane thought to be shed by a variety of cell types. Exosomes generally refer to secreted extracellular vesicles that may contain biomolecules such as proteins, lipids, and RNA and function in cellular signaling. In some embodiments, the soluble factors and/or particles of the donor cell sample that contact the receiver cell sample comprise extracellular vesicles. Exosomes and microvesicles belong to a broader group of extracellular vesicles (EVs) that represent an important mode of intercellular communication by serving as vehicles for transfer between cells of membrane and cytosolic proteins, lipids, and RNA. In some embodiments, disclosed herein are microRNAs within exosomes of young blood that can restore function to the aging lymphohematopoietic system as described herein and compositions comprising same, and methods of making same.

In some embodiments, the quality of the restoring composition can be adjusted by the presence of one or more materials that regulate the release of EVs. For example, the release of one or more EVs may be inhibited by the addition of small molecule inhibitors such as mannumycin A. Alternatively, the release of EVs may be promoted, for example, by activation of purinergic receptors with ATP, activation by lipopolysaccharides, plasma membrane depolarization, or increasing intracellular $Ca^{2+}$ concentrations.

In some embodiments, the RC may be formulated for administration to a subject in need thereof. In some embodiments, the subject is the receiver subject. For example, the RC may be a component of a formulation that is administered to the receiver subject to improve the receiver subject's general health. Such improvements may be identified by quantitative evaluation of one or more physiological or psychological parameters of the subject. In the alternative, such improvements may be identified by the qualitative evaluations of one or more physiological or psychological parameters of the subject. In an embodiment, the receiver subject is prophylactically administered the RC.

The RC may be administered to a subject (e.g., receiver subject) via any suitable methodology. In some embodiments, the methodologies disclosed herein comprise systemic administration of the RC to the subject. For example, the RC may be administered systemically in dosage unit formulations containing conventional nontoxic pharmaceutically acceptable carriers, adjuvants, and vehicles as desired. In a specific embodiment, administration of the RC may be by intravenous injection, endobronchial administration, intraaterial injection, intramuscular injection, intracardiac injection, subcutaneous injection, intraperitoneal injection, intraperitoneal infusion, transdermal diffusion, transmucosal diffusion, intracranial, intrathecal, or combinations thereof. A means of administering the RC may include, but is not limited to, infusion. Systemically may also include, for example, by a pump, by an intravenous line, or by bolus injection. Bolus injection can include subcutaneous, intramuscular, or intraperitoneal routes.

In some embodiments, one or more RNAi(s) and/or compounds as disclosed elsewhere herein are administered locally or systemically to a subject in need thereof. In some aspects, the appropriate route of administration of one or more RNAi(s) and/or compounds as disclosed elsewhere herein is selected based upon various factors such as the type of medical condition, the underlying cause, the severity of the condition, etc. In some embodiments, suitable routes of administration include, but are not limited to, oral, intravenous, rectal, aerosol, parenteral, ophthalmic, pulmonary, transmucosal, transdermal, vaginal, optic, nasal, and topical administration. In some embodiments, parenteral delivery includes but is not limited to intramuscular, subcutaneous, intravenous, intramedullary injections, as well as intrathecal, direct intraventricular, intraperitoneal, intralymphatic, and intranasal injections.

In some embodiments, one or more RNAi(s) and/or compounds as disclosed elsewhere herein is formulated for oral administration. In some embodiments, one or more RNAi(s) and/or compounds as disclosed elsewhere herein are formulated by combining the active agent or agents with, e.g., pharmaceutically acceptable carriers or excipients. In some embodiments, one or more RNAi(s) and/or compounds as disclosed elsewhere herein, such as a cell-free composition, is formulated in oral dosage forms that include tablets, powders, pills, dragees, capsules, liquids, gels, syrups, elixirs, slurries, suspensions and the like.

In some embodiments, one or more RNAi(s) and/or compounds as disclosed elsewhere herein are administered topically. Topical administration may be particularly useful for treatment or prevention of scarring resulting from injury or surgery. In some embodiments, one or more RNAi(s) and/or compounds as disclosed elsewhere herein may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In some embodiments, one or more RNAi(s) and/or compounds as disclosed elsewhere herein is formulated for transdermal administration. In some embodiments, transdermal formulations may employ transdermal delivery devices and transdermal delivery patches and can be lipophilic emulsions or buffered, aqueous solutions, dissolved and/or dispersed in a polymer or an adhesive. In some embodiments, such patches are constructed for continuous, pulsatile, or on demand delivery of pharmaceutical agents. In some embodiments, the transdermal delivery of the one or more RNAi(s) and/or compounds as disclosed elsewhere herein is accomplished by means of iontophoretic patches and the like. In some embodiments, transdermal patches provide controlled delivery. In some embodiments, the rate of absorption is slowed by using rate-controlling membranes or by trapping the one or more RNAi(s) and/or compounds as disclosed elsewhere herein within a polymer matrix or gel. In some embodiments, absorption enhancers are used to increase absorption. Absorption enhancers or carriers may include absorbable pharmaceutically acceptable solvents that assist passage through the skin. In some embodiments, transdermal devices are in the form of a bandage comprising a backing member, a reservoir containing an active agent optionally with carriers, optionally a rate controlling barrier to deliver the compound to the skin of the host at a controlled and predetermined rate over a prolonged period of time, and means to secure the device to the skin.

In some embodiments, the active agent or agents are formulated for administration by inhalation. Various forms suitable for administration by inhalation include, but are not limited to, aerosols, mists or powders. In some embodiments, the active agent or agents are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide, and/or other suitable gases). In some embodiments, the dosage unit of a pressurized aerosol is determined by providing a valve to deliver a metered amount. In some embodiments, capsules and cartridges of, such as, by way of example only, gelatins for use in an inhaler or insufflator are formulated containing a powder mix of one or more RNAi(s) and/or compounds as disclosed elsewhere herein and a suitable powder base such as lactose or starch.

As addressed above, other routes of administration, useful for the treatment of particular conditions or delivery to particular cells, tissues, organs, etc. are contemplated. A means of administering the one or more RNAi(s), compounds, or target cells as disclosed elsewhere herein may include, but are not limited to, infusion. Systemically may also include, for example, by a pump, by an intravenous line, or by bolus injection. In some embodiments, bolus injection can include subcutaneous, intramuscular, or intraperitoneal routes.

The phrases "systemic administration" or "administered systemically," as used herein, mean the administration of one or more RNAi(s), compounds, or cells as disclosed elsewhere herein, a composition, drug, or other material such that it enters the subject's system and, thus, is subject to metabolism and other like processes, for example, subcutaneous administration.

In some embodiments, the one or more RNAi(s), compounds, and/or cells as disclosed elsewhere herein is locally administered by means such as, but not limited to, injection, implantation, grafting, or epicutaneous. For example, the active agent or agents may be administered proximal to a wound site on the subject and functions to ameliorate the symptoms associated with the wound or increase the rate of wound-healing. Administration of the one or more RNAi(s), compounds, and/or cells as disclosed elsewhere herein may be conducted in any manner compatible with the compositions disclosed herein and to meet one or more user and/or process goals.

In some embodiments, the one or more RNAi(s), compounds, or target cells as disclosed elsewhere herein may be formulated for administration to a subject in order to improve the subject's general health. Such improvements may be identified by quantitative evaluation of one or more physiological or psychological parameters of the subject. In some embodiments, such improvements may be identified by the qualitative evaluations of one or more physiological or psychological parameters of the subject.

In some embodiments, the patient (e.g., receiver subject) is administered the one or more RNAi(s), compounds, or target cells as disclosed elsewhere herein as a component of a therapeutic procedure designed to ameliorate the effects of a medical condition. In some embodiments, the the one or more RNAi(s), compounds, or target cells as disclosed elsewhere herein, present in a therapeutically effective amount, may function as an active agent in a pharmaceutical composition.

In some embodiments, a subject being administered one or more RNAi(s), compounds, or target cells as disclosed elsewhere as disclosed elsewhere herein may be administered additional active agents as considered beneficial for the treatment of the medical condition. Such additional active agents may be administered prior to, concurrent with, or subsequent to the administration of the one or more RNAi(s), compounds, or target cells as disclosed elsewhere. Such additional active agents may be administered by the same route or by a different route, including any route disclosed herein for another active agent. Examples of additional active agents include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; or (h) combinations thereof. In some embodiments, additional active agents may also be present in a therapeutically effective amount. In some embodiments, the therapeutically effective amount is lower than would be required if the additional active agents were administered without the one or more RNAi(s), compounds, or target cells.

Examples of additional active agents for administration with one or more RNAi(s), compounds, or target cells include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor, or combinations thereof.

In some embodiments, specific compounds suitable for use with the one or more RNAi(s), compounds, or target cells include but are not limited to silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), NEOSPORIN® (i.e., Bacitracin, Polymyxin B, and Neomycin), POLYSPORIN® (i.e., Bacitracin and Polymyxin B). Additional antimicrobials include topical antimicrobials (i.e., antiseptics), examples of which include silver salts, iodine, benzalkonium chloride, alcohol, hydrogen peroxide, chlorhexidine, acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin, Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tiernynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine, Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium or combinations thereof.

Although the compositions provided herein are suitable for administration to humans, such compositions are generally suitable for administration to animals of all sorts. Modification of compositions suitable for administration to humans of the type disclosed herein (i.e., one or more RNAi(s), compounds, or target cells) in order to render the compositions suitable for administration to various animals can be accomplished by the ordinarily skilled veterinary pharmacologist, with the benefit of this disclosure, who can design and perform such modifications with routine, if any, experimentation. Subjects to which administration of the pharmaceutical compositions of this disclosure is contemplated include, but are not limited to, humans and other primates; mammals including commercially relevant mammals such as cattle, pigs, horses, and sheep; companion animals such as cats and dogs; and birds including commercially relevant birds such as chickens, ducks, geese, and turkeys.

In some embodiments, the composition may contain additional ingredients as suitable for the formulation of a pharmaceutical composition. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

In some embodiments, the composition may be administered systemically in dosage unit formulations containing conventional nontoxic pharmaceutically acceptable carriers, adjuvants, and vehicles as desired, or may be locally administered by means such as, but not limited to, injection, implantation, or grafting. In some embodiments, administration may be by intravenous injection, endobronchial adminstration, intraaterial injection, intramuscular injection, intracardiac injection, subcutaneous injection, intraperitoneal injection, intraperitoneal infusion, transdermal diffusion, transmucosal diffusion, intracranial, intrathecal, or combinations thereof. In some embodiments, the compositions are administered by infusion. Systemic administration may also include, for example, by a pump, by an intravenous line, or by bolus injection. Bolus injection can include subcutaneous, intramuscular, or intraperitoneal routes.

In some embodiments, the one or more RNAi(s), compounds, or target cells is formulated for topical administration into forms such as creams, lotions, serums, powders, ointments, or drops. A formulation of the one or more RNAi(s), compounds, or target cells for topical administration may also contain pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition or combinations thereof.

Nonlimiting exemplary pharmaceutically acceptable carriers that may be used in the compositions for topical administration or other forms of administration include water, mixtures of water and water-miscible solvents (e.g., lower alkanols, vegetable oils, DMSO, etc.), and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN®), white petrolatum (VASELINE®), triethanolamine, emu oil, aloe vera extract, lanolin, cocoa butter, LIPODERM® base, and the like or combinations thereof. In some embodiments, the one or more RNAi(s), compounds, or target cells formulated for topical administration may be applied to one or more areas of the skin including the face, hands, and neck.

In some embodiments, the methodologies disclosed herein result in therapies that are prophylactic, palliative, curative, or combinations thereof. Methodologies and compositions of the type disclosed herein may be utilized in the treatment of a wide variety of medical conditions related to decreases in cellular function and viability such as age-related medical conditions that include neurological disorders; autoimmune diseases; infectious disease; cancer and disorders associated with radiation overexposure (chronic or acute).

It is contemplated the methodologies and compositions disclosed herein may result in an increased expression of genes associated with improved cellular health with a concomitant decrease in the expression of genes associated with adverse cellular events. In some embodiments, the methodologies and compositions disclosed herein result in an increased expression of genes associated with beneficial cellular events.

According to another aspect of the disclosure, kits are provided. Kits, according to the present disclosure, include package(s) or containers comprising the compositions disclosed herein (e.g., RC, cell-free culture media) and may include defined culture medium and cell culture medium supplement. The kit may further include an instruction letter or package-associated instruction for the treatment and/or prophylaxis of a medical condition. The phrase "package" means any vessel containing the compositions (including stem cells, media, and/or media supplement) presented herein. For example, the package can be a box or wrapping. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. The kit can also contain items that are not contained within the package but are attached to the outside of the package, for example, pipettes. Kits may optionally contain instructions for administering compositions of the present disclosure to a subject having a condition in need of treatment. Kits may also comprise instructions for approved uses of compounds herein by regulatory agencies, such as the United States Food and Drug Administration. Kits may optionally contain labeling or product inserts for the present compositions. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another. The kit may optionally also contain one or more other compounds for use in combination therapies as described herein. In certain embodiments, the package(s) is a container for intravenous administration.

In an embodiment, a subject having undergone a restoration method of the type disclosed herein may be subsequently monitored for some time period. Monitoring of the subject may comprise qualitative and quantitative evaluations of the subject's general health and/or medical condition. In some embodiments, a subject may be subjected to a plurality of cellular restoration methods of the type disclosed herein. For example, a receiver subject having undergone a cellular restoration method of the type disclosed herein may display quantitative and/or qualitative improvements in the subject's general health and/or medical condition for some time period. Subsequently, the receiver subject may experience some decline in their general health and/or medical condition and another cellular restoration process may be carried out. The cellular restoration process may involve obtaining a donor cell sample and/or receiver cell sample utilizing the methodologies disclosed herein, performing cellular restoration of the receiver cell sample and administering the restored cell sample to the receiver subject. Alternatively, the receiver subject may be administered at least a portion of the restored cell sample remaining from a prior cellular restoration process.

In some embodiments, evaluations of the subject comprise determinations based on analyses disclosed herein (e.g., natural killer assay, telomere length, gene and protein biomarker arrays). In such embodiments, the subject may provide a receiver cell sample and the quality of the sample evaluated as disclosed herein. In some embodiments, the receiver cell sample quality value at some point post-restoration may be compared to the receiver cell sample quality value pre-restoration and this information utilized to assess whether additional treatment is needed. For example, a subject having a receiver cell sample pre-restoration quality value of 5 may have a receiver cell sample post-restoration quality value of 9 for a time period of up to about 1 year subsequent to the restoration process. The subject's post-restoration receiver cell sample quality value after 1.5 years may have decreased to 7 while after 3 years the value may be 5. In such instances, the subject may be administered another RC.

Figure 3N:
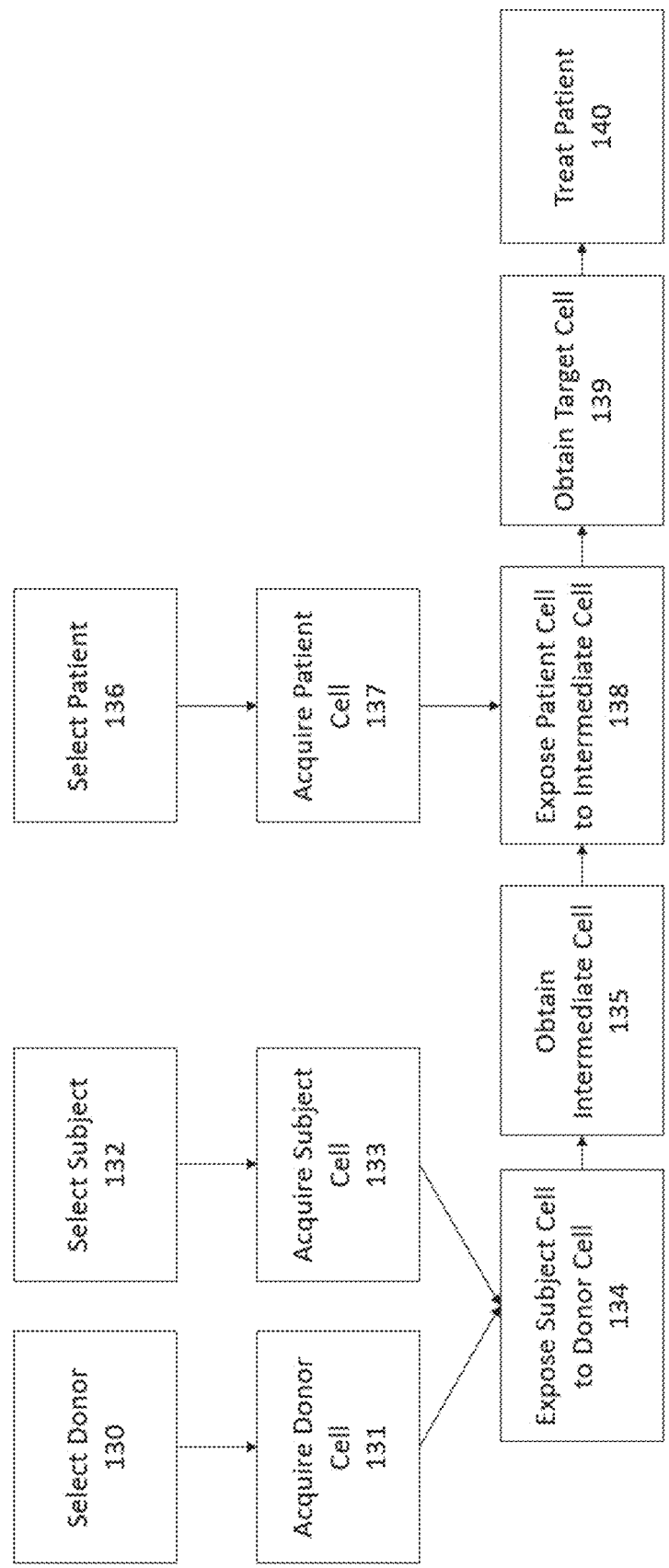

Some embodiments, as shown in FIG. 3N, pertain to a method of preparing at least one cell. In some embodiments, the method comprises selecting a donor 130. In some embodiments, the method comprises providing at least one donor cell from the donor 131. In some embodiments, the method comprises selecting a subject 132. In some embodiments, the method comprises providing at least one subject cell from the subject 133. In some embodiments, the method comprises selecting a patient 136. In some embodiments, the method comprises providing at least one patient cell from the patient 137. In some embodiments, the method comprises exposing the subject cell to the donor cell 134 to provide at least one intermediate cell 135. In some embodiments, the method comprises exposing the patient cell to the intermediate cell to provide a target cell 139. In some embodiments, the target cell is administered to the patient to treat the patient 140. In some embodiments, the donor is the subject (e.g., at an earlier age and/or in a state of improved health). In some embodiments, the donor is the patient (e.g., at an earlier age and/or in a state of improved health). In some embodiments, the subject is the patient (e.g., at an earlier age and/or in a state of improved health).

Figure 3O:
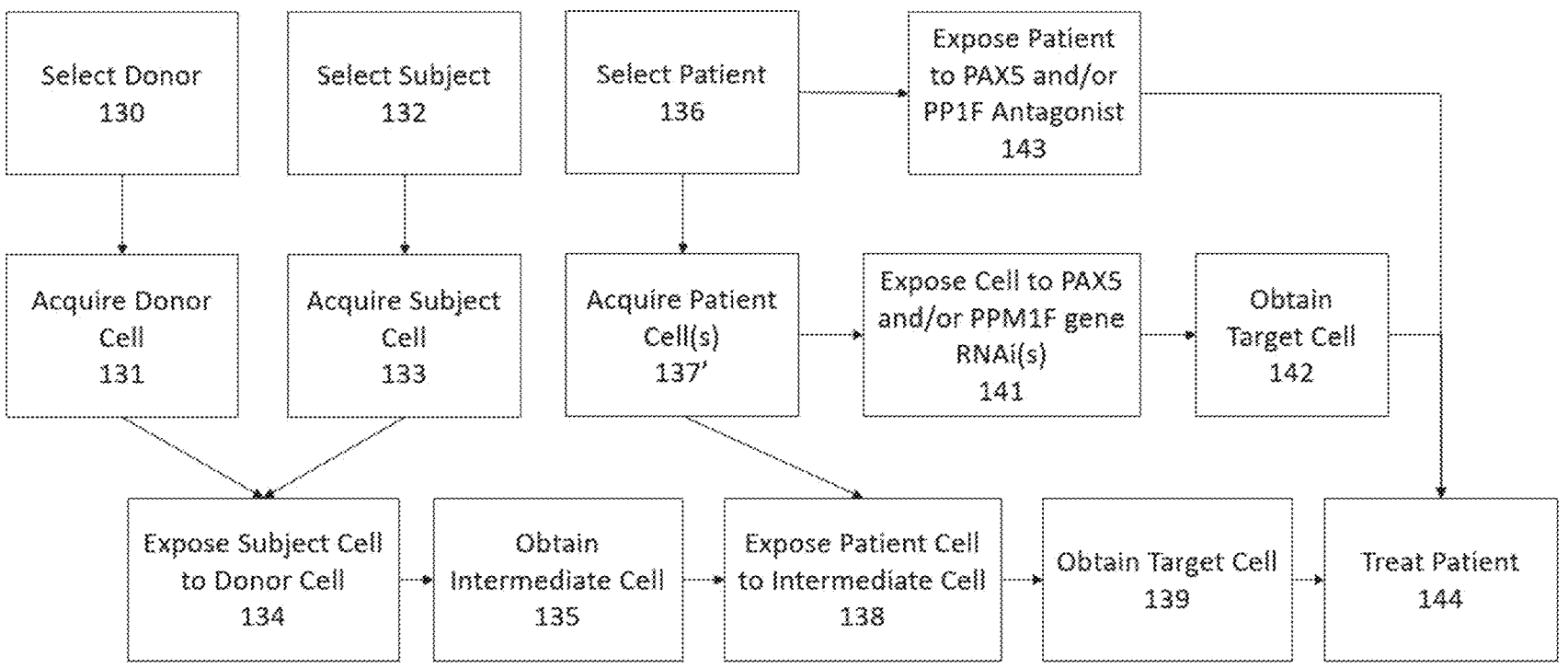

As shown in FIG. 3O, multiple strategies can be combined to provide treatments for patients. In some embodiments, as shown, the method comprises selecting a donor 130. In some embodiments, the method comprises providing at least one donor cell from the donor 131. In some embodiments, the method comprises selecting a subject 132. In some embodiments, the method comprises providing at least one subject cell from the subject 133. In some embodiments, the method comprises selecting a patient 136. In some embodiments, the method comprises providing at least one patient cell from the patient 137. In some embodiments, the method comprises exposing the subject cell to the donor cell 134 to provide at least one intermediate cell 135. In some embodiments, the method comprises exposing the patient cell to the intermediate cell to provide a target cell 139. In some embodiments, as shown, a cell is acquired and treated by exposing it to one or more different PAX5 gene RNAi(s) and/or PPM1G gene RNAi(s) 141. In some embodiments, as shown, this results in a target cell 142. In some embodiments, as shown in FIG. 3O, the cell can be reintroduced to the patient (e.g. where it was initially isolated from the patient). In some embodiments, one or more small molecule PAX5 and/or PP1F inhibitors are also administered to the patient 143. In some embodiments, the target cell 139 is administered to the patient to treat the patient 140. In some embodiments, as shown, the patient is thereby treated 122. In some embodiments, a method of reducing expression of a paired box 5 (PAX5) gene and reducing expression of a protein phosphatase 1F enzyme (PPM1F) gene in a cell is provided. In some embodiments, the method comprises contacting the cell with one or more interfering RNA(s) (RNAi(s)) comprising one or more of SEQ ID NOs:9-20 maintaining the cell for a time sufficient to obtain inhibition of the PAX5 gene and the PPM1F gene, thereby reducing expression of the PAX5 gene and the PPM1F gene in that cell to provide a target cell. In some embodiments, the RNAi(s) act on the patent cell and/or the subject cell to provide the intermediate cell and/or the target cell. In some embodiments, the method comprises contacting the cell with one or more polycyclic aromatic compounds that antagonize or reduce the expression of PAX5 and/or PPM1F. In some embodiments, one or more of the donor, the subject, and/or the cells therefrom can be treated with the RNAi(s) and/or small molecule PAX5/PP1F inhibitors prior to the exposure of the patient cell to the intermediate cell. For instance, in some embodiments, any one of the donor cell, the subject cell, the intermediate cell, or the target cell, can be treated with the RNAi(s). In some embodiments, any one of the donor, the subject, or the patient can be administered small molecule PAX5/PP1F inhibitors prior to cell harvesting.

ENUMERATED EMBODIMENTS

The following provide exemplary illustrative enumerated embodiments:

1. A method of reducing expression of a paired box 5 (PAX5) gene and reducing expression of a protein phosphatase 1F enzyme (PPM1F) gene in a cell, the method comprising: contacting the cell with one or more interfering RNA(s) (RNAi(s)) comprising one or more of SEQ ID NO:15, SEQ ID NO:16, SEQ ID NO:17, SEQ ID NO:18, SEQ ID NO:19, SEQ ID NO:20; and maintaining the cell for a time sufficient to obtain inhibition of the PAX5 gene and the PPM1F gene, thereby reducing expression of the PAX5 gene and the PPM1F gene in that cell to provide a target cell.

2. The method of embodiment 1, wherein the one or more RNAi(s) comprises SEQ ID NO:15.

3. The method of embodiment 1 or 2, wherein the one or more RNAi(s) comprises at least one of SEQ ID NO:15, SEQ ID NO:17, and SEQ ID NO:19.

4. The method of any one of embodiments 1 to 3, wherein the one or more RNAi(s) comprises at least one of SEQ ID NO:16, SEQ ID NO:18, and SEQ ID NO:20.

5. The method of any one of embodiments 1 to 4, wherein the one or more RNAi(s) further comprises at least one of SEQ ID NO:9, SEQ ID NO:10, SEQ ID NO:11, SEQ ID NO:12, SEQ ID NO:13, and SEQ ID NO:14.

6. The method of any one of embodiments 1 to 5, wherein the cell is isolated from a subject.

7. The method of any one of embodiments 1 to 6, wherein the cell is inside a subject.

8. The method of any one of embodiments 1 to 7, wherein the cell is a human cell.

9. The method of any one of embodiments 1 to 8, wherein the PAX5 expression is reduced by at least about 30%, 40%, 50%, 60%, 70%, 80%, 90%, 95%, 98%, 99%, or 99.9%.

10. The method of any one of embodiments 1 to 9, wherein the PAX5 expression is reduced by at least about 70%.

11. The method of any one of embodiments 1 to 10, wherein the PPM1F expression is reduced by at least about 30%, 40%, 50%, 60%, 70%, 80%, 90%, 95%, 98%, 99%, or 99.9%.

12. The method of any one of embodiments 1 to 11, wherein the PPM1F expression is reduced by at least about 70%.

13. The method of any one of embodiments 1 to 12, wherein the cell is contacted with the one or more RNAi(s) for a period of equal to or at least about 16 hours, 48 hours, or 72 hours.

14. A target cell made by the method of any one of embodiments 1 to 13.

15. The target cell of embodiment 14, wherein the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

16. A composition for reducing expression of a PAX5 gene and reducing the expression of a PPM1F gene, the composition comprising an acceptable carrier and an RNAi that is at least 80% to 100% identical to SEQ ID NO:15.

17. The composition of embodiment 16, further comprising a microRNA that is at least 80% to 100% identical to SEQ ID NO:16.

18. The composition of embodiment 16 or 17, further comprising a microRNA that is at least 80% to 100% identical to SEQ ID NO:17.

19. The composition of any one of embodiments 16 to 18, further comprising a microRNA that is at least 80% to 100% identical to SEQ ID NO:18.

20. The composition of any one of embodiments 16 to 19, further comprising a microRNA that is at least 80% to 100% identical to SEQ ID NO:19.

21. The composition of any one of embodiments 16 to 20, further comprising a microRNA that is at least 80% to 100% identical to SEQ ID NO:20.

22. A method of treating a subject having a disease or disorder that would benefit from reduction in expression of a PAX5 gene and a reduction in expression of a PPM1F gene, the method comprising administering to the subject a therapeutically effective amount of the target cell of any one of embodiments 1 to 15 or the composition of any one of embodiments 16 to 21, thereby treating the subject.

23. An interfering RNA (RNAi) for reducing the expression of a paired box 5 (PAX5) gene, wherein the RNAi comprises 4 to 50 contiguous nucleotides having a polynucleotide sequence that is at least 80% to 100% complementary to a region of SEQ ID NO:1.

24. The RNAi of embodiment 23, wherein the RNAi is a short interfering RNA (siRNA), microRNA (miRNA), circular RNAs (circRNAs), short hairpin RNAs (shRNAs), long non-coding RNAs (lncRNAs); piwi-interacting RNAs (piRNA), small nucleolar RNA (snoRNAs), tRNA-derived small RNA (tsRNA), small rDNA-derived RNA (srRNA), or a small nuclear RNA (U-RNA).

25. The RNAi of embodiment 23, wherein the RNAi is an siRNA.

26. The RNAi of any one of embodiments 23 to 25, wherein the RNAi hybridizes to the complimentary region of SEQ ID NO: 1.

27. The RNAi of embodiment any one of embodiments 23 to 26, wherein the RNAi comprises about 20 to 30 contiguous nucleotides.

28. The RNAi of any one of embodiments 23 to 27, wherein the RNAi is at least 80% to 100% identical to the nucleotide sequence of SEQ ID NO:9.

29. The RNAi of any one of embodiments 23 to 27, wherein the RNAi is at least 80% to 100% identical to the nucleotide sequence of SEQ ID NO: 10.

30. The RNAi of any one of embodiments 23 to 27, wherein the RNAi is at least 80% to 100% identical to the nucleotide sequence of SEQ ID NO:11.

31. A composition for reducing expression of a PAX5 gene comprising the RNAi of any one of embodiments 23 to 30.

32. The composition of embodiment 31, wherein the composition comprises two or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, or SEQ ID NO:20.

33. The composition of embodiment 31 or 32, further comprising a pharmaceutically acceptable carrier.

34. A method of reducing expression of a PAX5 gene in a cell, the method comprising:
 contacting the cell with the RNAi of any one of embodiments 1 to 30 or the composition of any one of embodiments 31 to 33; and
 maintaining the cell for a time sufficient to obtain inhibition of the PAX5 gene, thereby reducing expression of the PAX5 gene in the cell.

35. The method of embodiment 34, wherein the cell is isolated from or is inside a subject.

36. The method of embodiment 35, wherein the subject is a human.

37. The method of any one of embodiments 34 to 36, wherein the PAX5 expression is reduced by at least about 30%, 40%, 50%, 60%, 70%, 80%, 90%, 95%, 98%, 99%, or 99.9%.

38. The method of any one of embodiments 34 to 36, wherein the PAX5 expression is reduced by at least about 70%.

39. The method of any one of embodiments 34 to 38, wherein the cell is contacted with the RNAi for a period of equal to or at least about 16 hours, 48 hours, or 72 hours.

40. A cell made by the method any one of embodiments 34 to 39.

41. The target cell of embodiment 40, wherein the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

42. A method of treating a subject having a disease or disorder that would benefit from reduction in expression of a PAX5 gene, the method comprising administering to the subject a therapeutically effective amount of cells that have been treated with the RNAi of any one of embodiments 1 to 30 or the composition of any one of embodiments 31 to 33, thereby treating the subject.

43. An RNAi for reducing the expression of a protein phosphatase 1F enzyme (PPM1F) gene, wherein the RNAi comprises 4 to 50 contiguous nucleotides having a polynucleotide sequence that is at least 80% to 100% complementary to a region of SEQ ID NO:5.

44. The RNAi of embodiment 43, wherein the interfering RNA is a short interfering RNA (siRNA).

45. The RNAi of embodiment 43 or 44, wherein the RNAi hybridizes to the complimentary region of SEQ ID NO: 1.

46. The RNAi of any one of embodiments 43 to 45, wherein the RNAi comprises about 20 to 30 contiguous nucleotides.

47. The RNAi of any one of embodiments 43 to 46, wherein the RNAi is at least 80% to 100% identical to the nucleotide sequence of SEQ ID NO: 12.

48. The RNAi of any one of embodiments 43 to 46, wherein the RNAi is at least 80% to 100% identical to the nucleotide sequence of SEQ ID NO:13.

49. The RNAi of any one of embodiments 43 to 46, wherein the RNAi is at least 80% to 100% identical to the nucleotide sequence of SEQ ID NO: 14.

50. A composition for reducing expression of a PPM1F gene comprising the RNAi of any one of embodiments 43 to 49.

51. The composition of embodiment 50, wherein the composition comprises two or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

52. The composition of embodiment 50 or 51, further comprising a pharmaceutically acceptable carrier.

53. The composition of embodiment 52, wherein the pharmaceutically acceptable carrier comprises one or more 54. A method of reducing expression of a PPM1F gene in a cell, the method comprising: contacting the cell with the RNAi of any one of embodiments 43 to 49 or the composition of any one of embodiments 50 to 52; and maintaining the cell for a time sufficient to obtain inhibition of the PPM1F gene, thereby reducing expression of the PPM1F gene in the cell.

55. The method of embodiment 54, wherein the cell is isolated from or is inside a subject.

56. The method of embodiment 55, wherein the subject is a human.

57. The method of any one of embodiments 52 to 56, wherein the PPM1F expression is reduced by at least about 30%, 40%, 50%, 60%, 70%, 80%, 90%, 95%, 98%, 99%, or 99.9%.

58. A cell made by the method any one of embodiments 54 to 57.

59. The target cell of embodiment 58, wherein the target cell is non-senescent or has decreased senescent behavior, has increased innate immune function, increased telomere length, lower replicative stress relative to the patient cell, increased stem cell clonogenicity, increased cytotoxic function, increased mitogen- and antigen-induced lymphocyte proliferation and activation, decreased myeloid to lymphoid ratio, increased CD4 to CD8 T lymphocyte ratio, decreased expression of senescence-associated secretory proteins, and/or decreased expression of senescence- and aging-related genes.

60. A method of treating a subject having a disease or disorder that would benefit from reduction in expression of a PPM1F gene, the method comprising administering to the subject a therapeutically effective amount of cells that have been treated with the RNAi of any one of embodiments 43 to 49 or the composition of any one of embodiments 50 to 52, thereby treating the subject.

61. A method for treating or preventing a disease state, comprising administering to a patient in need thereof a therapeutically effective dose of cells treated with one or more RNAi(s) of a PAX5 gene and/or of a PPM1F gene.

62. The method of embodiment 61, wherein the one or more RNAi(s) is selected from any one or more of the RNA is as recited in any one of the preceding embodiments.

63. The method of embodiment 61 or 62, wherein the disease state is an age related dysfunction.

64. The method of any one of embodiments 61 to 63, wherein the disease state comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

65. A method for preparing a target cell comprising: obtaining cells from a subject to provide at least one subject cell; exposing the at least one subject cell to one or more RNA is as recited in any one of the preceding embodiments to provide at least one target cell.

66. The method of embodiment 65, wherein the at least one target cell is member of a population of cells comprising equal to or at least about 100, 1000, 10,000, 100,000, 1,000,000, or 10,000,000 cells.

67. A method for treating or preventing cellular dysfunction in a patient, comprising administering to a patient in need thereof a therapeutically effective dose of the target cell of embodiment 65 or 66.

68. The method of embodiment 67, wherein the cellular dysfunction is an age-related dysfunction.

69. A cell made by the method of 65 or 66.

70. An interfering RNA (RNAi) for reducing the expression of a paired any one of the CAMK2G/CAMK-II, PAK, C21orf62-AS1, CASP14, CATSPER2, DNAH100S, ELMOD1, GALNT6, HEPN1, LANCL2, LL22NC03-63E9.3, PPTC7, PROSC, RAB3B, RRP7A, SERF1A/SERF1B, SLC35E3, SMIM10, SPRY3, SUMO2, TPP1, TPPP, WBP1L, ZNF33A, or ZNF549 gene, wherein the RNAi comprises 4 to 50 contiguous nucleotides having a polynucleotide sequence that is at least 80% to 100% complementary to a region of any one or more of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

71. A method of reducing expression of a paired box 5 (PAX5) gene in a cell, the method comprising: contacting the cell with one or more interfering RNA(s) (RNAi(s)) wherein the one or more RNAi(s) comprises one or more of SEQ ID NO:9, SEQ ID NO:10, SEQ ID NO:11, SEQ ID NO:15, SEQ ID NO:16, SEQ ID NO:17, SEQ ID NO:18, SEQ ID NO:19, SEQ ID NO:20; and maintaining the cell for a time sufficient to obtain inhibition of the PAX5 gene, thereby reducing expression of the PAX5 gene in that cell to provide a target cell.

72. The method of embodiment 71, wherein the one or more RNAi(s) comprises at least one of SEQ ID NO:9, SEQ ID NO:10, and SEQ ID NO:11.

73. The method of embodiment 71, wherein the one or more RNAi(s) comprises at least one of SEQ ID NO:15, SEQ ID NO:17, and SEQ ID NO:19.

74. The method of embodiment 71, wherein the one or more RNAi(s) comprises at least one of SEQ ID NO:16, SEQ ID NO:18, and SEQ ID NO:20.

75. The method of embodiment 71, wherein the cell is isolated from a subject or is inside the subject.

76. The method of embodiment 75, wherein the subject is a human.

77. The method of embodiment 71, wherein the PAX5 expression is reduced by at least about 30%, 40%, 50%, 60%, 70%, 80%, 90%, 95%, 98%, 99%, or 99.9%.

78. The method of embodiment 71, wherein the PAX5 expression is reduced by at least about 70%.

79. The method of embodiment 71, wherein the cell is contacted with the one or more RNAi(s) for a period of equal to or at least about 16 hours, 48 hours, or 72 hours.

80. A target cell made by the method embodiment 71.

81. The target cell of embodiment 80, wherein the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

82. A method of treating a subject having a disease or disorder that would benefit from reduction in expression of a PAX5 gene, the method comprising administering to the subject a therapeutically effective amount of one or more RNAi(s) selected from the group consisting of SEQ ID NO:9, SEQ ID NO:10, SEQ ID NO:11, SEQ ID NO:15, SEQ ID NO:16, SEQ ID NO:17, SEQ ID NO:18, SEQ ID NO:19, and SEQ ID NO:20 or a therapeutically effective amount of cells that have been treated with the one or more RNAi(s), thereby treating the subject.

83. A method of reducing expression of a protein phosphatase 1F enzyme (PPM1F) gene in a cell, the method comprising: contacting the cell with one or more interfering RNA(s) (RNAi(s)) wherein the one or more RNAi(s) comprises one or more of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20; and maintaining the cell for a time sufficient to obtain inhibition of the PAX5 gene, thereby reducing expression of the PAX5 gene in that cell to provide a target cell.

84. The method of embodiment 83, wherein the one or more RNAi(s) comprises at least one of SEQ ID NO:12, SEQ ID NO:13, and SEQ ID NO:14.

85. The method of embodiment 83, wherein the one or more RNAi(s) comprises at least one of SEQ ID NO:15, SEQ ID NO:17, and SEQ ID NO:19.

86. The method of embodiment 83, wherein the one or more RNAi(s) comprises at least one of SEQ ID NO:16, SEQ ID NO:18, and SEQ ID NO:20.

87. The method of embodiment 83, wherein the cell is isolated from a subject or is inside the subject.

88. The method of embodiment 87, wherein the subject is a human.

89. The method of embodiment 83, wherein the PPM1F expression is reduced by at least about 30%, 40%, 50%, 60%, 70%, 80%, 90%, 95%, 98%, 99%, or 99.9%.

90. The method of embodiment 83, wherein the PPM1F expression is reduced by at least about 70%.

91. The method of embodiment 83, wherein the cell is contacted with the one or more RNAi(s) for a period of equal to or at least about 16 hours, 48 hours, or 72 hours.

92. A target cell made by the method embodiment 83.

93. The target cell of embodiment 92, wherein the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

94. A method of treating a subject having a disease or disorder that would benefit from reduction in expression of a PPM1F gene, the method comprising administering to the subject a therapeutically effective amount of one or more RNAi(s) selected from the group consisting of SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 or a therapeutically effective amount of cells that have been treated with the one or more RNAi(s), thereby treating the subject.

95. A method for reducing the expression of a PAX5 gene, comprising exposing a cell to a composition comprising at least one isolated microRNA, wherein the at least one microRNA is at least 80% to 100% identical to SEQ ID NO:15.

96. A method for reducing the expression of a PAX5 gene, comprising exposing a cell to a composition comprising at least one isolated microRNA, wherein the at least one microRNA is at least 80% to 100% identical to SEQ ID NO:16.

97. The method of embodiment 95 or 96, wherein the composition comprises both SEQ ID NO: 15 and SEQ ID NO: 16.

98. The method of any one of embodiments 95 to 97, wherein the composition further comprises a microRNA that is at least 80% to 100% identical to SEQ ID NO:17.

99. The method of any one of embodiments 95 to 98, wherein the composition further comprises a microRNA that is at least 80% to 100% identical to SEQ ID NO:18.

100. The method of any one of embodiments 95 to 99, wherein the composition further comprises a microRNA that is at least 80% to 100% identical to SEQ ID NO:19.

101. The method of any one of embodiments 95 to 100, wherein the composition further comprises a microRNA that is at least 80% to 100% identical to SEQ ID NO:20.

102. A composition for reducing expression of a PAX5 gene comprising an acceptable carrier and at least one isolated microRNA that is at least 80% to 100% identical to SEQ ID NO:15.

103. The composition of embodiment 102, further comprising a microRNA that is at least 80% to 100% identical to SEQ ID NO:16.

104. The composition of embodiment 102 or 103, further comprising a microRNA that is at least 80% to 100% identical to SEQ ID NO:17.

105. The composition of any one of embodiments 102 to 104, further comprising a microRNA that is at least 80% to 100% identical to SEQ ID NO:18.

106. The composition of any one of embodiments 102 to 105, further comprising a microRNA that is at least 80% to 100% identical to SEQ ID NO:19.

107. The composition of any one of embodiments 102 to 106, further comprising a microRNA that is at least 80% to 100% identical to SEQ ID NO:20.

108. A method of reducing expression of a PAX5 gene in a cell, the method comprising: contacting the cell with the composition of any one of embodiments 102 to 104; and maintaining the cell for a time sufficient to obtain inhibition of a PAX5 gene, thereby reducing expression of the PAX5 gene in the cell.

109. The method of embodiment 108, wherein the cell is isolated from a subject.

110. The method of embodiment 109, wherein the subject is a human.

111. The method of any one of embodiments 108 to 110, wherein the PAX5 expression is reduced by at least about 30%, 40%, 50%, 60%, 70%, 80%, 90%, 95%, 98%, 99%, or 99.9%.

112. A method of treating a subject having a disease or disorder that would benefit from reduction in expression of a PAX5 gene, the method comprising administering to the subject a therapeutically effective amount of cells treated with the composition of any one of embodiments 102 to 104, thereby treating the subject.

113. The method of embodiment 112, wherein the disease or disorder comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

114. A method for reducing the expression of a PPM1F gene, comprising exposing a cell to a composition comprising at least one isolated microRNA, wherein the at least one microRNA is at least 80% to 100% identical to SEQ ID NO:15.

115. The method of embodiment 114, wherein the composition further comprises a microRNA that is at least 80% to 100% identical to SEQ ID NO:16.

116. The method of embodiment 114 or 115, wherein the composition further comprises a microRNA that is at least 80% to 100% identical to SEQ ID NO:17.

117. The method of any one of embodiments 114 to 116, wherein the composition further comprises a microRNA that is at least 80% to 100% identical to SEQ ID NO:18.

118. The method of any one of embodiments 114 to 117, wherein the composition further comprises a microRNA that is at least 80% to 100% identical to SEQ ID NO:19.

119. The method of any one of embodiments 114 to 118, wherein the composition further comprises a microRNA that is at least 80% to 100% identical to SEQ ID NO:20.

120. A composition for reducing expression of a PPM1F gene comprising an acceptable carrier and at least one isolated microRNA that is at least 80% to 100% identical to SEQ ID NO:15.

121. The composition of embodiment 120, wherein the composition further comprises a microRNA that is at least 80% to 100% identical to SEQ ID NO:16.

122. The composition of embodiment 120 or 121, wherein the composition further comprises a microRNA that is at least 80% to 100% identical to SEQ ID NO:17.

123. The composition of any one of embodiments 120 to 122, wherein the composition further comprises a microRNA that is at least 80% to 100% identical to SEQ ID NO:18.

124. The composition of any one of embodiments 120 to 123, wherein the composition further comprises a microRNA that is at least 80% to 100% identical to SEQ ID NO:19.

125. The composition of any one of embodiments 120 to 124, wherein the composition further comprises a microRNA that is at least 80% to 100% identical to SEQ ID NO:20.

126. A method of reducing expression of a PPM1F gene in a cell, the method comprising: contacting the cell with the composition of any one of embodiments 120 to 125; and maintaining the cell for a time sufficient to obtain inhibition of a PPM1F gene, thereby reducing expression of the PPM1F gene in the cell.

127. The method of embodiment 126, wherein the cell is isolated from a subject.

128. The method of embodiment 127, wherein the subject is a human.

129. The method of any one of embodiments 126 to 128, wherein the PPM1F expression is reduced by at least about 30%, 40%, 50%, 60%, 70%, 80%, 90%, 95%, 98%, 99%, or 99.9%.

130. A method of treating a subject having a disease or disorder that would benefit from reduction in expression of a PPM1F gene, the method comprising administering to the subject a therapeutically effective amount of the composition of any one of embodiments 120 to 125, thereby treating the subject.

131. The method of embodiment 130, wherein the disease or disorder comprises one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

132. A method of treating a subject having a disease or disorder that would benefit from reduction in expression of a PAX5 gene and a reduction in expression of the PPM1F gene, the method comprising administering to the subject a therapeutically effective amount of the composition of any one of embodiments 102 to 107 and/or of any one of embodiments 120 to 125, thereby treating the subject.

133. The method of embodiment 132, wherein the subject is suffering from one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

134. A method for preparing a target cell comprising: obtaining cells from a subject to provide at least one subject cell; exposing the at least one subject cell to miRNA including one or more SEQ ID NOS:10-12 to provide at least one target cell.

135. The method of embodiment 134, wherein the at least one target cell is member of a population of cells comprising equal to or at least about 100, 1000, or 10,000 cells.

136. A method for treating or preventing cellular dysfunction in a patient, comprising administering to a patient in need thereof a therapeutically effective dose of the target cell of embodiment 134 or 135.

137. The method of embodiment 136, wherein the cellular dysfunction is an age related dysfunction.

138. The method of embodiment 136 or 137, wherein the cellular dysfunction one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, Alzheimer's disease, leukemia, lymphoma, multiple sclerosis, Crohn's disease, HIV, influenza, pneumonia, lung cancer, melanoma, stroke, Parkinson's disease, and multiple drug resistant *Staphylococcus aureus* (MRSA).

139. An miRNA for reducing the expression of PAX5 gene, wherein the miRNA comprises 4 to 50 contiguous nucleotides having a polynucleotide sequence that is at least 80% to 100% complementary to a region of SEQ ID NO:1.

140. An miRNA for reducing the expression of a PPM1F, wherein the miRNA comprises 4 to 50 contiguous nucleotides having a polynucleotide sequence that is at least 80% to 100% complementary to a region of SEQ ID NO:5.

141. A method for treating or preventing age related dysfunction, comprising administering to a patient in need thereof a therapeutically effective dose of one or more polycyclic aromatic compounds that antagonize or reduce the expression of PAX5 and/or PPM1F.

142. The method of embodiment 141, wherein the polycyclic compound is of formula I:

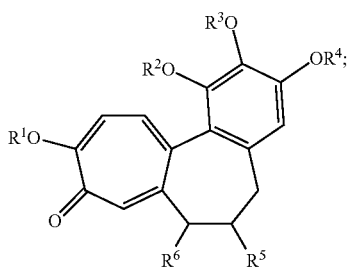

Formula I wherein each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether-having 1 to 6 repeat units.

143. The method of embodiment 142, wherein each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, and a —$(OR_B—)_oOH$, where $R_B$ is an optionally substituted $C_1$ to $C_6$ alkyl.

144. The method of embodiment 141, wherein the polycyclic compound is of formula II:

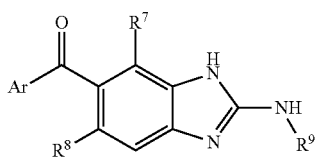

Formula II wherein each of $R_7$, $R_8$, and $R_9$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units.

145. The method of embodiment 144, wherein each of $R_7$, $R_8$, and $R_9$ is independently selected from —H, hydroxyl, halogen, $C_1$ to $C_6$ alkyl optionally substituted with halogen or hydroxy, and a —$(OR_B—)_oOH$, where $R_B$ is an optionally substituted $C_1$ to $C_6$ alkyl.

146. The method of embodiment 141, wherein the polycyclic compound is of formula III:

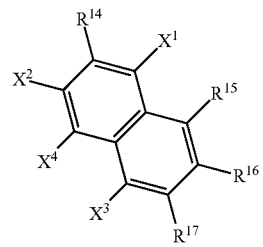

Formula III wherein each of $X_1$, $X_2$, $X_3$, $X_4$ is independently selected from —H, hydroxyl, halogen, —$NH_2$, optionally substituted —$SO_2OR_{18}$;

each of $R_{14}$, $R_{15}$, $R_{16}$, $R_{17}$, and $R_{18}$ is independently selected from —H, hydroxyl, halogen, —$NH_2$, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units.

147. The method of embodiment 146, wherein $R_{14}$, $R_{15}$, $R_{16}$, $R_{17}$, and $R_{18}$ are independently selected from —H, hydroxyl, halogen, $C_1$ to $C_6$ alkyl optionally substituted with halogen or hydroxy, and a —$(OR_B—)_oOH$, where $R_B$ is an optionally substituted $C_1$ to $C_6$ alkyl.

148. The method of embodiment 146, wherein the compound of formula III is represented by the following structure:

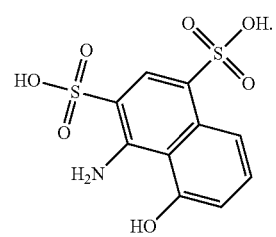 [SMILES: Nc1c(S(=O)(=O)O)cc(S(=O)(=O)O)c2cccc(O)c12]

149. The method of embodiment 141, wherein the polycyclic compound is selected from the group consisting of:

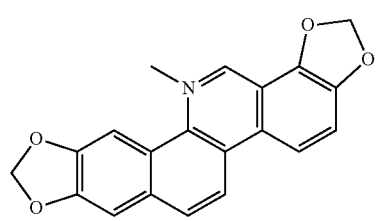

121
-continued

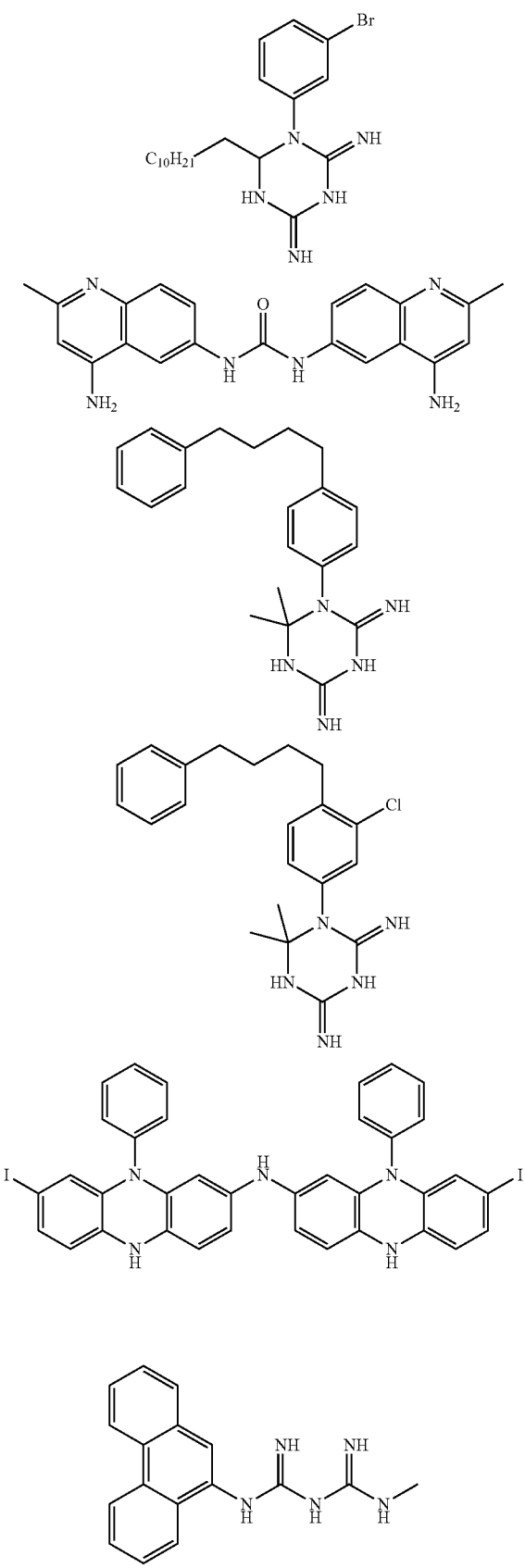

122
-continued

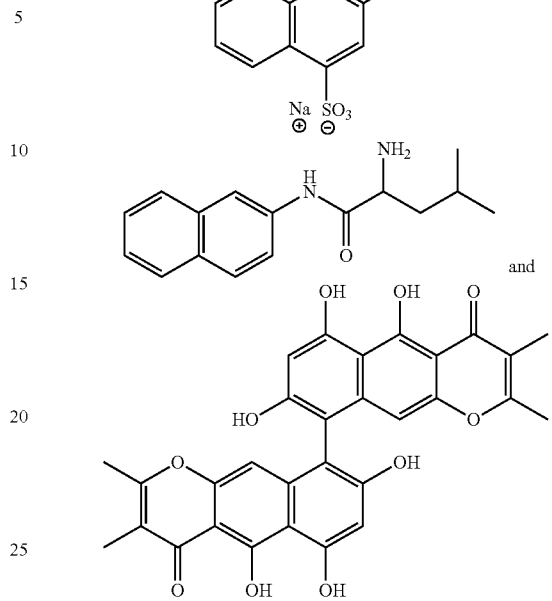

150. The method of any one of embodiments 141 to 149, wherein the polycyclic compound is provided as a pharmaceutically acceptable salt.

151. A pharmaceutical composition comprising a polycyclic aromatic compound as recited in any one of embodiments 141 to 150 and a pharmaceutically acceptable carrier.

152. A method of preparing at least one cell, the method comprising: providing at least one donor cell from a donor; providing at least one subject cell from a subject; providing at least one patient cell from a patient; exposing the subject cell to the donor cell to provide at least one intermediate cell; and exposing the patient cell to the intermediate cell to provide a target cell.

153. The method of embodiment 152, wherein exposing the subject cell to the donor cell comprises co-incubating the subject cell and the donor cell.

154. The method of embodiment 152 or 153, wherein exposing the intermediate cell to the patient cell comprises co-incubating the intermediate cell and the patient cell.

155. The method of any one of embodiments 152 to 154, wherein the subject cell is exposed to the donor cell for a time sufficient for cellular material from the donor cell to interact with the subject cell, thereby providing the intermediate cell.

156. The method of any one of embodiments 152 to 155, wherein the patient cell is exposed to the intermediate cell for a time sufficient for cellular material from the intermediate cell to interact with the patient cell, thereby providing the target cell.

157. The method of any one of embodiments 152 to 156, wherein each of the subject and the patient is older than the donor.

158. The method of any one of embodiments 152 to 157, wherein the donor cell is a cell mobilized from blood from the donor.

159. The method of any one of embodiments 152 to 158, wherein the subject cell is a cell mobilized from blood from the subject.

160. The method of any one of embodiments 152 to 159, wherein the patient cell is a cell that is mobilized from blood from the patient.

161. The method of any one of embodiments 158 to 160, further comprising administering a mobilizing agent to one or more of the donor, the subject, and the patient, wherein the mobilizing agent is an organic molecule, synthetic or naturally derived, or a polypeptide, such as a growth factor or colony-stimulating factor or an active fragment or mimic thereof, a nucleic acid, a carbohydrate, an antibody, or another agent that acts to enhance migration of stem cells from bone marrow to peripheral blood.

162. The method of any one of embodiments 152 to 161, wherein one or more of the donor cell, the subject cell, and/or the patient cell are harvested directly from the bone marrow of the donor, the subject, and/or the patient.

163. The method of any one of embodiments 152 to 162, wherein the subject is the patient.

164. The method of any one of embodiments 152 to 163, wherein the donor is the patient at an earlier age.

165. The method of any one of embodiments 152 to 164, wherein the target cell is provided in a formulation or culture suitable for administration to the patient to provide a therapeutic effect to the patient.

166. The method of any one of embodiments 152 to 165, wherein the at least one donor cell is member of a population of cells comprising equal to or at least about 10,000, 1,000,000, 10,000,000 cells.

167. The method of any one of embodiments 152 to 166, wherein the at least one subject cell is member of a population of cells comprising equal to or at least about 10,000, 1,000,000, 10,000,000 cells.

168. The method of any one of embodiments 152 to 167, wherein the at least one intermediate cell is member of a population of cells comprising equal to or at least about 10,000, 1,000,000, 10,000,000 cells.

169. The method of any one of embodiments 152 to 168, wherein the at least one target cell is member of a population of cells comprising equal to or at least about 10,000, 1,000,000, 10,000,000 cells.

170. The method of any one of embodiments 166 to 169, wherein one or more of the population of cells comprising the at least one donor cell, the population of cells comprising the at least one subject cell, the population of cells comprising the at least one intermediate cell, and/or the population of cells comprising the at least one target cell comprises one or more non-hematopoietic cells, mesenchymal stem cells, endothelial progenitor cells, hematopoietic stem cells, primitive hematopoietic stem cells, hematopoietic progenitor cells, differentiated hematopoietic cells, T-lymphocytes, natural killer cells, or combinations thereof.

171. A target cell made by the method any one of embodiments 152 to 170.

172. The target cell of embodiment 171, wherein the target cell is non-senescent or has decreased senescent behavior, has increased innate immune function, increased telomere length, lower replicative stress relative to the patient cell, increased stem cell clonogenicity, increased cytotoxic function, increased mitogen- and antigen-induced lymphocyte proliferation and activation, decreased myeloid to lymphoid ratio, increased CD4 to CD8 T lymphocyte ratio, decreased expression of senescence-associated secretory proteins, and/or decreased expression of senescence- and aging-related genes.

173. A composition comprising a population of cells comprising the target cell of any one of embodiments 152 to 172.

174. The composition of embodiment 173, wherein the composition comprises a pharmaceutically acceptable carrier.

175. The composition of embodiment 174, wherein the pharmaceutically acceptable carrier comprises one or more of an aqueous solution, cell culture media, or an aqueous buffered solution.

176. The composition of embodiment 174, wherein the pharmaceutically acceptable carrier comprises an aqueous solution of sodium chloride.

177. The composition of embodiment 176, wherein the pharmaceutically acceptable carrier further comprises human serum albumin.

178. The composition of embodiment 177, wherein the sodium chloride is present at about 0.9% by weight and/or wherein the human serum albumin is present at about 0.5% by weight.

179. A method for treating or preventing age-related dysfunction, comprising administering the target cell of any one of embodiments 152 to 171 or the composition of any one of embodiments 173 to 178 to the patient.

180. The method of embodiment 179, wherein the dysfunction is age-related dysfunction.

181. The method of embodiment 179 or 180, wherein the dysfunction includes one or more of arthritis, atherosclerosis, breast cancer, cardiovascular disease, cataracts, chronic obstructive pulmonary disease, colorectal cancer, hypertension, osteoporosis, periodontitis, type 2 diabetes, immune dysfunction, and Alzheimer's disease, leukemia, lymphoma, multiple sclerosis, Crohn's disease, HIV, influenza, pneumonia, lung cancer, melanoma, stroke, Parkinson's disease, multiple drug resistant Staphylococcus aureus (MRSA).

182. A method of reducing expression of a paired box 5 (PAX5) gene or reducing expression of a protein phosphatase 1F enzyme (PPM1F) gene in a cell, the method comprising: contacting a cell with one or more interfering RNAs (RNAi(s)) wherein the RNAi(s) comprises: one or more sequences comprising 4 to 50 contiguous nucleotides of a polynucleotide sequence that is at least 80% to 100% complementary to a region of SEQ ID NO:1, one or more sequences comprising a polynucleotide sequence that is at least 80% to 100% complementary to a region of SEQ ID NO:5, and/or one or more sequences comprising a polynucleotide sequence that is at least 80% to 100% identical to one or more of SEQ ID Nos: 9-20; and maintaining the cell for a time sufficient to obtain inhibition of the PAX5 gene or the PPM1F gene, thereby reducing expression of a PAX5 gene or a PPM1F gene in that cell to provide a target cell.

183. The method of embodiment 182, wherein the one or more RNAi(s) comprises at least one small interfering RNA (siRNA).

184. The method of embodiment 182 or 183, wherein the one or more RNAi(s) comprises at least one microRNA (miRNA).

185. The method of any one of embodiments 182 to 184, wherein the one or more RNAi(s) comprises at least one short hairpin RNA (shRNA).

186. The method of any one of embodiments 182 to 185, wherein the one or more RNAi(s) comprises SEQ ID NO:9.

187. The method of any one of embodiments 182 to 186, wherein the one or more RNAi(s) comprises SEQ ID NO:10.

188. The method of any one of embodiments 182 to 187, wherein the one or more RNAi(s) comprises SEQ ID NO: 11.

189. The method of any one of embodiments 182 to 188, wherein the one or more RNAi(s) comprises SEQ ID NO:12.

190. The method of any one of embodiments 182 to 189, wherein the one or more RNAi(s) comprises SEQ ID NO:13.

191. The method of any one of embodiments 182 to 190, wherein the one or more RNAi(s) comprises SEQ ID NO:14.

192. The method of any one of embodiments 182 to 191, wherein the one or more RNAi(s) comprises SEQ ID NO:15.

193. The method of any one of embodiments 182 to 192, wherein the one or more RNAi(s) comprises SEQ ID NO:16.

194. The method of any one of embodiments 182 to 193, wherein the one or more RNAi(s) comprises SEQ ID NO:17.

195. The method of any one of embodiments 182 to 194, wherein the one or more RNAi(s) comprises SEQ ID NO:18.

196. The method of any one of embodiments 182 to 195, wherein the one or more RNAi(s) comprises SEQ ID NO:19.

197. The method of any one of embodiments 182 to 197, wherein the one or more RNAi(s) comprises SEQ ID NO:20.

198. The method of any one of embodiments 182 to 197, wherein the cell is a human cell.

199. The method of any one of embodiments 182 to 198, wherein the PAX5 expression is reduced by at least about 70% or wherein the PPM1F expression by at least about 70%.

200. The method of any one of embodiments 182 to 199, wherein the cell is contacted with the one or more RNAi(s) for a period of equal to or at least about 16 hours.

201. The method of any one of embodiments 182 to 200, wherein the target cell is non-senescent and/or has decreased senescent behavior, has increased innate immune function, increased telomere length, lower replicative stress relative to the patient cell, increased stem cell clonogenicity; increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

202. A composition comprising: a pharmaceutically acceptable excipient; and one or more interfering RNAs (RNAi(s)); wherein the RNAi(s) comprises one or more sequences comprising: 4 to 50 contiguous nucleotides with a polynucleotide sequence that is at least 80% to 100% complementary to a region of SEQ ID NO:1, one or more sequences comprising a polynucleotide sequence that is at least 80% to 100% complementary to a region of SEQ ID NO:5, and/or one or more sequences comprising a polynucleotide sequence that is at least 80% to 100% identical to one or more of SEQ ID Nos: 9-20; wherein the composition is configured to reduce an expression of a paired box 5 (PAX5) gene or an expression of a protein phosphatase 1F enzyme (PPM1F) gene in a cell.

203. A method for treating or preventing age related dysfunction, comprising administering to a patient in need thereof a therapeutically effective dose of one or more polycyclic aromatic compounds that: antagonize a PAX5 protein and/or antagonize PP1F protein or reduce an expression of a PAX5 gene and/or a PPM1F gene.

204. The method of embodiment 203, wherein the polycyclic compound is of formula I:

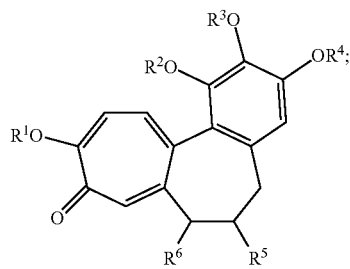

Formula I wherein each of $R_1$, $R_2$, $R_3$, $R_4$, $R_5$, and $R_6$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units.

205. The method of embodiment 203, wherein the polycyclic compound is of formula II:

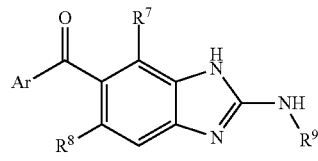

Formula II wherein each of $R_7$, $R_8$, and $R_9$ is independently selected from —H, hydroxyl, halogen, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether-having 1 to 6 repeat units.

206. The method of embodiment 203, wherein the polycyclic compound is of formula III:

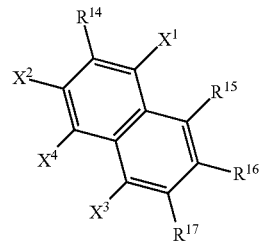

Formula III wherein each of $X_1$, $X_2$, $X_3$, $X_4$ is independently selected from —H, hydroxyl, halogen, —$NH_2$, optionally substituted —$SO_2OR_{18}$; each of $R_{14}$, $R_{15}$, $R_{16}$, $R_{17}$, and $R_{18}$ is independently selected from —H, hydroxyl, halogen, —$NH_2$, $C_1$ to $C_6$ alkyl optionally substituted with halogen or hydroxy, optionally substituted $C_1$ to $C_6$ alkenyl, optionally substituted $C_1$ to $C_6$ alkynyl, optionally substituted $C_1$ to $C_6$ alkoxy, optionally substituted $C_1$ to $C_6$ haloalkyl, optionally substituted $C_1$ to $C_6$ haloalkoxy, mono-substituted amine($C_1$ to $C_6$ alkyl optionally substituted), a di-substituted amine($C_1$ to $C_6$ alkyl optionally substituted), a diamino-group, and an optionally substituted polyether—having 1 to 6 repeat units.

207. The method of embodiment 203, wherein the polycyclic compound is selected from the group consisting of:

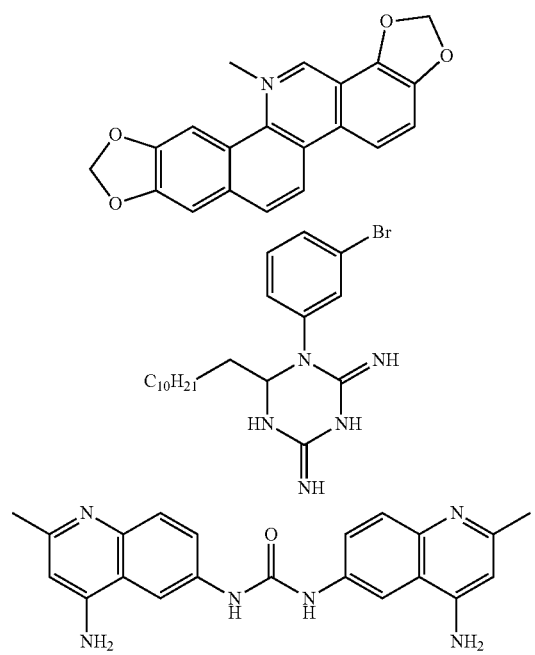

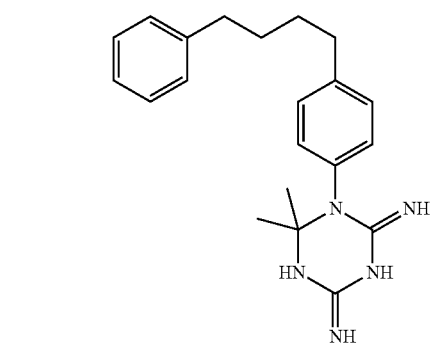

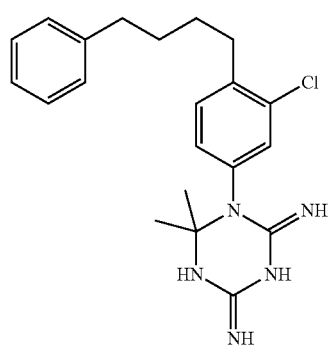

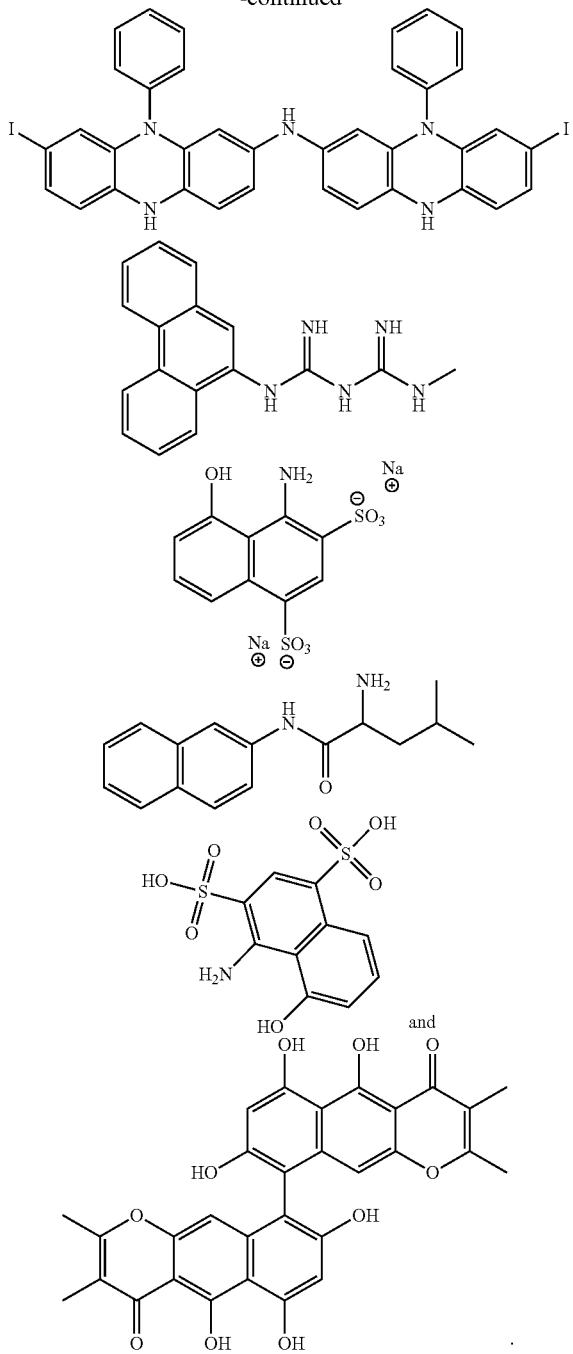

208. A method of preparing at least one cell, the method comprising: providing at least one donor cell from a donor; providing at least one subject cell from a subject; providing at least one patient cell from a patient; exposing the subject cell to the donor cell to provide at least one intermediate cell; and exposing the patient cell to the intermediate cell to provide a target cell.

209. The method of embodiment 208, wherein exposing the subject cell to the donor cell comprises co-incubating the subject cell and the donor cell; and wherein exposing the intermediate cell to the patient cell comprises co-incubating the intermediate cell and the patient cell.

210. The method of embodiment 208 or 209, wherein the subject cell is exposed to the donor cell for a time sufficient for cellular material from the donor cell to interact with the subject cell, thereby providing the intermediate cell; wherein the patient cell is exposed to the intermediate cell for a time sufficient for cellular material from the intermediate cell to interact with the patient cell, thereby providing the target cell.

211. The method of any one of embodiments 207 to 210, wherein the donor is the patient at an earlier age and the donor is the subject at an earlier age.

Examples

A variety of experiments are described below to illustrate various examples that may be employed to achieve one or more desired improvements. These examples are only illustrative and not intended in any way to restrict the general inventions presented and the various aspects and features of these inventions. Furthermore, the phraseology and terminology used herein is for the purpose of description and should not be regarded as limiting. No features, structure, or step disclosed herein is essential or indispensible.

Example 1: Novel microRNAs Improve Function of Aged and Defective Biological Systems
Overview Blood of healthy subjects (e.g., the blood of subjects that are younger or are generally healthier than particular patients) may compartmentalize pleiotropic factors that prevent age-associated tissue dysfunction or other dysfunction. The diminishing function of the hematopoietic and immune systems, for example, throughout an organism's lifetime as the organism ages, leads to compensatory increases in immune-related diseases, including cancer. While these dysfunctional processes can occur in the young and aged alike, for the purposes of this study, healthy aged individuals and young healthy individuals were used to determine the efficacy of using pleiotropic factors to improve dysfunctional cells. To this end, a heterochronic culture model was developed to target the declining function of hematopoietic stem (HSCs) and progenitor cells (HPCs) in aged patients, which allowed the study of various therapeutic factors (e.g., restorative factors) released from young blood cells. It was postulated that young adults (18-29 y/o) with healthy lifestyles could yield robust blood samples to identify factors that could restore and/or act as a therapeutic to aged or dysfunctional tissues and cells. To evaluate impairments related to, in this instance age, without co-morbidities, healthy aged donors (>60 y/o) were recruited. In other instances it is envisioned that the techniques disclosed herein could be used more generally with patients of any age that suffer dysfunction in part based on cellular factors. In this study, enrichment of HSCs, HPCs and stroma in donor blood samples was performed by granulocyte-colony stimulating factor (G-CSF)-mobilization (though other mobilization techniques are envisioned). Heterochronic cultures were established in a transwell system that allowed for exchange of soluble factors but no direct interaction of younger aged cells and aged cells. It was found that young paracrine factors induced increases in aged stem and progenitor clonogenicity, T cell activity and cell-mediated cytotoxicity. These findings were validated in humanized mice engrafted with an aged lymphohematopoietic system. Exploration of the restorative and/or therapeutic mechanism revealed a causal role for downstream targets in aged cells, PAX 5 and PPM1F and the interaction thereof with miRNAs from, for example, exosomes of younger subjects, including but not limited to miR-619-5p, miR-1303 and miR-4497. It was also determined that these systems could be targeted directly with one or more of these miRNAs to induce restoration without the need for heterochronic culture. Thus, in some embodiments, exploitation of miRNAs can provide an immunotherapy and/or therapeutic mechanism to restore and/or repair dysfunction in the patients (e.g., restoring or repairing an aging body's endogenous immune system and/or restoring or repairing a body's endogenous immune system where that system is dysfunctional). This therapeutic system was also demonstrated to have potential benefit in treating and/or preventing cancer.

INTRODUCTION

Aging is a highly complex biological process and the leading risk factor for the chronic diseases that account for the bulk of morbidity, mortality and health costs. Regrettably, there is no evidence to suggest that aging might be controlled by a single, hidden "master switch". Rather, the complexity of organismal aging is driven by cellular dysfunction at the macromolecular and/or organelle level, which ultimately leads to a decline in tissue function and the manifestation of disease.

As cells age (or otherwise become dysfunctional) they undergo epigenetic alterations that lead to dynamic changes in gene expression and increased likelihood of oncogenesis and cellular transformation. Cell entry into the non-proliferative, yet metabolically active, state of senescence serves a protective role to avert transformation. The frequency of senescent cells in the body increases as organisms age. Senescent cells exhibit a unique profile of enhanced secretory factor production, termed the senescent-associated secretory phenotype (SASP). Many of these factors are pro-inflammatory and/or tumor-supportive, thus cellular senescence is a fundamental aging mechanism tied to the progressive breakdown of tissue function with age. A new class of small molecule drugs, termed senolytics, may directly target senescent cells and lead to significant health span extension in mice. Lifespan extension in transgenic mice that selectively expressed suicide genes in senescent cells can also be accomplished. Physiologically, lifespan-extending effects may be observed for miRNAs, such as miR-17, that inhibit senescence signaling.

Interventions that attempt restoration of aging tissues have been researched for many years, often utilizing younger tissues as the source of restoration. This age-old concept has been documented as early as the 19th century in the form of animal graft experimentation. The first grafting experiments to study heterochronic parabiosis, which is the surgical suturing of two animals of different ages to enable development of a single, shared circulatory system between young and old, were carried out in the late 1950s and early 1960s. Several recent studies have revived the experimental procedure to demonstrate that the young circulatory system contains restorative factors that can rejuvenate aged tissues and cells. Further, other groups expanded on the heterochronic parabiosis model to show a role for systemic factors in the circulation of young parabionts that induce rejuvenation of cognitive, cardiac and skeletal muscle of the matched aged animal. While these factors were able to restore select tissue function, the infusion of young plasma and/or factors therefrom into aged animals have not been demonstrated to increase longevity, nor has its effects on the aged lymphohematopoietic system been explored.

Diminishing function of the aging lymphohematopoietic system leads to compensatory increases in immune-related diseases, including cancer. This system critically depends on adult hematopoietic stem cells (HSCs) throughout an organism's lifetime to generate progenitor cells and mature effector blood cells. The decline of HSCs and the adaptive immune response is a major source of morbidity and mortality, as decreased immune surveillance leads to increased incidence of cancer, infectious disease and immune-related disorders. Described herein is an approach to restore and/or repair the aging lymphohematopoietic system. The approach utilizes a cell culture adaptation of the heterochronic model to harness restorative factors from young blood that promote aged HSC function and reduce immune senescence.

Apheresis System using continuous flow centrifugal technology directly into the collection bag. Leukapheresis was performed according to the manufacturer's instructions to process 18 L of blood at a flow rate of 50 to 100 mL per min. Participants had only one mononuclear cells (MNC) collection performed immediately following mobilization. The product of 1 full MNC collection is referred to herein as a Leukopak. Mobilized MNC collections generally required 4 to 6 hours for completion, at which time cells were shipped to Rutgers for processing and biobanking. The research use of these cells followed a protocol approved by the institutional review board (IRB) of Rutgers Biomedical Health Sciences.

TABLE 4

Inclusion and Exclusion Criteria for Study Donors

| Aged Donor Inclusion Criteria | |
|---|---|
| ≥60 years old | Have adequate peripheral veins for apheresis |
| Healthy and feeling well | Review and sign an IRB- approved procedure- |
| BMI of 18.5-29 | specific consent form prior to the collection |
| Weigh at least 140 lbs | Fill out donor history questionnaire |
| Successful Leukopak donation | Non-smoker |
| Meet protocol specifications, i.e. CBC lab test | |
| Vaccination record current | |
| Aged Exclusion Criteria | |
| Current or recent (<30 days) illness | History of heart, lung, liver, kidney disease |
| Underweight (<18.5) or Obese (>29) BMI | Blood or bleeding disorders |
| Cannot be pregnant | Neurologic disorders |
| Prior cancer diagnosis | Diabetes |
| Previously mobilized | Autoimmune disorders |
| HIV, HPV, HBV or HCV positive test | |
| Young Inclusion Criteria | |
| 18-29 years old | Non-smoker |
| Healthy and feeling well | Between 5-15% body fat for men; 12.5-25% |
| Normal BMI (18.5-25) | body fat for women |
| Weigh at least 120 lbs | Healthy eating habits/diet with consumption of |
| Vaccination record current | fish 2x per week regularly |
| Successful Leukopak donation | Obtains 6-8 hours of sleep per night on a |
| Meet protocol specifications, i.e. CBC lab test | regular basis |
| At least 5 days/week of moderate to | Have adequate peripheral veins for apheresis |
| strenuous exercise (minimum of 30 min) | Review and sign an IRB- approved procedure- |
| Successful completion of physical | specific consent form prior to the collection |
| examination | Fill out Donor History Questionnaire |
| Young Exclusion Criteria | |
| Current or recent (<30 days) illness | Prior cancer diagnosis |
| Abnormal BMI (underweight, overweight, obese) | Previously mobilized |
| Diet consisting of fast food more than | HIV, HPV, HBV or HCV positive test |
| once per week | History of heart, lung, liver, kidney disease |
| Moderate to heavy regular alcohol consumption | Blood or bleeding disorders |
| Cannot be pregnant | Neurologic disorders |
| | Diabetes |
| | Autoimmune disorders |

Materials and Methods
Stem Cell Mobilization and Leukapheresis

Healthy aged (>60 y/o) and young (18-29 y/o) individuals were recruited according to specified inclusion and exclusion criteria (Table 4), with qualified donors enrolled for stem cell mobilization and leukapheresis. All recruitment, mobilization and leukapheresis were conducted under an approved IRB and informed consents by HemaCare Corporation (Van Nuys, Calif.), an FDA-registered, AABB-accredited collection center operating under GMP-compliant, validated procedures and equipment. Study participants were dosed subcutaneously with Neupogen® (G-CSF) at 5 µg/kg/day for 5 days to stimulate the bone marrow (BM) to expand the HSC/HPC compartment and mobilize it into the peripheral blood stream. On the 6th day, mobilized peripheral blood (MPB) was collected with the Spectra Optia®

Umbilical Cord Blood Collection

Umbilical cord blood (UCB) collected from mothers delivering at participating hospitals was obtained by Community Blood Services (Montvale, N.J.), an AABB-accredited blood bank registered with the FDA. Individual collections of less than 100 mL were designated for research use, and donated under a protocol approved by the IRB of Rutgers. 10 whole UCB units were obtained and processed within 24 h of collection by Ficoll-Hypaque (Sigma) density gradient to isolate the mononuclear fraction and remove red blood cells and granulocytes. MNCs were cryopreserved for later use in transwell cultures.

Isolation of CD34+ Cells and Cryopreservation of Blood Products

Immediately following collection, mobilized Leukopaks (400 mL) were split into 2 bags (200 mL each) and shipped overnight at 4° C. for subsequent processing and biobanking. All samples were processed within 16 h of donor leukapheresis. Total nucleated cells (TNCs) from the first collection bag were pelleted at 4° C. for 10 min, washed with cold buffer containing 2% human serum albumin (HSA; Irvine Scientific) and then resuspended in the original 200 mL supernatant. Chilled cryopreservation media with 3.6% HSA and 20% DMSO was added dropwise to the TNC suspension at a 1:1 ratio while gently shaking, for a final TNC concentration of approximately 50×106 cells/mL. The second half of the collection was used to purify CD34+ cells. TNCs were pelleted at 4° C. for 10 min and then resuspended in cold MACS buffer (0.5% bovine serum albumin, 2 mM EDTA in PBS, pH 7.2) at a concentration of 108 cells per 300 µL buffer. Cells were incubated in 100 µL each of FcR Blocking Reagent and CD34 MicroBeads (Miltenyi Biotec) per $10^8$ total TNCs for 30 min at 4° C., then washed in MACS buffer. Magnetic separation was performed by positive selection with LS columns (Miltenyi), and purified CD34+ cells immediately resuspended in cold cryopreservation media (80% FBS, 10% RPMI-1640 and 10% DMSO). Similar media was used for MNCs isolated from UCB. All cells were frozen using a controlled rate freezer at a rate of –1° C./min until at temperature of –100° C. was reached, at which time vials were transferred into liquid nitrogen for long term storage.

Heterochronic Transwell Culture

TNC vials were quickly thawed at 37° C. and cells added dropwise 1:10 to pre-warmed RPMI-1640 equilibration solution containing 5% HSA, 30 U/mL DNase I (Sigma), 5 mM MgCl2 and 5 mM $CaCl_2$), and incubated at 37° C. for 3-4 hrs. After equilibration, cells were pelleted, washed in RPMI-1640 with 2% BSA and resuspended in complete media containing 10% FBS. Cells were seeded at densities of 10 or 30×106 cells/well in 12- or 6-well plates, respectively, containing 0.4 µm transwell inserts (BD Falcon). Heterochronic cultures were established with young cells in the upper chamber and aged cells in the lower chamber. Cells were incubated at 37° C. for 7 days, with 15% of culture media replenished with fresh media on the 4th day. On the 7th day, cells were harvested by centrifugation and evaluated.

Cell Phenotyping by Flow Cytometry

Cell surface staining was performed by incubation with lineage-specific antibodies. Briefly, 106 cells were resuspended in PBS and incubated with appropriate antibodies for 30 min at RT in the dark. Antibody dilutions were performed according to manufacturer's recommendations. Isotype IgGs were used as controls. Cells were washed with PBS and acquired on a FACSCalibur flow cytometer (BD Biosciences). Data were analyzed using BD CellQuest Pro™ software (BD Biosciences). All antibodies were purchased from BD Biosciences: CD3-APC (UCHT1), CD3-PerCP-Cy5.5 (UCHT1), CD4-PE (RPA-T4), CD8-APC (RPA-T8), CD19-PE (HIB19), CD25-PerCP-Cy5.5 (M-A25), CD33-APC (WM53), CD34-APC (581), CD38-FITC (HIT2), CD45-PerCP-Cy5.5 (HI30), CD45-FITC (HI30), CD45-PE (HI30), CD56-PE (B159) and HLA-DR-PE (G46-6). In some embodiments, one or more of these antibodies is used in methods of preparing target cells as disclosed herein.

Modified Long-Term Culture-Initiating Cell Assay

A good in vitro system to study long-term HSC function is the long-term culture-initiating cell assay (LTC-IC). Briefly, LTC-IC assays were initiated by seeding an aliquot of cells from heterochronic or isochronic culture onto irradiated (1,500 cGy) BM stromal cells (3×104/cm2) that had been previously sub-cultured. Beginning at week 6, 103 non-adherent cells were assayed every 2 weeks, up to week 12, for primitive hematopoietic progenitors in clonogenic assays (as discussed in further detail elsewhere herein).

Clonogenic Assay

Non-adherent cells from LTC-IC assays, as well as cells from isochronic and heterochronic cultures, were studied for progenitors in short-term methylcellulose culture using a CFU-GM readout. Briefly, cultures were initiated by seeding 150 cells/mm$^2$ in clonogenic media containing 3 U/mL of rhGM-CSF (R&D Systems). After 10 days, cultures were scored by a single blinded observer, and colonies enumerated for CFU-GM.

Cell Vitality and Mitosox Assays

106 TNCs were labeled with anti-CD34-APC and -CD45-PerCp-Cy5.5. For Cell Vitality assay, cells were washed and co-stained with 10 nM Sytox and 200 nM C12-resazurin (Molecular Probes) in 100 µl volume. Cells were incubated for 15 min at 37° C., then diluted 5 times with PBS. For Mitosox assay, cells were washed and incubated with 5 µM MitoSox™ Red (Molecular Probes) for 10 min at 37° C. in the dark and then washed again with warm HBSS/Ca/Mg buffer. A FACSCalibur flow cytometer was used for data acquisition in both assays.

Cytotoxicity Assay

Cell cytotoxicity was determined with the CFSE/7-AAD Cell Cytotoxicity Kit (Cayman Chemical) according to manufacturer's specified instructions. Briefly, the human chronic myelogenous leukemia cell line, K562, (ATCC # CCL-243) was used as target cells. 107 K562 cells were labeled for 15 min with CFSE dye, washed twice and diluted 100-fold for 30 min incubation at 37° C. Cells from 7-day isochronic or heterochronic cultures were used as effectors. Effector and target cells were added to 6-well plates at the following effector-to-target (E:T) ratios: 0:1, 6.25:1, 12.5:1 and 25:1, and cell mixtures incubated for 4 h at 37° C. Cells were harvested and counter-stained with 7-AAD. 50,000 events were acquired on the FACSCalibur flow cytometer, and data analyzed using BD CellQuest Pro™ software. Target cells incubated alone with 7-AAD served as control to calculate spontaneous lysis, while effector cells alone with 7-AAD served as control to detect dead effector cells. Percent lysis was calculated according the following formula: [(cells positive for both CFSE and 7-AAD/total CFSE-labeled cells)*100−spontaneous % lysis].

T Cell Activation Assay

T cell activation was determined using the T Cell Activation/Expansion Kit (Miltenyi). Briefly, anti-biotin MACSiBead Particles were loaded with CD2, CD3, and CD28 antibodies. Cells from 7-day isochronic or heterochronic cultures, or MNCs isolated from huNSG mouse blood by Ficoll-Hypaque density gradient, were incubated with loaded anti-biotin MACSiBead Particles at a 1:2 bead to cell ratio for 72 h to activate T cells. Addition of unloaded MACSiBead Particles served as negative control. After 72 h, cells were fluorescently labeled using CD45-FITC, CD4-PE, CD25-PerCP-Cy5.5 and CD8-APC to determine T cell activation status by flow cytometry.

Mixed Lymphocyte Reaction

One-way mixed lymphocyte reaction (MLR) was performed. Briefly, cells from 7-day isochronic or heterochronic cultures were seeded in 96-well, flat-bottom plates (Corning) and equal volumes (0.1 ml) of stimulators (gamma-irradiated, freshly thawed aged cells) and responders (aged cells from heterochronic or isochronic culture) added to each well in triplicate. Thawed aged cells incubated with cells from young isochronic culture served as positive control. Cultures were pulsed with 1 µCi/well of [methyl-3H]TdR (70-90 Ci/mmol; NEN) during the last 16 h of a 4-day culture. Cells were harvested with a PhD cell harvester (Cambridge Technologies) onto glass-fiber filters, and [3H]TdR incorporation quantified in a scintillation counter (Beckman Coulter). Results were expressed as the stimulation index (S.I.), which is the mean dpm of experimental cultures (responders+gamma-irradiated stimulators)/dpm of responder cells with only medium.

Humanization of NSG Mice and Adoptive Transplant 5-week old, female NOD/scid IL2Rγnull (NSG) mice were purchased from Jackson Labs and housed in an AALAC-accredited facility at Rutgers, N.J. Medical School (Newark, N.J.). The protocol was approved by the Institutional Animal Care and Use Committee, Rutgers School of Biomedical Health Sciences (Newark, N.J.). Mice were acclimated in the Rutgers barrier animal facility for 1 week prior to experimental use. 6-week old mice were subjected to 150 cGy whole body gamma irradiation using a Mark-I cesium irradiator unit. 5 hours post-irradiation, mice were injected i.v. with 5×105 human CD34+ cells isolated from aged or young study donor Leukopaks. Engraftment proceeded over 15-19 weeks, with peripheral blood chimerism monitored at 9 and 13 weeks post-transplant. % Chimerism was detected by co-labeling blood with anti-human CD45-APC (HI30) and anti-mouse CD45-FITC (30-F11) for monitoring by flow cytometry. Humanized NSG (huNSG) enrolled in the treatment arm of the transwell-based animal study were given a 2nd i.v. injection of 5×105 autologous aged cells from 7-day isochronic (non-restored) or heterochronic (restored) cultures that were CD3-depleted (Miltenyi) prior to transplant, or saline control. The miRNA-based animal study was performed as above, except that the treatment arm utilized autologous aged cells transfected with 60 nmol total of either miR-619 alone, miR-combo (miR-619, -1303, 4497) or control RNA. Transfections utilized the HiPerFect reagent (Qiagen), and cells were transfected for a total of 7 days prior to CD3 depletion and i.v. injection as above. Mice were sacrificed at 14-15 weeks post-transplant, and blood, BM and speen harvested for biochemical, phenotypic and functional analyses. Major organs were also harvested for histological assessment. Tissue embedding, processing and staining were performed by the Digital Imaging and Histology Core of Rutgers-New Jersey Medical School Cancer Center (Newark, N.J.). Histologic findings were confirmed on H&E slides by a board-certified veterinary pathologist.

Senescence Protein Array and T Cell Cytokine Array

Detection of senescence associated secretory factors (SASFs) in plasma of huNSG mice was performed using Custom C-Series Human Antibody Arrays (Ray Biotech). Arrays were labeled with antibodies to 68 different factors linked to cellular senescence. Briefly, blood from huNSG mice was pelleted for 10 min at 300 g and plasma supernatant collected in siliconized microfuge tubes for SASF determination. Incubation and detection of factors within plasma followed the manufacturer's suggested protocol. Background levels were calculated by incubating the arrays with plasma from non-humanized NSG mice and then subtracting the obtained values from each huNSG sample.

For the T Cell Cytokine Array (Ray Biotech), conditioned media was collected from cells isolated from huNSG peripheral blood that were stimulated as per the T cell activation assay (see above) after 72 h and stored in protein lo-bind tubes. The protocol followed manufacturer's suggested recommendations. For both the custom SASF and T cell cytokine arrays, densitometry was performed using the UN-SCAN-IT densitometry software (Silk Scientific). Hierarchical clustering and heat map generation were perfomed with Heatmapper software.

Senescence and Aging Gene Arrays

BM from huNSG were flushed with a 26-gauge needle and collected for subsequent purification of engrafted human cells with the Mouse Cell Depletion Kit (Miltenyi). Total RNA (2 µg) was extracted from purified cells using the RNeasy Mini Kit (Qiagen) and reverse-transcribed with the RT2 First Strand Kit (Qiagen). 20 ng of cDNA was used for qPCR with the Human Cellular Senescence and Human Aging RT$^2$ Profiler™ PCR Arrays (Qiagen). Arrays were run on the 7300 Real Time PCR System (Life Technologies) with the cycling profile (40 cycles): 94° C. for 15 seconds and 60° C. for 45 seconds. Gene expression analysis was performed using Qiagen PCR Array Data Analysis Software and normalized to five housekeeping genes provided within each array. Hierarchical clustering and heat map generation were perfomed with Heatmapper software.

Exosome Isolation and Nanoparticle Tracking Analysis

Exosomes were isolated from cell culture media by the Total Exosome Isolation Kit (Life Technologies), using a modified version of the manufacturer's protocol. Briefly, 7-day isochronic and heterochronic cultures were established with Exosome-depleted FBS Media Supplement (System Biosciences), and culture media collected on the 4th and 7th days. Cells were pelleted and supernatant transferred to another tube for further clarification at 2000 g for 30 min to remove residual cells and debris. The remaining supernatant was transferred to a fresh tube and 0.5 volumes of Total Exosome Isolation reagent added for overnight incubation at 4° C. The following day samples were centrifuged at 10,000 g for 1 hr at 4° C. to pellet the exosomes for subsequent nanoparticle tracking analysis (NTA) or long-term storage at −80° C. Analysis of absolute size distribution of exosomes was performed using the NanoSight LM10 with NTA3.1 software (Malvern). Particles were automatically tracked and sized based on Brownian motion and the diffusion coefficient. For NTA, exosomes were re-suspended in 0.5 mL of PBS and measured using the following parameters: Temperature=25.6+/−0.5° C.; Viscosity=(Water) 0.99+/−0.01 cP; Measurement time=30 sec; Syringe pump speed=30. The detection threshold was similar in all samples. Three recordings were performed for each sample.

miRNA Profiling by NGS

Total RNA from exosomes and cells was isolated using the miRCURY RNA Isolation Kit (Exiqon) with small and large RNAs fractionated with the RNeasy MinElute Cleanup Kit (Qiagen), both according to manufacturer's recommended specifications. Half of the small RNA fraction (200 ng) was used in library preparation with the NEBNext Multiplex Small RNA Sample Prep Set for Illumina—Set 1 (NEB), according to the following protocol: (1) ligation of the 3' SR Adaptor, (2) hybridization of the reverse transcription primer, (3) ligation of the 5' SR Adaptor, (4) reverse transcription for first strand cDNA synthesis and (5) PCR enrichment. After PCR, samples were cleaned up and size selection performed. Briefly, 2 µl of sample was subjected to Tapestation analysis to ascertain band sizes. Samples were run on 8% acrylamide gel at 100V for 1 hr, with correct size bands excised for gel purification. Small RNA libraries were diluted to 2 nM and run on a miSeq System (Illumina) for NGS using the V2 kit (Illumina). Data analysis was performed using the CLC Genomics Workbench (Qiagen) according the following data workflow: (1) Fastq files imported into the analysis suite, (2) sequences trimmed to remove poor quality and short reads, (3) trimmed reads run through the Small RNA Analysis pipeline, (4) extraction and counting, (5) annotation and count merging to identify expression level of each mapped miRNA. Mapped reads from individual samples were then compared to determine fold change for each miRNA.

miRNA Microarray and qPCR

Total RNA (500 ng) was isolated from exosomes using the miRCURY RNA Isolation Kit (Exiqon) and reverse-transcribed with the miScript II RT Kit (Qiagen). 20 ng of cDNA was used for qPCR with the human miFinder miRNA Array (Qiagen), with cycling conditions of 94° C. for 15 minutes, 40 cycles at 94° C. for 10 seconds, 55° C. for 30 seconds, 70° C. for 30 seconds, followed by melt curve analysis. The data were analyzed with the online miScript miRNA PCR Array data analysis tool. For validation of miRNAs identified by microarray and NGS, individual qPCR experiments were performed with miScript primer assays (Qiagen) using similar cycling and analysis schemes. Total RNA (2 μg) was also isolated from cells, as described above, for profiling of downstream miRNA targets by qPCR. The following custom primers were designed: CASP14 (F) 5' gtt ccg aag aag acct gg at 3', (R) 5' ttc tcc agc ttg acc atc tc 3'; GALNT6 (F) 5' gga gca cct aaa gga gaa gc 3', (R) 5' ctg tct tgt cct cag cga tt 3'; PAX 5 (F) 5' cat ccg gac aaa agt aca gc 3', (R) 5' acc gga gac tcc tga ata cc 3'; PPM1F (F) 5' ctt ggc ttt cct gag aaa ca 3', (R) 5' ctt ggc ttt cct gag aaa ca 3'; SUMO2 (F) 5' atg gtt ctg tgg tgc agt tt 3', (R) 5' ctg ctg ttg gaa cac atc aa 3'; β-Actin (F) 5' atc ctc acc ctg aag tac cc 3', (R) 5' agc ctg gat agc aac gta ca 3', with cycling conditions of 95° C. for 15 minutes, 40 cycles at 94° C. for 15 seconds, 51° C. for 30 seconds, 72° C. for 30 seconds, followed by melt curve analysis. In some embodiments, the methods of preparing miRNA includes one or more of the above steps, including the use of the primers disclosed herein. Analyses were performed with Qiagen PCR Array Data Analysis Software, as described above.

Nucleofection of miRNA Mimics, miRNA Inhibitors and siRNA

Aged TNCs (10×106 cells per sample) were nucleofected with microRNA mimics (Qiagen), miRNA inhibitors (Qiagen), negative control siRNA (Qiagen), negative control miRNA inhibitor (Qiagen) or downstream target candidate siRNAs (Origene) using the Amaxa P3 Primary Cell 4D-Nucleofector X Kit (Lonza) on a 4D Nucleofector device (Lonza), according to manufacturer's specific protocol. Briefly, for nucleofection of CD34+ cells used in clonogenic assays, cells were nucleofected with 60 nmol total miRNA mimics, miRNA inhibitors or siRNA using the "human CD34+ cell" program. For nucleofection of T cells used in T cell activation and cell-mediated cytotoxicity assays, cells were nucleofected with 240 nmol total miRNA mimics, miRNA inhibitors or siRNA using the "human unstimulated T cell, high functionality" program.

miRNA Target Prediction and Network Analysis

Expression data from NGS was analyzed in silico by Ingenuity Pathway Analysis (IPA—Qiagen) to predict miRNA targets and downstream signaling networks. Differentially expressed exosomal and intracellular miRNA (1.4-fold cutoff) among young and aged isochronic, and aged isochronic and heterochronic samples, respectively, were uploaded to the IPA suite for Core Network Analysis. Predicted networks from the Core Analysis were then simultaneously likened using Comparison Analysis to identify the exosome-cell interactome during heterochronic restoration. Potential mRNA targets of candidate miRNAs were determined using the miRNA Target Filter. The source of the miRNA-mRNA relationship and the confidence of the relationship predictions were from TargetScan and the experimentally observed relationships were from TarBase. mRNA target selection was based on target rank score, where the highest ranked targets were common to the most candidate miRNA (score=6) and the lowest ranked targets to the least candidate miRNA (score=1). Potential interaction with the exosome-cell interactome was evaluated by creating a mock mRNA target expression profile (10-fold downregulation) to generate a Core Analysis network that could be likened using the Comparison Analysis tool. Candidates whose predicted networks converged with the interactome were selected for additional evaluation.

Statistical Analysis

Statistical analyses were performed with ANOVA and Tukey-Kramer multiple comparisons test. For array and NGS expression analyses, average linkage was used for clustering and Pearson correlation analysis used for distance measurement to generate heatmaps and hierarchically cluster genes. $p \leq 0.05$ was considered significant.

Results

Differences in Lymphohematopoietic Function Among Healthy Aged and Young Donors

The hematopoietic and immune systems are dependent on adult hematopoietic stem cell (HSC) function throughout an organism's lifetime to generate hematopoietic progenitor cells (HPCs) and mature effector blood cells. As these systems age or otherwise become dysfunctional, their diminishing functions lead to compensatory increases in immune-related diseases, including cancer. To this end, the overarching goal of this study was to identify novel factors produced by young healthy blood cells that could restore function to the aging or otherwise dysfunctional hematopoietic and immune systems.

To determine how blood cell function is solely impaired by temporal aging, without age-related co-morbidities, healthy study donors were recruited. Aged ($\geq 60$ y/o) and young (18-29 y/o) donors were screened using a set of inclusion and exclusion criteria to select for the desired donor type (Table 4). General inclusion criteria such as normal BMI and no smoking, and exclusion criteria such no concurrent illness, abnormal BMI or co-morbidities yielded healthy aged donors. The criteria for young donors was more rigorous, as it was hypothesized that young individuals with extremely healthy lifestyles should yield the healthiest blood samples to identify anti-aging, restorative factors. Additional inclusion and exclusion criteria for the young cohort included exercise, diet and sleep requirements.

Compared to other stem cell-rich organs such as bone marrow (BM) and spleen, the systemic circulation contains minimal numbers of stem cells. To circumvent this, G-CSF-mobilized peripheral blood (MPB) was collected from aged and young study donors. MPB comprises a heterogeneous population of cells, including HSCs, HPCs, mesenchymal stem cells (MSCs), endothelial progenitor cells (EPCs), stroma and mature immune cells. In total, MPB from 5 young and 4 aged donors, with an average age of 22.2 and 60.8 y/o, respectively (Table 5) was obtained. Umbilical cord blood (UCB) was also collected for comparison to young MPB, since UCB comprises a similar hematopoietic matrix.

TABLE 5

Aged and Young Mobilized Blood Donor Demographics

| | Donor ID | Age | Sex | Height (in) | Weight (lb) | Ethnicity | TNC count ($10^9$) | CD34+ count ($10^6$) |
|---|---|---|---|---|---|---|---|---|
| 1 | A01 | 61 | M | 70 | 162 | Caucas. | 71.9 | 90.0 |
| 2 | A02 | 60 | M | 70 | 190 | Caucas. | 43.6 | 185 |
| 3 | A03 | 61 | M | 68 | 149 | Caucas. | 32.2 | 46.8 |
| 4 | A04 | 61 | M | 67 | 172 | Caucas. | 47.0 | 93.9 |
| 5 | Y01 | 28 | M | 67 | 140 | Afr. Am. | 42.2 | 354 |
| 6 | Y02 | 22 | M | 66 | 146 | Hispan. | 79.2 | 192 |
| 7 | Y03 | 20 | M | 67 | 160 | Caucas. | 45.5 | 200 |
| 8 | Y04 | 20 | F | 60 | 120 | Hispan. | 43.2 | 82.2 |
| 9 | Y05 | 21 | M | 69 | 130 | Hispan. | 20.1 | 47.1 |
| Aged (n = 4) | — | 60.8 | — | 68.8 | 168 | — | 48.7 | 103.9 |
| Young (n = 5) | — | 22.2 | — | 65.8 | 139 | — | 46.0 | 175.1 |

*Values for Aged and Young are averages of the 4 aged and 5 young donors enrolled in this study
**UCB was collected from 10 different donors. Information related to each donor was not made available Collection of MPB from aged and young donors yielded a similar number of total nucleated (Table 5) and CD45+ cells (FIG. 4A), however young mobilization was more efficient as it yielded greater numbers of CD34+ cells (Table 5, FIG. 4B). Young CD34+ cells displayed significantly greater clonogenicity compared to aged, and were comparable to UCB (FIG. 5A). MPB cells from young donors also exhibited decreased oxidative stress (FIG. 5B), and increased cell-mediated cytotoxicity (FIG. 5C) compared to aged. These findings illustrate the striking impact of aging on the lymphohematopoietic system, even for donors with excellent health, on both the stem and mature effector cell compartments.

Development of a Heterochronic Culture Model to Restore Aging Blood Cell Function The functional decline of aging MPB was targeted through an adaptation of the heterochronic parabiosis model. The approach utilized heterochronic culture to harness production of paracrine factors from young MPB that could potentially restore aged function or function from dysfunction. Here, aged and young cells were separated by a transwell membrane that allowed contact-independent, cell-cell communication through exchange of soluble factors (FIG. 5D). The effect of heterochronic culture on aged MPB clonogenicity at periodic timepoints over 15 days in comparison to aged and young isochronic controls was tested. At day 7, a significant improvement in heterochronic vs. isochronic aged cell function was observed (FIG. 5E), and this effect was sustainable for up to 12 weeks as shown by LTC-IC assay (FIG. 5C). Induction of aged cell restoration was not restricted to young MPB cells, as a similar phenotype was observed in heterochronic cultures with UCB (FIG. 5F). Heterochronic culture altered aged MPB oxidative stress to a degree (FIG. 5G) and did significantly boost cell-mediated cytotoxicity (FIG. 5H). These effects were not due to potential transfer of immunogenic molecules secreted by young cells across the transwell membrane, as there were no differences in HLA-DR expression nor stimulation of naïve aged cells in one-way MLR (FIG. 4D and FIG. 4E).

To determine whether restoration can be propagated, aged restored ("hetero aged") and non-restored ("iso aged") cells were harvested after 7-day culture and seeded into fresh isochronic culture with naïve aged cells for an additional 7 days (FIG. 5I). Culture with cells from initial heterochronic culture (gray hatch bar) induced a significant increase in clonogenicity compared to cells from initial isochronic culture, although these effects were not as robust as initial heterochronic culture (FIG. 5F).

Preliminary investigation into the young MPB population exerting these restorative effects revealed a role for CD34+ cells (FIG. 5J), as depletion significantly reduced heterochronic restoration. Similarly, culture of aged MPB with purified young CD34+ cells alone increased aged clonogenicity compared to isochronic control (light gray bar). The effect was not as robust as unfractionated heterochronic culture (dark grey bar), thus implicating other young populations in the restorative mechanism.

A Humanized Model of the Aging Lymphohematopoietic System to Study Restoration

To translate the restorative findings from heterochronic MPB cultures, a sophisticated animal model was used that could recapitulate the aging human lymphohematopoietic system. NSG mice are a severely immunocompromised strain that lack an adaptive immune system and NK cells, thereby constituting a good model for human hematolymphoid engraftment. Most NSG humanization (huNSG) studies utilize young or primitive CD34+ cells isolated from sources such as MPB, UCB or fetal liver (FL). Implantation of these cell types would not be beneficial for the disclosed approach, since aged cell engraftment and hematopoiesis was required to study the therapeutic benefit of heterochronically-restored, autologous transplants. To this end, CD34+ cells isolated from aged study donor MPB collections were used to create aged huNSG mice. Pilot studies demonstrated a dose-escalating effect of aged CD34+ engraftment at 8 weeks post-transplant (FIG. 6A), which regressed and stabilized after 20 weeks (FIG. 6B).

Next, this model was applied to study the effect of heterochronically-restored cells in autologous huNSG. Mice were transplanted with aged or young CD34+ cells and monitored for human engraftment and hematopoiesis over 19 weeks (FIG. 7A, FIG. 6C). Variability in huCD45+ chimerism was observed among individual aged donors (FIG. 6D, A01 vs. A02) as well among aged vs. young donor cell recipients (middle panel), with young transplants demonstrating significantly greater engraftment than aged. Mice exhibiting a minimum of 1% peripheral blood chimerism were enrolled in the treatment arm of the study and given a second autologous transplant of CD3-depleted MPB cells from heterochronic or isochronic culture. Mice exhibiting detectable chimerism less than 1% were injected with saline and utilized solely for safety profile comparison. After 14 weeks, mice were sacrificed and lymphohematopoietic phenotype and toxicological analyses performed.

No significant safety concerns were observed for all treatment groups (FIG. 5E, FIG. 5F, FIG. 5G), with mice receiving heterochronically-restored (herein termed "restored huNSG") and isochronically-non-restored (herein termed "non-restored huNSG") cells exhibiting mean overall survivals of 100% and 91%, respectively (FIG. 5E). Histologic evaluation of immune tissues and major organs showed no evidence of tissue pathology or tumorigenesis (FIG. 8).

Phenotypic evaluation of human hematopoiesis was performed in blood, BM and spleen of treated huNSG (FIG. 7B-FIG. 7G, FIG. 9). Increased human chimerism was observed in BM of restored huNSG vs. non-restored (FIG. 7B, left plot). Restored transplants also demonstrated increased huCD3+(FIG. 7C) and decreased huCD33+(FIG. 7D) cell frequencies in blood compared to non-restored. No differences were observed in huCD34+ cell frequency in BM of all groups (FIG. 7E). To understand the phenotype in the context of relevant lymphohematopoietic aging-related metrics, the ratios of were determined huCD4+/CD8+ T cells (FIG. 7F) and lymphoid/myeloid cells (FIG. 7G) in blood and BM. Restored huNSG showed increased huCD4+/CD8+ T cell and lymphoid/myeloid ratios. These findings suggest that either the hematopoietic output, the autologous transplant itself or both in restored huNSG shows a decrease in age-related phenotype.

Next, human HSC/HPC and T cell function in BM and blood, respectively, of huNSG was evaluated. BM clonogenicity was significantly increased to levels comparable to young in restored huNSG (FIG. 7H). PBMCs harvested from restored mice and cultured ex vivo also showed increased frequency of huCD4+ cells (FIG. 7I, left plot). Stimulation of PBMCs with anti-CD3/CD28 elicited increased activation of huCD8+ cells from restored huNSG compared to non-restored (right plot).

Figure 10A:
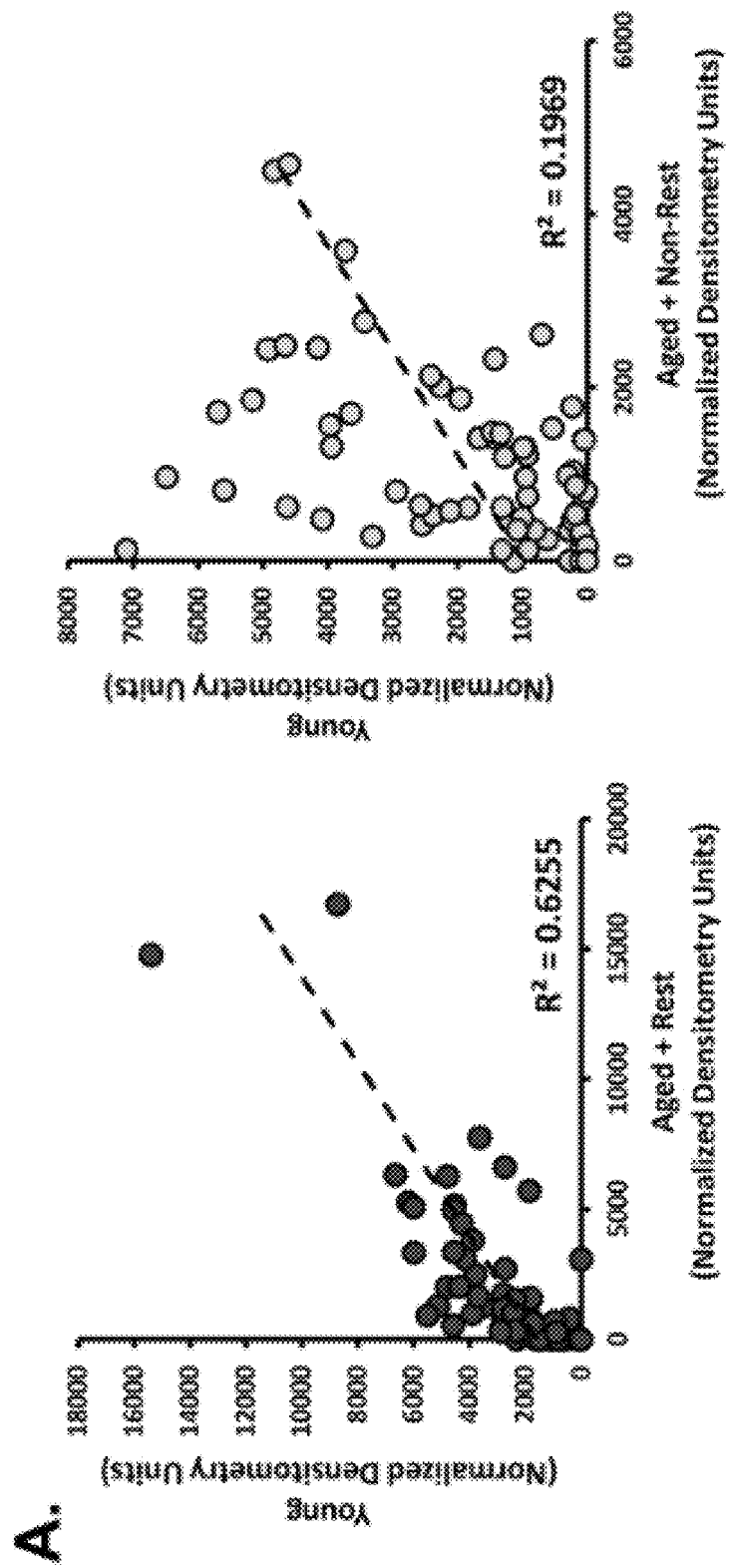

The final set of studies examined the effect of restoration on aging-related gene and protein expression in huNSG. Blood plasma isolated from restored and non-restored mice was probed for 68 factors linked to the senescence-associated secretory phenotype (SASP). Restored huNSG displayed decreased expression for 47% of factors and increased expression for only 12% of factors compared to non-restored (FIG. 7J, FIG. 10A-B). To determine whether these results were consistent with changes in gene expression for engrafted human cells, human cells were purified from chimeric BM and pathway-focused qPCR arrays were performed to evaluate 145 genes related to human senescence and aging. Similar to the expression pattern of the SASP study, purified cells from restored huNSG displayed decreased expression for 44% of factors and increased expression for only 8% of factors compared to non-restored (FIG. 7K, FIG. 10C). These findings illustrate that heterochronic restoration targets underlying pathways related to cellular aging and senescence. Further, the results suggest that the effect is propagated from the ectopically restored cells to the engrafted huBM compartment post-transplant.

Young Exosomes Promote Heterochronic Restoration

The next set of studies sought to elucidate the mechanism of heterochronic restoration. It was surmised that due to the 0.4 μm pore size restriction of the transwell membrane, restorative young factors would likely be a complex acellular mixture of molecules capable of inducing global intracellular changes in aged target cells. Exosomes are small membrane vesicles released by all cell types, which contain a subset of proteins, lipids and nucleic acids derived from the parent cell. Exosomes have important roles in intercellular communication, both locally and systemically, as well as in regulating a number of aging-related signaling pathways in targeted cells. A role for exosomes in the restorative mechanism was investigated.

Examination of exosomes harvested from 7-day heterochronic and isochronic cultures showed minimal difference in particle size (FIG. 11A), and a modest increase in exosome production in aged vs. young isochronic cultures (FIG. 12A). Collected exosomes were then added to aged isochronic cultures to determine the effect on clonogenicity (FIG. 12B). Young (checkered bar) and heterochronic (hatched bar), but not aged (black checkered bar), exosomes produced a significant increase in aged isochronic clonogenicity. Blocking global exosome production with the nSmase inhibitor, GW4869, abrogated the restorative phenotype, but was also extremely toxic to the aged cultures (data not shown).

Figure 11F:
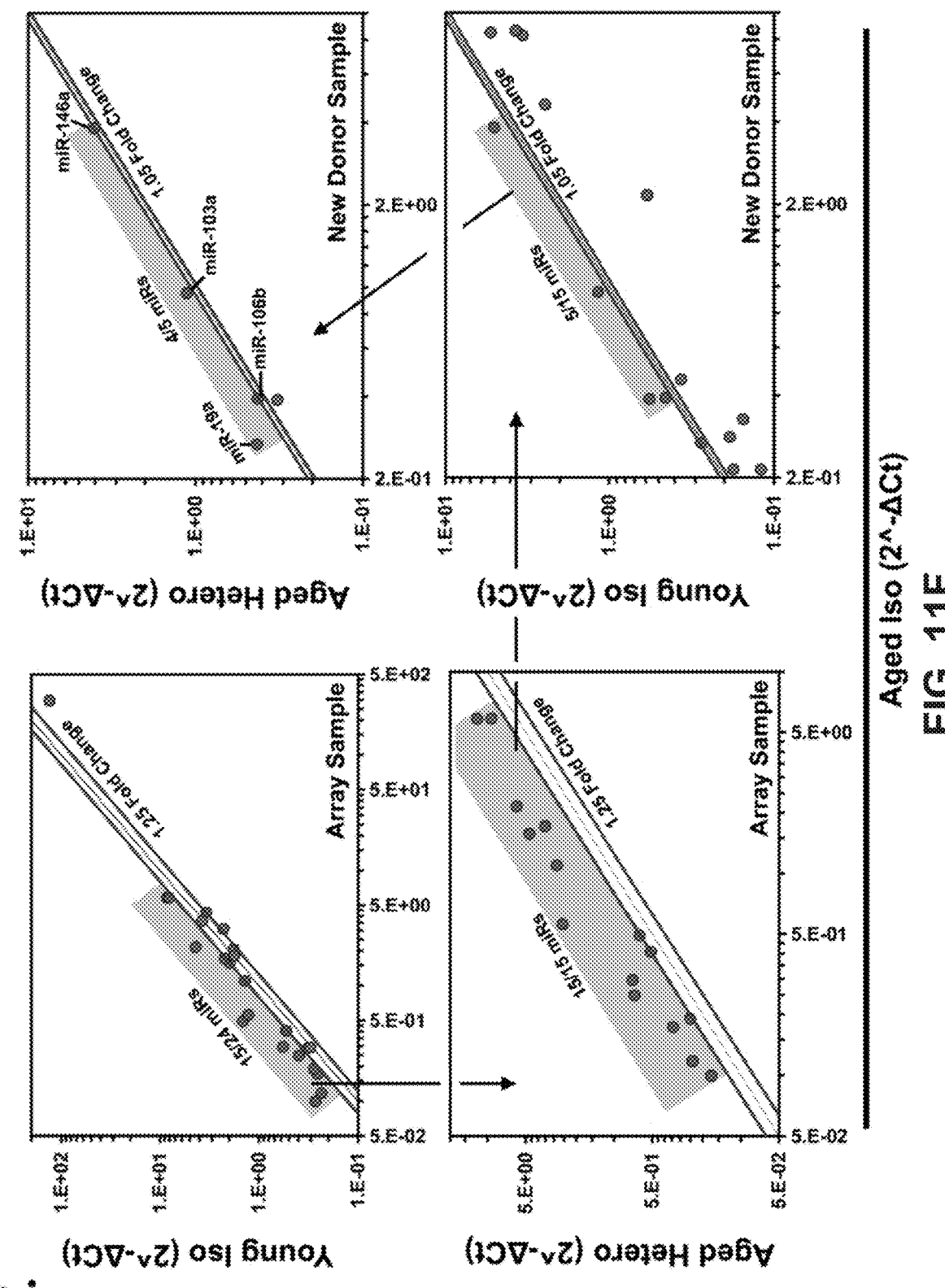

Though only a modest difference in exosome production was observed among aged and young cultures, the total RNA content of young exosomes was significantly greater than aged (FIG. 12C). Considering the importance of miRNAs in exosome-mediated intercellular communication, the role of miRNA in restoration was then investigated. The AGO2 inhibitor, BCI-137, was used to ablate miRNA packaging during exosome biogenesis. Treatment of heterochronic cultures with BCI-137 had minimal effect on exosome production and total RNA content (FIG. 11B and FIG. 11C), however it depleted the small and miRNA payload (FIG. 11D) and was coincident with a significant decrease in aged MPB clonogenicity (FIG. 12D, dotted bar). These findings led us to evaluate the miRNA profile of exosomes from isochronic and heterochronic cultures by utilizing an array with 84 probes for commonly expressed miRNA (FIG. 12E). A striking difference in exosomal miRNA expression was observed, with miRNA enrichment in young and heterochronic exosomes compared to aged, and only 25 of 68 detectable miRNAs expressed at similar levels for all cultures (FIG. 12F). Network analysis of the differential expression profile of young vs. aged demonstrated a number of predicted targets, including p53 (FIG. 11E). Differentially expressed miRNAs were validated in cultures from different donors, with miR-19a, miR-103a, miR-106b and miR-146a found to be consistently upregulated in young and heterochronic cultures compared to aged, although only minimally (FIG. 12G, FIG. 11E and FIG. 13G). Taken together, these data ascribed a putative role for young exosomes and their miRNA payload in the restorative mechanism.

Sequencing the Exosomal miRnome for Identification of Restorative miRNAs

Initial exosome profiling of 84 commonly expressed miRNAs provided preliminary indication that young and aged exosomes exhibit distinctly different expression patterns. However, thousands of human miRNAs have been identified, thus a more comprehensive assessment of the exosomal miRnome was needed. To this end, deep sequencing was utilized and small RNA-Seq was performed to define the exosomal miRnome of aged, young, UCB and heterochronic cultures. An expression cutoff of 100 mappable reads in the sequencing dataset was defined, and 13 and 17 miRNAs were identified that met this criteria in aged and young exosomes, respectively (FIG. 14A). Interestingly, 12 of 17 exosomal miRNAs detected in young were expressed at significantly higher levels than aged, while only 3 of 17 were observed at lower levels. Examination of exosomes from UCB illustrated a vastly different miRnome, with 70 miRNAs of greater than 100 mapped reads and only 4 commonly expressed miRNAs as young observed. Similar findings were seen when comparing intracellular miRnomes among aged, young, and UCB cultures (FIG. 13A).

Next, the exosomal miRnome of aged cells was examined following heterochronic culture and a dramatic increase in miRNAs with expression above the 100-read threshold was found (FIG. 14B and FIG. 14C). The effect was ubiquitous to heterochronic culture, as similar exosomal and intracellular expression patterns were observed with aged culture of either young or UCB cells (FIG. 13B-D). Of the 12 differentially expressed young miRNAs (FIG. 14A), 8 were up-regulated following heterochronic culture (FIG. 14D) and 6 were validated for greater than 5-fold differential expression in young and heterochronic exosomes of additional study donors (FIG. 14E). Of note, due to a lack of widely accepted small RNAs for exosomal miRNA qPCR normalization, hsa-miR-7641-2 (FIG. 13E) was utilized since it was highly expressed in exosomes across all sequencing samples (aged, young, UCB, heterochronic) and significantly correlated with total mapped reads ($p \leq 0.0001$). Of the 6 remaining candidates, only miR-223 and miR-619 were propagated in naïve aged cells after heterochronic restoration (FIG. 13F).

Figure 14G:
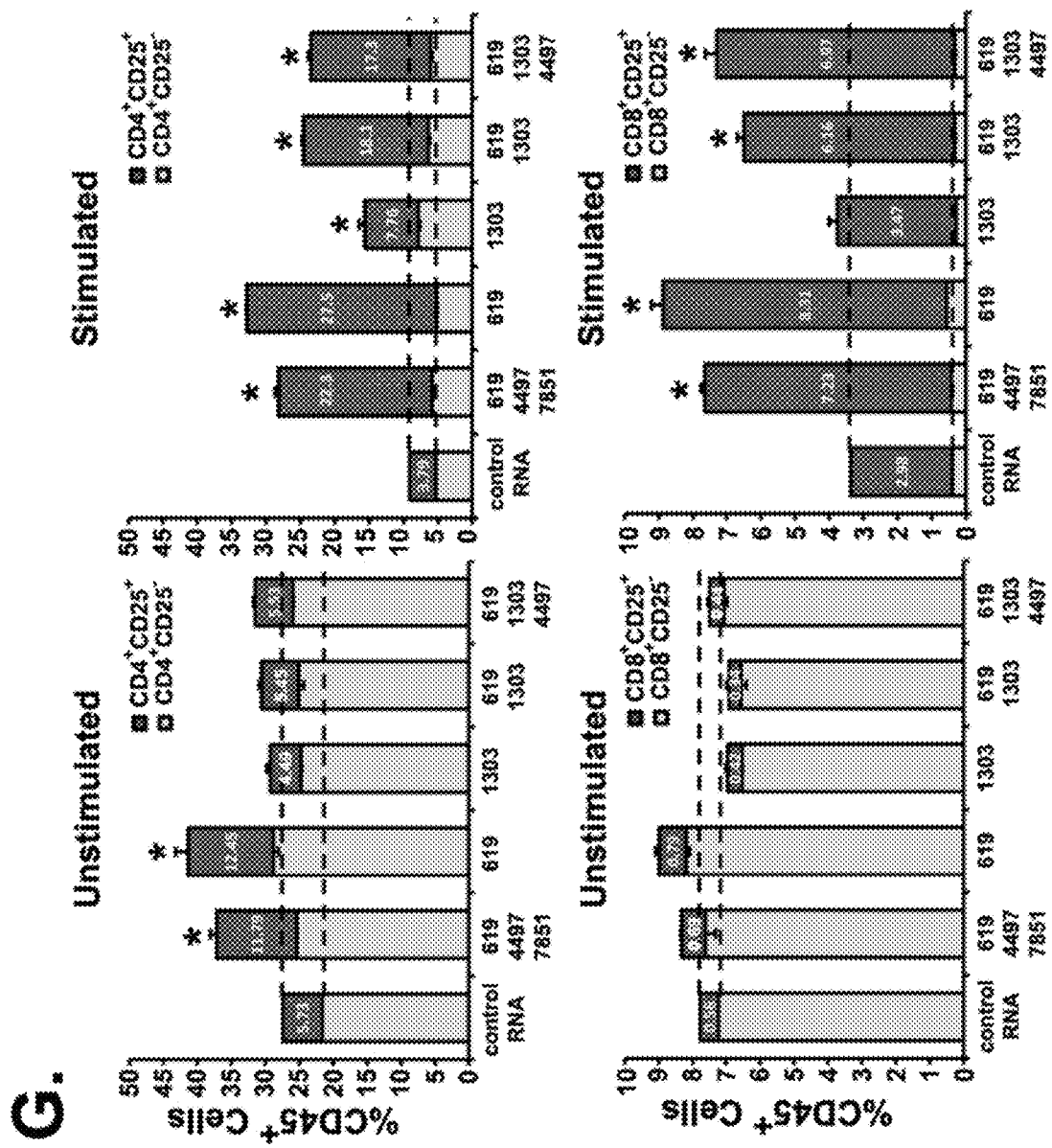
Figure 15B:
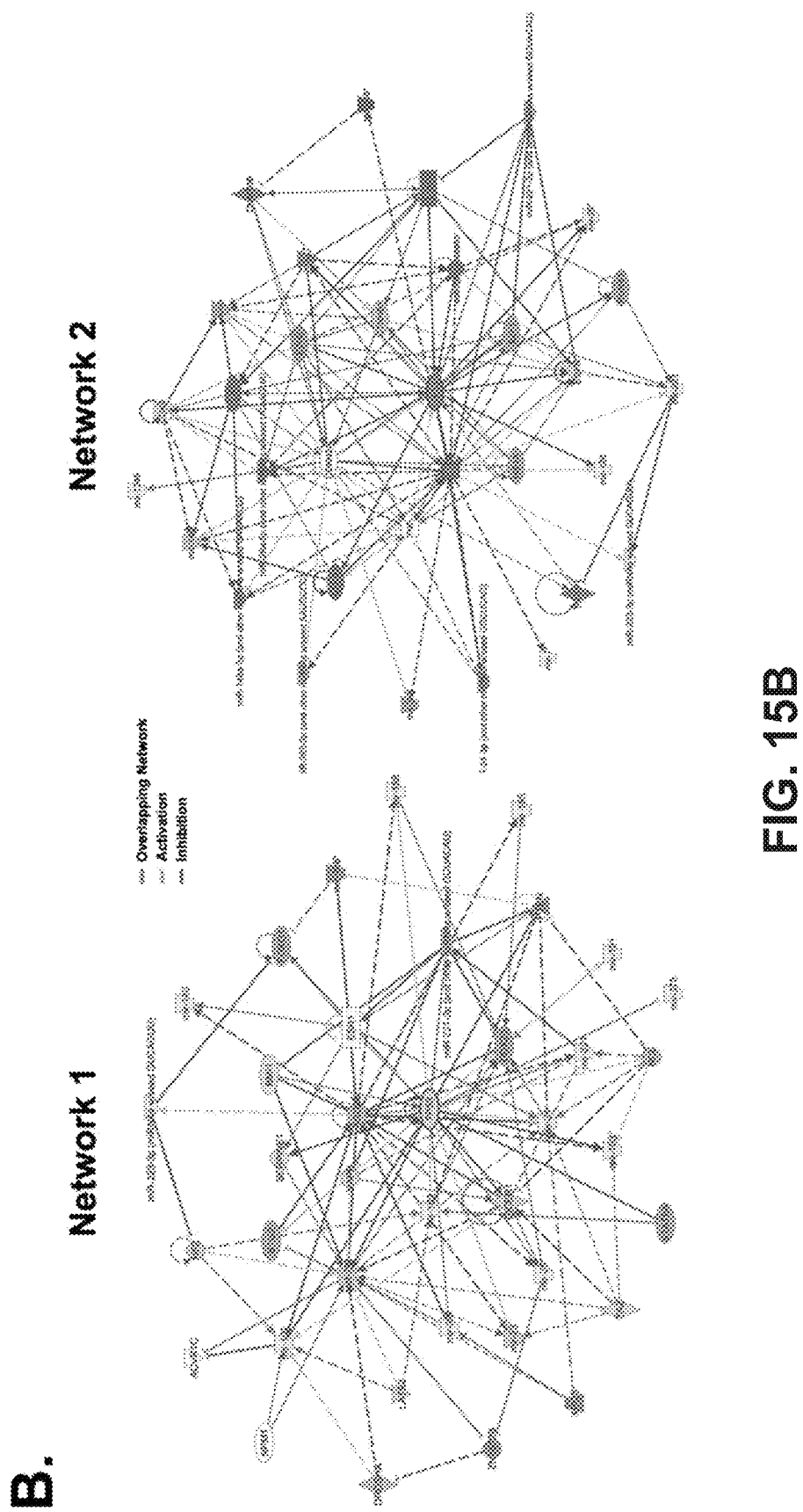
Figure 15E:
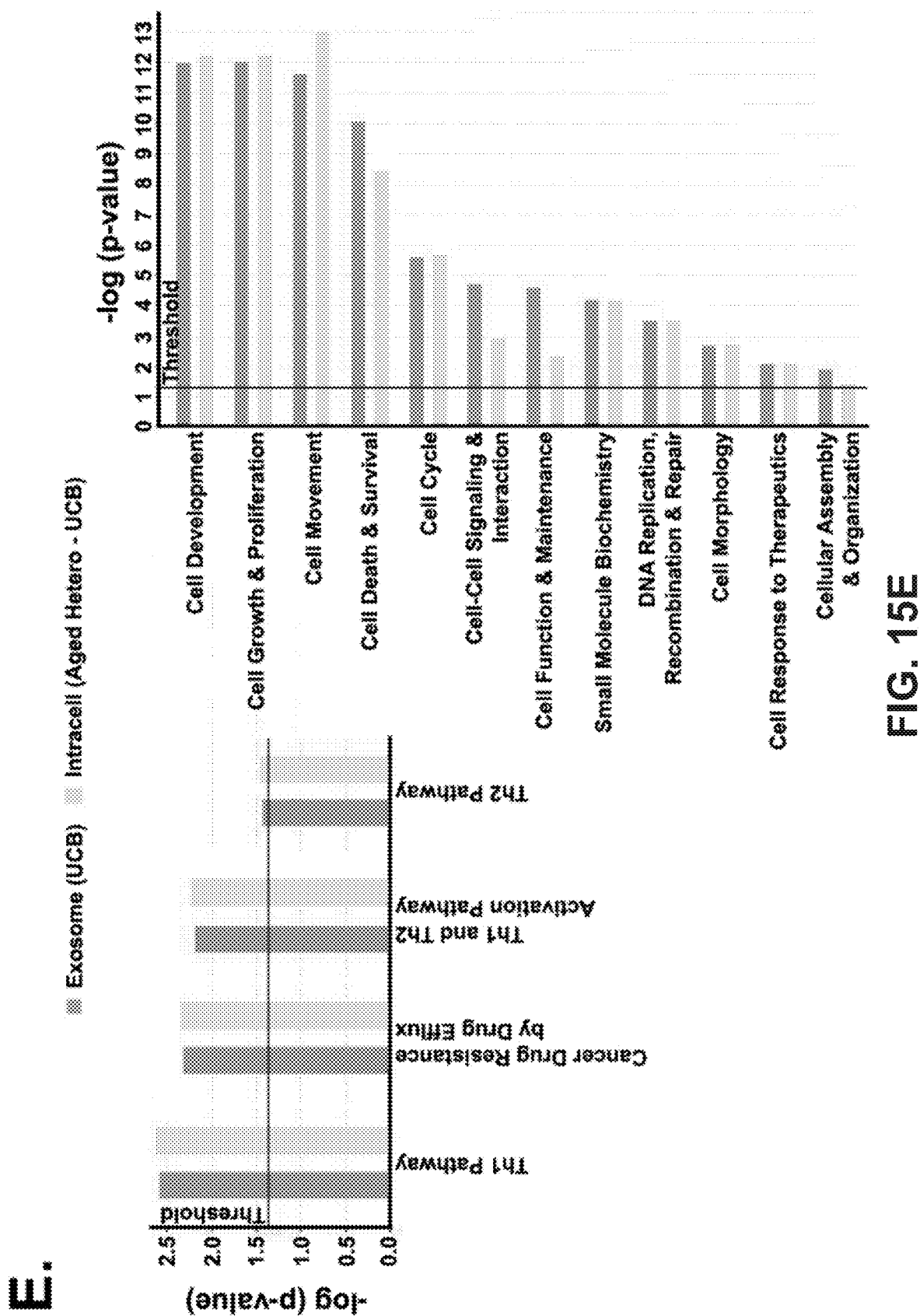

To screen the 6 miRNAs for restorative properties, first evaluated was the clonogenic effect of overexpressing candidate miRNAs in aged isochronic cultures (FIG. 14F). Individual expression of miR-619 or miR-1303 (left plot), or combinatorial expression of select miRNA formulations (right plot), elicited a significant effect on aged colony formation. Interestingly, of 5 formulations that caused a significant increase, 4 included miR-619 and 3 included miR-1303. These formulations were further evaluated to measure their effect on aged T cell activation (FIG. 14G). 2 formulations increased CD4+ T cell activation in unstimulated cells (top left plot), while 4 increased both CD4+ and CD8+ activation after stimulation (right plots). The 4 formulations underwent final screening by measuring their effect on cell-mediated cytotoxicity (FIG. 14H), with miR-619 alone (light purple circles) or in combination with miR-1303 and miR-4497 (dark purple circles) showing significant increases in target lysis. Ascribing a definitive role for these miRNAs within young cells was not obvious from studies inhibiting miR-619 alone or in combination with miR-1303 and miR-4497 and evaluating the effect on clonogenicity (FIG. 14I), T cell activation (FIG. 14J) and cell-mediated cytotoxicity (FIG. 14K). No effect was observed in any of the assays after miR-combo inhibition, while inhibition of miR-619 alone produced a significant increase in young clonogenicity (FIG. 14I, light purple bar) and decrease in cell-mediated cytotoxicity (FIG. 14K, light purple circles).

Identification of Downstream Targets of Restorative miRNAs

Figure 16A:
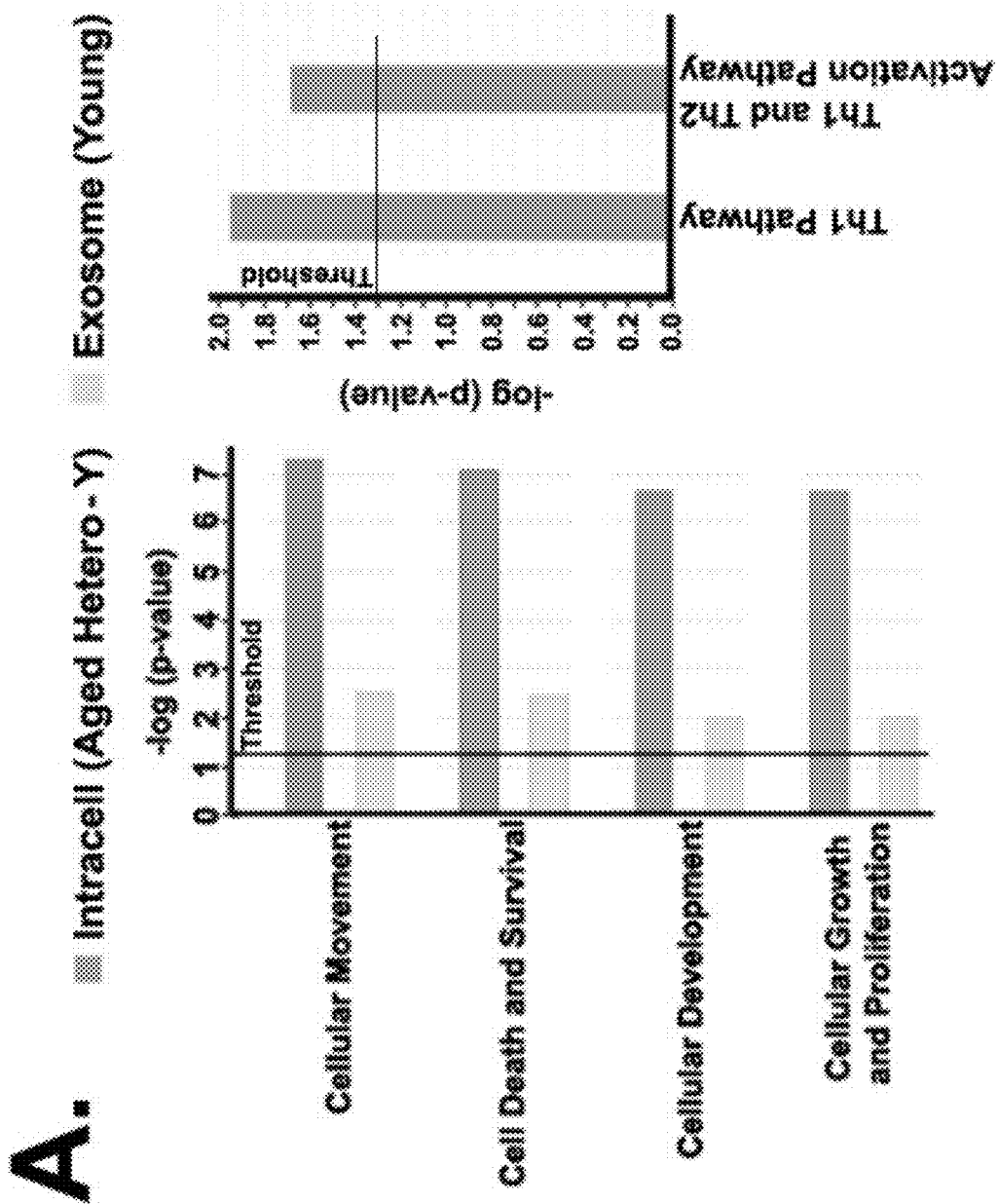
Figure 16B:
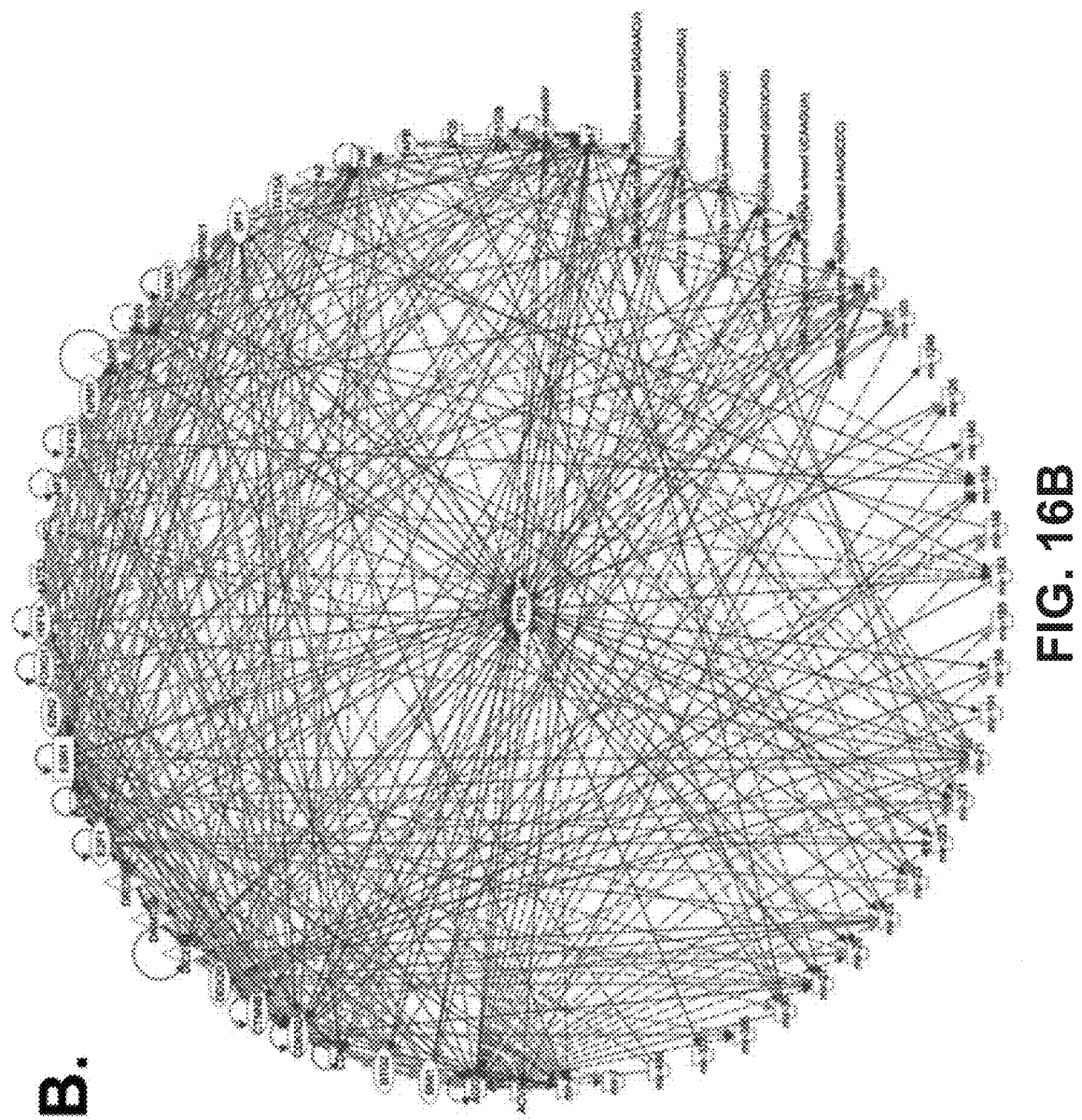

To fully describe the mechanism of heterochronic restoration, the downstream effector pathways targeted by the restorative miRNAs in aged cells was mapped. Network analysis utilizing the young exosomal (FIG. 14A) and aged heterochronic (young) intracellular (FIG. 8A and FIG. 15B) sequencing datasets was performed to map the miRNA interactome (FIG. 16A and FIG. 16B). A number of cellular functions (FIG. 16A, left plot) and canonical pathways (right plot), specifically in Th1 and Th2 cells, were predicted to be involved in this effector-target network. Many of the predicted molecules in the interactome are regulators of cellular senescence, including CDKN2A and p53, the latter of which displayed the greatest network convergence of the 2 datasets (FIG. 16B). Similar network analysis of the UCB exosomal (FIG. 15C) and aged heterochronic (UCB) intracellular (FIG. 15D) sequencing datasets identified related cellular functions, canonical pathways (FIG. 15E) and predicted molecules (FIG. 15F) as for young.

Next, miRNA target prediction software was used to identify direct targets of the 6 restorative miRNA candidates in aged cells. A total of 6101 targets were predicted for the individual miRNAs, so stratifying the number of common targets among the group was done (FIG. 16C). Targets sharing greater than 3 miRNA hits were further evaluated based on the presence or absence of miR-619 and miR-1303, which were shown as significant to restoration (FIG. 14). The remaining targets were first scanned for known expression in relevant tissues, as targets encoding hypothetical proteins and whose expression was restricted to neural tissues were eliminated, and then predicted pathway analysis (FIG. 16D) in the context of the effector-target interactome (FIG. 16D; FIG. 16E) to reveal 5 target candidates (FIG. 16F). Of these 5 candidates, PAX5 was significantly down-regulated in aged cells from heterochronic culture (FIG. 16G, top panel), while both PAX5 and PPM1F were down-regulated in human cells purified from BM of huNSG restored mice compared to non-restored (bottom panel). Basal expression of PAX5 and PPM1F in aged vs. young cells was drastically different, as PAX5 was significantly elevated in aged vs. young cells (FIG. 16H, left bars), while the opposite was true for PPM1F (right bars).

To demonstrate a cause-effect relationship between the miRNA candidates and the predicted downstream targets, aged cells were treated with miR-619 alone or in combination with miR-1303 and miR-4497 (miR-combo), or control RNA, and measured the effect on target gene expression (FIG. 16I, left bar sets). Both targets were significantly decreased following treatment with the miR-combo formulation. A similar effect on target expression was not observed after inhibiting miR-619, alone or in combination, in young cells (right bar sets).

The next set of studies knocked down PAX5 or PPM1F in aged cells (FIG. 15G) and measured effects on T cell activation, clonogenicity and cell-mediated cytotoxicity (FIG. 16J-L). Knockdown of either candidate did not significantly alter T cell activation of unstimulated cells (FIG. 16J, left panels), however both knockdowns displayed a significantly greater percentage of activated CD4+(top right panel) and CD8+(bottom right panel) T cells following stimulation. siRNA knockdown of PPM1F but not PAX5 yielded an increase in aged cell clonogenicity (FIG. 16K) compared to both scrambled RNA (gray bar) and isochronic controls (white bar). No significant difference between PPM1F knockdown and heterochronic control (black bar) was observed, while all other variables were significantly decreased. No effect on cell-mediated cytotoxicity was observed for either knockdown in aged cells (FIG. 16L).

Aged Cell Restoration with miRNA Candidates in the Humanized Mouse Model

The study then examined whether the restorative phenotype induced by the candidate miRNAs (FIG. 17) could produce a similar effect as heterochronic restoration (FIG. 6) in mice engrafted with an aged human immune system. Mice were again transplanted with aged or young CD34+ cells and monitored for human engraftment and hematopoiesis over 15 weeks (FIG. 17A, FIG. 9A). Variability in huCD45+ chimerism was observed among individual young (FIG. 9B, Y03 vs. Y04) and aged (A03 vs. A04) donors. Mice exhibiting a minimum of 1% peripheral blood chimerism were enrolled in the treatment arm of the study and given a second autologous transplant of CD3-depleted MPB cells from 7-day cultures of cells transfected with miR-619 alone or in combination (miR-combo) with miR-1303 and miR-4497, or control RNA. After 15 weeks, mice were sacrificed and lymphohematopoietic phenotype and toxicological analyses performed.

Figure 19A:
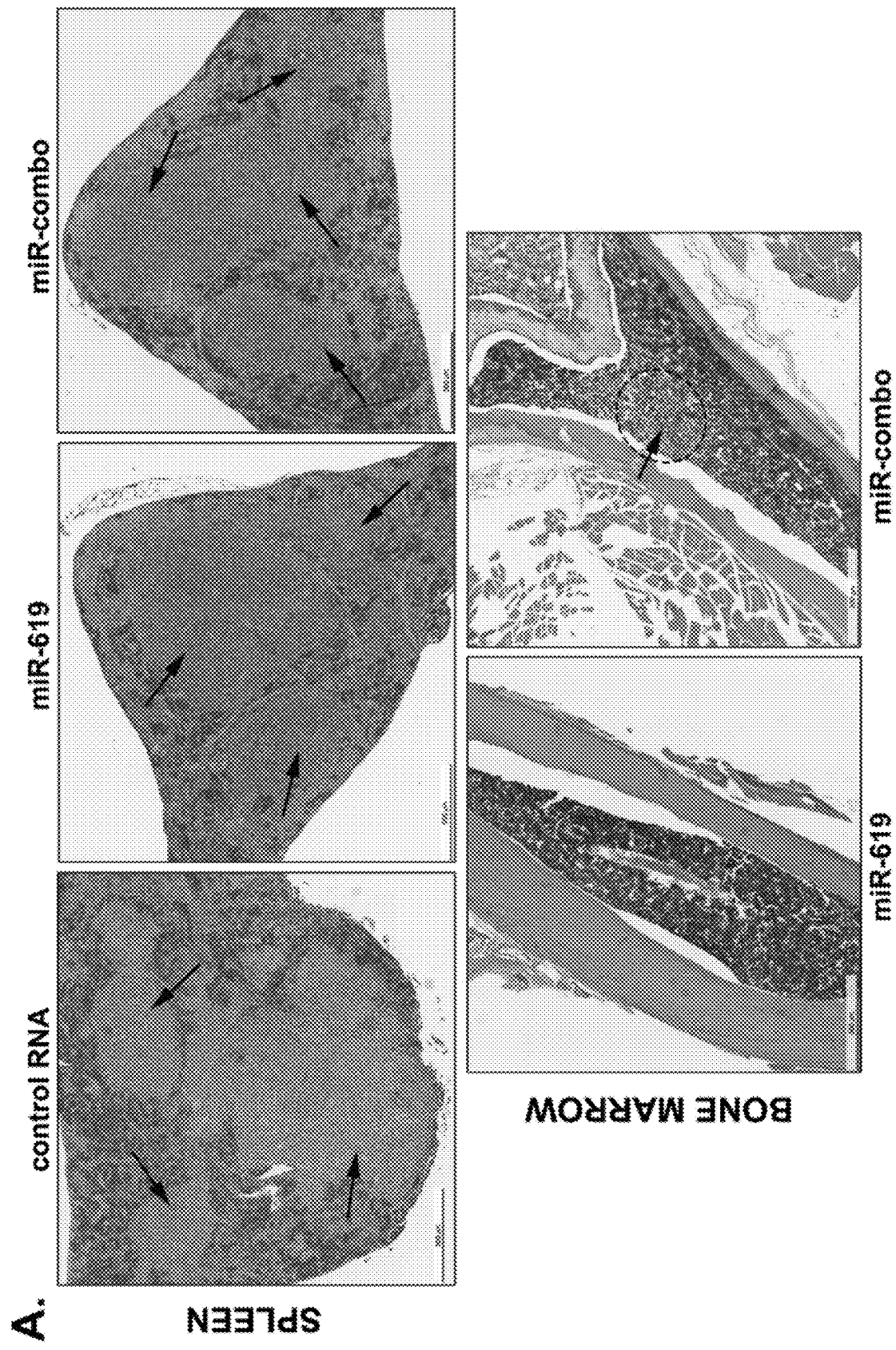

No significant safety concerns were observed for all treatment groups (Supplemental FIG. 18C-E), with mice receiving aged cells treated with miR-619 alone or in combination exhibiting mean overall survivals of 89% and 89%, respectively, compared to 95% for control (FIG. 18C). Total cellularity in BM and spleen from mice transplanted with aged and young cells were unremarkable for all groups (FIG. 18F). Histologic evaluation of immune tissues and major organs showed no evidence of tissue pathology or tumorigenesis (FIG. 19). Enlarged spleens were observed among several mice within both study treatment and control arms. These mice showed increased splenic cellularity due to extramedullary hematopoiesis.

Phenotypic evaluation of human hematopoiesis was performed in blood and BM of miRNA-treated huNSG (FIG. 17B-17F). No significant difference in human chimerism was observed in BM or blood of aged miR-619- or miR-combo-treated transplants compared to control (left black circles) (FIG. 17B). Mice transplanted with aged miR-619 cells demonstrated increased huCD3+(FIG. 17C, far left panel) and significantly increased huCD4+(middle, left panel) cells in blood compared to RNA control (left black circles). These findings were concomitant with decreased huCD8+ cells (middle, right panel) and increased huCD4+/CD8+ ratio (far right panel) in blood of aged miR-619 transplants vs. control. When the mice receiving aged cells treated with either miRNA formulation were grouped into a single cohort, a statistically significant increase was observed in huCD19+ output in blood compared to control (FIG. 17D). Coincident with the increase in lymphoid output, a significant decrease in aged huCD33+ myeloid production in the BM of miR-treated mice compared to control (FIG. 17E) was observed. Together, these data yielded an increased aged lymphoid to myeloid ratio in BM of miR-treated mice compared to control (FIG. 17F). These findings suggest that in aged huNSG transplanted with miR-treated cells, the hematopoietic output demonstrates a decrease in age-related phenotype.

Next, human HSC/HPC and T cell function was evaluated in BM and blood, respectively, of huNSG transplanted with miR-treated aged cells. BM clonogenicity was significantly increased in mice receiving aged cells treated with either miR-619 or miR-combo compared to control (FIG. 17G). PBMCs harvested from all treatment groups were cultured ex vivo but did not show any significant difference in huCD4+ or huCD8+ activation following stimulation with anti-CD3/CD28 compared to control (FIG. 17H).

The final set of studies examined the effect of miRNA-based restoration on aging-related gene and protein expression in huNSG, as well as the effect on the predicted targets PAX5 and PPM1F (FIG. 16). Human cells were purified from chimeric BM to first evaluate target gene expression (FIG. 17I), and second to perform pathway-focused qPCR arrays to evaluate 145 genes related to human senescence and aging (FIG. 17J, FIG. 20). Human cells isolated from the BM of huNSG transplanted with aged cells treated with the miR-combo formulation showed a significant decrease in PAX5 (FIG. 17I, left set of bars) and PPM1F (right set of bars) expression.

For the gene expression arrays, cells isolated from mice treated with the miR-combo formulation also displayed a decrease in more than half of all genes linked to senescence and aging (FIG. 17J, heat maps and pie charts). This correlated with a significant fold-decrease in the senescence array (left bar graph) and a substantial fold-decrease in the aging array (right bar graph). Next, blood plasma isolated from miR-treated and control mice was probed for 68 factors linked to the SASP (FIG. 17K). Similar to the expression pattern of the gene array studies, plasma from miR-619 and miR-combo treated mice showed decreases in 51.4% and 45.6% of SASFs, respectively (heat map and pie charts), with significant decreases in total expression (bar graph) compared to control.

It was then examined whether PBMCs harvested from the blood of all treatment groups, cultured ex vivo and stimulated with anti-CD3/CD28 differentially produced T cell cytokines (FIG. 17L). Conditioned media collected from the cultures after 72 h were used to probe human T cell cytokine arrays. Results showed a predominantly Th2 cytokine profile (IL-4, IL-5, IL-9) in miR-treated cells compared to control prior to stimulation (left heat map), with a switch to Th1 cytokine profile (IFNγ, IL-12, IL-10) following stimulation (right heat map). Increased production of both TGFβ and IL-17 following stimulation also indicated the presence of regulatory T cells and Th17 cells, respectively. Taken together, these data suggest a functional response to a T cell stimulus by phenotypic switching and immune activation.

Comparison of Heterochronic Vs. miRNA-Based Restoration in the huNSG Model

The findings from both animal studies illustrated that both heterochronic- and miRNA-based approaches to aged immune restoration was feasible. Thus, the results of both animal studies were indirectly studied by normalizing each study's treatment group(s) to the control group for key experimental readouts (FIG. 21). For the 1st animal study, heterochronic was normalized to isochronic data, and for the 2nd animal study, miRNA treatments were normalized to RNA control data.

For the blood T cell phenotypic panels (CD3+, CD4+, CD8+, CD4+/CD8+), similar results were observed among the heterochronic—(FIG. 21A) and miR-619-treated groups. However, the miRNA-treated groups showed significantly increased levels of CD19+ cells in blood (FIG. 21B), and significantly decreased levels of CD33+ cells in BM (FIG. 21C, left panel) compared to heterochronic treatment. No differences were observed for lymphoid/myeloid ratio (right panel). For the clonogenic assay, significant increases in clonogenicity for all treatment groups were observed, but treatment with miR-619 alone or in combination produced a more robust finding (FIG. 21D). Interestingly, for the gene array studies (FIG. 21E), the miR-combo treatment yielded the most dramatic downregulation of senescence-related genes (right panel) compared to either miR-619 alone or heterochronic treatment and was comparable to heterochronic for the aging array (left panel). Last, both miRNA treatments produced a significant decrease in SASF production (FIG. 21F) compared to heterochronic treatment.

Collectively, the findings from this comparative analysis suggest that treatment of autologous aged cells with either miRNA formulation yields a more robust immune and stem cell restoration compared to heterochronic culture and lends support to further develop these formulations in other relevant preclinical models of disease as an immune therapy.

DISCUSSION

Research of the past decade has provided a fundamental understanding of aging biology that has driven new and innovative approaches to extend organismal lifespan and healthspan. The utilization of young blood and factors present in the young systemic circulation to rejuvenate aged tissues, elegantly demonstrated by studies of heterochronic parabionts, is among these innovations. However, while young blood has been evidenced to contain factors that restore select tissue function, attempts to identify the restorative factors have been limited and identification of causal molecules refuted. Further, these initial findings were restricted to mouse blood, as only recently has a study of human UCB demonstrated a comparable effect in the CNS. To build on these limitations, the goal of these studies was to develop an adaptation of the heterochronic parabiosis model that would be immediately translational through utilization of blood from young and aged human donors. It was rationalized that young individuals with extremely healthy lifestyles should encompass high levels of restorative factors within their blood. A number of strict inclusion and exclusion criteria to select for good sleeping habits, diet and regular exercise were employed for young donor recruitment (Table 4). Selecting healthy aged donors was done in a diligent way, as it was desired to have any differential correlates to be associated with the temporal aspect of aging rather than age-related co-morbidities. This allowed for therapeutic factors that were uncovered to be applied in both preventative and interventional settings.

A facet of parabiotic studies that remained to be addressed was the effect of the young systemic circulation on the lymphohematopoietic system of the aged parabiont. The hematopoietic and immune systems are vital components of how organisms function. Blood cells perfuse most tissues of the body and serve local housekeeping and surveillance roles within the tissue microenvironment. The goal of these studies was to target the declining function of aging HSCs as a means to treat and delay the onset of age-related diseases. This approach modulated aging-related pathways to restore function to the aged HSC compartment. For the current investigation, it was important to develop a sophisticated animal model that could recapitulate the aging human lymphohematopoietic system and allow translational studies. This is believed to be the first study to engraft aged CD34+ cells for creation of humanized mice, as most approaches utilize young or primitive cells from UCB or fetal tissues. The aged huNSG model allowed the simulation of an adoptive cell therapy product, in which aged blood cells were restored ex vivo and then autologously transplanted into the aged individual. It was found that huNSG mice receiving adoptive restoration therapy exhibited significant increases in BM clonogenicity and lymphopoiesis compared to age-matched controls (FIG. 7). These findings are therapeutically-relevant, as many of the age-related increases in morbidity and mortality of the aging immune system can be attributed to HSC exhaustion and myeloid bias.

This study primarily utilized cells from MPB to establish heterochronic cultures. MPB comprises a heterogeneous population that is representative of both BM and the systemic circulation. It was rationalized that cultivation of such a complex cell matrix would simulate an ectopic microenvironment for paracrine communication among young and aged cells. Several unexpected observations were made from these culture studies. First, a partial role for young CD34+ cells was identified in the restorative mechanism (FIG. 5). This population encompasses HSCs, HPCs and EPCs, however other young immune or stromal populations likely contribute to the restorative phenotype, as CD34- depletion was not completely mitigating. Second, hetero- chronic restoration was sustainable. Restored aged cells propagated restoration in culture (FIG. 5) and in huNSG mice (FIG. 7). The latter conclusion was supported by gene expression studies of purified human cells from restored mouse BM. Here, it could be argued that decreases in senescence- and aging-related gene expression occur primarily in cells from the original graft, since the second transplant comprised a relatively low cell dose compared to the number of cells that would be the product of endogenous human hematopoiesis. Further, no spike in human chimerism was observed following the second transplant to suggest massive expansion in the BM compartment (FIG. 6).

Investigation into the paracrine mechanism of heterochronic restoration revealed a causal role for exosomes and miRNAs (FIGS. 12 and 14). Exosomes contain a subset of proteins, lipids and nucleic acids that are derived from the parent cell and which are shuttled between cells. miRNAs taken up by target cells can change target cell behavior by classical miRNA-induced silencing of target mRNAs. This form of intercellular communication is involved in numerous physiological processes, including immune regulation. Exosomes have gained substantial traction as a therapeutic for a number of indications ranging from cancer to immune-related diseases to regenerative medicine. A mechanistic role was attributed to exosomes and miRNA based on findings from studies of purified young exosomes and inhibition of exosomal miRNA biogenesis, respectively (FIG. 12). There is a distinct possibility that other soluble factors beyond exosomes contribute to restoration, since proteins found in UCB and young mouse plasma, such as TIMP2, have restored cognitive function in aged mice. Further, exosomes also house other species of non-coding RNA, such as long non-coding RNAs (lncRNAs) and circular RNAs, that could be involved in restoration. miR-619-5p was identified as a stand-alone restorative factor found within young exosomes that could induce restoration independently of young cells (FIG. 14). While little is known regarding physiological function, miR-619 may be a unique miRNA (umiRNA). umiRNAs are known to have hundreds of target genes and bind to mRNAs with high affinity, thus the suggested downstream effect of miR-619 would be broad-acting and consistent with gene expression changes observed during restoration. In silico prediction of pathways targeted by young exosomal miRNA included master regulators of cell senescence, such p53, p21 and p16INK4a (FIG. 16). Network analysis of restorative miRNA (FIG. 14) in the context of these pathways predicted 5 direct targets in aged cells, of which PAX5 and PPM1F were validated. The PAX5 gene encodes the B-cell lineage specific activator protein (BSAP) that is expressed at early, but not late stages of B-cell differentiation, while the PPM1F gene encodes a member of the PP2C family of Ser/Thr protein phosphatases that are negative regulators of the cell stress response pathways. FIG. 22 summarizes the downstream pathways engaged by young exosomal miRNA following PAX5 and PPM1F mRNA target engagement in the aged cell. Both PAX5 and PPM1F directly and indirectly regulate pathways involved in cellular senescence, respectively. PAX 5 can directly activate p53 and p21 signaling, while PPM1F can activate similar pathways indirectly through CaMKIIγ.

A second huNSG study was performed, this time utilizing two separate formulations of candidate miRNAs to induce aged cell restoration prior to autologous transplant (FIG. 17). The first formulation contained a high dose of miR-619 alone (90 nmol), while the second contained a combinatorial formulation including miR-619, miR-1303 and miR-4497 transfected at 30 nmol each to yield an equal total RNA dose as the standalone treatment. Interestingly, with the miRNA treatments it was again observed therapeutic benefit as defined by significant increases in BM clonogenicity and lymphopoiesis, as well as decreases in aging- and senescence-related gene and protein expression. When indirect comparative analyses were performed among the heterochronic-vs. miRNA-based treatments (FIG. 21), a similar effect on T cell phenotype was observed; however, the miRNA-treatments were more efficacious in boosting B cell production, decreasing myeloid output and increasing clonogenicity. Further, the miRNA combination treatment of miR-619, miR-1303 and miR-4497 proved to be efficacious in improving stem cell function and decreasing aging-related gene and protein expression. These findings provide support to further develop this combination as a novel therapeutic.

These studies highlight at least 3 potential approaches that could be implemented clinically: (1) an adoptive, autologous cell product derived from heterochronic cultivation; (2) similar as 1 but replacing young cells with a miRNA combinatorial formulation to induce restoration; or (3) a pharmacological inhibitor of PAX5, PPM1F or a downstream component of their signaling pathways. It is shown that the disclosed model is restorative for aged cells harvested from healthy donors, thus development of these approaches as a preventative therapy to enhance endogenous stem cell and immune function before the onset of disease is logical (FIG. 23). Further, there is also the exciting possibility of applying these approaches as an interventional therapy for aged patients afflicted with cancer or infectious disease, as either an autologous cell-based or cell-free restoration therapy. Existing immuno-oncology (I-O) biological therapies, such as checkpoint inhibitors and bispecific antibodies, and cell-based therapies, such as chimeric antigen receptor (CAR) T cells, utilize a targeted approach to coax the immune system to recognize and attack cancer cells. A restorative product could be administered in combination with these therapies to bolster the endogenous immune system in advance of the targeted response, an approach shown recently to be effective in mice. Additional studies will test patient blood samples to evaluate and demonstrate that the disclosed approach enhances tumor clearance either alone or in combination with existing I-O drugs.

Studies have relied on CD34-rich sources such as MPB and UCB. However, the translating these data to non-mobilized blood may be attractive and possible, since mobilization is costly and potentially impractical for cancer patients. Beyond blood, determining whether this approach could functionally restore other aging tissues, such as stromal vascular fraction (SVF) harvested from adipose is attractive. SVF is a rich source of preadipocytes, adipose-derived stem cells (ADSCs), EPCs and other resident immune cells, which can be utilized clinically for various orthopedic applications. Since restorative factors directly target ubiquitous pathways related to aging and senescence, this approach should be therapeutic for a number of aging tissues. Extrapolation of these findings to these other aging systems is possible in view of these studies.

Example 2: Small Molecules Inhibit Proteins Having Roles in Cellular Dysfuntion Aged TNCs (20×106 cells per sample) were cultured with CaMKP inhibitor (FT-0640107 shown below) at the following concentrations 25 uM, 10 uM, 5 uM, 1 uM & 0 (vehicle). After 48 and 72 hours, cells were harvested, counted using Turk's solution and percent viability assessed using Trypan blue exclusion.

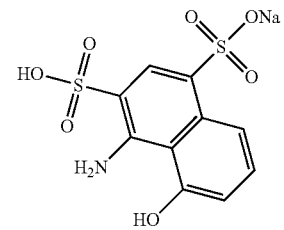

At 72 hours following treatment with the CaMPK inhibitor, FT-0640107, or vehicle, cells were harvested, counted and viability measured using Trypan blue exclusion. Cells treated with 1 μM FT-0640107 for 72 hours demonstrated an average cell viability of 96.3%, whereas treatment with vehicle alone yielded an average cell viability of 95.7% and cells treated with a high dose of 25 μM of the compound exhibited a viability of 93%. Further, cells treated with 1 μM FT-0640107 for 72 hours yielded an increase in cell number compared to both vehicle control and high dose treatment (25 μM). The data were observed for donor A04, with no significant difference observed for donor A03 at 48 or 72 hour timepoints. These findings demonstrate that pharmacological inhibition of CaMPK with FT-0640107 can exert a therapeutic benefit on aged mobilized blood cells by improving cell viability and survival in culture.

Example 3

Sample and Techniques

Peripheral blood mononuclear cells were collected from subjects having undergone a Stage B preparation involving the administration of the mobilizer NEUPOGEN® (filagrastim). For the following experiments peripheral blood mononuclear cells (1×5 mL vial per subject) were found to contain the following number of nucleated cells:

| Subject | Approximate Age | Sex | Cell Number |
|---------|-----------------|--------|-------------|
| R1 | 70 | Male | $1.8 \times 10^8$ |
| R2 | 70 | Male | $2.7 \times 10^8$ |
| R3 | 60 | Male | $2.2 \times 10^8$ |
| D1 | 26 | Male | $3.3 \times 10^8$ |
| D2 | 30 | Male | $1.8 \times 10^8$ |
| D3 | 28 | Female | $1.9 \times 10^8$ |

The cells following harvest were cryopreserved and upon thawing were determined by trypan blue dye exclusion and flow cytometry to be greater than 95%.

The percentages of stem cell, progenitor cell and mature cell populations were determined by flow cytometry. Table 6 shows the average percentage of hematopoietic stem cells (HSCs) and early hematopoietic progenitor cells (HPCs) to be ~0.5% and 1.0% respectively of the total mobilized cell collection.

TABLE 6

|  | Hematopoietic Cells CD45+ | Hematopoietic Stem Cells CD34+ CD38− | Hematopoietic Progenitor Cells CD34+ CD38+ | T Cells CD3+ | NK Cells CD56+ |
|---|---|---|---|---|---|
| % Total Cell Population | | | | | |
| R1 | 64.4 | 0.5 | 0.3 | 39.6 | 4.2 |
| R2 | 59.9 | 0.4 | 1.6 | 29.7 | 7.5 |
| R3 | 86.3 | 0.4 | 0.3 | 56.7 | 2.9 |
| D1 | 64.0 | 1.0 | 1.5 | 32.4 | 5.7 |
| D2 | 59.9 | 0.3 | 0.8 | 36.0 | 4.1 |
| D3 | 59.0 | 4.1 | 1.0 | 10.5 | 5.5 |
| % Hematopoietic (CD45+) Population | | | | | |
| R1 | 100 | 0.7 | 0.4 | 61.5 | 6.5 |
| R2 | 100 | 0.7 | 2.8 | 49.5 | 12.5 |
| R3 | 100 | 0.4 | 0.4 | 65.7 | 3.4 |
| D1 | 100 | 1.5 | 2.4 | 50.5 | 8.9 |
| D2 | 100 | 0.5 | 1.3 | 60.1 | 6.9 |
| D3 | 100 | 7.0 | 1.7 | 51.7 | 9.3 |

TABLE 7

|  | Non-Hematopoietic Cells CD45− | Mesenchymal Stem Cells CD29+ CD44+ CD105+ | Endothelial Progenitor Cells CD31+ CD105+ |
|---|---|---|---|
| % Total Cell Population | | | |
| R1 | 17.9 | 0.11 | 0.06 |
| R2 | 38.7 | 0.91 | 0.79 |
| R3 | 11.1 | 0.22 | 0.18 |
| D1 | 33.4 | 0.52 | 0.44 |
| D2 | 26.7 | 0.69 | 0.65 |
| D3 | 40.4 | 0.63 | 0.46 |
| % Non-Hematopoietic (CD45−) Population | | | |
| R1 | 100 | 0.60 | 0.35 |
| R2 | 100 | 2.34 | 2.05 |
| R3 | 100 | 1.94 | 1.58 |
| D1 | 100 | 1.57 | 1.32 |
| D2 | 100 | 2.57 | 2.43 |
| D3 | 100 | 1.56 | 1.14 |

Receiver cell samples (i.e., R1, R2, and R3) were individually paired with donor cell samples (i.e., D1, D2, and D3) and the pairs co-cultured in a transwell culture cell for four weeks. The morphology of the cells was studied at 2 weeks into the co-culture and at 4 weeks of co-culture. Gene expression arrays, protein arrays, and telomere length experiments compared freshly defrosted cells from the collection tubes (referred to as the baseline donor cell sample or baseline receiver cell sample) with cells at the 4-week study endpoint (referred to as restored cell samples).

At the midpoint of the co-culture (i.e., 2 weeks) baseline receiver cell samples displayed morphologies consistent with low viability. Restored cell samples displayed a robust cellular morphology that included colony formation.

Example 4

Protein array analyses were carried out using conditioned media from the baseline donor cell sample or baseline receiver cell sample. The conditioned media was mixed with like cellular protein extracts and applied to the custom-designed arrays which consisted of antibody probes for 68 factors linked to cellular aging and senescence, collectively referred to as the senescence-associated secretory factors (SASF). Quantitative PCR gene array analyses were carried out by extracting RNA from the baseline samples or the co-cultured donor and receiver samples. The data presented represents the average metric determined for either the baseline donor cell sample, the baseline receiver cell sample, or the restored cell sample.

The results of the gene array analyses demonstrated that there was less than a 2-fold difference in the majority of senescence-related genes for the baseline donor cell samples and the baseline receiver cell samples, FIGS. 27 and 28. In all of the figures presented as plots of the gene expression analysis, the squares represent genes which are expressed at a lower level following the cellular restoration, triangles represent genes expressed at a higher level following restoration and circles represent genes whose expression level was determined to be substantially similar to the expression level prior to cellular restoration. The designation of "substantially similar" is qualitative and reflects the close proximity of the value to the line. The data suggests the techniques disclosed herein for the mobilization and collection of donor cell samples and receiver cell samples select for non-senescent cells. The results of the protein-based arrays, which assessed levels of senescence-related factors produced either within the cells or released into the culture media, similarly displayed little difference between the senescence-related factors among the donor cell sample and receiver cell sample, FIG. 29. The mean telomere length between the donor cell samples and receiver cell samples were not found to be significantly different, FIG. 30.

The results demonstrate that the gene expression profiles and protein expression profiles of the donor cell samples and receiver cell samples were similar despite the difference in age of the subjects. Further, despite the difference in age between the donor subjects and receiver subjects, the cells had similar telomere lengths.

Example 5

The restored cell samples were investigated using the gene and protein arrays of Example 2 and are shown in FIGS. 31 and 32, respectively. For each of the restored cell samples investigated, approximately half of the examined genes (as designated by the "Xs" on the Figure) were expressed at a lower level in the restored cell samples when compared to the baseline donor cell sample. The genes that were expressed at a lower level were genes associated with improving cellular function and decreasing the extent of cellular senescence and aging. The data suggests the gene expression profile of the restored cell samples were altered by the transwell restoration and more closely approximated that of the baseline donor cell sample than that of the baseline receiver cell sample. The data demonstrate the restore cell sample exhibited a decreased expression of senescence-related genes of receiver cells and/or cell types compared to the receiver cell sample, wherein senescence-related genes are defined as the RBGEP, by quantitative polymerase chain reaction as shown in FIGS. 31 and 32.

Further, examination of the clustering analyses revealed a subset of genes (designated gene set A) whose expression was consistently elevated in the baseline receiver cell sample but whose expression was reduced in the restored cell sample. The expression of Gene Set A in the restored cell sample was reduced to levels comparable to those observed in the baseline donor cell sample. Similarly, as shown in FIG. 33A, stratification of the protein arrays identified 13 factors that showed a similar elevated trend in the baseline receiver cell samples when compared to that of the baseline donor cell samples. Likewise, as shown in FIG. 33B, the restored cell samples exhibit a level of expression of the identified 13 factors comparable to that observed in the baseline donor samples. These findings demonstrate a methodology for monitoring the restoration of the receiver cell sample by gene and protein array analyses. Further, these data demonstrate the restored cell sample exhibited a decreased expression of senescence-associated secretory factors compared to the receiver cell sample at baseline, wherein senescence-associated secretory factors are defined in Table 2, as measured by antibody array, as in FIGS. 33, 34 and 35, or enzyme-linked immunosorbant assay.

Example 6

Gene and protein arrays of restored cell samples for individual pairs of baseline donor cell samples and receiver cell samples were investigated. Specifically, receiver cell sample R1 was co-cultured in a transwell experiment with donor cell samples from D1 (FIG. 34B), D2 (FIG. 34C), and D3 (FIG. 34D) respectively. Hierarchical clustergrams showed that all of the genes investigated are elevated in the receiver cell sample (FIG. 34A) while these same genes are expressed at low to modest levels in D1, D2 and D3. The restored cell sample was found to have a gene expression comparable to that of the level of expression observed for D1, D2, and D3. Experiments carried out using receiver cell samples R2 or R3 with donor cell samples D1, D2, or D3 exhibited similar results.

Example 7

The nature of the soluble particles passing through the permeable membrane in the transwell co-culture experiments was investigated. Specifically, transwell co-culture experiments were carried out in the presence or absence of manumycin. Manumycin, -[(1S,5S,6R)-5-hydroxy-5-[(1E, 3E,5E)-7-[(2-hydroxy-5-oxo-1-cyclopenten-1-yl)amino]-7-oxo-1,3,5-heptatrien-1-yl]-2-oxo-7-oxabicyclo[4.1.]hept-3-en-3-yl]-2E,4E,6R-trimethyl,2,4-decadienamide, is an antibiotic that acts a potent and selective farnesytransferase inhibitor. Mannumycin is also known to inhibit the release of exosomes. Restored cells co-cultured in the presence of 5 µM manumycin displayed less robust morphology than restored cells cultured in the absence of manumycin. Gene expression analysis of restored cell samples co-cultured in the presence of manumycin did not display a change in expression levels similar to those observed in the absence of manumycin. In contrast, protein expression analyses of restored cell samples co-cultured in the presence of manumycin found elevated levels of all proteins investigated when compared to the proteins levels for restored cell samples co-cultured in the absence of manumycin, FIG. 35. The data suggests the role of exosome/microvesicles in mediating the disclosed cellular restoration process. Further support for the role of exosome/microvesicles in mediating the disclosed cellular restoration process is shown in FIG. 36. FIG. 36 displays the telomere length for a restored cell sample co-cultured in the presence or absence of manumycin. The telomere length in the presence of manumycin is decreased suggesting exosome/microvesicles play a role in the restoration process.

Example 8

The innate immune function of the baseline donor cell samples and receiver cell samples were evaluated using a natural killer cell assay, FIG. 37. The assay was also performed on restored samples, FIG. 38. The restored cell samples are identified by the receiver cell sample-donor cell sample that were contacted, for example, receiver cell sample 3 and donor cell sample D2 are listed as R3-D2. The data demonstrate that the restored cell samples R1-D3, R1-D2, R3-D2, and R2-D2 maintained proper immune function while restored cell sample R1-D1 had decreased immune function. The data illustrate that for D2 and D3 the restored cell samples are characterized by an improvement in cellular immune function as quantified by natural killer cell cytotoxicity assay, as illustrated in FIGS. 37 and 14, and/or T-cell mitogen response assay.

The hematopoietic function of the baseline donor cell samples and receiver cell samples were evaluated using a clonogenic assay, FIG. 39. The data demonstrate that the restored cell samples R1-D3, R1-D2, R3-D2, and R2-D2 maintained proper hematopoietic function while restored cell sample R1-D1 had decreased hematopoietic function. The data illustrate that the restored cell sample is characterized by an improvement in cellular hematopoietic function as quantified by hematopoietic stem cell clonogenic assay, as observed in FIG. 39.

Figure 40A:
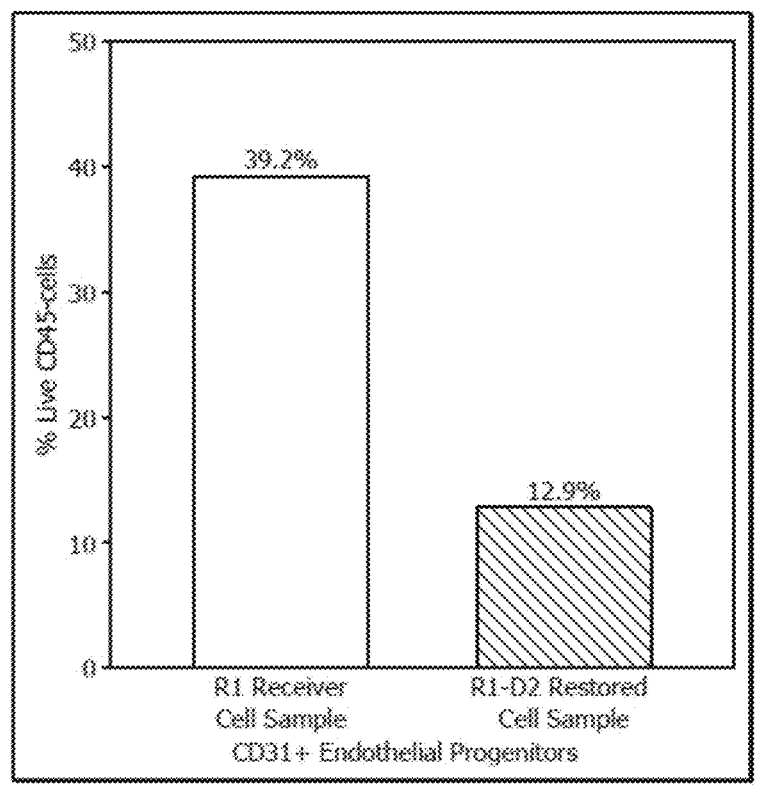
Figure 40B:
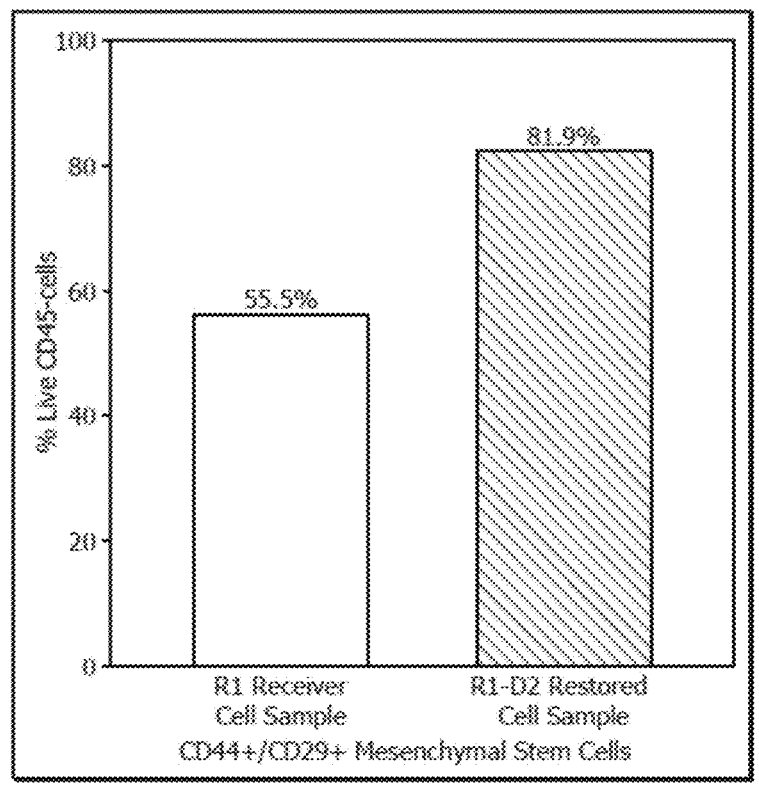
Figure 40C:
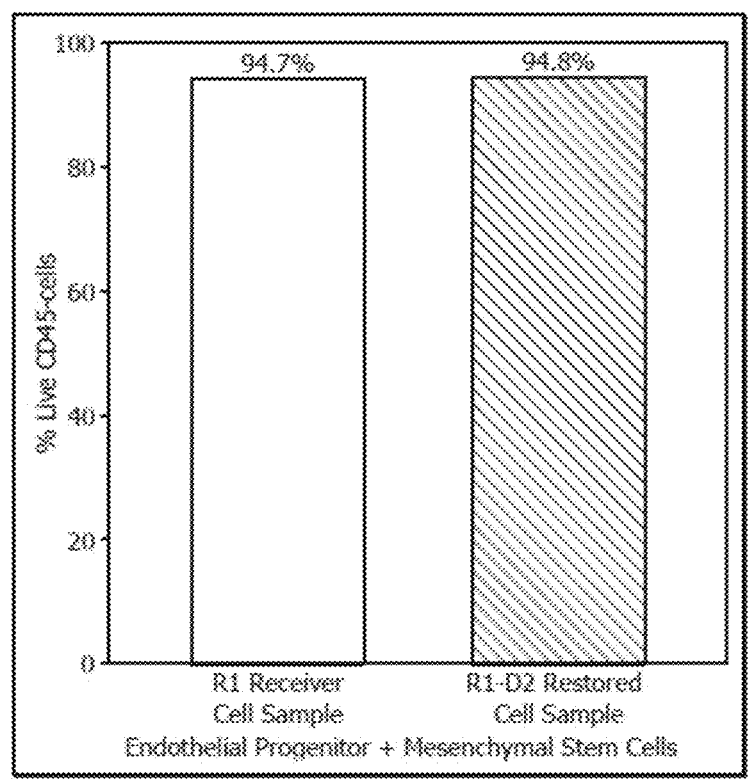
Figure 40D:
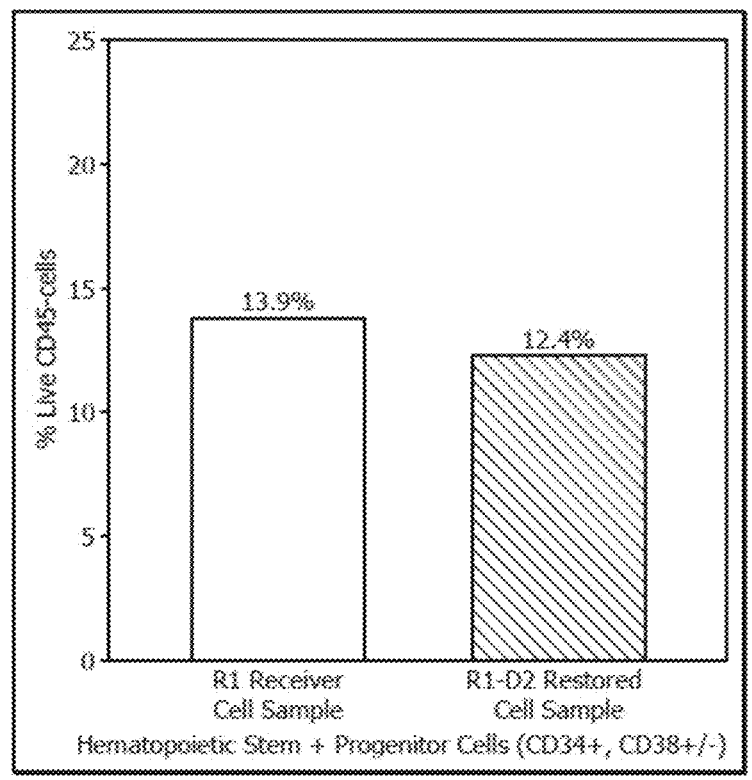

Cell population analyses were performed by flow cytometry to investigate whether the original distribution of cell types in the receiver cell sample, R1, was altered by the 4-week restoration process with donor cell sample D2. The results, shown in FIGS. 40A-40D, demonstrated that although there was some loss in the percentage of endothelial progenitor cells (FIG. 40A), there was an expansion of the mesenchymal stem cell compartment (FIG. 40B). As shown in FIG. 40C, a combination of the percentages of non-hematopoietic cells (i.e., from FIGS. 40A and B) indicated that the total percentages of these populations were maintained during the restoration process. Similarly, as shown in FIG. 40D, the percentages of hematopoietic stem and progenitor cells were insignificantly changed. These data demonstrate that the restored composition prepared by the methodologies disclosed herein is characterized by a lack of change in the percentage of hematopoietic stem cells, hematopoietic progenitor cells, mesenchymal stem cells and endothelial progenitor cells, herein termed the "stem cell pool", in receiver cells after cellular restoration compared to receiver samples at baseline, as observed in FIG. 40, by flow cytometry.

Example 9

To evaluate whether in vitro restoration could be propagated, aged and young cells from isochronic cultures (+iso aged+young) or aged cells from heterochronic culture (+heteroaged) were harvested at day 7 and transferred to fresh transwell cultures with naïve aged cells. As control, naïve aged cells were also placed in isochronic culture (gray bar). After an additional seven days, aged cells from the 2nd set of cultures were evaluated by clonogenic assay. The results are presented in FIG. 41.

Example 10: Administration of a Combination Therapy

This is a prophetic example. 200 healthy aged (>60 y/o) individuals are recruited. The study participants are split into a group of 100 experimental patients and 100 control patients. All patients are dosed subcutaneously with STEM-GEN® for 5 days to stimulate the bone marrow (BM) to expand the HSC/HPC compartment and mobilize it into the peripheral blood stream. On the 5th day, mobilized peripheral blood (MPB) are collected with the Spectra Optia® Apheresis System using continuous flow centrifugal technology directly into the collection bag. Leukapheresis is performed according to the manufacturer's instructions to process 18 L of blood at a flow rate of 50 to 100 mL per min. The cells of the experimental patients are cultured and treated with RNAi(s) (SEQ ID NOs: 15, 17, and 19) along with a small molecule CaMKP inhibitor shown here:

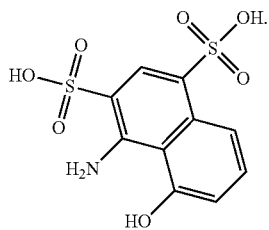 [SMILES: Nc1c(S(=O)(=O)O)cc(S(=O)(=O)O)c2cccc(O)c12]

After treatment of the cells by the combination of RNAi(s) and the small molecule inhibitor, the treated cells are analyzed. It is noted that the treated cells in the experimental group have statistically significant increased innate immune function, increased telomere length, and lower replicative stress relative to the cells from the control group. The experimental cells are reintroduced to the experimental patients and the control cells to the control patients. After 5 years of patient tracking, the experimental patients report becoming sick less often (25% reduction) than the control group, having a lower incidence of cancer (60% reduction), having less soreness in their joints (45% reduction as measured using the VAS score), and generally report feeling better. The experimental patients also report improved cognitive performance and function (35% increase relative to control as measured using the Cognitive Function Composite Score), have measured improvements in cardiovascular output (increase in cardiac output of 42%), and muscular health (as measured by strength increases relative to controls during weight training). The results are statistically significant.

Example 11: Administration of RNAi(s)

This is a prophetic example. 100 healthy aged (>60 y/o) individuals are recruited. The study participants are split into a group of 50 experimental patients and 50 control patients. All patients are dosed subcutaneously with Neupogen® for 5 days to stimulate the bone marrow (BM) to expand the HSC/HPC compartment and mobilize it into the peripheral blood stream. On the 5th day, mobilized peripheral blood (MPB) are collected with the Spectra Optia® Apheresis System using continuous flow centrifugal technology directly into the collection bag. Leukapheresis is performed according to the manufacturer's instructions to process 18 L of blood at a flow rate of 50 to 100 mL per min. The cells of the experimental patients are cultured and treated with RNAi(s) (SEQ ID NOs: 9-15).

After treatment of the cells by the combination of RNAi(s), the treated cells are analyzed. It is noted that the treated cells in the experimental group have statistically significantly increased stem cell clonogenicity, increased cytotoxic function, increased mitogen- and antigen-induced lymphocyte proliferation and activation relative to the cells from the control group. The experimental cells are reintroduced to the experimental patients and the control cells to the control patients. After 4 years of patient tracking, the experimental patients report more active lifestyles, feeling younger, and generally better health. After 5 years of patient tracking, the experimental patients report becoming sick less often (35% reduction) than the control group, having a lower incidence of cancer (40% reduction), and having less soreness in their joints (65% reduction as measured using the VAS score). The experimental patients also report improved cognitive performance and function (55% increase relative to control as measured using the Cognitive Function Composite Score), have measured improvements in cardiovascular output (increase in cardiac output of 62%), and muscular health (as measured by strength increases relative to controls during weight training). The results are statistically significant.

Example 12: Administration of RNA(i)s

This is a prophetic example. 100 healthy aged (>60 y/o) individuals are recruited. The study participants are split into a group of 50 experimental patients and 50 control patients. The experimental group receives a composition comprising RNAi(s) (SEQ ID NOs: 15-20) in liposomes intravenously one a week for two months. The control group receives a placebo.

After 6 months, the cells of the groups are mobilize and collected. After treatment of the cells by the combination of RNAi(s), the cells have decreased senescent behavior, has increased innate immune function, increased telomere length, lower replicative stress relative to the patient cell, increased stem cell clonogenicity, increased cytotoxic function, increased mitogen- and antigen-induced lymphocyte proliferation and activation, decreased myeloid to lymphoid ratio, increased CD4 to CD8 T lymphocyte ratio, decreased expression of senescence-associated secretory proteins, and/or decreased expression of senescence- and aging-related genes relative to the control cells. The patients indicate they have a feeling of better health. After 5 years of patient tracking, the experimental patients report becoming sick less often (75% reduction) than the control group, having a lower incidence of cancer (73% reduction), and having less soreness in their joints (55% reduction as measured using the VAS score). The experimental patients also report improved cognitive performance and function (75% increase relative to control as measured using the Cognitive Function Composite Score), have measured improvements in cardiovascular output (increase in cardiac output of 32%), and muscular health (as measured by strength increases relative to controls during weight training). The results are also statistically significant.

Example 13: Administration of a Small Molecule Compound

This is a prophetic example. 100 healthy aged (>60 y/o) individuals are recruited. The study participants are split into a group of 50 experimental patients and 50 control patients. The experimental group receives a composition comprising the following compounds orally one a week for two months. The control group receives a placebo.

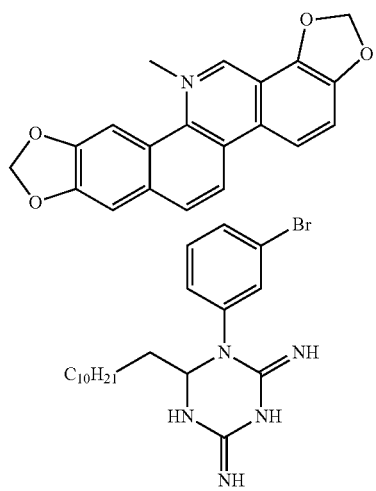

After 6 months, the cells of the groups are mobilize and collected. After treatment of the cells by the combination small molecules, the cells have decreased senescent behavior, has increased innate immune function, increased telomere length, lower replicative stress relative to the patient cell, increased stem cell clonogenicity, increased cytotoxic function, increased mitogen- and antigen-induced lymphocyte proliferation and activation, decreased myeloid to lymphoid ratio, increased CD4 to CD8 T lymphocyte ratio, decreased expression of senescence-associated secretory proteins, and/or decreased expression of senescence- and aging-related genes relative to the control cells. The patients indicate they have a feeling of better health. After 5 years of patient tracking, the experimental patients report becoming sick less often (22% reduction) than the control group, having a lower incidence of cancer (42% reduction), and having less soreness in their joints (46% reduction as measured using the VAS score). The experimental patients also report improved cognitive performance and function (39% increase relative to control as measured using the Cognitive Function Composite Score), have measured improvements in cardiovascular output (increase in cardiac output of 15%), and muscular health (as measured by strength increases relative to controls during weight training). The results also statistically significant.

What is claimed is:

1. A method of reducing expression of a paired box 5 (PAX5) gene in a cell, the method comprising:
   contacting a cell from a patient with one or more interfering RNAs (RNAi(s)), wherein the patient is one that will benefit from a reduction in expression of PAX5, wherein the RNAi(s) comprises:
      one or more sequences comprising a polynucleotide sequence that is at least 80% to 100% identical to one or more of SEQ ID Nos: 9-11 and 15-20; and
   maintaining the cell for a time sufficient to obtain inhibition of the PAX5 gene, thereby reducing expression of a PAX5 gene in that cell to provide a target cell, wherein the target cell is non-senescent and/or has decreased senescent behavior, has increased innate immune function, increased telomere length, lower replicative stress relative to the patient cell, increased stem cell clonogenicity, increased cytotoxic function, increased mitogen- and/or antigen-induced lymphocyte proliferation and/or activation, decreased myeloid to lymphoid ratio, increased CD4 to CD8 T lymphocyte ratio, decreased expression of senescence-associated secretory proteins, and/or decreased expression of senescence- and/or aging-related genes.

2. The method of claim 1, wherein the one or more RNAi(s) comprises at least one small interfering RNA (siRNA).

3. The method of claim 1, wherein the one or more RNAi(s) comprises at least one microRNA (miRNA).

4. The method of claim 1, wherein the one or more RNAi(s) comprises at least one short hairpin RNA (shRNA).

5. The method of claim 1, wherein the one or more RNAi(s) comprises SEQ ID NO:9.

6. The method of claim 1, wherein the one or more RNAi(s) comprises SEQ ID NO:10.

7. The method of claim 1, wherein the one or more RNAi(s) comprises SEQ ID NO:11.

8. The method of claim 1, wherein the one or more RNAi(s) comprises SEQ ID NO:15.

9. The method of claim 1, wherein the one or more RNAi(s) comprises SEQ ID NO:16.

10. The method of claim 1, wherein the one or more RNAi(s) comprises SEQ ID NO:17.

11. The method of claim 1, wherein the one or more RNAi(s) comprises SEQ ID NO:18.

12. The method of claim 1, wherein the one or more RNAi(s) comprises SEQ ID NO:19.

13. The method of claim 1, wherein the one or more RNAi(s) comprises SEQ ID NO:20.

14. The method of claim 1, wherein the cell is a human cell.

15. The method of claim 1, wherein the PAX5 expression is reduced by at least about 70%.

16. The method of claim 1, wherein the cell is contacted with the one or more RNAi(s) for a period of equal to or at least about 16 hours.

17. The method of claim 1, wherein contacting the cell with the one or more RNAi(s) comprises providing a dose of the one or more RNAi(s) that is equal to or less than 1000 µg.

18. The method of claim 17, wherein the cell is contacted with the one or more RNAi(s) for a period of time between 8 hours and 84 hours.

19. The method of claim 17, wherein the cell is in the patient and wherein the one or more RNAi(s) is administered using a pharmaceutically acceptable carrier.

20. The method of claim 1, wherein the cell is isolated from the patient prior to contacting the cell with one or more RNAi(s).

21. The method of claim 20, wherein the target cell is administered to the patient after contacting the cell with one or more RNAi(s).

22. The method of claim 21, wherein the target cell is part of a population of cells and wherein the population of cells comprises a therapeutically effective dose of cells.

23. The method of claim 22, wherein the therapeutically effective dose of cells is administered to a patient in need of treatment.

24. The method of claim 23, wherein the patient in need of treatment has an age that is greater than or equal to 50 years old.

\* \* \* \* \*